(12) United States Patent
Maianti et al.

(10) Patent No.: US 11,040,976 B2
(45) Date of Patent: Jun. 22, 2021

(54) SUBSTRATE SELECTIVE INHIBITORS OF INSULIN-DEGRADING ENZYME (IDE) AND USES THEREOF

(71) Applicant: President and Fellows of Harvard College, Cambridge, MA (US)

(72) Inventors: Juan Pablo Maianti, Revere, MA (US); David R. Liu, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/568,930

(22) PCT Filed: Apr. 22, 2016

(86) PCT No.: PCT/US2016/029051
§ 371 (c)(1),
(2) Date: Oct. 24, 2017

(87) PCT Pub. No.: WO2016/172631
PCT Pub. Date: Oct. 27, 2016

(65) Prior Publication Data
US 2018/0194768 A1     Jul. 12, 2018
US 2019/0016723 A9     Jan. 17, 2019

Related U.S. Application Data

(60) Provisional application No. 62/194,660, filed on Jul. 20, 2015, provisional application No. 62/152,723, filed on Apr. 24, 2015.

(51) Int. Cl.
*C07D 487/04*     (2006.01)
*A61K 31/397*     (2006.01)
(Continued)

(52) U.S. Cl.
CPC ............ *C07D 487/04* (2013.01); *A61K 45/06* (2013.01); *A61P 3/00* (2018.01); *C07C 311/16* (2013.01);
(Continued)

(58) Field of Classification Search
CPC ............................ C07D 487/04; A61K 31/397
See application file for complete search history.

(56) References Cited

U.S. PATENT DOCUMENTS

| 8,632,989 B1 | 1/2014 | Rodgers et al. |
| 8,975,232 B2 | 3/2015 | Liu et al. |

(Continued)

FOREIGN PATENT DOCUMENTS

| EP | 2 371 421 A1 | 10/2011 |
| WO | WO 2004/016767 A2 | 2/2004 |

(Continued)

OTHER PUBLICATIONS

Ex parte Cao, Decision rendered by Board of Patent Appeals and Interferences in U.S. Appl. No. 10/696,862 on Sep. 21, 2011 (Year: 2011).*

(Continued)

*Primary Examiner* — Karen Cheng
(74) *Attorney, Agent, or Firm* — Wolf, Greenfield & Sacks, P.C.

(57) ABSTRACT

Provided herein are compounds of Formulae (RL), (I), (II), (III), (IV), and (V), and pharmaceutically acceptable salts, solvates, hydrates, polymorphs, co-crystals, tautomers, stereoisomers, prodrugs, and isotopically labeled derivatives thereof. Also provided are pharmaceutical compositions, kits, and methods involving the inventive compounds for the treatment of metabolic disorders (e.g., diabetes, hyperglycemia, impaired glucose tolerance, insulin resistance, obesity). The compound are useful as substrate selective inhibitors of insulin-degrading enzyme (IDE).

(Continued)

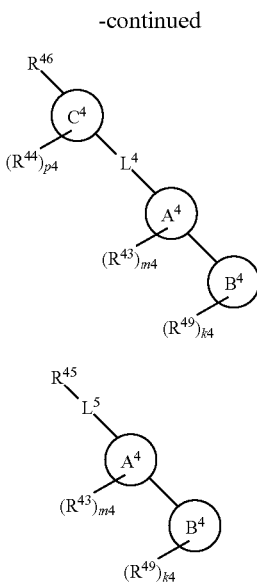

19 Claims, 42 Drawing Sheets

Specification includes a Sequence Listing.

(51) Int. Cl.
| | | |
|---|---|---|
| C07D 295/185 | (2006.01) | |
| C07D 295/26 | (2006.01) | |
| C07D 413/06 | (2006.01) | |
| C07D 493/10 | (2006.01) | |
| C07D 413/12 | (2006.01) | |
| C07D 405/06 | (2006.01) | |
| C07D 211/14 | (2006.01) | |
| C07D 211/16 | (2006.01) | |
| C07D 401/06 | (2006.01) | |
| C07D 401/12 | (2006.01) | |
| C07D 205/04 | (2006.01) | |
| C07D 211/96 | (2006.01) | |
| C07D 487/08 | (2006.01) | |
| C07D 405/12 | (2006.01) | |
| A61K 45/06 | (2006.01) | |
| A61P 3/00 | (2006.01) | |
| C07C 311/16 | (2006.01) | |
| C07D 241/44 | (2006.01) | |

(52) U.S. Cl.
CPC .......... *C07D 205/04* (2013.01); *C07D 211/14* (2013.01); *C07D 211/16* (2013.01); *C07D 211/96* (2013.01); *C07D 241/44* (2013.01); *C07D 295/185* (2013.01); *C07D 295/26* (2013.01); *C07D 401/06* (2013.01); *C07D 401/12* (2013.01); *C07D 405/06* (2013.01); *C07D 405/12* (2013.01); *C07D 413/06* (2013.01); *C07D 413/12* (2013.01); *C07D 487/08* (2013.01); *C07D 493/10* (2013.01)

(56) References Cited

U.S. PATENT DOCUMENTS

| | | | |
|---|---|---|---|
| 9,243,038 | B2 | 1/2016 | Liu et al. |
| 9,610,322 | B2 | 4/2017 | Liu et al. |
| 2002/0068301 | A1 | 6/2002 | Lai et al. |
| 2004/0067503 | A1 | 4/2004 | Tan et al. |
| 2006/0025566 | A1 | 2/2006 | Hoveyda et al. |
| 2008/0139456 | A1 | 6/2008 | Burke et al. |
| 2008/0242598 | A1 | 10/2008 | Fairlie et al. |
| 2010/0003232 | A1 | 1/2010 | Tang et al. |
| 2010/0105601 | A2 | 4/2010 | Brady et al. |
| 2013/0178429 | A1 | 7/2013 | Liu et al. |
| 2014/0213515 | A1 | 7/2014 | Liu et al. |
| 2016/0213744 | A1 | 7/2016 | Liu et al. |
| 2016/0282364 | A1 | 9/2016 | Maianti et al. |

FOREIGN PATENT DOCUMENTS

| | | | |
|---|---|---|---|
| WO | WO 2007/016441 A1 | 2/2007 | |
| WO | WO 2008/156701 A2 | 12/2008 | |
| WO | WO 2012/016186 A1 | 2/2012 | |
| WO | WO 2013/006451 A2 | 1/2013 | |
| WO | WO 2015/069876 A1 | 5/2015 | |
| WO | WO2015070204 | * | 5/2015 |

OTHER PUBLICATIONS

International Search Report and Written Opinion for Application No. PCT/US2011/045966, dated Dec. 16, 2011.
International Preliminary Report on Patentability for Application No. PCT/US2011/045966, dated Feb. 7, 2013.
International Search Report and Written Opinion for Application No. PCT/US2012/044977, dated Dec. 6, 2012.
International Preliminary Report on Patentability for Application No. PCT/US2012/044977, dated Jan. 16, 2014.
Extended European Search Report for Application No. EP 12807710.4, dated Jan. 5, 2015.
International Search Report and Written Opinion for Application No. PCT/US2014/064322, dated Mar. 5, 2015.
International Preliminary Report on Patentability for Application No. PCT/US2014/064322, dated May 19, 2016.
Invitation to Pay Additional Fees for Application No. PCT/US2016/029051, dated Aug. 4, 2016.
International Search Report and Written Opinion for Application No. PCT/US2016/029051, dated Oct. 11, 2016.
International Preliminary Report on Patentability for Application No. PCT/US2016/029051, dated Nov. 2, 2017.
[No Author Listed], Compound Summary for PubChem-CID-60191432. Create date Sep. 28, 2012. Accessed at https://pubchem.ncbi.nlm.nih.gov/compound/60191432. Accessed on Jun. 27, 2016.
[No Author Listed], Compound Summary for PubChem-CID-82283970. Create date Oct. 20, 2014. Accessed at https://pubchem.ncbi.nlm.nih.gov/compound/82283970#section=Top. Accessed on Jun. 10, 2016.
[No Author Listed], Compound Summary for PubChem-CID-71500599. Create date Jun. 10, 2013. Accessed at https://pubchem.ncbi.nlm.nih.gov/compound/71500599. Accessed on Jun. 13, 2016.
[No Author Listed], Compound Summary for PubChem-CID-65919020. Create date Oct. 24, 2012. Accessed at https://pubchem.ncbi.nlm.nih.gov/compound/82283970#section=Top. Accessed on Jun. 13, 2016.
Abdul-Hay et al., Deletion of insulin-degrading enzyme elicits antipodal, age-dependent effects on glucose and insulin tolerance. PLoS One. 2011;6(6):e20818. doi: 10.1371/journal.pone.0020818. Epub Jun. 9, 2011.
Abdul-Hay et al., Optimization of Peptide Hydroxamate Inhibitors of Insulin-Degrading Enzyme Reveals Marked Substrate-Selectivity. J Med Chem 2013;56(6):2246-2255. doi:10.1021/jm301280p. Epub Mar. 15, 2013.
Adams et al., PHENIX: A comprehensive Python-based system for macromolecular structure solution. Acta Crystallogr D Biol Crystallogr. Feb. 2010;66(Pt 2):213-21. doi: 10.1107/S0907444909052925. Epub Jan. 22, 2010.
Adams et al., PHENIX: building new software for automated crystallographic structure determination. Acta Crystallogr D Biol Crystallogr. Nov. 2002;58(Pt 11):1948-54. Epub Oct. 21, 2002.

(56) References Cited

OTHER PUBLICATIONS

Adrian et al., Allosteric inhibitors of Bcr-abl-dependent cell proliferation. Nat Chem Biol. Feb. 2006;2(2):95-102. Epub Jan. 15, 2006.
Ahren et al., The augmenting effect on insulin secretion by oral versus intravenous glucose is exaggerated by high-fat diet in mice. J Endocrinol. Apr. 2008;197(1):181-7. doi: 10.1677/JOE-07-0460.
Anderson et al., Discovery of selective aminothiazole aurora kinase inhibitors. ACS Chem Biol. Mar. 20, 2008;3(3):180-92. doi: 10.1021/cb700200w. Epub Feb. 29, 2008.
Andrikopoulos et al., Evaluating the glucose tolerance test in mice. Am J Physiol Endocrinol Metab. Dec. 2008;295(6):E1323-32. doi: 10.1152/ajpendo.90617.2008. Epub Sep. 23, 2008.
Authier et al., Proteolysis of glucagon within hepatic endosomes by membrane-associated cathepsins B and D. J Biol Chem. Jun. 30, 1995;270(26):15798-807.
Azam et al., Activation of tyrosine kinases by mutation of the gatekeeper threonine. Nat Struct Mol Biol. Oct. 2008;15(10):1109-18. doi: 10.1038/nsmb.1486. Epub Sep. 14, 2008.
Azam et al., Activity of dual SRC-ABL inhibitors highlights the role of BCR/ABL kinase dynamics in drug resistance. Proc Natl Acad Sci U S A. Jun. 13, 2006;103(24):9244-9. Epub Jun. 5, 2006.
Bannister et al., Probe Reports from the NIH Molecular Libraries Program [Online]. National Center for Biotechnology Information, Bethesda, MD 2012.
Barker et al., Characterization of pp60c-src tyrosine kinase activities using a continuous assay: autoactivation of the enzyme is an intermolecular autophosphorylation process. Biochemistry. Nov. 14, 1995;34(45):14843-51.
Barnard et al., In vitro inhibition of Ras-Raf association by short peptides. Biochem Biophys Res Commun. Jun. 9, 1998;247(1):176-80.
Barouch-Bentov et al, A conserved salt bridge in the G loop of multiple protein kinases is important for catalysis and for in vivo Lyn function. Mol Cell. Jan. 16, 2009;33(1):43-52. doi:10.1016/j.molcel.2008.12.024.
Bartl et al., Disorder-specific effects of polymorphisms at opposing ends of the Insulin Degrading Enzyme gene. BMC Med Genet. Nov. 22, 2011;12:151. doi: 10.1186/1471-2350-12-151.
Beaumont et al., Design of ester prodrugs to enhance oral absorption of poorly permeable compounds: challenges to the discovery scientist. Curr Drug Metab. Dec. 2003;4(6):461-85.
Becker et al., Insulysin and pitrilysin: insulin-degrading enzymes of mammals and bacteria. Methods Enzymol. 1995;248:693-703.
Bednarek et al., Selective high affinity peptide antagonist of alpha melanotropin action at human melanocortin recept or 4: their synthesis and biological evaluation in vitro. J Med Chem. 2001;44:3665-72.
Bennett et al., Degradation of amylin by insulin-degrading enzyme. J Biol Chem. Nov. 24, 2000;275(47):36621-5.
Bennett et al., Degradation of relaxin family peptides by insulin-degrading enzyme. Ann N Y Acad Sci. Apr. 2009;1160:38-41. doi:10.1111/j.1749-6632.2008.03782.x.
Bentley et al., Accurate whole human genome sequencing using reversible terminator chemistry. Nature. Nov. 6, 2008;456(7218):53-9.
Berge et al., Pharmaceutical salts. J Pharm Sci. Jan. 1977;66(1):1-19.
Bikker et al., Kinase domain mutations in cancer: implications for small molecule drug design strategies. J Med Chem. Mar. 26, 2009;52(6):1493-509.
Bradner et al., A robust small-molecule microarray platform for screening cell lysates. Chem Biol. May 2006;13(5):493-504.
Brudno et al., An in vitro translation, selection and amplification system for peptide nucleic acids. Nat Chem Biol. Feb. 2010;6(2):148-55. doi: 10.1038/nchembio.280. Epub Dec. 27, 2009.
Calderone et al., Small-molecule diversification from iterated branching reaction pathways enabled by DNA-templated synthesis. Angew Chem Int Ed Engl. Dec. 1, 2005;44(45):7383-6.

Capdeville et al., Glivec (STI571, imatinib), a rationally developed, targeted anticancer drug. Nat Rev Drug Discov. Jul. 2002;1(7):493-502.
Carrasquillo et al., Concordant association of insulin degrading enzyme gene (IDE) variants with IDE mRNA, Abeta, and Alzheimer's disease. PLoS One. Jan. 19, 2010;5(1):e8764.
Charton et al., Imidazole-derived 2-[N-carbamoylmethyl-alkylamino] acetic acids, substrate-dependent modulators of insulin-degrading enzyme in amyloid-β hydrolysis. Eur J Med Chem. May 22, 2014;79:184-93. doi: 10.1016/j.ejmech.2014.04.009. Epub Apr. 4, 2014.
Cheetham et al., Crystal structure of aurora-2, an oncogenic serine/threonine kinase. J Biol Chem. Nov. 8, 2002;277(45):42419-22. Epub Sep. 16, 2002.
Chen et al., A biomolecule-compatible visible-light-induced azide reduction from a DNA-encoded reaction-discovery system. Nat Chem. Feb. 2011;3(2):146-53. doi: 10.1038/nchem.932. Epub Jan. 9, 2011.
Chene et al., A small synthetic peptide, which inhibits the p53-hdm2 interaction, stimulates the p53 pathway in tumour cell lines. J Mol Biol. May 26, 2000;299(1):245-53.
Chudakov et al., Fluorescent proteins and their applications in imaging living cells and tissues. Physiol Rev. Jul. 2010;90(3):1103-63. doi: 10.1152/physrev.00038.2009. Review.
Church, Genomes for all. Sci Am. Jan. 2006;294(1):46-54.
Ciaccio et al., Somatostatin: a novel substrate and a modulator of insulin-degrading enzyme activity. J Mol Biol. Feb. 6, 2009;385(5):1556-67. doi:10.1016/j.jmb.2008.11.025. Epub Nov. 25, 2008.
Clark et al., Design, synthesis and selection of DNA-encoded small-molecule libraries. Nat Chem Biol. Sep. 2009;5(9):647-54. doi:10.1038/nchembio.211. Epub Aug. 2, 2009. Erratum in: Nat Chem Biol. Oct. 2009;5(10):772.
Coan et al., Stoichiometry and physical chemistry of promiscuous aggregate-based inhibitors. J Am Chem Soc. Jul. 23, 2008;130(29):9606-12. doi:10.1021/ja802977h. Epub Jun. 28, 2008. Epub Jun. 28, 2008.
Cohen, Protein kinases—the major drug targets of the twenty-first century? Nat Rev Drug Discov. Apr. 2002;1(4):309-15.
Cools et al., PKC412 overcomes resistance to imatinib in a murine model of FIP1L1-PDGFRα-induced myeloproliferative disease. Cancer Cell. May 2003;3(5):459-69.
Cowan-Jacob et al., The crystal structure of a c-Src complex in an active conformation suggests possible steps in c-Src activation. Structure. Jun. 2005;13(6):861-71.
Cronican et al., Potent delivery of functional proteins into Mammalian cells in vitro and in vivo using a supercharged protein. ACS Chem Biol. Aug. 20, 2010;5(8):747-52. doi:10.1021/cb1001153. With Supporting Information. 18 pages.
Crowell et al., The effects of tegaserod, a 5-HT receptor agonist, on gastric emptying in a murine model of diabetes mellitus. Neurogastroenterol Motil. Oct. 2005;17(5):738-43.
Das et al., 2-aminothiazole as a novel kinase inhibitor template. Structure-activity relationship studies toward the discovery of N-(2-chloro-6-methylphenyl)-2-[[6-[4-(2-hydroxyethyl)-1-piperazinyl]]-2-methyl-4-pyrimidinyl]amino)]-1,3-thiazole-5-carboxamide (dasatinib, BMS-354825) as a potent pan-Src kinase inhibitor. J Med Chem. Nov. 16, 2006;49(23):6819-32.
Dewey et al., New uridine derivatives for systematic evolution of RNA ligands by exponential enrichment. J. Am. Chem. Soc. Aug. 1995;117(32):8474-5.
Ditchfield et al., Aurora B couples chromosome alignment with anaphase by targeting BubR1, Mad2, and Cenp-E to kinetochores. J Cell Biol. Apr. 28, 2003;161(2):267-80.
Doyon et al., Highly sensitive in vitro selections for DNA-linked synthetic small molecules with protein binding affinity and specificity. J Am Chem Soc. Oct. 15, 2003;125(41):12372-3.
Drag et al., Emerging principles in protease-based drug discovery. Nat Rev Drug Discov. Sep. 2010;9(9):690-701. doi: 10.1038/nrd3053. Review.
Driggers et al., The exploration of macrocycles for drug discovery—an underexploited structural class. Nat Rev Drug Discov. Jul. 2008;7(7):608-24. doi: 10.1038/nrd2590.

(56) References Cited

OTHER PUBLICATIONS

Drucker., The biology of incretin hormones. Cell Metab. Mar. 2006;3(3):153-65. Review.
Duckworth et al., Insulin and glucagon degradation by the same enzyme. Diabetes. Jun. 1974;23(6):536-43.
Duckworth et al., Insulin degradation: progress and potential. Endocr Rev. Oct. 1998;19(5):608-24. Review.
Dumelin et al., Selection of streptavidin binders from a DNA-encoded chemical library. Bioconjug Chem. Mar.-Apr. 2006;17(2):366-70.
Durham et al., Dual Exosite-binding Inhibitors of Insulin-degrading Enzyme Challenge Its Role as the Primary Mediator of Insulin Clearance in Vivo. J. Biol. Chem. Aug. 2015;290:20044-20059.
Emsley et al., Coot: model-building tools for molecular graphics. Acta Crystallogr D Biol Crystallogr. Dec. 2004;60(Pt 12 Pt 1):2126-32. Epub Nov. 26, 2004.
Ettmayer et al., Lessons learned from marketed and investigational prodrugs. J Med Chem. May 6, 2004;47(10):2393-404.
Fancelli et al., Potent and selective Aurora inhibitors identified by the expansion of a novel scaffold for protein kinase inhibition. J Med Chem. Apr. 21, 2005;48(8):3080-4.
Farris et al., Insulin-degrading enzyme regulates the levels of insulin, amyloid beta-protein, and the beta-amyloid precursor protein intracellular domain in vivo. Proc Natl Acad Sci U S A. Apr. 1, 2003;100(7):4162-7. Epub Mar. 12, 2003.
Fontes et al., Miniglucagon (MG)-generating endopeptidase, which processes glucagon into MG, is composed of N-arginine dibasic convertase and aminopeptidase B. Endocrinology. Feb. 2005;146(2):702-12. Epub Nov. 11, 2004.
Forster et al., Programming peptidomimetic syntheses by translating genetic codes designed de novo. Proc Natl Acad Sci U S A. May 27, 2003;100(11):6353-7. Epub May 16, 2003.
Fu et al., Roles of Aurora kinases in mitosis and tumorigenesis. Mol Cancer Res. Jan. 2007;5(1):1-10. Review.
García-Echeverría et al., Discovery of potent antagonists of the interaction between human double minute 2 and tumor suppressor p53. J Med Chem. Aug. 24, 2000;43(17):3205-8.
Gartner et al. DNA-templated organic synthesis and selection of a library of macrocycles. Science. Sep. 10, 2004;305(5690):1601-5. Epub Aug. 19, 2004.
Gartner et al., Expanding the reaction scope of DNA-templated synthesis. Angew Chem Int Ed Engl. May 17, 2002;41(10):1796-800.
Gartner et al., Multistep small-molecule synthesis programmed by DNA templates. J Am Chem Soc. Sep. 4, 2002;124(35):10304-6.
Gartner et al., The generality of DNA-templated synthesis as a basis for evolving non-natural small molecules. J Am Chem Soc. Jul. 18, 2001;123(28):6961-3.
Gazit et al., Tyrphostins I: synthesis and biological activity of protein tyrosine kinase inhibitors. J Med Chem. Oct. 1989;32(10):2344-52.
Gedulin et al., Role of endogenous amylin in glucagon secretion and gastric emptying in rats demonstrated with the selective antagonist, AC187. Regul Pept. Dec. 10, 2006;137(3):121-7. Epub Aug. 17, 2006.
Gelling et al., Lower blood glucose, hyperglucagonemia, and pancreatic alpha cell hyperplasia in glucagon receptor knockout mice. Proc Natl Acad Sci U S A. Feb. 4, 2003;100(3):1438-43. Epub Jan. 24, 2003.
Georghiou et al., Highly specific, bisubstrate-competitive Src inhibitors from DNA-templated macrocycles. Nat Chem Biol. Feb. 19, 2012;8(4):366-74. doi: 10.1038/nchembio.792.
Golas et al., SKI-606, a Src/Abl inhibitor with in vivo activity in colon tumor xenograft models. Cancer Res. Jun. 15, 2005;65(12):5358-64.
Gu et al., Quantitative trait loci near the insulin-degrading enzyme (IDE) gene contribute to variation in plasma insulin levels. Diabetes. Aug. 2004;53(8):2137-42.
Guo et al., Molecular basis for the recognition and cleavages of IGF-II, TGF-alpha, and amylin by human insulin-degrading enzyme. J Mol Biol. Jan. 15, 2010;395(2):430-43. doi:10.1016/j.jmb.2009.10.072. Epub Nov. 5, 2009.
Hall, Advanced sequencing technologies and their wider impact in microbiology. J Exp Biol. May 2007;210(Pt 9):1518-25. Review.
Halpin et al., DNA display I. Sequence-encoded routing of DNA populations. PLoS Biology. Jul. 2004; 2(7):1015-21.
Halpin et al., DNA display II. Genetic manipulation of combinatorial chemistry libraries for small-molecule evolution. PLoS Biology. Jul. 2004; 2(7):1022-30.
Halpin et al., DNA display III. Solid-phase organic synthesis on unprotected DNA. PLoS Biology. Jul. 2004; 2(7):1031-8.
Hamel et al., Identification of the cleavage sites of transforming growth factor alpha by insulin-degrading enzymes. Biochim Biophys Acta. Apr. 4, 1997;1338(2):207-14.
Han et al., Targeted prodrug design to optimize drug delivery AAPS PharmSci. 2000;2(1):E6.
Hanke et al., Discovery of a novel, potent, and Src family-selective tyrosine kinase inhibitor. Study of Lck- and FynT-dependent T cell activation. J Biol Chem. Jan. 12, 1996;271(2):695-701.
Hanks et al., Protein kinase catalytic domain sequence database: identification of conserved features of primary structure and classification of family members. Methods Enzymol. 1991;200:38-62.
Hanks et al., The eukaryotic protein kinase superfamily: kinase (catalytic) domain structure and classification. FASEB J. May 1995;9(8):576-96. Review.
Hanks et al., The protein kinase family: conserved features and deduced phylogeny of the catalytic domains. Science. Jul. 1, 1988;241(4861):42-52. Review.
Hansen et al., A yoctoliter-scale DNA reactor for small-molecule evolution. J Am Chem Soc. Jan. 28, 2009;131(3):1322-7. doi: 10.1021/ja808558a.
Harrington et al., VX-680, a potent and selective small-molecule inhibitor of the Aurora kinases, suppresses tumor growth in vivo. Nat Med. Mar. 2004;10(3):262-7. Epub Feb. 22, 2004. Erratum in: Nat Med. Apr. 2007;13(4):511.
Heid et al., Real time quantitative PCR. Genome Res. Oct. 1996;6(10):986-94.
Higuchi et al., Simultaneous amplification and detection of specific DNA sequences. Biotechnology (N Y). Apr. 1992;10(4):413-7.
Hill et al., A chemical genetic method for generating bivalent inhibitors of protein kinases. J Am Chem Soc. May 20, 2009;131(19):6686-8. doi:10.1021/ja900871y.
Hollander et al., Effect of pramlintide on weight in overweight and obese insulin-treated type 2 diabetes patients. Obes Res. Apr. 2004;12(4):661-8.
Holmes et al., Vascular endothelial growth factor receptor-2: structure, function, intracellular signalling and therapeutic inhibition. Cell Signal. Oct. 2007;19(10):2003-12. Epub Jun. 12, 2007. Review.
Horhota et al., Kinetic analysis of an efficient DNA-dependent TNA polymerase. J Am Chem Soc. May 25, 2005;127(20):7427-34.
Hruby et al., Synthesis of oligopeptide and peptidomimetic libraries. Curr Opin Chem Biol. Jun. 1997;1(1):114-9.
Hubbard., Crystal structure of the activated insulin receptor tyrosine kinase in complex with peptide substrate and ATP analog. EMBO J. Sep. 15, 1997;16(18):5572-81.
Irby et al., Activating SRC mutation in a subset of advanced human colon cancers. Nat Genet. Feb. 1999;21(2):187-90.
Jameson et al., Fluorescence polarization: past, present and future. Comb Chem High Throughput Screen. May 2003;6(3):167-73. Review.
Jameson et al., Fluorescence polarization/anisotropy in diagnostics and imaging. Chem Rev. May 12, 2010;110(5):2685-708. doi: 10.1021/cr900267p. Review.
Johnson et al., Development of an internally quenched fluorescent substrate selective for endothelin-converting enzyme-1. Anal Biochem. Nov. 1, 2000;286(1):112-8.
Josephson et al., Ribosomal synthesis of unnatural peptides. J Am Chem Soc. Aug. 24, 2005;127(33):11727-35.
Joyce., Directed evolution of nucleic acid enzymes. Annu Rev Biochem. 2004;73:791-836. Review.

(56) References Cited

OTHER PUBLICATIONS

Kanan et al., Reaction discovery enabled by DNA-templated synthesis and in vitro selection. Nature. Sep. 30, 2004;431(7008):545-9.
Kansy et al., Physicochemical high throughput screening: parallel artificial membrane permeation assay in the description of passive absorption processes. J Med Chem. Mar. 26, 1998;41(7):1007-10.
Karaman et al., A quantitative analysis of kinase inhibitor selectivity. Nat Biotechnol. Jan. 2008;26(1):127-32.
Karamohamed et al., Polymorphisms in the insulin-degrading enzyme gene are associated with type 2 diabetes in men from the NHLBI Framingham Heart Study. Diabetes. Jun. 2003;52(6):1562-7.
Kim et al., Peptidomics approach to elucidate the proteolytic regulation of bioactive peptides. Proc Natl Acad Sci U S A. May 29, 2012;109(22):8523-7. Epub May 14, 2012.
Kleiner et al., DNA-templated polymerization of side-chain-functionalized peptide nucleic acid aldehydes. J Am Chem Soc. Apr. 9, 2008;130(14):4646-59. Epub Mar. 15, 2008.
Kleiner et al., In vitro selection of a DNA-templated small-molecule library reveals a class of macrocyclic kinase inhibitors. J Am Chem Soc. Aug. 25, 2010;132(33):11779-91.
Kleiner et al., In vitro selection of a DNA-templated small-molecule library reveals a class of macrocyclic kinase inhibitors. J Am Chem Soc. Aug. 25, 2010;132(33):11779-91. Supporting Information. 36 pages.
Kleiner et al., Small-molecule discovery from DNA-encoded chemical libraries. Chem Soc Rev. Dec. 2011;40(12):5707-17. Epub Jun. 14, 2011.
Knight et al, Chemical genetics: where genetics and pharmacology meet. Cell. Feb. 9, 2007;128(3):425-30.
Knight et al., Features of selective kinase inhibitors. Chem Biol. Jun. 2005;12(6):621-37.
Kolterman et al., Reduction of postprandial hyperglycemia in subjects with IDDM by intravenous infusion of AC137, a human amylin analogue. Diabetes Care. Aug. 1995;18(8):1179-82.
Krishnamurty et al., Biochemical mechanisms of resistance to small-molecule protein kinase inhibitors. ACS Chem Biol. Jan. 15, 2010;5(1):121-38. doi: 10.1021/cb9002656. Review.
Kurochkin et al., Alzheimer's beta-amyloid peptide specifically interacts with and is degraded by insulin degrading enzyme. FEBS Lett. May 23, 1994;345(1):33-7.
Kwon et al., Quantitative comparison of the relative cell permeability of cyclic and linear peptides. Chem Biol. Jun. 2007;14(6):671-7.
Lam et al., The "One-Bead-One-Compound" Combinatorial Library Method. Chem Rev. Apr. 1, 1997;97(2):411-448.
Lang et al., DOCK 6: combining techniques to model RNA-small molecule complexes. RNA. Jun. 2009;15(6):1219-30. doi: 10.1261/rna.1563609. Epub Apr. 15, 2009.
Latham et al., The application of a modified nucleotide in aptamer selection: novel thrombin aptamers containing 5-(1-pentynyl)-2'-deoxyuridine. Nucleic Acids Res. Jul. 25, 1994;22(14):2817-22.
Lee et al., Enhancing the catalytic repertoire of nucleic acids: a systematic study of linker length and rigidity. Nucleic Acids Res. Apr. 1, 2001;29(7):1565-73.
Lee et al., Metabolic manifestations of insulin deficiency do not occur without glucagon action. Proc Natl Acad Sci U S A. Sep. 11, 2012;109(37):14972-6. doi: 10.1073/pnas.1205983109. Epub Aug. 13, 2012.
Leissring et al., Designed inhibitors of insulin-degrading enzyme regulate the catabolism and activity of insulin. PLoS One. May 7, 2010;5(5):e10504. doi: 10.1371/journal.pone.0010504.
Leslie, Recent changes to the MOSFLM package for processing film and image plate data. Joint CCP4 + ESF-EAMCB Newsletter on Protein Crystallography, 1992;26:27-33.
Levinson et al., A Src-like inactive conformation in the abl tyrosine kinase domain. PLoS Biol. May 2006;4(5):e144. Epub May 2, 2006.
Levitzki, Protein tyrosine kinase inhibitors as novel therapeutic agents. Pharmacol Ther. May-Jun. 1999;82(2-3):231-9. Review.

Li et al., DNA-templated organic synthesis: nature's strategy for controlling chemical reactivity applied to synthetic molecules. Angew Chem Int Ed Engl. Sep. 20, 2004;43(37):4848-70. Review.
Li et al., The C-terminal domain of human insulin degrading enzyme is required for dimerization and substrate recognition. Biochem Biophys Res Commun. May 19, 2006;343(4):1032-7. Epub Mar. 22, 2006.
Lin et al., Screening and selection methods for large-scale analysis of protein function. Angew Chem Int Ed Engl. Dec. 2, 2002;41(23):4402-25. Review.
Liu et al., Synthesis and screening of a cyclic peptide library: Discovery of small molecule ligands against human prolactin receptor. Bioord Med Chem Lett. 2009;17:1026-33. doi:10.1016/j.bmc.2008.01.015. Epub Jan. 13, 2008.
Livak et al., Oligonucleotides with fluorescent dyes at opposite ends provide a quenched probe system useful for detecting PCR product and nucleic acid hybridization. PCR Methods Appl. Jun. 1995;4(6):357-62.
Llauger-Bufi et al., Synthesis of novel fluorescent probes for the molecular chaperone Hsp90. Bioorg Med Chem Lett. Nov. 17, 2003;13(22):3975-8.
Llovera et al., The catalytic domain of insulin-degrading enzyme forms a denaturant-resistant complex with amyloid beta peptide: implications for Alzheimer disease pathogenesis. J Biol Chem. Jun. 20, 2008;283(25):17039-48. doi: 10.1074/jbc.M706316200. Epub Apr. 14, 2008.
Löber et al., Palladium-catalyzed hydroamination of 1,3-dienes: a colorimetric assay and enantioselective additions. J Am Chem Soc. May 9, 2001;123(18):4366-7.
Lombardo et al., Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Lowe et al., Synthesis and Profiling of a Diverse Collection of Azetidine-Based Scaffolds for the Development of CNS-Focused Lead-Like Libraries. J. Org. Chem Aug. 2012;77(17):7187-7211.
Maianti et al., Anti-diabetic activity of insulin-degrading enzyme inhibitors mediated by multiple hormones. Nature. Jul. 3, 2014;511(7507):94-8. doi: 10.1038/nature13297. Epub May 21, 2014.
Malito et al., Molecular bases for the recognition of short peptide substrates and cysteine-directed modifications of human insulin-degrading enzyme. Biochemistry. Dec. 2, 2008;47(48):12822-34. doi: 10.1021/bi801192h.
Manning et al., The protein kinase complement of the human genome. Science. Dec. 6, 2002;298(5600):1912-34. Review.
Manolopoulou et al., Molecular basis of catalytic chamber-assisted unfolding and cleavage of human insulin by human insulin-degrading enzyme. J Biol Chem. May 22, 2009;284(21):14177-88. doi:10.1074/jbc.M900068200. Epub Mar. 25, 2009.
Maresso et al., Sortase as a target of anti-infective therapy. Pharmacol Rev. Mar. 2008;60(1):128-41. Review.
Martens et al., PREPL: A putative novel oligopeptidase propelled into the limelight. Biol Chem. Jul. 2006;387(7):879-83. Review.
Matulic-Adamic et al., Functionalized nucleoside 5'-triphosphates for in vitro selection of new catalytic ribonucleic acids. Bioorg Med Chem Lett. Jun. 5, 2000;10(11):1299-302.
McCoy et al. Likelihood-enhanced fast translation functions. Acta Crystallogr D Biol Crystallogr. Apr. 2005;61(Pt 4):458-64. Epub Mar. 24, 2005.
McCoy et al., Phaser crystallographic software. J Appl Crystallogr. Aug. 1, 2007;40(Pt 4):658-674. Epub Jul. 13, 2007.
Melkko et al., Encoded self-assembling chemical libraries. Nat Biotechnol. May 2004;22(5):568-74. Epub Apr. 18, 2004.
Melkko et al., Isolation of high-affinity trypsin inhibitors from a DNA-encoded chemical library. Angew Chem Int Ed Engl. 2007;46(25):4671-4.
Miller et al., Amyloid-beta peptide levels in brain are inversely correlated with insulysin activity levels in vivo. Proc Natl Acad Sci U S A. May 13, 2003;100(10):6221-6. Epub May 5, 2003.
Mirsky et al, Effect of insulinase-inhibitor on hypoglycemic action of insulin. Science. Sep. 23, 1955;122(3169):559-60.

(56) References Cited

OTHER PUBLICATIONS

Mirsky et al., The inactivation of insulin by tissue extracts; the distribution and properties of insulin inactivating extracts. Arch Biochem. Jan. 1949;20(1):1-9.
Misbin et al., Inhibition of insulin degradation by insulin-like growth factors. Endocrinology. Oct. 1983;113(4):1525-7.
Mol et al., Structural basis for the autoinhibition and STI-571 inhibition of c-Kit tyrosine kinase. J Biol Chem. Jul. 23, 2004;279(30):31655-63. Epub Apr. 29, 2004.
Momiyama et al., Synthesis of acyclic alpha,beta-unsaturated ketones via Pd(II)-catalyzed intermolecular reaction of alkynamides and alkenes. J Am Chem Soc. Feb. 28, 2007;129(8):22301. Epub Feb. 6, 2007.
Müller et al., Atrial natriuretic peptide (ANP) is a high-affinity substrate for rat insulin-degrading enzyme. Eur J Biochem. Dec. 5, 1991;202(2):285-92.
Muller et al., Prodrug approaches for enhancing the bioavailability of drugs with low solubility. Chem Biodivers. Nov. 2009;6(11):2071-83. doi: 10.1002/cbdv.200900114.
Musich et al, Synthesis of anthopleurine, the alarm pheromone from Anthopleura elegantissima. J. Am. Chem. Soc. Jul. 1987;100(15):4865-72.
Ohren et al., Structures of human MAP kinase kinase 1 (MEK1) and MEK2 describe novel noncompetitive kinase inhibition. Nat Struct Mol Biol. Dec. 2004;11(12):1192-7. Epub Nov. 14, 2004. Erratum in: Nat Struct Mol Biol. Mar. 2005;12(3):278.
Otwinowski et al., Processing of x-ray diffraction data collected in oscillation mode. Methods in Enzymology. 276 (Macromolecular Crystallography, part A):307-26.
Owicki., Fluorescence polarization and anisotropy in high throughput screening: perspectives and primer. J Biomol Screen. Oct. 2000;5(5):297-306. Review.
Parker et al., The regulation of *Acinetobacter* sp. alpha-oxoglutarate dehydrogenase complex. Biochem J. Nov. 1972;130(1):39P.
Patick et al., Protease inhibitors as antiviral agents. Clin Microbiol Rev. Oct. 1998;11(4):614-27. Review.
Perrin et al., Bridging the gap between proteins and nucleic acids: a metal-independent RNAseA mimic with two protein-like functionalities. J Am Chem Soc. Feb. 28, 2001;123(8):1556-63.
Pirrung, Spatially Addressable Combinatorial Libraries. Chem Rev. Apr. 1, 1997;97(2):473-488.
PubChem CID 46938796. Nov. 15, 2010. [Retrieved from the internet Dec. 2, 2011:http://pubchem.ncbi.nim.nih.gov/summary/summary.cgi?cid=46938796&loc=ec_rcs].
Qiu et al., Insulin-degrading enzyme regulates extracellular levels of amyloid beta-protein by degradation. J Biol Chem. Dec. 4, 1998;273(49):32730-8.
Riddle et al., Emerging therapies mimicking the effects of amylin and glucagon-like peptide 1. Diabetes Care. Feb. 2006;29(2):435-49. Review.
Riediger et al., The anorectic hormone amylin contributes to feeding-related changes of neuronal activity in key structures of the gut-brain axis. Am J Physiol Regul Integr Comp Physiol. Jan. 2004;286(1):R114-22. Epub Sep. 4, 2003.
Roh et al., Overexpression of the oncogenic kinase Pim-1 leads to genomic instability. Cancer Res. Dec. 1, 2003;63(23):8079-84.
Rosenbaum et al., Efficient and sequence-specific DNA-templated polymerization of peptide nucleic acid aldehydes. J Am Chem Soc. Nov. 19, 2003;125(46):13924-5.
Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.
Ruff et al., Enhanced functional potential of nucleic acid aptamer libraries patterned to increase secondary structure. J Am Chem Soc. Jul. 14, 2010;132(27):9453-64. doi: 10.1021/ja103023m.
Ruff et al., Enhanced functional potential of nucleic acid aptamer libraries patterned to increase secondary structure. J Am Chem Soc. Jul. 14, 2010;132(27):9453-64. Supporting Information. 25 pages.
Sadry et al., Emerging combinatorial hormone therapies for the treatment of obesity and T2DM. Nat Rev Endocrinol. Jul. 2013;9(7):425-33. doi: 10.1038/nrendo.2013.47. Epub Mar. 12, 2013. Review.
Safavi et al., Identification of gamma-endorphin-generating enzyme as insulin-degrading enzyme. Biochemistry. Nov. 12, 1996;35(45):14318-25.
Saghatelian et al., Activity-based probes for the proteomic profiling of metalloproteases. Proc Natl Acad Sci U S A. Jul. 6, 2004;101(27):10000-5. Epub Jun. 25, 2004.
Sattler et al., Structure of Bcl-xL-Bak peptide complex: recognition between regulators of apoptosis. Science. Feb. 14, 1997;275(5302):983-6.
Scheuermann et al., DNA-encoded chemical libraries for the discovery of MMP-3 inhibitors. Bioconjug Chem. Mar. 2008;19(3):778-85. Epub Feb. 7, 2008.
Schmitz et al., Amylin agonists: a novel approach in the treatment of diabetes. Diabetes. Dec. 2004;53 Suppl 3:S233-8. Review.
Seeliger et al., c-Src binds to the cancer drug imatinib with an inactive Abl/c-Kit conformation and a distributed thermodynamic penalty. Structure. Mar. 2007;15(3):299-311.
Seeliger et al., Equally potent inhibition of c-Src and Abl by compounds that recognize inactive kinase conformations. Cancer Res. Mar. 15, 2009;69(6):2384-92. Epub Mar. 10, 2009.
Seeliger et al., High yield bacterial expression of active c-Abl and c-Src tyrosine kinases. Protein Sci. Dec. 2005;14(12):3135-9. Epub Oct. 31, 2005.
Shan et al., How does a drug molecule find its target binding site? J Am Chem Soc. Jun. 22, 2011;133(24):9181-3. Epub May 13, 2011.
Sharma et al., Targeting Akt3 signaling in malignant melanoma using isoselenocyanates. Clin Cancer Res. Mar. 1, 2009;15(5):1674-85. Epub Feb. 10, 2009.
Shen et al., Structures of human insulin-degrading enzyme reveal a new substrate recognition mechanism. Nature. Oct. 19, 2006;443(7113):870-4. Epub Oct. 11, 2006.
Shoichet, Interpreting steep dose-response curves in early inhibitor discovery. J Med Chem. Dec. 14, 2006;49(25):7274-7.
Sicheri et al., Crystal structure of the Src family tyrosine kinase Hck. Nature. Feb. 13, 1997;385(6617):602-9.
Singh et al., Recent trends in targeted anticancer prodrug and conjugate design. Curr Med Chem. 2008;15(18):1802-26.
Snyder et al., Ordered multistep synthesis in a single solution directed by DNA templates. Angew Chem Int Ed Engl. Dec. 1, 2005;44(45):7379-82.
Songyang et al., Catalytic specificity of protein-tyrosine kinases is critical for selective signalling. Nature. Feb. 9, 1995;373(6514):536-9.
Songyang et al., Recognition and specificity in protein tyrosine kinase-mediated signalling. Trends Biochem Sci. Nov. 1995;20(11):470-5.
Souza-Fagundes et al., A high-throughput fluorescence polarization anisotropy assay for the 70N domain of replication protein A. Anal Biochem. Feb. 15, 2012;421(2):742-9. doi: 10.1016/j.ab.2011.11.025. Epub Dec. 1, 2011.
Stella et al., Cyclodextrins. Toxicol Pathol. Jan. 2008;36(1):30-42. doi: 10.1177/0192623307310945. Review.
Stout et al., High-throughput structural biology in drug discovery: protein kinases. Curr Pharm Des. 2004;10(10):1069-82. Review.
Sugimura et al., Mutation of the SRC gene in endometrial carcinoma. Jpn J Cancer Res. Apr. 2000;91(4):395-8.
Tan., Diversity-oriented synthesis: exploring the intersections between chemistry and biology. Nat Chem Biol. Jul. 2005;1(2):74-84. Review.
Tatton et al., The Src-selective kinase inhibitor PP1 also inhibits Kit and Bcr-Abl tyrosine kinases. J Biol Chem. Feb. 14, 2003;278(7):4847-53. Epub Dec. 9, 2002.
Taylor et al., Investigating and Engineering Enzymes by Genetic Selection. Angew Chem Int Ed Engl. Sep. 17, 2001;40(18):3310-3335.
Testa, Prodrug research: futile or fertile? Biochem Pharmacol. Dec. 1, 2004;68(11):2097-106.
Thompson et al., Attenuation of androgen receptor-dependent transcription by the serine/threonine kinase Pim-1. Lab Invest. Sep. 2003;83(9):1301-9.

(56) References Cited

OTHER PUBLICATIONS

Trebbien et al., Neutral endopeptidase 24.11 is important for the degradation of both endogenous and exogenous glucagon in anesthetized pigs. Am J Physiol Endocrinol Metab. Sep. 2004;287(3):E431-8. Epub May 4, 2004.

Tse et al., Translation of DNA into a library of 13,000 synthetic small-molecule macrocycles suitable for in vitro selection. J Am Chem Soc. Nov. 19, 2008;130(46):15611-26. doi: 10.1021/ja805649f. Epub Oct. 29, 2008.

Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008, supporting information.

Unger et al., Glucagonocentric restructuring of diabetes: a pathophysiologic and therapeutic makeover. J Clin Invest. Jan. 3, 2012;122(1):4-12. doi: 10.1172/JCI60016. Epub Jan. 3, 2012. Review.

Vonrhein et al., Data processing and analysis with the autoPROC toolbox. Acta Crystallogr D Biol Crystallogr. Apr. 2011;67(Pt 4):293-302. doi: 10.1107/S0907444911007773. Epub Mar. 18, 2011.

Walters et al., Designing screens: how to make your hits a hit. Nat Rev Drug Discov. Apr. 2003;2(4):259-66. Review.

Wilson et al., In vitro Selection of Functional Nucleic Acids. Ann. Rev. Biochem., 1999; 68:611-48.

Winzell et al., The high-fat diet-fed mouse: a model for studying mechanisms and treatment of impaired glucose tolerance and type 2 diabetes. Diabetes. Dec. 2004;53 Suppl 3:S215-9.

Workman et al., Probing the probes: fitness factors for small molecule tools. Chem Biol. Jun. 25, 2010;17(6):561-77. doi: 10.1016/j.chembiol.2010.05.013. Review.

Wrenn et al., Synthetic ligands discovered by in vitro selection. J Am Chem Soc. Oct. 31, 2007;129(43):13137-43. Epub Oct. 6, 2007.

Xu et al., Crystal structures of c-Src reveal features of its autoinhibitory mechanism. Mol Cell. May 1999;3(5):629-38.

Xu et al., Three-dimensional structure of the tyrosine kinase c-Src. Nature. Feb. 13, 1997;385(6617):595-602.

Zhang et al., In vitro degradation of insulin-like peptide 3 by insulin-degrading enzyme. Protein J. Feb. 2010;29(2):93-8. doi:10.1007/s10930-009-9226-8.

Zhang et al., Targeting cancer with small molecule kinase inhibitors. Nat Rev Cancer. Jan. 2009;9(1):28-39. doi: 10.1038/nrc2559. Review.

U.S. Appl. No. 13/812,431, filed Mar. 26, 2013, Liu et al.
U.S. Appl. No. 14/643,709, filed Mar. 10, 2015, Liu et al.
U.S. Appl. No. 14/130,336, filed Mar. 3, 2014, Liu et al.
U.S. Appl. No. 15/004,862, filed Jan. 22, 2016, Liu et al.
U.S. Appl. No. 15/034,731, filed May 5, 2016, Maianti et al.
PCT/US2011/045966, Dec. 16, 2011, International Search Report and Written Opinion.
PCT/US2011/045966, Feb. 7, 2013, International Preliminary Report on Patentability.
PCT/US2012/044977, Dec. 6, 2012, International Search Report and Written Opinion.
PCT/US2012/044977, Jan. 16, 2014, International Preliminary Report on Patentability.
12807710.4, Jan. 5, 2015, Extended European Search Report.
PCT/US2014/064322, Mar. 5, 2015, International Search Report and Written Opinion.
PCT/US2014/064322, May 19, 2016, International Preliminary Report on Patentability.
PCT/US2016/029051, Aug. 4, 2016, Invitiation to Pay Additional Fees.
PCT/US2016/029051, Oct. 11, 2016, International Search Report and Written Opinion.
PCT/US2016/029051, Nov. 2, 2017, International Preliminary Report on Patentability.

\* cited by examiner

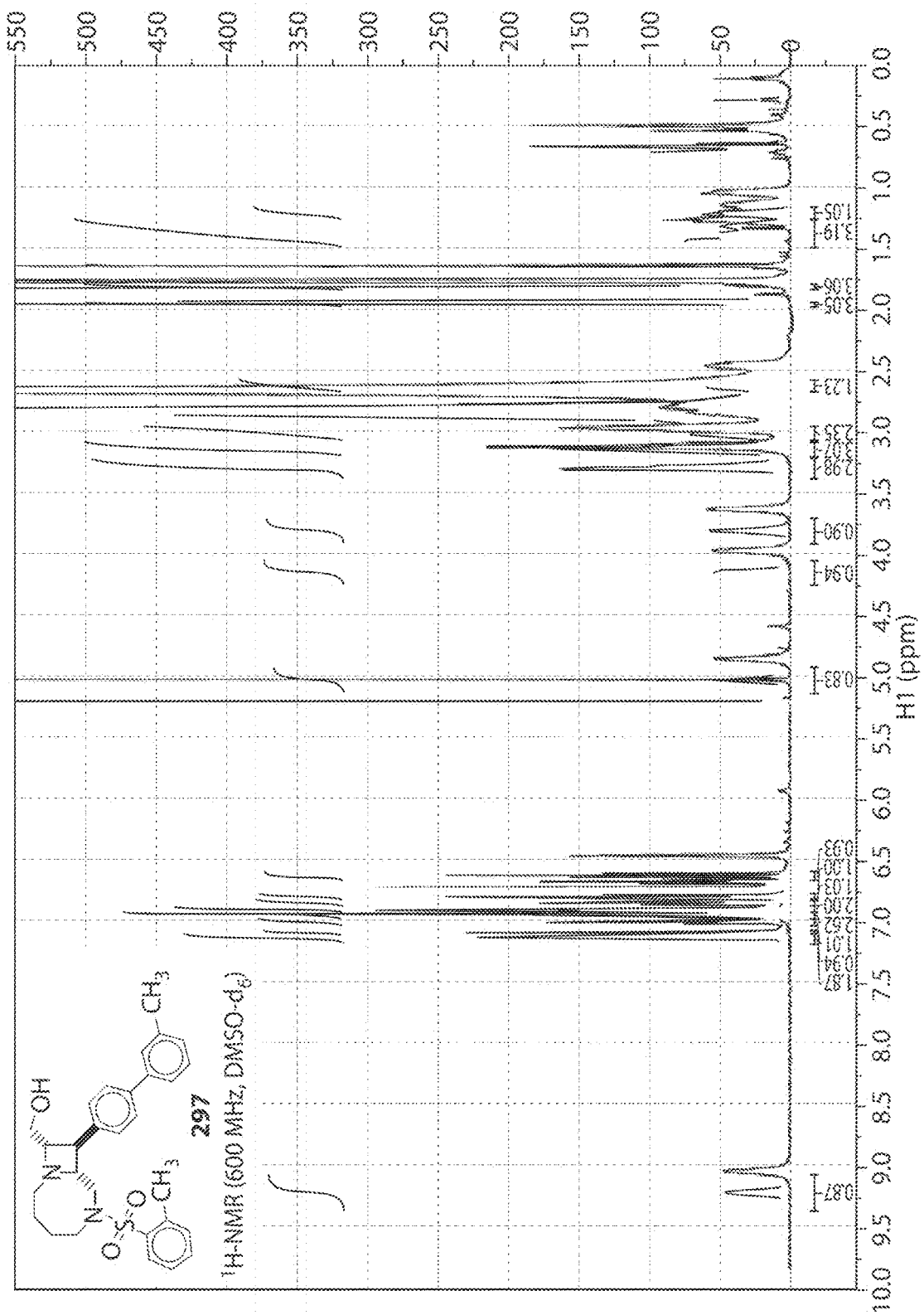

Amylin (fp)  KCNTATCATXRLANFLVHSSNNZGAILSSTNVGSNTY-NH$_2$
hAmylin      KCNTATCATQRLANFLVHSSNNFGAILSSTNVGSNTY-NH$_2$
(X = Lys-γN-anthranilamide; Z = 3-NO$_2$-Y)

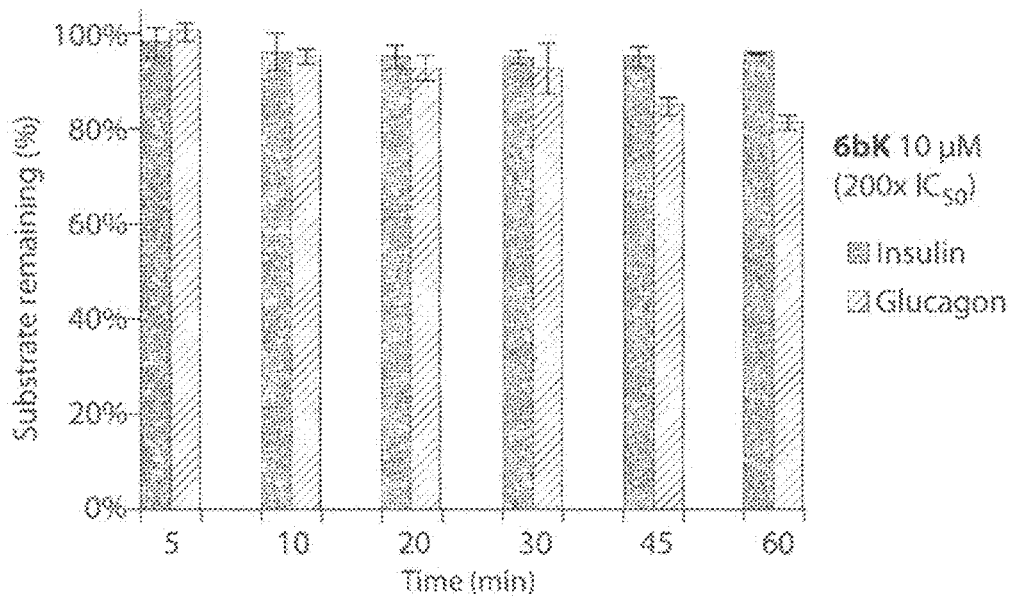
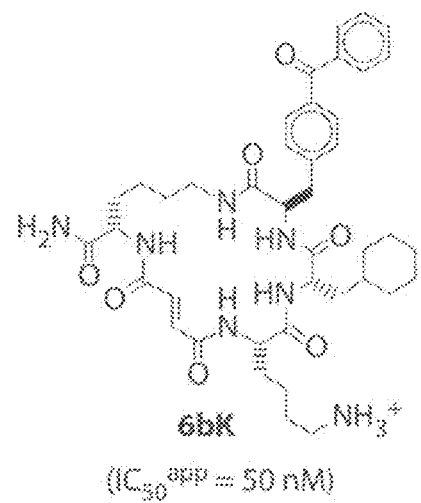
FIG. 26A

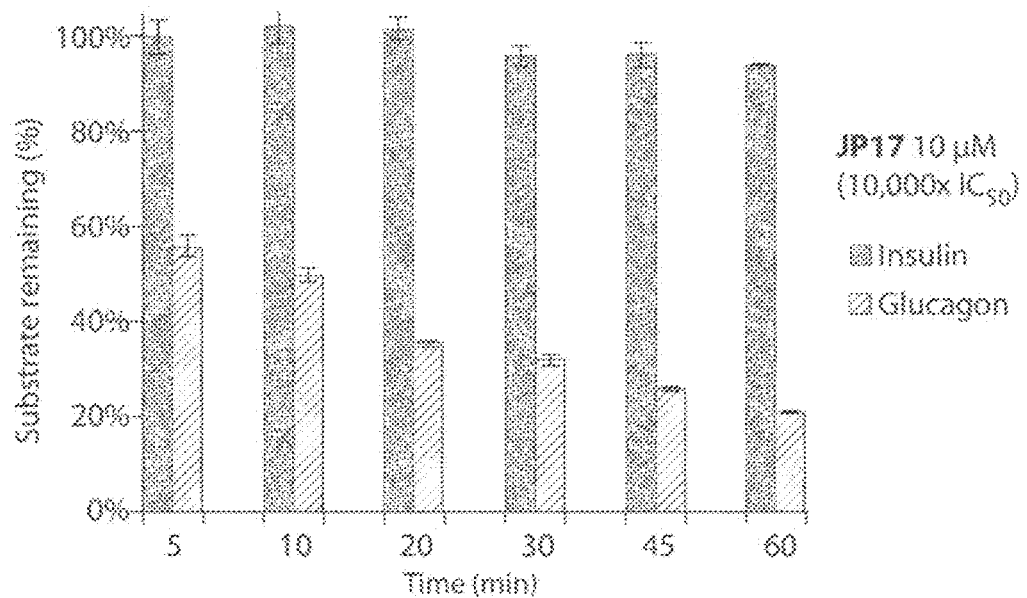
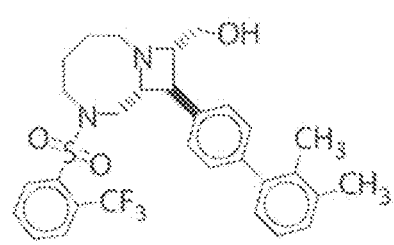
JP17 (IC$_{50}^{app}$ = 1 nM)
FIG. 26B

```
                          SEQUENCE LISTING

<160> NUMBER OF SEQ ID NOS: 54

<210> SEQ ID NO 1
<211> LENGTH: 1019
<212> TYPE: PRT
<213> ORGANISM: Homo sapiens

<400> SEQUENCE: 1

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
                20                  25                  30

Gly Phe Gln Lys Lys Thr Tyr Ser Lys Met Asn Asn Pro Ala Ile Lys
            35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
                100                 105                 110

Met Leu Phe Leu Gly Thr Lys Lys Tyr Pro Lys Glu Asn Glu Tyr Ser
            115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
    195                 200                 205

Gly Asn Pro Lys His Pro Phe Ser Lys Phe Gly Thr Gly Asn Lys Tyr
210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
    275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335
```

-continued

```
Leu Ile Gly His Gly Pro Gly Ser Leu Ser Glu Leu Lys Ser
            340                 345                 350

Lys Gly Trp Val Asn Thr Leu Val Gly Gly Gln Lys Glu Gly Ala Arg
        355                 360                 365

Gly Phe Met Phe Phe Ile Ile Asn Val Asp Leu Thr Glu Glu Gly Leu
        370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
                420                 425                 430

Tyr Thr Ser Lys Ile Ala Gly Ile Leu His Tyr Tyr Pro Leu Glu Glu
        435                 440                 445

Val Leu Thr Ala Glu Tyr Leu Leu Glu Glu Phe Arg Pro Asp Leu Ile
        450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                485                 490                 495

Gly Thr Gln Tyr Lys Gln Glu Ala Ile Pro Asp Glu Val Ile Lys Lys
        500                 505                 510

Trp Gln Asn Ala Asp Leu Asn Gly Lys Phe Lys Leu Pro Thr Lys Asn
        515                 520                 525

Glu Phe Ile Pro Thr Asn Phe Glu Ile Leu Pro Leu Glu Lys Glu Ala
    530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
            580                 585                 590

Ala Tyr Leu Tyr Leu Glu Leu Leu Lys Asp Ser Leu Asn Glu Tyr Ala
        595                 600                 605

Tyr Ala Ala Glu Leu Ala Gly Leu Ser Tyr Asp Leu Gln Asn Thr Ile
610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                645                 650                 655

Lys Arg Phe Glu Ile Ile Lys Glu Ala Tyr Met Arg Ser Leu Asn Asn
                660                 665                 670

Phe Arg Ala Glu Gln Pro His Gln His Ala Met Tyr Tyr Leu Arg Leu
        675                 680                 685

Leu Met Thr Glu Val Ala Trp Thr Lys Asp Glu Leu Lys Glu Ala Leu
        690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750
```

Ala His Thr Lys Pro Leu Leu Pro Ser Gln Leu Val Arg Tyr Arg Glu
755 760 765

Val Gln Leu Pro Asp Arg Gly Trp Phe Val Tyr Gln Gln Arg Asn Glu
770 775 780

Val His Asn Asn Cys Gly Ile Glu Ile Tyr Tyr Gln Thr Asp Met Gln
785 790 795 800

Ser Thr Ser Glu Asn Met Phe Leu Glu Leu Phe Cys Gln Ile Ile Ser
805 810 815

Glu Pro Cys Phe Asn Thr Leu Arg Thr Lys Glu Gln Leu Gly Tyr Ile
820 825 830

Val Phe Ser Gly Pro Arg Arg Ala Asn Gly Ile Gln Gly Leu Arg Phe
835 840 845

Ile Ile Gln Ser Glu Lys Pro Pro His Tyr Leu Glu Ser Arg Val Glu
850 855 860

Ala Phe Leu Ile Thr Met Glu Lys Ser Ile Glu Asp Met Thr Glu Glu
865 870 875 880

Ala Phe Gln Lys His Ile Gln Ala Leu Ala Ile Arg Arg Leu Asp Lys
885 890 895

Pro Lys Lys Leu Ser Ala Glu Cys Ala Lys Tyr Trp Gly Glu Ile Ile
900 905 910

Ser Gln Gln Tyr Asn Phe Asp Arg Asp Asn Thr Glu Val Ala Tyr Leu
915 920 925

Lys Thr Leu Thr Lys Glu Asp Ile Ile Lys Phe Tyr Lys Glu Met Leu
930 935 940

Ala Val Asp Ala Pro Arg Arg His Lys Val Ser Val His Val Leu Ala
945 950 955 960

Arg Glu Met Asp Ser Cys Pro Val Val Gly Glu Phe Pro Cys Gln Asn
965 970 975

Asp Ile Asn Leu Ser Gln Ala Pro Ala Leu Pro Gln Pro Glu Val Ile
980 985 990

Gln Asn Met Thr Glu Phe Lys Arg Gly Leu Pro Leu Phe Pro Leu Val
995 1000 1005

Lys Pro His Ile Asn Phe Met Ala Ala Lys Leu
1010 1015

<210> SEQ ID NO 2
<211> LENGTH: 464
<212> TYPE: PRT
<213> ORGANISM: Homo sapiens

<400> SEQUENCE: 2

Met Ser Lys Leu Trp Phe Lys Gln Asp Asp Lys Phe Leu Pro Lys
1 5 10 15

Ala Cys Leu Asn Phe Glu Phe Phe Ser Pro Phe Ala Tyr Val Asp Pro
20 25 30

Leu His Cys Asn Met Ala Tyr Leu Tyr Leu Glu Leu Leu Lys Asp Ser
35 40 45

Leu Asn Glu Tyr Ala Tyr Ala Ala Glu Leu Ala Gly Leu Ser Tyr Asp
50 55 60

Leu Gln Asn Thr Ile Tyr Gly Met Tyr Leu Ser Val Lys Gly Tyr Asn
65 70 75 80

Asp Lys Gln Pro Ile Leu Leu Lys Lys Ile Ile Glu Lys Met Ala Thr
85 90 95

Phe Glu Ile Asp Glu Lys Arg Phe Glu Ile Ile Lys Glu Ala Tyr Met
100 105 110

```
Arg Ser Leu Asn Asn Phe Arg Ala Glu Gln Pro His Gln His Ala Met
            115                 120                 125

Tyr Tyr Leu Arg Leu Leu Met Thr Glu Val Ala Trp Thr Lys Asp Glu
130                 135                 140

Leu Lys Glu Ala Leu Asp Asp Val Thr Leu Pro Arg Leu Lys Ala Phe
145                 150                 155                 160

Ile Pro Gln Leu Leu Ser Arg Leu His Ile Glu Ala Leu Leu His Gly
                165                 170                 175

Asn Ile Thr Lys Gln Ala Ala Leu Gly Ile Met Gln Met Val Glu Asp
            180                 185                 190

Thr Leu Ile Glu His Ala His Thr Lys Pro Leu Leu Pro Ser Gln Leu
        195                 200                 205

Val Arg Tyr Arg Glu Val Gln Leu Pro Asp Arg Gly Trp Phe Val Tyr
210                 215                 220

Gln Gln Arg Asn Glu Val His Asn Asn Cys Gly Ile Glu Ile Tyr Tyr
225                 230                 235                 240

Gln Thr Asp Met Gln Ser Thr Ser Glu Asn Met Phe Leu Glu Leu Phe
                245                 250                 255

Cys Gln Ile Ile Ser Glu Pro Cys Phe Asn Thr Leu Arg Thr Lys Glu
            260                 265                 270

Gln Leu Gly Tyr Ile Val Phe Ser Gly Pro Arg Arg Ala Asn Gly Ile
        275                 280                 285

Gln Gly Leu Arg Phe Ile Ile Gln Ser Glu Lys Pro Pro His Tyr Leu
290                 295                 300

Glu Ser Arg Val Glu Ala Phe Leu Ile Thr Met Glu Lys Ser Ile Glu
305                 310                 315                 320

Asp Met Thr Glu Glu Ala Phe Gln Lys His Ile Gln Ala Leu Ala Ile
                325                 330                 335

Arg Arg Leu Asp Lys Pro Lys Lys Leu Ser Ala Glu Cys Ala Lys Tyr
            340                 345                 350

Trp Gly Glu Ile Ile Ser Gln Gln Tyr Asn Phe Asp Arg Asp Asn Thr
        355                 360                 365

Glu Val Ala Tyr Leu Lys Thr Leu Thr Lys Glu Asp Ile Ile Lys Phe
370                 375                 380

Tyr Lys Glu Met Leu Ala Val Asp Ala Pro Arg Arg His Lys Val Ser
385                 390                 395                 400

Val His Val Leu Ala Arg Glu Met Asp Ser Cys Pro Val Val Gly Glu
                405                 410                 415

Phe Pro Cys Gln Asn Asp Ile Asn Leu Ser Gln Ala Pro Ala Leu Pro
            420                 425                 430

Gln Pro Glu Val Ile Gln Asn Met Thr Glu Phe Lys Arg Gly Leu Pro
        435                 440                 445

Leu Phe Pro Leu Val Lys Pro His Ile Asn Phe Met Ala Ala Lys Leu
450                 455                 460

<210> SEQ ID NO 3
<211> LENGTH: 1019
<212> TYPE: PRT
<213> ORGANISM: Mus musculus

<400> SEQUENCE: 3

Met Arg Asn Gly Leu Val Trp Leu Leu His Pro Ala Leu Pro Gly Thr
1               5                   10                  15

Leu Arg Ser Ile Leu Gly Ala Arg Pro Pro Ala Lys Arg Leu Cys
            20                  25                  30
```

-continued

```
Gly Phe Pro Lys Gln Thr Tyr Ser Thr Met Ser Asn Pro Ala Ile Gln
             35                  40                  45

Arg Ile Glu Asp Gln Ile Val Lys Ser Pro Glu Asp Lys Arg Glu Tyr
 50                  55                  60

Arg Gly Leu Glu Leu Ala Asn Gly Ile Lys Val Leu Leu Ile Ser Asp
 65                  70                  75                  80

Pro Thr Thr Asp Lys Ser Ser Ala Ala Leu Asp Val His Ile Gly Ser
                 85                  90                  95

Leu Ser Asp Pro Pro Asn Ile Pro Gly Leu Ser His Phe Cys Glu His
                100                 105                 110

Met Leu Phe Leu Gly Thr Lys Lys Tyr Pro Lys Glu Asn Glu Tyr Ser
            115                 120                 125

Gln Phe Leu Ser Glu His Ala Gly Ser Ser Asn Ala Phe Thr Ser Gly
            130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Ala
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
            195                 200                 205

Gly Asn Pro Lys His Pro Phe Ser Lys Phe Gly Thr Gly Asn Lys Tyr
210                 215                 220

Thr Leu Glu Thr Arg Pro Asn Gln Glu Gly Ile Asp Val Arg Glu Glu
225                 230                 235                 240

Leu Leu Lys Phe His Ser Thr Tyr Tyr Ser Ser Asn Leu Met Ala Ile
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
            275                 280                 285

Pro Glu His Pro Phe Gln Glu Glu His Leu Arg Gln Leu Tyr Lys Ile
            290                 295                 300

Val Pro Ile Lys Asp Ile Arg Asn Leu Tyr Val Thr Phe Pro Ile Pro
305                 310                 315                 320

Asp Leu Gln Gln Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
            340                 345                 350

Lys Gly Trp Val Asn Thr Leu Val Gly Gly Gln Lys Glu Gly Ala Arg
            355                 360                 365

Gly Phe Met Phe Phe Ile Ile Asn Val Asp Leu Thr Glu Glu Gly Leu
            370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Lys Leu His Tyr Tyr Pro Leu Asn Gly
            435                 440                 445
```

```
Val Leu Thr Ala Glu Tyr Leu Leu Glu Glu Phe Arg Pro Asp Leu Ile
450                 455                 460

Asp Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Gln Trp Tyr
                485                 490                 495

Gly Thr Gln Tyr Lys Gln Glu Ala Ile Pro Glu Asp Ile Ile Gln Lys
                500                 505                 510

Trp Gln Asn Ala Asp Leu Asn Gly Lys Phe Lys Leu Pro Thr Lys Asn
                515                 520                 525

Glu Phe Ile Pro Thr Asn Phe Glu Ile Leu Ser Leu Glu Lys Asp Ala
530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
                580                 585                 590

Ala Tyr Leu Tyr Leu Glu Leu Leu Lys Asp Ser Leu Asn Glu Tyr Ala
                595                 600                 605

Tyr Ala Ala Glu Leu Ala Gly Leu Ser Tyr Asp Leu Gln Asn Thr Ile
610                 615                 620

Tyr Gly Met Tyr Leu Ser Val Lys Gly Tyr Asn Asp Lys Gln Pro Ile
625                 630                 635                 640

Leu Leu Lys Lys Ile Thr Glu Lys Met Ala Thr Phe Glu Ile Asp Lys
                645                 650                 655

Lys Arg Phe Glu Ile Ile Lys Glu Ala Tyr Met Arg Ser Leu Asn Asn
                660                 665                 670

Phe Arg Ala Glu Gln Pro His Gln His Ala Met Tyr Tyr Leu Arg Leu
                675                 680                 685

Leu Met Thr Glu Val Ala Trp Thr Lys Asp Glu Leu Lys Glu Ala Leu
690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Val Met Gln Met Val Glu Asp Thr Leu Ile Glu His
                740                 745                 750

Ala His Thr Lys Pro Leu Leu Pro Ser Gln Leu Val Arg Tyr Arg Glu
                755                 760                 765

Val Gln Leu Pro Asp Arg Gly Trp Phe Val Tyr Gln Gln Arg Asn Glu
                770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
                820                 825                 830

Val Phe Ser Gly Pro Arg Arg Ala Asn Gly Ile Gln Gly Leu Arg Phe
                835                 840                 845

Ile Ile Gln Ser Glu Lys Pro Pro His Tyr Leu Glu Ser Arg Val Glu
850                 855                 860
```

Ala Phe Leu Ile Thr Met Glu Lys Ala Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910

Ser Gln Gln Tyr Asn Tyr Asp Arg Asp Asn Ile Glu Val Ala Tyr Leu
        915                 920                 925

Lys Thr Leu Thr Lys Asp Asp Ile Ile Arg Phe Tyr Gln Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Ser Gln Asn
                965                 970                 975

Asp Ile Asn Leu Ser Glu Ala Pro Pro Leu Pro Gln Pro Glu Val Ile
            980                 985                 990

His Asn Met Thr Glu Phe Lys Arg Gly Leu Pro Leu Phe Pro Leu Val
        995                 1000                1005

Lys Pro His Ile Asn Phe Met Ala Ala Lys Leu
    1010                1015

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Arg is modified with (7-methoxycoumarin-4-yl)
      acetyl
<220> FEATURE:
<221> NAME/KEY: MISC_FEATURE
<222> LOCATION: (9)..(9)
<223> OTHER INFORMATION: Lys is modified with 2,4-dinitrophenyl

<400> SEQUENCE: 4

Arg Pro Pro Gly Phe Ser Ala Phe Lys
1               5

<210> SEQ ID NO 5
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 6
<211> LENGTH: 30
<212> TYPE: PRT
<213> ORGANISM: Artificial Sequence
<220> FEATURE:
<223> OTHER INFORMATION: Synthetic Polypeptide

```
<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 8
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: Xaa is Lys-(gamma)N-anthrinilamide
<220> FEATURE:
<221> NAME/KEY: MISC_FEATURE
<222> LOCATION: (23)..(23)
<223> OTHER INFORMATION: Xaa is 3-nitro-Tyr

<400> SEQUENCE: 8

Lys Cys Asn Thr Ala Thr Cys Ala Thr Xaa Arg Leu Ala Asn Phe Leu
1               5                   10                  15

Val His Ser Ser Asn Asn Xaa Gly Ala Ile Leu Ser Ser Thr Asn Val
            20                  25                  30

Gly Ser Asn Thr Tyr
        35

<210> SEQ ID NO 9
<211> LENGTH: 37
<212> TYPE: PRT
<213> ORGANISM: Homo sapiens

<400> SEQUENCE: 9

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<222> LOCATION: (1)..(1)
<223> OTHER INFORMATION: Arg is modified with (7-methoxycoumarin-4-yl)
      acetyl
<220> FEATURE:
<221> NAME/KEY: MISC_FEATURE
<222> LOCATION: (7)..(7)
<223> OTHER INFORMATION: Xaa is norvaline
<220> FEATURE:
<221> NAME/KEY: MISC_FEATURE
<222> LOCATION: (10)..(10)
<223> OTHER INFORMATION: Lys is modified with 2,4-dinitrophenyl

<400> SEQUENCE: 10

Arg Pro Lys Pro Val Glu Xaa Trp Arg Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Pro is modified with (7-methoxycoumarin-4-yl)
      acetyl
<220> FEATURE:
<221> NAME/KEY: MISC_FEATURE
<222> LOCATION: (6)..(7)
<223> OTHER INFORMATION: Modified with N-3-(2,4-dinitrophenyl)-L-2,3-
      diaminopropionyl

<400> SEQUENCE: 11

Pro Leu Ala Gln Ala Val Arg Ser Ser Ser Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Ser is modified with (7-methoxycoumarin-4-yl)
      acetyl
<220> FEATURE:
<221> NAME/KEY: MISC_FEATURE
<222> LOCATION: (11)..(12)
<223> OTHER INFORMATION: Modified with 2,4-dinitrophenyl

<400> SEQUENCE: 12

Ser Glu Val Asn Leu Asp Ala Glu Phe Arg Lys Arg Arg
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Pro is modified with (7-methoxycoumarin-4-yl)
      acetyl
```

```
<220> FEATURE:
<221> NAME/KEY: MISC_FEATURE
<222> LOCATION: (4)..(5)
<223> OTHER INFORMATION: Modified with N-3-(2,4-dinitrophenyl)-L-2,3-
      diaminopropionyl

<400> SEQUENCE: 13

Pro Leu Gly Leu Ala Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Tyr is modified with PO3

<400> SEQUENCE: 14

Asp Ala Asp Glu Tyr Leu Ile Pro Gln Gln Gly
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tyr is modified with (7-methoxycoumarin-4-yl)
      acetyl
<220> FEATURE:
<221> NAME/KEY: MISC_FEATURE
<222> LOCATION: (5)..(5)
<223> OTHER INFORMATION: Lys is modified with 2,4-dinitrophenyl

<400> SEQUENCE: 15

Tyr Val Ala Asp Ala Pro Lys
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Ala is acetylated
<220> FEATURE:
<221> NAME/KEY: MISC_FEATURE
<222> LOCATION: (4)..(4)
<223> OTHER INFORMATION: Asp is modified with 7-amino-4-methylcoumarin

<400> SEQUENCE: 16

Ala Ser Thr Asp
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Polypeptide
```

-continued

```
<220> FEATURE:
<221> NAME/KEY: MISC_FEATURE
<222> LOCATION: (1)..(1)
<223> OTHER INFORMATION: Ala is modified with benzyloxycarbonyl
<220> FEATURE:
<221> NAME/KEY: MISC_FEATURE
<222> LOCATION: (4)..(4)
<223> OTHER INFORMATION: Asp is modified with 7-amino-4-
      trifluoromethylcoumarin

<400> SEQUENCE: 17

Asp Gln Met Asp
1

<210> SEQ ID NO 18
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: Met is modified with p-nitroanilide

<400> SEQUENCE: 18

Lys Thr Glu Glu Ile Ser Glu Val Lys Met
1               5                   10

<210> SEQ ID NO 19
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Ala is modified with succinyl
<220> FEATURE:
<221> NAME/KEY: MISC_FEATURE
<222> LOCATION: (4)..(4)
<223> OTHER INFORMATION: Xaa is norvaline
<220> FEATURE:
<221> NAME/KEY: MISC_FEATURE
<222> LOCATION: (4)..(4)
<223> OTHER INFORMATION: Xaa is modified with p-nitroanilide

<400> SEQUENCE: 19

Ala Ala Pro Xaa
1

<210> SEQ ID NO 20
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Lys is modified with 2-aminobenzoic acid
<220> FEATURE:
<221> NAME/KEY: MISC_FEATURE
<222> LOCATION: (5)..(6)
<223> OTHER INFORMATION: Modified with L-alpha,beta-diaminopropionic
      acid and 2,4-dinitrophenyl

<400> SEQUENCE: 20

Lys Pro Leu Gly Leu Ala Arg
1               5
```

```
<210> SEQ ID NO 21
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tyr is modified with 4-
      (4-dimethylaminophenylazo)benzoyl

<400> SEQUENCE: 21

Tyr Val Ala Asp
1

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(2)
<223> OTHER INFORMATION: Modified with 5-[(2-aminoethyl)
      amino]naphthalene-1-sulfonic acid
<220> FEATURE:
<221> NAME/KEY: MISC_FEATURE
<222> LOCATION: (9)..(9)
<223> OTHER INFORMATION: Lys is modified with 4-(4-
      dimethylaminophenylazo)benzoyl

<400> SEQUENCE: 22

Glu Lys Pro Ala Lys Phe Phe Arg Lys
1               5

<210> SEQ ID NO 23
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Gly is modified with 5-[(2-aminoethyl)amino]
      naphthalene-1-sulfonic acid
<220> FEATURE:
<221> NAME/KEY: MISC_FEATURE
<222> LOCATION: (13)..(13)
<223> OTHER INFORMATION: Xaa is retro-m-nitro-Tyr-H

<400> SEQUENCE: 23

Gly Gly Trp Thr Leu Asn Ser Ala Gly Tyr Leu Lys Xaa
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Arg is modified with (7 methoxycourmarin-4-yl)
      acetyl
<220> FEATURE:
<221> NAME/KEY: MISC_FEATURE
<222> LOCATION: (9)..(9)
<223> OTHER INFORMATION: Lys is modified with 2,4-dinitrophenyl
```

<400> SEQUENCE: 24

Arg Pro Pro Gly Phe Ser Ala Phe Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Pro is modified with (7 methoxycourmarin-4-yl)
      acetyl
<220> FEATURE:
<221> NAME/KEY: MISC_FEATURE
<222> LOCATION: (5)..(5)
<223> OTHER INFORMATION: Lys is modified with 2,4-dinitrophenyl

<400> SEQUENCE: 25

Pro Leu Gly Pro Lys
1               5

<210> SEQ ID NO 26
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 26
atcatcatat gaataatcca gccaucaaga gaatagg                              37

<210> SEQ ID NO 27
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 27
atgctagcca tacctcagag utttgcagcc atgaag                               36

<210> SEQ ID NO 28
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 28
atggctggat tattcatatg atgaugatga tgatgagaac cc                        42

<210> SEQ ID NO 29
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 29
actctgaggt atggctagca ugactggtg                                       29

```
<210> SEQ ID NO 30
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 30
agactctttc aattggaaaa agcuacaggg                                    30

<210> SEQ ID NO 31
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 31 agcttttcc aattgaaaga gtcuccaggt atcattcatc acattcttct catgttc       57

<210> SEQ ID NO 32
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 32
agactctttc aattggaaaa agcuacaggg                                    30

<210> SEQ ID NO 33
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 33 agcttttcc aattgaaaga gtcugaaggc atcattcatc acattcttct c             51

<210> SEQ ID NO 34
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 34
agactctttc aattggaaaa agcuacaggg                                    30

<210> SEQ ID NO 35
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 35
atgaatgatg cctggagacu ccgtcaattg gaaaaagcta caggg                   45

<210> SEQ ID NO 36
<211> LENGTH: 53
<212> TYPE: DNA
<213> ORGANISM: Artificial Sequence
<220> FEATURE:
<223> OTHER INFORMATION: Synthetic Polynucleotide
```

<400> SEQUENCE: 36
acccattaaa gatattagga atctcutcgt gacatttccc atacctgacc ttc        53

<210> SEQ ID NO 37
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 37
agagattcct aatatcttta atggguacta ttttg                            35

<210> SEQ ID NO 38
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 38
aaagggctgg gttaatactc tucagggtgg gcag                             34

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 39
aagagtatta acccagccct tugacttaag                                  30

<210> SEQ ID NO 40
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 40
aaagggctgg gttaatactc tugttggtca gcagaaggaa ggagcccgag             50

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
aagagtatta acccagccct tugacttaag                                  30

<210> SEQ ID NO 42
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 42
atgttttttc agattaatgt ggactugacc gaggaagg                         38

```
<210> SEQ ID NO 43
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 43
aagtccacat taatctgaaa aaacauaaaa cctcgggctc cttc                    44

<210> SEQ ID NO 44
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 44
atgtccgggt tctgatagtt tctaaauctt ttgaaggaaa aactg                   45

<210> SEQ ID NO 45
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 45
atttagaaac tatcagaacc cggacautttt ctggtctgag                       40

<210> SEQ ID NO 46
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 46
gattaacttt attattaaaa attaaagagg                                    30

<210> SEQ ID NO 47
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 47
caacatgtaa taatccttcc tcggtc                                        26

<210> SEQ ID NO 48
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 48
gcatgaaggt cctggaagtc tg                                            22

<210> SEQ ID NO 49
<211> LENGTH: 24
<212> TYPE: DNA
<213> ORGANISM: Artificial Sequence
<220> FEATURE:
<223> OTHER INFORMATION: Synthetic Polynucleotide
```

```
<400> SEQUENCE: 49
aggaagggtt acatcatcca gagc                                          24

<210> SEQ ID NO 50
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 50
ccatgtacta cctccgcttg c                                             21

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 51
gcagatctcg agctcggatc                                               20

<210> SEQ ID NO 52
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 52
gcttatgtgg accccttgca ctg                                           23

<210> SEQ ID NO 53
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 53

Arg Ala Gln Asp Phe Val Gln Trp Leu Met Asn Thr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 54

Arg Arg Ala Gln Asp Phe Val Gln Trp Leu Met Asn Thr
1               5                   10
```

SUBSTRATE SELECTIVE INHIBITORS OF INSULIN-DEGRADING ENZYME (IDE) AND USES THEREOF

RELATED APPLICATIONS

The present application is a national stage filing under 35 U.S.C. § 371 of international PCT application, PCT/US2016/029051, filed Apr. 22, 2016, which claims priority under 35 U.S.C. § 119(e) to U.S. provisional patent applications, U.S. Ser. No. 62/152,723, filed Apr. 24, 2015, and U.S. Ser. No. 62/194,660, filed Jul. 20, 2015, each of which is incorporated herein by reference.

GOVERNMENT SUPPORT

This invention was made with Government support under grant number R01 GM065865 awarded by the National Institutes of Health (National Institute of General Medical Sciences). The Government has certain rights in the invention.

BACKGROUND

Diabetes and other diabetic conditions are endocrinological disorders that are characterized by impaired insulin signaling or insulin resistance. Conventional therapeutic approaches for diabetic patients aim to enhance insulin signaling, for example, by administration of exogenous insulin, by stimulating the generation and secretion of endogenous insulin, or by activating downstream targets of the insulin receptor (IR) signaling cascade. Inhibitors of insulin catabolism open another therapeutic avenue to improve insulin signaling.

Insulin-degrading enzyme (IDE) and its involvement in insulin catabolism has been known for several decades, however, the development of small-molecule inhibitors of IDE has been surprisingly difficult. As a result, there is need for the development of clinically useful IDE inhibitors.

SUMMARY

Most treatments for metabolic disorders such as diabetes and other diabetic conditions rely on the regulation of metabolic hormones, most notably insulin. An alternative therapeutic approach to the enhancement of insulin signaling (e.g., by administering exogenous insulin, stimulating insulin secretion) is the inhibition of insulin catabolism. The enzyme responsible for the degradation (i.e., catabolism) of insulin is insulin-degrading enzyme (IDE). Insulin-degrading enzyme, also referred to as insulysin, insulinase, or insulin protease, is a 110 kDa zinc-binding protease of the M16A metalloprotease subfamily (EC 3.4.24.56). IDE was first identified by its ability to degrade the β chain of insulin and has since been shown to target additional substrates, including the pathophysiologically important peptide β-amyloid, the signaling peptides glucagon, amylin, TGF-alpha, β-endorphin, and atrial natriuretic peptide. While IDE is the main protease responsible for insulin degradation, most other IDE substrates are known to be targeted and degraded by other proteases as well. Despite great interest in the pharmacological targeting of IDE, the enzyme has remained an elusive target. Only a handful of types of IDE inhibitors are known.

One group of IDE inhibitors includes peptide hydroxamic acids, e.g., Ii1 (see, e.g., Leissring et al., *PLoS ONE* (2010) 5(5): e10504).

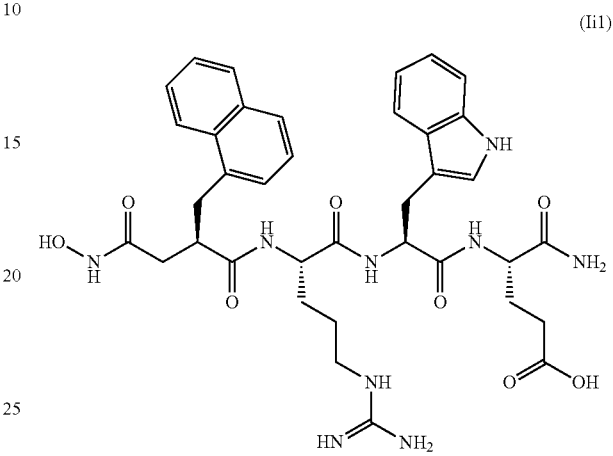

(Ii1)

The isothiazoline inhibitor ML345 (see, e.g., Bannister et al., *Probe Reports from the NIH Molecular Libraries Program* [Online] (2012), National Center for Biotechnology Information: Bethesda, Md.) and imidazole-derived amyloid beta inhibitors, e.g., BDM41367 (see, e.g., Charton et al., *Eur. J. Med. Chem.* (2014), 79, 184-193), have also been identified as IDE inhibitors and are shown below.

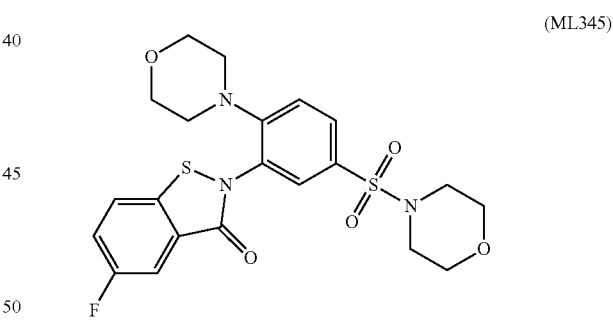

(ML345)

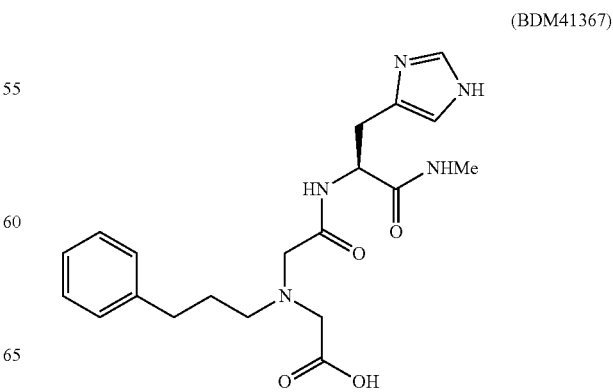

(BDM41367)

Additional IDE inhibitors include macrocyclic peptide-like compounds, e.g., 6b and 6bK (see, e.g., Maianti et al., *Nature* (2014), 511, 94-98, which is incorporated herein by reference).

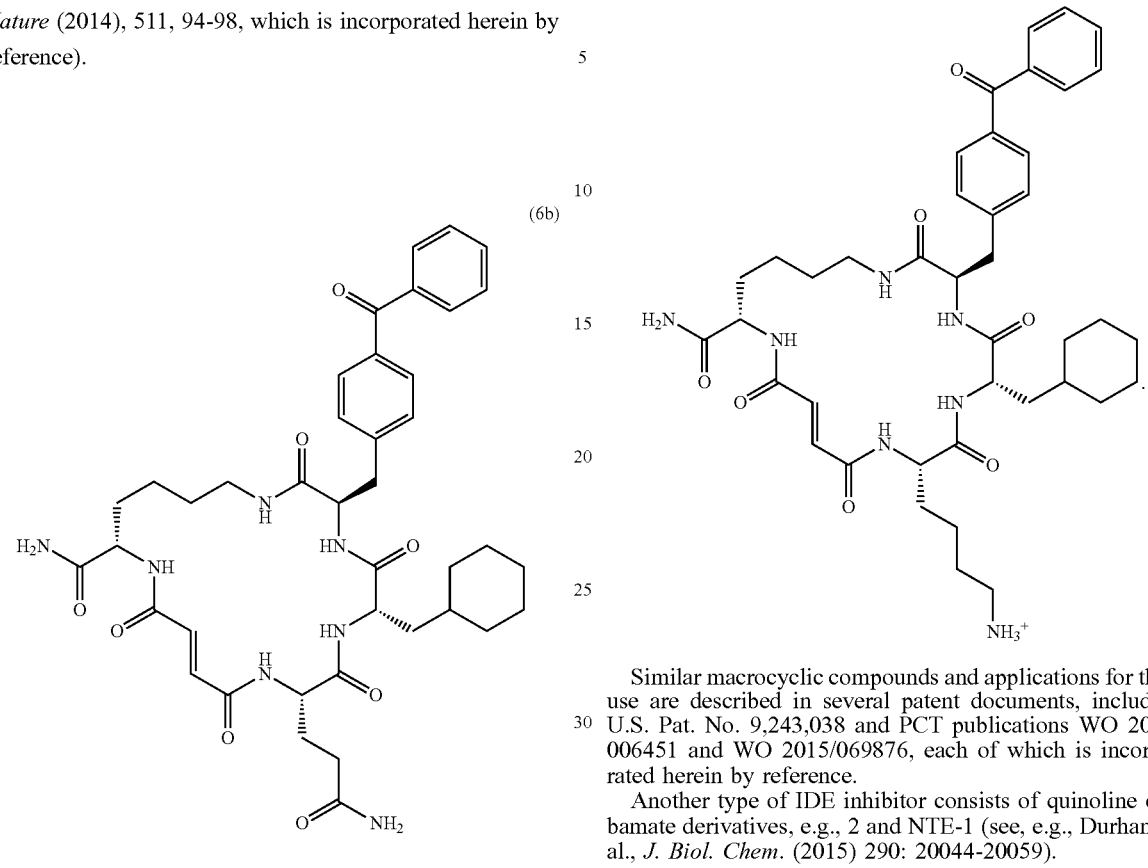

Similar macrocyclic compounds and applications for their use are described in several patent documents, including U.S. Pat. No. 9,243,038 and PCT publications WO 2013/006451 and WO 2015/069876, each of which is incorporated herein by reference.

Another type of IDE inhibitor consists of quinoline carbamate derivatives, e.g., 2 and NTE-1 (see, e.g., Durham et al., *J. Biol. Chem.* (2015) 290: 20044-20059).

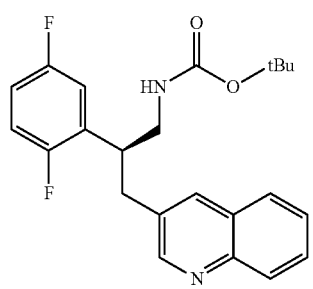

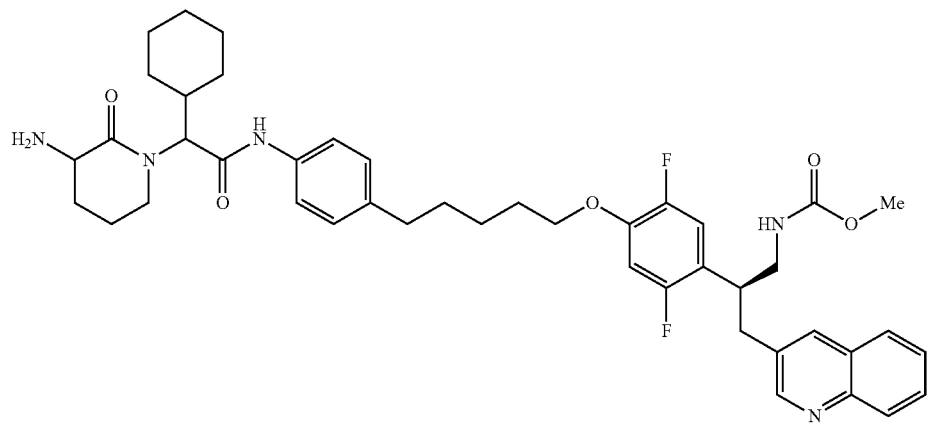

In addition to insulin, IDE also degrades other hormones including glucagon. The effect of glucagon on metabolism opposes that of insulin. Glucagon signaling causes the release of glucose into the bloodstream. Non-selective inhibition of IDE may lead to increased levels of both insulin and glucagon, whereas the selective inhibition of IDE to block insulin degradation but allow IDE to continue to catabolize glucagon could enhance insulin concentrations without effecting glucagon concentrations. The compounds provided herein may be selective or non-selective inhibitors of IDE. Substrate selectivity between other substrates besides insulin and glucagon are also contemplated.

The selectivity of a substrate selective inhibitor may be a result of the manner in which the compound binds to IDE and the differences between the interaction of insulin and glucagon with IDE. Insulin and glucagon interact differently with IDE due to different physical properties (e.g., size, volume, charge, conformation, location of specific residues and sequences). Therefore, a provided compound, in some embodiments, may affect the ability of one substrate (e.g., insulin) to bind to IDE and be cleaved, more than said compound affects the ability of a second substrate (e.g., glucagon) to bind to IDE and be cleaved.

In certain embodiments, the inhibitor binds to IDE (e.g., human IDE isoform 1) in a distal binding pocket at the interface of IDE domains 1 and 2. For inhibitor 6b the catalytic Zn center is located about 11 Å from the nearest atom of 6b (See, e.g., FIG. 9B and FIG. 9D, and Maianti et al., *Nature* (2014), 511, 94-98, which is incorporated herein by reference). The distal binding pocket comprises a deep hydrophobic pocket about 10 Å in length, defined by the residues Leu201, Glu205, Tyr302, Thr316, and Ala479. The involvement of the deep hydrophobic pocket in the binding of inhibitors described herein to IDE has been demonstrated by site-directed mutagenesis experiments where Ala479 was replaced with leucine, leading to an increase in the $IC_{50}$ for inhibition of proteolysis of about 100-200 fold for compounds 204 and 297 (See FIG. 8A and FIG. 8B).

Binding of the inhibitor in the distal binding pocket may affect the conformation of IDE at the peptide (e.g., insulin, glucagon) binding site, affect the ability of the peptide to achieve a conformation necessary for peptide cleavage during binding, or sterically impede binding of the peptide (e.g., insulin, glucagon), or a combination thereof. In certain embodiments, these effects reduce the binding affinity of IDE for peptide substrates and/or the degradation activity of IDE towards those substrates. In certain embodiments, for a substrate selective inhibitor, the binding of the inhibitor to the distal site will have a greater effect on the binding affinity and/or degradation activity of IDE for one substrate (e.g., insulin) than for a second substrate (e.g., glucagon). This concept is depicted in FIG. 9A and FIG. 9C which shows a model of a binding pocket of IDE with a compound of the invention bound, and with either insulin or glucagon docked with the enzyme. In the model with insulin bound there are unfavorable steric interactions between insulin and the inhibitor, however, when glucagon is bound such interactions do not occur between glucagon and the inhibitor.

In one aspect, provided is a compound which inhibits IDE selectively or non-selectively and comprises a locked ring moiety, linker moiety, and cavity-interacting moiety, wherein the linker moiety connects the locked ring moiety and the cavity-interacting moiety. In certain embodiments, the locked ring moiety, linker moiety, and cavity-interacting moiety may each independently be hydrophobic or moderately hydrophobic.

In certain embodiments, the locked ring moiety is capable of interacting with the deep hydrophobic pocket defined by IDE residues Leu201, Glu205, Tyr302, Thr316, and Ala479. In certain embodiments, the cavity-interacting moiety is capable of interacting with a first hydrophobic patch defined by IDE residues Val360, Gly361, Gly362, Lys364, and Ile374. In certain embodiments, the cavity-interacting moiety is capable of interacting with a second hydrophobic patch defined by IDE residues Ala198, Trp199, and Phe202. Unless otherwise specified, specific residues of IDE referred to herein are residues in the protein sequence for human insulin-degrading enzyme isoform 1 (see, e.g., SEQ ID NO: 1), though the compounds and uses thereof described herein are not limited to human isoform 1 and contemplate IDE's from other species, other isoforms, and naturally occurring or synthetic IDE sequence variants or mutations.

In certain embodiments, the locked ring moiety is about 6 to 12 Å in length, and capable of interacting with the deep hydrophobic pocket of IDE, defined by the residues Leu201, Glu205, Tyr302, Thr316, and Ala479. In some embodiments, the locked ring moiety comprises two aryl or heteroaryl rings joined by a bond or linker. In some embodiments, the two rings are directly attached and comprise no substituents ortho to bond connecting the two rings. In some embodiments, the two rings are directly attached and comprise at least one substituent ortho to the bond connecting the two rings. In some embodiments, the two rings are rotationally locked.

As used herein "rotationally locked" refers to a bond about which there is a barrier to rotation greater than for rotation about the same bond in an unsubstituted system, that is, in a compound consisting of the two rings and no non-hydrogen substituents. A two ring system that is not rotationally locked may adopt a conformation that is co-planar or near co-planar (e.g., with a dihedral of less than 10°). In the unsubstituted case, the co-planar conformation may be energetically favorable due to conjugation between π orbitals on each ring. The presence of an ortho substituent may make the co-planar configuration higher in energy depending on the energy of the conjugation interaction and the energy of the steric interaction between groups of each ring when the rings are co-planar. The barrier to rotation may be provided by steric interactions between groups on the two rings, e.g., a non-hydrogen group ortho to the bond connecting the rings. In some embodiments, the barrier is at least about at least about 3 kcal/mol, at least about at least about 6 kcal/mol, at least about 10 kcal/mol, at least about 15 kcal/mol, at least about 20 kcal/mol, at least about 30 kcal/mol, e.g., at about room temperature (about 25-27° C.).

Inhibitors comprising a locked ring moiety may have a higher binding affinity for IDE versus analogous compounds with a homologous moiety in which the two rings are not rotationally locked. For example, compound B8 is identical to compound 297, but has an ortho methyl substituent on the biphenyl unit in place of a hydrogen (on 297). As shown in FIG. 12 the $IC_{50}$ for proteolysis for B8 (2 nM) is two orders of magnitude lower than the $IC_{50}$ for 297 (0.25 µM).

In one aspect, provided herein is a compound comprising:

(a) a locked ring moiety, wherein the locked ring moiety is hydrophobic or moderately hydrophobic, and is capable of interacting with a deep hydrophobic pocked defined by residues Leu201, Glu205, Tyr302, Thr316, and Ala479;

(b) a cavity-interacting moiety, wherein the cavity-interacting moiety is hydrophobic or moderately hydrophobic, and is capable of interacting with a first hydrophobic patch defined by residues Val360, Gly361, Gly362, Lys364, and Ile374, or second hydrophobic patch defined by residues Ala198, Trp199, and Phe202; and (c) a linker moiety, wherein the linker moiety connects the locked ring moiety and the cavity-interacting moiety; wherein when the compound is bound to insulin degrading enzyme (IDE), at least one of conditions (i), (ii) and (iii) are met:

(i) the locked ring moiety is within about 5 Å of at least one of Leu201, Glu205, Tyr302, Thr316, and Ala479;

(ii) the cavity-interacting moiety is within about 5 Å of at least one of Val360, Gly361, Gly362, Lys364, and Ile374, or within about 5 Å of at least one of Ala198, Trp199, and Phe202; or (iii) the linker moiety has a length, as measured between the atom connected to the locked ring moiety and the atom connected to the cavity-interacting moiety, between about 3 Å and about 10 Å;

wherein the compound inhibits insulin degrading enzyme (IDE).

In certain embodiments, only one of the three conditions (i)-(iii) are met. In certain embodiments, only two of the three conditions (i)-(iii) are met. In certain embodiments, all three of conditions (i)-(iii) are met.

In certain embodiments, the inhibitor selectively inhibits the activity of IDE for the degradation of insulin over the activity of IDE for the degradation of glucagon. Substrate selectivity may be between about 2-fold and about 5-fold, between about 5-fold and about 10-fold, between about 10-fold and about 50-fold, between about 50-fold and about 100-fold, or between about 100-fold and about 500-fold, or between about 500-fold and about 1000-fold, inclusive. In some embodiments, the substrate selectivity is between about 2 fold and 100-fold, inclusive.

Compounds comprising a locked ring moiety may be of Formula (RL):

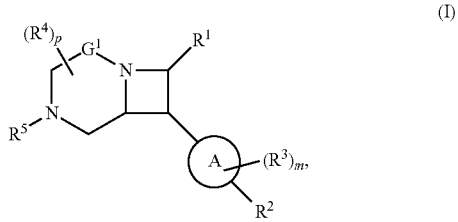

(RL)

or a pharmaceutically acceptable salt, solvate, hydrate, polymorph, co-crystal, tautomer, stereoisomer, prodrug, or isotopically labeled derivative thereof;
wherein at least one substituent on Ring $A^4$ or Ring $B^4$ is attached ortho to the bond connecting Rings $A^4$ and $B^4$, providing a barrier to rotation and preventing the rings from being co-planar.

In another aspect, provided herein are compounds of Formula (I):

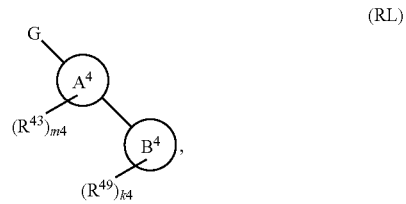

(I)

or a pharmaceutically acceptable salt, solvate, hydrate, polymorph, co-crystal, tautomer, stereoisomer, prodrug, or isotopically labeled derivative thereof.

The azetidines of Formula (I) are polycyclic and may be comprise a 4,6-bicyclic ring system or 4,8-bicyclic ring system according to Formula (I-a) or (I-b):

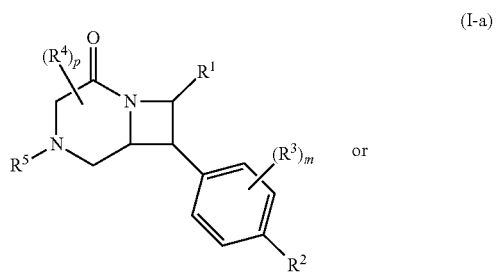

(I-a)

or

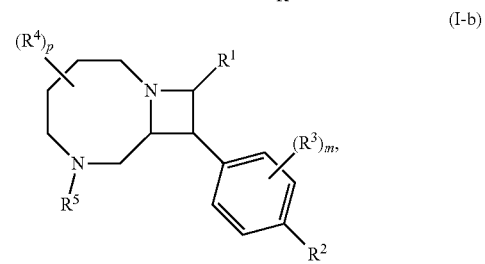

(I-b)

or a pharmaceutically acceptable salt, solvate, hydrate, polymorph, co-crystal, tautomer, stereoisomer, prodrug, or isotopically labeled derivative thereof.

In another aspect, provided herein are compounds of Formula (II):

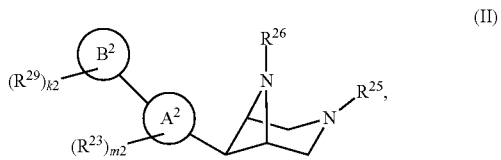

(II)

or a pharmaceutically acceptable salt, solvate, hydrate, polymorph, co-crystal, tautomer, stereoisomer, prodrug, or isotopically labeled derivative thereof.

In another aspect, provided herein are compounds of Formula (III):

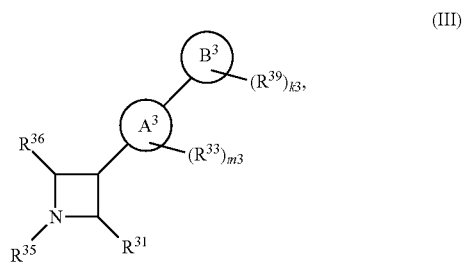

(III)

or a pharmaceutically acceptable salt, solvate, hydrate, polymorph, co-crystal, tautomer, stereoisomer, prodrug, or isotopically labeled derivative thereof.

In another aspect, provided herein are compounds of Formula (IV) or (V):

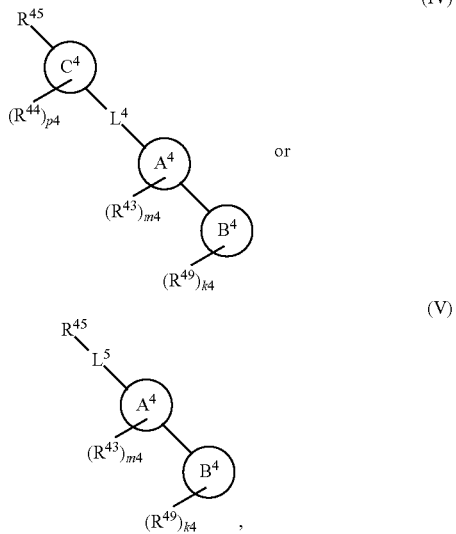

or a pharmaceutically acceptable salt, solvate, hydrate, polymorph, co-crystal, tautomer, stereoisomer, prodrug, or isotopically labeled derivative thereof, wherein the Rings $A^4$ and $B^4$ represent a locked ring moiety.

Pharmaceutical compositions of the compounds are also provided, in addition to methods of treating a metabolic disorder using the compounds, or compositions thereof. The metabolic disorder may be a diabetic condition or an obesity-related condition (e.g., obesity). The diabetic condition may be diabetes (e.g., type I diabetes, type II diabetes, gestational diabetes), hyperglycemia, impaired glucose tolerance, or insulin resistance.

Also provided are methods useful for inhibiting insulin degradation, inhibiting amylin degradation, inhibiting glucagon degradation, and/or inhibiting insulin-degrading enzyme (IDE). The method comprises administering an inventive compound or composition thereof to a subject in need thereof or contacting a biological sample with the compound or composition. In certain embodiments, the inhibition of IDE selectively inhibits the insulin degrading activity of IDE, and in other embodiments, the inhibition of IDE selectively inhibits the glucagon degrading activity of IDE. In still other embodiments, the compound is not selective or is only minimally selective.

In another aspect, also provided are methods for enhancing the glucagon degrading activity of IDE. A compound provided herein may enhance the glucagon degrading activity of IDE, or may both enhance the glucagon degrading activity and inhibit the insulin degrading activity of IDE. A compound provided herein may enhance the glucagon degrading activity of IDE, or may both enhance the glucagon degrading activity and inhibit the degrading activity of IDE towards another substrate.

Provided herein are also methods of identifying a compound that may selectively inhibit insulin-degrading enzyme for degradation of one substrate over another. The method comprises a an assay to determine the inhibition maximum ($I_{MAX}$) of a potential inhibitor. In certain embodiments, a fluorogenic peptide is used to probe the activity of IDE in the presence of a candidate inhibitor. In some embodiments, when the fluorogenic peptide is cleaved by IDE, the peptide fragments exhibit greater fluorescence than the intact peptide. The maximum inhibition ($I_{MAX}$) is the greatest extent (i.e. the highest percent of uncleaved peptide as measured by fluorescence or by measurement of another detectable label) to which IDE is inhibited by any concentration of the candidate inhibitor. In some embodiments, the maximum inhibition will be the value at which a dosage-response curve plateaus at high inhibitor concentration. In some embodiments, an $I_{MAX}$ of less than 100% will identify a candidate compound as a substrate selective inhibitor.

In another aspect, also provided is a compound of compound comprising a locked ring moiety, cavity-interacting moiety, and linker moiety or a compound Formula (RL), (I), (II), (III), (IV), or (V), wherein the compound further comprises a detectable label. In some aspects the detectable label is a fluorophore.

In another aspect, provided herein is a method of preparing a compound a compound comprising a locked ring moiety, cavity-interacting moiety, and linker moiety or a compound Formula (RL), (I), (II), (III), (IV), or (V), and further comprising a detectable label, wherein the method comprises coupling a compound comprising a locked ring moiety, cavity-interacting moiety, and linker moiety or a compound Formula (RL), (I), (II), (III), (IV), or (V) with a reagent comprising a detectable label. In some embodiments, the detectable label is a fluorophore. In some embodiments, the reagent comprising a detectable label comprises a leaving group. In some embodiments, the compound comprises a leaving group.

The compound with a detectable label may be used in an assay to identify selective or non-selective inhibitors of insulin-degrading enzyme, as described herein and in PCT application PCT/US2014/064322, which is incorporated herein by reference.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

FIG. 1A: Unbiased screen using "DOS informer set" plates comprising 10,000 compounds originating from multiple compound collections. FIG. 1B: Focused screen using a sub-library of 10,304 azetidine compounds comprised of 76% bicyclic- or biaryl-substituted analogs. Human N-His6-IDE42-1019 (*E. coli* expressed) was mixed with fluorescein-labeled macrocycle FL-6b generating a high anisotropy signal in the presence of negative control DMSO, or with inactive compounds. The inhibitor 6bK (1 μM), used here as a positive control displaces analog FL-6b, lowering fluorescence anisotropy with an excellent signal-to-noise ratio (Z-factor >0.6). The top 100 compounds display low anisotropy signal for FL-6b (e.g., Z-score <−10 in replicate plates)

FIG. 2A: Representative examples of the concentration-dependent profiles of IDE inhibition for pan-substrate competitive inhibitors, which display complete inhibition of IDE-mediated proteolysis of the fluorogenic Mca-RPPGFSAFK(Dnp)-OH (SEQ ID NO: 4). The inhibition maximum ($I_{MAX}$) is approximately 100% at high inhibitor concentrations. FIG. 2B: Representative examples of the concentration-dependent IDE inhibition profiles for IDE binders that allow partial IDE-mediated proteolysis of the fluorogenic nonapeptide at all concentrations ($I_{MAX}$<100%), and that display proteolytic activity as a ternary IDE-inhibitor-substrate complex.

FIGS. 8A and 8B: Activity assays for wild type or mutant human IDE variants in the presence of IDE inhibitors. FIG. 8C: These results are consistent with the highest docking score pose for compound 297 within human IDE (PDB: 4LTE, ligand 6b removed). Molecular docking simulations are consistent with the placement of the N-arylsulfonyl moiety interacting with the exo-site residues Ile374 and Gly362.

FIG. 10. $^1$H NMR of compound 297 in DMSO-$d_6$ at 600 MHz.

FIG. 14A: Concentration dependence profile for inhibition of IDE to proteolysis of a fluorogenic decapeptide in the presence of 297, J1, J2, J3, J6, and J7. FIG. 14B: Concentration dependence profiles measured with the HTRF endpoint degradation assay for the inhibition of insulin degradation by IDE with inhibitors 6bK, J1, J2, J3, J6, and J7.

FIGS. 26A-26B. Substrate-selective inhibition with compound 6bK (FIG. 26A) and compound JP17 (FIG. 26B) protects insulin for >1 hour.

FIG. 27B is a zoom of the cleavage products at 1400-1800 Da. The sequences, from left to right, correspond to SEQ ID NOs: 53-54.

DETAILED DESCRIPTION OF CERTAIN EMBODIMENTS

Figure 1A:
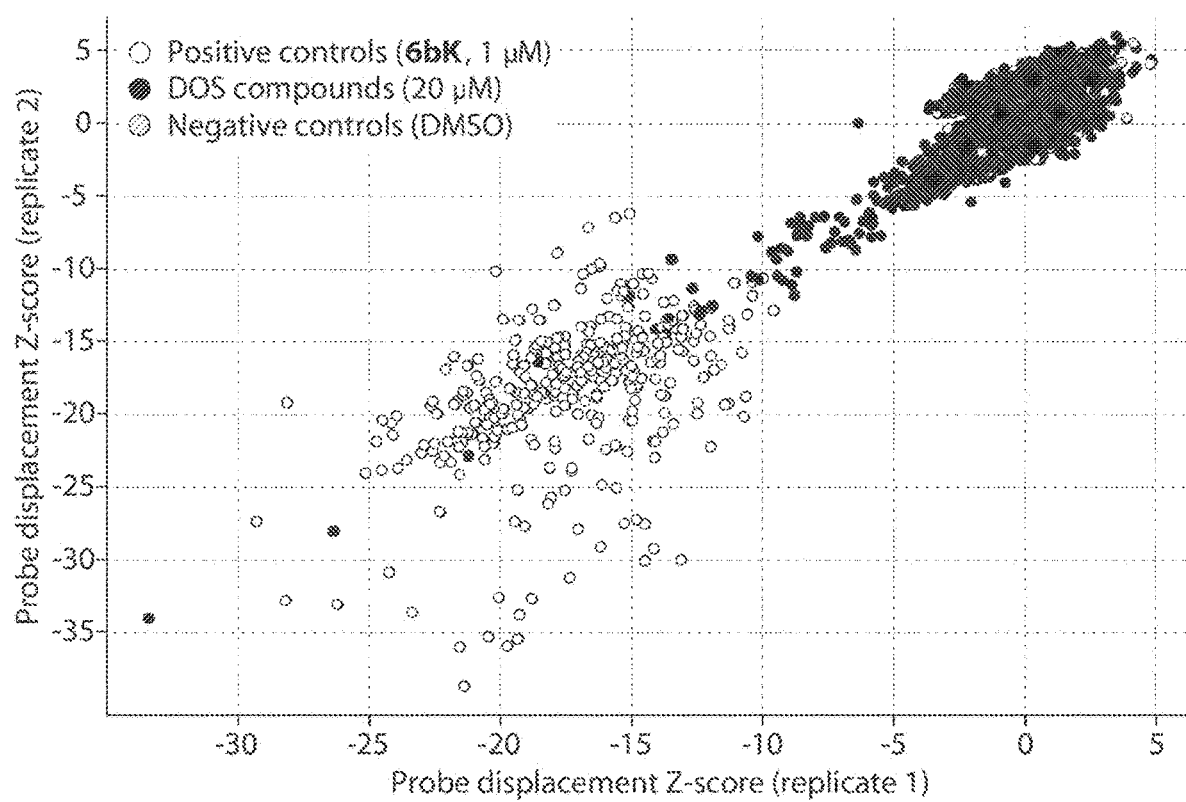
FIGS. 1A-1B. Anisotropy-based high-throughput screening assays using the fluorescent probe FL-6b, based on the selective IDE inhibitor 6bK.

Provided herein are compounds which may be inhibitors of insulin-degrading enzyme (IDE). The compounds may interact with IDE so as to disrupt the activity of IDE to degrade insulin, glucagon, amylin, or other substrates, or multiple substrates. In certain embodiments, a compound may selectively inhibit the activity of IDE for degrading insulin over the activity of IDE for degrading glucagon.

In on aspect, the invention contemplates any compound which selectively inhibits the activity of IDE for degradation of a first substrate over the activity of IDE for degradation of a second substrate. In some embodiments, the compound selectively inhibits the activity of IDE for degradation of insulin over the activity of IDE for degradation of a second substrate (e.g., glucagon, amylin). In some embodiments, the compound selectively inhibits the activity of IDE for degradation of insulin over the activity of IDE for degradation of glucagon. In some embodiments, the compound selectively inhibits the activity of IDE for degradation of insulin over the activity of IDE for degradation of more than one other substrate (e.g., glucagon and amylin).

Exemplary substrates of IDE include, but are not limited to, insulin, glucagon, amylin, TGF alpha, beta-endorphin, amyloid beta, bradykinin, kallidin, calcitonin-gene related peptide (CGRP), somatostatin, and atrial natriuretic peptide. In certain embodiments, the compound selectively inhibits insulin degradation over the degradation of another substrate. In some embodiments, the compound selectively inhibits insulin degradation over glucagon degradation. In some embodiments, the compound selectively inhibits insulin degradation over amylin degradation. In some embodiments, the compound selectively inhibits insulin degradation over degradation of TGF alpha, beta-endorphin, amyloid beta, bradykinin, kallidin, calcitonin-gene related peptide (CGRP), somatostatin, or atrial natriuretic peptide. In certain embodiments, the selectivity for inhibiting degradation of one substrate over another is between about 1.1-fold and about 2-fold, inclusive, between about 2-fold and about 5-fold, inclusive, between about 5-fold and about 10-fold, inclusive, between about 10-fold and about 50-fold, inclusive, between about 50-fold and about 100-fold, inclusive, or greater than about 100-fold. In certain embodiments, there is no selectivity for one substrate over another substrate.

Substrate selective inhibitors may have an inhibition maximum for IDE which is less than complete (e.g., less than 100%) inhibition of activity of the enzyme for degradation of a specific substrate. The maximum inhibition ($I_{MAX}$) is defined to be the greatest extent to which IDE is inhibited by any concentration of the candidate inhibitor. The maximum inhibition may be determined by probing the activity of IDE for a specific peptide (e.g., a peptide with a detectable label) in the presence of a candidate inhibitor. In the absence of an inhibitor when the peptide is contacted by IDE, no peptide remains uncleaved. Contrastingly, in the presence of a sufficient concentration of a non-selective inhibitor, the IDE may be fully inhibited, and all peptide remains uncleaved, i.e. $I_{MAX}$ is about 100%.

Thus, in certain embodiments, the invention contemplates compounds with an inhibition maximum of less than 100%. In some embodiments, the compound has an inhibition maximum for IDE of less than 100%, and selectively inhibits the activity of IDE for degradation of a first substrate over the activity of IDE for degradation of a second substrate. In some embodiments, the compound has an inhibition maximum for IDE of less than 100%, and selectively inhibits the activity of IDE for degradation of insulin over the activity of IDE for degradation of a second substrate (e.g., glucagon, amylin). In some embodiments, the compound has an inhibition maximum for IDE of less than 100%, and selectively inhibits the activity of IDE for degradation of a first substrate over degradation of more than one other substrate.

In certain embodiments, the inventive compounds are non-selective inhibitors of IDE for insulin, amylin, glucagon, and/or other substrates. In certain embodiments, a compound may enhance the degradation of insulin, amylin, glucagon, and/or another substrate of IDE. For example, the presence of the inventive compound in the binding pocket of IDE may increase the rate of enzymatic activity for a particular substrate (e.g., glucagon) versus an uninhibited IDE (i.e., with no exogenous inhibitor/activator present). This may be due to a change in the binding affinity of the substrate, a change in affinity for the substrate versus competitive substrates, or a change in the conformation of the enzyme or substrate caused by the presence of the compound that otherwise affects the reaction rate.

In one aspect, the invention provides a compound which inhibits IDE selectively or non-selectively and comprises a locked ring moiety, a linker moiety, and a cavity-interacting moiety, wherein the linker moiety connects the locked ring moiety and the cavity-interacting moiety.

The locked ring moiety, linker moiety, and cavity-interacting moiety may be hydrophobic or moderately hydrophobic. As used herein "hydrophobic" refers to a moiety which tends to not dissolve in water and is fat soluble. Hydrophobic moieties include but are not limited to, groups comprising hydrocarbon radicals, such as alkyl, alkenyl, alkynyl, carbocylyl and aryl. Hydrophobic moieties may also include groups selected from heteroalkyl, heteroalkenyl, heteroalkynyl, heterocyclyl, and heteroaryl, wherein the heteroatom containing group is substantially similar to a hydrocarbon group. Hydrophobic moieties may contain groups that are the same as or are derivatives of the side chains of hydrophobic amino acids, including but not limited to, glycine, alanine, valine, leucine, isoleucine, methionine, phenylalanine, amino isobutyric acid, alloisoleucine, tyrosine, and tryptophan. As used herein "moderately hydrophobic" refers to a hydrophobic moiety in which 1, 2, 3, or 4 carbon atoms have been replaced with more polar atoms, such as oxygen, nitrogen, or sulfur, or more polar function groups, such as carbonyl, sulfonyl, or heteroaryl.

Unless otherwise specified, specific residues of IDE referred to herein are residues in the protein sequence for human insulin-degrading enzyme isoform 1, a 1019 amino acid (See SEQ ID NO: 1). Also contemplated are inhibitors that interact with naturally occurring or synthetic sequence variants or mutations of human isoform 1. In certain embodiments, a residue referred to herein to define a binding region or specific interaction may be replaced with another amino acid. In certain embodiments, the inhibitor may interact with an amino acid adjacent to one of the specific amino acids referred to herein.

Locked Ring Moiety

Figure 8C:
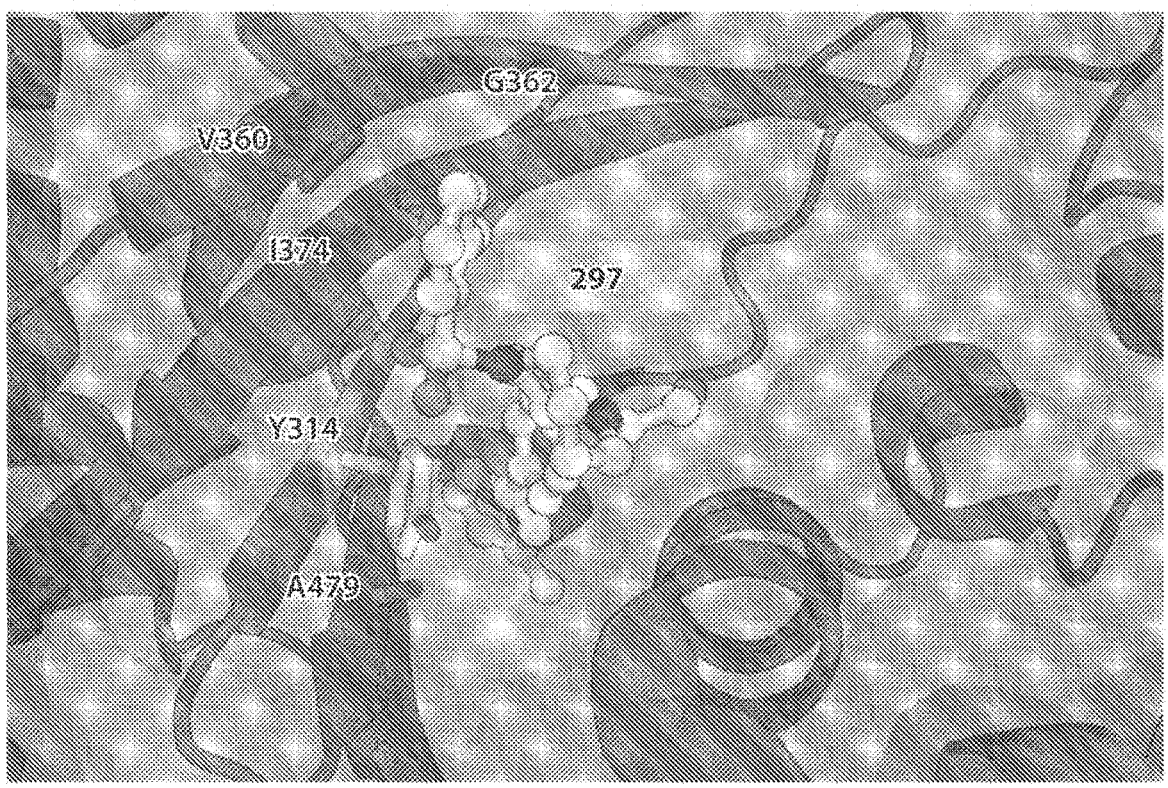
Figure 9A:
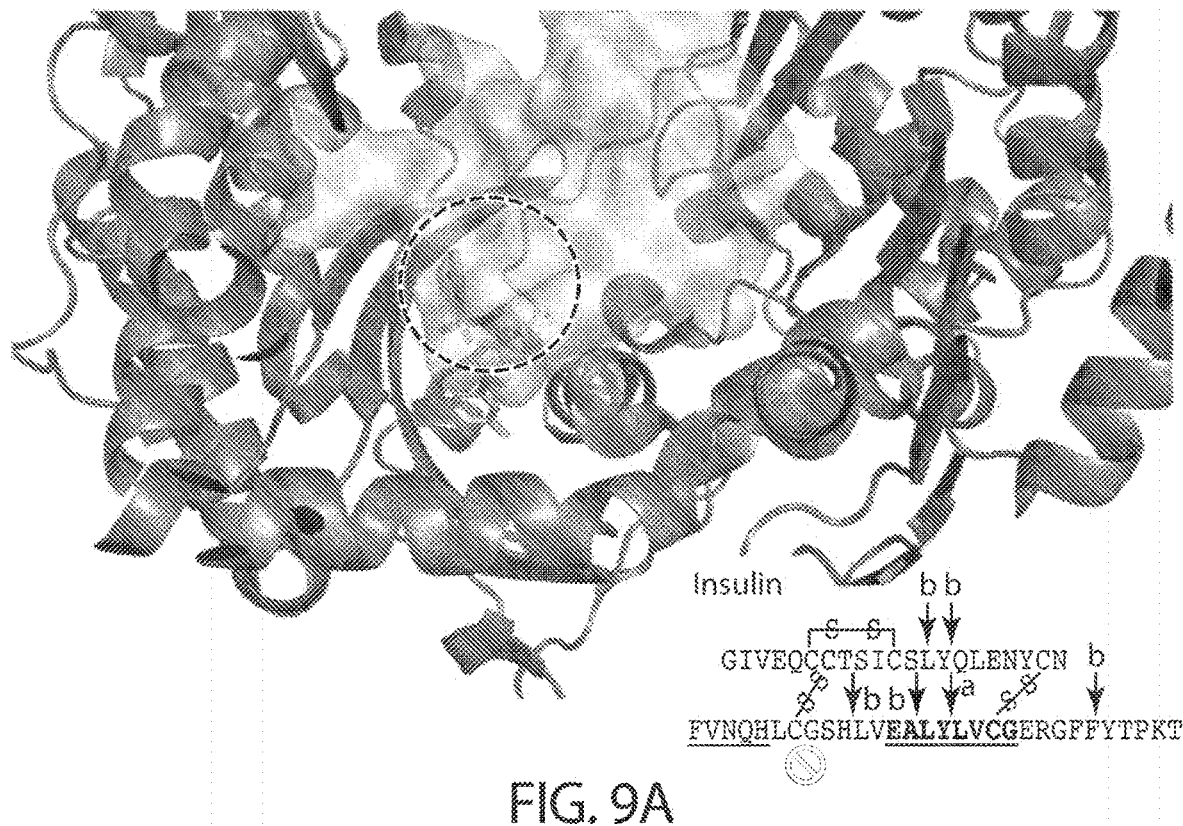
FIGS. 9A-9D. Model of structural basis for substrate-selective IDE inhibition. The IDE-insulin X-ray co-crystal structure (PDB: 2WBY) was overlaid with the model of compound 297 docked in the IDE structure (FIG. 9A) and the IDE-6b inhibitor co-crystal structure (FIG. 9B). The sequences in FIGS. 9A-9B, from top to bottom, correspond to SEQ ID NOs: 5-6. Similarly, the IDE-glucagon X-ray co-crystal structure (PDB: 2G49) was overlaid with the model of compound 297 docked in the IDE structure (FIG. 9C) and the IDE-6b inhibitor co-crystal structure (FIG. 9D). The sequence in FIGS. 9C-9D corresponds to SEQ ID NO: 7. Insulin and glucagon are shown as grey surfaces, and the inhibitors as stick models.
Figure 9B:
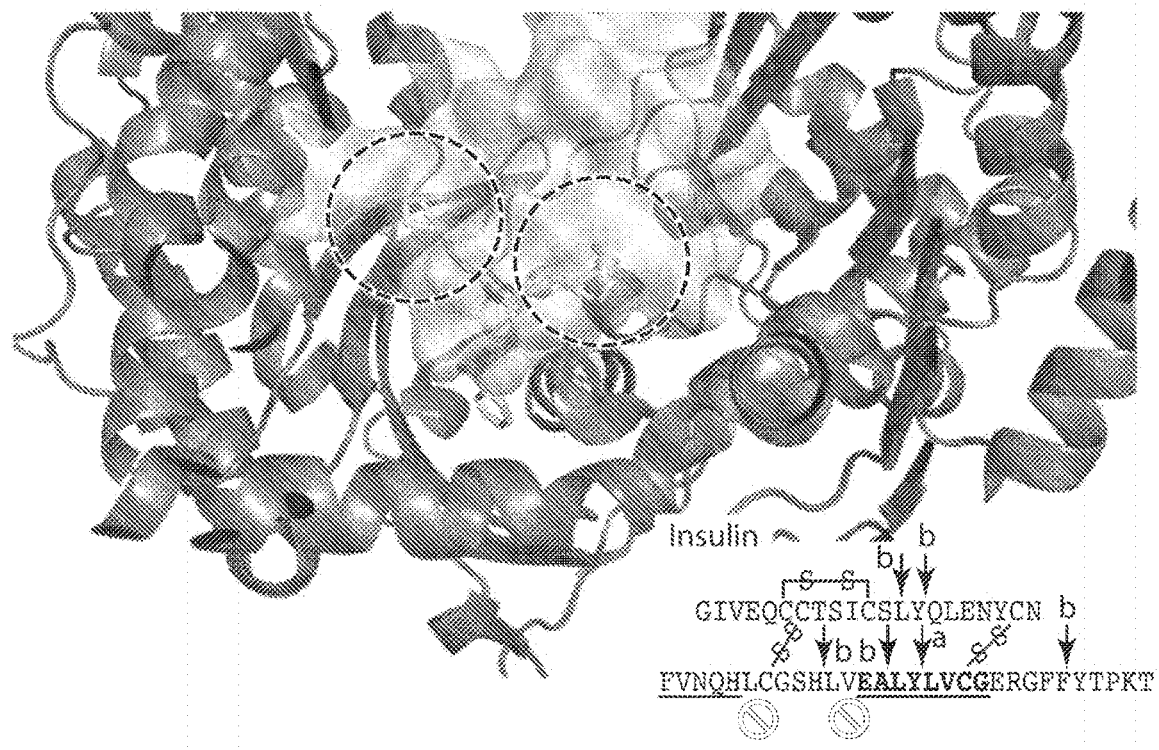
Figure 9C:
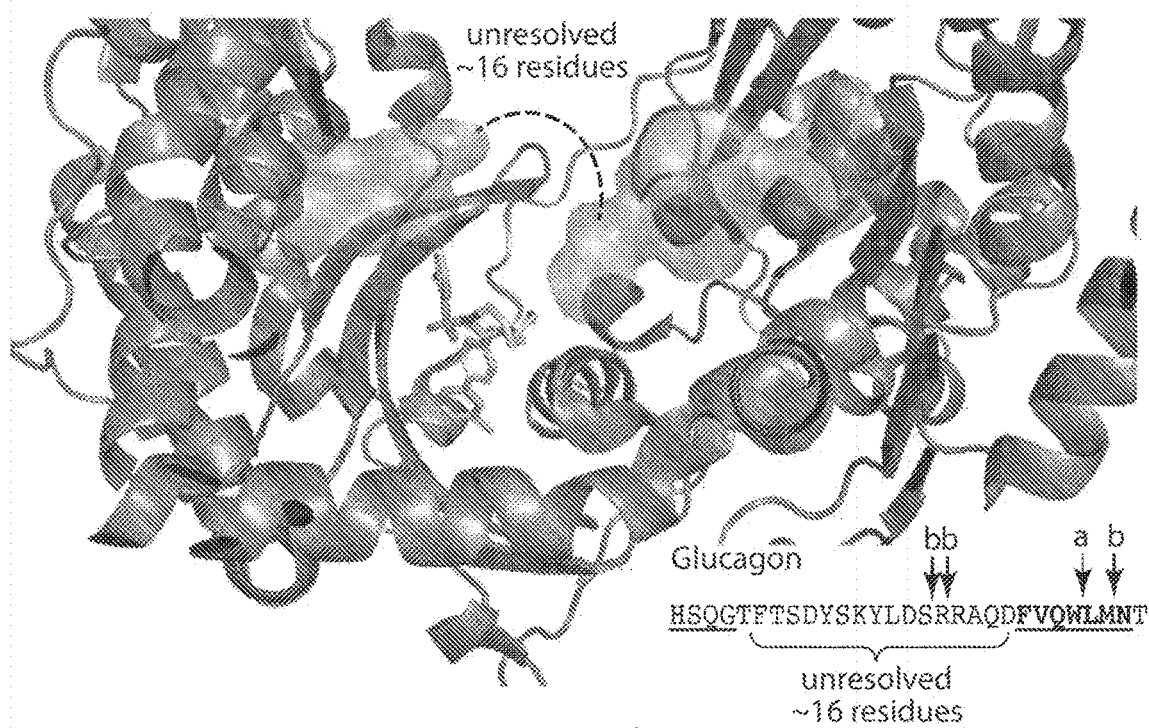

The locked ring moiety is a hydrophobic moiety or moderately hydrophobic moiety comprising two rings, wherein the rings are rotationally locked with respect to rotation about the bond or linker connecting the two rings. In certain embodiments, the locked ring moiety may bind in a deep hydrophobic pocket of IDE, defined by residues Leu201, Glu205, Tyr302, Thr316, and Ala479. The deep hydrophobic pocket is shown interacting with the biphenyl moiety of compound 297 in FIG. 8C, FIG. 9A, and FIG. 9C. In certain embodiments, the two rings of the locked ring moiety are directly bonded through a single bond. In certain embodiments, the two rings of the locked ring moiety are connected by a linker. In some embodiments, the linker is a rigid linker. In some embodiments, the linker is alkynyl (e.g., —C≡C—). In some embodiments, the two rings are directly attached and comprise no non-hydrogen substituents ortho to bond connecting the two rings. In some embodiments, the two rings are directly attached and comprise at least one non-hydrogen substituent ortho to the bond connecting the two rings. In some embodiments, the two rings are rotationally locked.

As used herein "rotationally locked" refers to a bond or linker about which there is a barrier to rotation greater than for rotation about the same bond in an unsubstituted system, that is, in a compound consisting of the two rings and no non-hydrogen substituents. A two ring system that is not rotationally locked may adopt a conformation that is co-planar or nearly co-planar due to conjugation between it orbitals on each ring. The presence of an ortho substituent may make the co-planar configuration higher in energy depending on the energy of the conjugation interaction and the energy of the steric interaction between groups of each ring when the rings are co-planar.

For example, the rotational barrier for biphenyl ($C_6H_5$—$C_6H_5$), is between about 3.0 and about 6.0 kcal/mol at room temperature, but this rotational barrier will be higher for biphenyls with one or more ortho substituent. In some embodiments, the compound comprises a moiety comprising two rings, wherein the barrier for rotation about the bond or linker connecting the two rings is at least about 3 kcal/mol. In some embodiments, the compound comprises a moiety comprising two rings, wherein the barrier for rotation about the bond or linker connecting the two rings is at least about 6 kcal/mol. In some embodiments, the barrier is at least about 10 kcal/mol, at least about 15 kcal/mol, at least about 20 kcal/mol, or at least about 30 kcal/mol.

The term "ortho" is used to indicate substitution at the position on the ring adjacent to the bond or linker between the two rings, and may be applied to indicate the positions on the ring adjacent to the bond or linker between two rings for a ring of any size, not only for a phenyl ring.

The term "dihedral angle" refers to the angle between the two planes defined by the two rings which are connected by a bond or linker. A dihedral angle of 00 means the two rings are coplanar. In certain embodiments, the rings are not coplanar.

The locked ring moiety may have an equilibrium dihedral angle greater than 00. In certain embodiments, the equilibrium dihedral angle is between about 20° and about 160°. In certain embodiments, the equilibrium dihedral angle is between about 40° and about 140°. In certain embodiments, the equilibrium dihedral angle is between about 60° and about 120°. In certain embodiments, the equilibrium dihedral angle is between about 80° and 100°.

The locked ring moiety may have an equilibrium dihedral angle greater than 0° when bound to IDE. In certain embodiments, the equilibrium dihedral angle is between about 20° and about 160° when bound to IDE. In certain embodiments, the equilibrium dihedral angle is between about 40° and about 140° when bound to IDE. In certain embodiments, the equilibrium dihedral angle is between about 60° and about 120° when bound to IDE. In certain embodiments, the equilibrium dihedral angle is between about 80° and 100° when bound to IDE.

In certain embodiments, when the inhibitor is bound the locked ring moiety interacts with Leu201. In certain embodiments, the linker moiety interacts with Leu201 and at least one of Glu205, Tyr302, Thr316, and Ala479. In certain embodiments, when the inhibitor is bound the locked ring moiety interacts with Glu205. In certain embodiments, the linker moiety interacts with Glu205 and at least one of Leu201, Tyr302, Thr316, and Ala479. In certain embodiments, when the inhibitor is bound the locked ring moiety interacts with Tyr302. In certain embodiments, the linker moiety interacts with Tyr302 and at least one of Leu201, Glu205, Thr316, and Ala479. In certain embodiments, when the inhibitor is bound the locked ring moiety interacts with Thr316. In certain embodiments, the linker moiety interacts with Thr316 and at least one of Leu201, Glu205, Tyr302, and Ala479. In certain embodiments, when the inhibitor is bound the locked ring moiety interacts with Ala479. In certain embodiments, the linker moiety interacts with Ala479 and at least one of Leu201, Glu205, Tyr302, and Thr316.

In certain embodiments, when the inhibitor is bound the locked ring moiety interacts with Leu201 and Glu205. In certain embodiments, when the inhibitor is bound the locked ring moiety interacts with Leu201 and Tyr302. In certain embodiments, when the inhibitor is bound the locked ring moiety interacts with Leu201 and Thr316. In certain embodiments, when the inhibitor is bound the locked ring moiety interacts with Leu201 and Ala479. In certain embodiments, when the inhibitor is bound the locked ring moiety interacts with Glu205 and Tyr302. In certain embodiments, when the inhibitor is bound the locked ring moiety interacts with Glu205 and Thr316. In certain embodiments, when the inhibitor is bound the locked ring moiety interacts with Glu205 and Ala479. In certain embodiments, when the inhibitor is bound the locked ring moiety interacts with Tyr302 and Thr316. In certain embodiments, when the inhibitor is bound the locked ring moiety interacts with Tyr302 and Ala479. In certain embodiments, when the inhibitor is bound the locked ring moiety interacts with Thr316 and Ala479.

In certain embodiments, when the inhibitor is bound the locked ring moiety interacts with Leu201, Glu205, and Tyr302. In certain embodiments, when the inhibitor is bound the locked ring moiety interacts with Leu201, Glu205, and Thr316. In certain embodiments, when the inhibitor is bound the locked ring moiety interacts with Leu201, Glu205, and Ala479. In certain embodiments, when the inhibitor is bound the locked ring moiety interacts with Leu201, Tyr302, and Thr316. In certain embodiments, when the inhibitor is bound the locked ring moiety interacts with Leu201, Tyr302, and Ala479. In certain embodiments, when the inhibitor is bound the locked ring moiety interacts with Leu201, Thr316, and Ala49. In certain embodiments, when the inhibitor is bound the locked ring moiety interacts with Glu205, Tyr302, and Thr316. In certain embodiments, when the inhibitor is bound the locked ring moiety interacts with Glu205, Tyr302, and Ala479. In certain embodiments, when the inhibitor is bound the locked ring moiety interacts with Glu205, Thr316, and Ala479. In certain embodiments, when the inhibitor is bound the locked ring moiety interacts with Tyr302, Thr316, and Ala479. In certain embodiments, when the inhibitor is bound the locked ring moiety interacts with Leu201, Glu205, Tyr302, and Thr316. In certain embodiments, when the inhibitor is bound the locked ring moiety interacts with Leu201, Glu205, Tyr302, and Ala479. In certain embodiments, when the inhibitor is bound the locked ring moiety interacts with Leu201, Glu205, Thr316, and Ala479. In certain embodiments, when the inhibitor is bound the locked ring moiety interacts with Leu201, Tyr302, Thr316, and Ala479. In certain embodiments, when the inhibitor is bound the locked ring moiety interacts with Glu205, Tyr302, Thr316, and Ala479. In certain embodiments, when the inhibitor is bound the locked ring moiety interacts with Leu201, Glu205, Tyr302, Thr316, and Ala479.

In certain embodiments, the interaction between the locked ring moiety and Leu201 comprises a hydrophobic-hydrophobic interaction or van der Waals interaction. In certain embodiments, the interaction between the locked ring moiety and Leu201 comprises a hydrogen bonding interaction. In certain embodiments, the interaction between the locked ring moiety and Glu205 comprises a hydrophobic-hydrophobic interaction or van der Waals interaction. In certain embodiments, the interaction between the locked ring moiety and Glu205 comprises a hydrogen bonding interaction. In certain embodiments, the interaction between the locked ring moiety and Tyr302 comprises a hydrophobic-hydrophobic interaction, van der Waals interaction, or π-stacking interaction. In certain embodiments, the interaction between the locked ring moiety and Tyr302 comprises a hydrogen bonding interaction. In certain embodiments, the interaction between the locked ring moiety and Thr316 comprises a hydrophobic-hydrophobic interaction, van der Waals interaction, or π-stacking interaction. In certain embodiments, the interaction between the locked ring moiety and Thr316 comprises a hydrogen bonding interaction. In certain embodiments, the interaction between the locked ring moiety and Ala479 comprises a hydrophobic-hydrophobic interaction or van der Waals interaction. In certain embodiments, the interaction between the locked ring moiety and Ala479 comprises a hydrogen bonding interaction.

In certain embodiments, when the inhibitor is bound the linker moiety is within about 6 Å of at least one of residues Leu201, Glu205, Tyr302, Thr316, and Ala479. In certain embodiments, the linker moiety is within about 5 Å of at least one of residues Leu201, Glu205, Tyr302, Thr316, and Ala479. In some embodiments, is within about 4 Å of at least one of residues Leu201, Glu205, Tyr302, Thr316, and Ala479. In some embodiments, is within about 3 Å of at least one of residues Leu201, Glu205, Tyr302, Thr316, and Ala479. In certain embodiments, when the inhibitor is bound the linker moiety is within about 6 Å of at least two of residues Leu201, Glu205, Tyr302, Thr316, and Ala479. In certain embodiments, the linker moiety is within about 5 Å of at least two of residues Leu201, Glu205, Tyr302, Thr316, and Ala479. In some embodiments, is within about 4 Å of at least two of residues Leu201, Glu205, Tyr302, Thr316, and Ala479. In some embodiments, is within about 3 Å of at least two of residues Leu201, Glu205, Tyr302, Thr316, and Ala479. In certain embodiments, when the inhibitor is bound the linker moiety is within about 6 Å of at least three of residues Leu201, Glu205, Tyr302, Thr316, and Ala479. In certain embodiments, the linker moiety is within about 5 Å of at least three of residues Leu201, Glu205, Tyr302, Thr316, and Ala479. In some embodiments, is within about 4 Å of at least three of residues Leu201, Glu205, Tyr302, Thr316, and Ala479. In some embodiments, is within about 3 Å of at least three of residues Leu201, Glu205, Tyr302, Thr316, and Ala479. In certain embodiments, when the inhibitor is bound the linker moiety is within about 6 Å of at least four of residues Leu201, Glu205, Tyr302, Thr316, and Ala479. In certain embodiments, the linker moiety is within about 5 Å of at least four of residues Leu201, Glu205, Tyr302, Thr316, and Ala479. In some embodiments, is within about 4 Å of at least four of residues Leu201, Glu205, Tyr302, Thr316, and Ala479. In some embodiments, is within about 3 Å of at least four of residues Leu201, Glu205, Tyr302, Thr316, and Ala479. In certain embodiments, when the inhibitor is bound the linker moiety is within about 6 Å of each of residues Leu201, Glu205, Tyr302, Thr316, and Ala479. In certain embodiments, the linker moiety is within about 5 Å of each of residues Leu201, Glu205, Tyr302, Thr316, and Ala479. In some embodiments, is within about 4 Å of each of residues Leu201, Glu205, Tyr302, Thr316, and Ala479. In certain embodiments, the linker moiety is within about 3 Å of each of residues Leu201, Glu205, Tyr302, Thr316, and Ala479.

In certain embodiments, the compound comprises a locked ring moiety comprising two rings directly attached by a single bond, wherein the rings are independently optionally substituted aryl or optionally substituted heteroaryl. In certain embodiments, the locked ring moiety comprises two rings directly attached by a single bond, wherein the rings are independently optionally substituted aryl or optionally substituted heteroaryl, and at least one of the rings has a non-hydrogen group ortho to the single bond.

In certain embodiments, the locked ring moiety has a molecular weight between about 100 and about 500 Da. In certain embodiments, the locked ring moiety has a molecular weight between about 150 and about 350 Da. In certain embodiments, the locked ring moiety has a molecular weight between about 150 and about 250 Da. In certain embodiments, the locked ring moiety has a molecular weight between about 150 and about 200 Da.

Certain embodiments of the locked ring moiety are described herein as moieties comprising Ring $A^4$ and Ring $B^4$, Ring A and Ring B, Ring $A^2$ and Ring $B^2$, or Ring $A^3$ and Ring $B^3$.

Linker Moiety

In certain embodiments, the linker moiety is a hydrophobic moiety or moderately hydrophobic moiety connecting the locked ring moiety and the cavity-interacting moiety. In some embodiments, the linker moiety is hydrophobic. In some embodiments, the linker moiety is moderately hydrophobic. In some embodiments, the linker moiety is not hydrophobic. The region to which the linker moiety binds is generally defined by residues Lys364, Glu205, Tyr314, Thr316, Gln376, and Ala198. In certain embodiments, the linker moiety is rigid, e.g., arylene, heteroarylene. In certain embodiments, the linker moiety is flexible, e.g., alkylene, heteroalkylene, carbocyclylene, heterocyclylene.

In certain embodiments, when the inhibitor is bound the linker moiety interacts with Lys364. In certain embodiments, the linker moiety interacts with Lys364 and at least one of Glu205, Tyr314, Thr316, Gln376, and Ala198. In certain embodiments, when the inhibitor is bound the linker moiety interacts with Glu205. In certain embodiments, the linker moiety interacts with Glu205 and at least one of Lys364, Tyr314, Thr316, Gln376, and Ala198. In certain embodiments, when the inhibitor is bound the linker moiety interacts with Tyr314. In certain embodiments, the linker moiety interacts with Tyr314 and at least one of Lys364, Glu205, Thr316, Asn376, and Ala198. In certain embodiments, when the inhibitor is bound the linker moiety interacts with Thr316. In certain embodiments, the linker moiety interacts with Thr316 and at least one of Lys364, Glu205, Tyr314, Asn376, and Ala198. In certain embodiments, when the inhibitor is bound the linker moiety interacts with Asn376. In certain embodiments, the linker moiety interacts with Asn376 and at least one of Lys364, Glu205, Tyr314, Asn376, Thr316, and Ala198. In certain embodiments, when the inhibitor is bound the linker moiety interacts with Ala198. In certain embodiments, the linker moiety interacts with Ala198 and at least one of Lys364, Glu205, Tyr314, Asn376, and Thr316.

In certain embodiments, when the inhibitor is bound the linker moiety interacts with Lys364 and Glu205. In certain embodiments, when the inhibitor is bound the linker moiety interacts with Lys364 and Tyr314. In certain embodiments, when the inhibitor is bound the linker moiety interacts with Lys364 and Thr316. In certain embodiments, when the inhibitor is bound the linker moiety interacts with Lys364 and Asn376. In certain embodiments, when the inhibitor is bound the linker moiety interacts with Lys364 and Ala198. In certain embodiments, when the inhibitor is bound the linker moiety interacts with Glu205 and Tyr314. In certain embodiments, when the inhibitor is bound the linker moiety interacts with Glu205 and Thr316. In certain embodiments, when the inhibitor is bound the linker moiety interacts with Glu205 and Asn376. In certain embodiments, when the inhibitor is bound the linker moiety interacts with Glu205 and Ala198. In certain embodiments, when the inhibitor is bound the linker moiety interacts with Tyr314 and Thr316. In certain embodiments, when the inhibitor is bound the linker moiety interacts with Tyr314 and Asn376. In certain embodiments, when the inhibitor is bound the linker moiety interacts with Tyr314 and Ala198. In certain embodiments, when the inhibitor is bound the linker moiety interacts with Thr316 and Ala198. In certain embodiments, when the inhibitor is bound the linker moiety interacts with Thr316 and Asn376. In certain embodiments, when the inhibitor is bound the linker moiety interacts with Asn376 and Ala198.

In certain embodiments, when the inhibitor is bound the linker moiety interacts with Lys364, Glu205, and Tyr314. In certain embodiments, when the inhibitor is bound the linker moiety interacts with Lys364, Glu205, and Thr316. In certain embodiments, when the inhibitor is bound the linker moiety interacts with Lys364, Gsn376, and Ala198. In certain embodiments, when the inhibitor is bound the linker moiety interacts with Lys364, Glu205, and Ala198. In certain embodiments, when the inhibitor is bound the linker moiety interacts with Lys364, Tyr314, and Thr316. In certain embodiments, when the inhibitor is bound the linker moiety interacts with Lys364, Tyr314, and Asn376. In certain embodiments, when the inhibitor is bound the linker moiety interacts with Lys364, Tyr314, and Ala198. In certain embodiments, when the inhibitor is bound the linker moiety interacts with Lys364, Thr316, and Asn376. In certain embodiments, when the inhibitor is bound the linker moiety interacts with Lys364, Thr316, and Ala198. In certain embodiments, when the inhibitor is bound the linker moiety interacts with Lys364, Asn376, and Ala198. In certain embodiments, when the inhibitor is bound the linker moiety interacts with Glu205, Tyr314, and Thr316. In certain embodiments, when the inhibitor is bound the linker moiety interacts with Glu205, Tyr314, and Asn376. In certain embodiments, when the inhibitor is bound the linker moiety interacts with Glu205, Tyr314, and Ala198. In certain embodiments, when the inhibitor is bound the linker moiety interacts with Glu205, Thr316, and Asn376. In certain embodiments, when the inhibitor is bound the linker moiety interacts with Glu205, Thr316, and Ala198. In certain embodiments, when the inhibitor is bound the linker moiety interacts with Glu205, Asn376, and Ala198. In certain embodiments, when the inhibitor is bound the linker moiety interacts with Tyr314, Thr316, and Asn376. In certain embodiments, when the inhibitor is bound the linker moiety interacts with Tyr314, Thr316, and Ala198. In certain embodiments, when the inhibitor is bound the linker moiety interacts with Tyr314, Asn376, and Ala198. In certain embodiments, when the inhibitor is bound the linker moiety interacts with Thr316, Asn376, and Ala198.

In certain embodiments, when the inhibitor is bound the linker moiety interacts with Lys364, Glu205, Tyr314, and Thr316. In certain embodiments, when the inhibitor is bound the linker moiety interacts with Lys364, Glu205, Tyr314, and Asn376. In certain embodiments, when the inhibitor is bound the linker moiety interacts with Lys364, Glu205, Tyr314, and Ala198. In certain embodiments, when the inhibitor is bound the linker moiety interacts with Lys364, Glu205, Thr316, and Asn376. In certain embodiments, when the inhibitor is bound the linker moiety interacts with Lys364, Glu205, Thr316, and Ala198. In certain embodiments, when the inhibitor is bound the linker moiety interacts with Lys364, Glu205, Asn376, and Ala198. In certain embodiments, when the inhibitor is bound the linker moiety interacts with Lys364, Tyr314, Thr316, and Asn376. In certain embodiments, when the inhibitor is bound the linker moiety interacts with Lys364, Tyr314, Thr316, and Ala198. In certain embodiments, when the inhibitor is bound the linker moiety interacts with Lys364, Tyr314, Asn376, and Ala198. In certain embodiments, when the inhibitor is bound the linker moiety interacts with Lys364, Thr316, Asn376, and Ala198. In certain embodiments, when the inhibitor is bound the linker moiety interacts with Glu205, Tyr314, Thr316, and Asn376. In certain embodiments, when the inhibitor is bound the linker moiety interacts with Glu205, Tyr314, Thr316, and Ala198. In certain embodiments, when the inhibitor is bound the linker moiety interacts with Glu205, Tyr314, Asn376, and Ala198. In certain embodiments, when the inhibitor is bound the linker moiety interacts with Glu205, Thr316, Asn376, and Ala198. In certain embodiments, when the inhibitor is bound the linker moiety interacts with Tyr314, Thr316, Asn376, and Ala198.

In certain embodiments, when the inhibitor is bound the linker moiety interacts with Lys364, Glu205, Tyr314, Thr316, and Asn376. In certain embodiments, when the inhibitor is bound the linker moiety interacts with Lys364, Glu205, Tyr314, Thr316, and Ala198. In certain embodiments, when the inhibitor is bound the linker moiety interacts with Lys364, Glu205, Tyr314, Asn376, and Ala198. In certain embodiments, when the inhibitor is bound the linker moiety interacts with Lys364, Glu205, Thr316, Asn376, and Ala198. In certain embodiments, when the inhibitor is bound the linker moiety interacts with Lys364, Tyr314, Thr316, Asn376, and Ala198. In certain embodiments, when the inhibitor is bound the linker moiety interacts with Glu205, Tyr314, Thr316, Asn376, and Ala198. In certain embodiments, when the inhibitor is bound the linker moiety interacts with Lys364, Glu205, Tyr314, Thr316, Asn376, and Ala198.

In certain embodiments, the interaction between the linker moiety and Lys364 comprises a hydrophobic-hydrophobic interaction or van der Waals interaction. In certain embodiments, the interaction between the linker moiety and Lys364 comprises a hydrogen bonding interaction. In certain embodiments, the interaction between the linker moiety and Glu205 comprises a hydrophobic-hydrophobic interaction or van der Waals interaction. In certain embodiments, the interaction between the linker moiety and Glu205 comprises a hydrogen bonding interaction. In certain embodiments, the interaction between the linker moiety and Tyr314 comprises a hydrophobic-hydrophobic interaction, van der Waals interaction, or π-stacking interaction. In certain embodiments, the interaction between the linker moiety and Tyr314 comprises a hydrogen bonding interaction. In certain embodiments, the interaction between the linker moiety and Thr316 comprises a hydrophobic-hydrophobic interaction or van der Waals interaction. In certain embodiments, the interaction between the linker moiety and Thr316 comprises a hydrogen bonding interaction. In certain embodiments, the interaction between the linker moiety and Asn376 comprises a hydrophobic-hydrophobic interaction or van der Waals interaction. In certain embodiments, the interaction between the linker moiety and Asn376 comprises a hydrogen bonding interaction. In certain embodiments, the interaction between the linker moiety and Ala198 comprises a hydrophobic-hydrophobic interaction or van der Waals interaction. In certain embodiments, the interaction between the linker moiety and Ala198 comprises a hydrogen bonding interaction.

In certain embodiments, when the inhibitor is bound the linker moiety is within about 6 Å of at least one of residues Lys364, Glu205, Tyr314, Thr316, Asn376, and Ala198. In certain embodiments, the linker moiety is within about 5 Å of at least one of residues Lys364, Glu205, Tyr314, Thr316, Asn376, and Ala198. In some embodiments, is within about 4 Å of at least one of residues Lys364, Glu205, Tyr314, Thr316, Asn376, and Ala198. In some embodiments, is within about 3 Å of at least one of residues Lys364, Glu205, Tyr314, Thr316, Asn376, and Ala198. In certain embodiments, when the inhibitor is bound the linker moiety is within about 6 Å of at least two of residues Lys364, Glu205, Tyr314, Thr316, Asn376, and Ala198. In certain embodiments, the linker moiety is within about 5 Å of at least two of residues Lys364, Glu205, Tyr314, Thr316, Asn376, and Ala198. In some embodiments, is within about 4 Å of at least two of residues Lys364, Glu205, Tyr314, Thr316, Asn376, and Ala198. In some embodiments, is within about 3 Å of at least two of residues Lys364, Glu205, Tyr314, Thr316, Asn376, and Ala198. In certain embodiments, when the inhibitor is bound the linker moiety is within about 6 Å of at least three of residues Lys364, Glu205, Tyr314, Thr316, Asn376, and Ala198. In certain embodiments, the linker moiety is within about 5 Å of at least three of residues Lys364, Glu205, Tyr314, Thr316, Asn376, and Ala198. In some embodiments, is within about 4 Å of at least three of residues Lys364, Glu205, Tyr314, Thr316, Asn376, and Ala198. In some embodiments, is within about 3 Å of at least three of residues Lys364, Glu205, Tyr314, Thr316, Asn376, and Ala198. In certain embodiments, when the inhibitor is bound the linker moiety is within about 6 Å of at least four of residues Lys364, Glu205, Tyr314, Thr316, Asn376, and Ala198. In certain embodiments, the linker moiety is within about 5 Å of at least four of residues Lys364, Glu205, Tyr314, Thr316, Asn376, and Ala198. In some embodiments, is within about 4 Å of at least four of residues Lys364, Glu205, Tyr314, Thr316, Asn376, and Ala198. In some embodiments, is within about 3 Å of at least four of residues Lys364, Glu205, Tyr314, Thr316, Asn376, and Ala198. In certain embodiments, when the inhibitor is bound the linker moiety is within about 6 Å of at least five of residues Lys364, Glu205, Tyr314, Thr316, Asn376, and Ala198. In certain embodiments, the linker moiety is within about 5 Å of at least five of residues Lys364, Glu205, Tyr314, Thr316, Asn376, and Ala198. In some embodiments, is within about 4 Å of at least five of residues Lys364, Glu205, Tyr314, Thr316, Asn376, and Ala198. In some embodiments, is within about 3 Å of at least five of residues Lys364, Glu205, Tyr314, Thr316, Asn376, and Ala198. In certain embodiments, when the inhibitor is bound the linker moiety is within about 6 Å of each of residues Lys364, Glu205, Tyr314, Thr316, Asn376, and Ala198. In certain embodiments, the linker moiety is within about 5 Å of each of residues Lys364, Glu205, Tyr314, Thr316, Asn376, and Ala198. In some embodiments, is within about 4 Å of each of residues Lys364, Glu205, Tyr314, Thr316, Asn376, and Ala198. In certain embodiments, the linker moiety is within about 3 Å of each of residues Lys364, Glu205, Tyr314, Thr316, Asn376, and Ala198.

In certain embodiments, the length of the linker moiety, as measured between the atom connected to Ring $A^4$ and the atom connected to the cavity-interacting moiety when the compound is bound to IDE is between about 2 Å and about 15 Å. In certain embodiments, the length of the linker moiety, as measured between the atom connected to Ring $A^4$ and the atom connected to the cavity-interacting moiety when the compound is bound to IDE is between about 3 Å and about 10 Å. In certain embodiments, the length of the linker moiety, as measured between the atom connected to Ring $A^4$ and the atom connected to the cavity-interacting moiety when the compound is bound to IDE is between about 3 Å and about 6 Å.

In certain embodiments, Ring $A^4$ is a 6-membered ring (e.g., phenyl) and the linker moiety and Ring $B^4$ are arranged meta or para to each other. In certain embodiments, Ring $A^4$ is a 6-membered ring (e.g., phenyl) and the linker moiety and Ring $B^4$ are arranged meta to each other. In certain embodiments, Ring $A^4$ is a 6-membered ring (e.g., phenyl) and the linker moiety and Ring $B^4$ are arranged para to each other.

In certain embodiments, the shortest number of atoms in the linker moiety between Ring $A^4$ and the cavity-interacting moiety is between 2 and 8 atoms. In certain embodiments, the shortest number of atoms in the linker moiety between Ring $A^4$ and the cavity-interacting moiety is between 3 and 5 atoms. In certain embodiments, the shortest number of atoms in the linker moiety between Ring $A^4$ and the cavity-interacting moiety is 2 atoms, e.g., the linker moiety is —$CH_2CH_2$—. In certain embodiments, the shortest number of atoms in the linker moiety between Ring $A^4$ and the cavity-interacting moiety is 3 atoms, e.g., the linker moiety is —$NHCH_2CH_2$—, the linker moiety is phenylene wherein the cavity-interacting moiety and Ring $A^4$ are arranged meta to each other. In certain embodiments, the shortest number of atoms in the linker moiety between Ring $A^4$ and the cavity-interacting moiety is 4 atoms, e.g., the linker moiety is a piperazine ring wherein the cavity-interacting moiety and Ring $A^4$ are attached at the nitrogen atoms, the linker moiety is phenylene wherein the cavity-interacting moiety and Ring $A^4$ are arranged para to each other. In certain embodiments, the shortest number of atoms in the linker moiety between Ring $A^4$ and the cavity-interacting moiety is 5 atoms. In certain embodiments, the shortest number of atoms in the linker moiety between Ring $A^4$ and the cavity-interacting moiety is 6 atoms. In certain embodiments, the shortest number of atoms in the linker moiety between Ring $A^4$ and the cavity-interacting moiety is 7 atoms. In certain embodiments, the shortest number of atoms in the linker moiety between Ring $A^4$ and the cavity-interacting moiety is 8 atoms.

In some embodiments, the linker moiety comprises a carbocyclic ring. In some embodiments, the linker moiety comprises a 4-8 membered carbocyclic ring. In some embodiments, the linker moiety comprises a heterocyclic ring. In some embodiments, the linker moiety comprises a 4-8 membered heterocyclic ring wherein the ring contains 1 or 2 heteroatoms selected from O, N, or S. In some embodiments, the linker moiety comprises a 4 membered ring. In some embodiments, the linker comprises an azetidine ring. In some embodiments, the linker moiety comprises a bicyclic azetidine, wherein the azetidine is fused to a 4-8 membered carbocyclic or 4-8 membered heterocyclic ring. In some embodiments, the linker moiety comprises a piperazine. In some embodiments, the linker moiety comprises a piperidine. In some embodiments, the linker moiety comprises a phenyl ring. In some embodiments, the linker moiety comprises a 4-8 membered heteroaryl ring. In some embodiments, the linker moiety comprises an amino group, acyl group, or sulfonyl group. In some embodiments, the linker moiety comprises an amino group, acyl group, or sulfonyl group, wherein the amine, acyl or sulfonyl group is attached to an alkylene group or a carbocyclyl, heterocyclyl, aryl, or heteroaryl ring, and the amine, acyl or sulfonyl group is attached to the cavity-interacting moiety.

In certain embodiments, the linker moiety has a molecular weight between about 50 Da and about 500 Da. In certain embodiments, the linker moiety has a molecular weight between about 50 Da and about 350 Da. In certain embodiments, the linker moiety has a molecular weight between about 50 Da and about 250 Da. In certain embodiments, the linker moiety has a molecular weight between about 50 Da and about 150 Da.

Cavity-Interacting Moiety

In certain embodiments, the cavity-interacting moiety is a hydrophobic moiety or moderately hydrophobic moiety connecting the locked ring moiety and the cavity-interacting moiety. In some embodiments, the cavity-interacting moiety is hydrophobic. In some embodiments, the cavity-interacting moiety is moderately hydrophobic. The cavity-interacting moiety may interact with a first hydrophobic patch defined by residues Val360, Gly361, Gly362, Lys364, and Ile374, a second hydrophobic patch defined by residues Ala198, Trp199 and Phe202, or both hydrophobic patches. In certain embodiments, the cavity-interacting moiety is capable of interacting with the first hydrophobic patch defined by residues Val360, Gly361, Gly362, Lys364, and Ile374. In certain other embodiments, the cavity-interacting moiety is capable of interacting with the second hydrophobic patch defined by residues Ala198, Trp199 and Phe202. In still other embodiments, the cavity-interacting moiety is capable of interacting with both the first hydrophobic patch defined by residues Val360, Gly361, Gly362, Lys364, and Ile374, and the second hydrophobic patch defined by residues Ala198, Trp199, and Phe202.

Figure 9D:
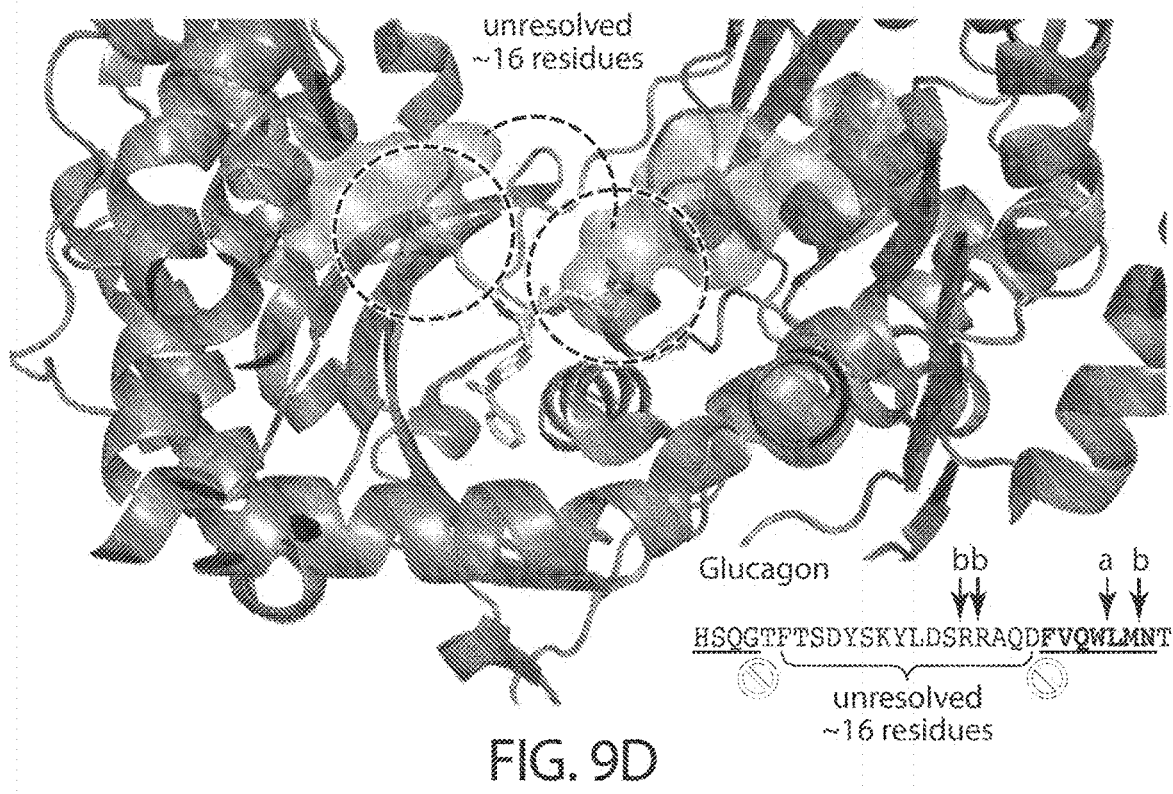
Figure 15A:
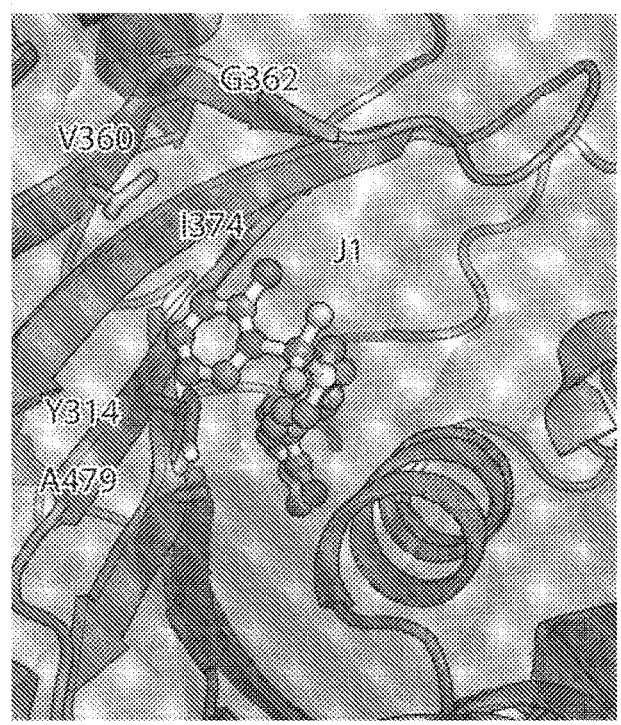
FIGS. 15A-15B. Molecular docking simulations for inhibitors J1 (FIG. 15A) and J6 (FIG. 15B).
Figure 15B:
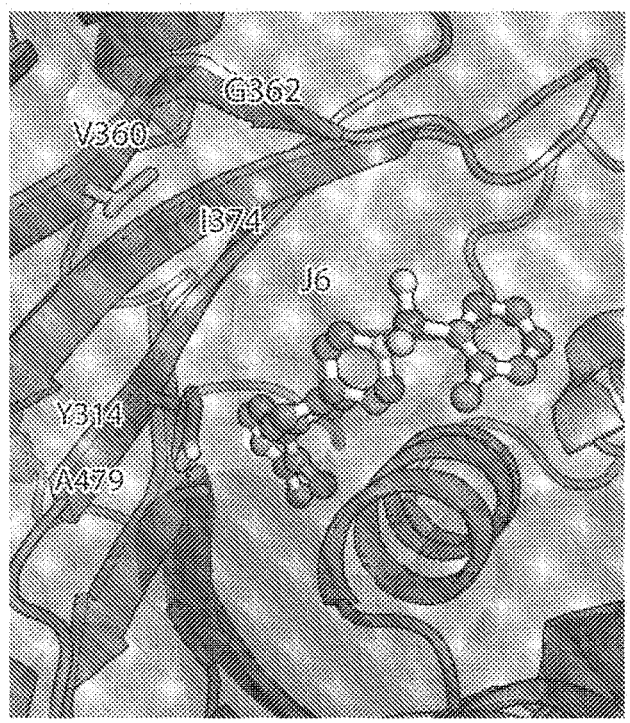
Figure 16:
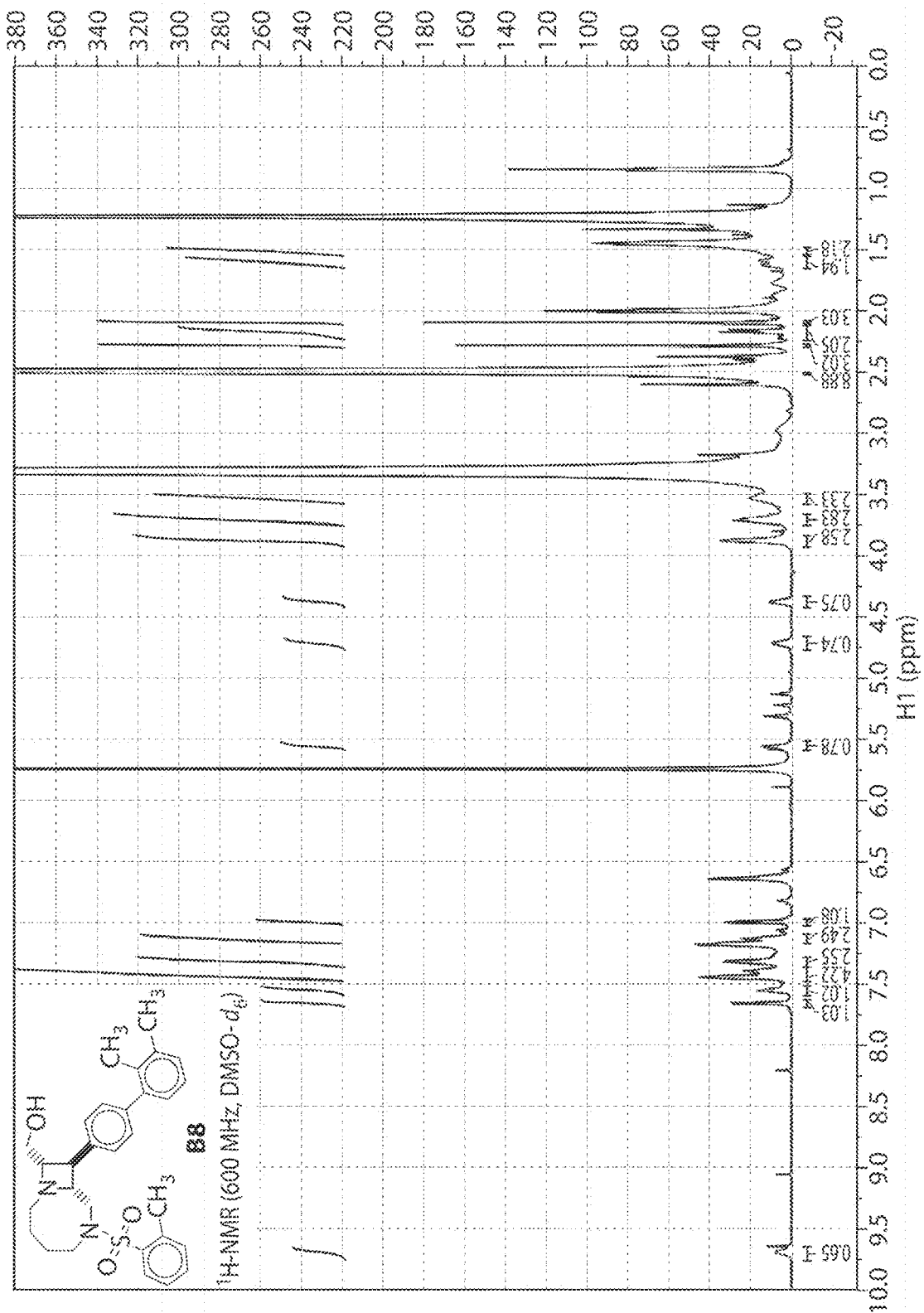
FIG. 16. $^1$H NMR of compound B8 in DMSO-$d_6$ at 600 MHz.
Figure 17:
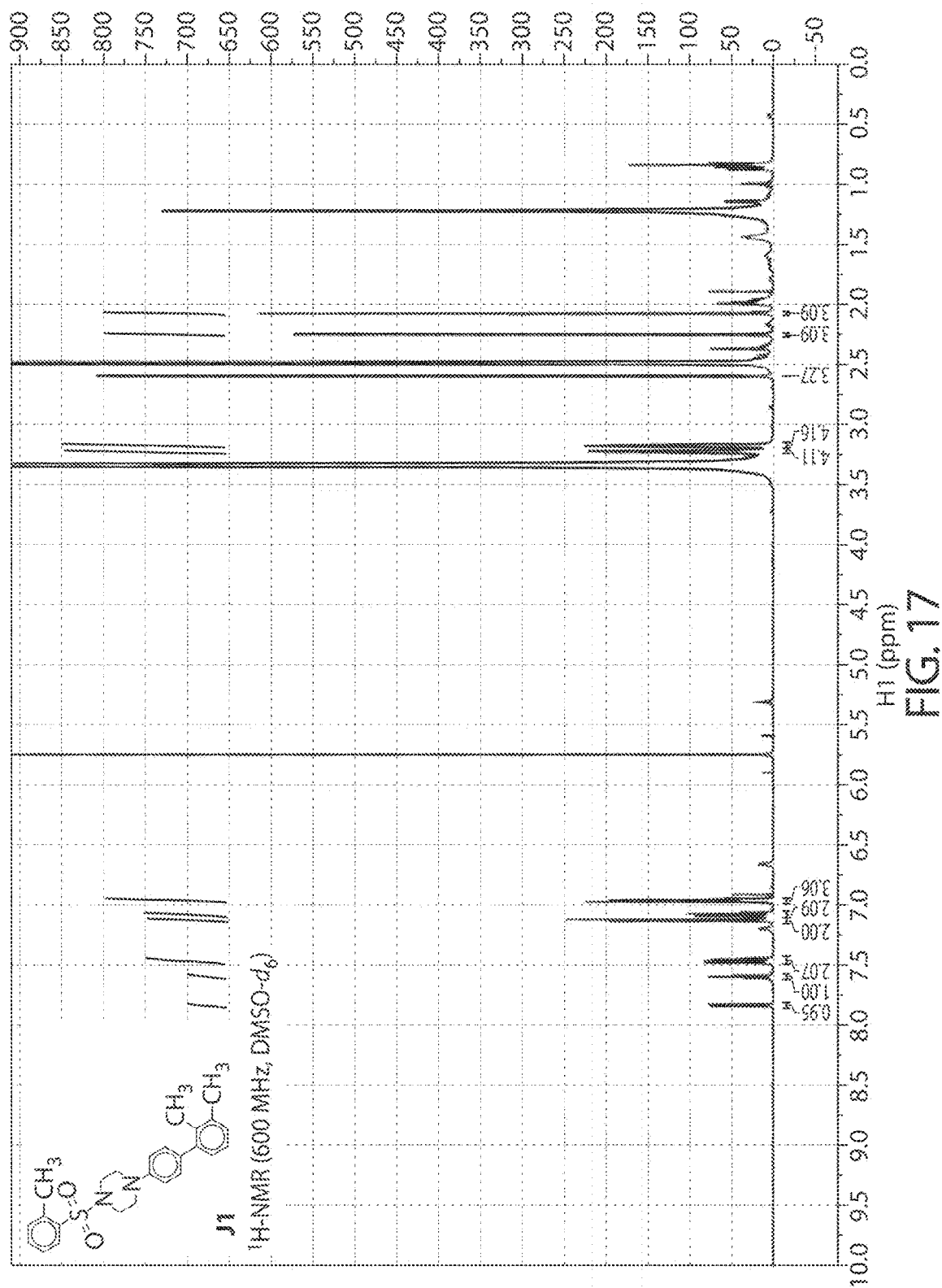
FIG. 17. $^1$H NMR of compound J1 in DMSO-$d_6$ at 600 MHz.
Figure 18:
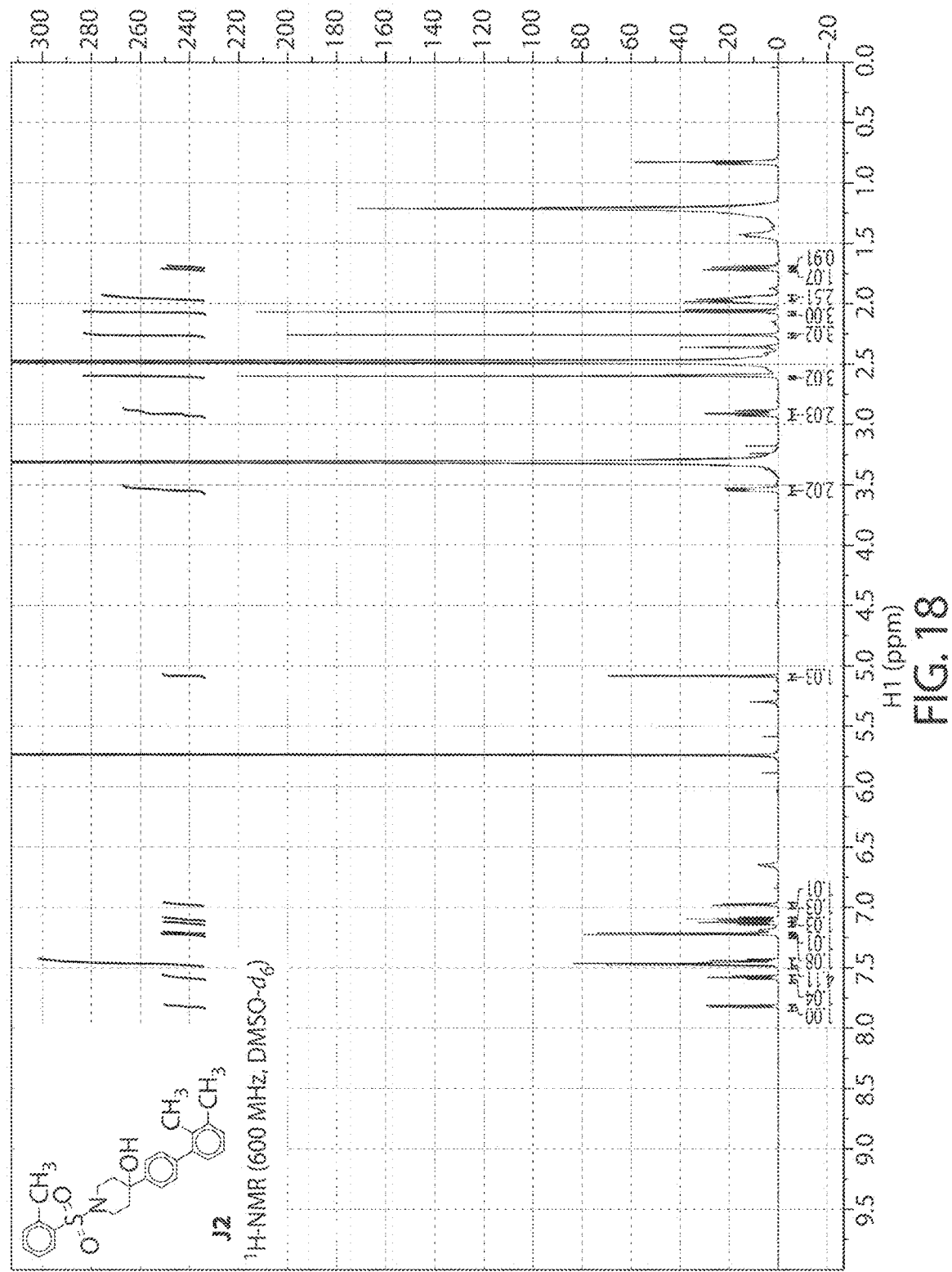
FIG. 18. $^1$H NMR of compound J2 in DMSO-$d_6$ at 600 MHz.
Figure 19:
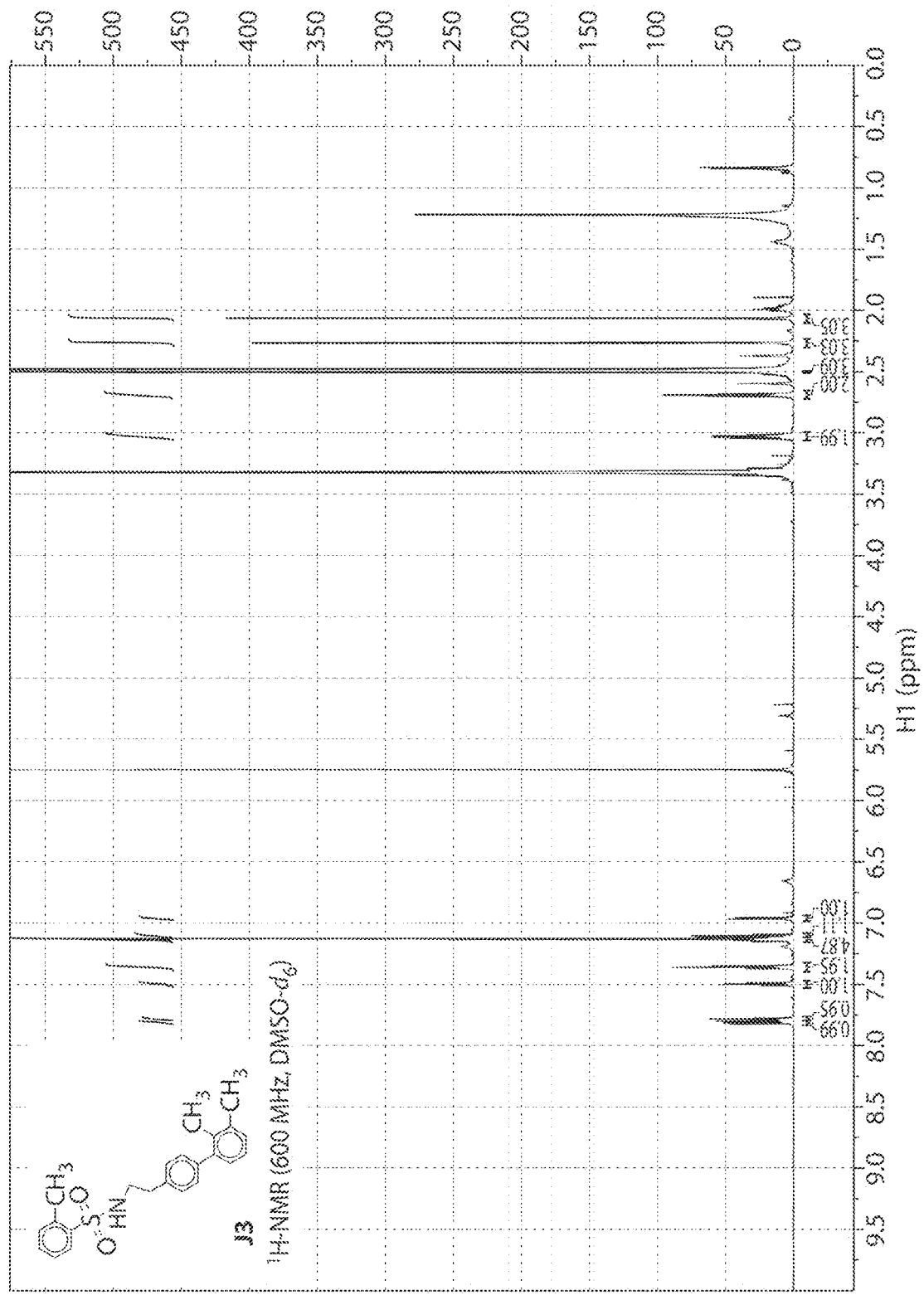
FIG. 19. $^1$H NMR of compound J3 in DMSO-$d_6$ at 600 MHz.
Figure 20:
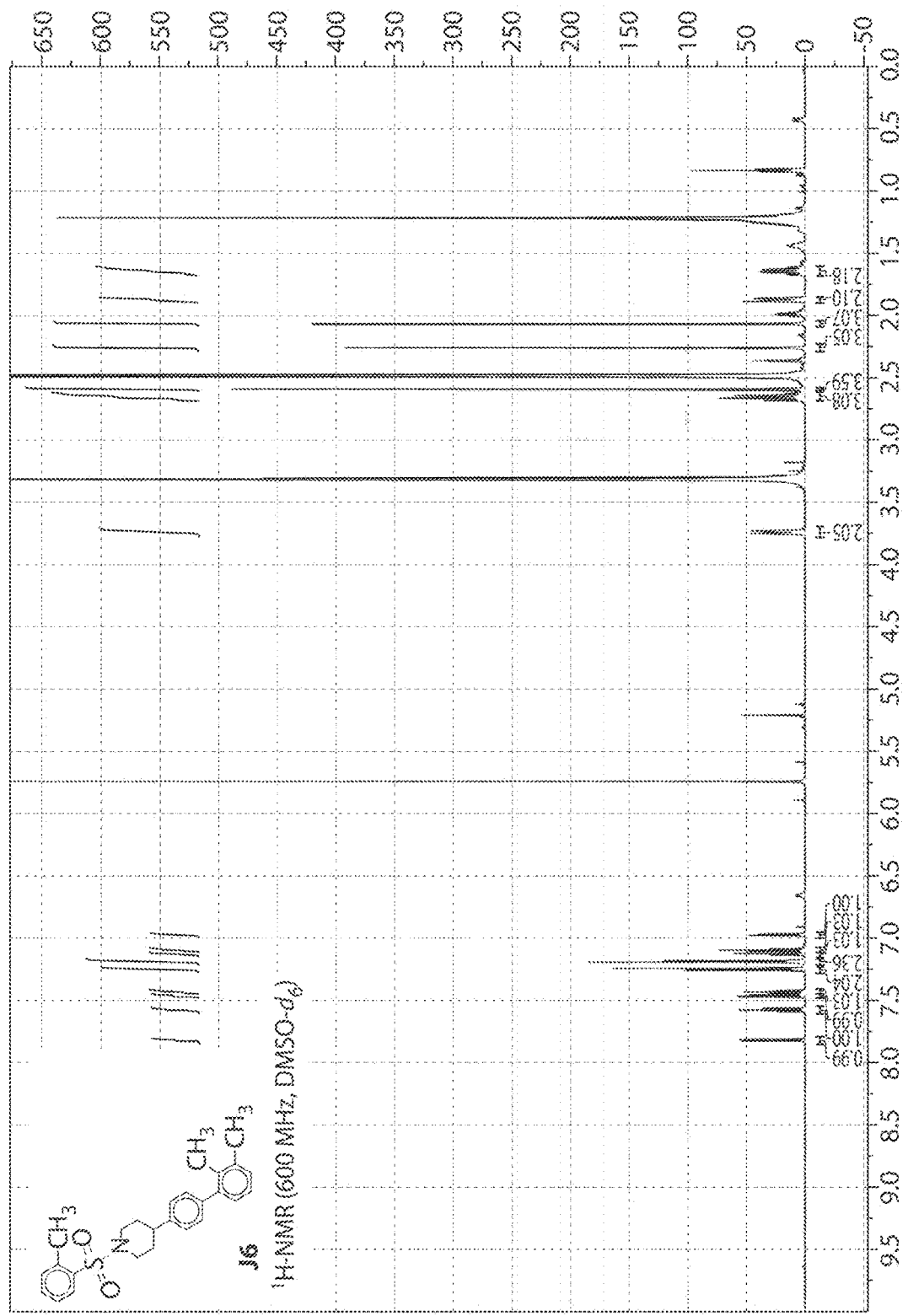
FIG. 20. $^1$H NMR of compound J6 in DMSO-$d_6$ at 600 MHz.
Figure 21:
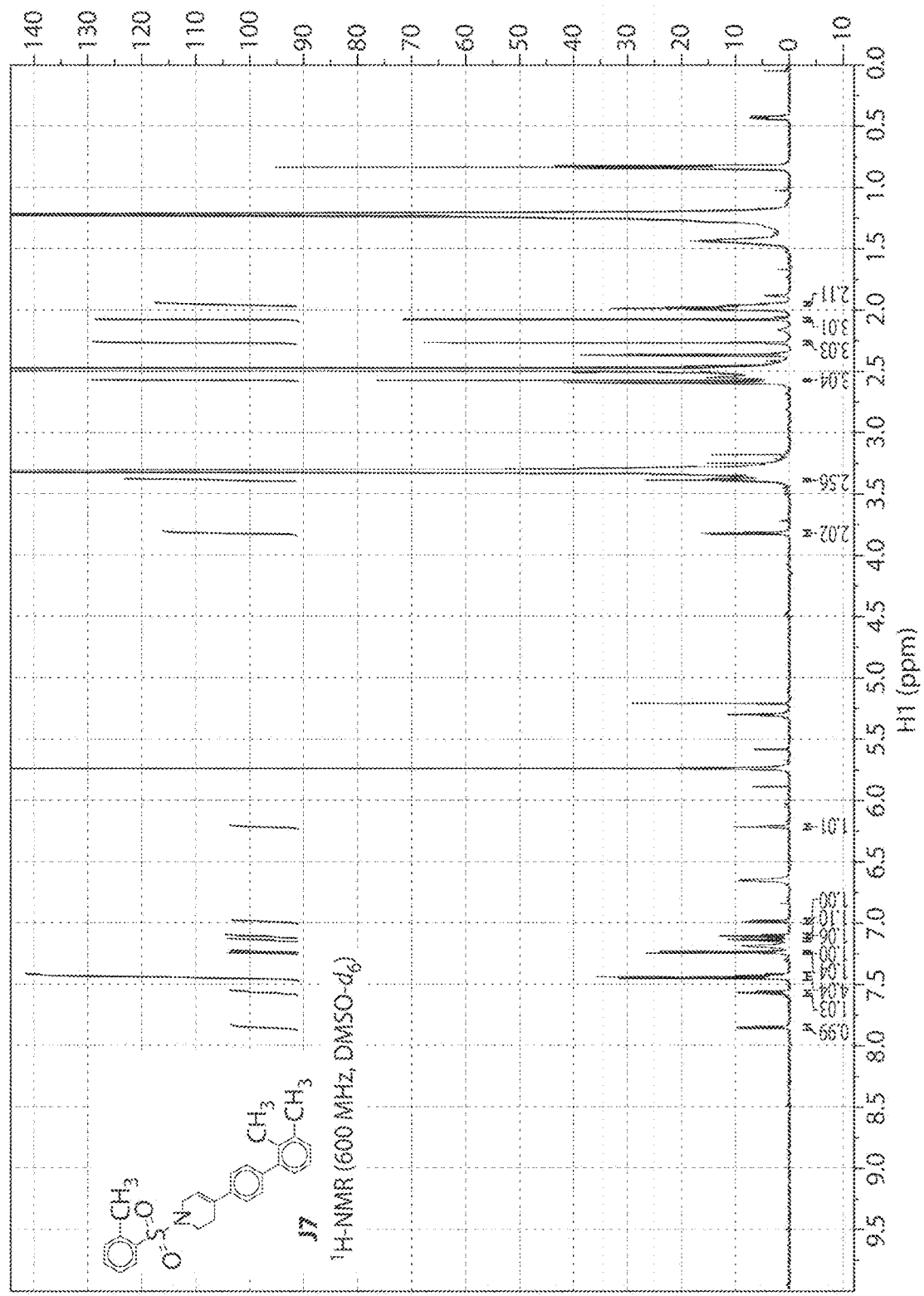
FIG. 21. $^1$H NMR of compound J7 in DMSO-$d_6$ at 600 MHz.
Figure 22:
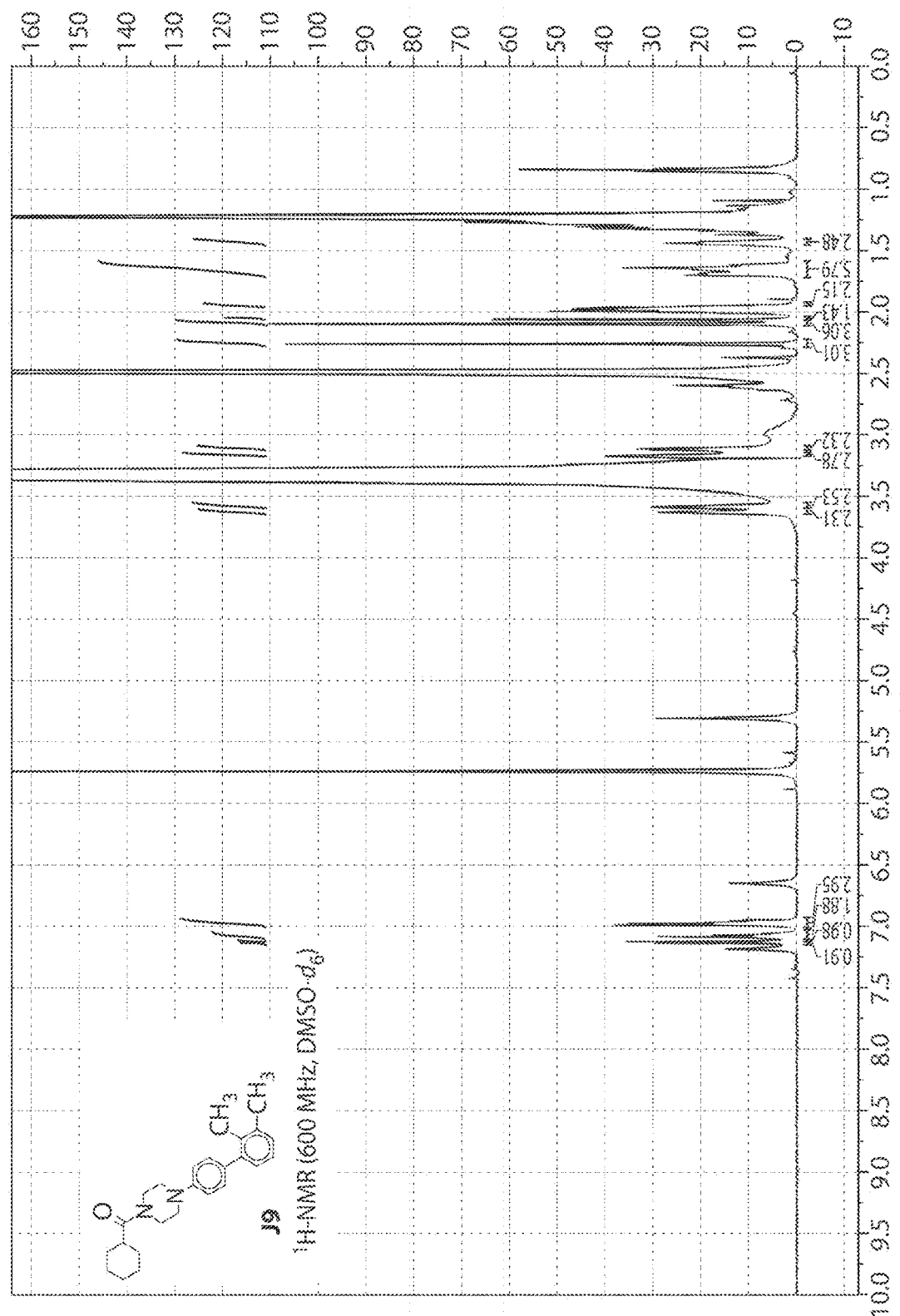
FIG. 22. $^1$H NMR of compound J9 in DMSO-$d_6$ at 600 MHz.
Figure 23:
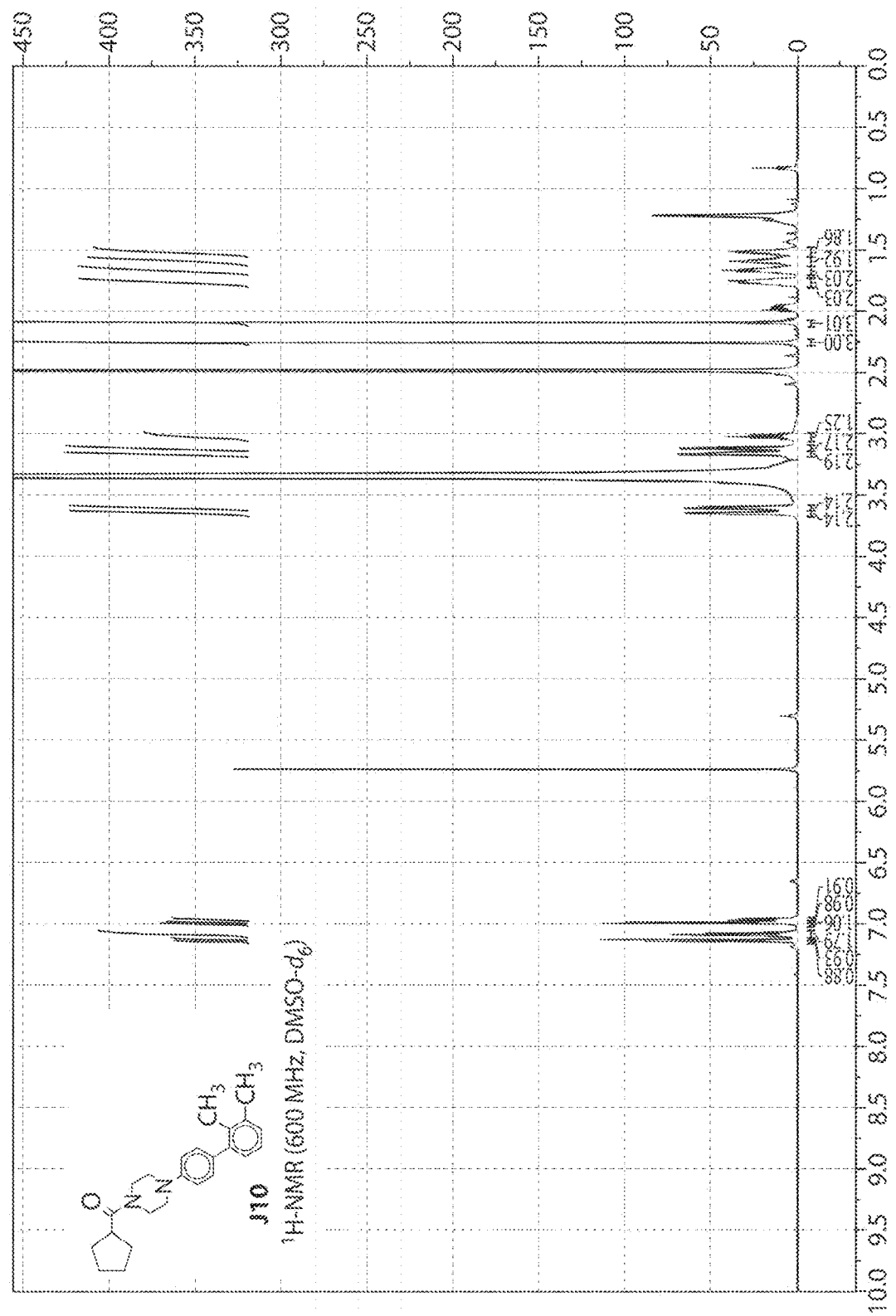
FIG. 23. $^1$H NMR of compound J10 in DMSO-$d_6$ at 600 MHz.
Figure 24:
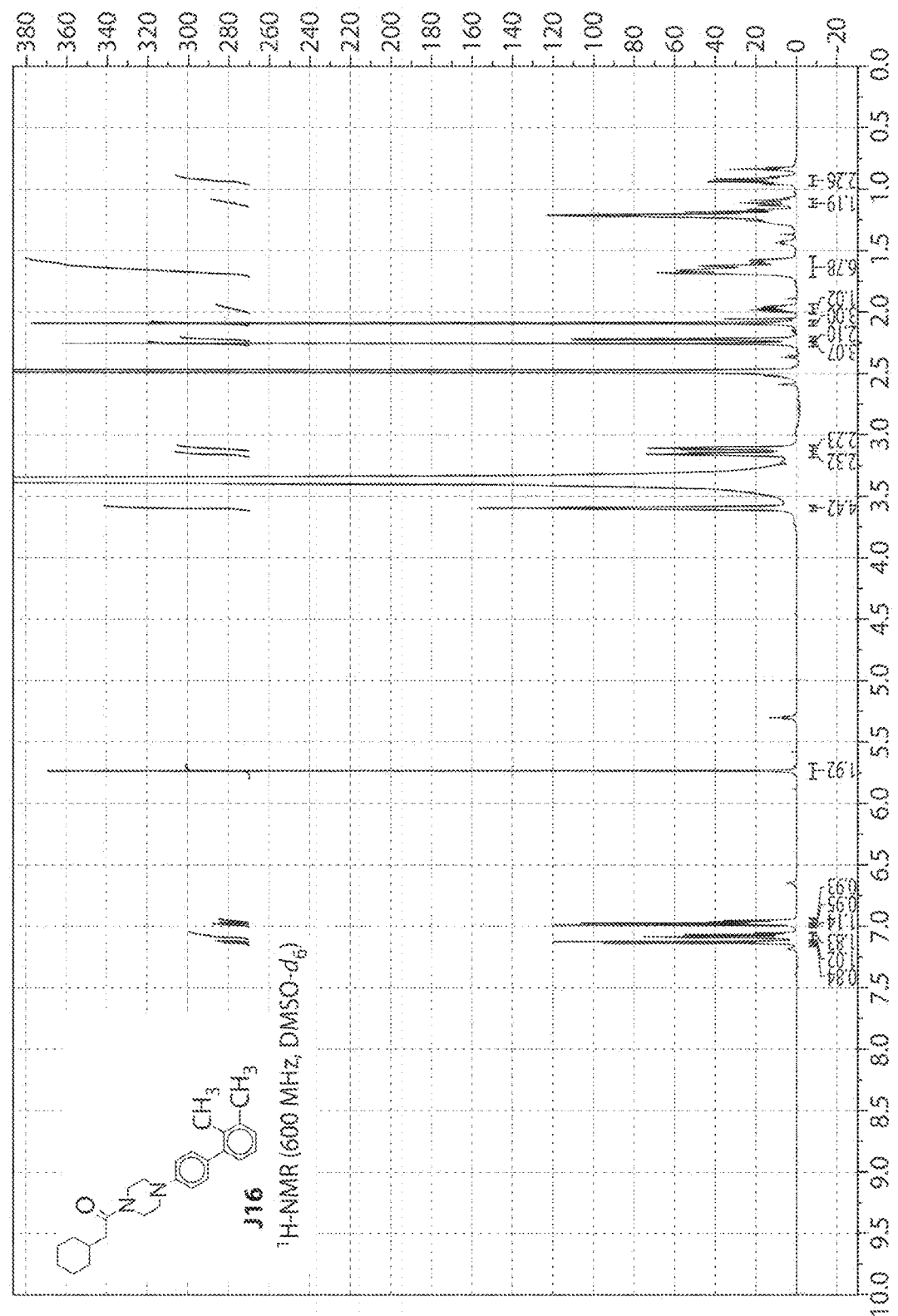
FIG. 24. $^1$H NMR of compound J16 in DMSO-$d_6$ at 600 MHz.
Figure 25:
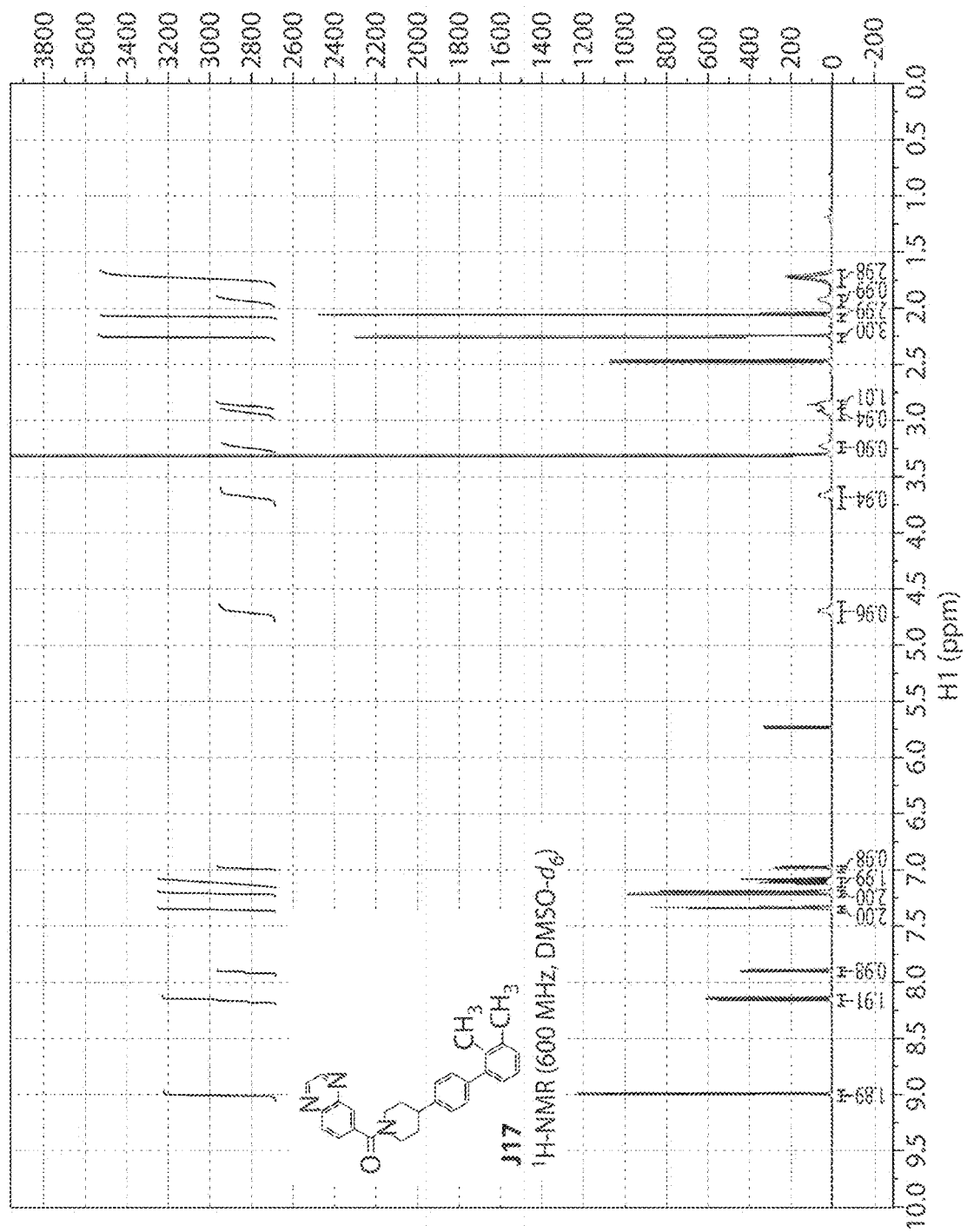
FIG. 25. $^1$H NMR of ompound J17 in DMSO-$h_6$ at 600 MHz.
Figure 27A:
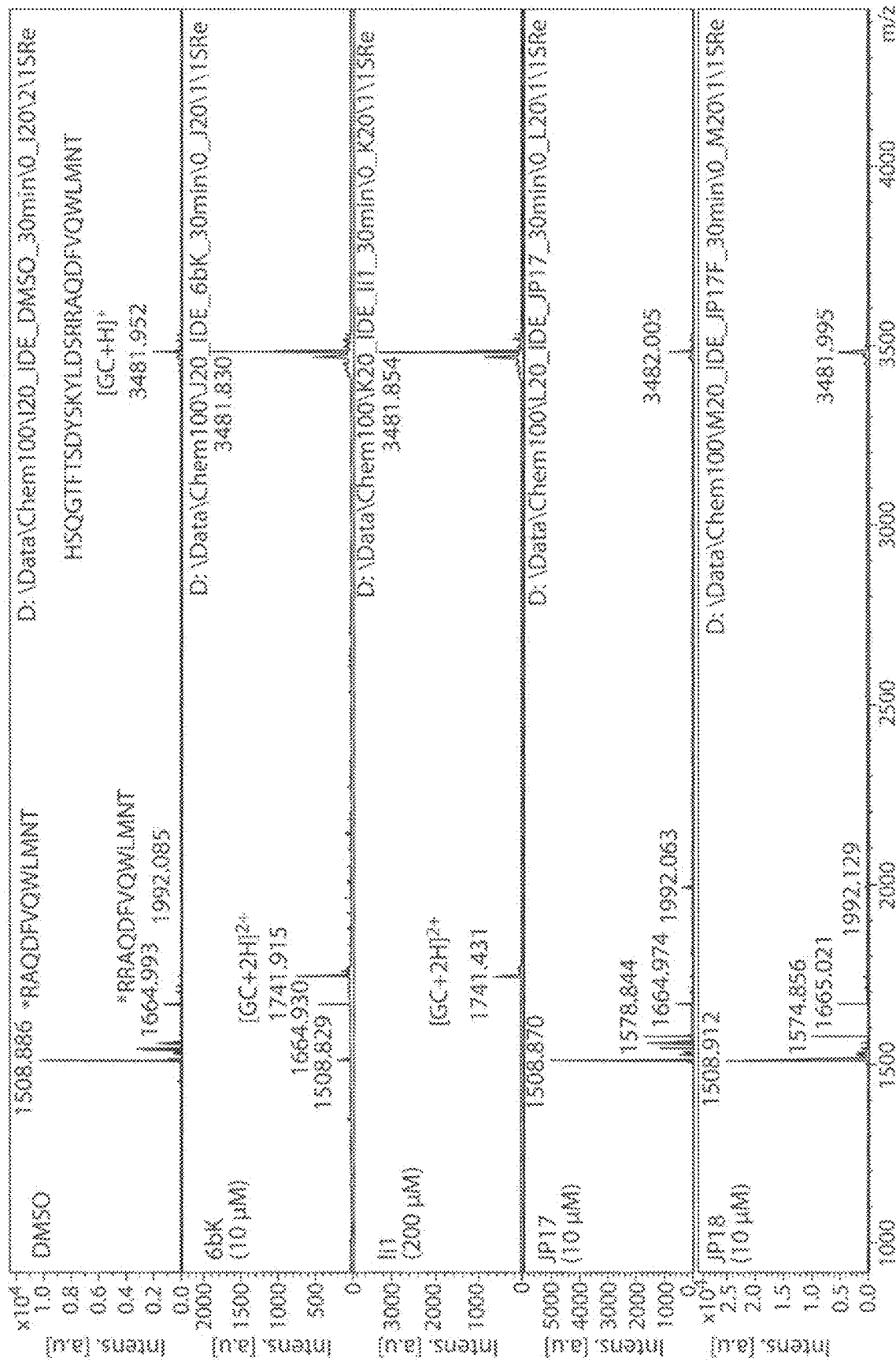
FIGS. 27A-27B. Matrix Assisted Laser Desorption/Ionization (MALDI) results for DMSO (control), 6bK (positive control), Ii1 (positive control), and compounds JP-17 and JP-18, indicates no change in the main glucagon cleavage site (FIG. 27A). The sequences, from top to bottom and left to right, correspond to SEQ ID NOs: 53, 54, and 7.
Figure 27B:
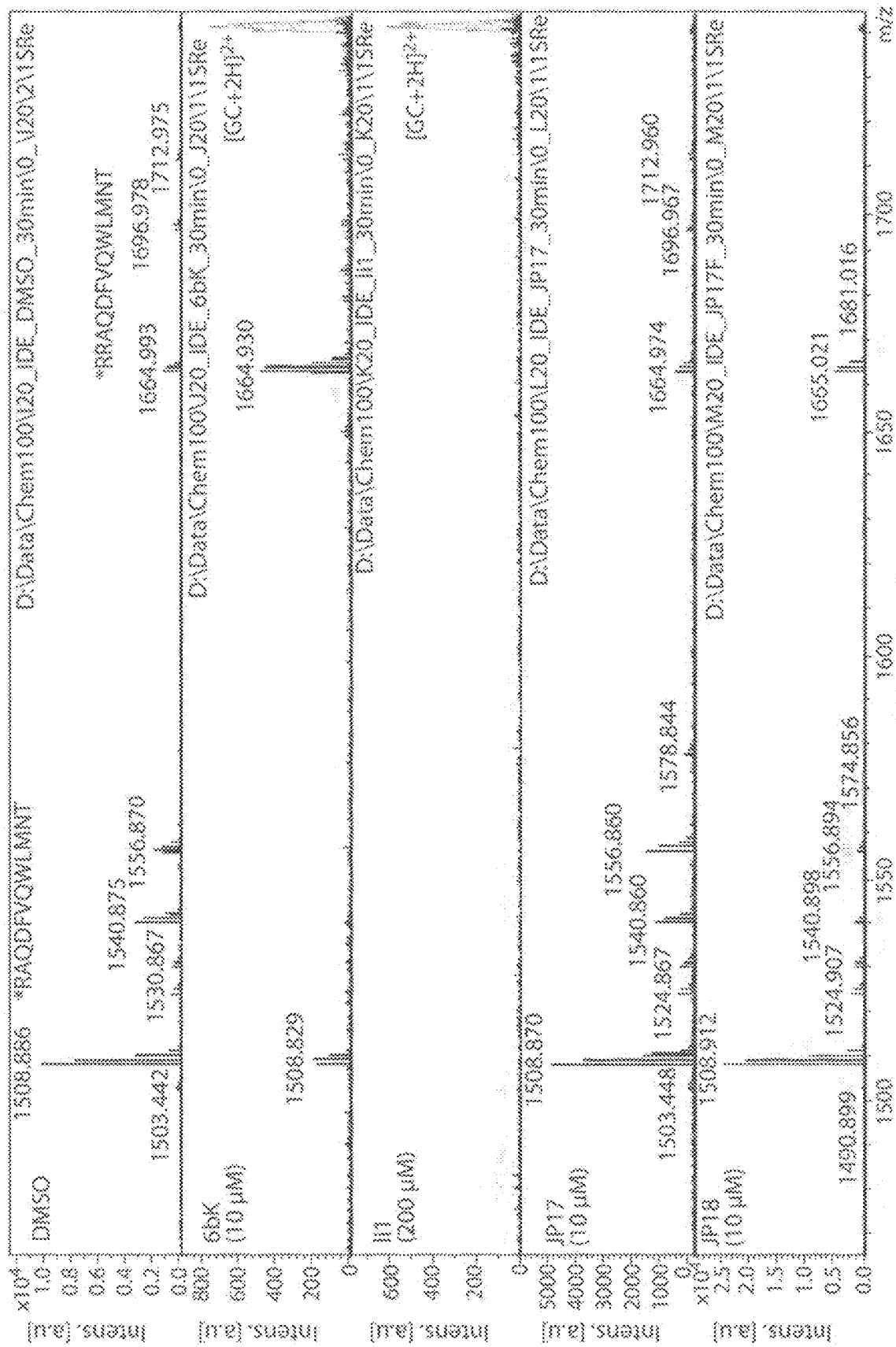
Figure 28:
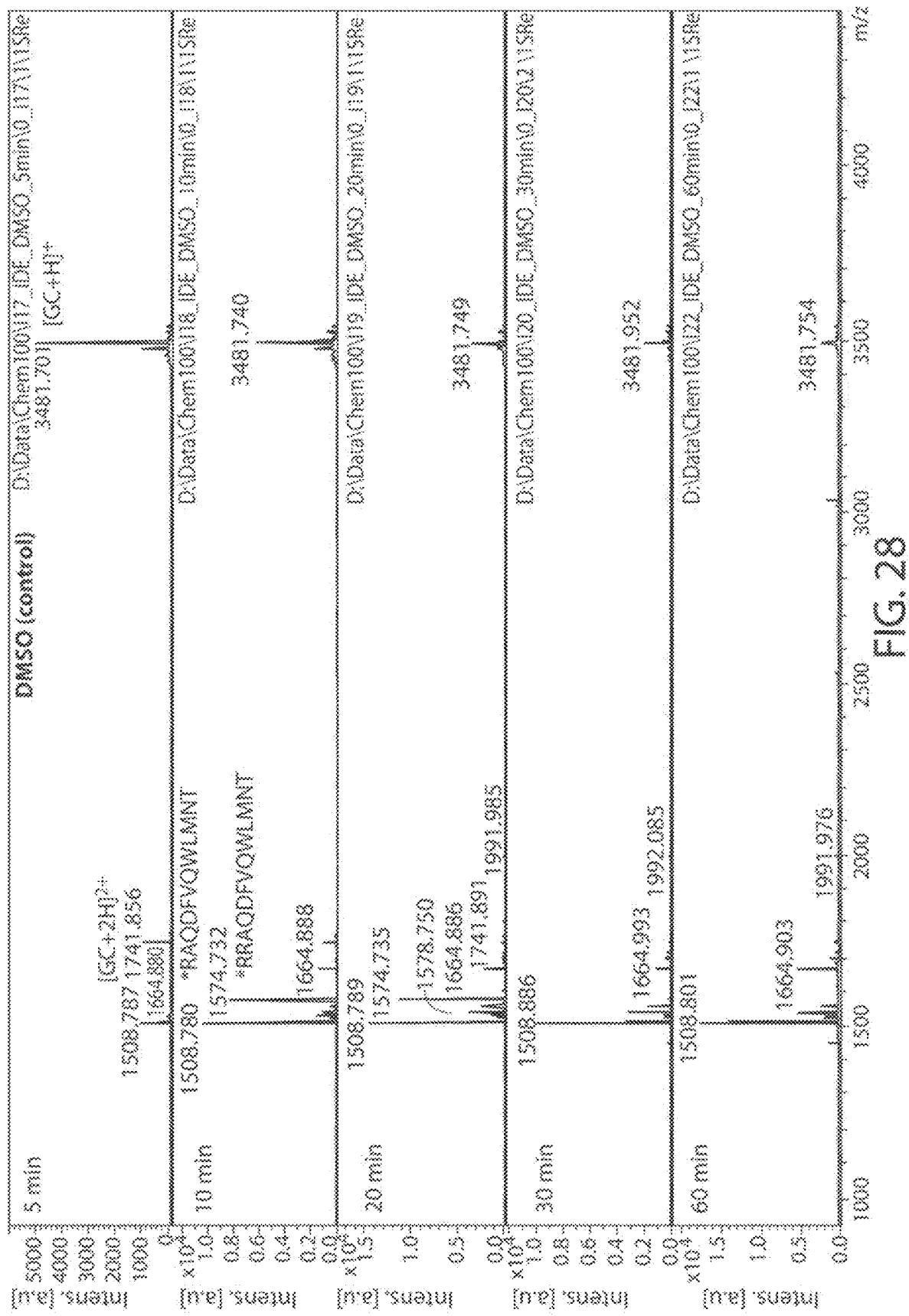
FIG. 28. Matrix Assisted Laser Desorption/Ionization (MALDI) results for DMSO control at 5, 10, 20, 30, and 60 minutes. The sequences, from top to bottom, correspond to SEQ ID NOs: 53-54.
Figure 29:
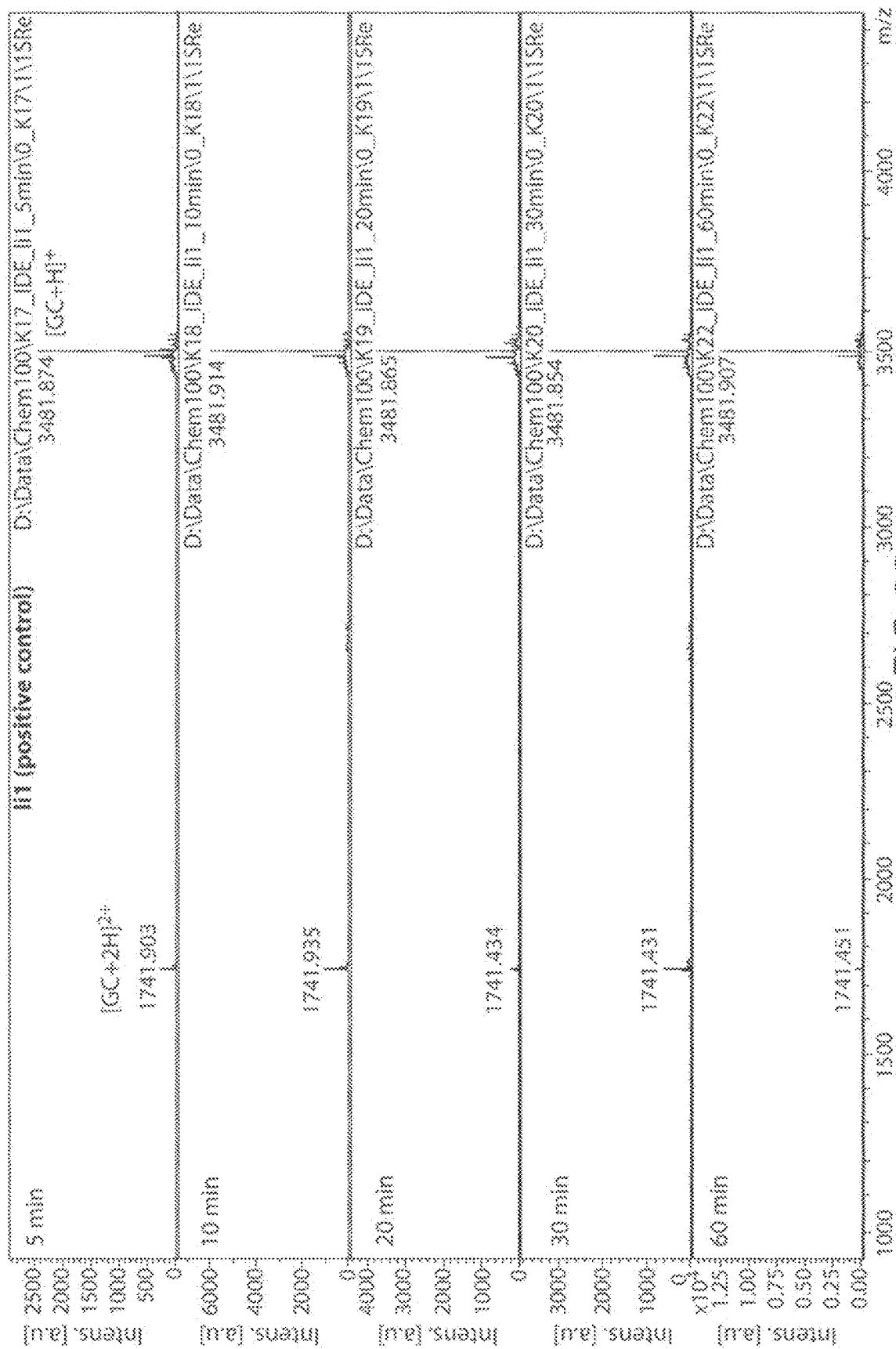
FIG. 29. Matrix Assisted Laser Desorption/Ionization (MALDI) results for Ii1 at 5, 10, 20, 30, and 60 minutes.
Figure 30:
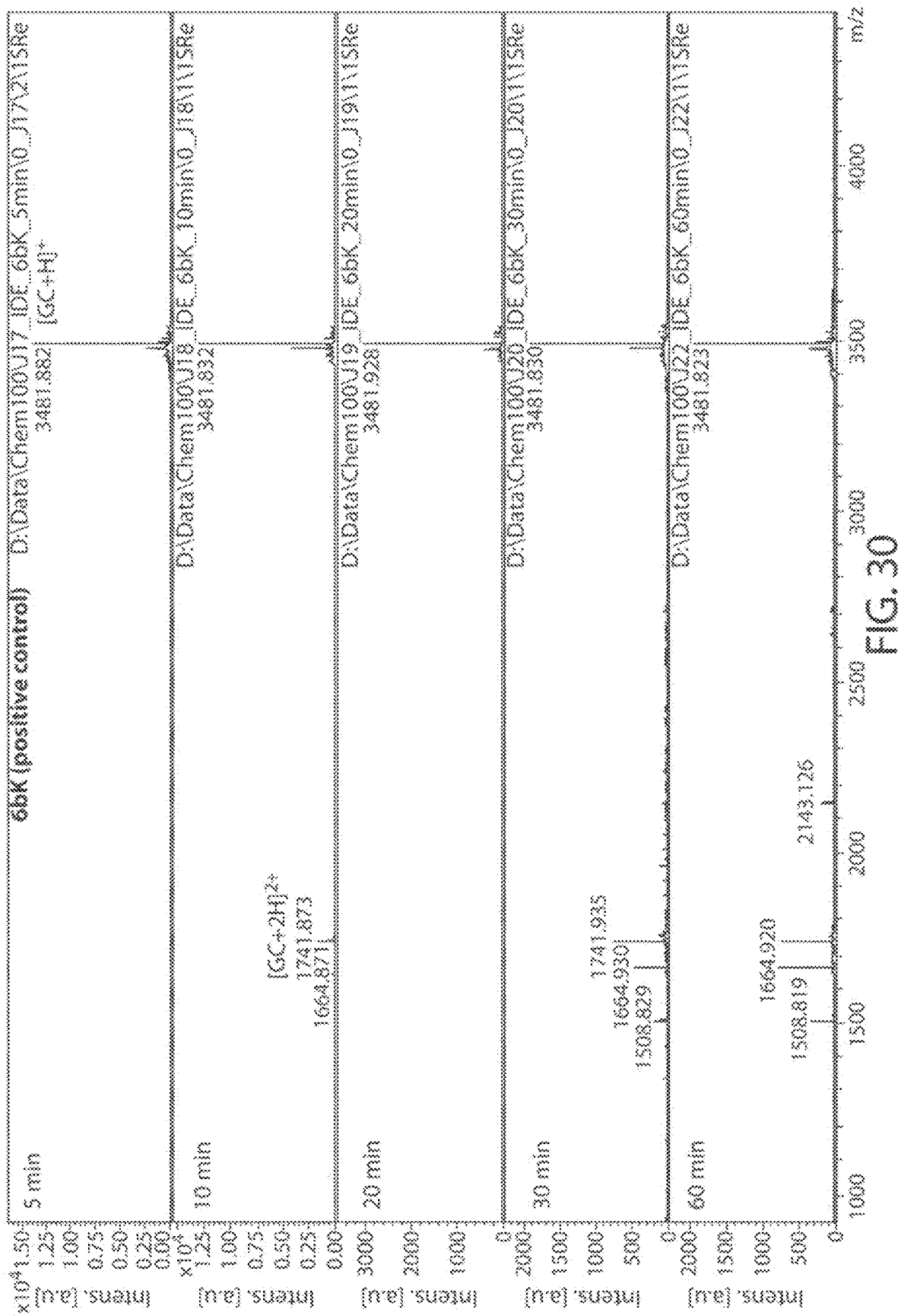
FIG. 30. Matrix Assisted Laser Desorption/Ionization (MALDI) results for compound 6bK at 5, 10, 20, 30, and 60 minutes.
Figure 31:
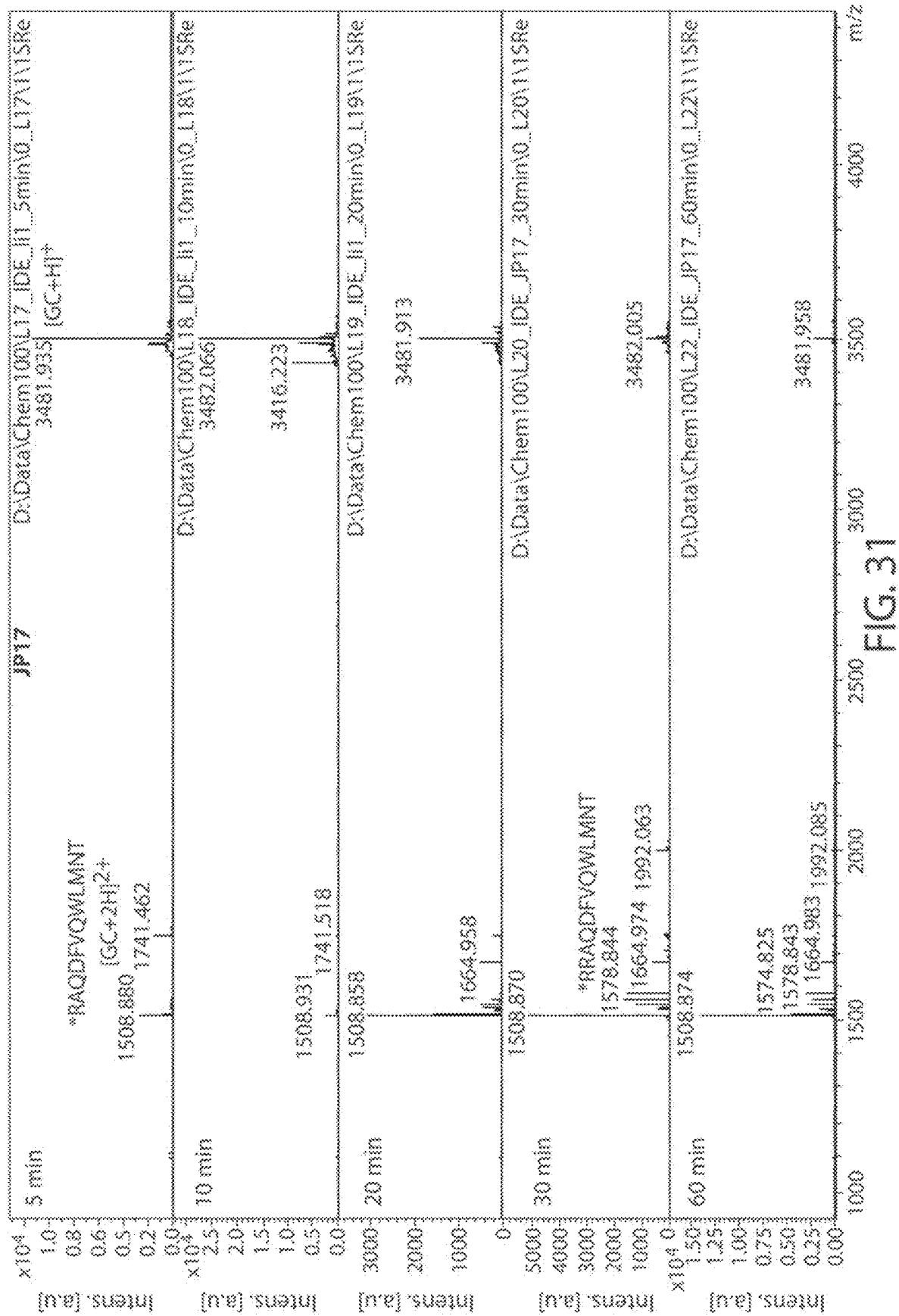
FIG. 31. Matrix Assisted Laser Desorption/Ionization (MALDI) results for compound JP17 at 5, 10, 20, 30, and 60 minutes. The sequences, from top to bottom, correspond to SEQ ID NOs: 53-54.
Figure 32:
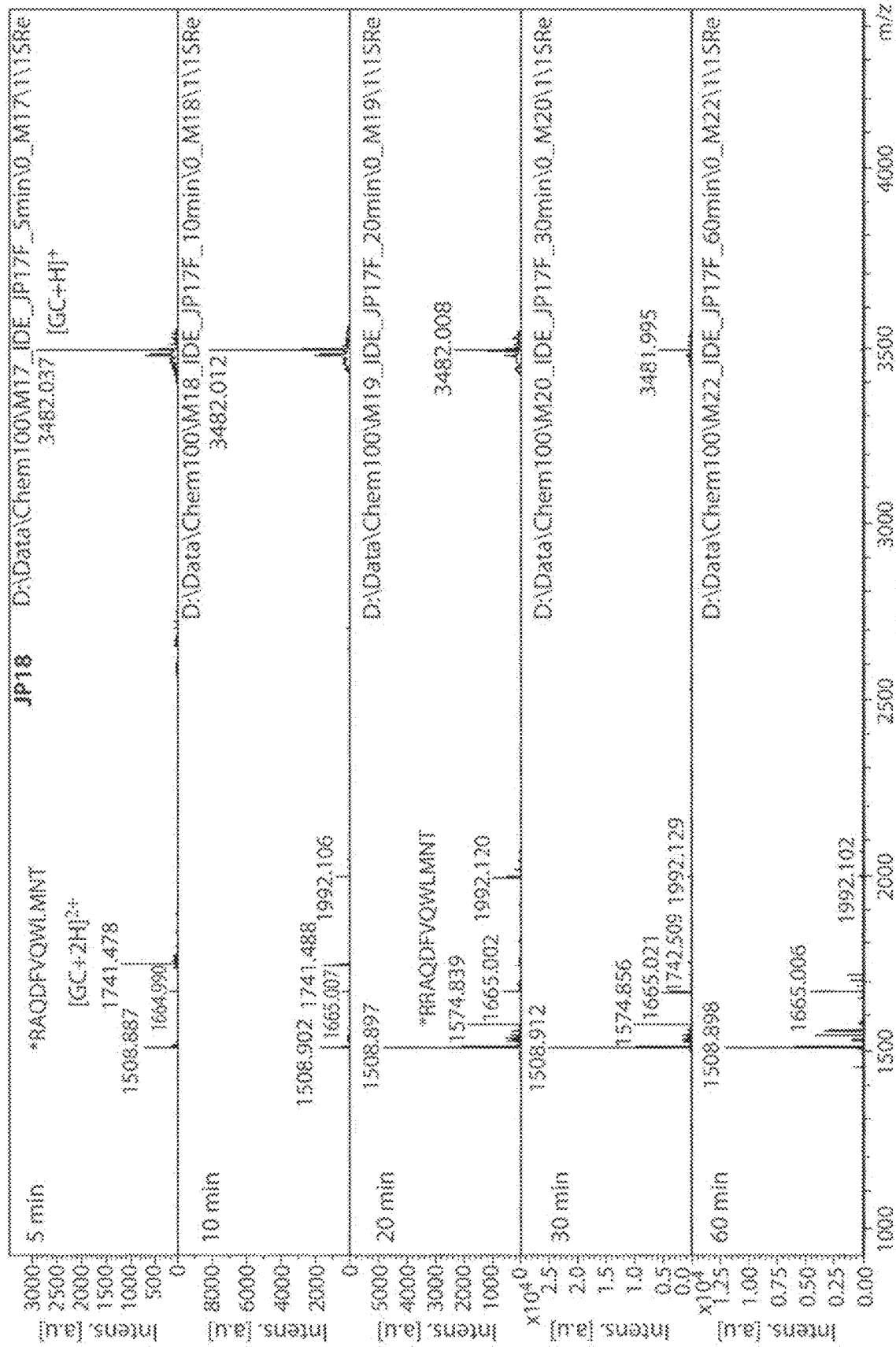
FIG. 32. Matrix Assisted Laser Desorption/Ionization (MALDI) results for compound JP18 at 5, 10, 20, 30, and 60 minutes. The sequences, from top to bottom, correspond to SEQ ID NOs: 53-54.

FIGS. 15A and 15B demonstrate the two hydrophobic pockets with which the cavity-interacting moiety may interact. For compounds J1 and J6 the cavity-interacting moiety is 2-methylphenylsulfonyl. For J1 the 2-methylphenylsulfonyl group interacts with the first hydrophobic pocket defined by residues Val360, Gly361, Gly362, Lys364, and Ile374. For J6 the 2-methylphenylsulfonyl group interacts with the first hydrophobic pocket defined by residues defined by residues Ala198, Trp199 and Phe202. Inhibitors 6b and 6bK interact with both hydrophobic pockets. See, e.g., FIGS. 9B and 9D, and Maianti et al., Nature (2014), 511, 94-98, which is incorporated herein by reference.

In certain embodiments, the cavity-interacting moiety interacts with Val360. In certain embodiments, the cavity-interacting moiety interacts with Val360 and at least one of Gly361, Gly362, Lys364, and Ile374. In certain embodiments, the cavity-interacting moiety interacts with Gly361 360. In certain embodiments, the cavity-interacting moiety interacts with Gly361 and at least one of Val360, Gly362, Lys364, and Ile374. In certain embodiments, the cavity-interacting moiety interacts with Gly362. In certain embodiments, the cavity-interacting moiety interacts with Gly362 and at least one of Val360, Gly361, Lys364, and Ile374. In certain embodiments, the cavity-interacting moiety interacts with Lys364. In certain embodiments, the cavity-interacting moiety interacts with Lys364 and at least one of Val360, Gly361, Gly362, and Ile374. In certain embodiments, the cavity-interacting moiety interacts with Ile374. In certain embodiments, the cavity-interacting moiety interacts with Ile374 and at least one of Val360, Gly361, Gly362, and Lys364.

In certain embodiments, the cavity-interacting moiety interacts with Val360 and Gly361. In certain embodiments, the cavity-interacting moiety interacts with Val360 and Gly362. In certain embodiments, the cavity-interacting moiety interacts with Val360 and Lys364. In certain embodiments, the cavity-interacting moiety interacts with Val360 and Ile374. In certain embodiments, the cavity-interacting moiety interacts with Gly361 and Gly362. In certain embodiments, the cavity-interacting moiety interacts with Gly361 and Lys364. In certain embodiments, the cavity-interacting moiety interacts with Gly361 and Ile374. In certain embodiments, the cavity-interacting moiety interacts with Gly362 and Lys364. In certain embodiments, the cavity-interacting moiety interacts with Gly362 and Ile374. In certain embodiments, the cavity-interacting moiety interacts with Lys364 and Ile374.

In certain embodiments, the cavity-interacting moiety interacts with Val360, Gly361, and Gly362. In certain embodiments, the cavity-interacting moiety interacts with Val360, Gly361, and Lys364. In certain embodiments, the cavity-interacting moiety interacts with Val360, Gly361, and Ile374. In certain embodiments, the cavity-interacting moiety interacts with Val360, Gly362, and Lys364. In certain embodiments, the cavity-interacting moiety interacts with Val360, Gly362, and Ile374. In certain embodiments, the cavity-interacting moiety interacts with Val360, Lys364, and Ile374. In certain embodiments, the cavity-interacting moiety interacts with Gly361, Gly362, and Lys364. In certain embodiments, the cavity-interacting moiety interacts with Gly361, Gly362, and Ile374. In certain embodiments, the cavity-interacting moiety interacts with Gly361, Lys364, and Ile374. In certain embodiments, the cavity-interacting moiety interacts with Gly362, Lys364, and Ile374. In certain embodiments, the cavity-interacting moiety interacts with Val360, Gly361, Gly362, and Lys364. In certain embodiments, the cavity-interacting moiety interacts with Val360, Gly361, Gly362, and Ile374. In certain embodiments, the cavity-interacting moiety interacts with Val360, Gly361, Lys364, and Ile374. In certain embodiments, the cavity-interacting moiety interacts with Val360, Gly362, Lys364, and Ile374. In certain embodiments, the cavity-interacting moiety interacts with Gly361, Gly362, Lys364, and Ile374. In certain embodiments, the cavity-interacting moiety interacts with Val360, Gly361, Gly362, Lys364, and Ile374.

In certain embodiments, the interaction between the cavity-interacting moiety and Val360 comprises a hydrophobic-hydrophobic interaction or van der Waals interaction. In certain embodiments, the interaction between the cavity-interacting moiety and Val360 comprises a hydrogen bonding interaction. In certain embodiments, the interaction between the cavity-interacting moiety and Gly361 comprises a hydrophobic-hydrophobic interaction or van der Waals interaction. In certain embodiments, the interaction between the cavity-interacting moiety and Gly361 comprises a hydrogen bonding interaction. In certain embodiments, the interaction between the cavity-interacting moiety and 362 comprises a hydrophobic-hydrophobic interaction or van der Waals interaction. In certain embodiments, the interaction between the cavity-interacting moiety and Gly362 comprises a hydrogen bonding interaction. In certain embodiments, the interaction between the cavity-interacting moiety and Lys364 comprises a hydrophobic-hydrophobic interaction or van der Waals interaction. In certain embodiments, the interaction between the cavity-interacting moiety and Lys364 comprises a hydrogen bonding interaction. In certain embodiments, the interaction between the cavity-interacting moiety and Ile374 comprises a hydrophobic-hydrophobic interaction or van der Waals interaction. In certain embodiments, the interaction between the cavity-interacting moiety and Ile374 comprises a hydrogen bonding interaction.

In certain embodiments, when the inhibitor is bound the linker moiety is within about 6 Å of at least one of residues Val360, Gly361, Gly362, Lys364, and Ile374. In certain embodiments, the linker moiety is within about 5 Å of at least one of residues Val360, Gly361, Gly362, Lys364, and Ile374. In some embodiments, is within about 4 Å of at least one of residues Val360, Gly361, Gly362, Lys364, and Ile374. In some embodiments, is within about 3 Å of at least one of residues Val360, Gly361, Gly362, Lys364, and Ile374. In certain embodiments, when the inhibitor is bound the linker moiety is within about 6 Å of at least two of residues Val360, Gly361, Gly362, Lys364, and Ile374. In certain embodiments, the linker moiety is within about 5 Å of at least two of residues Val360, Gly361, Gly362, Lys364, and Ile374. In some embodiments, is within about 4 Å of at least two of residues Val360, Gly361, Gly362, Lys364, and Ile374. In some embodiments, is within about 3 Å of at least two of residues Val360, Gly361, Gly362, Lys364, and Ile374. In certain embodiments, when the inhibitor is bound the linker moiety is within about 6 Å of at least three of residues Val360, Gly361, Gly362, Lys364, and Ile374. In certain embodiments, the linker moiety is within about 5 Å of at least three of residues Val360, Gly361, Gly362, Lys364, and Ile374. In some embodiments, is within about 4 Å of at least three of residues Val360, Gly361, Gly362, Lys364, and Ile374. In some embodiments, is within about 3 Å of at least three of residues Val360, Gly361, Gly362, Lys364, and Ile374. In certain embodiments, when the inhibitor is bound the linker moiety is within about 6 Å of at least four of residues Val360, Gly361, Gly362, Lys364, and Ile374. In certain embodiments, the linker moiety is within about 5 Å of at least four of residues Val360, Gly361, Gly362, Lys364, and Ile374. In some embodiments, is within about 4 Å of at least four of residues Val360, Gly361, Gly362, Lys364, and Ile374. In some embodiments, is within about 3 Å of at least four of residues Val360, Gly361, Gly362, Lys364, and Ile374. In certain embodiments, when the inhibitor is bound the linker moiety is within about 6 Å of each of residues Val360, Gly361, Gly362, Lys364, and Ile374. In certain embodiments, the linker moiety is within about 5 Å of each of residues Val360, Gly361, Gly362, Lys364, and Ile374. In some embodiments, is within about 4 Å of each of residues Val360, Gly361, Gly362, Lys364, and Ile374. In certain embodiments, the linker moiety is within about 3 Å of each of residues Val360, Gly361, Gly362, Lys364, and Ile374.

In certain embodiments, the cavity-interacting moiety interacts with Ala198. In certain embodiments, the cavity-interacting moiety interacts with Ala198 and at least one of Trp199 and Phe202. In certain embodiments, the cavity-interacting moiety interacts with Trp199. In certain embodiments, the cavity-interacting moiety interacts with Trp199 and at least one of Ala198 and Phe202. In certain embodiments, the cavity-interacting moiety interacts with Phe202. In certain embodiments, the cavity-interacting moiety interacts with Phe202 and at least one of Ala198 and Trp199.

In certain embodiments, the cavity-interacting moiety interacts with Ala198 and Trp199. In certain embodiments, the cavity-interacting moiety interacts with Ala198 and Phe202. In certain embodiments, the cavity-interacting moiety interacts with Trp199 and Phe202. In certain embodiments, the cavity-interacting moiety interacts with Ala198, Trp199, and Phe202.

In certain embodiments, the interaction between the cavity-interacting moiety and Ala198 comprises a hydrophobic-hydrophobic interaction or van der Waals interaction. In certain embodiments, the interaction between the cavity-interacting moiety and Ala198 comprises a hydrogen bonding interaction. In certain embodiments, the interaction between the cavity-interacting moiety and Trp199 comprises a hydrophobic-hydrophobic interaction, van der Waals interaction, or π-stacking interaction. In certain embodiments, the interaction between the cavity-interacting moiety and Trp199 comprises a hydrogen bonding interaction. In certain embodiments, the interaction between the cavity-interacting moiety and Phe202 comprises a hydrophobic-hydrophobic interaction, van der Waals interaction, or π-stacking interaction. In certain embodiments, the interaction between the cavity-interacting moiety and Phe202 comprises a hydrogen bonding interaction.

In certain embodiments, when the inhibitor is bound the linker moiety is within about 6 Å of at least one of residues Ala198, Trp199, and Phe202. In certain embodiments, the linker moiety is within about 5 Å of at least one of residues Ala198, Trp199, and Phe202. In some embodiments, is within about 4 Å of at least one of residues Ala198, Trp199, and Phe202. In some embodiments, is within about 3 Å of at least one of residues Ala198, Trp199, and Phe202. In certain embodiments, when the inhibitor is bound the linker moiety is within about 6 Å of at least two of residues Ala198, Trp199, and Phe202. In certain embodiments, the linker moiety is within about 5 Å of at least two of residues Ala198, Trp199, and Phe202. In some embodiments, is within about 4 Å of at least two of residues Ala198, Trp199, and Phe202. In some embodiments, is within about 3 Å of at least two of residues Ala198, Trp199, and Phe202. In certain embodiments, when the inhibitor is bound the linker moiety is within about 6 Å of each of residues Ala198, Trp199, and Phe202. In certain embodiments, the linker moiety is within about 5 Å of each of residues Ala198, Trp199, and Phe202. In some embodiments, is within about 4 Å of each of residues Ala198, Trp199, and Phe202. In certain embodiments, the linker moiety is within about 3 Å of each of residues Ala198, Trp199, and Phe202.

In certain embodiments, the cavity-interacting moiety comprises a carbocyclic ring. In certain embodiments, the cavity-interacting moiety comprises a 4-8 membered carbocyclic ring. In certain embodiments, the cavity-interacting moiety comprises a heterocyclic ring. In certain embodiments, the cavity-interacting moiety comprises a 4-8 membered heterocyclic ring. In certain embodiments, the cavity-interacting moiety comprises a phenyl ring. In certain embodiments, the cavity-interacting moiety comprises a 4-8 membered heteroaryl ring. In certain embodiments, the cavity-interacting moiety comprises an acyl group. In certain embodiments, the cavity-interacting moiety comprises an amide group. In certain embodiments, the cavity-interacting moiety comprises a ketone group. In certain embodiments, the cavity-interacting moiety comprises a sulfonyl group.

In certain embodiments, the cavity-interacting moiety and the linker moiety are attached via a carbonyl (e.g., ketone, amide). In certain embodiments, the cavity-interacting moiety and the linker moiety are attached via a sulfonyl. In certain embodiments, the cavity-interacting moiety and the linker moiety are attached via an amine. In certain embodiments, the carbonyl, sulfonyl, or amine is part of the linker moiety. In certain embodiments, the carbonyl, sulfonyl, or amine is part of the cavity-interacting moiety.

In certain embodiments, the cavity-interacting moiety has a molecular weight between about 50 Da and about 1000 Da. In certain embodiments, the cavity-interacting moiety has a molecular weight between about 50 Da and about 500 Da. In certain embodiments, the cavity-interacting moiety has a molecular weight between about 50 Da and about 350 Da. In certain embodiments, the cavity-interacting moiety has a molecular weight between about 50 Da and about 250 Da. In certain embodiments, the cavity-interacting moiety has a molecular weight between about 50 Da and about 150 Da. In certain embodiments, the cavity-interacting moiety has a molecular weight between about 100 Da and about 350 Da. In certain embodiments, the cavity-interacting moiety has a molecular weight between about 100 Da and about 250 Da. In certain embodiments, the cavity-interacting moiety has a molecular weight between about 100 Da and about 200 Da.

Certain embodiments of the linker moiety and cavity-interacting moiety are described for compounds of Formula (I), (II), (III), (IV), and (V).

Compounds of Formula (RL)

In certain embodiments, provided herein is a compound of Formula (RL):

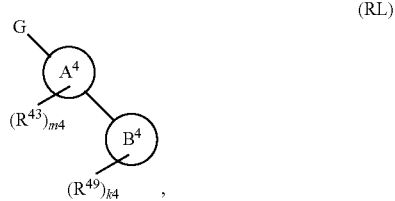

(RL)

or a pharmaceutically acceptable salt, stereoisomer, or tautomer thereof, wherein:

G is an organic substituent comprising a linker moiety and cavity-interacting moiety, wherein the linker moiety connects Ring $A^4$ to the cavity-interacting moiety;

Ring $A^4$ is 6-membered arylene or 5-7 membered heteroarylene;

Ring $B^4$ is 6 membered aryl, or 5-7 membered heteroaryl;

each $R^{43}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{43a}$, or —$N(R^{43a})_2$, or two $R^{43}$ are joined to form an optionally substituted carbocyclic, heterocyclic, aryl, or heteroaryl ring, wherein each $R^{43a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{43a}$ are joined to form an optionally substituted heteroaryl or optionally substituted heterocyclic ring;

each $R^{49}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{49a}$, —$N(R^{49a})_2$, —$S(=O)_2R^{49a}$, —$S(=O)_2OR^{49a}$, or —$S(=O)_2N(R^{49a})_2$, or two $R^{49}$ are joined to form an optionally substituted carbocyclic, heterocyclic, aryl, or heteroaryl ring, wherein each $R^{49a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{49a}$ are joined to form an optionally substituted heteroaryl or optionally substituted heterocyclic ring;

m4 is 0, 1, 2, 3, or 4; and k4 is 0, 1, 2, 3, 4, or 5;

wherein the sum of m4 and k4 is at least one, and at least one $R^{43}$ or $R^{49}$ is attached ortho to the bond between Rings $A^4$ and $B^4$.

In certain embodiments, G comprises a linker moiety and a cavity-interacting moiety, as described above wherein the linker moiety connects Ring $A^4$ and the IDE cavity-interacting moiety.

In certain embodiments, the compound of Formula (RL) selectively inhibits the activity of IDE for degradation of a first substrate over the activity of IDE for degradation of a second substrate. In certain embodiments, the compound of Formula (RL) selectively inhibits the activity of IDE for degradation of insulin over the activity of IDE for degradation of a second substrate (e.g., glucagon, amylin). In certain embodiments, the compound of Formula (RL) selectively inhibits the activity of IDE for degradation of insulin over the activity of IDE for degradation of glucagon. In certain embodiments, the compound of Formula (RL) selectively inhibits the activity of IDE for degradation of insulin over the activity of IDE for degradation of more than one other substrate.

In certain embodiments, the rotational energy barrier between rings $A^4$ and $B^4$ is at least about 3 kcal/mol. In certain embodiments, the rotational energy barrier between rings $A^4$ and $B^4$ is at least about 6 kcal/mol, is at least about 10 kcal/mol, at least about 15 kcal/mol, at least about 20 kcal/mol, or at least about 30 kcal/mol. In certain embodiments, the equilibrium dihedral angle between rings $A^4$ and $B^4$ is between about 20° and between about 1600. In certain embodiments, the equilibrium dihedral angle between rings $A^4$ and $B^4$ is between about 40° and between about 140°, between about 60° and between about 120°, or between about 90° and between about 100°. In certain embodiments, the equilibrium dihedral angle between rings $A^4$ and $B^4$ is between about 20° and between about 160° when bound to IDE. In certain embodiments, the equilibrium dihedral angle between rings $A^4$ and $B^4$ is between about 40° and between about 140°, between about 60° and between about 120°, or between about 90° and between about 100° when bound to IDE.

In certain embodiments, the compound of Formula (RL) is a compound of Formula (RL-a):

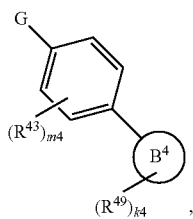

(RL-a)

or a pharmaceutically acceptable salt, solvate, hydrate, polymorph, co-crystal, tautomer, stereoisomer, prodrug, or isotopically labeled derivative thereof, wherein Ring $B^4$, G, $R^{43}$, $R^{49}$, m4, and k4 are as described herein.

In certain embodiments, the compound of Formula (RL) is a compound of Formula (RL-b):

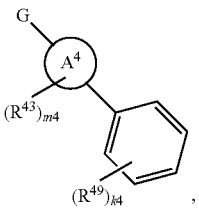

(RL-b)

or a pharmaceutically acceptable salt, solvate, hydrate, polymorph, co-crystal, tautomer, stereoisomer, prodrug, or isotopically labeled derivative thereof, wherein Ring $A^4$, G, $R^{43}$, $R^{49}$, m4, and k4 are as described herein.

In certain embodiments, the compound of Formula (RL) is a compound of Formula (RL-c):

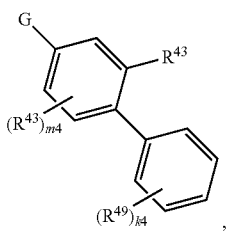

(RL-c)

or a pharmaceutically acceptable salt, solvate, hydrate, polymorph, co-crystal, tautomer, stereoisomer, prodrug, or iso-topically labeled derivative thereof, wherein G, $R^{43}$, $R^{49}$, m4, and k4 are as described herein.

In certain embodiments, the compound of Formula (RL) is a compound of Formula (RL-d):

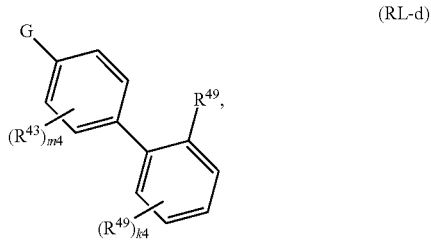

(RL-d)

or a pharmaceutically acceptable salt, solvate, hydrate, polymorph, co-crystal, tautomer, stereoisomer, prodrug, or isotopically labeled derivative thereof, wherein G, $R^{43}$, $R^{49}$, m4, and k4 are as described herein.

In certain embodiments, the compound of Formula (RL) is a compound of Formula (RL-e):

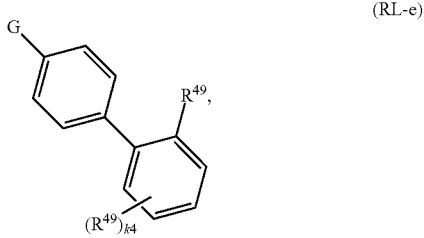

(RL-e)

or a pharmaceutically acceptable salt, solvate, hydrate, polymorph, co-crystal, tautomer, stereoisomer, prodrug, or isotopically labeled derivative thereof, wherein G, $R^{49}$, and k4 are as described herein.

In certain embodiments, the compound of Formula (RL) is a compound of Formula:

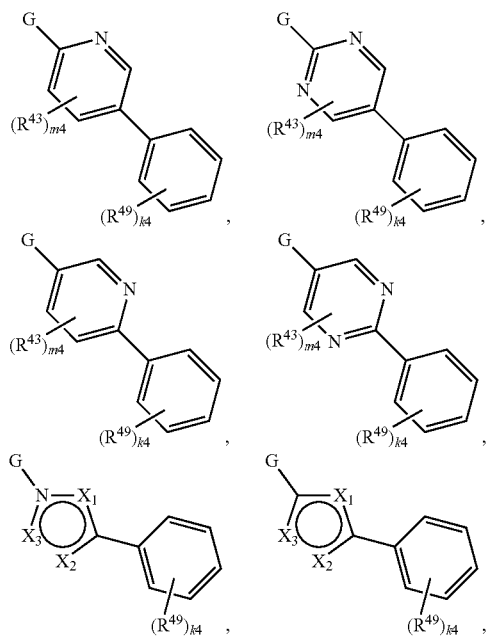

or a pharmaceutically acceptable salt, solvate, hydrate, polymorph, co-crystal, tautomer, stereoisomer, prodrug, or isotopically labeled derivative thereof, and
wherein:
m4 is 0, 1, or 2;
k4 is 0, 1, 2, 3, 4, or 5;
$X_1$, $X_2$, and $X_3$ are selected from the group consisting of C, CH, C($R^{43}$), O, S, N, and N($R^{43a}$), as valency permits.

In certain embodiments, the compound comprising a locked ring moiety, and further comprises a fragment of an inhibitor known in the art, for example, a fragment of (Ii1), (ML345), (BDM41367), (6b), (6bK), (2), or (NTE-1), or an analog thereof. In certain embodiments, for a compound of Formula (RL), G comprises a fragment of an inhibitor known in the art, for example, (Ii1), (ML345), (BDM41367), (6b), (6bK), (2), or (NTE-1), or an analog thereof.

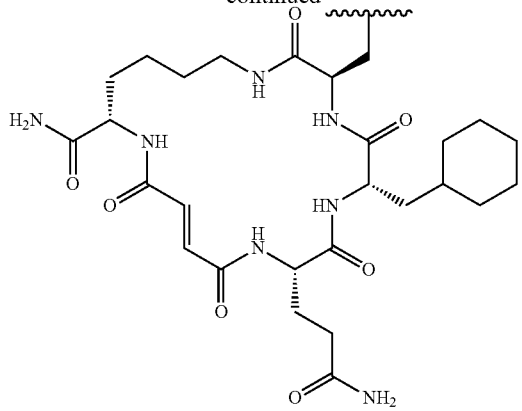

In some embodiments, G is of formula:

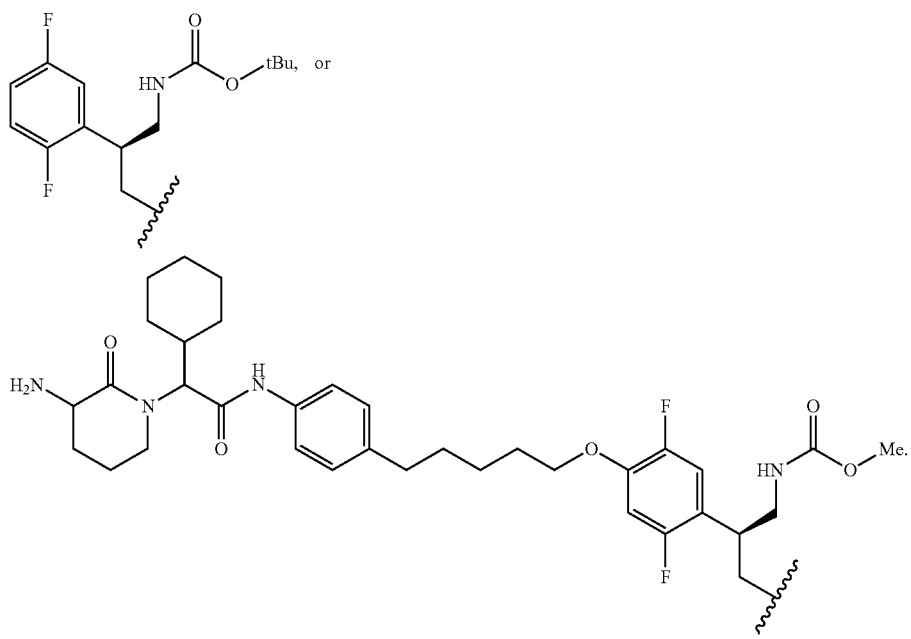

In some embodiments, G is of formula:

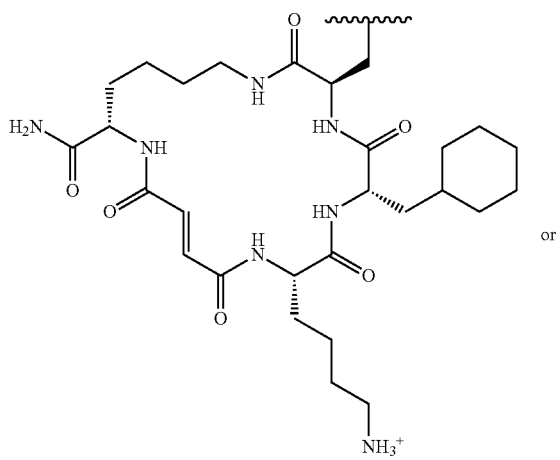

or

Ring $A^4$ and $R^{43}$

As generally defined herein, Ring $A^4$ is a 6-membered arylene or 5-7 membered heteroarylene. In certain embodiments, Ring $A^4$ and Ring $B^4$ are both phenyl rings, such that Ring $A^4$ and $B^4$ together form a biphenyl group. In certain embodiments, Ring $A^4$ is a phenylene ring. In certain embodiments, Ring $A^4$ is a 5-membered heteroarylene ring. In some embodiments, Ring $A^4$ is a pyrrole, imidazole, pyrazole, or triazole ring. In some embodiments, Ring $A^4$ is a furan, thiophene, oxazole, isoxazole, thiazole, or isothiazole ring. In certain embodiments, Ring $A^4$ is a 6-membered heteroarylene ring. In some embodiments, Ring $A^4$ is a pyridine ring. In some embodiments, Ring $A^4$ is a pyrimidine, pyrazine, or pyridazine ring. In certain embodiments, Ring A is a 6-membered heteroarylene ring, and Ring $B^4$ is a 6-membered heteroaryl ring. In certain embodiments, Ring A is a phenylene ring and Ring $B^4$ is a 6-membered heteroaryl ring. In some embodiments, Ring $A^4$ is a 7-membered heteroarylene ring.

Ring $A^4$ may be substituted with 0, 1, 2, 3, or 4 independent $R^{44}$, valency permitting. In certain embodiments, m4 is 0 or 1. In certain embodiments, m4 is 0. In certain embodiments, m4 is 1. In certain embodiments, m4 is 2. In certain embodiments, m4 is 3. In certain embodiments, m4 is 4.

In certain embodiments, Ring $A^4$ is of formula:

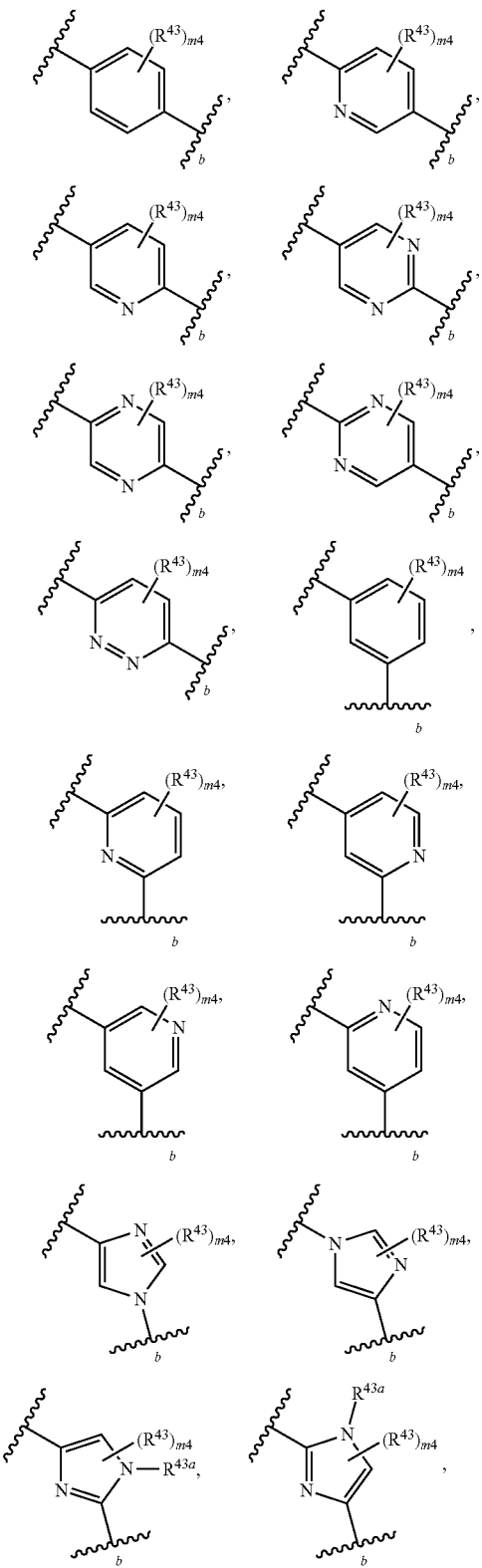

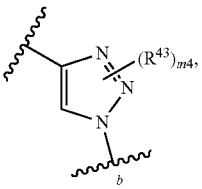

wherein the position labeled b is attached to Ring $B^4$, and m4 is 0, 1, 2, 3, or 4, valency permitting.

In certain embodiments, Ring $A^4$ is of formula:

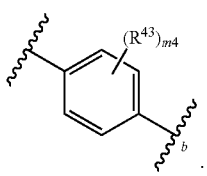

In certain embodiments, Ring $A^4$ is of formula:

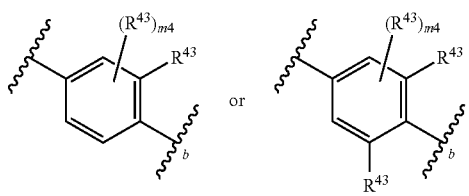

In certain embodiments, Ring $A^4$ is of formula:

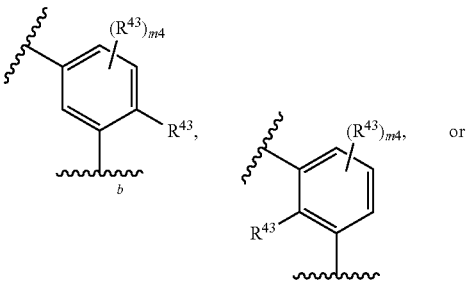

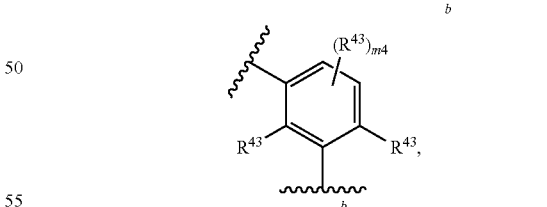

In certain embodiments, Ring $A^4$ is of formula:

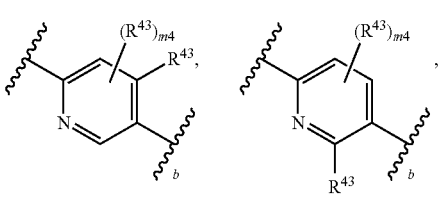

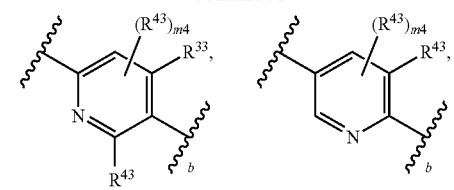
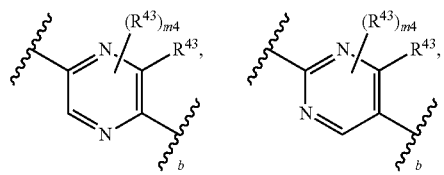
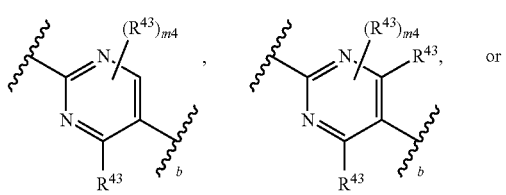
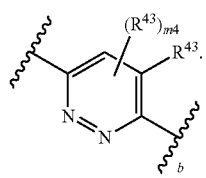
In certain embodiments, Ring A⁴ is of formula:
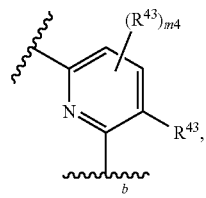 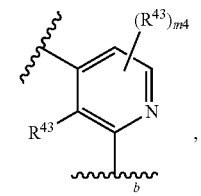
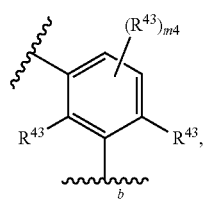 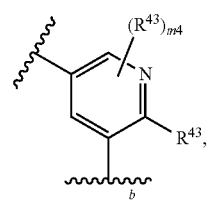
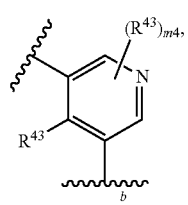
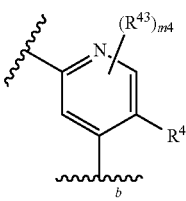
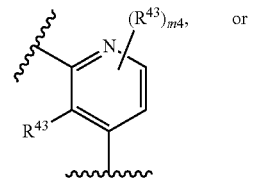 or
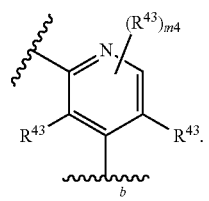
In certain embodiments, Ring A⁴ is of formula:
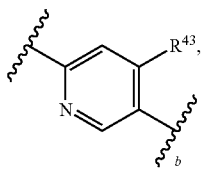 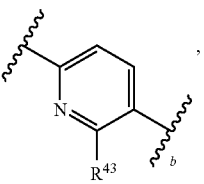
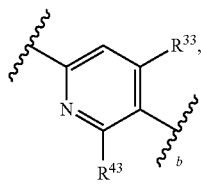 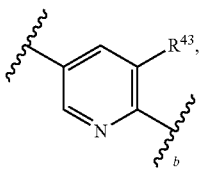
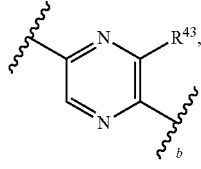 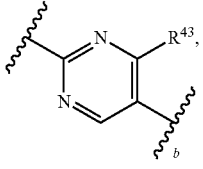
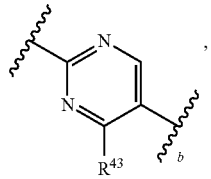 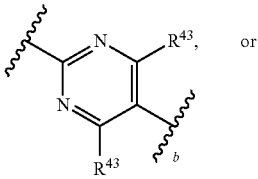 or
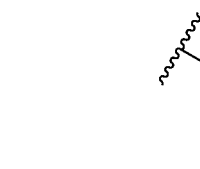

In certain embodiments, Ring A⁴ is of formula:
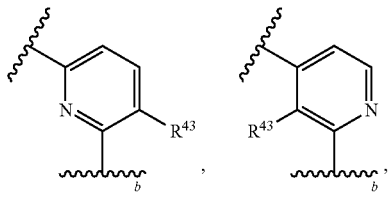
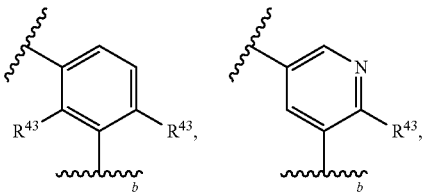
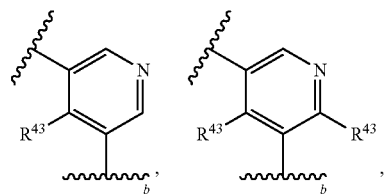
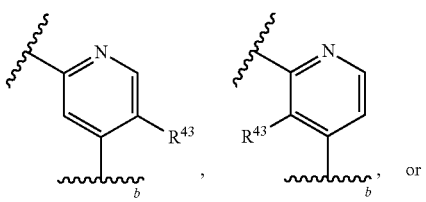
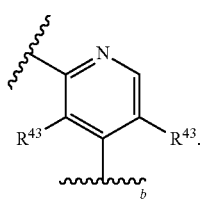
In certain embodiments, Ring A⁴ is of formula:
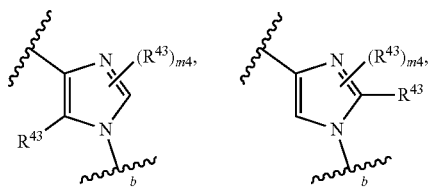
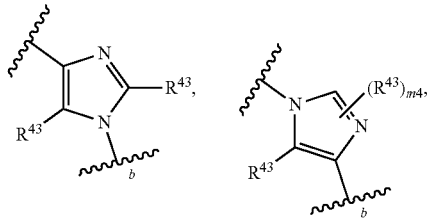
-continued
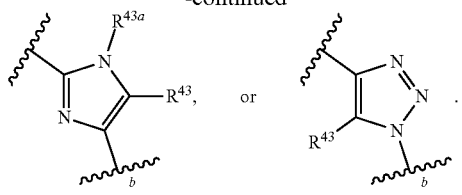
In certain embodiments, Ring A⁴ is of formula:
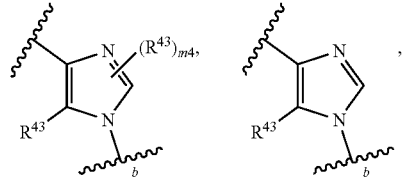
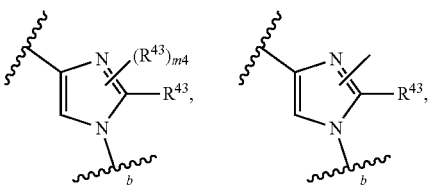
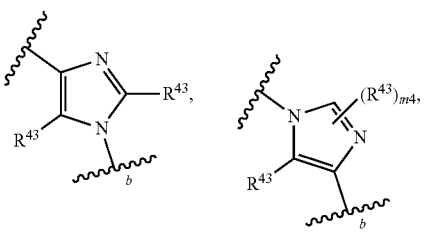
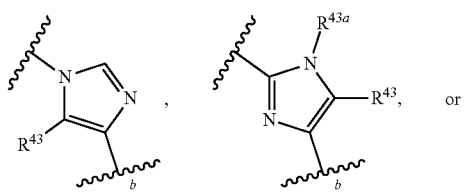
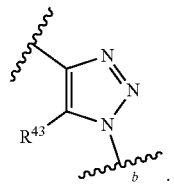
In certain embodiments, Ring A⁴ is of formula:
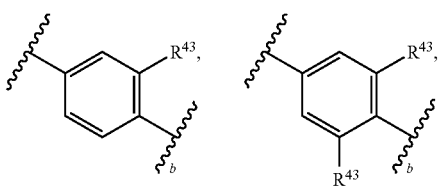

-continued
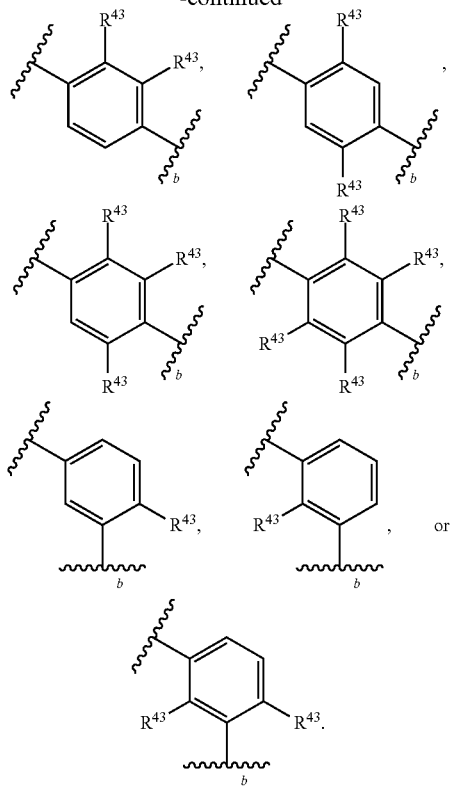
In certain embodiments, Ring $A^4$ is of formula:
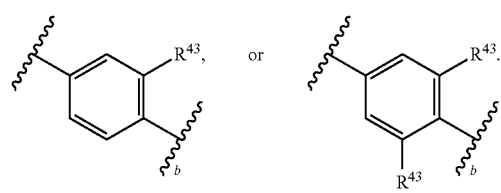
In certain embodiments, Ring $A^4$ is of formula:
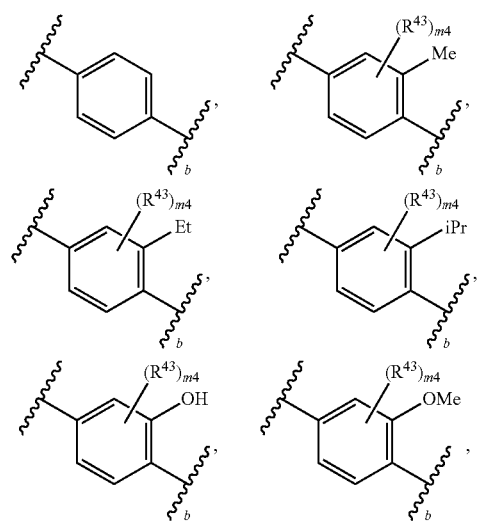
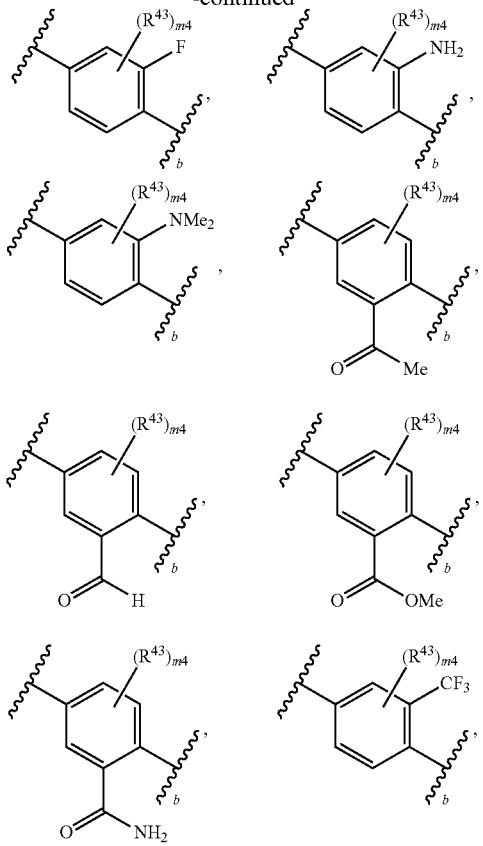
In certain embodiments, Ring $A^4$ is of formula:
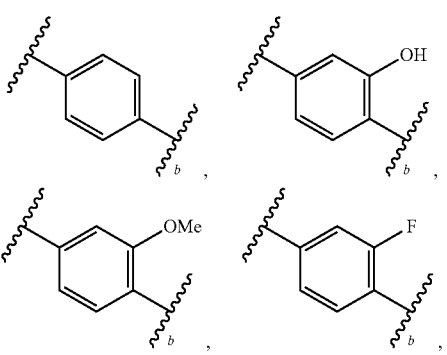

-continued

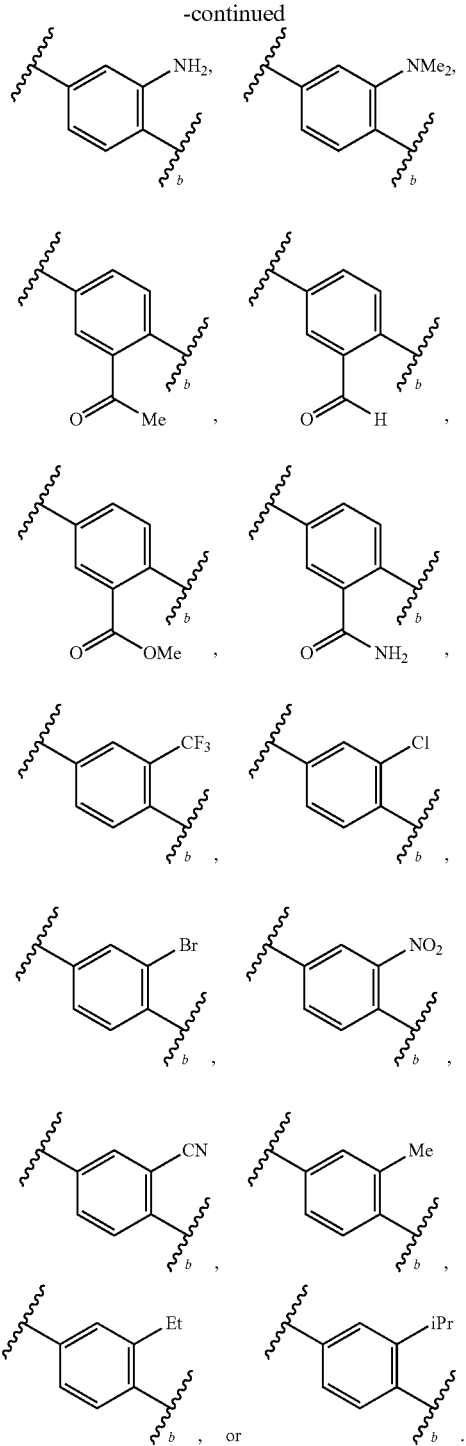

In certain embodiments, Ring $A^4$ is of formula:

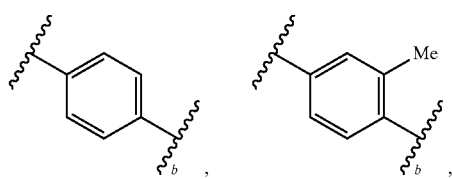

-continued

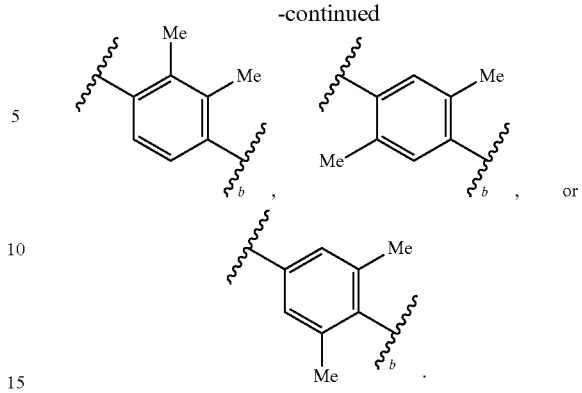

As generally defined herein, each $R^{43}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{43a}$, or —N(R$^{43a}$)$_2$, wherein each R$^{43a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R$^{43a}$ are joined to form an optionally substituted heteroaryl or optionally substituted heterocyclic ring.

In certain embodiments, at least one $R^{43}$ is —NO$_2$. In certain embodiments, at least one $R^{43}$ is —CN. In certain embodiments, at least one $R^{43}$ is halogen. In some embodiments, at least one $R^{43}$ is —F. In some embodiments, at least one $R^{43}$ is —Cl, —Br, or —I. In certain embodiments, at least one $R^{43}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{43}$ is methyl. In certain embodiments, at least one $R^{43}$ is ethyl, propyl, or butyl. In certain embodiments, at least one $R^{43}$ is optionally substituted alkenyl, e.g., optionally substituted $C_{2-6}$ alkenyl. In certain embodiments, at least one $R^{43}$ is vinyl, allyl, or prenyl. In certain embodiments, at least one $R^{43}$ is optionally substituted alkynyl, e.g., $C_{2-6}$ alkynyl.

In certain embodiments, at least one $R^{43}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{43}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{43}$ is optionally substituted aryl, e.g., optionally substituted phenyl. In certain embodiments, at least one $R^{43}$ is optionally substituted heteroaryl, e.g., optionally substituted 5-6 membered heteroaryl or optionally substituted 9-10 membered bicyclic heteroaryl. In certain embodiments, at least one $R^{43}$ is optionally substituted aralkyl, e.g., optionally substituted benzyl. In certain embodiments, at least one $R^{43}$ is optionally substituted heteroaralkyl, e.g., methyl substituted with a 5-6 membered heteroaryl ring.

In certain embodiments, at least one $R^{43}$ is optionally substituted acyl, e.g., —CHO, —CO$_2$H, or —C(=O)NH$_2$. In certain embodiments, at least one $R^{43}$ is —C(=O)R$^{43a}$, —C(=O)OR$^{43a}$, —C(=O)NH(R$^{43a}$), or —C(=O)N(R$^{43a}$)$_2$. In certain embodiments, at least one $R^{43}$ is —C(=O)R$^{43a}$, and R$^{43a}$ is optionally substituted alkyl, e.g., $R^{43}$ is —C(=O)Me. In certain embodiments, at least one $R^{43}$ is —C(=O)R$^{43a}$, and R$^{43a}$ is optionally substituted alkenyl. In certain embodiments, at least one $R^{43}$ is —C(=O)R$^{43a}$, and R$^{43a}$ is optionally substituted carbocyclyl, heterocyclyl, aryl, or heteroaryl. In certain embodiments, at least one $R^{43}$ is —C(=O)OR$^{43a}$, and R$^{43a}$ is optionally substituted alkyl. In certain embodiments, at least one $R^{43}$ is —C(=O)OR$^{43a}$, and R$^{43a}$ is optionally substituted alkenyl. In certain embodiments, at least one $R^{43}$ is —C(=O)OR$^{43a}$, and R$^{43a}$ is optionally substituted carbocyclyl, heterocyclyl, aryl, or heteroaryl. In certain embodiments, at least one $R^{43}$ is —C(=O)N(R$^{43a}$)$_2$, and at least one R$^{43a}$ is optionally substituted alkyl. In certain embodiments, at least one $R^{43}$ is —C(=O)NHR$^{43a}$, and R$^{43a}$ is optionally substituted alkyl. In certain embodiments, at least one $R^{43}$ is —C(=O)NHR$^{43a}$, and R$^{43a}$ is optionally substituted alkenyl. In certain embodiments, at least one $R^{43}$ is —C(=O)NHR$^{43a}$, and R$^{43a}$ is optionally substituted carbocyclyl, heterocyclyl, aryl, or heteroaryl.

In certain embodiments, at least one $R^{43}$ is —OR$^{43a}$, e.g., —OH. In certain embodiments, at least one $R^{43}$ is —OR$^{43a}$, and R$^{43a}$ is optionally substituted alkyl. In certain embodiments, at least one $R^{43}$ is —OR$^{43a}$, and R$^{43a}$ is optionally alkenyl. In certain embodiments, at least one $R^{43}$ is —OR$^{43a}$, and R$^{43a}$ is optionally substituted carbocyclyl, optionally substituted heterocyclyl, optionally substituted aryl or optionally substituted heteroaryl. In certain embodiments, at least one $R^{43}$ is —OR$^{43a}$, and R$^{43a}$ is optionally substituted acyl, e.g., $R^{43}$ is —OC(=O)R$^{43a}$, —OC(=O)OR$^{43a}$, or —OC(=O)N(R$^{43a}$)$_2$. In certain embodiments, at least one $R^{43}$ is —OR$^{43a}$, and R$^{43a}$ is an oxygen protecting group.

In certain embodiments, at least one $R^{43}$ is —N(R$^{43a}$)$_2$, e.g., —NH$_2$, —NHR$^{43a}$. In certain embodiments, at least one $R^{43}$ is —NH(R$^{43a}$), and R$^{43a}$ is optionally substituted alkyl. In certain embodiments, at least one $R^{43}$ is —N(R$^{43a}$)$_2$, and at least one R$^{43a}$ is optionally substituted alkyl. In certain embodiments, at least one $R^{43}$ is —NHR$^{43a}$, and R$^{43a}$ is optionally substituted carbocyclyl, optionally substituted heterocyclyl, optionally substituted aryl, or optionally substituted heteroaryl. In certain embodiments, at least one $R^{43}$ is —NHR$^{43a}$, and R$^{43a}$ is optionally substituted acyl, e.g., $R^{43}$ is —NHC(=O)R$^{43a}$, —NHC(=O)OR$^{43a}$, or —NHC(=O)NHR$^{43}$a. In certain embodiments, at least one $R^{43}$ is —N(R$^{43a}$)$_2$, and at least one R$^{43a}$ is a nitrogen protecting group. In certain embodiments, at least one $R^{43}$ is —N(R$^{43a}$)$_2$, and R$^{43a}$ are joined to form an optionally substituted heterocyclic or optionally substituted heteroaryl ring.

In certain embodiments, an $R^{43}$ ortho to the bond between Ring A$^4$ and Ring B$^4$ is —NO$_2$. In certain embodiments, an $R^{43}$ ortho to the bond between Ring A$^4$ and Ring B$^4$ is —CN. In certain embodiments, an $R^{43}$ ortho to the bond between Ring A$^4$ and Ring B$^4$ is halogen. In some embodiments, an $R^{43}$ ortho to the bond between Ring A$^4$ and Ring B$^4$ is —F. In some embodiments, an $R^{43}$ ortho to the bond between Ring A$^4$ and Ring B$^4$ is —Cl, —Br, or —I. In certain embodiments, an $R^{43}$ ortho to the bond between Ring A$^4$ and Ring B$^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^{43}$ ortho to the bond between Ring A$^4$ and Ring B$^4$ is methyl. In certain embodiments, an $R^{43}$ ortho to the bond between Ring A$^4$ and Ring B$^4$ is ethyl, propyl, or butyl. In certain embodiments, an $R^{43}$ ortho to the bond between Ring A$^4$ and Ring B$^4$ is optionally substituted alkenyl, e.g., optionally substituted $C_{2-6}$ alkenyl. In certain embodiments, an $R^{43}$ ortho to the bond between Ring A$^4$ and Ring B$^4$ is vinyl, allyl, or prenyl. In certain embodiments, an $R^{43}$ ortho to the bond between Ring A$^4$ and Ring B$^4$ is optionally substituted alkynyl, e.g., $C_{2-6}$ alkynyl.

In certain embodiments, an $R^{43}$ ortho to the bond between Ring A$^4$ and Ring B$^4$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^{43}$ ortho to the bond between Ring A$^4$ and Ring B$^4$ is optionally substituted heterocyclyl, e.g., optionally substituted 3-6 membered heterocyclyl, optionally substituted 3-$^4$ membered heterocyclyl, optionally substituted $^4$-5 membered heterocyclyl, or optionally substituted 5-6 membered heterocyclyl.

In certain embodiments, an $R^{43}$ ortho to the bond between Ring A$^4$ and Ring B$^4$ is optionally substituted aryl, e.g., optionally substituted phenyl. In certain embodiments, an $R^{43}$ ortho to the bond between Ring A$^4$ and Ring B$^4$ is optionally substituted heteroaryl, e.g., optionally substituted 5-6 membered heteroaryl or optionally substituted 9-10 membered bicyclic heteroaryl. In certain embodiments, an $R^{43}$ ortho to the bond between Ring A$^4$ and Ring B$^4$ is optionally substituted aralkyl, e.g., optionally substituted benzyl. In certain embodiments, an $R^{43}$ ortho to the bond between Ring A$^4$ and Ring B$^4$ is optionally substituted heteroaralkyl, e.g., methyl substituted with a 5-6 membered heteroaryl ring.

In certain embodiments, an $R^{43}$ ortho to the bond between Ring A$^4$ and Ring B$^4$ is optionally substituted acyl, e.g., —CHO, —CO$_2$H, or —C(=O)NH$_2$. In certain embodiments, an $R^{43}$ ortho to the bond between Ring A$^4$ and Ring B$^4$ is —C(=O)R$^{43a}$, —C(=O)OR$^{43a}$, —C(=O)NH(R$^{43a}$), or —C(=O)N(R$^{43a}$)$_2$. In certain embodiments, an $R^{43}$ ortho to the bond between Ring A$^4$ and Ring B$^4$ is —C(=O)R$^{43a}$, and R$^{43a}$ is optionally substituted alkyl, e.g., $R^{43}$ is —C(=O)Me. In certain embodiments, an $R^{43}$ ortho to the bond between Ring A$^4$ and Ring B$^4$ is —C(=O)R$^{43a}$, and R$^{43a}$ is optionally substituted alkenyl. In certain embodiments, an $R^{43}$ ortho to the bond between Ring A$^4$ and Ring B$^4$ is —C(=O)R$^{43a}$, and R$^{43a}$ is optionally substituted carbocyclyl, heterocyclyl, aryl, or heteroaryl. In certain embodiments, an $R^{43}$ ortho to the bond between Ring A$^4$ and Ring B$^4$ is —C(=O)OR$^{43a}$, and R$^{43a}$ is optionally substituted alkyl. In certain embodiments, an $R^{43}$ ortho to the bond between Ring A$^4$ and Ring B$^4$ is —C(=O)OR$^{43a}$, and R$^{43a}$ is optionally substituted alkenyl. In certain embodiments, an $R^{43}$ ortho to the bond between Ring A$^4$ and Ring B$^4$ is —C(=O)OR$^{43a}$, and R$^{43a}$ is optionally substituted carbocyclyl, heterocyclyl, aryl, or heteroaryl. In certain embodiments, an $R^{43}$ ortho to the bond between Ring A$^4$ and Ring B$^4$ is —C(=O)N(R$^{43a}$)$_2$, and at least one R$^{43a}$ is optionally substituted alkyl. In certain embodiments, an $R^{43}$ ortho to the bond between Ring A$^4$ and Ring B$^4$ is —C(=O)NHR$^{43a}$, and R$^{43a}$ is optionally substituted alkyl. In certain embodiments, an R$^{43}$ ortho to the bond between Ring A$^4$ and Ring B$^4$ is —C(=O)NHR$^{43a}$, and R$^{43a}$ is optionally substituted alkenyl. In certain embodiments, an R$^{43}$ ortho to the bond between Ring A$^4$ and Ring B$^4$ is —C(=O)NHR$^{43a}$, and R$^{43a}$ is optionally substituted carbocyclyl, heterocyclyl, aryl, or heteroaryl.

In certain embodiments, an R$^{43}$ ortho to the bond between Ring A$^4$ and Ring B$^4$ is —OR$^{43a}$, e.g., —OH. In certain embodiments, an R$^{43}$ ortho to the bond between Ring A$^4$ and Ring B$^4$ is —OR$^{43a}$, and R$^{43a}$ is optionally substituted alkyl. In certain embodiments, an R$^{43}$ ortho to the bond between Ring A$^4$ and Ring B$^4$ is —OR$^{43a}$, and R$^{43a}$ is optionally substituted alkenyl. In certain embodiments, an R$^{43}$ ortho to the bond between Ring A$^4$ and Ring B$^4$ is —OR$^{43a}$, and R$^{43a}$ is optionally substituted carbocyclyl, optionally substituted heterocyclyl, optionally substituted aryl or optionally substituted heteroaryl. In certain embodiments, an R$^{43}$ ortho to the bond between Ring A$^4$ and Ring B$^4$ is —OR$^{43a}$, and R$^{43a}$ is optionally substituted acyl, e.g., R$^{43}$ is —OC(=O)R$^{43a}$, —OC(=O)OR$^{43a}$, or —OC(=O)N(R$^{43a}$)$_2$. In certain embodiments, an R$^{43}$ ortho to the bond between Ring A$^4$ and Ring B$^4$ is —OR$^{43a}$, and R$^{43a}$ is an oxygen protecting group.

In certain embodiments, an R$^{43}$ ortho to the bond between Ring A$^4$ and Ring B$^4$ is —N(R$^{43a}$)$_2$, e.g., —NH$_2$, —NHR$^{43a}$. In certain embodiments, an R$^{43}$ ortho to the bond between Ring A$^4$ and Ring B$^4$ is —NH(R$^{43a}$), and R$^{43a}$ is optionally substituted alkyl. In certain embodiments, an R$^{43}$ ortho to the bond between Ring A$^4$ and Ring B$^4$ is —N(R$^{43a}$)$_2$, and at least one R$^{43a}$ is optionally substituted alkyl. In certain embodiments, an R$^{43}$ ortho to the bond between Ring A$^4$ and Ring B$^4$ is —NHR$^{43a}$, and R$^{43a}$ is optionally substituted carbocyclyl, optionally substituted heterocyclyl, optionally substituted aryl, or optionally substituted heteroaryl. In certain embodiments, an R$^{43}$ ortho to the bond between Ring A$^4$ and Ring B$^4$ is —NHR$^{43a}$, and R$^{43a}$ is optionally substituted acyl, e.g., R$^{43}$ is —NHC(=O)R$^{43a}$, —NHC(=O)OR$^{43}$, or —NHC(=O)NHR$^{43a}$. In certain embodiments, an R$^{43}$ ortho to the bond between Ring A$^4$ and Ring B$^4$ is —N(R$^{43a}$)$_2$, and at least one R$^{43a}$ is a nitrogen protecting group. In certain embodiments, an R$^{43}$ ortho to the bond between Ring A$^4$ and Ring B$^4$ is —N(R$^{43a}$)$_2$, and R$^{43a}$ are joined to form an optionally substituted heterocyclic or optionally substituted heteroaryl ring.

Ring B$^4$ and R$^{49}$

As generally defined herein, is Ring B$^4$ is 6-membered aryl or 5-7-membered heteroaryl. In certain embodiments, Ring A$^4$ and Ring B$^4$ are both phenyl rings, such that Ring A$^4$ and B$^4$ together form a biphenyl group. In certain embodiments, Ring B$^4$ is phenyl. In certain embodiments, Ring B$^4$ is a 5-membered heteroaryl ring. In some embodiments, Ring B$^4$ is a pyrrole, imidazole, pyrazole, or triazole ring. In some embodiments, Ring B$^4$ is a furan, thiophene, oxazole, isoxazole, thiazole, or isothiazole ring. In certain embodiments, Ring B$^4$ is a 6-membered heteroaryl ring. In some embodiments, Ring B$^4$ is a pyridine ring. In some embodiments, Ring B$^4$ is a pyrimidine, pyrazine, or pyridazine ring. In certain embodiments, Ring A is a 6-membered heteroarylene ring and Ring B$^4$ is a 6-membered heteroaryl ring. In certain embodiments, Ring A is a phenylene ring and Ring B$^4$ is a 6-membered heteroaryl ring. In some embodiments, Ring B$^4$ is a 7-membered heteroaryl ring.

Ring B$^4$ may be substituted with 0, 1, 2, 3, 4, or 5 independent R$^{49}$, valency permitting. In certain embodiments, k4 is 0 or 1. In certain embodiments, k4 is 0. In certain embodiments, k4 is 1. In certain embodiments, k4 is 2. In certain embodiments, k4 is 3. In certain embodiments, k4 is 4. In certain embodiments, k4 is 5.

In certain embodiments, Ring B$^4$ is of formula:

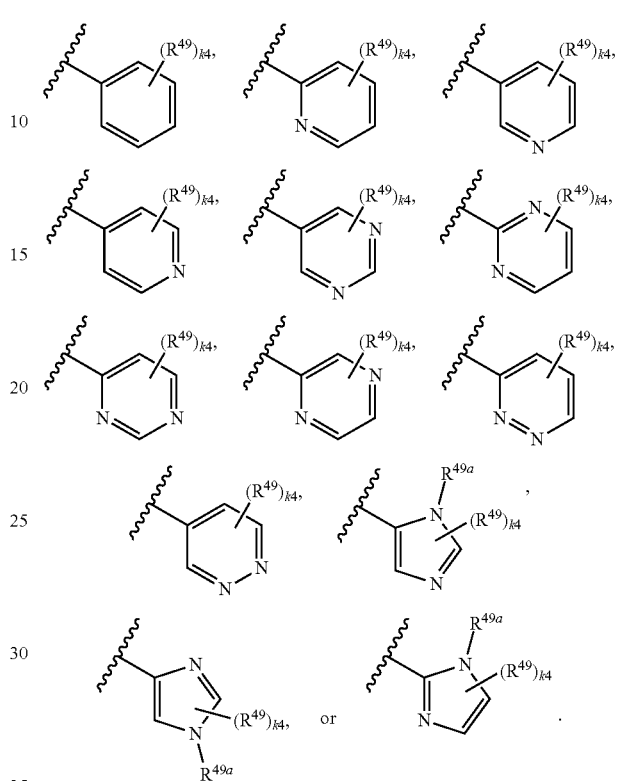

wherein k4 is 0, 1, 2, 3, 4, or 5, valency permitting.

In certain embodiments, Ring B$^4$ is of formula:

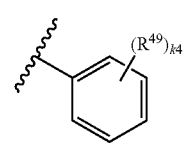

In certain embodiments, Ring B$^4$ is of formula:

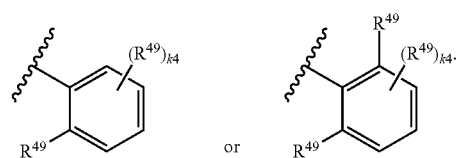

In certain embodiments, Ring B$^4$ is of formula:

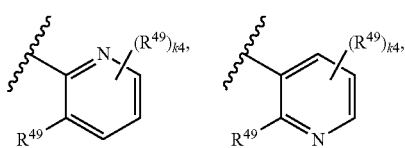

-continued
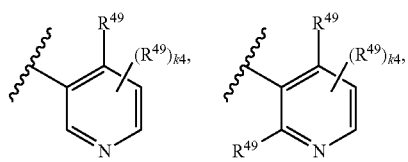
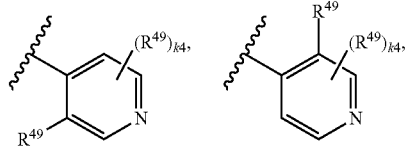
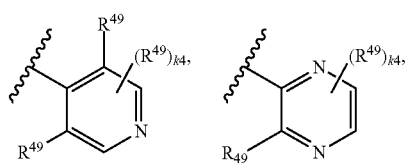
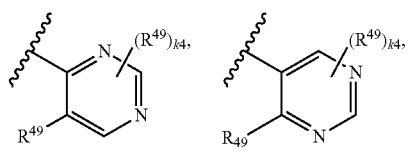
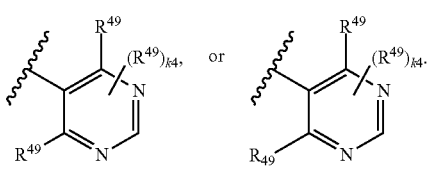
In certain embodiments, Ring B⁴ is of formula:
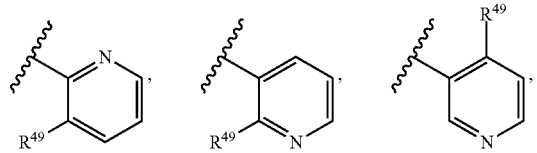
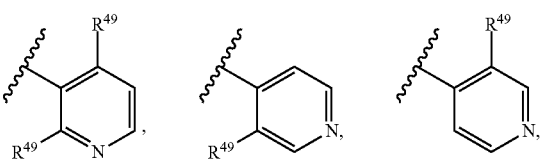
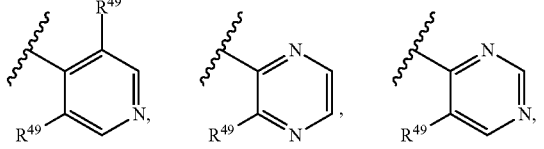
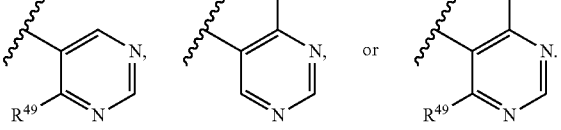
In certain embodiments, Ring B⁴ is of formula:
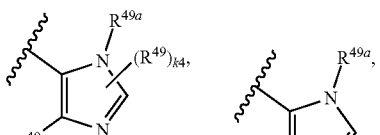
In certain embodiments, Ring B⁴ is of formula:
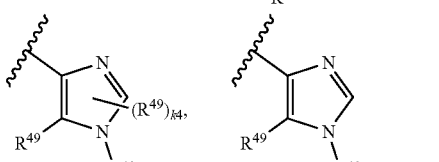
In certain embodiments, Ring B⁴ is of formula:
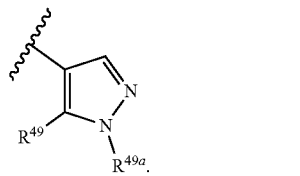
In certain embodiments, Ring B⁴ is of formula:
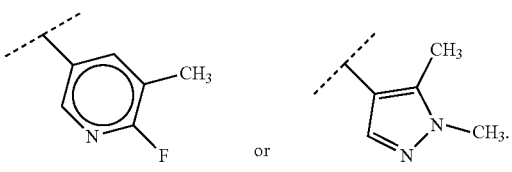
In certain embodiments, Ring B⁴ is of formula:
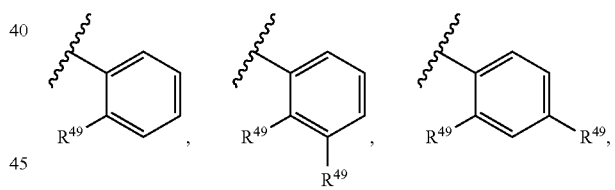
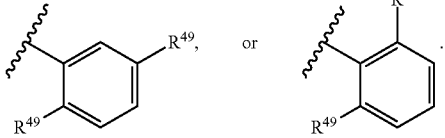
In certain embodiments, Ring B⁴ is of formula:
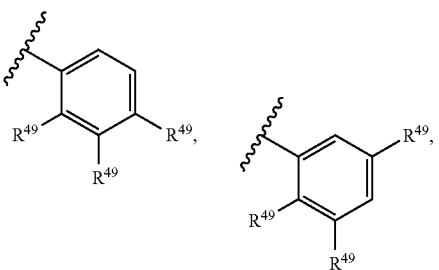

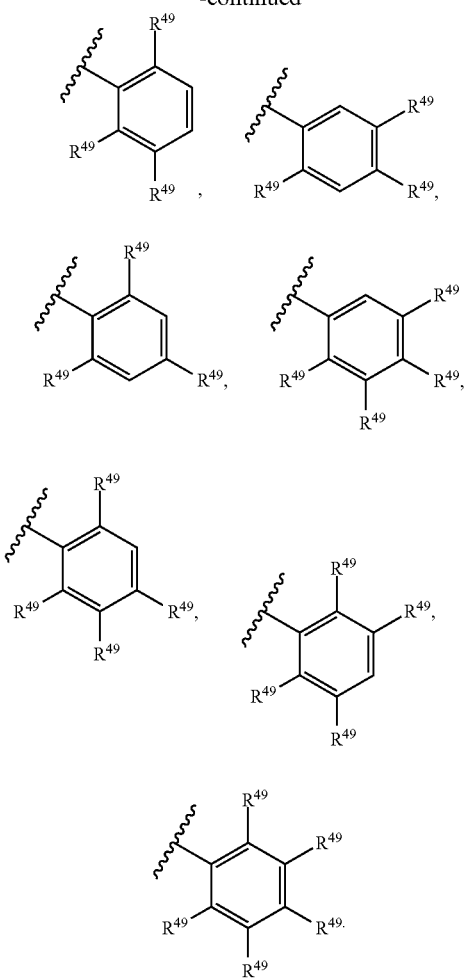
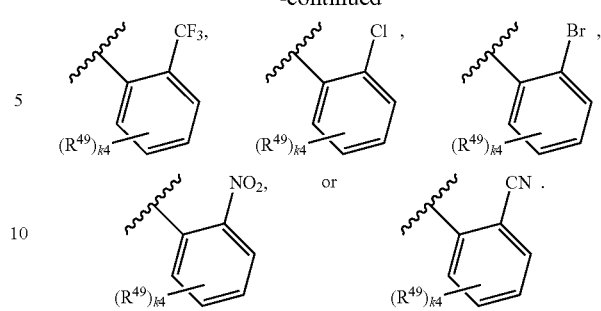
In certain embodiments, Ring $B^4$ is of formula:
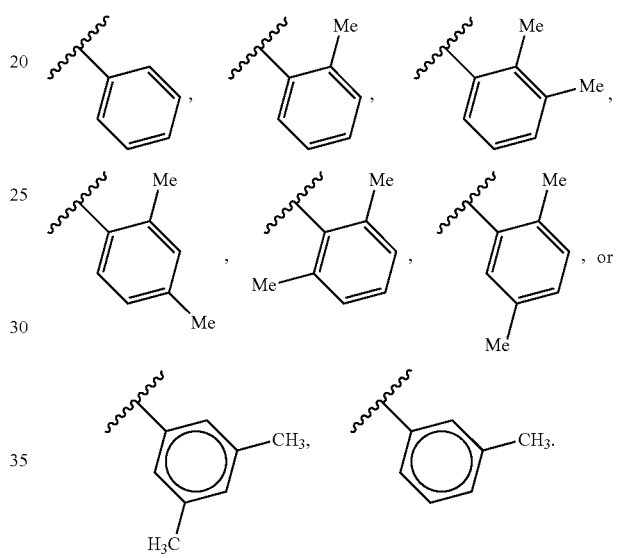
In certain embodiments, Ring $B^4$ is of formula:
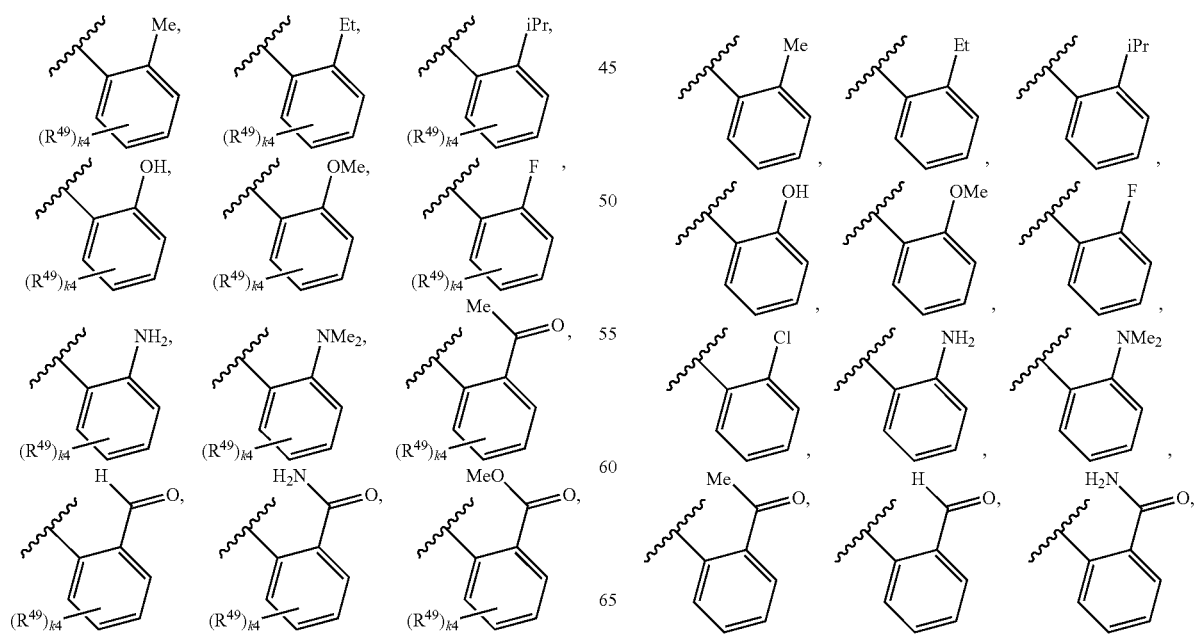
In certain embodiments, Ring $B^4$ is of formula:

-continued

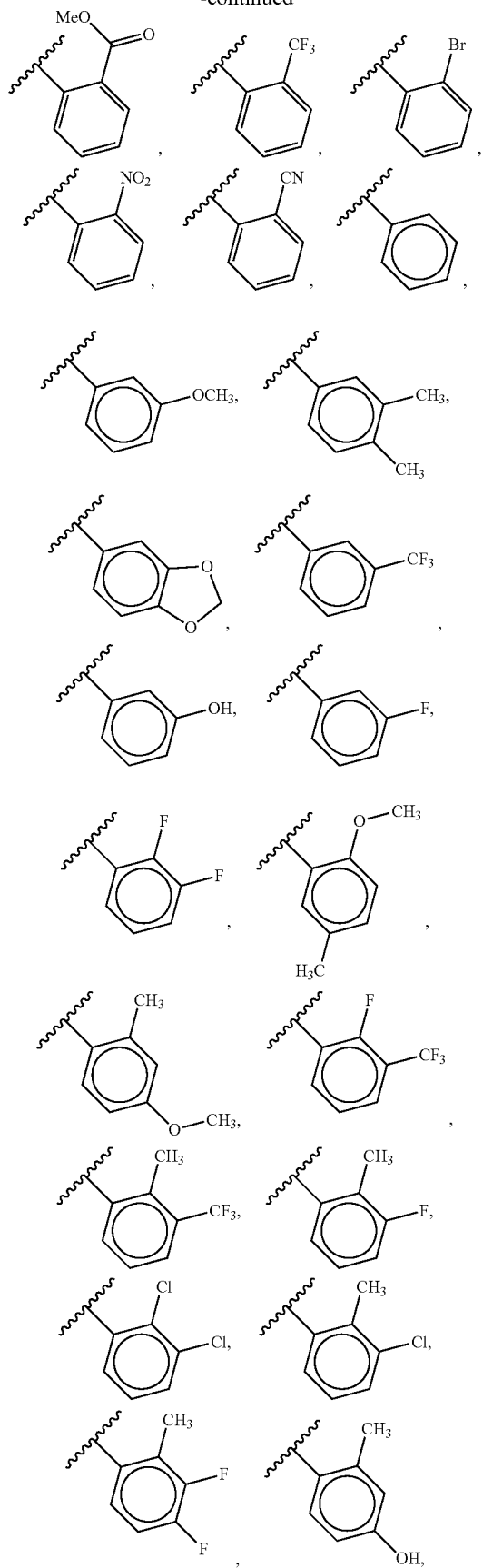

-continued

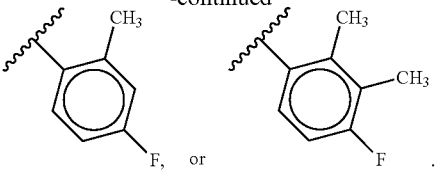

As generally described herein, each $R^{49}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{49a}$, —$N(R^{49a})_2$, —$S(=O)_2R^{49a}$, —$S(=O)_2OR^{49a}$, or —$S(=O)_2N(R^{49a})_2$, wherein each $R^{49a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{49a}$ are joined to form an optionally substituted heteroaryl or optionally substituted heterocyclic ring.

In certain embodiments, at least one $R^{49}$ is —$NO_2$. In certain embodiments, at least one $R^{49}$ is —CN. In certain embodiments, at least one $R^{49}$ is halogen. In some embodiments, at least one $R^{49}$ is —F. In some embodiments, at least one $R^{49}$ is —Cl, —Br, or —I. In certain embodiments, at least one $R^{49}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{49}$ is methyl. In certain embodiments, at least one $R^{49}$ is ethyl, propyl, or butyl. In certain embodiments, at least one $R^{49}$ is optionally substituted alkenyl, e.g., optionally substituted $C_{2-6}$ alkenyl. In certain embodiments, at least one $R^{49}$ is vinyl, allyl, or prenyl. In certain embodiments, at least one $R^{49}$ is optionally substituted alkynyl, e.g., $C_{2-6}$ alkynyl.

In certain embodiments, at least one $R^{49}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{49}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{49}$ is optionally substituted aryl, e.g., optionally substituted phenyl. In certain embodiments, at least one $R^{49}$ is optionally substituted heteroaryl, e.g., optionally substituted 5-6 membered heteroaryl or optionally substituted 9-10 membered bicyclic heteroaryl. In certain embodiments, at least one $R^{49}$ is optionally substituted aralkyl, e.g., optionally substituted benzyl. In certain embodiments, at least one $R^{49}$ is optionally substituted heteroaralkyl, e.g., methyl substituted with a 5-6 membered heteroaryl ring.

In certain embodiments, at least one $R^{49}$ is optionally substituted acyl, e.g., —CHO, —$CO_2H$, or —C(=O)$NH_2$. In certain embodiments, at least one $R^{49}$ is —C(=O)$R^{49a}$, —C(=O)OR$^{49a}$, —C(=O)NH(R$^{49a}$), or —C(=O)N(R$^{49a}$)$_2$. In certain embodiments, at least one R$^{49}$ is —C(=O)R$^{49a}$, and R$^{49a}$ is optionally substituted alkyl, e.g., R$^{49}$ is —C(=O)Me. In certain embodiments, at least one R$^{49}$ is —C(=O)R$^{49a}$, and R$^{49a}$ is optionally substituted alkenyl. In certain embodiments, at least one R$^{49}$ is —C(=O)R$^{49a}$, and R$^{49a}$ is optionally substituted carbocyclyl, heterocyclyl, aryl, or heteroaryl. In certain embodiments, at least one R$^{49}$ is —C(=O)OR$^{49a}$, and R$^{49a}$ is optionally substituted alkyl. In certain embodiments, at least one R$^{49}$ is —C(=O)OR$^{49a}$, and R$^{49a}$ is optionally substituted alkenyl. In certain embodiments, at least one R$^{49}$ is —C(=O)OR$^{49a}$, and R$^{49a}$ is optionally substituted carbocyclyl, heterocyclyl, aryl, or heteroaryl. In certain embodiments, at least one R$^{49}$ is —C(=O)N(R$^{49a}$)$_2$, and at least one R$^{49a}$ is optionally substituted alkyl. In certain embodiments, at least one R$^{49}$ is —C(=O)NHR$^{49a}$, and R$^{49a}$ is optionally substituted alkyl. In certain embodiments, at least one R$^{49}$ is —C(=O)NHR$^{49a}$, and R$^{49a}$ is optionally substituted alkenyl. In certain embodiments, at least one R$^{49}$ is —C(=O)NHR$^{49a}$, and R$^{49a}$ is optionally substituted carbocyclyl, heterocyclyl, aryl, or heteroaryl.

In certain embodiments, at least one R$^{49}$ is —OR$^{49a}$, e.g., —OH. In certain embodiments, at least one R$^{49}$ is —OR$^{49a}$, and R$^{49a}$ is optionally substituted alkyl. In certain embodiments, at least one R$^{49}$ is —OR$^{49a}$, and R$^{49a}$ is optionally alkenyl. In certain embodiments, at least one R$^{49}$ is —OR$^{49a}$, and R$^{49a}$ is optionally substituted carbocyclyl, optionally substituted heterocyclyl, optionally substituted aryl optionally substituted heteroaryl. In certain embodiments, at least one R$^{49}$ is —OR$^{49a}$, and R$^{49a}$ is optionally substituted acyl, e.g., R$^{49}$ is —OC(=O)R$^{49a}$, —OC(=O)OR$^{49a}$, or —OC(=O)N(R$^{49a}$)$_2$. In certain embodiments, at least one R$^{49}$ is —OR$^{49a}$, and R$^{49a}$ is an oxygen protecting group.

In certain embodiments, at least one R$^{49}$ is —N(R$^{49a}$)$_2$, e.g., —NH$_2$, —NHR$^{49a}$. In certain embodiments, at least one R$^{49}$ is —NH(R$^{49a}$), and R$^{49a}$ is optionally substituted alkyl. In certain embodiments, at least one R$^{49}$ is —N(R$^{49a}$)$_2$, and at least one R$^{49a}$ is optionally substituted alkyl. In certain embodiments, at least one R$^{49}$ is —NHR$^{49a}$, and R$^{49a}$ is optionally substituted carbocyclyl, optionally substituted heterocyclyl, optionally substituted aryl, or optionally substituted heteroaryl. In certain embodiments, at least one R$^{49}$ is —NHR$^{49a}$, and R$^{49a}$ is optionally substituted acyl, e.g., R$^{49}$ is —NHC(=O)R$^{49a}$, —NHC(=O)OR$^{49a}$, or —NHC(=O)NHR$^{49a}$. In certain embodiments, at least one R$^{49}$ is —N(R$^{49a}$)$_2$, and at least one R$^{49a}$ is a nitrogen protecting group. In certain embodiments, at least one R$^{49}$ is —N(R$^{49a}$)$_2$, and R$^{49a}$ are joined to form an optionally substituted heterocyclic or optionally substituted heteroaryl ring.

In certain embodiments, at least one R$^{49}$ is —S(=O)$_2$R$^{49a}$. In certain embodiments, at least one R$^{49}$ is —S(=O)$_2$R$^{49a}$, and R$^{49a}$ is optionally substituted alkyl, e.g., R$^{49}$ is —S(=O)$_2$Me. In certain embodiments, at least one R$^{49}$ is —S(=O)$_2$R$^{49a}$ and R$^{49a}$ is optionally substituted alkenyl. In certain embodiments, at least one R$^{49}$ is —S(=O)$_2$R$^{49a}$, and R$^{49a}$ is optionally substituted carbocyclyl, heterocyclyl, aryl, or heteroaryl. In certain embodiments, at least one R$^{49}$ is —S(=O)$_2$OR$^{49a}$. In certain embodiments, at least one R$^{49}$ is —S(=O)$_2$OR$^{49}$, and R$^{49a}$ is optionally substituted alkyl. In certain embodiments, at least one R$^{49}$ is —S(=O)$_2$OR$^{49a}$, and R$^{49a}$ is optionally substituted alkenyl. In certain embodiments, at least one R$^{49}$ is —S(=O)$_2$OR$^{49a}$, and R$^{49a}$ is optionally substituted carbocyclyl, heterocyclyl, aryl, or heteroaryl. In certain embodiments, at least one R$^{49}$ is —S(=O)$_2$N(R$^{49a}$)$_2$ or —S(=O)$_2$NHR$^{49a}$. In certain embodiments, at least one R$^{49}$ is —S(=O)$_2$N(R$^{49a}$)$_2$, and at least one R$^{49a}$ is optionally substituted alkyl. In certain embodiments, at least one R$^{49}$ is —S(=O)$_2$NHR$^{49a}$, and R$^{49a}$ is optionally substituted alkyl. In certain embodiments, at least one R$^{49}$ is —S(=O)$_2$NHR$^{49a}$, and R$^{49a}$ is optionally substituted alkenyl. In certain embodiments, at least one R$^{49}$ is —S(=O)$_2$NHR$^{49a}$, and R$^{49a}$ is optionally substituted carbocyclyl, heterocyclyl, aryl, or heteroaryl.

In certain embodiments, an R$^{49}$ ortho to the bond connecting Ring A$^4$ and Ring B$^4$ is —NO$_2$. In certain embodiments, an R$^{49}$ ortho to the bond connecting Ring A$^4$ and Ring B$^4$ is —CN. In certain embodiments, an R$^{49}$ ortho to the bond connecting Ring A$^4$ and Ring B$^4$ is halogen. In some embodiments, an R$^{49}$ ortho to the bond connecting Ring A$^4$ and Ring B$^4$ is —F. In some embodiments, an R$^{49}$ ortho to the bond connecting Ring A$^4$ and Ring B$^4$ is —Cl, —Br, or —I. In certain embodiments, an R$^{49}$ ortho to the bond connecting Ring A$^4$ and Ring B$^4$ is optionally substituted alkyl, e.g., optionally substituted C$_{1-6}$ alkyl, optionally substituted C$_{1-2}$ alkyl, optionally substituted C$_{2-3}$ alkyl, optionally substituted C$_{3-4}$ alkyl, optionally substituted C$_{4-5}$ alkyl, or optionally substituted C$_{5-6}$ alkyl. In certain embodiments, an R$^{49}$ ortho to the bond connecting Ring A$^4$ and Ring B$^4$ is methyl. In certain embodiments, an R$^{49}$ ortho to the bond connecting Ring A$^4$ and Ring B$^4$ is ethyl, propyl, or butyl. In certain embodiments, an R$^{49}$ ortho to the bond connecting Ring A$^4$ and Ring B$^4$ is optionally substituted alkenyl, e.g., optionally substituted C$_{2-6}$ alkenyl. In certain embodiments, an R$^{49}$ ortho to the bond connecting Ring A$^4$ and Ring B$^4$ is vinyl, allyl, or prenyl. In certain embodiments, an R$^{49}$ ortho to the bond connecting Ring A$^4$ and Ring B$^4$ is optionally substituted alkynyl, e.g., C$_{2-6}$ alkynyl.

In certain embodiments, an R$^{49}$ ortho to the bond connecting Ring A$^4$ and Ring B$^4$ is optionally substituted carbocyclyl, e.g., optionally substituted C$_{3-6}$ carbocyclyl, optionally substituted C$_{3-4}$ carbocyclyl, optionally substituted C$_{4-5}$ carbocyclyl, or optionally substituted C$_{5-6}$ carbocyclyl. In certain embodiments, an R$^{49}$ ortho to the bond connecting Ring A$^4$ and Ring B$^4$ is optionally substituted heterocyclyl, e.g., optionally substituted 3-6 membered heterocyclyl, optionally substituted 3-$^4$ membered heterocyclyl, optionally substituted $^4$-5 membered heterocyclyl, or optionally substituted 5-6 membered heterocyclyl.

In certain embodiments, an R$^{49}$ ortho to the bond connecting Ring A$^4$ and Ring B$^4$ is optionally substituted aryl, e.g., optionally substituted phenyl. In certain embodiments, an R$^{49}$ ortho to the bond connecting Ring A$^4$ and Ring B$^4$ is optionally substituted heteroaryl, e.g., optionally substituted 5-6 membered heteroaryl or optionally substituted 9-10 membered bicyclic heteroaryl. In certain embodiments, an R$^{49}$ ortho to the bond connecting Ring A$^4$ and Ring B$^4$ is optionally substituted aralkyl, e.g., optionally substituted benzyl. In certain embodiments, an R$^{49}$ ortho to the bond connecting Ring A$^4$ and Ring B$^4$ is optionally substituted heteroaralkyl, e.g., methyl substituted with a 5-6 membered heteroaryl ring.

In certain embodiments, an R$^{49}$ ortho to the bond connecting Ring A$^4$ and Ring B$^4$ is optionally substituted acyl, e.g., —CHO, —CO$_2$H, or —C(=O)NH$_2$. In certain embodiments, an R$^{49}$ ortho to the bond connecting Ring A$^4$ and Ring B$^4$ is —C(=O)R$^{49a}$, —C(=O)OR$^{49a}$, —C(=O)NH(R$^{49a}$), or —C(=O)N(R$^{49a}$)$_2$. In certain embodiments, an R$^{49}$ ortho to the bond connecting Ring A$^4$ and Ring B$^4$ is —C(=O)R$^{49a}$, and R$^{49a}$ is optionally substituted alkyl, e.g., R$^{49}$ is —C(=O)Me. In certain embodiments, an R$^{49}$ ortho to the bond connecting Ring A$^4$ and Ring B$^4$ is —C(=O)R$^{49a}$, and R$^{49a}$ is optionally substituted alkenyl. In certain embodiments, an R$^{49}$ ortho to the bond connecting Ring A$^4$ and Ring B$^4$ is —C(=O)R$^{49a}$, and R$^{49a}$ is optionally substituted carbocyclyl, heterocyclyl, aryl, or heteroaryl. In certain embodiments, an $R^{49}$ ortho to the bond connecting Ring $A^4$ and Ring $B^4$ is —C(=O)O$R^{49a}$, and $R^{49a}$ is optionally substituted alkyl. In certain embodiments, an $R^{49}$ ortho to the bond connecting Ring $A^4$ and Ring $B^4$ is —C(=O)O$R^{49a}$, and $R^{49a}$ is optionally substituted alkenyl. In certain embodiments, an $R^{49}$ ortho to the bond connecting Ring $A^4$ and Ring $B^4$ is —C(=O)O$R^{49a}$, and $R^{49a}$ is optionally substituted carbocyclyl, heterocyclyl, aryl, or heteroaryl. In certain embodiments, an $R^{49}$ ortho to the bond connecting Ring $A^4$ and Ring $B^4$ is —C(=O)N($R^{49a}$)$_2$, and at least one $R^{49a}$ is optionally substituted alkyl. In certain embodiments, an $R^{49}$ ortho to the bond connecting Ring $A^4$ and Ring $B^4$ is —C(=O)NH$R^{49a}$, and $R^{49a}$ is optionally substituted alkyl. In certain embodiments, an $R^{49}$ ortho to the bond connecting Ring $A^4$ and Ring $B^4$ is —C(=O)NH$R^{49a}$, and $R^{49a}$ is optionally substituted alkenyl. In certain embodiments, an $R^{49}$ ortho to the bond connecting Ring $A^4$ and Ring $B^4$ is —C(=O)NH$R^{49a}$, and $R^{49a}$ is optionally substituted carbocyclyl, heterocyclyl, aryl, or heteroaryl.

In certain embodiments, an $R^{49}$ ortho to the bond connecting Ring $A^4$ and Ring $B^4$ is —O$R^{49a}$, e.g., —OH. In certain embodiments, an $R^{49}$ ortho to the bond connecting Ring $A^4$ and Ring $B^4$ is —O$R^{49a}$, and $R^{49a}$ is optionally substituted alkyl. In certain embodiments, an $R^{49}$ ortho to the bond connecting Ring $A^4$ and Ring $B^4$ is —O$R^{49a}$, and $R^{49a}$ is optionally alkenyl. In certain embodiments, an $R^{49}$ ortho to the bond connecting Ring $A^4$ and Ring $B^4$ is —O$R^{49a}$, and $R^{49a}$ is optionally substituted carbocyclyl, optionally substituted heterocyclyl, optionally substituted aryl optionally substituted heteroaryl. In certain embodiments, an $R^{49}$ ortho to the bond connecting Ring $A^4$ and Ring $B^4$ is —O$R^{49a}$, and $R^{49a}$ is optionally substituted acyl, e.g., $R^{49}$ is —OC(=O)$R^{49a}$, —OC(=O)O$R^{49a}$, or —OC(=O)N($R^{49a}$)$_2$. In certain embodiments, an $R^{49}$ ortho to the bond connecting Ring $A^4$ and Ring $B^4$ is —O$R^{49a}$, and $R^{49a}$ is an oxygen protecting group.

In certain embodiments, an $R^{49}$ ortho to the bond connecting Ring $A^4$ and Ring $B^4$ is —N($R^{49a}$)$_2$, e.g., —NH$_2$, —NHR$^{49a}$. In certain embodiments, an $R^{49}$ ortho to the bond connecting Ring $A^4$ and Ring $B^4$ is —NH($R^{49a}$), and $R^{49a}$ is optionally substituted alkyl. In certain embodiments, an $R^{49}$ ortho to the bond connecting Ring $A^4$ and Ring $B^4$ is —N($R^{49a}$)$_2$, and at least one $R^{49a}$ is optionally substituted alkyl. In certain embodiments, an $R^{49}$ ortho to the bond connecting Ring $A^4$ and Ring $B^4$ is —NHR$^{49a}$, and $R^{49a}$ is optionally substituted carbocyclyl, optionally substituted heterocyclyl, optionally substituted aryl, or optionally substituted heteroaryl. In certain embodiments, an $R^{49}$ ortho to the bond connecting Ring $A^4$ and Ring $B^4$ is —NHR$^{49a}$, and $R^{49a}$ is optionally substituted acyl, e.g., $R^{49}$ is —NHC(=O)$R^{49a}$, —NHC(=O)O$R^{49a}$, or —NHC(=O)NH$R^{49a}$. In certain embodiments, an $R^{49}$ ortho to the bond connecting Ring $A^4$ and Ring $B^4$ is —N($R^{49a}$)$_2$, and at least one $R^{49a}$ is a nitrogen protecting group. In certain embodiments, an $R^{49}$ ortho to the bond connecting Ring $A^4$ and Ring $B^4$ is —N($R^{49a}$)$_2$, and $R^{49a}$ are joined to form an optionally substituted heterocyclic or optionally substituted heteroaryl ring.

In certain embodiments, an $R^{49}$ ortho to the bond connecting Ring $A^4$ and Ring $B^4$ is —S(=O)$_2$$R^{49}$. In certain embodiments, an $R^{49}$ ortho to the bond connecting Ring $A^4$ and Ring $B^4$ is —S(=O)$_2$$R^{49a}$, and $R^{49a}$ is optionally substituted alkyl, e.g., $R^{49}$ is —S(=O)$_2$Me. In certain embodiments, an $R^{49}$ ortho to the bond connecting Ring $A^4$ and Ring $B^4$ is —S(=O)$_2$$R^{49a}$, and $R^{49a}$ is optionally substituted alkenyl. In certain embodiments, an $R^{49}$ ortho to the bond connecting Ring $A^4$ and Ring $B^4$ is —S(=O)$_2$$R^{49a}$, and $R^{49a}$ is optionally substituted carbocyclyl, heterocyclyl, aryl, or heteroaryl. In certain embodiments, an $R^{49}$ ortho to the bond connecting Ring $A^4$ and Ring $B^4$ is —S(=O)$_2$O$R^{49a}$. In certain embodiments, an $R^{49}$ ortho to the bond connecting Ring $A^4$ and Ring $B^4$ is —S(=O)$_2$O$R^{49a}$, and $R^{49a}$ is optionally substituted alkyl. In certain embodiments, an $R^{49}$ ortho to the bond connecting Ring $A^4$ and Ring $B^4$ is —S(=O)$_2$O$R^{49a}$, and $R^{49a}$ is optionally substituted alkenyl. In certain embodiments, an $R^{49}$ ortho to the bond connecting Ring $A^4$ and Ring $B^4$ is —S(=O)$_2$O$R^{49a}$, and $R^{49a}$ is optionally substituted carbocyclyl, heterocyclyl, aryl, or heteroaryl. In certain embodiments, an $R^{49}$ ortho to the bond connecting Ring $A^4$ and Ring $B^4$ is —S(=O)$_2$N($R^{49a}$)$_2$ or —S(=O)$_2$NH$R^{49a}$. In certain embodiments, an $R^{49}$ ortho to the bond connecting Ring $A^4$ and Ring $B^4$ is —S(=O)$_2$N($R^{49a}$)$_2$, and at least one $R^{49a}$ is optionally substituted alkyl. In certain embodiments, an $R^{49}$ ortho to the bond connecting Ring $A^4$ and Ring $B^4$ is —S(=O)$_2$NH$R^{49a}$ and $R^{49a}$ is optionally substituted alkyl. In certain embodiments, an $R^{49}$ ortho to the bond connecting Ring $A^4$ and Ring $B^4$ is —S(=O)$_2$NH$R^{49a}$, and $R^{49a}$ is optionally substituted alkenyl. In certain embodiments, an $R^{49}$ ortho to the bond connecting Ring $A^4$ and Ring $B^4$ is —S(=O)$_2$NH$R^{49a}$, and $R^{49a}$ is optionally substituted carbocyclyl, heterocyclyl, aryl, or heteroaryl.

In certain embodiments, Ring $B^4$ is of formula:

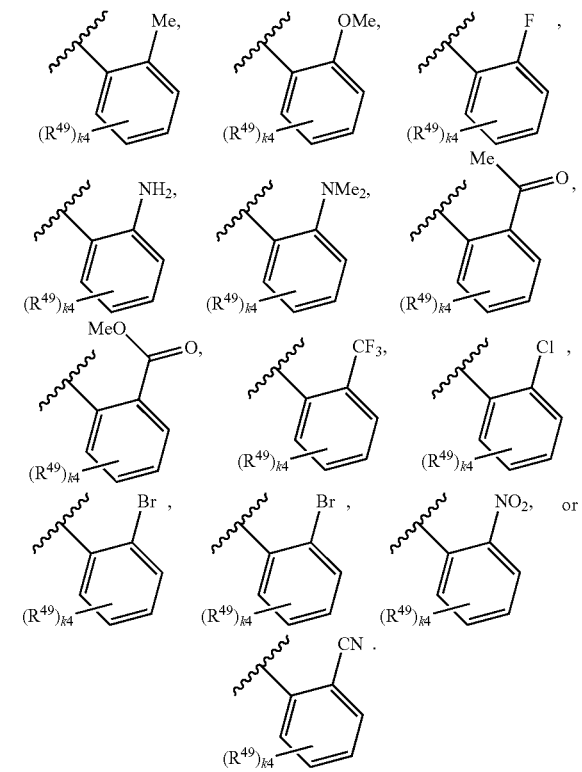

In certain embodiments, Ring $B^4$ is of formula:

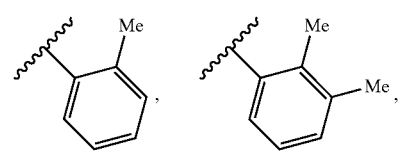

-continued
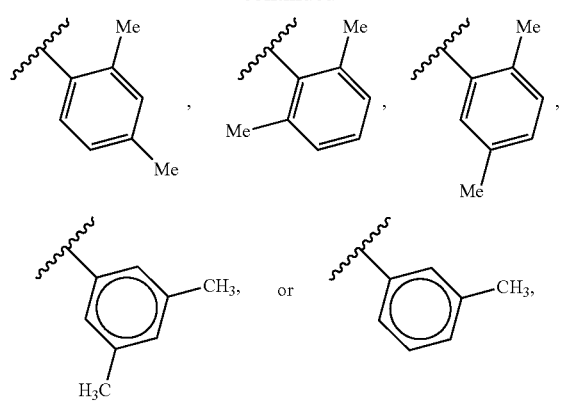
In certain embodiments, Ring B⁴ is of formula:
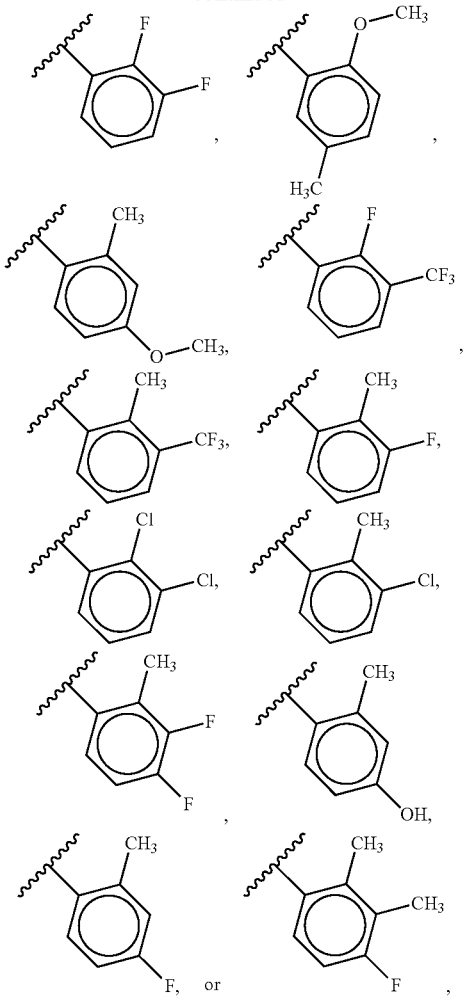
Compounds of Formula (I)
In certain embodiments, the invention provides a compound of Formula (I):
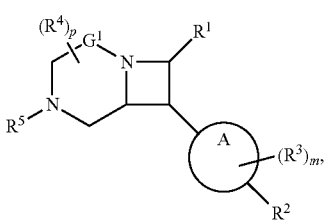
(I)
or a pharmaceutically acceptable salt, solvate, hydrate, polymorph, co-crystal, tautomer, stereoisomer, prodrug, or isotopically labeled derivative thereof, wherein:
G¹ is of formula:
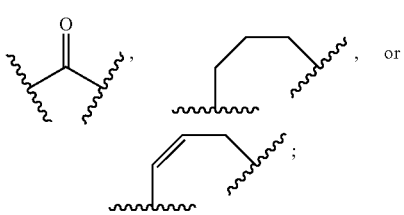

Ring A is carbocyclylene, heterocyclylene, arylene, or heteroarylene;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH$_2$-halo, —CH$_2$OR$^{1a}$, —CH$_2$SR$^{1a}$, or —CH$_2$N(R$^{1a}$)$_2$, wherein each $R^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, a sulfur protecting group when attached to a sulfur atom, or a nitrogen protecting group when attached to a nitrogen atom, or two $R^{1a}$ are joined to form an optionally substituted heteroaryl or optionally substituted heterocyclic ring;

$R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —OR$^{2a}$, —N(R$^{2a}$)$_2$, —S(=O)$_2$R$^{2a}$, —S(=O)$_2$OR$^{2a}$, or —S(=O)$_2$N(R$^{2a}$)$_2$, wherein each $R^{2a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, an oxygen protecting group when attached to an oxygen atom, or a nitrogen protecting group when attached to a nitrogen atom, or two $R^{2a}$ are joined to form an optionally substituted heteroaryl or optionally substituted heterocyclic ring;

each $R^3$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{3a}$, —N(R$^{3a}$)$_2$, or two $R^3$ are joined to form an optionally substituted carbocyclic, heterocyclic, aryl, or heteroaryl ring, wherein each $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{3a}$ are joined to form an optionally substituted heteroaryl or optionally substituted heterocyclic ring;

each $R^4$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —OR$^{4a}$, or —N(R$^{4a}$)$_2$, wherein each $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{4a}$ are joined to form an optionally substituted heteroaryl or optionally substituted heterocyclic ring;

$R^5$ is hydrogen, optionally substituted alkyl, optionally substituted alkenyl, optionally substituted alkynyl, optionally substituted aralkyl, optionally substituted heteroaralkyl, optionally substituted acyl, —C(=O)R$^{5a}$, —C(=O)OR$^{5a}$, —C(=O)N(R$^{5a}$)$_2$, —S(=O)$_2$R$^{5a}$, —S(=O)$_2$OR$^{5a}$, —S(=O)$_2$N(R$^{5a}$)$_2$, or a nitrogen protecting group, wherein each $R^{5a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{5a}$ are joined to form an optionally substituted heteroaryl or optionally substituted heterocyclic ring;

m is 0, 1, 2, 3, or 4; and p is 0, 1, 2, 3, or 4.

In certain embodiments, the compound of Formula (I) selectively inhibits the activity of IDE for degradation of a first substrate over the activity of IDE for degradation of a second substrate. In certain embodiments, the compound of Formula (I) selectively inhibits the activity of IDE for degradation of insulin over the activity of IDE for the degradation of a second substrate (e.g., glucagon, amylin). In certain embodiments, the compound of Formula (I) selectively inhibits the activity of IDE for degradation of insulin over the activity of IDE for degradation of glucagon. In certain embodiments, the compound of Formula (I) selectively inhibits the activity of IDE for degradation of insulin over the activity of IDE for degradation of more than one other substrate.

Unless otherwise stated, any formulae described herein are also meant to include salts, solvates, hydrates, polymorphs, co-crystals, tautomers, stereoisomers, prodrugs, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is an isotopically labeled form of any of the formulae described herein. For example, compounds having the present structures except for the replacement of hydrogen by deuterium or tritium, replacement of $^{19}$F with $^{18}$F, or the replacement of a $^{12}$C by a $^{13}$C or $^{14}$C are within the scope of the disclosure. In certain embodiments, the provided compound is a deuterated form of any of the formulae described herein.

In certain embodiments, $G^1$ is of formula:

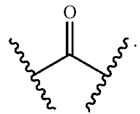

In certain embodiments, $G^1$ is of formula:

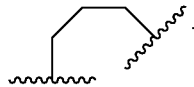

In certain embodiments, G1 is of formula:

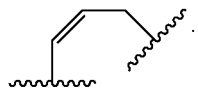 [SMILES: */C=C\C*]

A provided compound may be any possible stereoisomer of Formula (I). The azetidines ring comprises three chiral centers, which each may independently be in either the (R)- or (S)-configuration. In certain embodiments, a compound of Formula (I) is a stereoisomer of formula:

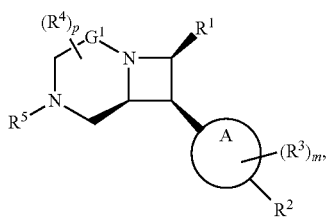

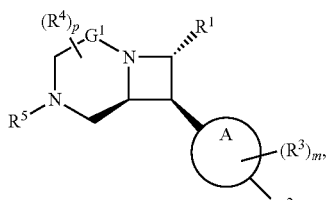

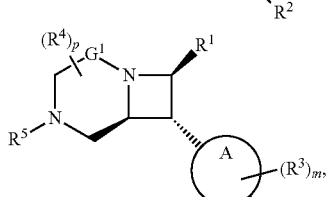

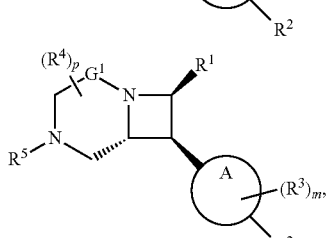

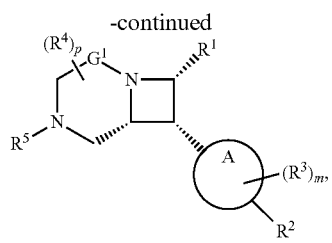

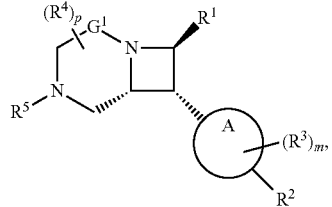

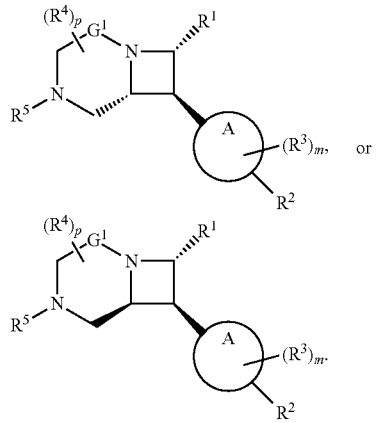

or

In certain embodiments, a compound of Formula (I) is a stereoisomer of formula:

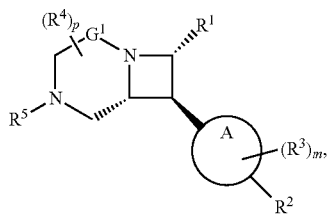

or a pharmaceutically acceptable salt, solvate, hydrate, polymorph, co-crystal, prodrug, or isotopically labeled derivative thereof.

In certain embodiments, the compound of Formula (I) is a compound of Formula (I-a):

(I-a)

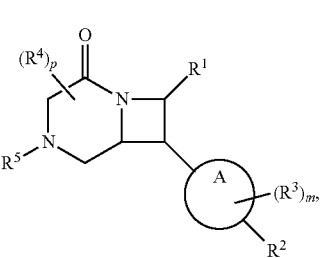

or a pharmaceutically acceptable salt, solvate, hydrate, polymorph, co-crystal, tautomer, stereoisomer, prodrug, or isotopically labeled derivative thereof, wherein Ring A, $R^1$, $R^2$, $R^3$, $R^4$, $R^5$, m, and p are as described herein.

In certain embodiments, the compound of Formula (I) is a compound of Formula (I-b):

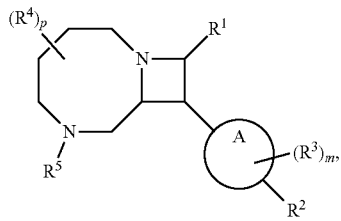

(I-b)

or a pharmaceutically acceptable salt, solvate, hydrate, polymorph, co-crystal, tautomer, stereoisomer, prodrug, or isotopically labeled derivative thereof, wherein Ring A, $R^1$, $R^2$, $R^3$, $R^4$, $R^5$, m, and p are as described herein.

In certain embodiments, a compound of Formula (I-b) is a stereoisomer of formula:

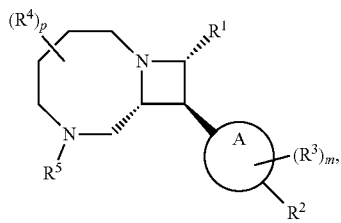

or a pharmaceutically acceptable salt, solvate, hydrate, polymorph, co-crystal, prodrug, or isotopically labeled derivative thereof.

In certain embodiments, the compound of Formula (I) is a compound of Formula (I-c):

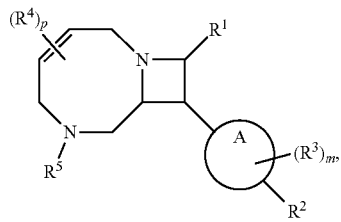

(I-c)

or a pharmaceutically acceptable salt, solvate, hydrate, polymorph, co-crystal, tautomer, stereoisomer, prodrug, or isotopically labeled derivative thereof, wherein Ring A, $R^1$, $R^2$, $R^3$, $R^4$, $R^5$, m, and p are as described herein.

In certain embodiments, the compound of Formula (I) is a compound of Formula (I-d):

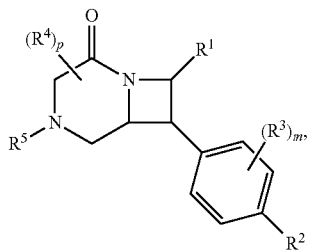

(I-d)

or a pharmaceutically acceptable salt, solvate, hydrate, polymorph, co-crystal, tautomer, stereoisomer, prodrug, or isotopically labeled derivative thereof, wherein $R^1$, $R^2$, $R^3$, $R^4$, $R^5$, m, and p are as described herein.

In certain embodiments, the compound of Formula (I) is a compound of Formula (I-e):

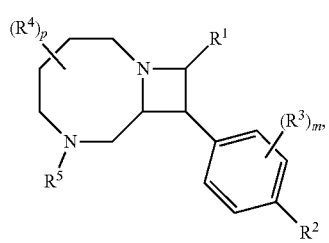

(I-e)

or a pharmaceutically acceptable salt, solvate, hydrate, polymorph, co-crystal, tautomer, stereoisomer, prodrug, or isotopically labeled derivative thereof, wherein $R^1$, $R^2$, $R^3$, $R^4$, $R^5$, m, and p are as described herein.

In certain embodiments, the compound of Formula (I) is a compound of Formula (I-f):

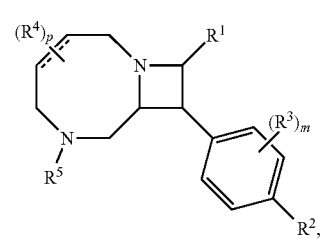

(I-f)

or a pharmaceutically acceptable salt, solvate, hydrate, polymorph, co-crystal, tautomer, stereoisomer, prodrug, or isotopically labeled derivative thereof, wherein $R^1$, $R^2$, $R^3$, $R^4$, $R^5$, m, and p are as described herein.

In certain embodiments, the compound of Formula (I) is a compound of Formula (I-g):

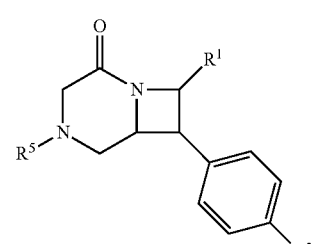

(I-g)

or a pharmaceutically acceptable salt, solvate, hydrate, polymorph, co-crystal, tautomer, stereoisomer, prodrug, or isotopically labeled derivative thereof, wherein $R^1$, $R^2$, and $R^5$ are as described herein.

In certain embodiments, the compound of Formula (I) is a compound of Formula (I-h):

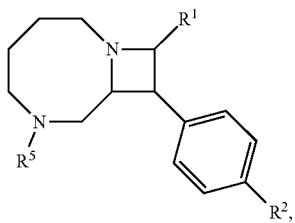 (I-h)

or a pharmaceutically acceptable salt, solvate, hydrate, polymorph, co-crystal, tautomer, stereoisomer, prodrug, or isotopically labeled derivative thereof, wherein $R^1$, $R^2$, and $R^5$ are as described herein.

In certain embodiments, the compound of Formula (I) is a compound of Formula (Ii):

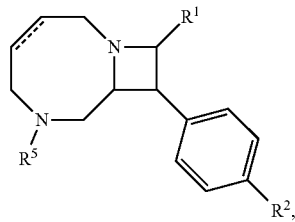 (I-i)

or a pharmaceutically acceptable salt, solvate, hydrate, polymorph, co-crystal, tautomer, stereoisomer, prodrug, or isotopically labeled derivative thereof, wherein $R^1$, $R^2$, and $R^5$ are as described herein, and wherein ===== corresponds to a single or double bond.

In certain embodiments, the compound of Formula (I) is a compound of Formula:

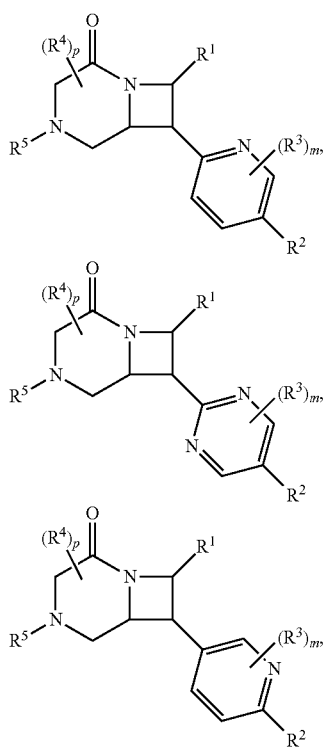

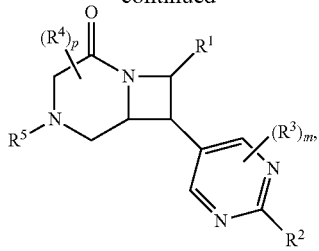

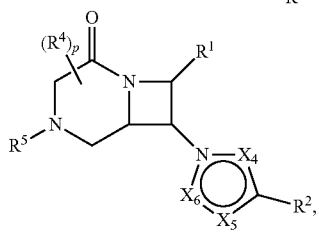

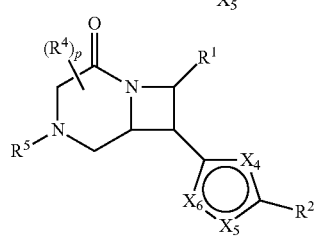

or a pharmaceutically acceptable salt, solvate, hydrate, polymorph, co-crystal, tautomer, stereoisomer, prodrug, or isotopically labeled derivative thereof, wherein $R^1$, $R^2$, $R^3$, $R^4$, $R^5$, and p are as described herein, m is 0, 1, or 2; and $X_4$, $X_5$, and $X_6$ are selected from the group consisting of C, CH, $C(R^3)$, O, S, N, and $N(R^3)$, as valency permits.

In certain embodiments, the compound of Formula (I) is a compound of Formula:

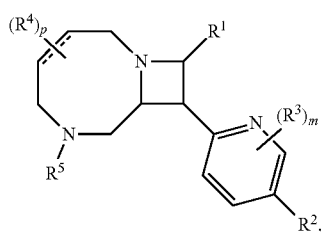

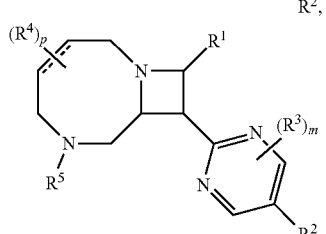

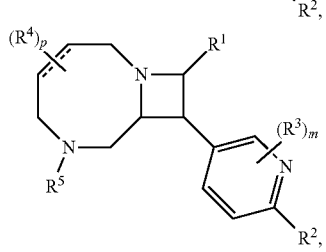

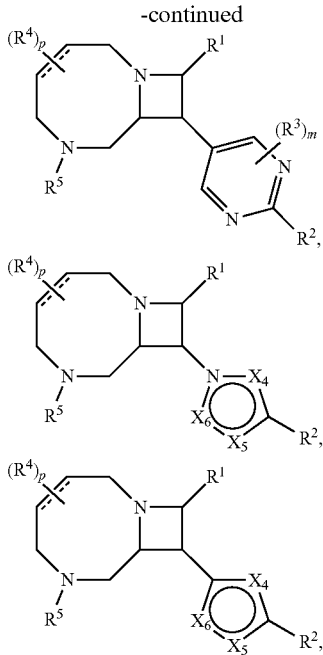

or a pharmaceutically acceptable salt, solvate, hydrate, polymorph, co-crystal, tautomer, stereoisomer, prodrug, or isotopically labeled derivative thereof, wherein $R^1$, $R^2$, $R^3$, $R^4$, $R^5$, m, and p are as described herein, and wherein:

----- corresponds to a single or double bond;

m is 0, 1, or 2; and $X_4$, $X_5$, and $X_6$ are selected from the group consisting of C, CH, $C(R^3)$, O, S, N, and $N(R^{3a})$, as valency permits.

In certain embodiments, $R^2$ is of formula:

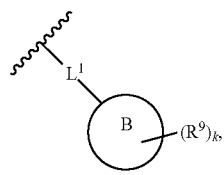

wherein:

$L^1$ is a bond, optionally substituted alkylene, optionally substituted alkenylene, optionally substituted alkynylene, —O—, —$NR^L$—, —C(=O)—, —C(=O)$NR^L$—, —$NR^L$C(=O)—, wherein $R^L$ is hydrogen, optionally substituted $C_{1-6}$ alkyl, or a nitrogen protecting group;

Ring B is a carbocyclic, heterocyclic, aryl or heteroaryl ring;

each $R^9$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{9a}$, —$N(R^{9a})_2$, —$S(=O)_2R^{9a}$, —$S(=O)_2OR^{9a}$, or —$S(=O)_2N(R^{9a})_2$, or two $R^9$ are joined to form an optionally substituted carbocyclic, heterocyclic, aryl, or heteroaryl ring, wherein each $R^{9a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{9a}$ are joined to form an optionally substituted heteroaryl or optionally substituted heterocyclic ring; and k is 0, 1, 2, 3, 4, or 5.

In certain embodiments, the compound of Formula (I) is a compound of Formula (I-j):

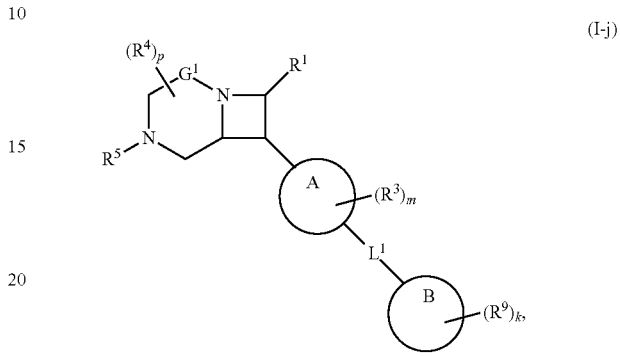

or a pharmaceutically acceptable salt, solvate, hydrate, polymorph, co-crystal, tautomer, stereoisomer, prodrug, or isotopically labeled derivative thereof, wherein Ring A, Ring B, $L^1$, $R^1$, $R^2$, $R^3$, $R^4$, $R^9$, m, p, and k are as described herein.

In certain embodiments, the compound of Formula (I) is a compound of Formula (I-k):

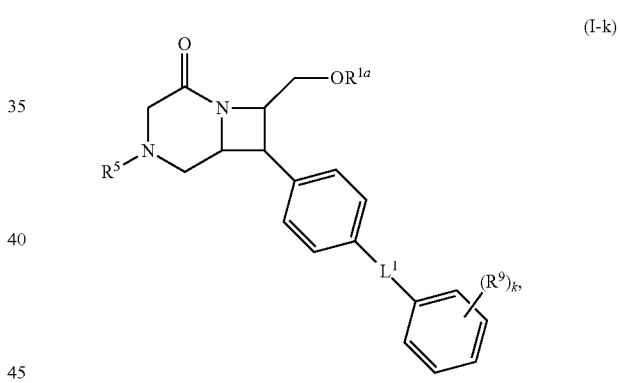

or a pharmaceutically acceptable salt, solvate, hydrate, polymorph, co-crystal, tautomer, stereoisomer, prodrug, or isotopically labeled derivative thereof, wherein $R^{1a}$, $R^5$, $R^9$, and k are as described herein.

In certain embodiments, the compound of Formula (I) is a compound of Formula (I-l):

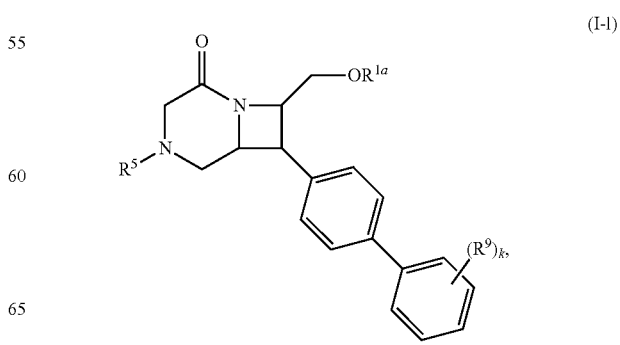

In certain embodiments, the compound of Formula (I) is a compound of Formula (I-m):

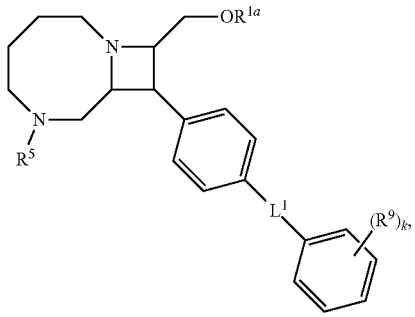
(I-m)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-n):

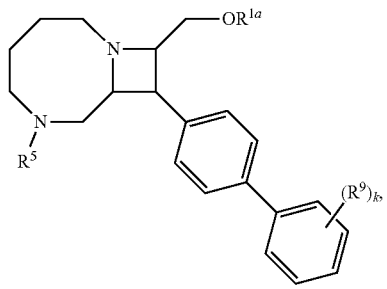
(I-n)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein In certain embodiments, the compound of Formula (I-n) is a stereoisomer of formula:

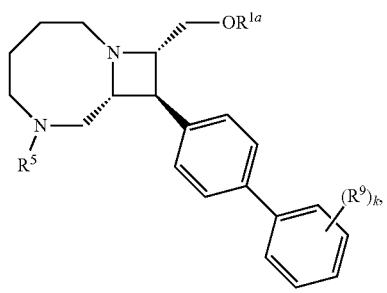

or a pharmaceutically acceptable salt, solvate, hydrate, polymorph, co-crystal, prodrug, or isotopically labeled derivative thereof.

In certain embodiments, the compound of Formula (I) is a compound of Formula (I-o):

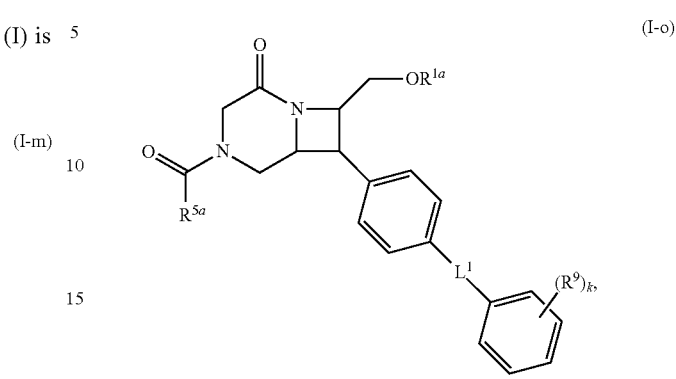
(I-o)

or a pharmaceutically acceptable salt, solvate, hydrate, polymorph, co-crystal, tautomer, stereoisomer, prodrug, or isotopically labeled derivative thereof, wherein $R^{1a}$, $R^5$, $R^9$, and k are as described herein.

In certain embodiments, the compound of Formula (I) is a compound of Formula (I-p)

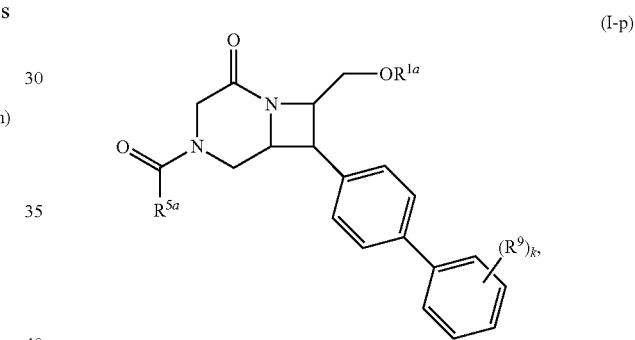
(I-p)

or a pharmaceutically acceptable salt, solvate, hydrate, polymorph, co-crystal, tautomer, stereoisomer, prodrug, or isotopically labeled derivative thereof, wherein $R^{1a}$, $R^5$, $R^9$, and k are as described herein.

In certain embodiments, the compound of Formula (I) is a compound of Formula (I-q):

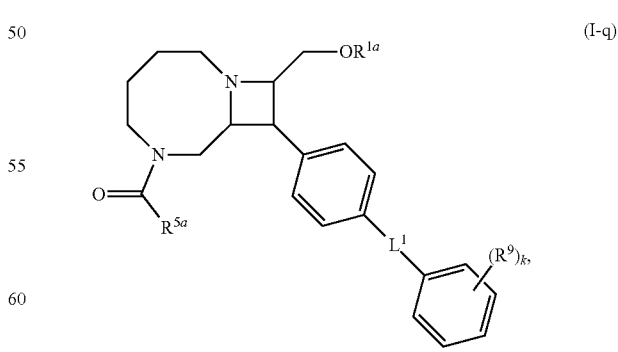
(I-q)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-r):

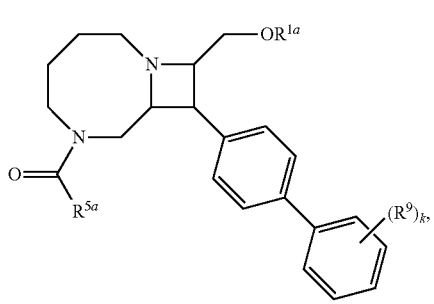
(I-r)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein.

In certain embodiments, the compound of Formula (I) is a compound of Formula (I-s):

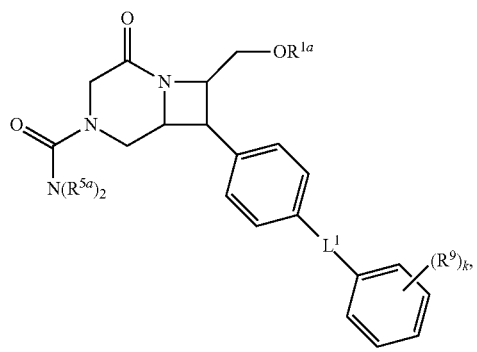
(I-s)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-t):

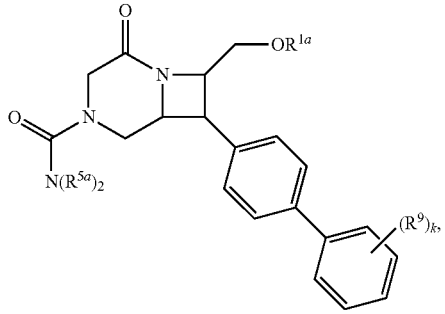
(I-t)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein.

In certain embodiments, the compound of Formula (I) is a compound of Formula (I-u):

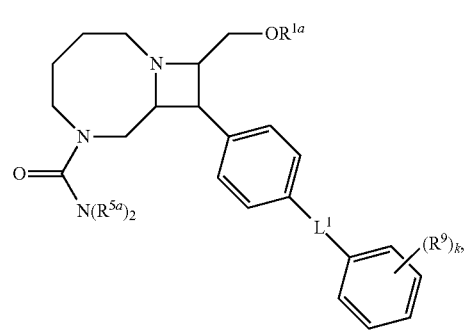
(I-u)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-v):

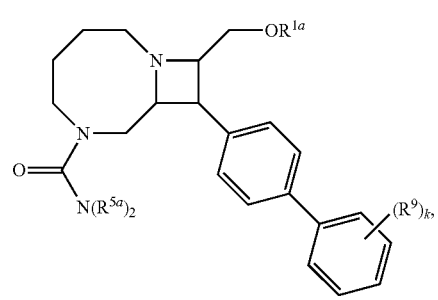
(I-v)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein.

In certain embodiments, the compound of Formula (I) is a compound of Formula (I-w):

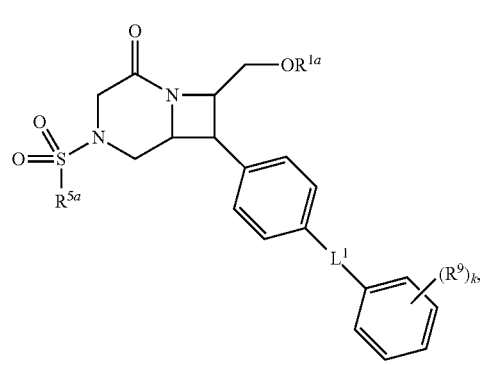
(I-w)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-x):

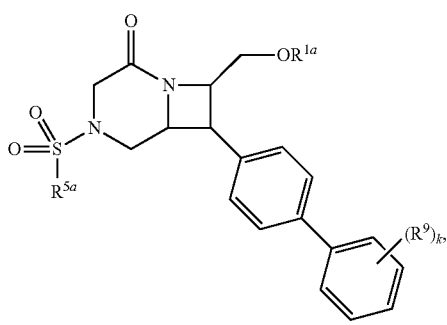

(I-x)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein.

In certain embodiments, the compound of Formula (I) is a compound of Formula (I-y):

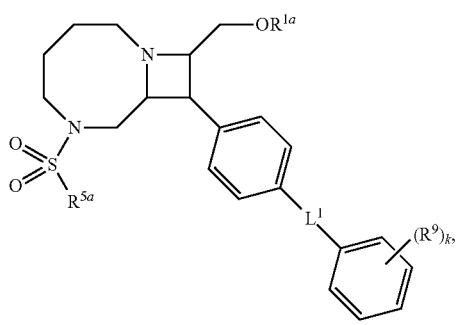

(I-y)

or a pharmaceutically acceptable salt, solvate, hydrate, polymorph, co-crystal, tautomer, stereoisomer, prodrug, or isotopically labeled derivative thereof, wherein $L^1$, $R^{1a}$, $R^{5a}$, $R^9$, and k are as described herein.

In certain embodiments, the compound of Formula (I) is a compound of Formula (I-z):

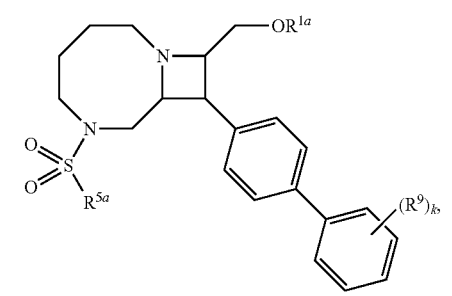

(I-z)

or a pharmaceutically acceptable salt, solvate, hydrate, polymorph, co-crystal, tautomer, stereoisomer, prodrug, or isotopically labeled derivative thereof, wherein $R^{1a}$, $R^{5a}$, $R^9$, and k are as described herein.

$R^1$

As generally defined herein, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH$_2$-halo, —CH$_2$OR$^{1a}$, —CH$_2$SR$^{1a}$, or —CH$_2$N(R$^{1a}$)$_2$, wherein each $R^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{1a}$ are joined to form an optionally substituted heteroaryl or optionally substituted heterocyclic ring.

In certain embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH$_2$-halo, —CH$_2$OR$^{1a}$, —CH$_2$SR$^{1a}$, or —CH$_2$N(R$^{1a}$)$_2$.

In certain embodiments, $R^1$ is hydrogen. In certain embodiments, $R^1$ is a non-hydrogen group, and the carbon to which $R^1$ attached is a stereocenter of the (R)-configuration. In certain embodiments, $R^1$ is a non-hydrogen group, and the carbon to which $R^1$ attached is a stereocenter of the (S)-configuration.

In certain embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH$_2$-halo, —CH$_2$OR$^{1a}$, —CH$_2$SR$^{1a}$, or —CH$_2$N(R$^{1a}$)$_2$.

In certain embodiments, $R^1$ is halogen. In some embodiments, $R^1$ is —F. In some embodiments, $R^1$ is —Cl, —Br, or —I. In certain embodiments, $R^1$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^1$ is methyl. In certain embodiments, $R^1$ is ethyl, propyl, or butyl. In certain embodiments, $R^1$ is optionally substituted alkenyl, e.g., optionally substituted $C_{2-6}$ alkenyl. In certain embodiments, $R^1$ is vinyl, allyl, or prenyl. In certain embodiments, $R^1$ is optionally substituted alkynyl, e.g., $C_{2-6}$ alkynyl.

In certain embodiments, $R^1$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^1$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^1$ is optionally substituted aryl, e.g., optionally substituted phenyl. In certain embodiments, $R^1$ is optionally substituted heteroaryl, e.g., optionally substituted 5-6 membered heteroaryl, or optionally substituted 9-10 membered bicyclic heteroaryl. In certain embodiments, $R^1$ is optionally substituted aralkyl, e.g., optionally substituted benzyl. In certain embodiments, $R^1$ is optionally substituted heteroaralkyl, e.g., methyl substituted with a 5-6 membered heteroaryl ring.

In certain embodiments, $R^1$ is optionally substituted acyl, e.g., —CHO, —CO$_2$H, or —C(=O)NH$_2$. In certain embodiments, $R^1$ is —C(=O)R$^{1a}$, —C(=O)OR$^{1a}$, —C(=O)NH(R$^{1a}$), or —C(=O)N(R$^{1a}$)$_2$. In certain embodiments, $R^1$ is —C(=O)R$^{1a}$, and $R^{1a}$ is optionally substituted alkyl, e.g., —C(=O)Me. In certain embodiments, $R^1$ is —C(=O)R$^{1a}$, and $R^{1a}$ is optionally substituted alkenyl. In certain embodiments, $R^1$ is —C(=O)R$^{1a}$, and $R^{1a}$ is optionally substituted carbocyclyl, heterocyclyl, aryl, or heteroaryl. In certain embodiments, $R^1$ is —C(=O)OR$^{1a}$, and $R^{1a}$ is optionally substituted alkyl. In certain embodiments, $R^1$ is —C(=O)OR$^{1a}$, and $R^{1a}$ is optionally substituted alkenyl. In certain embodiments, $R^1$ is —C(=O)OR$^{1a}$, and $R^{1a}$ is optionally substituted carbocyclyl, heterocyclyl, aryl, or heteroaryl.

In certain embodiments, $R^1$ is —C(=O)N(R$^{1a}$)$_2$, and at least one $R^{1a}$ is optionally substituted alkyl. In certain embodiments, $R^1$ is —C(=O)NHR$^{1a}$, and $R^{1a}$ is optionally substituted alkyl. In certain embodiments, $R^1$ is —C(=O)NHR$^{1a}$, and $R^{1a}$ is optionally substituted alkenyl. In certain embodiments, $R^1$ is —C(=O)NHR$^{1a}$, and $R^{1a}$ is optionally substituted carbocyclyl, heterocyclyl, aryl, or heteroaryl.

In certain embodiments, $R^1$ is —(CH$_2$)$_n$OR$^{1a}$, wherein n is 0, 1, 2, 3, or 4. In certain embodiments, $R^1$ is —CH$_2$OR$^{1a}$, e.g., —CH$_2$OH. In certain embodiments, $R^1$ is —CH$_2$OR$^{1a}$, and $R^{1a}$ is hydrogen, optionally substituted alkyl, or an oxygen protecting group. In certain embodiments, $R^1$ is —CH$_2$OR$^{1a}$, and $R^{1a}$ is optionally substituted alkyl or an oxygen protecting group. In certain embodiments, $R^1$ is —CH$_2$OR$^{1a}$, and $R^{1a}$ is optionally substituted alkyl. In certain embodiments, $R^1$ is —CH$_2$OR$^{1a}$, and $R^{1a}$ is optionally alkenyl. In certain embodiments, $R^1$ is —CH$_2$OR$^{1a}$, and $R^{1a}$ is optionally substituted carbocyclyl, optionally substituted heterocyclyl, optionally substituted aryl optionally substituted heteroaryl. In certain embodiments, $R^1$ is —CH$_2$OR$^{1a}$, and $R^{1a}$ is optionally substituted acyl, e.g., $R^1$ is —CH$_2$OC(=O)R$^{1a}$, —CH$_2$OC(=O)OR$^{1a}$, or —CH$_2$OC(=O)N(R$^{1a}$)$_2$. In certain embodiments, $R^1$ is —OR$^{1a}$, and $R^{1a}$ is an oxygen protecting group, e.g., $R^1$ is —CH$_2$OCPh$_3$. In certain embodiments, $R^1$ is —CH$_2$OH. In certain embodiments, $R^1$ is not —CH$_2$OH.

In certain embodiments, $R^1$ is —(CH$_2$)$_n$SR$^{1a}$, wherein n is 0, 1, 2, 3, or 4. In certain embodiments, $R^1$ is —CH$_2$SR$^{1a}$, e.g., —CH$_2$SH. In certain embodiments, $R^1$ is —CH$_2$SR$^{1a}$, and $R^{1a}$ is hydrogen, optionally substituted alkyl, or a sulfur protecting group. In certain embodiments, $R^1$ is —CH$_2$SR$^{1a}$, and $R^{1a}$ is optionally substituted alkyl or a sulfur protecting group. In certain embodiments, $R^1$ is —CH$_2$SR$^{1a}$, and $R^{1a}$ is optionally substituted alkyl. In certain embodiments, $R^1$ is —CH$_2$SR$^{1a}$, and $R^{1a}$ is optionally alkenyl. In certain embodiments, $R^1$ is —CH$_2$SR$^{1a}$, and $R^{1a}$ is optionally substituted carbocyclyl, optionally substituted heterocyclyl, optionally substituted aryl optionally substituted heteroaryl. In certain embodiments, $R^1$ is —CH$_2$SR$^{1a}$, and $R^{1a}$ is optionally substituted acyl, e.g., $R^1$ is —CH$_2$SC(=O)R$^{1a}$, —CH$_2$SC(=O)OR$^{1a}$, or —CH$_2$SC(=O)N(R$^{1a}$)$_2$. In certain embodiments, $R^1$ is —SR$^{1a}$, and $R^{1a}$ is a sulfur protecting group.

In certain embodiments, $R^1$ is —(CH$_2$)$_n$N(R$^{1a}$)$_2$, wherein n is 0, 1, 2, 3, or 4. In certain embodiments, $R^1$ is —CH$_2$N(R$^{1a}$)$_2$, e.g., —CH$_2$NH$_2$, —CH$_2$NHR$^{1a}$. In certain embodiments, $R^1$ is —CH$_2$NH(R$^{1a}$), and $R^{1a}$ is optionally substituted alkyl. In certain embodiments, $R^1$ is —CH$_2$N(R$^{1a}$)$_2$, and at least one $R^{1a}$ is optionally substituted alkyl. In certain embodiments, $R^1$ is —CH$_2$NHR$^{1a}$, and $R^{1a}$ is optionally substituted carbocyclyl, optionally substituted heterocyclyl, optionally substituted aryl, or optionally substituted heteroaryl. In certain embodiments, $R^1$ is —CH$_2$NHR$^{1a}$, and $R^{1a}$ is optionally substituted acyl, e.g., $R^1$ is —CH$_2$NHC(=O)R$^{1a}$, —CH$_2$NHC(=O)OR$^{1a}$, or —CH$_2$NHC(=O)NHR$^{1a}$. In certain embodiments, $R^1$ is —CH$_2$N(R$^{1a}$)$_2$, and at least one $R^{1a}$ is a nitrogen protecting group. In certain embodiments, $R^1$ is —CH$_2$N(R$^{1a}$)$_2$, and both $R^{1a}$ are joined to form an optionally substituted heterocyclic or optionally substituted heteroaryl ring.

In certain embodiments, $R^1$ is —CH$_2$-halo, i.e., —CH$_2$F, —CH$_2$Br, —CH$_2$I, or —CH$_2$Cl. In certain embodiments, $R^1$ is —CH$_2$F.

$R^2$

As generally defined herein, $R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —OR$^{2a}$, or —N(R$^{2a}$)$_2$, wherein each $R^{2a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, an oxygen protecting group when attached to an oxygen atom, or a nitrogen protecting group when attached to a nitrogen atom, or two $R^{2a}$ are joined to form an optionally substituted heteroaryl or optionally substituted heterocyclic ring.

In certain embodiments, $R^2$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^2$ is methyl. In certain embodiments, $R^2$ is ethyl, propyl, or butyl. In certain embodiments, $R^2$ is optionally substituted alkenyl, e.g., optionally substituted $C_{2-6}$ alkenyl. In certain embodiments, $R^2$ is vinyl, allyl, or prenyl. In certain embodiments, $R^2$ is optionally substituted alkynyl, e.g., $C_{2-6}$ alkynyl.

In certain embodiments, $R^2$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^2$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^2$ is optionally substituted aryl, e.g., optionally substituted phenyl. In certain embodiments, $R^2$ is optionally substituted heteroaryl, e.g., optionally substituted 5-6 membered heteroaryl, or optionally substituted 9-10 membered bicyclic heteroaryl. In certain embodiments, $R^2$ is optionally substituted aralkyl, e.g., optionally substituted benzyl. In certain embodiments, $R^2$ is optionally substituted heteroaralkyl, e.g., methyl substituted with a 5-6 membered heteroaryl ring.

In certain embodiments, $R^2$ is optionally substituted acyl, e.g., —CHO, —CO$_2$H, or —C(=O)NH$_2$. In certain embodiments, $R^2$ is —C(=O)R$^{2a}$, —C(=O)OR$^{2a}$, —C(=O)NH(R$^{2a}$), or —C(=O)N(R$^{2a}$)$_2$. In certain embodiments, $R^2$ is —C(=O)R$^{2a}$, and $R^{2a}$ is optionally substituted alkyl, e.g., —C(=O)Me. In certain embodiments, $R^2$ is —C(=O)$R^{2a}$, and $R^{2a}$ is optionally substituted alkenyl. In certain embodiments, $R^2$ is —C(=O)$R^{2a}$, and $R^{2a}$ is optionally substituted carbocyclyl, heterocyclyl, aryl, or heteroaryl. In certain embodiments, $R^2$ is —C(=O)$OR^{2a}$, and $R^{2a}$ is optionally substituted alkyl. In certain embodiments, $R^2$ is —C(=O)$OR^{2a}$, and $R^{2a}$ is optionally substituted alkenyl. In certain embodiments, $R^2$ is —C(=O)$OR^{2a}$, and $R^{2a}$ is optionally substituted carbocyclyl, heterocyclyl, aryl, or heteroaryl. In certain embodiments, $R^2$ is —C(=O)N($R^{2a}$)$_2$, and at least one $R^{2a}$ is optionally substituted alkyl. In certain embodiments, $R^2$ is —C(=O)NH$R^{2a}$, and $R^{2a}$ is optionally substituted alkyl. In certain embodiments, $R^2$ is —C(=O)NH$R^{2a}$, and $R^{2a}$ is optionally substituted alkenyl. In certain embodiments, $R^2$ is —C(=O)NH$R^{2a}$, and $R^{2a}$ is optionally substituted carbocyclyl, heterocyclyl, aryl, or heteroaryl.

In certain embodiments, $R^2$ is —$OR^{2a}$, e.g., —OH. In certain embodiments, $R^2$ is —$OR^{2a}$, and $R^{2a}$ is optionally substituted alkyl. In certain embodiments, $R^2$ is —$OR^{2a}$, and $R^{2a}$ is optionally alkenyl. In certain embodiments, $R^2$ is —$OR^{2a}$, and $R^{2a}$ is optionally substituted carbocyclyl, optionally substituted heterocyclyl, optionally substituted aryl optionally substituted heteroaryl. In certain embodiments, $R^2$ is —$OR^{2a}$, and $R^{2a}$ is optionally substituted acyl, e.g., $R^2$ is —OC(=O)$R^{2a}$, —OC(=O)$OR^{2a}$, or —OC(=O)N($R^{2a}$)$_2$. In certain embodiments, $R^2$ is —$OR^{2a}$, and $R^{2a}$ is an oxygen protecting group.

In certain embodiments, $R^2$ is —N($R^{2a}$)$_2$, e.g., —NH$_2$, —NH$R^{2a}$. In certain embodiments, $R^2$ is —NH($R^{2a}$), and $R^{2a}$ is optionally substituted alkyl. In certain embodiments, $R^2$ is —N($R^{2a}$)$_2$, and at least one $R^{2a}$ is optionally substituted alkyl. In certain embodiments, $R^2$ is —NH$R^{2a}$, and $R^{2a}$ is optionally substituted carbocyclyl, optionally substituted heterocyclyl, optionally substituted aryl, or optionally substituted heteroaryl. In certain embodiments, $R^2$ is —NH$R^{2a}$, and $R^{2a}$ is optionally substituted acyl, e.g., $R^2$ is —NHC(=O)$R^{2a}$, —NHC(=O)$OR^{2a}$, or —NHC(=O)NH$R^{2a}$. In certain embodiments, $R^2$ is —N($R^{2a}$)$_2$, and at least one $R^{2a}$ is a nitrogen protecting group. In certain embodiments, $R^2$ is —N($R^{2a}$)$_2$, and $R^{2a}$ are joined to form an optionally substituted heterocyclic or optionally substituted heteroaryl ring.

In certain embodiments, $R^2$ is —C≡C$R^{2a}$. In certain embodiments, $R^2$ is —C≡C$R^{2a}$, and $R^{2a}$ is optionally substituted alkyl. In certain embodiments, $R^2$ is —C≡C$R^{2a}$, and $R^{2a}$ is optionally substituted carbocyclyl, heterocyclyl, or heteroaryl. In certain embodiments, $R^2$ is —C≡C$R^{2a}$, and $R^{2a}$ is optionally substituted aryl, e.g., $R^2$ is —C≡C (optionally substituted phenyl).

Ring A and $R^3$

As generally defined herein, Ring A is carbocyclylene, heterocyclylene, arylene, or heteroarylene. In certain embodiments, Ring A is a phenyl ring and $R^2$ is optionally substituted phenyl, such that Ring A and $R^2$ together form a biphenyl group. Ring A may be substituted with 0, 1, 2, 3, or 4 independent $R^3$, valency permitting. In certain embodiments, m is 0 or 1. In certain embodiments, m is 0. In certain embodiments, m is 1. In certain embodiments, m is 2. In certain embodiments, m is 3. In certain embodiments, m is 4.

In certain embodiments, Ring A is arylene, e.g., phenylene. In certain embodiments, Ring A is heteroarylene, e.g., 5- to 6-membered heteroarylene. In some embodiments, Ring A is pyridylene, pyrimidylene, or imidazylene. In certain embodiments, Ring A is carbocyclylene, e.g., 3- to 6-membered carbocyclylene. In some embodiments, Ring A is cyclohexylene, cyclopentylene, cyclobutylene, or cyclopropylene. In certain embodiments, Ring A is heterocyclylene, e.g., 5- to 6-membered heterocyclylene. In some embodiments, Ring A is piperidinylene or piperizinylene.

In certain embodiments, Ring A is of formula:

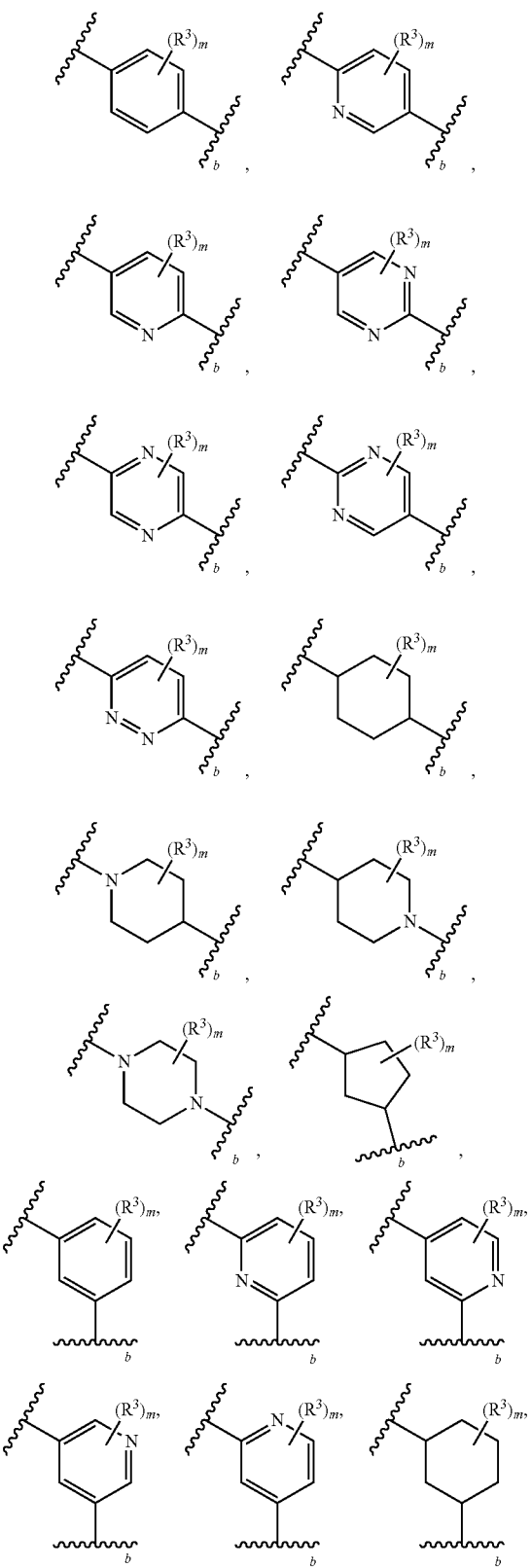

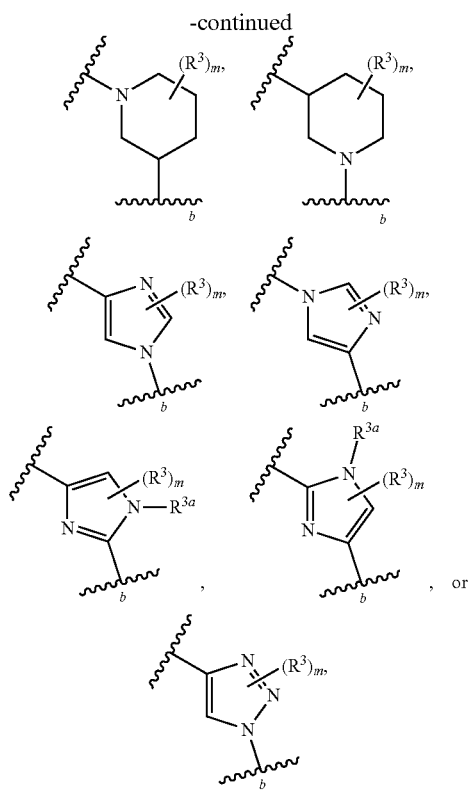
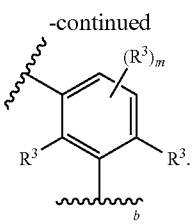
wherein the position labeled b is attached to R², and m is 0, 1, 2, 3, or 4, valency permitting.
In certain embodiments, Ring A is of formula:
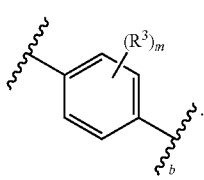
In certain embodiments, Ring A is of formula:
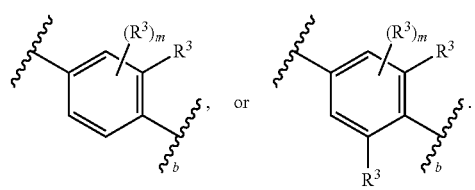
In certain embodiments, Ring A is of formula:
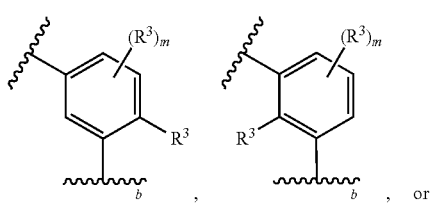
In certain embodiments, Ring A is of formula:
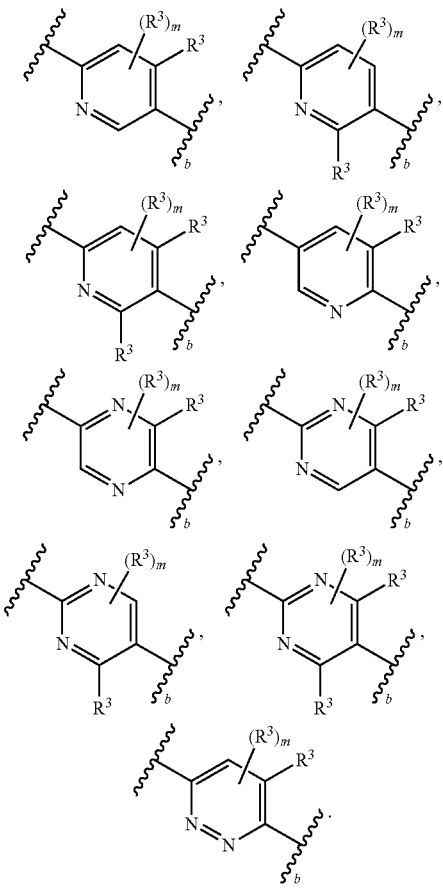
In certain embodiments, Ring A is of formula:
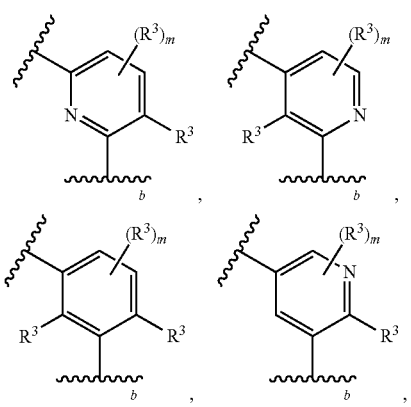

-continued
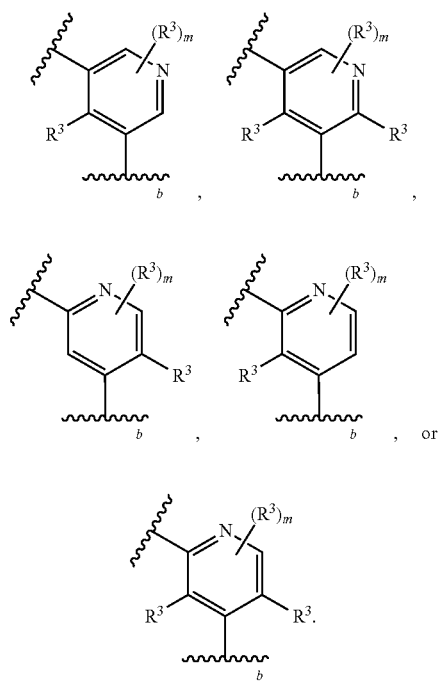
In certain embodiments, Ring A is of formula:
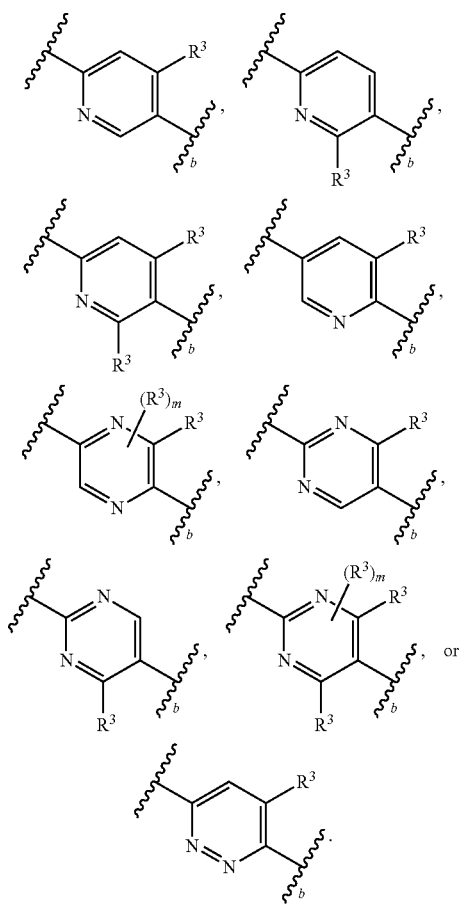
In certain embodiments, Ring A is of formula:
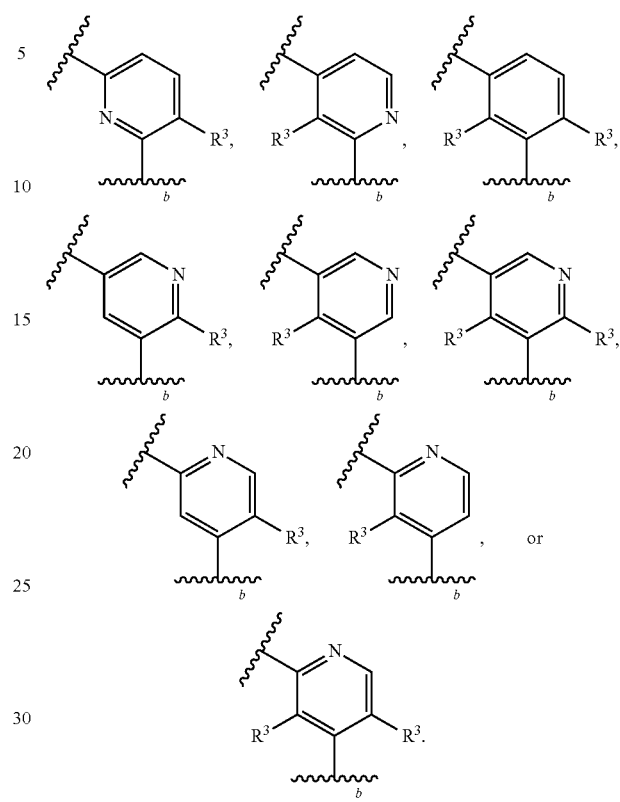
In certain embodiments, Ring A is of formula:
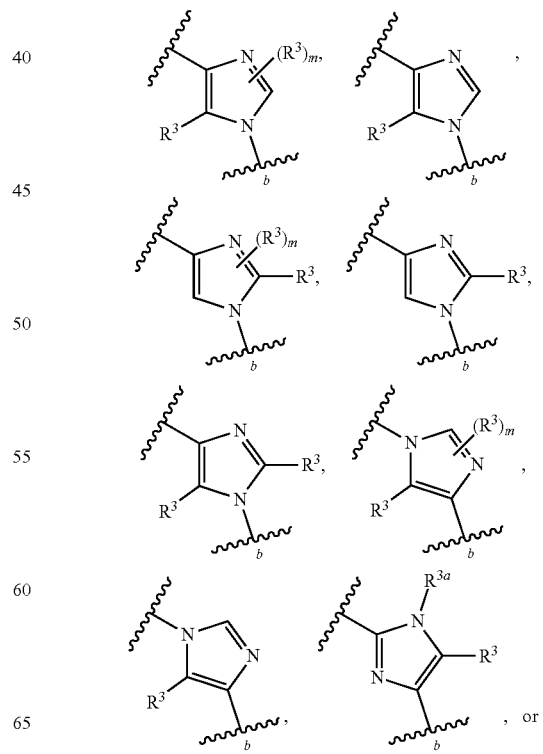

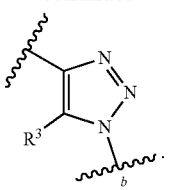
In certain embodiments, Ring A is of formula:
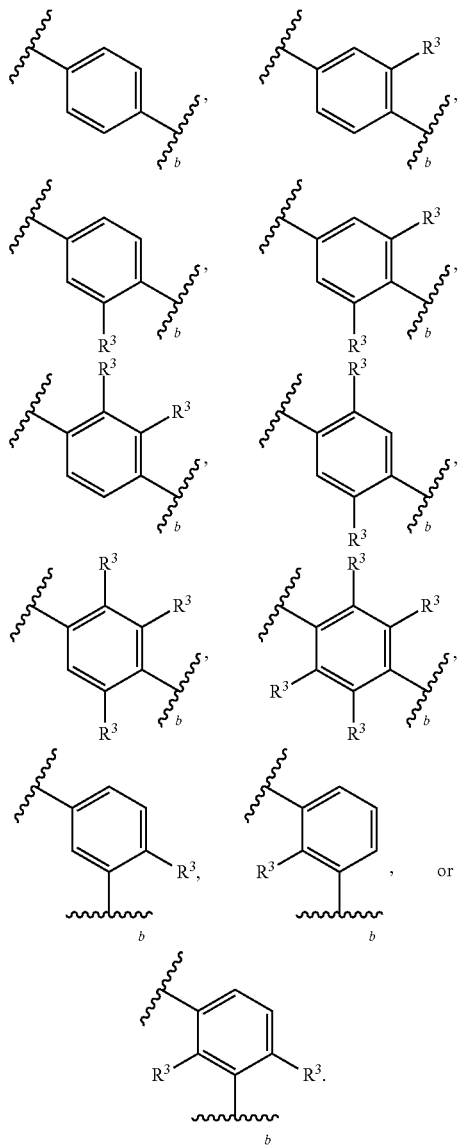
In certain embodiments, Ring $A^4$ is of formula:
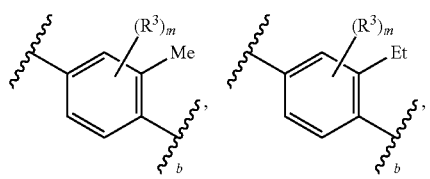
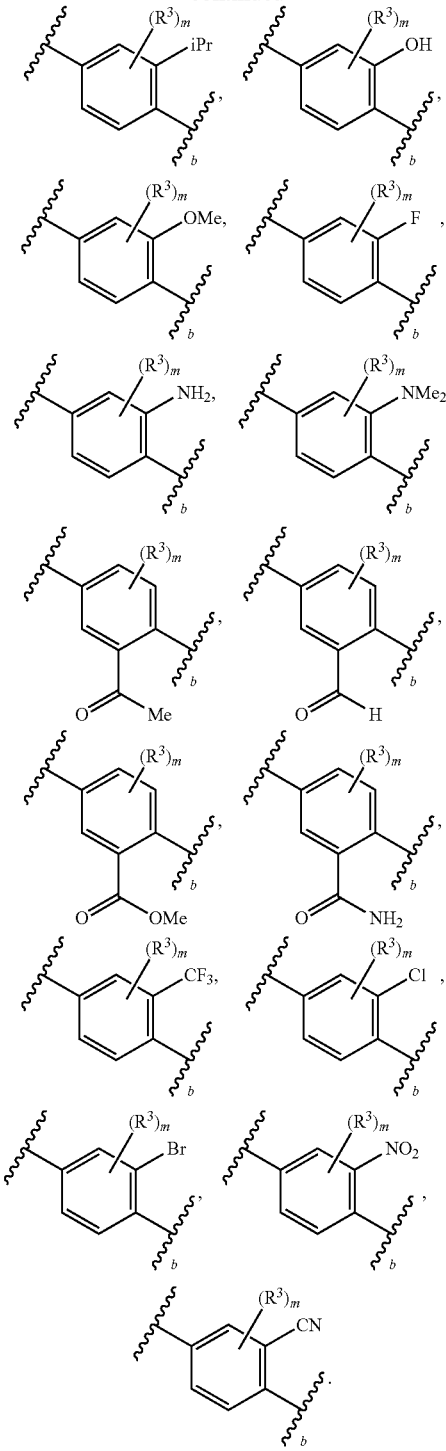
In certain embodiments, Ring $A^4$ is of formula:
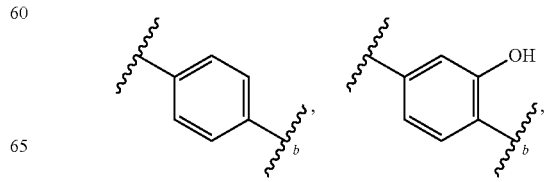

-continued

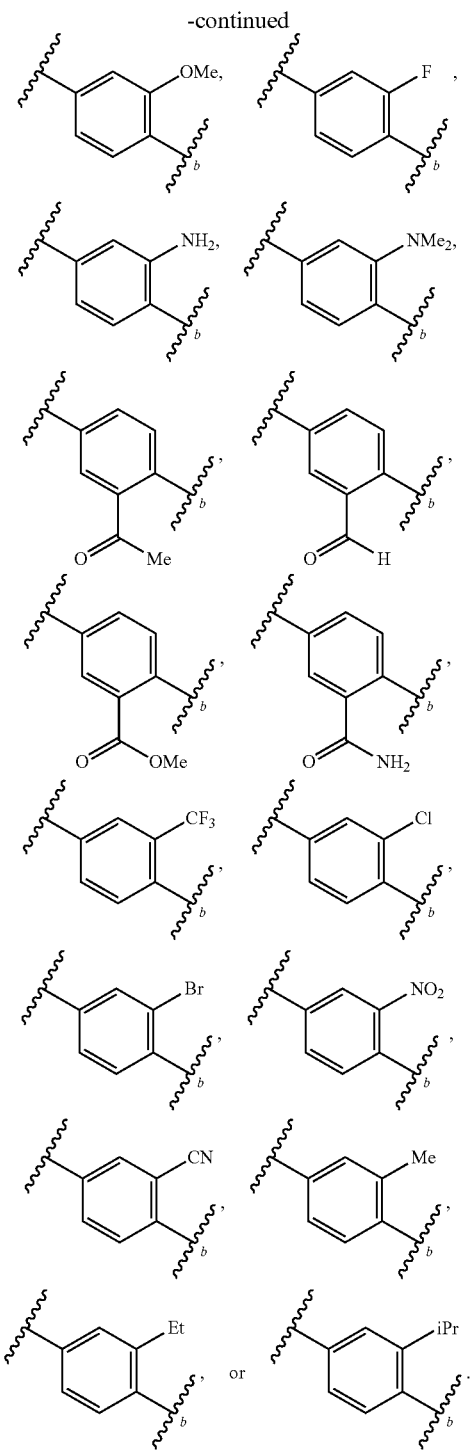

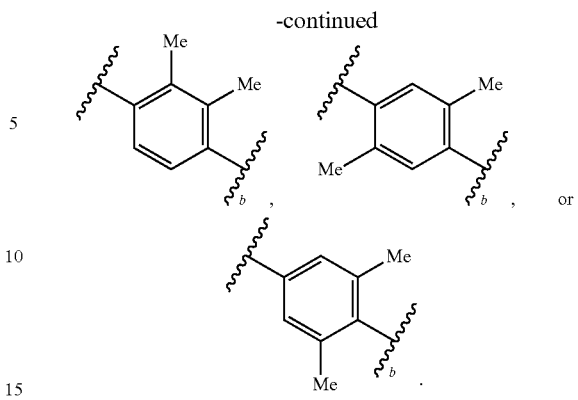

As generally defined herein, each $R^3$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{3a}$, or —$N(R^{3a})_2$, or two $R^3$ are joined to form an optionally substituted carbocyclic, heterocyclic, aryl, or heteroaryl ring, wherein each $R^{3a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{3a}$ are joined to form an optionally substituted heteroaryl or optionally substituted heterocyclic ring.

In certain embodiments, at least one $R^3$ is —$NO_2$. In certain embodiments, at least one $R^3$ is —CN. In certain embodiments, at least one $R^3$ is halogen. In some embodiments, at least one $R^3$ is —F. In some embodiments, at least one $R^3$ is —Cl, —Br, or —I. In certain embodiments, at least one $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^3$ is methyl. In certain embodiments, at least one $R^3$ is ethyl, propyl, or butyl. In certain embodiments, at least one $R^3$ is optionally substituted alkenyl, e.g., optionally substituted $C_{2-6}$ alkenyl. In certain embodiments, at least one $R^3$ is vinyl, allyl, or prenyl. In certain embodiments, at least one $R^3$ is optionally substituted alkynyl, e.g., $C_{2-6}$ alkynyl.

In certain embodiments, at least one $R^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^3$ is optionally substituted aryl, e.g., optionally substituted phenyl. In certain embodiments, at least one $R^3$ is optionally substituted heteroaryl, e.g., optionally substituted 5-6 membered heteroaryl or optionally substituted 9-10 membered bicyclic heteroaryl. In certain embodiments, at least one $R^3$ is optionally substituted aralkyl, e.g., optionally substituted benzyl. In certain embodiments, at least one $R^3$ is optionally substituted heteroaralkyl, e.g., methyl substituted with a 5-6 membered heteroaryl ring.

In certain embodiments, at least one $R^3$ is optionally substituted acyl, e.g., —CHO, —CO$_2$H, or —C(=O)NH$_2$. In certain embodiments, at least one $R^3$ is —C(=O)R$^{3a}$, —C(=O)OR$^{3a}$, —C(=O)NH(R$^{3a}$), or —C(=O)N(R$^{3a}$)$_2$. In certain embodiments, at least one $R^3$ is —C(=O)R$^{3a}$ and $R^{3a}$ is optionally substituted alkyl, e.g., $R^3$ is —C(=O)Me. In certain embodiments, at least one $R^3$ is —C(=O)R$^{3a}$, and $R^{3a}$ is optionally substituted alkenyl. In certain embodiments, at least one $R^3$ is —C(=O)R$^{3a}$, and $R^{3a}$ is optionally substituted carbocyclyl, heterocyclyl, aryl, or heteroaryl. In certain embodiments, at least one $R^3$ is —C(=O)OR$^{3a}$, and $R^{3a}$ is optionally substituted alkyl. In certain embodiments, at least one $R^3$ is —C(=O)OR$^{3a}$, and $R^{3a}$ is optionally substituted alkenyl. In certain embodiments, at least one $R^3$ is —C(=O)OR$^{3a}$, and $R^{3a}$ is optionally substituted carbocyclyl, heterocyclyl, aryl, or heteroaryl. In certain embodiments, at least one $R^3$ is —C(=O)N(R$^{3a}$)$_2$, and at least one $R^{3a}$ is optionally substituted alkyl. In certain embodiments, at least one $R^3$ is —C(=O)NHR$^{3a}$, and $R^{3a}$ is optionally substituted alkyl. In certain embodiments, at least one $R^3$ is —C(=O)NHR$^{3a}$, and $R^{3a}$ is optionally substituted alkenyl. In certain embodiments, at least one $R^3$ is —C(=O)NHR$^{3a}$, and $R^{3a}$ is optionally substituted carbocyclyl, heterocyclyl, aryl, or heteroaryl.

In certain embodiments, at least one $R^3$ is —OR$^{3a}$, e.g., —OH. In certain embodiments, at least one $R^3$ is —OR$^{3a}$, and $R^{3a}$ is optionally substituted alkyl. In certain embodiments, at least one $R^3$ is —OR$^{3a}$, and $R^{3a}$ is optionally alkenyl. In certain embodiments, at least one $R^3$ is —OR$^{3a}$, and $R^{3a}$ is optionally substituted carbocyclyl, optionally substituted heterocyclyl, optionally substituted aryl optionally substituted heteroaryl. In certain embodiments, at least one $R^3$ is —OR$^{3a}$, and $R^{3a}$ is optionally substituted acyl, e.g., $R^3$ is —OC(=O)R$^{3a}$, —OC(=O)OR$^{3a}$, or —OC(=O)N(R$^{3a}$)$_2$. In certain embodiments, at least one $R^3$ is —OR$^{3a}$, and $R^{3a}$ is an oxygen protecting group.

In certain embodiments, at least one $R^3$ is —N(R$^{3a}$)$_2$, e.g., —NH$_2$, —NHR$^{3a}$. In certain embodiments, at least one $R^3$ is —NH(R$^{3a}$), and $R^{3a}$ is optionally substituted alkyl. In certain embodiments, at least one $R^3$ is —N(R$^{3a}$)$_2$, and at least one $R^{3a}$ is optionally substituted alkyl. In certain embodiments, at least one $R^3$ is —NHR$^{3a}$, and $R^{3a}$ is optionally substituted carbocyclyl, optionally substituted heterocyclyl, optionally substituted aryl, or optionally substituted heteroaryl. In certain embodiments, at least one $R^3$ is —NHR$^{3a}$, and $R^{3a}$ is optionally substituted acyl, e.g., $R^3$ is —NHC(=O)R$^{3a}$, —NHC(=O)OR$^{3a}$, or —NHC(=O)NHR$^{3a}$ In certain embodiments, at least one $R^3$ is —N(R$^{3a}$)$_2$, and at least one $R^{3a}$ is a nitrogen protecting group. In certain embodiments, at least one $R^3$ is —N(R$^{3a}$)$_2$, and $R^{3a}$ are joined to form an optionally substituted heterocyclic or optionally substituted heteroaryl ring.

In certain embodiments, an $R^3$ ortho to the bond between Ring A and Ring B is —NO$_2$. In certain embodiments, an $R^3$ ortho to the bond between Ring A and Ring B is —CN. In certain embodiments, an $R^3$ ortho to the bond between Ring A and Ring B is halogen. In some embodiments, an $R^3$ ortho to the bond between Ring A and Ring B is —F. In some embodiments, an $R^3$ ortho to the bond between Ring A and Ring B is —Cl, —Br, or —I. In certain embodiments, an $R^3$ ortho to the bond between Ring A and Ring B is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^3$ ortho to the bond between Ring A and Ring B is methyl. In certain embodiments, an $R^3$ ortho to the bond between Ring A and Ring B is ethyl, propyl, or butyl. In certain embodiments, an $R^3$ ortho to the bond between Ring A and Ring B is optionally substituted alkenyl, e.g., optionally substituted $C_{2-6}$ alkenyl. In certain embodiments, an $R^3$ ortho to the bond between Ring A and Ring B is vinyl, allyl, or prenyl. In certain embodiments, an $R^3$ ortho to the bond between Ring A and Ring B is optionally substituted alkynyl, e.g., $C_{2-6}$ alkynyl.

In certain embodiments, an $R^3$ ortho to the bond between Ring A and Ring B is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^3$ ortho to the bond between Ring A and Ring B is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, an $R^3$ ortho to the bond between Ring A and Ring B is optionally substituted aryl, e.g., optionally substituted phenyl. In certain embodiments, an $R^3$ ortho to the bond between Ring A and Ring B is optionally substituted heteroaryl, e.g., optionally substituted 5-6 membered heteroaryl or optionally substituted 9-10 membered bicyclic heteroaryl. In certain embodiments, an $R^3$ ortho to the bond between Ring A and Ring B is optionally substituted aralkyl, e.g., optionally substituted benzyl. In certain embodiments, an $R^3$ ortho to the bond between Ring A and Ring B is optionally substituted heteroaralkyl, e.g., methyl substituted with a 5-6 membered heteroaryl ring.

In certain embodiments, an $R^3$ ortho to the bond between Ring A and Ring B is optionally substituted acyl, e.g., —CHO, —CO$_2$H, or —C(=O)NH$_2$. In certain embodiments, an $R^3$ ortho to the bond between Ring A and Ring B is —C(=O)R$^{3a}$, —C(=O)OR$^{3a}$, —C(=O)NH(R$^{3a}$), or —C(=O)N(R$^{3a}$)$_2$. In certain embodiments, an $R^3$ ortho to the bond between Ring A and Ring B is —C(=O)R$^{3a}$, and $R^{3a}$ is optionally substituted alkyl, e.g., $R^3$ is —C(=O)Me. In certain embodiments, an $R^3$ ortho to the bond between Ring A and Ring B is —C(=O)R$^{3a}$, and $R^{3a}$ is optionally substituted alkenyl. In certain embodiments, an $R^3$ ortho to the bond between Ring A and Ring B is —C(=O)R$^{3a}$, and $R^{3a}$ is optionally substituted carbocyclyl, heterocyclyl, aryl, or heteroaryl. In certain embodiments, an $R^3$ ortho to the bond between Ring A and Ring B is —C(=O)OR$^{3a}$, and $R^{3a}$ is optionally substituted alkyl. In certain embodiments, an $R^3$ ortho to the bond between Ring A and Ring B is —C(=O)OR$^{3a}$, and $R^{3a}$ is optionally substituted alkenyl. In certain embodiments, an $R^3$ ortho to the bond between Ring A and Ring B is —C(=O)OR$^{3a}$, and $R^{3a}$ is optionally substituted carbocyclyl, heterocyclyl, aryl, or heteroaryl. In certain embodiments, an $R^3$ ortho to the bond between Ring A and Ring B is —C(=O)N(R$^{3a}$)$_2$, and at least one $R^{3a}$ is optionally substituted alkyl. In certain embodiments, an $R^3$ ortho to the bond between Ring A and Ring B is —C(=O)NHR$^{3a}$, and $R^{3a}$ is optionally substituted alkyl. In certain embodiments, an $R^3$ ortho to the bond between Ring A and Ring B is —C(=O)NHR$^{3a}$, and $R^{3a}$ is optionally substituted alkenyl. In certain embodiments, an $R^3$ ortho to the bond between Ring A and Ring B is —C(=O)NHR$^{3a}$, and R$^{3a}$ is optionally substituted carbocyclyl, heterocyclyl, aryl, or heteroaryl.

In certain embodiments, an R$^3$ ortho to the bond between Ring A and Ring B is —OR$^{3a}$, e.g., —OH. In certain embodiments, an R$^3$ ortho to the bond between Ring A and Ring B is —OR$^{3a}$, and R$^{3a}$ is optionally substituted alkyl. In certain embodiments, an R$^3$ ortho to the bond between Ring A and Ring B is —OR$^{3a}$, and R$^{3a}$ is optionally alkenyl. In certain embodiments, an R$^3$ ortho to the bond between Ring A and Ring B is —OR$^{3a}$, and R$^{3a}$ is optionally substituted carbocyclyl, optionally substituted heterocyclyl, optionally substituted aryl or optionally substituted heteroaryl. In certain embodiments, an R$^3$ ortho to the bond between Ring A and Ring B is —OR$^{3a}$, and R$^{3a}$ is optionally substituted acyl, e.g., R$^3$ is —OC(=O)R$^{3a}$, —OC(=O)OR$^{3a}$, or —OC(=O)N(R$^{3a}$)$_2$. In certain embodiments, an R$^3$ ortho to the bond between Ring A and Ring B is —OR$^{3a}$, and R$^{3a}$ is an oxygen protecting group.

In certain embodiments, an R$^3$ ortho to the bond between Ring A and Ring B is —N(R$^{3a}$)$_2$, e.g., —NH$_2$, —NHR$^{3a}$. In certain embodiments, an R$^3$ ortho to the bond between Ring A and Ring B is —NH(R$^{3a}$), and R$^{3a}$ is optionally substituted alkyl. In certain embodiments, an R$^3$ ortho to the bond between Ring A and Ring B is —N(R$^{3a}$)$_2$, and at least one R$^{3a}$ is optionally substituted alkyl. In certain embodiments, an R$^3$ ortho to the bond between Ring A and Ring B is —NHR$^{3a}$, and R$^{3a}$ is optionally substituted carbocyclyl, optionally substituted heterocyclyl, optionally substituted aryl, or optionally substituted heteroaryl. In certain embodiments, an R$^3$ ortho to the bond between Ring A and Ring B is —NHR$^{3a}$, and R$^{3a}$ is optionally substituted acyl, e.g., R$^3$ is —NHC(=O)R$^{3a}$, —NHC(=O)OR$^{3a}$, or —NHC(=O)NHR$^{3a}$. In certain embodiments, an R$^3$ ortho to the bond between Ring A and Ring B is —N(R$^{3a}$)$_2$, and at least one R$^{3a}$ is a nitrogen protecting group. In certain embodiments, an R$^3$ ortho to the bond between Ring A and Ring B is —N(R$^{3a}$)$_2$, and R$^{3a}$ are joined to form an optionally substituted heterocyclic or optionally substituted heteroaryl ring. Ring B, L1, and R$^9$ In certain embodiments, R$^2$ is of formula:

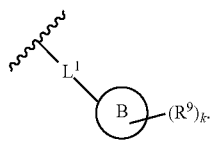

As generally defined herein, is Ring B is a carbocyclic, heterocyclic, aryl or heteroaryl ring. In certain embodiments, Ring A and B are both phenyl rings and L$^1$ is a bond, such that Ring A and B together form a biphenyl group. Ring B may be substituted with 0, 1, 2, 3, 4, or 5 independent R$^9$, valency permitting. In certain embodiments, k is 0 or 1. In certain embodiments, k is 0. In certain embodiments, k is 1. In certain embodiments, k is 2. In certain embodiments, k is 3. In certain embodiments, k is 4. In certain embodiments, k is 5.

In certain embodiments, Ring B is aryl, e.g., phenyl. In certain embodiments, Ring B is heteroaryl, e.g., 5- to 6-membered heteroaryl. In some embodiments, Ring B is pyridyl, pyrimidyl, or imidazyl. In certain embodiments, Ring B is carbocyclyl, e.g., 3- to 6-membered carbocyclyl. In some embodiments, Ring B is cyclohexyl, cyclopentyl, cyclobutyl, or cyclopropyl. In certain embodiments, Ring B is heterocyclyl, e.g., 5- to 6-membered heterocyclyl. In some embodiments, Ring B is piperidinyl, piperizinyl, or morpholinyl.

In certain embodiments, Ring B is of formula:

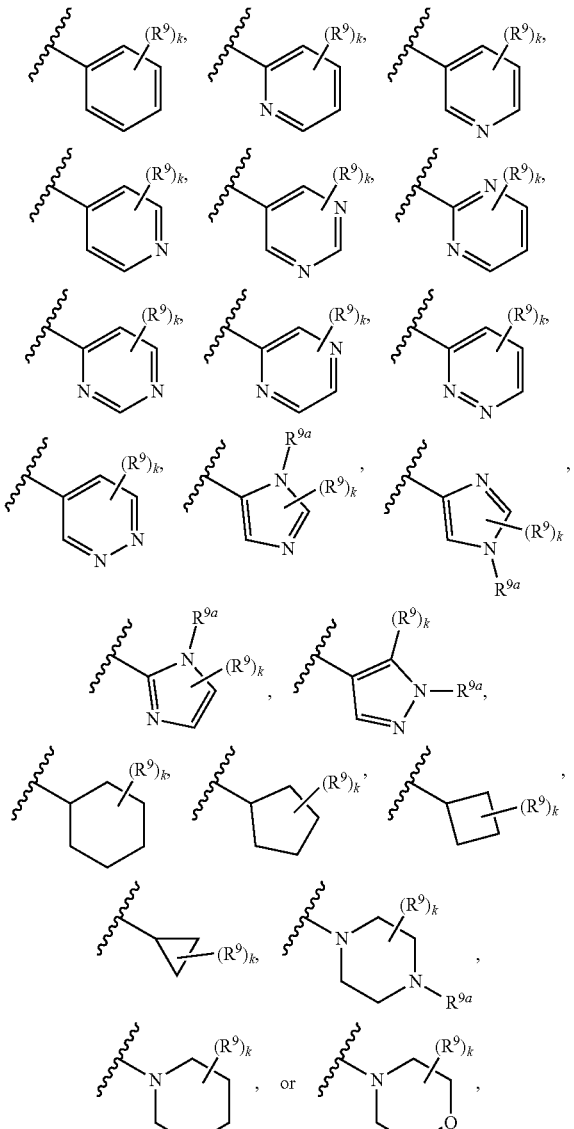

wherein k is 0, 1, 2, 3, 4, or 5, valency permitting.

In certain embodiments, Ring B is of formula:

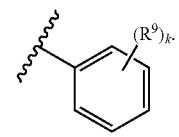

In certain embodiments, Ring B is of formula:

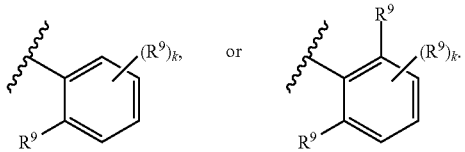

In certain embodiments, Ring B is of formula:
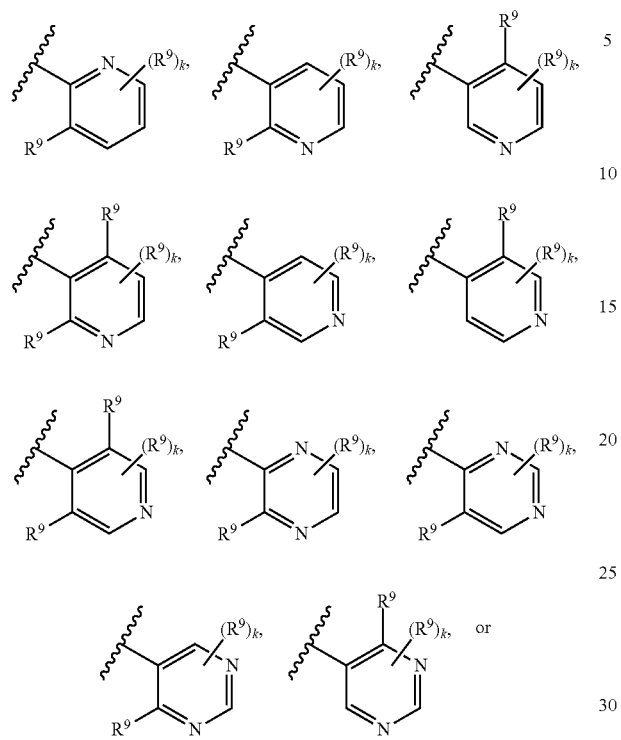
In certain embodiments, Ring B is of formula:
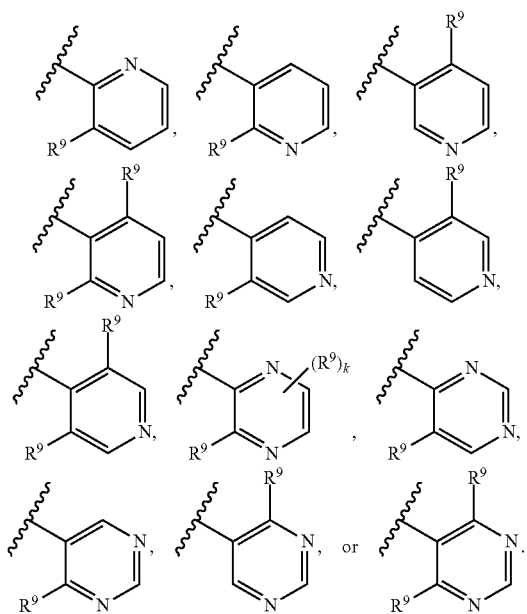
In certain embodiments, Ring B is of formula:
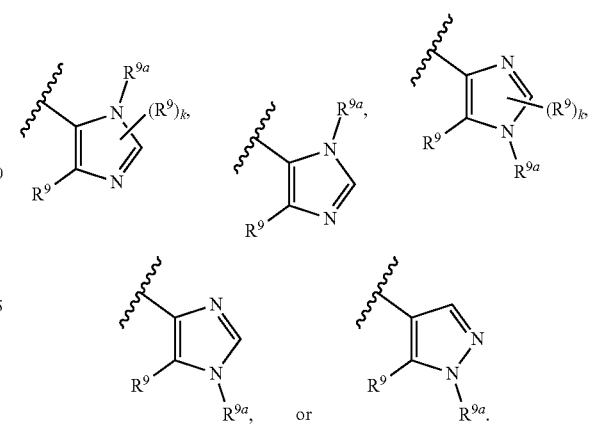
In certain embodiments, Ring B is of formula:
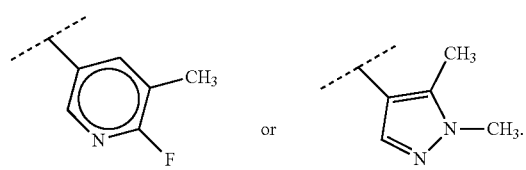
In certain embodiments, Ring B is of formula:
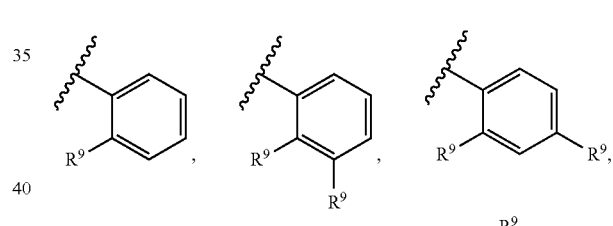
In certain embodiments, Ring B is of formula:
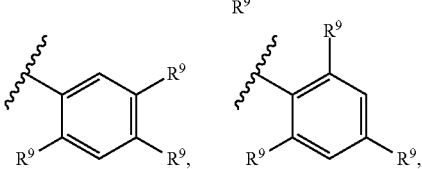

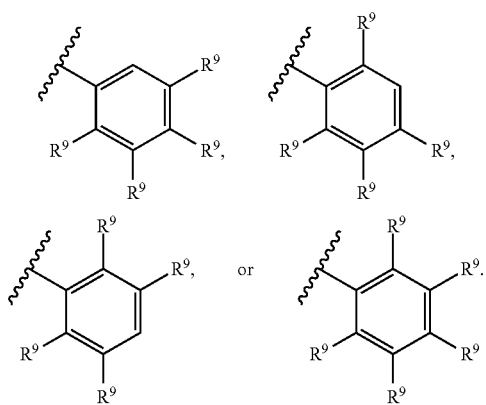
In certain embodiments, Ring B is of formula:
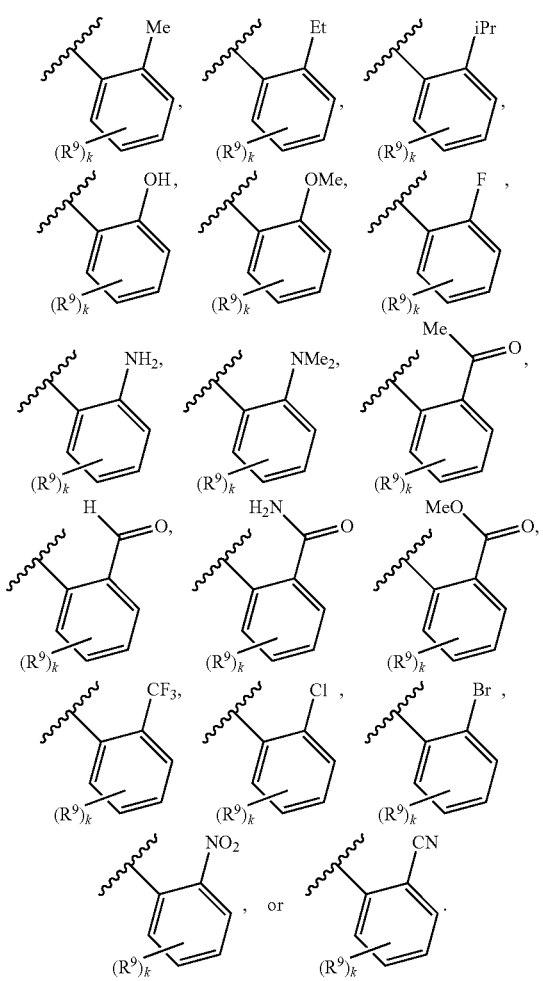
In certain embodiments, Ring B is of formula:
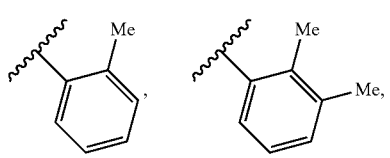
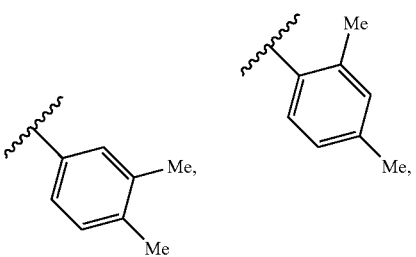
In certain embodiments, Ring B is of formula:
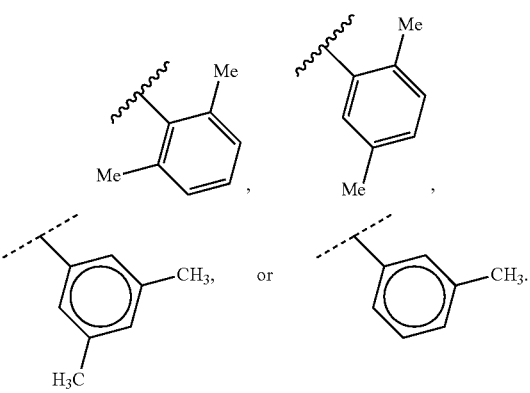
In certain embodiments, Ring B is of formula:
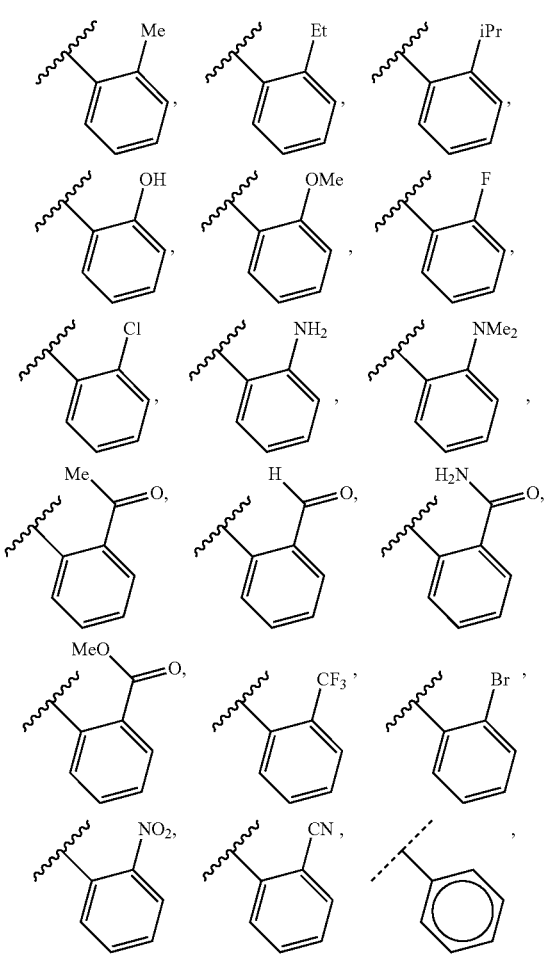

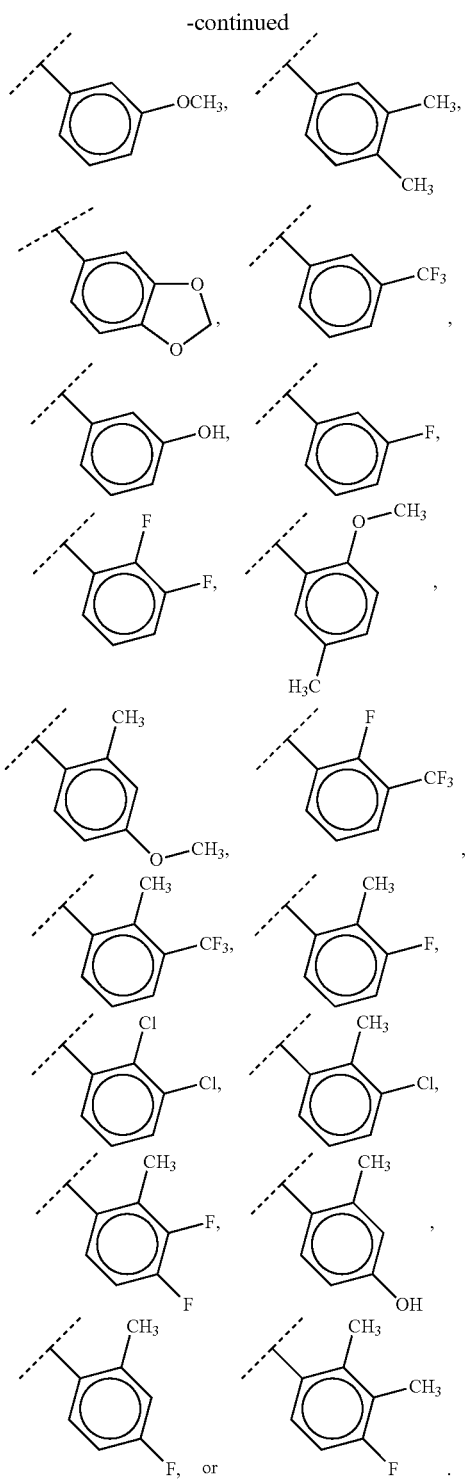

ments, $L^1$ is optionally substituted alkynylene. In certain embodiments, $L^1$ is —C≡C—. In certain embodiments, $L^1$ is —O—. In certain embodiments, $L^1$ is —NR$^L$—, e.g., —NH—. In certain embodiments, $L^1$ is —C(=O)—. In certain embodiments, L is —C(=O)NR$^L$—, e.g., —C(=O)NH—. In certain embodiments, $L^1$ is —NR$^L$C(=O)—, e.g., —NHC(=O)—.

In certain embodiments, $R^L$ is hydrogen. In certain embodiments, $R^L$ is optionally substituted $C_{1-6}$ alkyl. In certain embodiments, $R^L$ is a nitrogen protecting group.

As generally described herein, each $R^9$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^9$, —N(R$^{9a}$)$_2$, —S(=O)$_2$R$^{9a}$, —S(=O)$_2$OR$^{9a}$, or —S(=O)$_2$N(R$^{9a}$)$_2$, or two $R^9$ are joined to form an optionally substituted carbocyclic, heterocyclic, aryl, or heteroaryl ring, wherein each $R^{9a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{9a}$ are joined to form an optionally substituted heteroaryl or optionally substituted heterocyclic ring.

In certain embodiments, at least one $R^9$ is —NO$_2$. In certain embodiments, at least one $R^9$ is —CN. In certain embodiments, at least one $R^9$ is halogen. In some embodiments, at least one $R^9$ is —F. In some embodiments, at least one $R^9$ is —Cl, —Br, or —I. In certain embodiments, at least one $R^9$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^9$ is methyl. In certain embodiments, at least one $R^9$ is ethyl, propyl, or butyl. In certain embodiments, at least one $R^9$ is optionally substituted alkenyl, e.g., optionally substituted $C_{2-6}$ alkenyl. In certain embodiments, at least one $R^9$ is vinyl, allyl, or prenyl. In certain embodiments, at least one $R^9$ is optionally substituted alkynyl, e.g., $C_{2-6}$ alkynyl.

In certain embodiments, at least one $R^9$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^9$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^9$ is optionally substituted aryl, e.g., optionally substituted phenyl. In certain embodiments, at least one $R^9$ is optionally substituted heteroaryl, e.g., optionally substituted 5-6 membered heteroaryl or optionally substituted 9-10 membered bicyclic heteroaryl. In certain embodiments, at least one $R^9$ is optionally substituted aralkyl, e.g., optionally substituted benzyl. In certain embodiments, at least one $R^9$ is optionally substituted heteroaralkyl, e.g., methyl substituted with a 5-6 membered heteroaryl ring.

As generally described herein, $L^1$ is a bond, optionally substituted alkylene, optionally substituted alkenylene, optionally substituted alkynylene, —O—, —NR$^L$—, —C(=O)—, —C(=O)NR$^L$—, or —NR$^L$C(=O)—, wherein $R^L$ is hydrogen, optionally substituted $C_{1-6}$ alkyl, or a nitrogen protecting group.

In certain embodiments, $L^1$ is a bond, such that $R^2$ and ring B are directly attached. In certain embodiments, $L^1$ is optionally substituted alkylene. In certain embodiments, $L^1$ is optionally substituted alkenylene. In certain embodi- In certain embodiments, at least one $R^9$ is optionally substituted acyl, e.g., —CHO, —CO$_2$H, or —C(=O)NH$_2$. In certain embodiments, at least one $R^9$ is —C(=O)$R^{9a}$, —C(=O)O$R^{9a}$, —C(=O)NH($R^{9a}$), or —C(=O)N($R^{9a}$)$_2$. In certain embodiments, at least one $R^9$ is —C(=O)$R^{9a}$, and $R^{9a}$ is optionally substituted alkyl, e.g., $R^9$ is —C(=O)Me. In certain embodiments, at least one $R^9$ is —C(=O)$R^{9a}$, and $R^{9a}$ is optionally substituted alkenyl. In certain embodiments, at least one $R^9$ is —C(=O)$R^{9a}$, and $R^{9a}$ is optionally substituted carbocyclyl, heterocyclyl, aryl, or heteroaryl. In certain embodiments, at least one $R^9$ is —C(=O)O$R^{9a}$, and $R^{9a}$ is optionally substituted alkyl. In certain embodiments, at least one $R^9$ is —C(=O)O$R^{9a}$, and $R^{9a}$ is optionally substituted alkenyl. In certain embodiments, at least one $R^9$ is —C(=O)O$R^{9a}$, and $R^{9a}$ is optionally substituted carbocyclyl, heterocyclyl, aryl, or heteroaryl. In certain embodiments, at least one $R^9$ is —C(=O)N($R^{9a}$)$_2$, and at least one $R^{9a}$ is optionally substituted alkyl. In certain embodiments, at least one $R^9$ is —C(=O)NH$R^{9a}$, and $R^{9a}$ is optionally substituted alkyl. In certain embodiments, at least one $R^9$ is —C(=O)NH$R^{9a}$, and $R^{9a}$ is optionally substituted alkenyl. In certain embodiments, at least one $R^9$ is —C(=O)NH$R^{9a}$, and $R^{9a}$ is optionally substituted carbocyclyl, heterocyclyl, aryl, or heteroaryl.

In certain embodiments, at least one $R^9$ is —O$R^{9a}$, e.g., —OH. In certain embodiments, at least one $R^9$ is —O$R^{9a}$, and $R^{9a}$ is optionally substituted alkyl. In certain embodiments, at least one $R^9$ is —O$R^{9a}$, and $R^{9a}$ is optionally alkenyl. In certain embodiments, at least one $R^9$ is —O$R^{9a}$, and $R^{9a}$ is optionally substituted carbocyclyl, optionally substituted heterocyclyl, optionally substituted aryl optionally substituted heteroaryl. In certain embodiments, at least one $R^9$ is —O$R^{9a}$, and $R^{9a}$ is optionally substituted acyl, e.g., $R^9$ is —OC(=O)$R^{9a}$, —OC(=O)O$R^{9a}$, or —OC(=O)N($R^{9a}$)$_2$. In certain embodiments, at least one $R^9$ is —O$R^9$, and $R^{9a}$ is an oxygen protecting group.

In certain embodiments, at least one $R^9$ is —N($R^{9a}$)$_2$, e.g., —NH$_2$, —NH$R^{9a}$. In certain embodiments, at least one $R^9$ is —NH($R^{9a}$), and $R^{9a}$ is optionally substituted alkyl. In certain embodiments, at least one $R^9$ is —N($R^{9a}$)$_2$, and at least one $R^{9a}$ is optionally substituted alkyl. In certain embodiments, at least one $R^9$ is —NH$R^{9a}$, and $R^{9a}$ is optionally substituted carbocyclyl, optionally substituted heterocyclyl, optionally substituted aryl, or optionally substituted heteroaryl. In certain embodiments, at least one $R^9$ is —NH$R^{9a}$, and $R^{9a}$ is optionally substituted acyl, e.g., $R^9$ is —NHC(=O)$R^{9a}$, —NHC(=O)O$R^{9a}$, or —NHC(=O)NH$R^{9a}$ In certain embodiments, at least one $R^9$ is —N($R^{9a}$)$_2$, and at least one $R^{9a}$ is a nitrogen protecting group. In certain embodiments, at least one $R^9$ is —N($R^{9a}$)$_2$, and $R^{9a}$ are joined to form an optionally substituted heterocyclic or optionally substituted heteroaryl ring.

In certain embodiments, at least one $R^9$ is —S(=O)$_2$$R^{9a}$. In certain embodiments, at least one $R^9$ is —S(=O)$_2$$R^{9a}$, and $R^{9a}$ is optionally substituted alkyl, e.g., $R^9$ is —S(=O)$_2$Me. In certain embodiments, at least one $R^9$ is —S(=O)2R9a, and $R^{9a}$ is optionally substituted alkenyl. In certain embodiments, at least one $R^9$ is —S(=O)$_2$$R^{9a}$, and $R^{9a}$ is optionally substituted carbocyclyl, heterocyclyl, aryl, or heteroaryl. In certain embodiments, at least one $R^9$ is —S(=O)$_2$O$R^{9a}$. In certain embodiments, at least one $R^9$ is —S(=O)$_2$O$R^{9a}$, and $R^{9a}$ is optionally substituted alkyl. In certain embodiments, at least one $R^9$ is —S(=O)$_2$O$R^{9a}$, and $R^{9a}$ is optionally substituted alkenyl. In certain embodiments, at least one $R^9$ is —S(=O)$_2$O$R^{9a}$, and $R^{9a}$ is optionally substituted carbocyclyl, heterocyclyl, aryl, or heteroaryl. In certain embodiments, at least one $R^9$ is —S(=O)$_2$N($R^{9a}$)$_2$ or —S(=O)$_2$NH$R^{9a}$. In certain embodiments, at least one $R^9$ is —S(=O)$_2$N($R^{9a}$)$_2$, and at least one $R^{9a}$ is optionally substituted alkyl. In certain embodiments, at least one $R^9$ is —S(=O)$_2$NH$R^{9a}$, and $R^{9a}$ is optionally substituted alkyl. In certain embodiments, at least one $R^9$ is —S(=O)$_2$NH$R^{9a}$, and $R^{9a}$ is optionally substituted alkenyl. In certain embodiments, at least one $R^9$ is —S(=O)$_2$NH$R^{9a}$, and $R^{9a}$ is optionally substituted carbocyclyl, heterocyclyl, aryl, or heteroaryl.

In certain embodiments, an $R^9$ ortho to the bond connecting Ring A and Ring B is —NO$_2$. In certain embodiments, an $R^9$ ortho to the bond connecting Ring A and Ring B is —CN. In certain embodiments, an $R^9$ ortho to the bond connecting Ring A and Ring B is halogen. In some embodiments, an $R^9$ ortho to the bond connecting Ring A and Ring B is —F. In some embodiments, an $R^9$ ortho to the bond connecting Ring A and Ring B is —Cl, —Br, or —I. In certain embodiments, an $R^9$ ortho to the bond connecting Ring A and Ring B is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^9$ ortho to the bond connecting Ring A and Ring B is methyl. In certain embodiments, an $R^9$ ortho to the bond connecting Ring A and Ring B is ethyl, propyl, or butyl. In certain embodiments, an $R^9$ ortho to the bond connecting Ring A and Ring B is optionally substituted alkenyl, e.g., optionally substituted $C_{2-6}$ alkenyl. In certain embodiments, an $R^9$ ortho to the bond connecting Ring A and Ring B is vinyl, allyl, or prenyl. In certain embodiments, an $R^9$ ortho to the bond connecting Ring A and Ring B is optionally substituted alkynyl, e.g., $C_{2-6}$ alkynyl.

In certain embodiments, an $R^9$ ortho to the bond connecting Ring A and Ring B is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^9$ ortho to the bond connecting Ring A and Ring B is optionally substituted heterocyclyl, e.g., optionally substituted 3-6 membered heterocyclyl, optionally substituted 3-$^4$ membered heterocyclyl, optionally substituted $^4$-5 membered heterocyclyl, or optionally substituted 5-6 membered heterocyclyl.

In certain embodiments, an $R^9$ ortho to the bond connecting Ring A and Ring B is optionally substituted aryl, e.g., optionally substituted phenyl. In certain embodiments, an $R^9$ ortho to the bond connecting Ring A and Ring B is optionally substituted heteroaryl, e.g., optionally substituted 5-6 membered heteroaryl or optionally substituted 9-10 membered bicyclic heteroaryl. In certain embodiments, an $R^9$ ortho to the bond connecting Ring A and Ring B is optionally substituted aralkyl, e.g., optionally substituted benzyl. In certain embodiments, an $R^9$ ortho to the bond connecting Ring A and Ring B is optionally substituted heteroaralkyl, e.g., methyl substituted with a 5-6 membered heteroaryl ring.

In certain embodiments, an $R^9$ ortho to the bond connecting Ring A and Ring B is optionally substituted acyl, e.g., —CHO, —CO$_2$H, or —C(=O)NH$_2$. In certain embodiments, an $R^9$ ortho to the bond connecting Ring A and Ring B is —C(=O)$R^{9a}$, —C(=O)O$R^{9a}$, —C(=O)NH($R^{9a}$), or —C(=O)N($R^{9a}$)$_2$. In certain embodiments, an $R^9$ ortho to the bond connecting Ring A and Ring B is —C(=O)$R^{9a}$, and $R^{9a}$ is optionally substituted alkyl, e.g., $R^9$ is —C(=O)Me. In certain embodiments, an $R^9$ ortho to the bond connecting Ring A and Ring B is —C(=O)$R^{9a}$, and $R^{9a}$ is optionally substituted alkenyl. In certain embodiments, an $R^9$ ortho to the bond connecting Ring A and Ring B is —C(=O)$R^{9a}$, and $R^{9a}$ is optionally substituted carbocyclyl, heterocyclyl, aryl, or heteroaryl. In certain embodiments, an $R^9$ ortho to the bond connecting Ring A and Ring B is —C(=O)O$R^{9a}$, and $R^{9a}$ is optionally substituted alkyl. In certain embodiments, an $R^9$ ortho to the bond connecting Ring A and Ring B is —C(=O)O$R^{9a}$, and $R^{9a}$ is optionally substituted alkenyl. In certain embodiments, an $R^9$ ortho to the bond connecting Ring A and Ring B is —C(=O)O$R^{9a}$, and $R^{9a}$ is optionally substituted carbocyclyl, heterocyclyl, aryl, or heteroaryl. In certain embodiments, an $R^9$ ortho to the bond connecting Ring A and Ring B is —C(=O)N($R^{9a}$)$_2$, and at least one $R^{9a}$ is optionally substituted alkyl. In certain embodiments, an $R^9$ ortho to the bond connecting Ring A and Ring B is —C(=O)NH$R^{9a}$, and $R^{9a}$ is optionally substituted alkyl. In certain embodiments, an $R^9$ ortho to the bond connecting Ring A and Ring B is —C(=O)NH$R^{9a}$, and $R^{9a}$ is optionally substituted alkenyl. In certain embodiments, an $R^9$ ortho to the bond connecting Ring A and Ring B is —C(=O)NH$R^{9a}$, and $R^{9a}$ is optionally substituted carbocyclyl, heterocyclyl, aryl, or heteroaryl.

In certain embodiments, an $R^9$ ortho to the bond connecting Ring A and Ring B is —O$R^{9a}$, e.g., —OH. In certain embodiments, an $R^9$ ortho to the bond connecting Ring A and Ring B is —O$R^{9a}$, and $R^{9a}$ is optionally substituted alkyl. In certain embodiments, an $R^9$ ortho to the bond connecting Ring A and Ring B is —O$R^{9a}$, and $R^{9a}$ is optionally alkenyl. In certain embodiments, an $R^9$ ortho to the bond connecting Ring A and Ring B is —O$R^{9a}$, and $R^{9a}$ is optionally substituted carbocyclyl, optionally substituted heterocyclyl, optionally substituted aryl optionally substituted heteroaryl. In certain embodiments, an $R^9$ ortho to the bond connecting Ring A and Ring B is —O$R^{9a}$, and $R^{9a}$ is optionally substituted acyl, e.g., $R^9$ is —OC(=O)$R^{9a}$, —OC(=O)O$R^{9a}$, or —OC(=O)N($R^{9a}$)$_2$. In certain embodiments, an $R^9$ ortho to the bond connecting Ring A and Ring B is —O$R^{9a}$, and $R^{9a}$ is an oxygen protecting group.

In certain embodiments, an $R^9$ ortho to the bond connecting Ring A and Ring B is —N($R^{9a}$)$_2$, e.g., —NH$_2$, —NH$R^{9a}$. In certain embodiments, an $R^9$ ortho to the bond connecting Ring A and Ring B is —NH($R^{9a}$), and $R^{9a}$ is optionally substituted alkyl. In certain embodiments, an $R^9$ ortho to the bond connecting Ring A and Ring B is —N($R^{9a}$)$_2$, and at least one $R^{9a}$ is optionally substituted alkyl. In certain embodiments, an $R^9$ ortho to the bond connecting Ring A and Ring B is —NH$R^{9a}$, and $R^{9a}$ is optionally substituted carbocyclyl, optionally substituted heterocyclyl, optionally substituted aryl, or optionally substituted heteroaryl. In certain embodiments, an $R^9$ ortho to the bond connecting Ring A and Ring B is —NH$R^{9a}$, and $R^{9a}$ is optionally substituted acyl, e.g., $R^9$ is —NHC(=O)$R^{9a}$, —NHC(=O)O$R^{9a}$, or —NHC(=O)NH$R^{9a}$. In certain embodiments, an $R^9$ ortho to the bond connecting Ring A and Ring B is —N($R^{9a}$)$_2$, and at least one $R^{9a}$ is a nitrogen protecting group. In certain embodiments, an $R^9$ ortho to the bond connecting Ring A and Ring B is —N($R^{9a}$)$_2$, and $R^{9a}$ are joined to form an optionally substituted heterocyclic or optionally substituted heteroaryl ring.

In certain embodiments, an $R^9$ ortho to the bond connecting Ring A and Ring B is —S(=O)$_2$$R^{9a}$. In certain embodiments, an $R^9$ ortho to the bond connecting Ring A and Ring B is —S(=O)$_2$$R^{9a}$, and $R^{9a}$ is optionally substituted alkyl, e.g., $R^9$ is —S(=O)$_2$Me. In certain embodiments, an $R^9$ ortho to the bond connecting Ring A and Ring B is —S(=O)$_2$$R^{9a}$, and $R^{9a}$ is optionally substituted alkenyl. In certain embodiments, an $R^9$ ortho to the bond connecting Ring A and Ring B is —S(=O)$_2$$R^{9a}$, and $R^{9a}$ is optionally substituted carbocyclyl, heterocyclyl, aryl, or heteroaryl. In certain embodiments, an $R^9$ ortho to the bond connecting Ring A and Ring B is —S(=O)$_2$O$R^{9a}$. In certain embodiments, an $R^9$ ortho to the bond connecting Ring A and Ring B is —S(=O)$_2$O$R^{9a}$, and $R^{9a}$ is optionally substituted alkyl. In certain embodiments, an $R^9$ ortho to the bond connecting Ring A and Ring B is —S(=O)$_2$O$R^{9a}$, and $R^{9a}$ is optionally substituted alkenyl. In certain embodiments, an $R^9$ ortho to the bond connecting Ring A and Ring B is —S(=O)$_2$O$R^{9a}$, and $R^{9a}$ is optionally substituted carbocyclyl, heterocyclyl, aryl, or heteroaryl. In certain embodiments, an $R^9$ ortho to the bond connecting Ring A and Ring B is —S(=O)$_2$N($R^{9a}$)$_2$ or —S(=O)$_2$NH$R^{9a}$. In certain embodiments, an $R^9$ ortho to the bond connecting Ring A and Ring B is —S(=O)$_2$N($R^{9a}$)$_2$, and at least one $R^{9a}$ is optionally substituted alkyl. In certain embodiments, an $R^9$ ortho to the bond connecting Ring A and Ring B is —S(=O)$_2$NH$R^{9a}$, and $R^{9a}$ is optionally substituted alkyl. In certain embodiments, an $R^9$ ortho to the bond connecting Ring A and Ring B is —S(=O)$_2$NH$R^{9a}$, and $R^{9a}$ is optionally substituted alkenyl. In certain embodiments, an $R^9$ ortho to the bond connecting Ring A and Ring B is —S(=O)$_2$NH$R^{9a}$, and $R^{9a}$ is optionally substituted carbocyclyl, heterocyclyl, aryl, or heteroaryl.

In certain embodiments, $R^2$ is of formula:

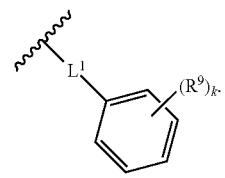

In certain embodiments, $R^2$ is of formula:

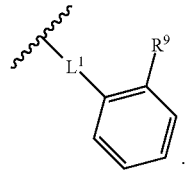

In certain embodiments, $R^2$ is of formula:

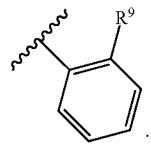

In certain embodiments, $R^2$ is of formula:

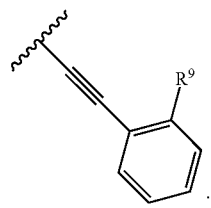

101
In certain embodiments, $R^2$ is of formula:
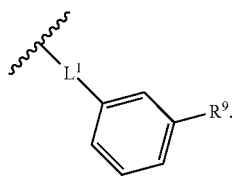
In certain embodiments, $R^2$ is of formula:
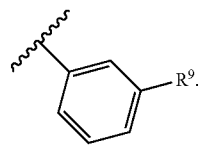
In certain embodiments, $R^2$ is of formula:
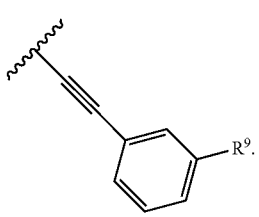
In certain embodiments, $R^2$ is of formula:
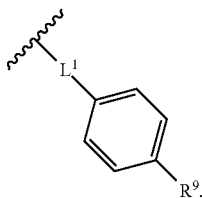
In certain embodiments, $R^2$ is of formula:
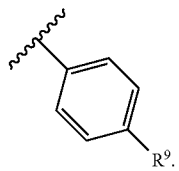
In certain embodiments, $R^2$ is of formula:
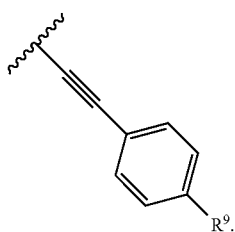
102
In certain embodiments, $R^2$ is of formula:
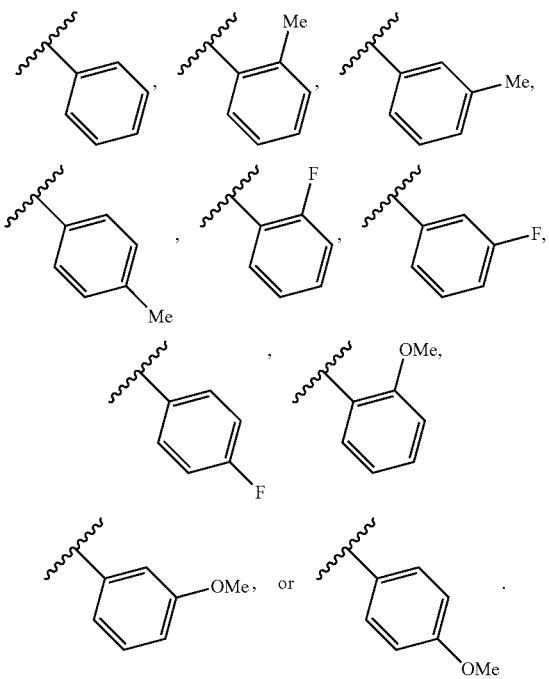
In certain embodiments, $R^2$ is of formula:
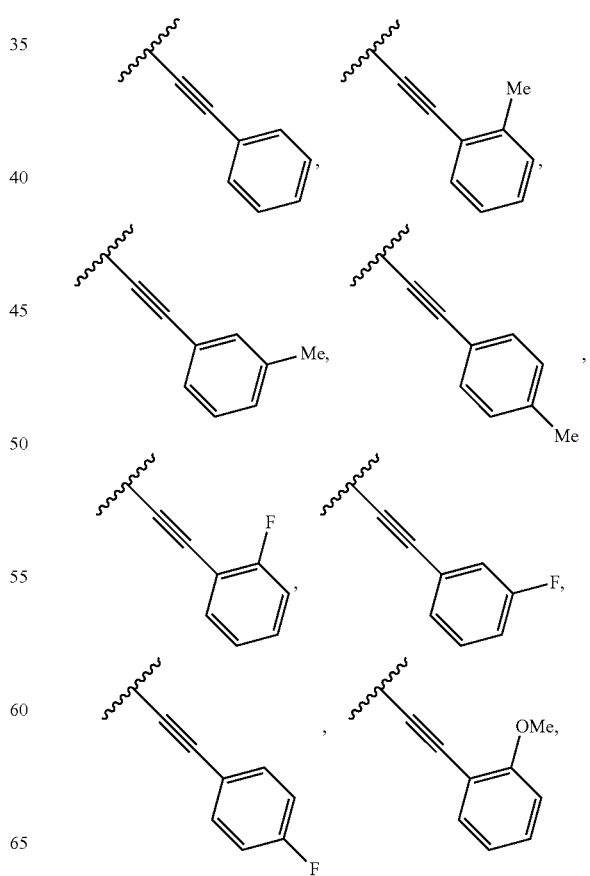

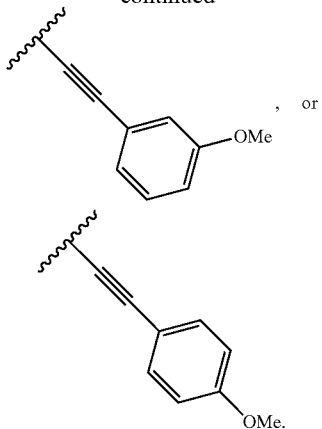

$R^4$

As generally defined herein, each independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$OR^{4a}$, or —$N(R^{4a})_2$, wherein each $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{4a}$ are joined to form an optionally substituted heteroaryl or optionally substituted heterocyclic ring.

In certain embodiments, p is 0 or 1. In certain embodiments, p is 0. In certain embodiments, p is 1. In certain embodiments, p is 2. In certain embodiments, p is 3. In certain embodiments, p is 4.

In certain embodiments, at least one $R^4$ is halogen. In some embodiments, at least one $R^4$ is —F. In some embodiments, at least one $R^4$ is —Cl, —Br, or —I. In certain embodiments, at least one $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^4$ is methyl. In certain embodiments, at least one $R^4$ is ethyl, propyl, or butyl. In certain embodiments, at least one $R^4$ is optionally substituted alkenyl, e.g., optionally substituted $C_{2-6}$ alkenyl. In certain embodiments, at least one $R^4$ is vinyl, allyl, or prenyl. In certain embodiments, at least one $R^4$ is optionally substituted alkynyl, e.g., $C_{2-6}$ alkynyl.

In certain embodiments, at least one $R^4$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^4$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^4$ is optionally substituted aryl, e.g., optionally substituted phenyl. In certain embodiments, at least one $R^4$ is optionally substituted heteroaryl, e.g., optionally substituted 5-6 membered heteroaryl or optionally substituted 9-10 membered bicyclic heteroaryl. In certain embodiments, at least one $R^4$ is optionally substituted aralkyl, e.g., optionally substituted benzyl. In certain embodiments, at least one $R^4$ is optionally substituted heteroaralkyl, e.g., methyl substituted with a 5- to 6-membered heteroaryl ring.

In certain embodiments, at least one $R^4$ is optionally substituted acyl, e.g., —CHO, —$CO_2H$, or —C(=O)$NH_2$. In certain embodiments, at least one $R^4$ is —C(=O)$R^{4a}$, —C(=O)$OR^{4a}$, —C(=O)NH($R^{4a}$), or —C(=O)$N(R^{4a})_2$. In certain embodiments, at least one $R^4$ is —C(=O)$R^{4a}$ and $R^{4a}$ is optionally substituted alkyl, e.g., $R^4$ is —C(=O)Me. In certain embodiments, at least one $R^4$ is —C(=O)$R^{4a}$, and $R^{4a}$ is optionally substituted alkenyl. In certain embodiments, at least one $R^4$ is —C(=O)$R^{4a}$, and $R^{4a}$ is optionally substituted carbocyclyl, heterocyclyl, aryl, or heteroaryl. In certain embodiments, at least one $R^4$ is —C(=O)$OR^{4a}$, and $R^{4a}$ is optionally substituted alkyl. In certain embodiments, at least one $R^4$ is —C(=O)$OR^{4a}$, and $R^{4a}$ is optionally substituted alkenyl. In certain embodiments, at least one $R^4$ is —C(=O)$OR^{4a}$, and $R^{4a}$ is optionally substituted carbocyclyl, heterocyclyl, aryl, or heteroaryl. In certain embodiments, at least one $R^4$ is —C(=O)$N(R^{4a})_2$, and at least one $R^{4a}$ is optionally substituted alkyl. In certain embodiments, at least one $R^4$ is —C(=O)$NHR^{4a}$, and $R^{4a}$ is optionally substituted alkyl. In certain embodiments, at least one $R^4$ is —C(=O)$NHR^{4a}$, and $R^{4a}$ is optionally substituted alkenyl. In certain embodiments, at least one $R^4$ is —C(=O)$NHR^{4a}$, and $R^{4a}$ is optionally substituted carbocyclyl, heterocyclyl, aryl, or heteroaryl.

In certain embodiments, at least one $R^4$ is —$OR^{4a}$, e.g., —OH. In certain embodiments, at least one $R^4$ is —$OR^{4a}$, and $R^{4a}$ is optionally substituted alkyl. In certain embodiments, at least one $R^4$ is —$OR^{4a}$, and $R^{4a}$ is optionally substituted alkenyl. In certain embodiments, at least one $R^4$ is —$OR^{4a}$, and $R^{4a}$ is optionally substituted carbocyclyl, optionally substituted heterocyclyl, optionally substituted aryl optionally substituted heteroaryl. In certain embodiments, at least one $R^4$ is —$OR^{4a}$, and $R^{4a}$ is optionally substituted acyl, e.g., $R^4$ is —OC(=O)$R^{4a}$, —OC(=O)$OR^{4a}$, or —OC(=O)$N(R^{4a})_2$. In certain embodiments, at least one $R^4$ is —$OR^{4a}$, and $R^{4a}$ is an oxygen protecting group.

In certain embodiments, at least one $R^4$ is —$N(R^{4a})_2$, e.g., —$NH_2$, —$NHR^{4a}$. In certain embodiments, at least one $R^4$ is —$NH(R^{4a})$, and $R^{4a}$ is optionally substituted alkyl. In certain embodiments, at least one $R^4$ is —$N(R^{4a})_2$, and at least one $R^{4a}$ is optionally substituted alkyl. In certain embodiments, at least one $R^4$ is —$NHR^{4a}$, and $R^{4a}$ is optionally substituted carbocyclyl, optionally substituted heterocyclyl, optionally substituted aryl, or optionally substituted heteroaryl. In certain embodiments, at least one $R^4$ is —$NHR^{4a}$, and $R^{4a}$ is optionally substituted acyl, e.g., $R^4$ is —NHC(=O)$R^{4a}$, —NHC(=O)$OR^{4a}$, or —NHC(=O)$NHR^{4a}$ In certain embodiments, at least one $R^4$ is —$N(R^{4a})_2$, and at least one $R^{4a}$ is a nitrogen protecting group. In certain embodiments, at least one $R^4$ is —$N(R^{4a})_2$, and $R^{4a}$ are joined to form an optionally substituted heterocyclic or optionally substituted heteroaryl ring.

$R^5$

As generally defined herein, $R^5$ is hydrogen, optionally substituted alkyl, optionally substituted alkenyl, optionally substituted alkynyl, optionally substituted aralkyl, optionally substituted heteroaralkyl, optionally substituted acyl, —C(=O)$R^{5a}$, —C(=O)$OR^{5a}$, —C(=O)$N(R^{5a})_2$, —S(=O)$_2R^{5a}$, —S(=O)$_2OR^{5a}$, —S(=O)$_2N(R^{5a})_2$, or a nitrogen protecting group, wherein each $R^{5a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{5a}$ are joined to form an optionally substituted heteroaryl or optionally substituted heterocyclic ring.

In certain embodiments, $R^5$ is hydrogen, optionally substituted $C_{2-6}$ alkyl, optionally substituted alkenyl, optionally substituted alkynyl, optionally substituted aralkyl, optionally substituted heteroaralkyl, optionally substituted acyl, —C(=O)$R^{5a}$, —C(=O)O$R^{5a}$, —C(=O)N($R^{5a}$)$_2$, —S(=O)$_2R^{5a}$, —S(=O)$_2$O$R^{5a}$, —S(=O)$_2$N($R^{5a}$)$_2$, or a nitrogen protecting group, wherein each $R^{5a}$ is independently hydrogen, optionally substituted $C_{2-6}$ alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{5a}$ are joined to form an optionally substituted heteroaryl or optionally substituted heterocyclic ring.

In certain embodiments, $R^5$ is hydrogen, optionally substituted $C_{2-6}$ alkyl, optionally substituted alkenyl, optionally substituted alkynyl, optionally substituted aralkyl, optionally substituted heteroaralkyl, —C(=O)$R^{5a}$, —C(=O)O$R^{5a}$, —C(=O)N($R^{5a}$)$_2$, —S(=O)$_2R^{5a}$, —S(=O)$_2$O$R^{5a}$, or —S(=O)$_2$N($R^{5a}$)$_2$, wherein each $R^{5a}$ is independently hydrogen, optionally substituted $C_{2-6}$ alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{5a}$ are joined to form an optionally substituted heteroaryl or optionally substituted heterocyclic ring. In certain embodiments, $R^5$ is hydrogen, optionally substituted alkenyl, optionally substituted alkynyl, optionally substituted aralkyl, optionally substituted heteroaralkyl, —S(=O)$_2$O$R^{5a}$, or —S(=O)$_2$N($R^{5a}$)$_2$.

In certain embodiments, $R^5$ is a non-hydrogen group. In certain embodiments, $R^5$ is not alkyl. In certain embodiments, $R^5$ is a non-hydrogen group and is not alkyl, —C(=O)$R^{5a}$, or —S(=O)$_2R^{5a}$. In certain embodiments, $R^5$ is a non-hydrogen group and is not methyl, —C(=O)$R^{5a}$, or —S(=O)$_2R^{5a}$. In certain embodiments, $R^5$ is not nosyl. In certain embodiments, $R^5$ is not —CH$_3$, —C(=O)Me, or —S(=O)$_2$Me. In certain embodiments, $R^5$ is a nitrogen protecting group.

In certain embodiments, $R^5$ is hydrogen. In certain embodiments, $R^5$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^5$ is optionally substituted $C_{2-6}$ alkyl. In certain embodiments, $R^5$ is methyl. In certain embodiments, $R^5$ is ethyl, propyl, or butyl. In certain embodiments, $R^5$ is optionally substituted alkenyl, e.g., optionally substituted $C_{2-6}$ alkenyl. In certain embodiments, $R^5$ is vinyl, allyl, or prenyl. In certain embodiments, $R^5$ is optionally substituted alkynyl, e.g., $C_{2-6}$ alkynyl.

In certain embodiments, $R^5$ is of formula:

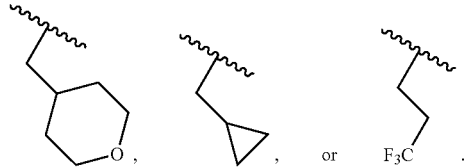 [SMILES: *CC1CCOCC1 ; *CC1CC1 ; *CCC(F)(F)F]

In certain embodiments, $R^5$ is optionally substituted aralkyl, e.g., optionally substituted benzyl. In certain embodiments, $R^5$ is optionally substituted heteroaralkyl, e.g., methyl substituted with a 5- to 6-membered heteroaryl ring.

In certain embodiments, $R^5$ is of formula:

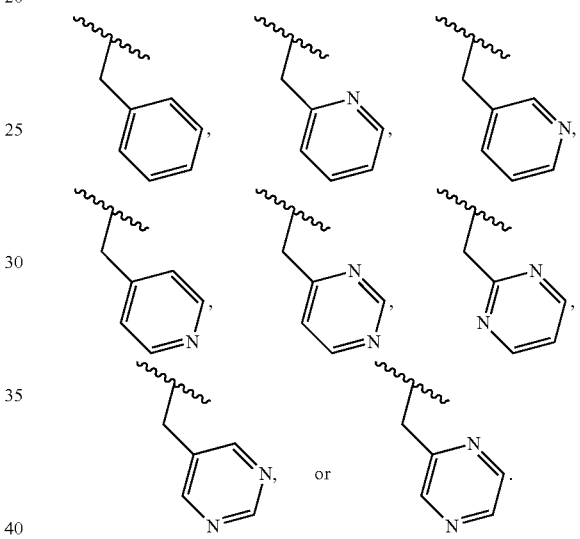

In certain embodiments, $R^5$ is optionally substituted acyl, e.g., —CHO, —CO$_2$H, or —C(=O)NH$_2$. In certain embodiments, $R^5$ is —C(=O)$R^{5a}$, —C(=O)O$R^{5a}$, —C(=O)NH($R^{5a}$), or —C(=O)N($R^{5a}$)$_2$. In certain embodiments, $R^5$ is —C(=O)$R^{5a}$, and $R^{5a}$ is optionally substituted alkyl, e.g., —C(=O)Me. In certain embodiments, $R^5$ is —C(=O)$R^{5a}$, and $R^{5a}$ is optionally substituted $C_{1-6}$ alkyl. In certain embodiments, $R^5$ is —C(=O)$R^{5a}$, and $R^{5a}$ is optionally substituted $C_{2-6}$ alkyl. In certain embodiments, $R^5$ is —C(=O)$R^{5a}$, and $R^{5a}$ is optionally substituted alkenyl. In certain embodiments, $R^5$ is —C(=O)$R^{5a}$, and $R^{5a}$ is optionally substituted carbocyclyl, heterocyclyl, aryl, or heteroaryl. In certain embodiments, $R^5$ is —C(=O)O$R^{5a}$, and $R^{5a}$ is optionally substituted alkyl. In certain embodiments, $R^5$ is —C(=O)O$R^{5a}$, and $R^{5a}$ is optionally substituted alkenyl. In certain embodiments, $R^5$ is —C(=O)O$R^{5a}$, and $R^{5a}$ is optionally substituted carbocyclyl, heterocyclyl, aryl, or heteroaryl. In certain embodiments, $R^5$ is —C(=O)N($R^{5a}$)$_2$, and at least one $R^{5a}$ is optionally substituted alkyl. In certain embodiments, $R^5$ is —C(=O)NH$R^{5a}$, and $R^{5a}$ is optionally substituted alkyl. In certain embodiments, $R^5$ is —C(=O)NH$R^{5a}$, and $R^{5a}$ is optionally substituted alkenyl. In certain embodiments, $R^5$ is —C(=O)NH$R^{5a}$, and $R^{5a}$ is optionally substituted carbocyclyl, heterocyclyl, aryl, or heteroaryl.

In certain embodiments, $R^5$ is of formula:
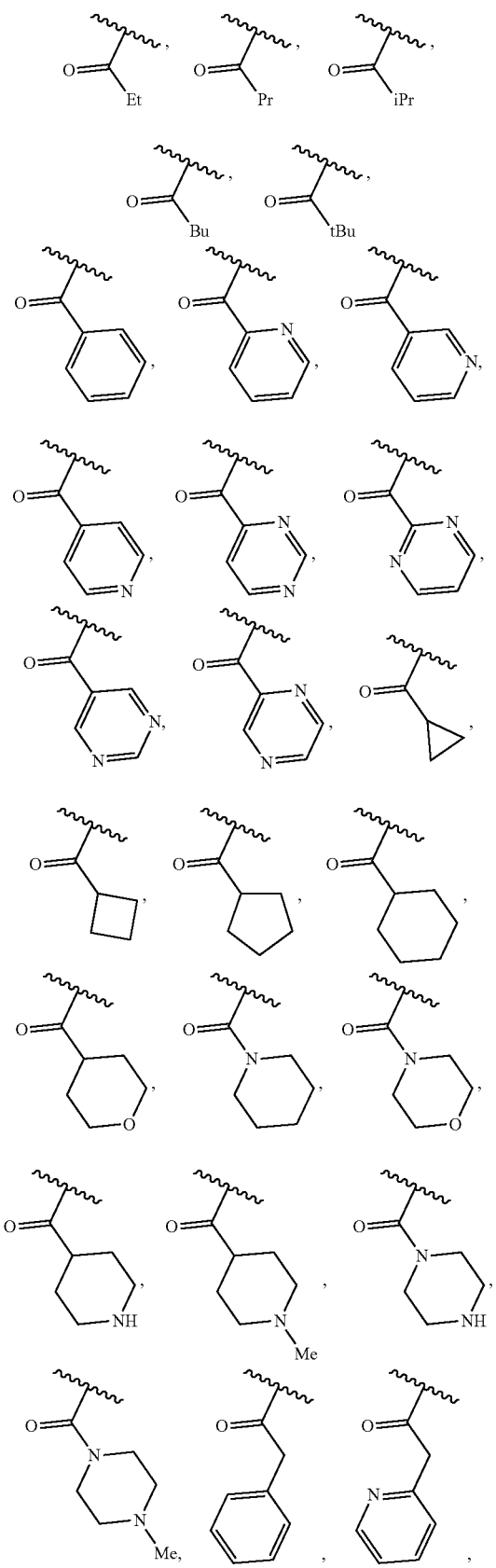
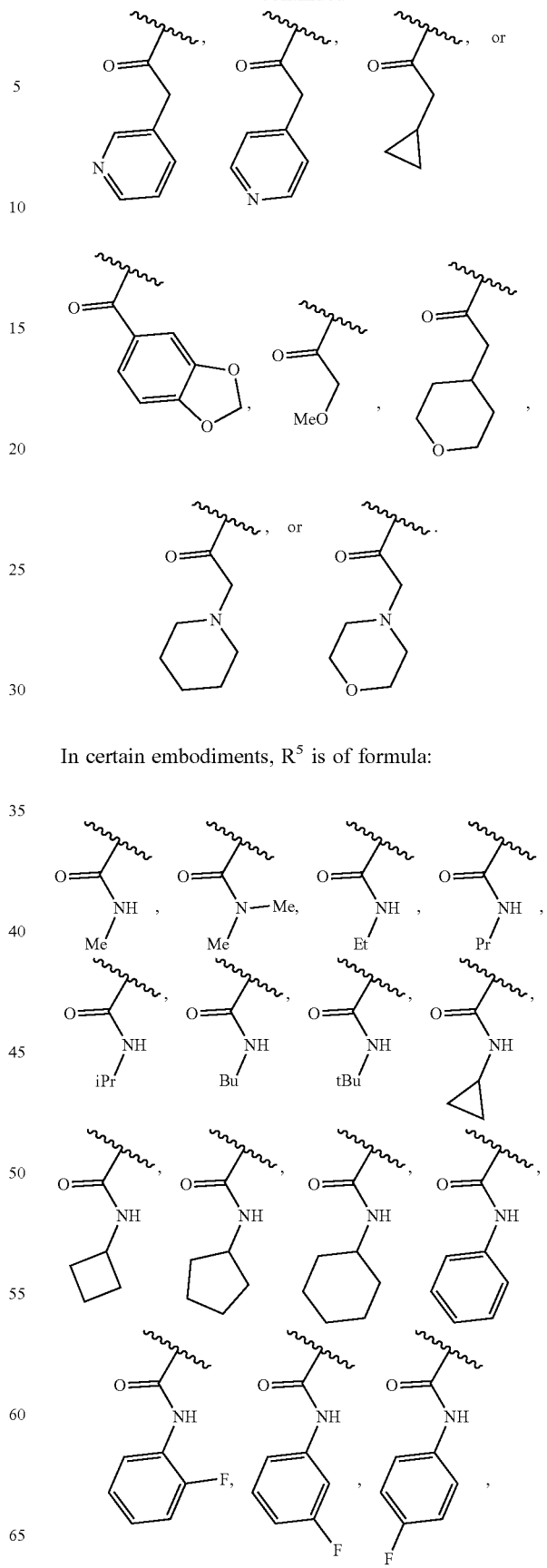
In certain embodiments, $R^5$ is of formula:

-continued

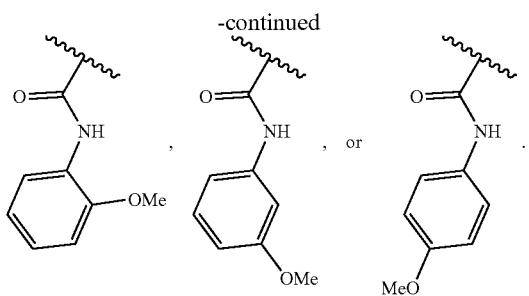

In certain embodiments, $R^5$ is $-S(=O)_2R^{5a}$. In certain embodiments, $R^5$ is $-S(=O)_2R^{5a}$, and $R^{5a}$ is optionally substituted alkyl, e.g., $R^5$ is $-S(=O)_2Me$. In certain embodiments, $R^5$ is $-S(=O)_2R^{5a}$, and $R^{5a}$ is optionally substituted $C_{1-6}$ alkyl. In certain embodiments, $R^5$ is $-S(=O)_2R^{5a}$, and $R^{5a}$ is optionally substituted $C_{2-6}$ alkyl. In certain embodiments, $R^5$ is $-S(=O)_2R^{5a}$, and $R^{5a}$ is optionally substituted alkenyl. In certain embodiments, $R^5$ is $-S(=O)_2R^{5a}$, and $R^{5a}$ is optionally substituted carbocyclyl, heterocyclyl, aryl, or heteroaryl. In certain embodiments, $R^5$ is $-S(=O)_2OR^{5a}$. In certain embodiments, $R^5$ is $-S(=O)_2OR^{5a}$, and $R^{5a}$ is optionally substituted alkyl. In certain embodiments, $R^5$ is $-S(=O)_2OR^{5a}$, and $R^{5a}$ is optionally substituted alkenyl. In certain embodiments, $R^5$ is $-S(=O)_2OR^{5a}$, and $R^{5a}$ is optionally substituted carbocyclyl, heterocyclyl, aryl, or heteroaryl. In certain embodiments, $R^5$ is $-S(=O)_2N(R^{5a})_2$ or $-S(=O)_2NHR^{5a}$. In certain embodiments, $R^5$ is $-S(=O)_2N(R^{5a})_2$, and at least one $R^{5a}$ is optionally substituted alkyl. In certain embodiments, $R^5$ is $-S(=O)_2NHR^{5a}$, and $R^{5a}$ is optionally substituted alkyl. In certain embodiments, $R^5$ is $-S(=O)_2NHR^{5a}$, and $R^{5a}$ is optionally substituted alkenyl. In certain embodiments, $R^5$ is $-S(=O)_2NHR^{5a}$, and $R^{5a}$ is optionally substituted carbocyclyl, heterocyclyl, aryl, or heteroaryl.

In certain embodiments, $R^5$ is of formula:

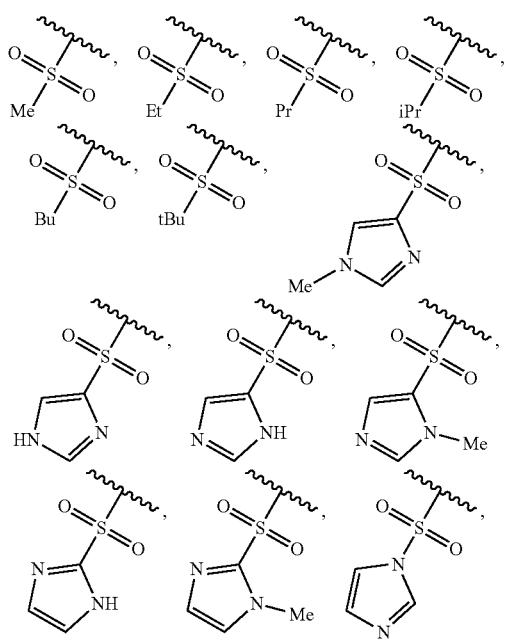

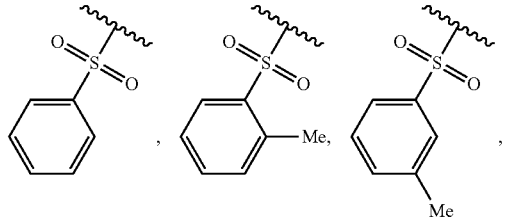

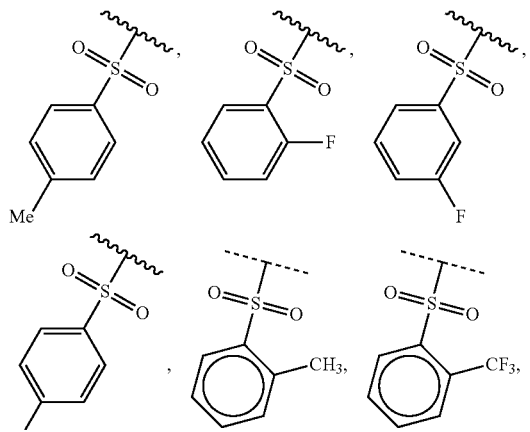

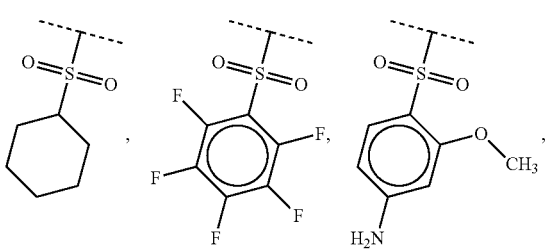

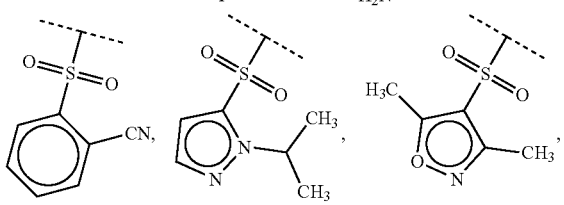

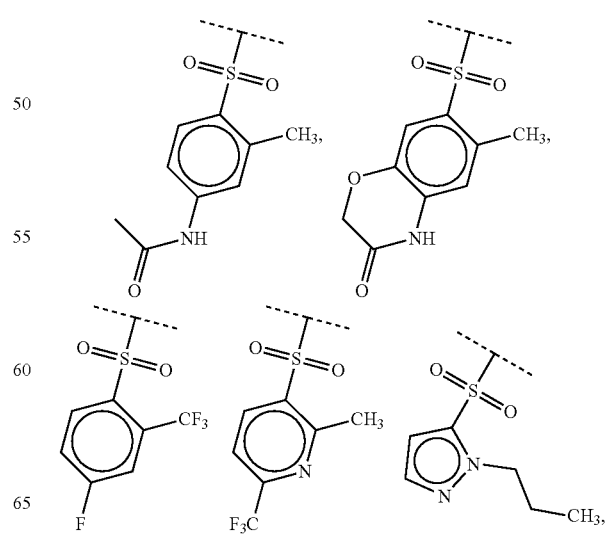

111
-continued
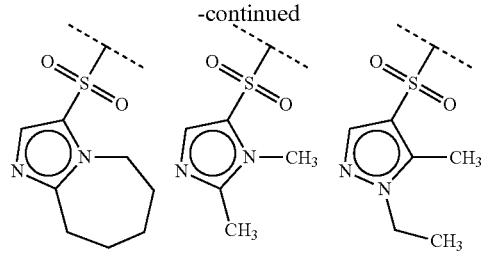
112
-continued
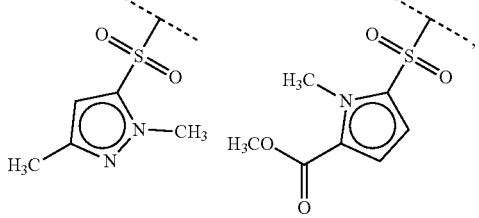
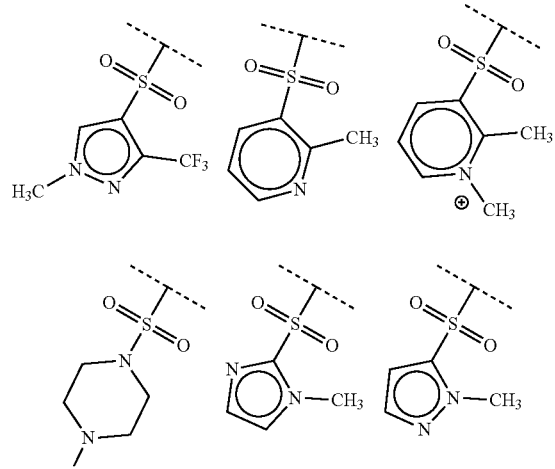
In certain embodiments, the compound of Formula (I) is a compound in Table 1 or 2, or a pharmaceutically acceptable salt, solvate, hydrate, polymorph, co-crystal, tautomer, stereoisomer, prodrug, or isotopically labeled derivative thereof.
TABLE 1
Exemplary compounds of Formula (I).
779
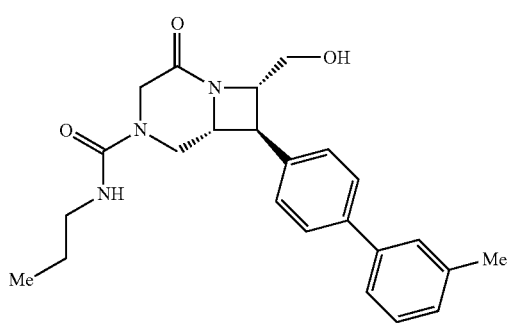 [SMILES: CCCNC(=O)N1CC(=O)N2[C@H](CO)[C@@H](c3ccc(-c4cccc(C)c4)cc3)[C@@H]2C1]
838
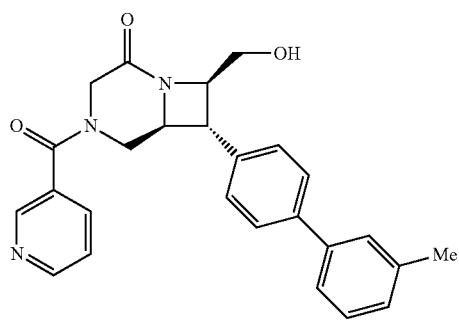 [SMILES: Cc1cccc(-c2ccc([C@@H]3[C@H]4CN(C(=O)c5cccnc5)CC(=O)N4[C@H]3CO)cc2)c1]

TABLE 1-continued

Exemplary compounds of Formula (I).

| Structure | No. |
|---|---|
| (structure) | 779-OMe |
| (structure) | 838-OMe |
| (structure) | 653 |
| (structure) | 904 |
| (structure) | 653-OMe |

TABLE 1-continued
Exemplary compounds of Formula (I).
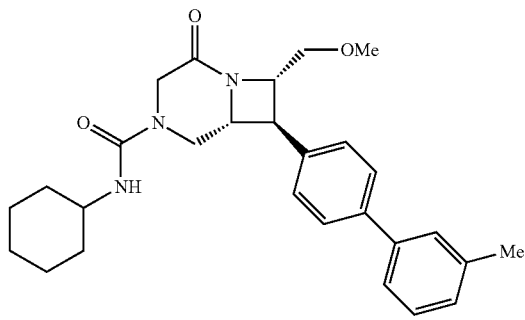 [SMILES: COC[C@@H]1[C@@H](c2ccc(-c3cccc(C)c3)cc2)[C@@H]2CN(C(=O)NC3CCCCC3)CC(=O)N12]
904-OMe
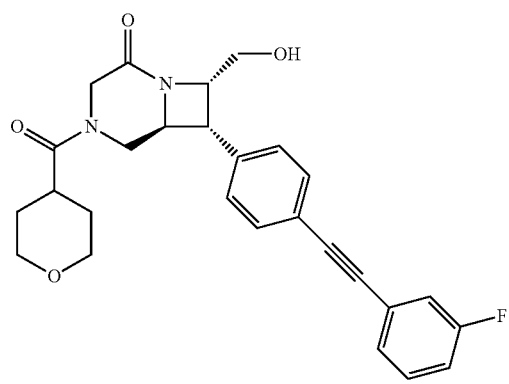 [SMILES: O=C(C1CCOCC1)N1CC(=O)N2[C@H](CO)[C@H](c3ccc(C#Cc4cccc(F)c4)cc3)[C@H]2C1]
142
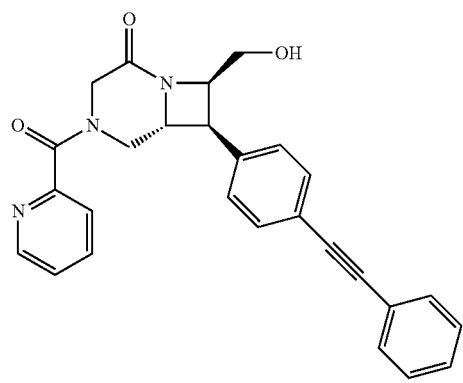 [SMILES: O=C(c1ccccn1)N1CC(=O)N2[C@@H](CO)[C@@H](c3ccc(C#Cc4ccccc4)cc3)[C@@H]2C1]
479
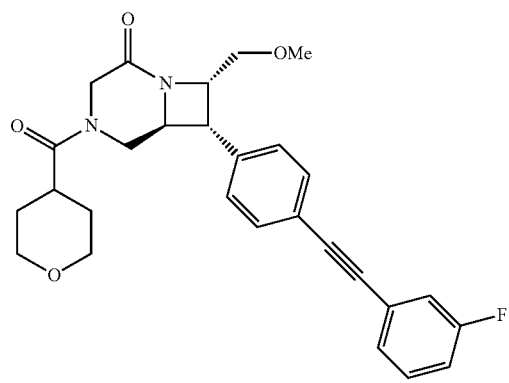 [SMILES: COC[C@@H]1[C@H](c2ccc(C#Cc3cccc(F)c3)cc2)[C@H]2CN(C(=O)C3CCOCC3)CC(=O)N12]
142-OMe TABLE 1-continued
Exemplary compounds of Formula (I).
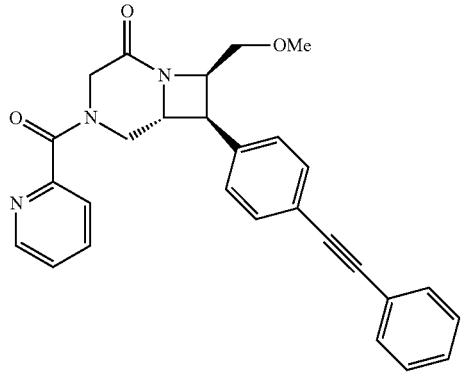 [SMILES: COC[C@H]1[C@@H](c2ccc(C#Cc3ccccc3)cc2)[C@@H]2CN(C(=O)c3ccccn3)CC(=O)N12]
479-OMe
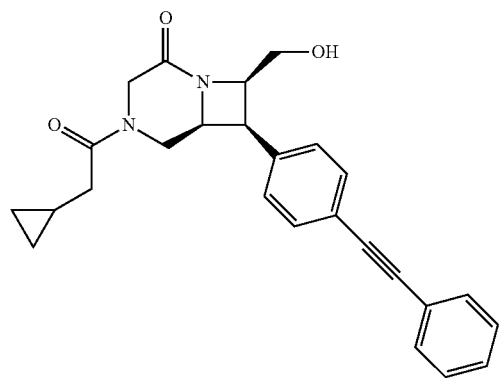 [SMILES: O=C(CC1CC1)N1CC(=O)N2[C@H](C1)[C@H](c1ccc(C#Cc3ccccc3)cc1)[C@@H]2CO]
187
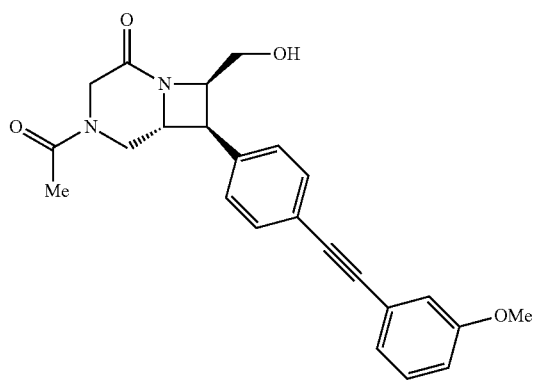 [SMILES: COc1cccc(C#Cc2ccc([C@@H]3[C@H](CO)N4C(=O)CN(C(C)=O)C[C@@H]34)cc2)c1]
608
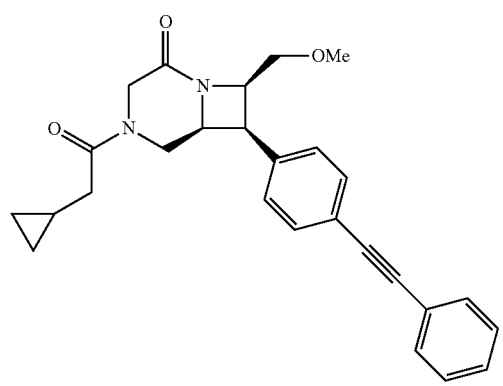 [SMILES: COC[C@H]1[C@@H](c2ccc(C#Cc3ccccc3)cc2)[C@H]2CN(C(=O)CC3CC3)CC(=O)N21]
187-OMe TABLE 1-continued
Exemplary compounds of Formula (I).
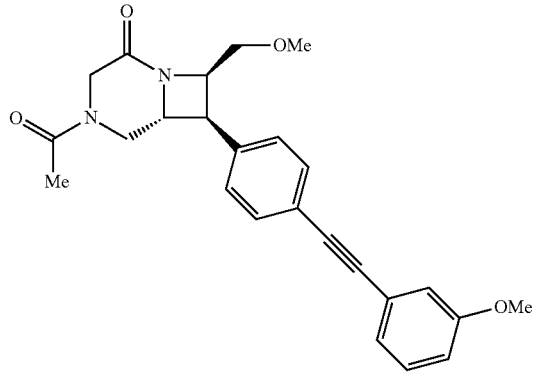 [SMILES: COC[C@H]1[C@@H](c2ccc(C#Cc3cccc(OC)c3)cc2)[C@@H]2CN(C(C)=O)CC(=O)N12]
608-OMe
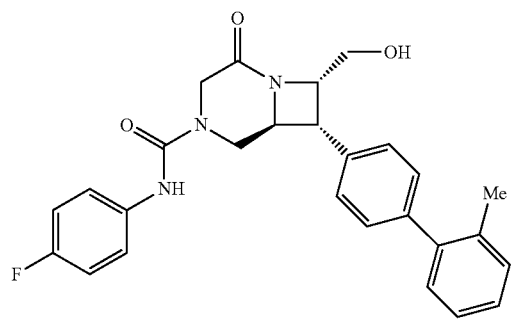 [SMILES: Cc1ccccc1-c1ccc([C@H]2[C@@H](CO)N3C(=O)CN(C(=O)Nc4ccc(F)cc4)C[C@H]23)cc1]
510
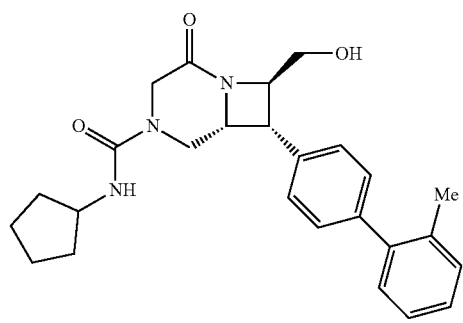 [SMILES: Cc1ccccc1-c1ccc([C@H]2[C@H](CO)N3C(=O)CN(C(=O)NC4CCCC4)C[C@@H]23)cc1]
504
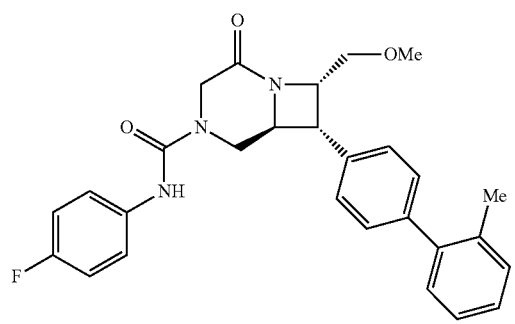 [SMILES: COC[C@@H]1[C@H](c2ccc(-c3ccccc3C)cc2)[C@H]2CN(C(=O)Nc3ccc(F)cc3)CC(=O)N12]
510-OMe TABLE 1-continued
Exemplary compounds of Formula (I).
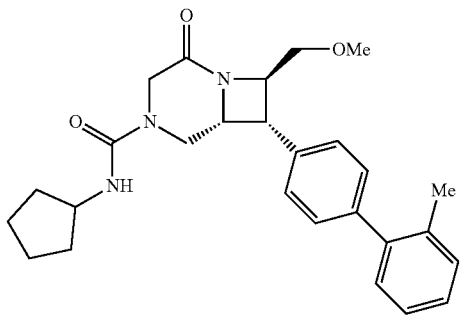
504-OMe
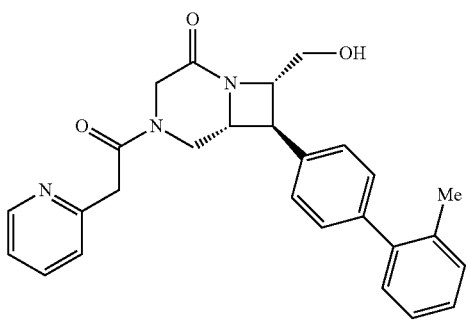 [SMILES: Cc1ccccc1-c1ccc([C@@H]2[C@@H](CO)N3C(=O)CN(C(=O)Cc4ccccn4)C[C@@H]23)cc1]
081
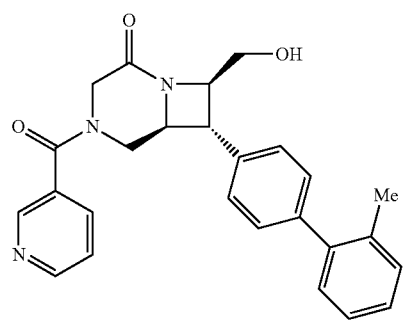 [SMILES: Cc1ccccc1-c1ccc([C@@H]2[C@H]3CN(C(=O)c4cccnc4)CC(=O)N3[C@H]2CO)cc1]
745
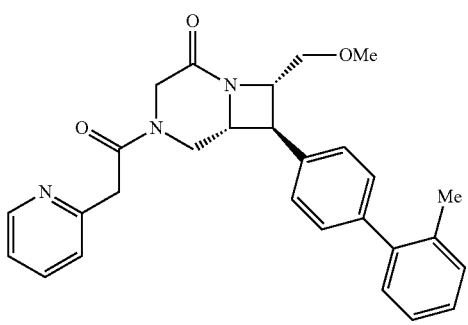 [SMILES: COC[C@@H]1[C@@H](c2ccc(-c3ccccc3C)cc2)[C@@H]2CN(C(=O)Cc3ccccn3)CC(=O)N12]
081-OMe
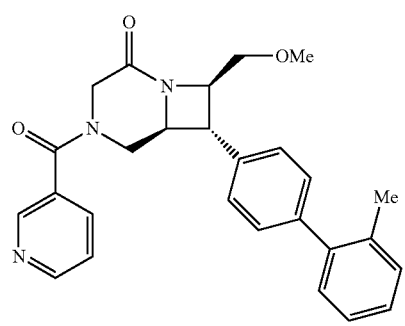 [SMILES: COC[C@H]1[C@H](c2ccc(-c3ccccc3C)cc2)[C@H]2CN(C(=O)c3cccnc3)CC(=O)N21]
745-OMe TABLE 1-continued
Exemplary compounds of Formula (I).
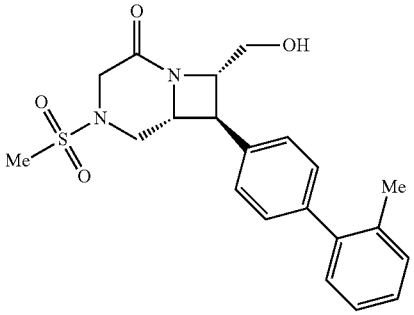 [SMILES: Cc1ccccc1-c1ccc([C@@H]2[C@@H](CO)N3C(=O)CN(S(C)(=O)=O)C[C@@H]23)cc1]
585
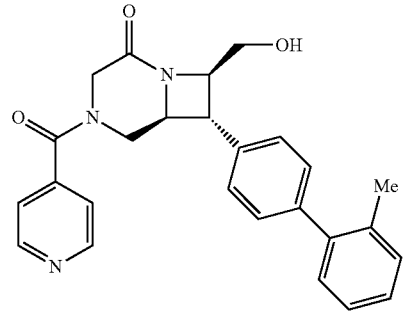 [SMILES: Cc1ccccc1-c1ccc([C@@H]2[C@H]3CN(C(=O)c4ccncc4)CC(=O)N3[C@H]2CO)cc1]
102
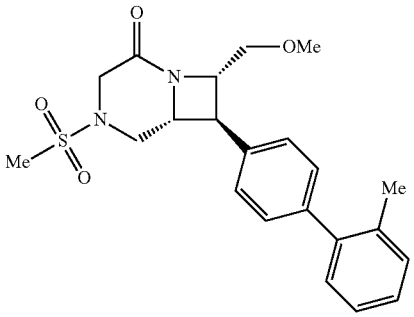 [SMILES: COC[C@@H]1[C@@H](c2ccc(-c3ccccc3C)cc2)[C@@H]2CN(S(C)(=O)=O)CC(=O)N12]
585-OMe
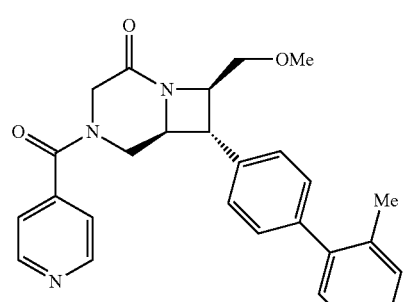
102-OMe TABLE 1-continued
Exemplary compounds of Formula (I).
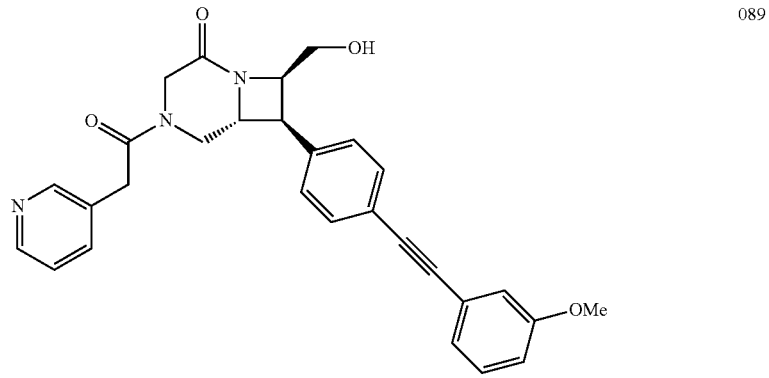
089
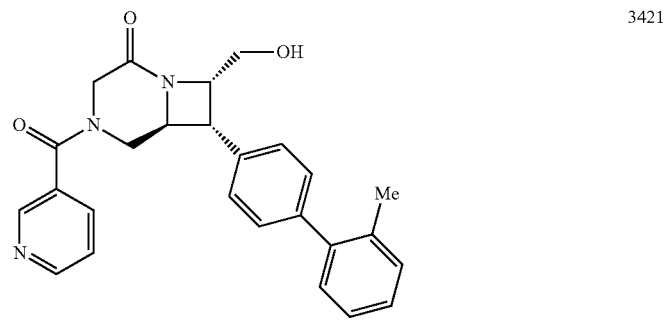
3421
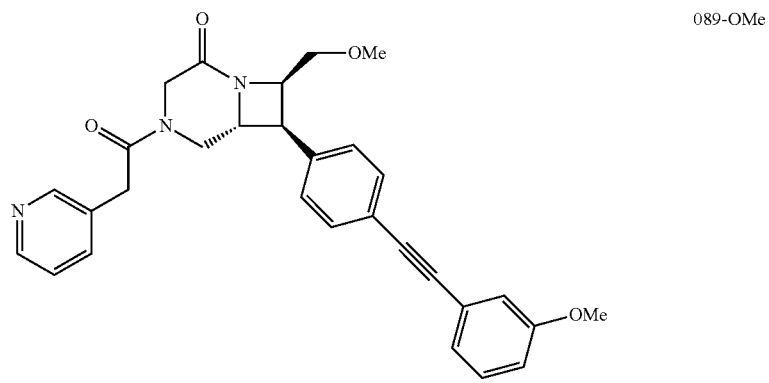
089-OMe
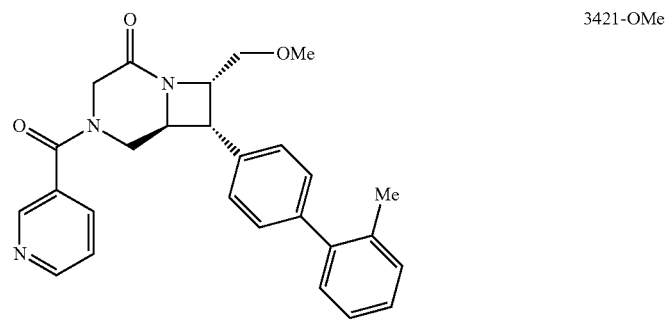
3421-OMe TABLE 1-continued Exemplary compounds of Formula (I).

140

805

140-OMe

805-OMe

580

TABLE 1-continued
Exemplary compounds of Formula (I).
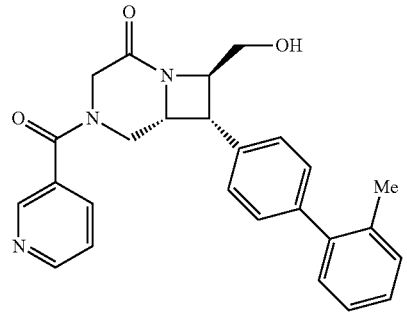 [SMILES: Cc1ccccc1-c1ccc([C@H]2[C@H](CO)N3C(=O)CN(C(=O)c4cccnc4)C[C@@H]23)cc1] 491
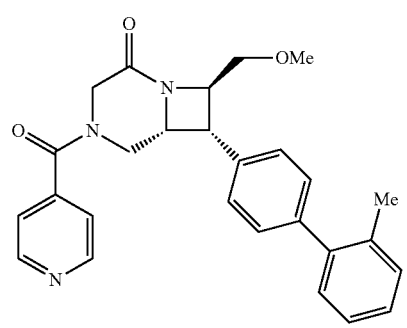 [SMILES: COC[C@H]1[C@H](c2ccc(-c3ccccc3C)cc2)[C@@H]2CN(C(=O)c3ccncc3)CC(=O)N12] 580-OMe
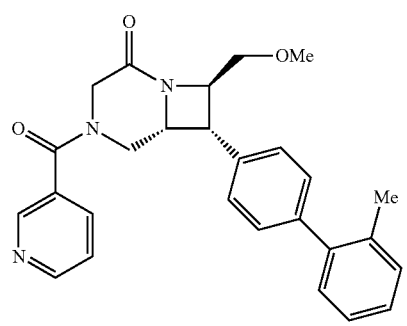 [SMILES: COC[C@H]1[C@H](c2ccc(-c3ccccc3C)cc2)[C@@H]2CN(C(=O)c3cccnc3)CC(=O)N12] 491-OMe
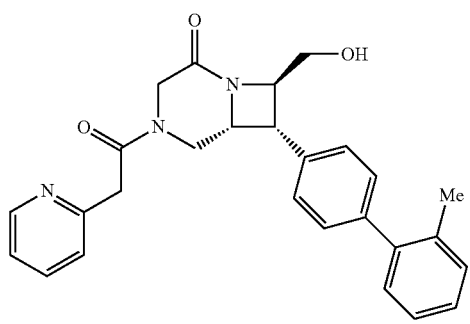 [SMILES: Cc1ccccc1-c1ccc([C@H]2[C@H](CO)N3C(=O)CN(C(=O)Cc4ccccn4)C[C@@H]23)cc1] 321
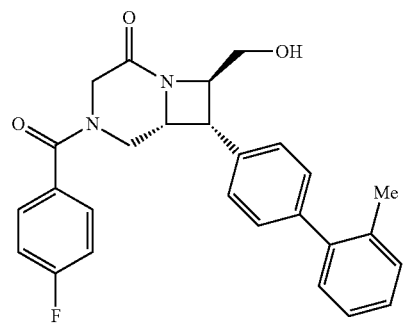 [SMILES: Cc1ccccc1-c1ccc([C@H]2[C@H](CO)N3C(=O)CN(C(=O)c4ccc(F)cc4)C[C@@H]23)cc1] 124

TABLE 1-continued
Exemplary compounds of Formula (I).
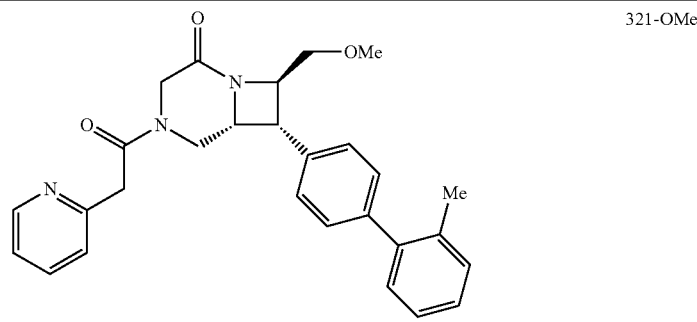
321-OMe
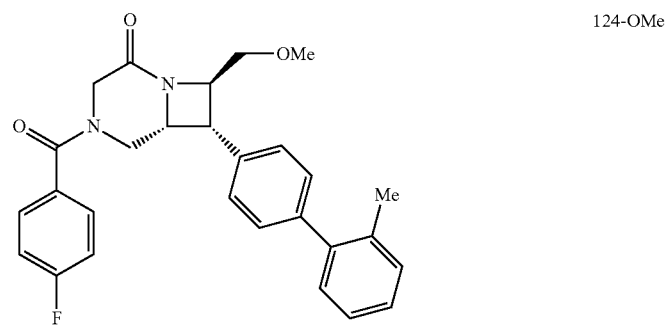
124-OMe
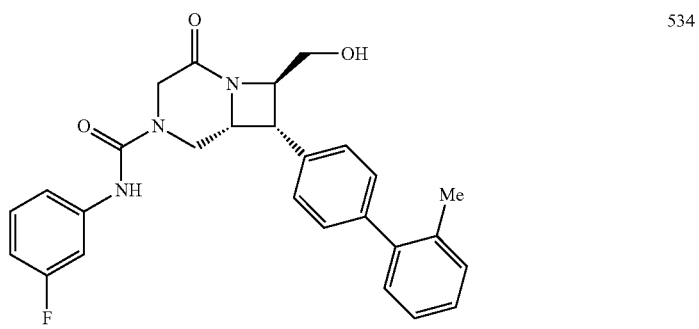
534
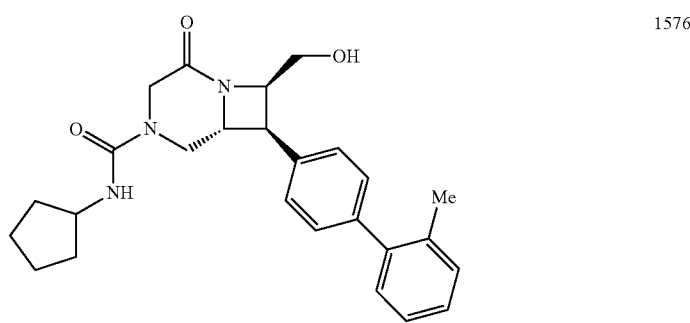
1576
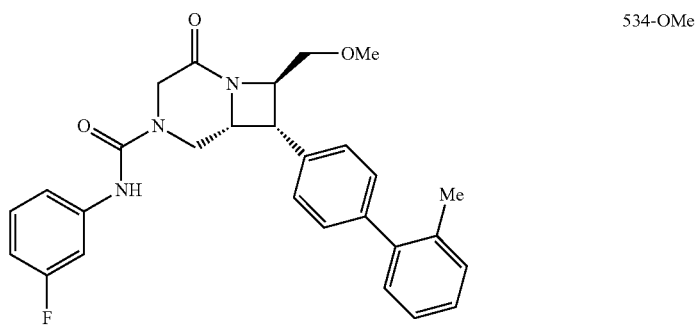
534-OMe TABLE 1-continued
Exemplary compounds of Formula (I).
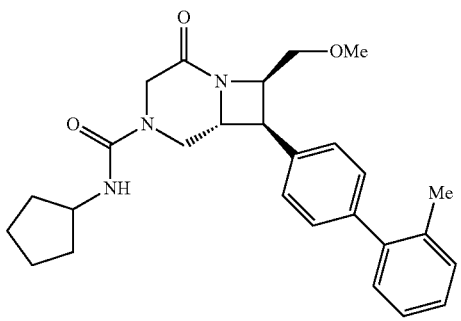 [SMILES: COC[C@H]1[C@@H](c2ccc(-c3ccccc3C)cc2)[C@@H]2CN(C(=O)NC3CCCC3)CC(=O)N12]
1576-OMe
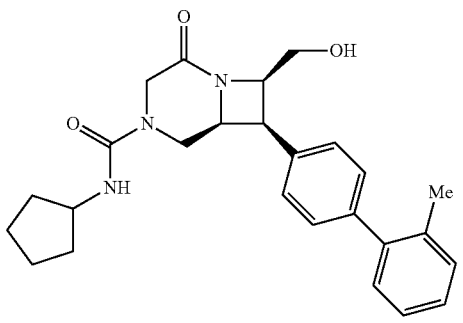 [SMILES: Cc1ccccc1-c1ccc([C@H]2[C@H]3CN(C(=O)NC4CCCC4)CC(=O)N3[C@H]2CO)cc1]
612
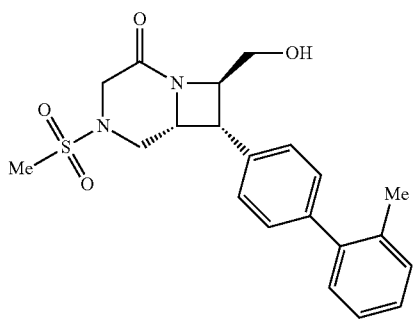 [SMILES: Cc1ccccc1-c1ccc([C@H]2[C@H](CO)N3C(=O)CN(S(C)(=O)=O)C[C@@H]23)cc1]
061
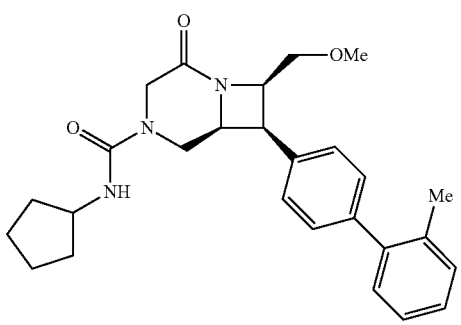 [SMILES: COC[C@H]1[C@@H](c2ccc(-c3ccccc3C)cc2)[C@H]2CN(C(=O)NC3CCCC3)CC(=O)N21]
612-OMe
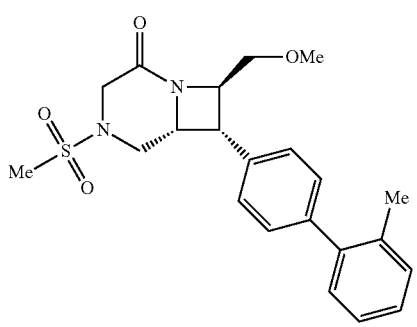 [SMILES: COC[C@H]1[C@H](c2ccc(-c3ccccc3C)cc2)[C@@H]2CN(S(C)(=O)=O)CC(=O)N12]
061-OMe TABLE 1-continued
Exemplary compounds of Formula (I).
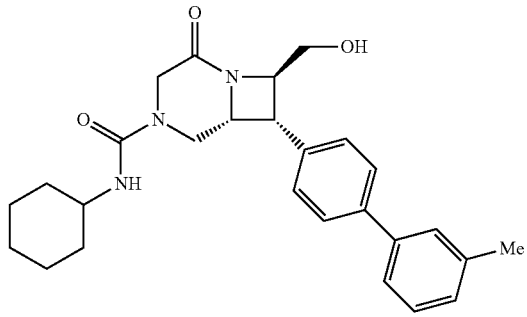 [SMILES: Cc1cccc(-c2ccc([C@H]3[C@H](CO)N4C(=O)CN(C(=O)NC5CCCCC5)C[C@@H]34)cc2)c1] 130
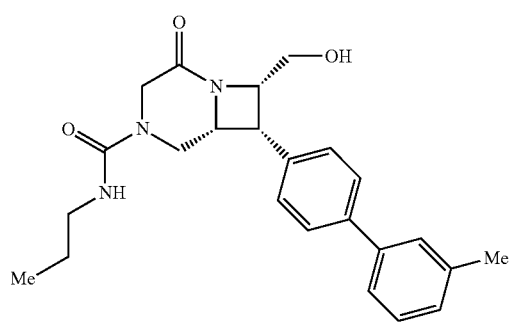 [SMILES: CCCNC(=O)N1CC(=O)N2[C@H](CO)[C@H](c3ccc(-c4cccc(C)c4)cc3)[C@@H]2C1] 782
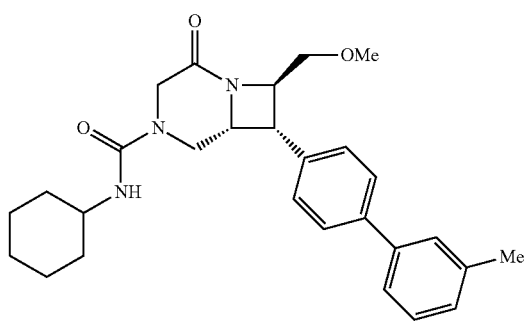 [SMILES: COC[C@H]1[C@H](c2ccc(-c3cccc(C)c3)cc2)[C@@H]2CN(C(=O)NC3CCCCC3)CC(=O)N12] 130-OMe
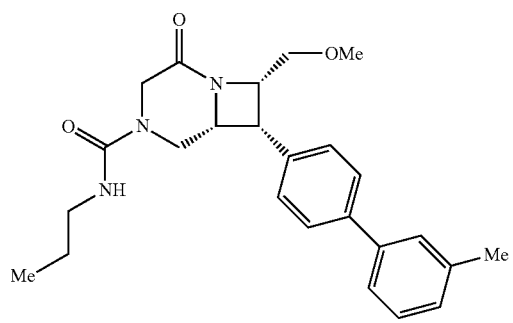 [SMILES: CCCNC(=O)N1CC(=O)N2[C@H](COC)[C@H](c3ccc(-c4cccc(C)c4)cc3)[C@@H]2C1] 782-OMe
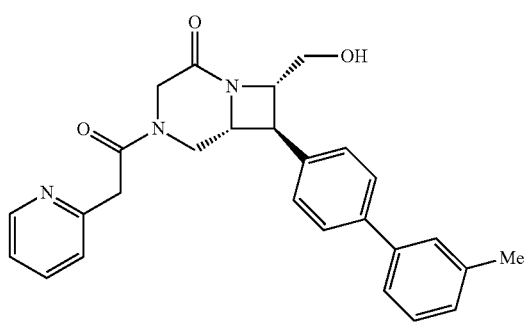 [SMILES: Cc1cccc(-c2ccc([C@@H]3[C@@H](CO)N4C(=O)CN(C(=O)Cc5ccccn5)C[C@@H]34)cc2)c1] 348

TABLE 1-continued
Exemplary compounds of Formula (I).
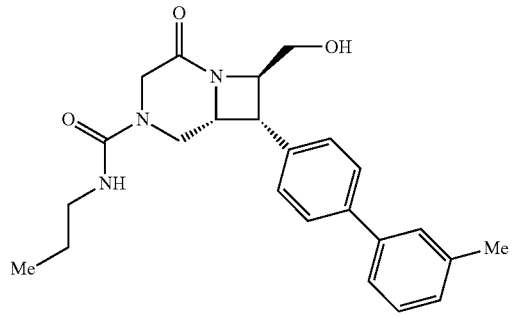 [SMILES: CCCNC(=O)N1CC(=O)N2[C@@H](CO)[C@H](c3ccc(-c4cccc(C)c4)cc3)[C@@H]2C1]
231
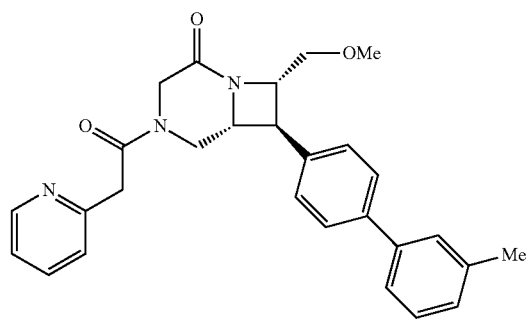 [SMILES: COC[C@@H]1[C@@H](c2ccc(-c3cccc(C)c3)cc2)[C@@H]2CN(C(=O)Cc3ccccn3)CC(=O)N12]
348-OMe
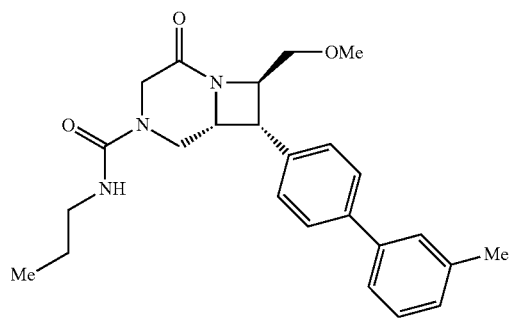 [SMILES: CCCNC(=O)N1CC(=O)N2[C@@H](COC)[C@H](c3ccc(-c4cccc(C)c4)cc3)[C@@H]2C1]
231-OMe
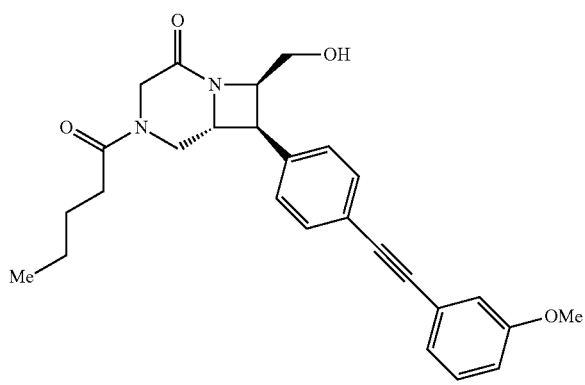 [SMILES: CCCCC(=O)N1CC(=O)N2[C@@H](CO)[C@@H](c3ccc(C#Cc4cccc(OC)c4)cc3)[C@@H]2C1]
564

TABLE 1-continued
Exemplary compounds of Formula (I).
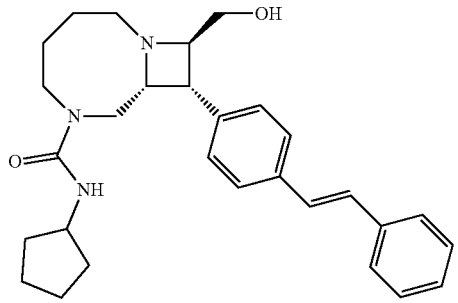 [SMILES: O=C(NC1CCCC1)N1CCCCN2[C@@H](CO)[C@H](c3ccc(/C=C/c4ccccc4)cc3)[C@@H]2C1] 900
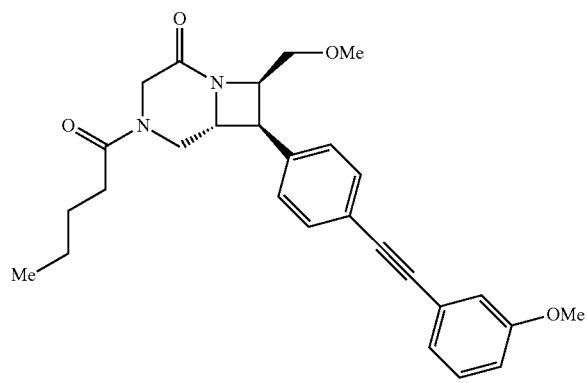 [SMILES: CCCCC(=O)N1CC(=O)N2[C@@H](COC)[C@@H](c3ccc(C#Cc4cccc(OC)c4)cc3)[C@@H]2C1] 564-OMe
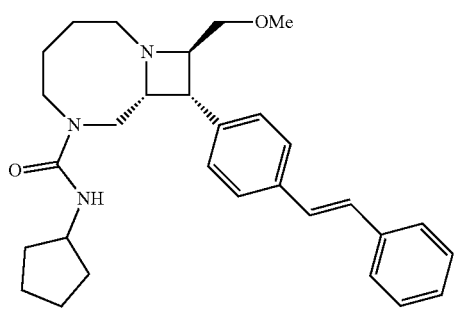 [SMILES: COC[C@H]1[C@H](c2ccc(/C=C/c3ccccc3)cc2)[C@@H]2CN(C(=O)NC3CCCC3)CCCCN12] 900-OMe
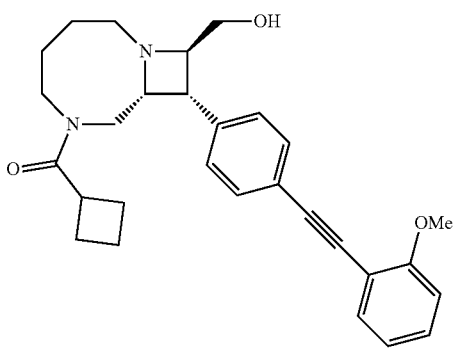 [SMILES: COc1ccccc1C#Cc1ccc([C@H]2[C@H](CO)N3CCCCN(C(=O)C4CCC4)C[C@@H]23)cc1] 180

TABLE 1-continued
Exemplary compounds of Formula (I).
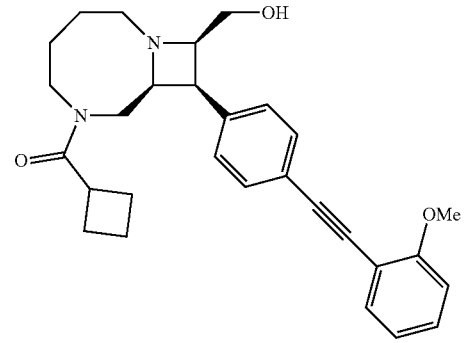 [SMILES: COc1ccccc1C#Cc1ccc([C@H]2[C@H]3CN(C(=O)C4CCC4)CCCCN3[C@H]2CO)cc1]
141
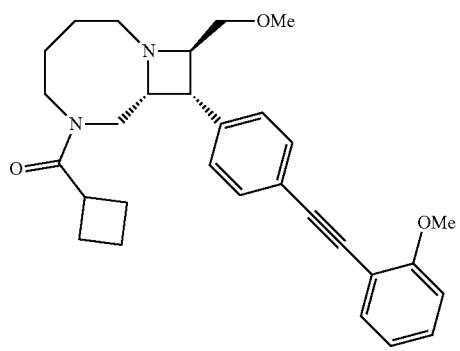 [SMILES: COC[C@H]1[C@H](c2ccc(C#Cc3ccccc3OC)cc2)[C@@H]2CN(C(=O)C3CCC3)CCCCN12]
180-OMe
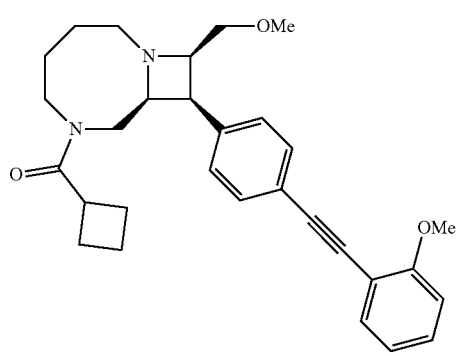 [SMILES: COC[C@H]1[C@@H](c2ccc(C#Cc3ccccc3OC)cc2)[C@H]2CN(C(=O)C3CCC3)CCCCN21]
141-OMe
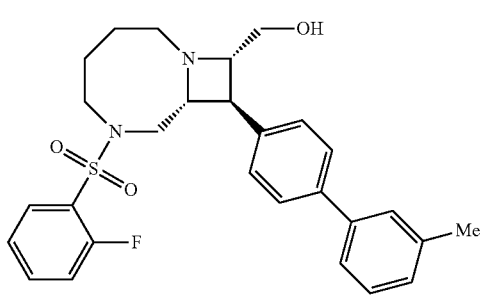 [SMILES: Cc1cccc(-c2ccc([C@@H]3[C@@H](CO)N4CCCCN(S(=O)(=O)c5ccccc5F)C[C@@H]34)cc2)c1]
688
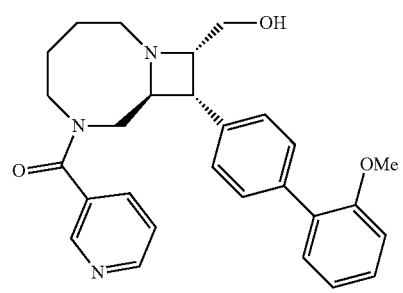 [SMILES: COc1ccccc1-c1ccc([C@H]2[C@@H](CO)N3CCCCN(C(=O)c4cccnc4)C[C@H]23)cc1]
983

TABLE 1-continued
Exemplary compounds of Formula (I).
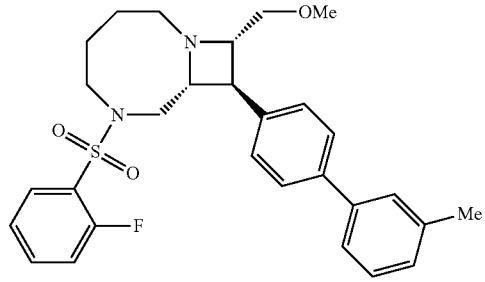 [SMILES: COC[C@@H]1[C@@H](c2ccc(-c3cccc(C)c3)cc2)[C@@H]2CN(S(=O)(=O)c3ccccc3F)CCCCN12] 688-OMe
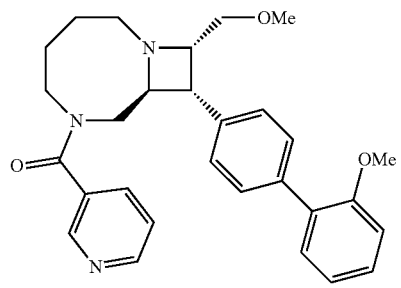 [SMILES: COC[C@@H]1[C@H](c2ccc(-c3ccccc3OC)cc2)[C@H]2CN(C(=O)c3cccnc3)CCCCN12] 983-OMe
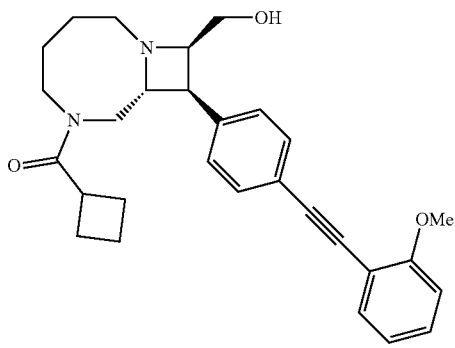 [SMILES: COc1ccccc1C#Cc1ccc([C@@H]2[C@H](CO)N3CCCCN(C(=O)C4CCC4)C[C@@H]23)cc1] 930
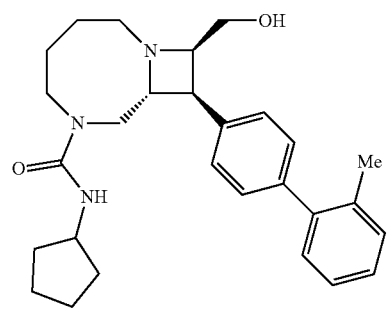 [SMILES: Cc1ccccc1-c1ccc([C@@H]2[C@H](CO)N3CCCCN(C(=O)NC4CCCC4)C[C@@H]23)cc1] 932
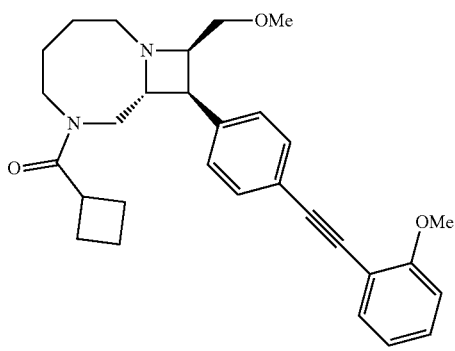 [SMILES: COC[C@H]1[C@@H](c2ccc(C#Cc3ccccc3OC)cc2)[C@@H]2CN(C(=O)C3CCC3)CCCCN12] 930-OMe TABLE 1-continued
Exemplary compounds of Formula (I).
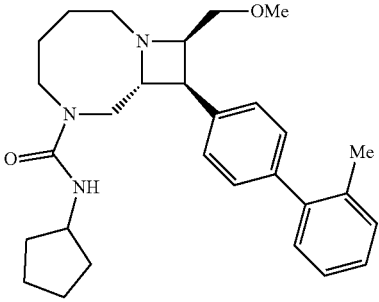 [SMILES: COC[C@H]1[C@@H](c2ccc(-c3ccccc3C)cc2)[C@@H]2CN(C(=O)NC3CCCC3)CCCCN12] 932-OMe
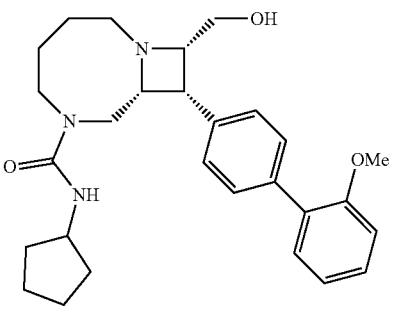 [SMILES: COc1ccccc1-c1ccc([C@H]2[C@@H](CO)N3CCCCN(C(=O)NC4CCCC4)C[C@@H]23)cc1] 204
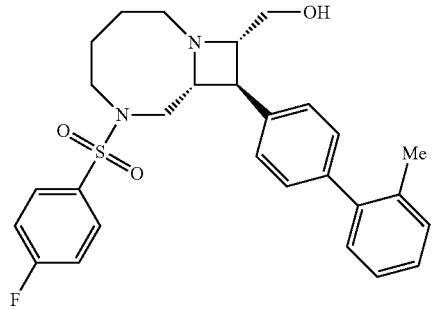 [SMILES: Cc1ccccc1-c1ccc([C@@H]2[C@@H](CO)N3CCCCN(S(=O)(=O)c4ccc(F)cc4)C[C@@H]23)cc1] 217
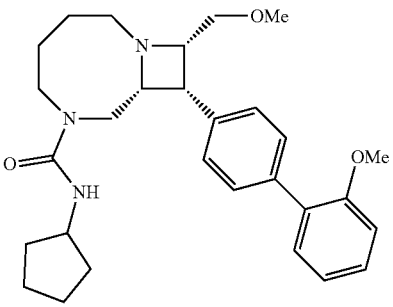 [SMILES: COC[C@@H]1[C@H](c2ccc(-c3ccccc3OC)cc2)[C@@H]2CN(C(=O)NC3CCCC3)CCCCN12] 204-OMe
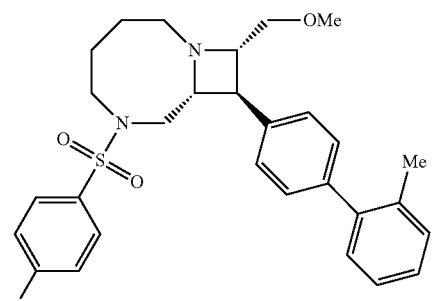 217-OMe TABLE 1-continued
Exemplary compounds of Formula (I).
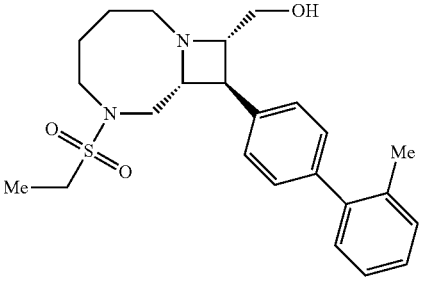 [SMILES: CCS(=O)(=O)N1CCCCN2[C@H](CO)[C@@H](c3ccc(-c4ccccc4C)cc3)[C@@H]2C1] 416
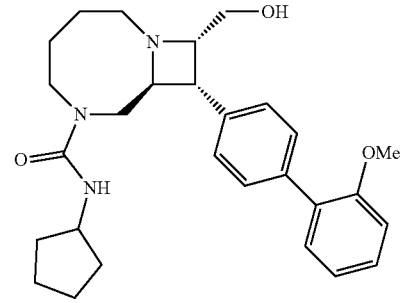 [SMILES: COc1ccccc1-c1ccc([C@H]2[C@@H](CO)N3CCCCN(C(=O)NC4CCCC4)C[C@H]23)cc1] 439
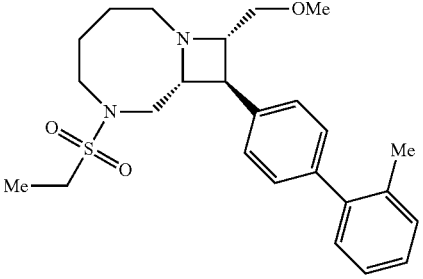 [SMILES: CCS(=O)(=O)N1CCCCN2[C@H](COC)[C@@H](c3ccc(-c4ccccc4C)cc3)[C@@H]2C1] 416-OMe
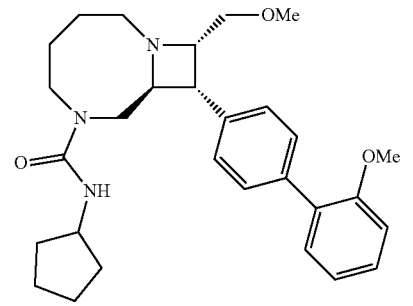 [SMILES: COC[C@@H]1[C@H](c2ccc(-c3ccccc3OC)cc2)[C@H]2CN(C(=O)NC3CCCC3)CCCCN12] 439-OMe
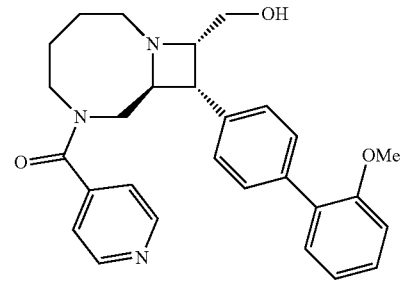 [SMILES: COc1ccccc1-c1ccc([C@H]2[C@@H](CO)N3CCCCN(C(=O)c4ccncc4)C[C@H]23)cc1] 586

TABLE 1-continued
Exemplary compounds of Formula (I).
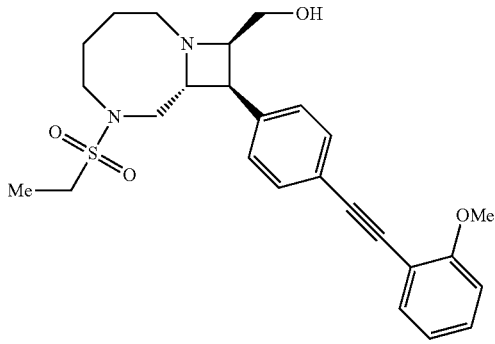 [SMILES: CCS(=O)(=O)N1CCCCN2[C@@H](CO)[C@@H](c3ccc(C#Cc4ccccc4OC)cc3)[C@@H]2C1]
964
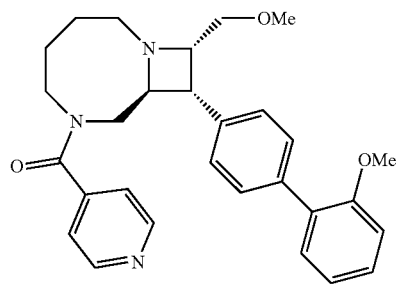 [SMILES: COC[C@@H]1[C@H](c2ccc(-c3ccccc3OC)cc2)[C@H]2CN(C(=O)c3ccncc3)CCCCN12]
586-OMe
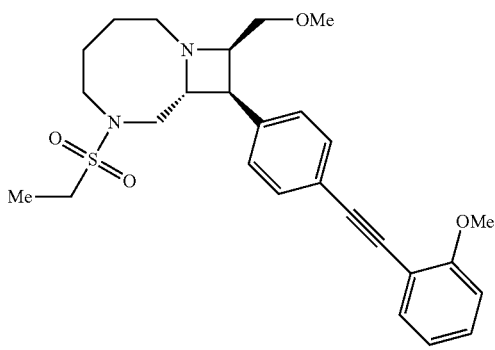 [SMILES: CCS(=O)(=O)N1CCCCN2[C@@H](COC)[C@@H](c3ccc(C#Cc4ccccc4OC)cc3)[C@@H]2C1]
964-OMe
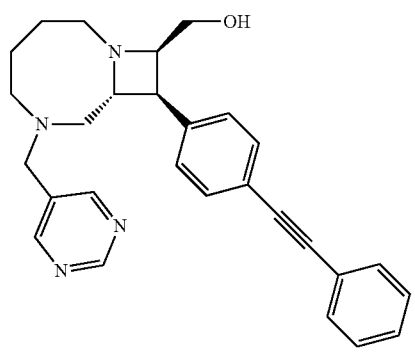 [SMILES: OC[C@H]1[C@@H](c2ccc(C#Cc3ccccc3)cc2)[C@@H]2CN(Cc3cncnc3)CCCCN12]
525

TABLE 1-continued
Exemplary compounds of Formula (I).
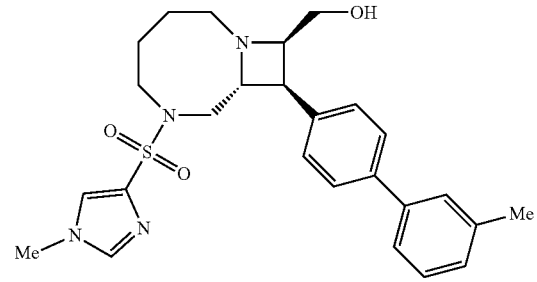 [SMILES: Cc1cccc(-c2ccc([C@@H]3[C@H](CO)N4CCCCN(S(=O)(=O)c5cn(C)cn5)C[C@@H]34)cc2)c1] 795
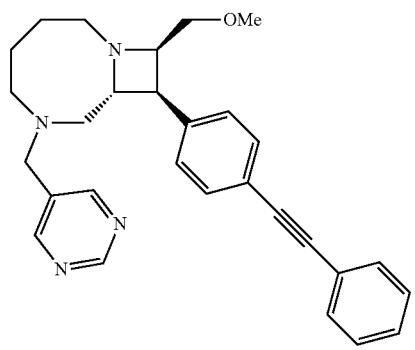 [SMILES: COC[C@H]1[C@@H](c2ccc(C#Cc3ccccc3)cc2)[C@@H]2CN(Cc3cncnc3)CCCCN12] 525-OMe
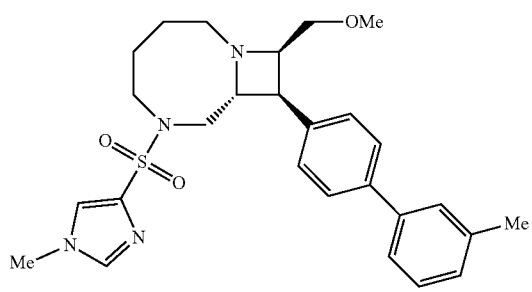 [SMILES: COC[C@H]1[C@@H](c2ccc(-c3cccc(C)c3)cc2)[C@@H]2CN(S(=O)(=O)c3cn(C)cn3)CCCCN12] 795-OMe
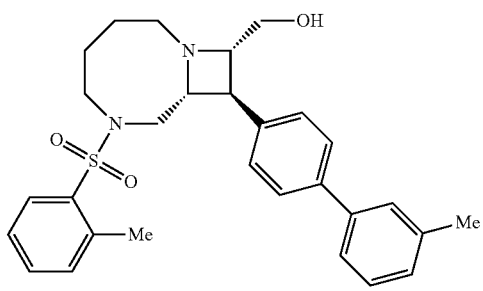 297
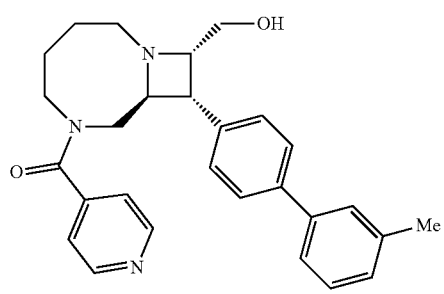 [SMILES: Cc1cccc(-c2ccc([C@H]3[C@@H](CO)N4CCCCN(C(=O)c5ccncc5)C[C@H]34)cc2)c1] 836

TABLE 1-continued
Exemplary compounds of Formula (I).
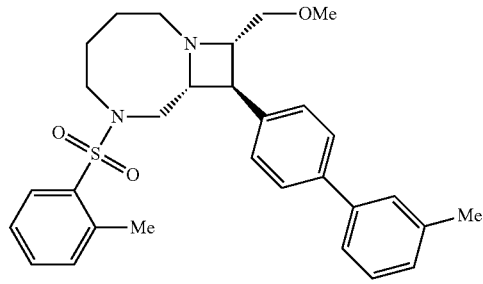 297-OMe
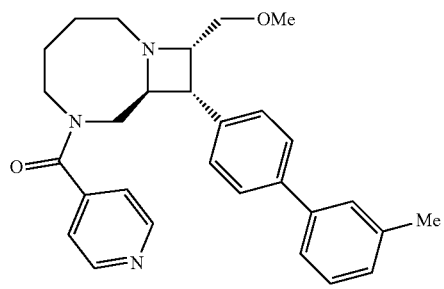 [SMILES: COC[C@@H]1[C@H](c2ccc(-c3cccc(C)c3)cc2)[C@H]2CN(C(=O)c3ccncc3)CCCCN12] 836-OMe
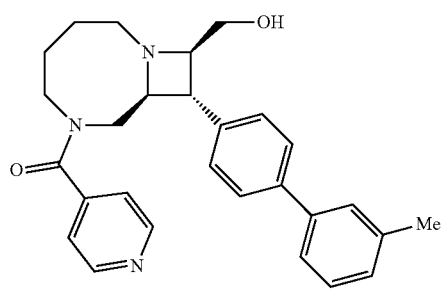 [SMILES: Cc1cccc(-c2ccc([C@@H]3[C@H]4CN(C(=O)c5ccncc5)CCCCN4[C@H]3CO)cc2)c1] 316
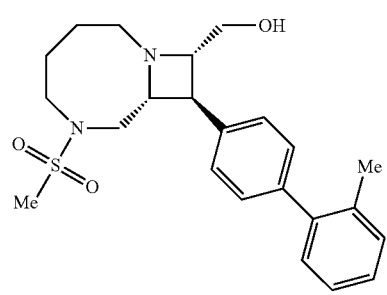 [SMILES: Cc1ccccc1-c1ccc([C@@H]2[C@@H](CO)N3CCCCN(S(C)(=O)=O)C[C@@H]23)cc1] 591
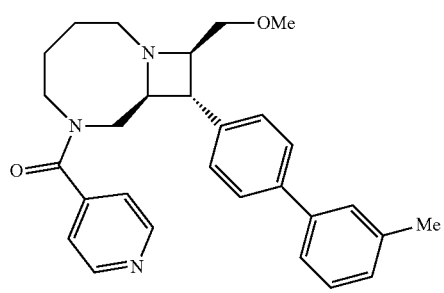 [SMILES: COC[C@H]1[C@H](c2ccc(-c3cccc(C)c3)cc2)[C@H]2CN(C(=O)c3ccncc3)CCCCN21] 316-OMe TABLE 1-continued
Exemplary compounds of Formula (I).
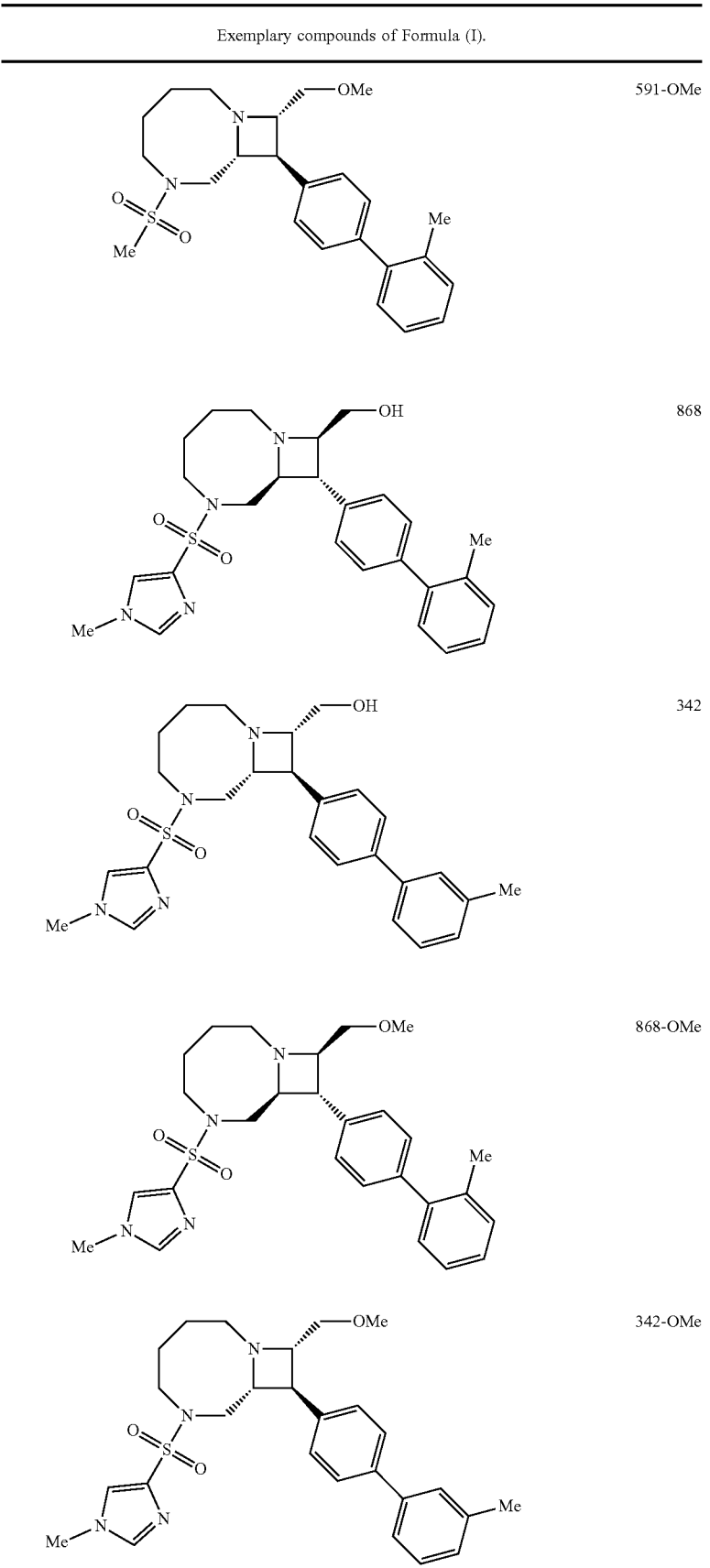
591-OMe
868
342
868-OMe
342-OMe TABLE 1-continued
Exemplary compounds of Formula (I).
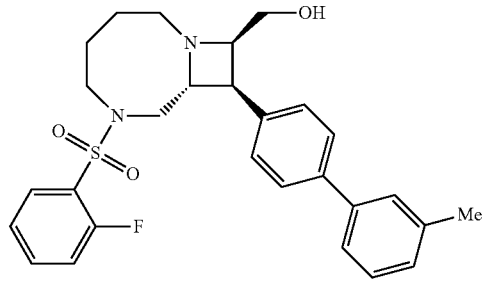 [SMILES: Cc1cccc(-c2ccc([C@@H]3[C@H](CO)N4CCCCN(S(=O)(=O)c5ccccc5F)C[C@@H]34)cc2)c1] 807
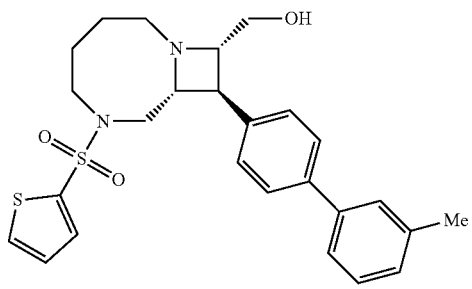 [SMILES: Cc1cccc(-c2ccc([C@@H]3[C@@H](CO)N4CCCCN(S(=O)(=O)c5cccs5)C[C@@H]34)cc2)c1] 945
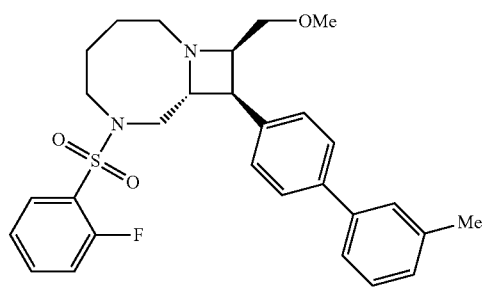 807-OMe
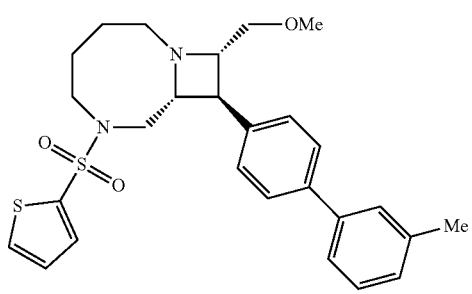 [SMILES: COC[C@@H]1[C@@H](c2ccc(-c3cccc(C)c3)cc2)[C@@H]2CN(S(=O)(=O)c3cccs3)CCCCN12] 945-OMe
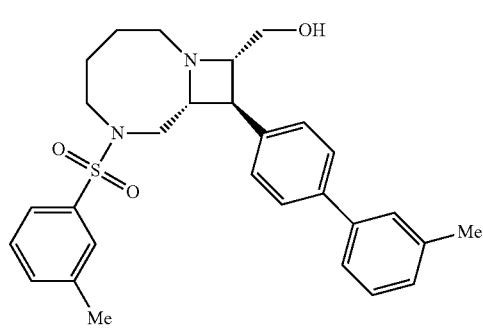 [SMILES: Cc1cccc(-c2ccc([C@@H]3[C@@H](CO)N4CCCCN(S(=O)(=O)c5cccc(C)c5)C[C@@H]34)cc2)c1] 496

TABLE 1-continued

Exemplary compounds of Formula (I).

| Structure | No. |
|---|---|
| (structure) | 091 |
| (structure) | 496-OMe |
| (structure) | 091-OMe |
| (structure) | 383 |
| (structure) | 443 |

TABLE 1-continued
Exemplary compounds of Formula (I).
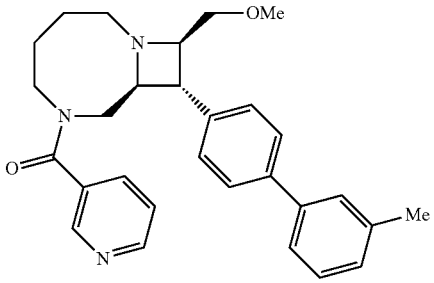 [SMILES: COC[C@H]1[C@H](c2ccc(-c3cccc(C)c3)cc2)[C@H]2CN(C(=O)c3cccnc3)CCCCN21] 383-OMe
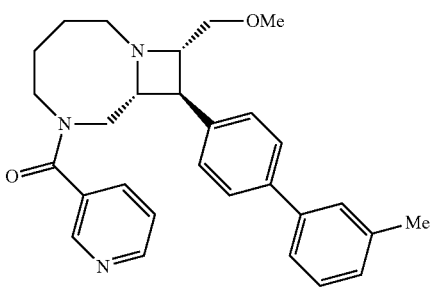 [SMILES: COC[C@@H]1[C@@H](c2ccc(-c3cccc(C)c3)cc2)[C@@H]2CN(C(=O)c3cccnc3)CCCCN12] 443-OMe
 296
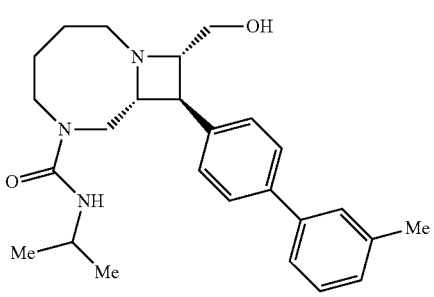 [SMILES: Cc1cccc(-c2ccc([C@@H]3[C@@H](CO)N4CCCCN(C(=O)NC(C)C)C[C@@H]34)cc2)c1] 777
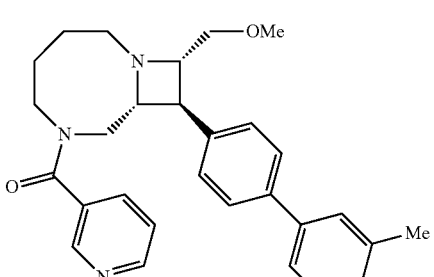 296-OMe TABLE 1-continued
Exemplary compounds of Formula (I).
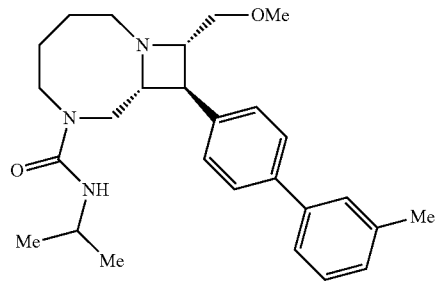 [SMILES: COC[C@@H]1[C@@H](c2ccc(-c3cccc(C)c3)cc2)[C@@H]2CN(C(=O)NC(C)C)CCCCN12] 777-OMe
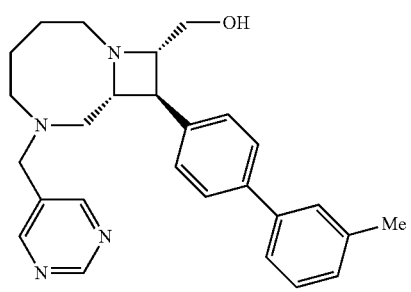 [SMILES: Cc1cccc(-c2ccc([C@@H]3[C@@H](CO)N4CCCCN(Cc5cncnc5)C[C@@H]34)cc2)c1] 654
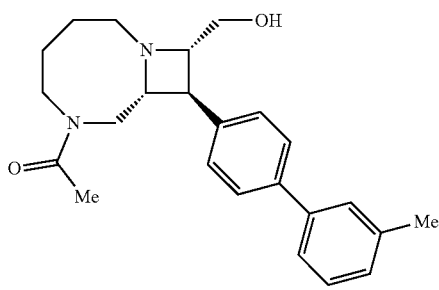 [SMILES: CC(=O)N1CCCCN2[C@H](CO)[C@@H](c3ccc(-c4cccc(C)c4)cc3)[C@@H]2C1] 507
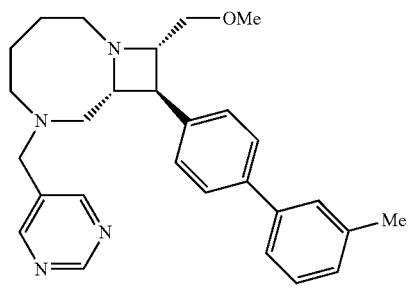 [SMILES: COC[C@@H]1[C@@H](c2ccc(-c3cccc(C)c3)cc2)[C@@H]2CN(Cc3cncnc3)CCCCN12] 654-OMe
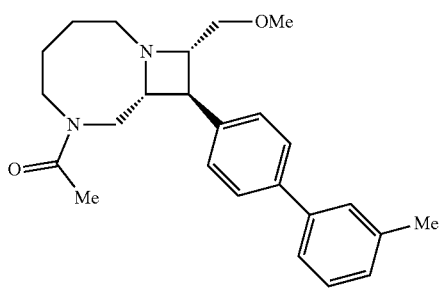 507-OMe TABLE 1-continued Exemplary compounds of Formula (I).

| Structure | No. |
|---|---|
| (chemical structure) | 291 |
| (chemical structure) | 154 |
| (chemical structure) | 291-OMe |
| (chemical structure) | 154-OMe |
| (chemical structure) | 073 |

TABLE 1-continued
Exemplary compounds of Formula (I).
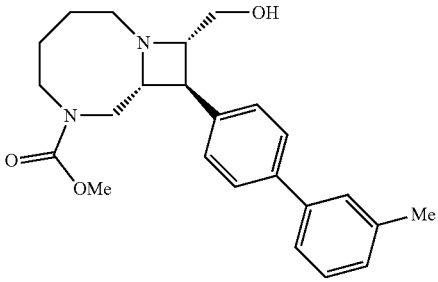 [SMILES: COC(=O)N1CCCCN2[C@H](CO)[C@@H](c3ccc(-c4cccc(C)c4)cc3)[C@@H]2C1] 559
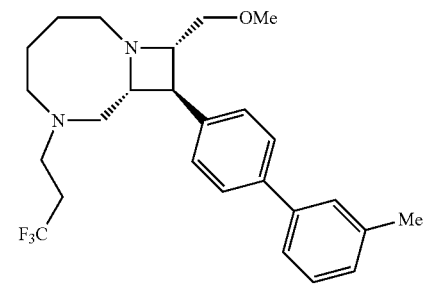 [SMILES: COC[C@@H]1[C@@H](c2ccc(-c3cccc(C)c3)cc2)[C@@H]2CN(CCC(F)(F)F)CCCCN12] 073-OMe
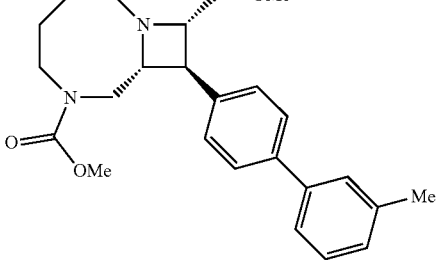 559-OMe
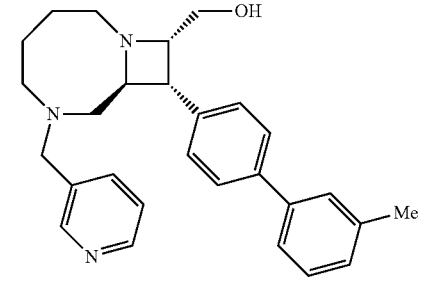 [SMILES: Cc1cccc(-c2ccc([C@H]3[C@@H](CO)N4CCCCN(Cc5cccnc5)C[C@H]34)cc2)c1] 959
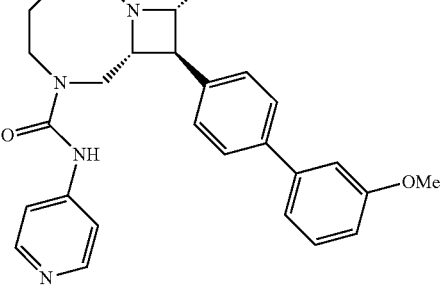 433

TABLE 1-continued
Exemplary compounds of Formula (I).
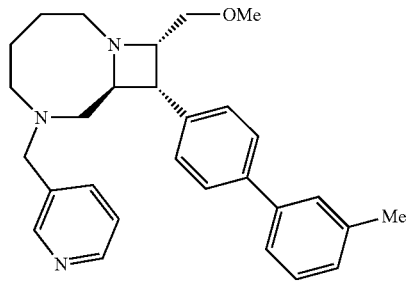 [SMILES: COC[C@@H]1[C@H](c2ccc(-c3cccc(C)c3)cc2)[C@H]2CN(Cc3cccnc3)CCCCN12] 959-OMe
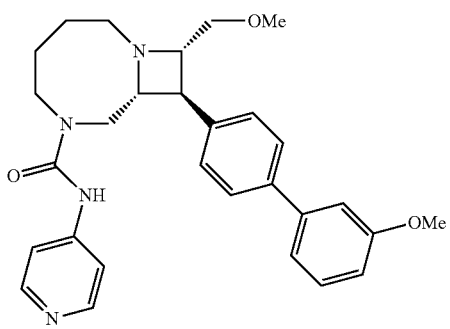 [SMILES: COC[C@@H]1[C@@H](c2ccc(-c3cccc(OC)c3)cc2)[C@@H]2CN(C(=O)Nc3ccncc3)CCCCN12] 433-OMe
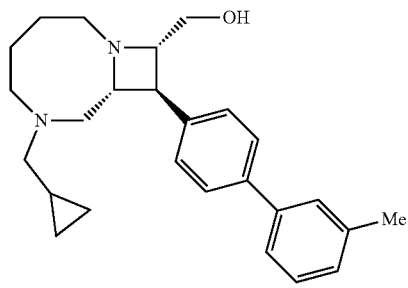 [SMILES: Cc1cccc(-c2ccc([C@@H]3[C@@H](CO)N4CCCCN(CC5CC5)C[C@@H]34)cc2)c1] 837
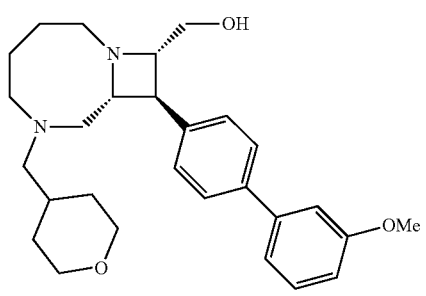 [SMILES: COc1cccc(-c2ccc([C@@H]3[C@@H](CO)N4CCCCN(CC5CCOCC5)C[C@@H]34)cc2)c1] 644
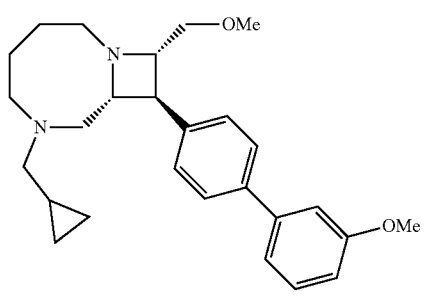 [SMILES: COC[C@@H]1[C@@H](c2ccc(-c3cccc(OC)c3)cc2)[C@@H]2CN(CC3CC3)CCCCN12] 837-OMe TABLE 1-continued
Exemplary compounds of Formula (I).
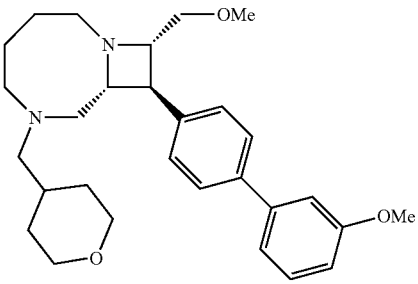 [SMILES: COC[C@@H]1[C@@H](c2ccc(-c3cccc(OC)c3)cc2)[C@@H]2CN(CC3CCOCC3)CCCCN12] 644-OMe
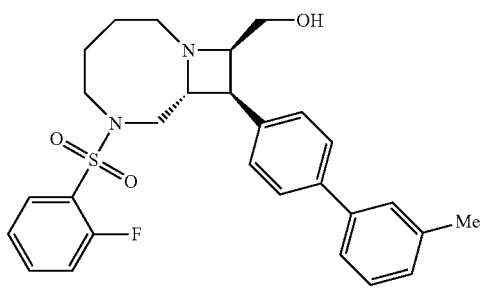 [SMILES: Cc1cccc(-c2ccc([C@@H]3[C@H](CO)N4CCCCN(S(=O)(=O)c5ccccc5F)C[C@@H]34)cc2)c1] 807
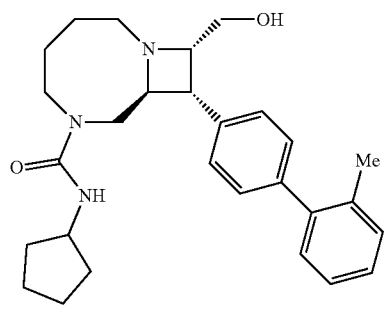 255
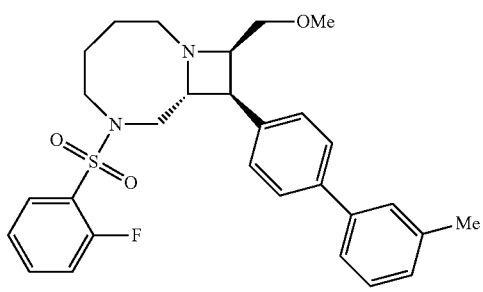 [SMILES: COC[C@H]1[C@@H](c2ccc(-c3cccc(C)c3)cc2)[C@@H]2CN(S(=O)(=O)c3ccccc3F)CCCCN12] 807-OMe
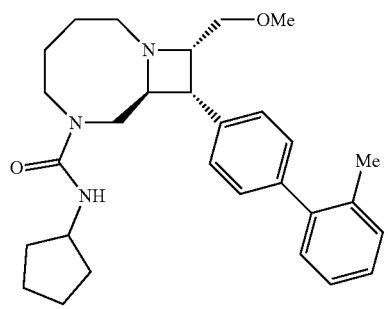 [SMILES: COC[C@@H]1[C@H](c2ccc(-c3ccccc3C)cc2)[C@H]2CN(C(=O)NC3CCCC3)CCCCN12] 255-OMe TABLE 1-continued
Exemplary compounds of Formula (I).
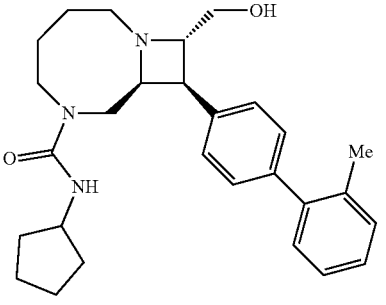 [SMILES: Cc1ccccc1-c1ccc([C@@H]2[C@@H](CO)N3CCCCN(C(=O)NC4CCCC4)C[C@H]23)cc1] 702
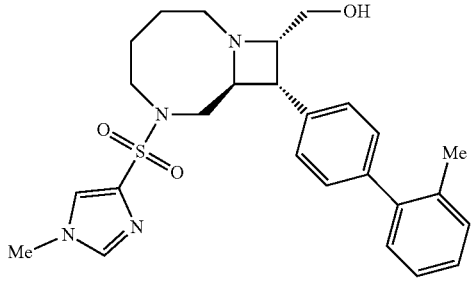 [SMILES: Cc1ccccc1-c1ccc([C@H]2[C@@H](CO)N3CCCCN(S(=O)(=O)c4cn(C)cn4)C[C@H]23)cc1] 736
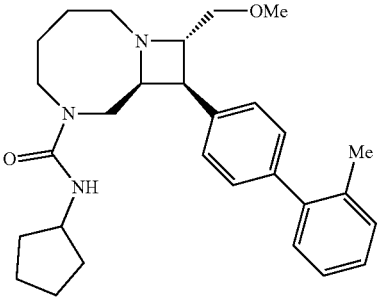 [SMILES: COC[C@@H]1[C@@H](c2ccc(-c3ccccc3C)cc2)[C@H]2CN(C(=O)NC3CCCC3)CCCCN12] 702-OMe
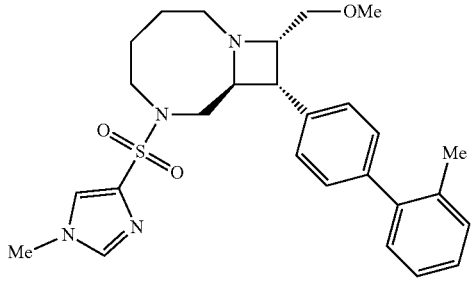 [SMILES: COC[C@@H]1[C@H](c2ccc(-c3ccccc3C)cc2)[C@H]2CN(S(=O)(=O)c3cn(C)cn3)CCCCN12] 736-OMe
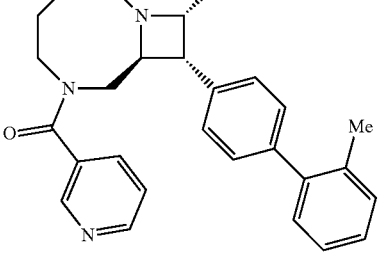 106

TABLE 1-continued
Exemplary compounds of Formula (I).
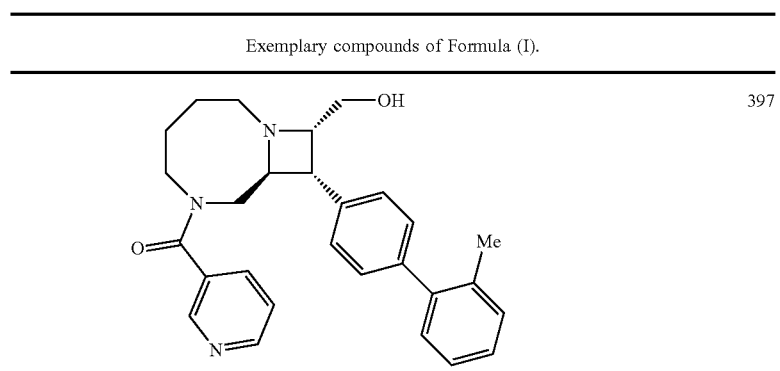 397
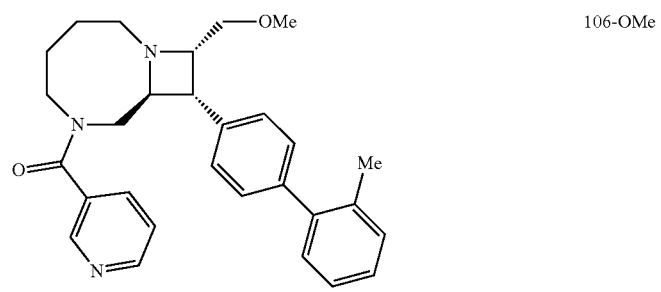 106-OMe
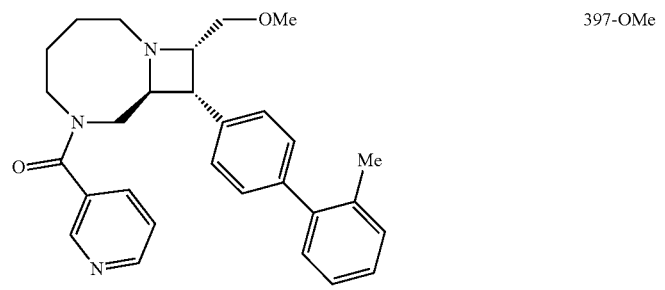 397-OMe
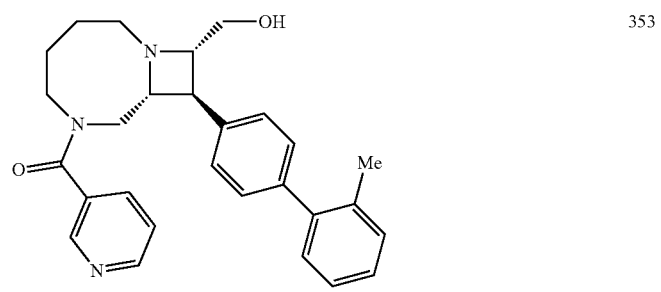 353
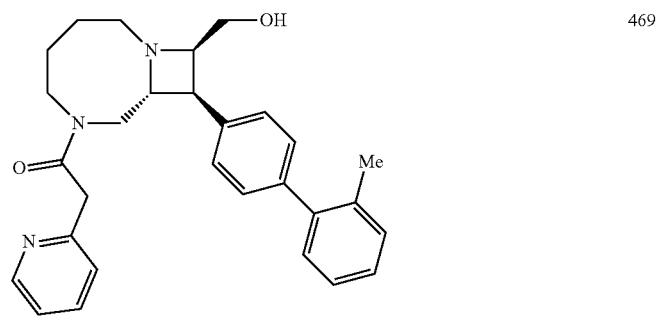 469

TABLE 1-continued
Exemplary compounds of Formula (I).
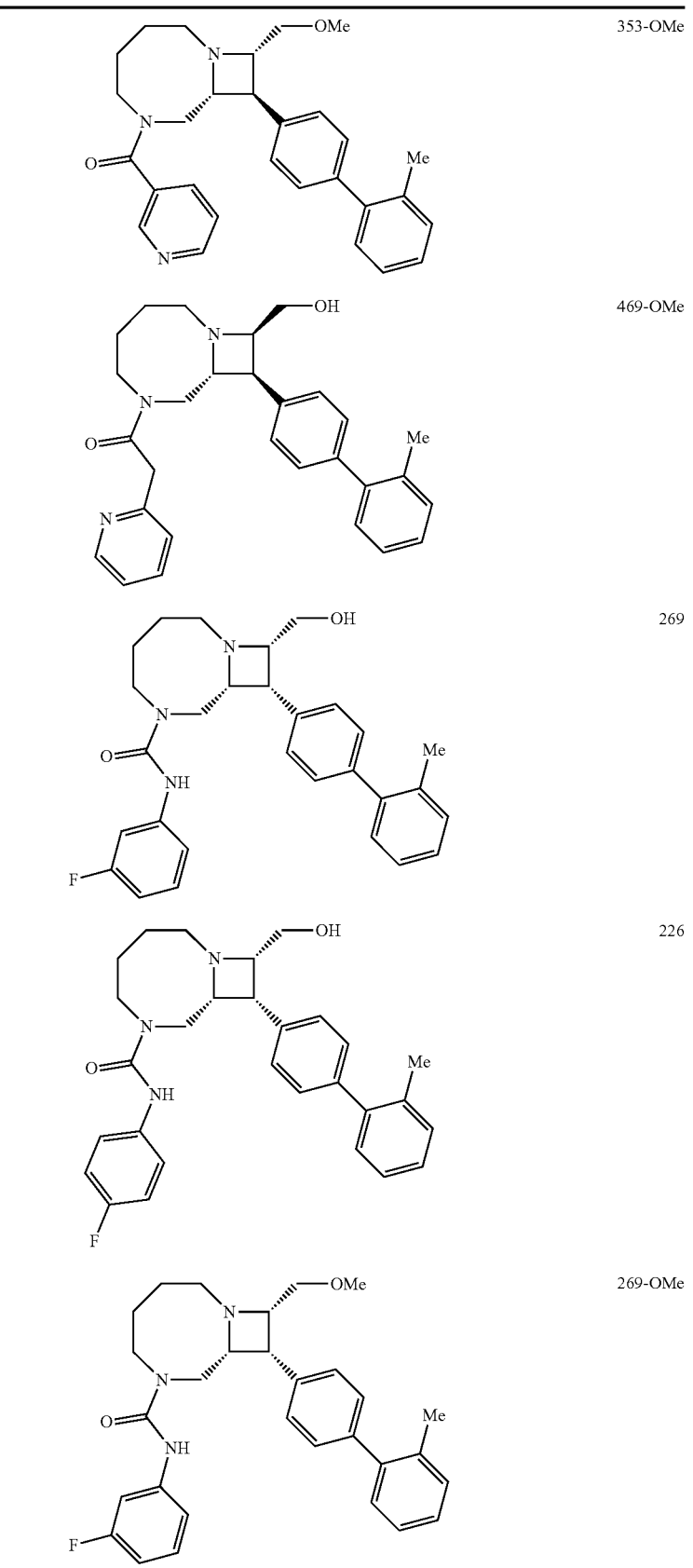
353-OMe
469-OMe
269
226
269-OMe TABLE 1-continued
Exemplary compounds of Formula (I).
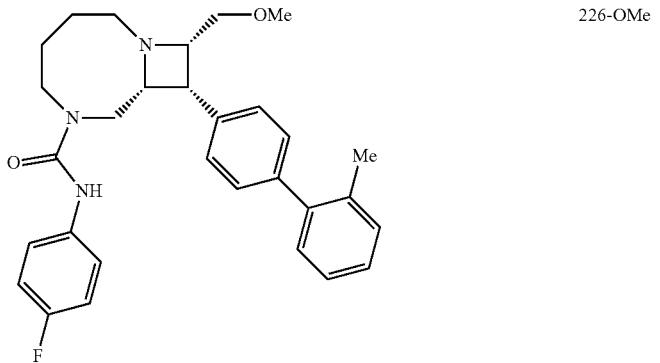 226-OMe
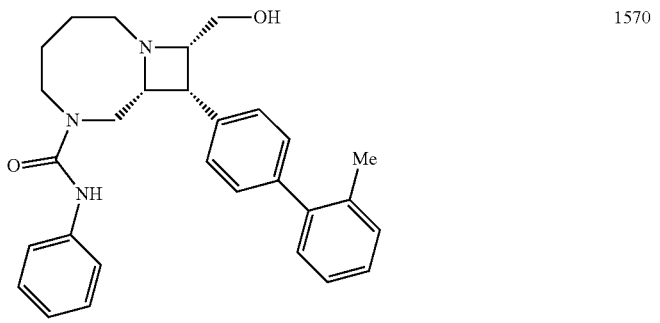 1570
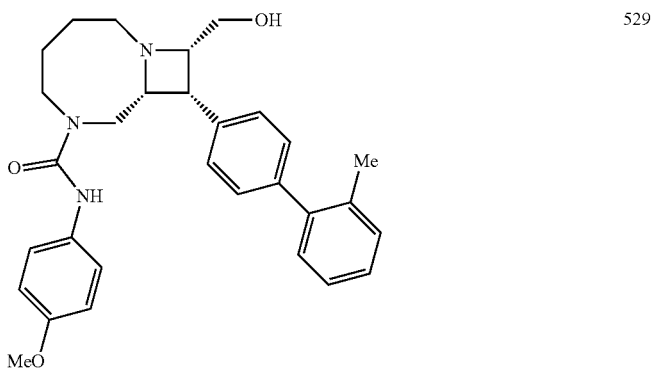 529
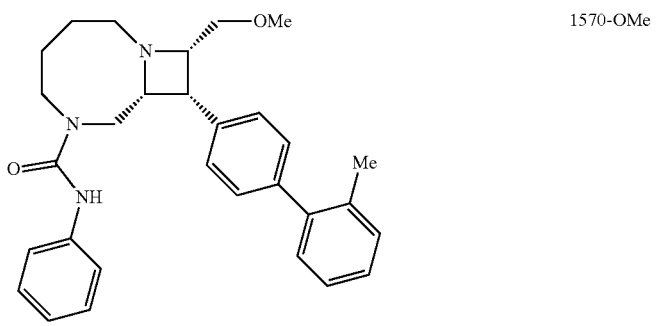 1570-OMe TABLE 1-continued
Exemplary compounds of Formula (I).
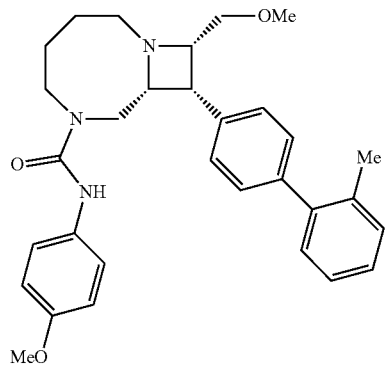 [SMILES: COC[C@@H]1[C@H](c2ccc(-c3ccccc3C)cc2)[C@@H]2CN(C(=O)Nc3ccc(F)cc3)CCCCN12] 529-OMe
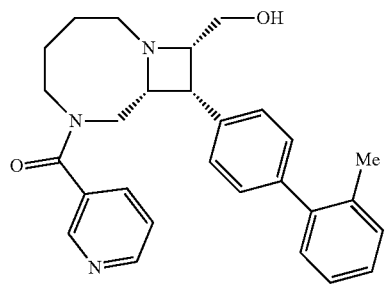 [SMILES: Cc1ccccc1-c1ccc([C@H]2[C@@H](CO)N3CCCCN(C(=O)c4cccnc4)C[C@@H]23)cc1] 712
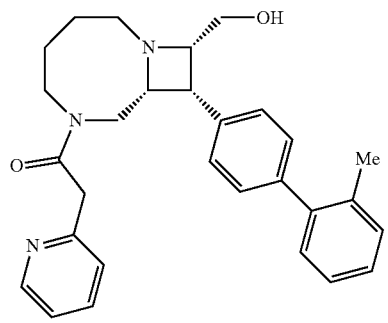 [SMILES: Cc1ccccc1-c1ccc([C@H]2[C@@H](CO)N3CCCCN(C(=O)Cc4ccccn4)C[C@@H]23)cc1] 890
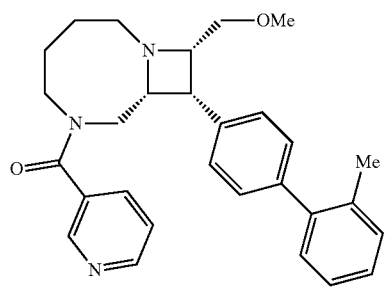 [SMILES: COC[C@@H]1[C@H](c2ccc(-c3ccccc3C)cc2)[C@@H]2CN(C(=O)c3cccnc3)CCCCN12] 712-OMe
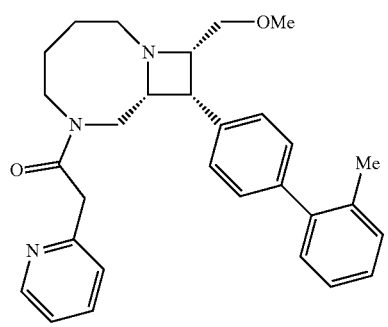 [SMILES: COC[C@@H]1[C@H](c2ccc(-c3ccccc3C)cc2)[C@@H]2CN(C(=O)Cc3ccccn3)CCCCN12] 890-OMe TABLE 1-continued
Exemplary compounds of Formula (I).
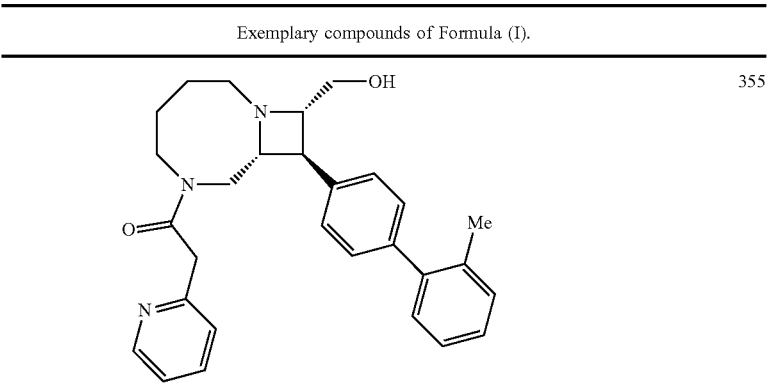
355
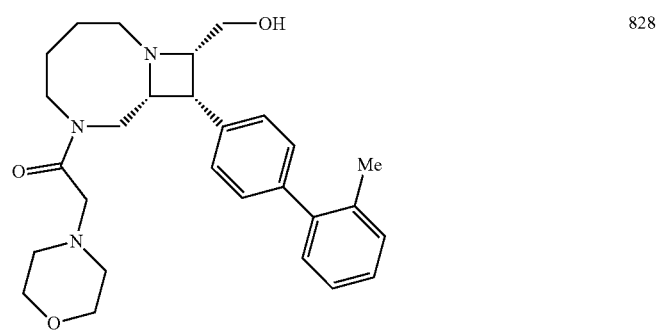
828
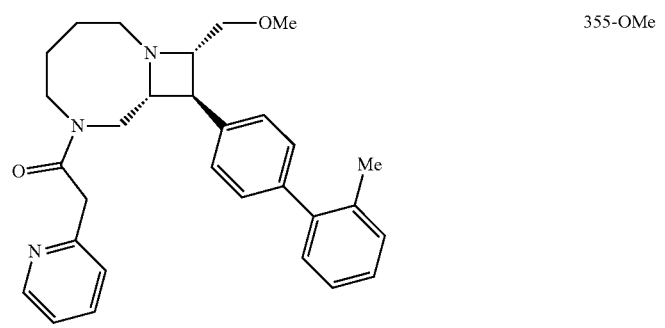
355-OMe
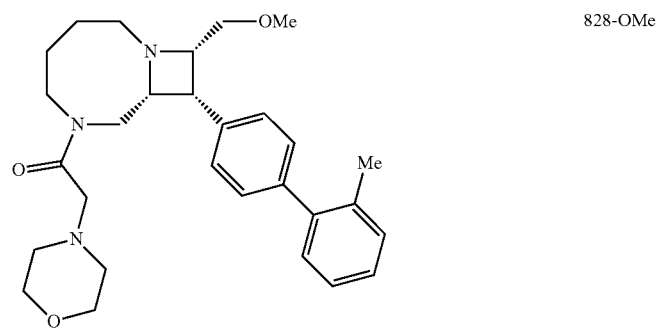
828-OMe TABLE 1-continued
Exemplary compounds of Formula (I).
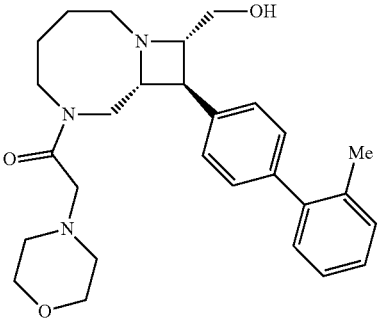 [SMILES: Cc1ccccc1-c1ccc([C@@H]2[C@@H](CO)N3CCCCN(C(=O)CN4CCOCC4)C[C@@H]23)cc1] 171
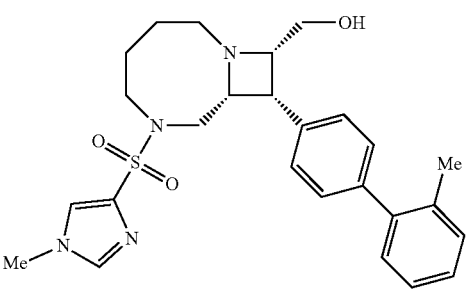 [SMILES: Cc1ccccc1-c1ccc([C@H]2[C@@H](CO)N3CCCCN(S(=O)(=O)c4cn(C)cn4)C[C@@H]23)cc1] 985
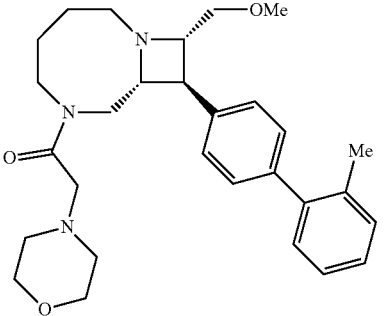 [SMILES: COC[C@@H]1[C@@H](c2ccc(-c3ccccc3C)cc2)[C@@H]2CN(C(=O)CN3CCOCC3)CCCCN12] 171-OMe
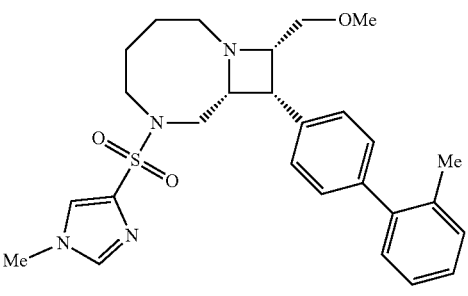 [SMILES: COC[C@@H]1[C@H](c2ccc(-c3ccccc3C)cc2)[C@@H]2CN(S(=O)(=O)c3cn(C)cn3)CCCCN12] 985-OMe
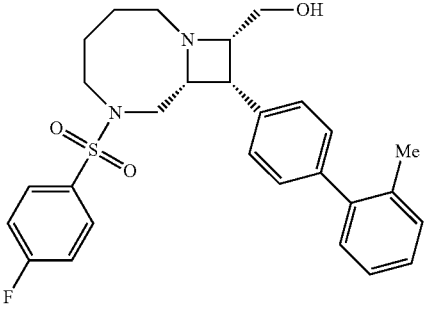 396

TABLE 1-continued
Exemplary compounds of Formula (I).
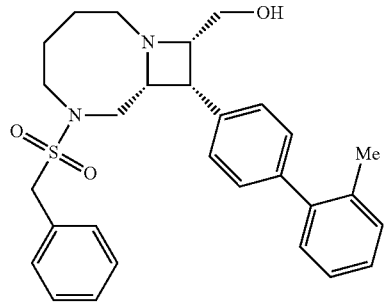 [SMILES: Cc1ccccc1-c1ccc([C@H]2[C@@H](CO)N3CCCCN(S(=O)(=O)Cc4ccccc4)C[C@@H]23)cc1]   236
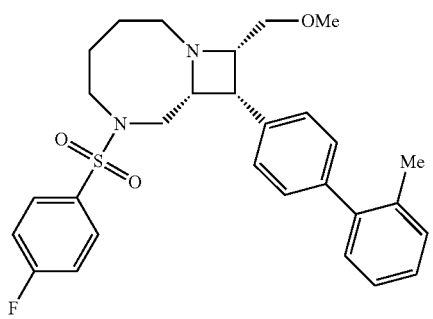 [SMILES: COC[C@@H]1[C@H](c2ccc(-c3ccccc3C)cc2)[C@@H]2CN(S(=O)(=O)c3ccc(F)cc3)CCCCN12]   396-OMe
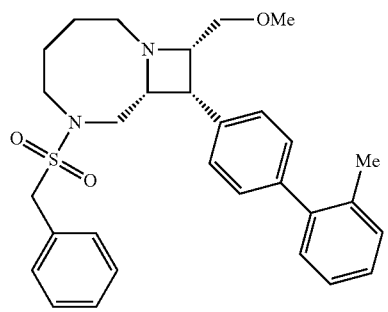 [SMILES: COC[C@@H]1[C@H](c2ccc(-c3ccccc3C)cc2)[C@@H]2CN(S(=O)(=O)Cc3ccccc3)CCCCN12]   236-OMe
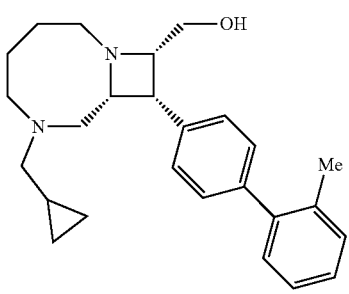 [SMILES: Cc1ccccc1-c1ccc([C@H]2[C@@H](CO)N3CCCCN(CC4CC4)C[C@@H]23)cc1]   768
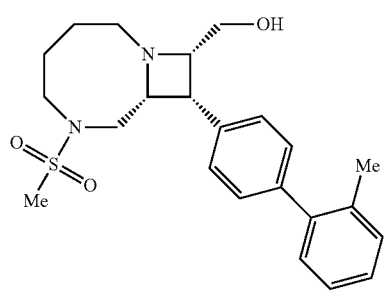 [SMILES: Cc1ccccc1-c1ccc([C@H]2[C@@H](CO)N3CCCCN(S(C)(=O)=O)C[C@@H]23)cc1]   077

TABLE 1-continued
Exemplary compounds of Formula (I).
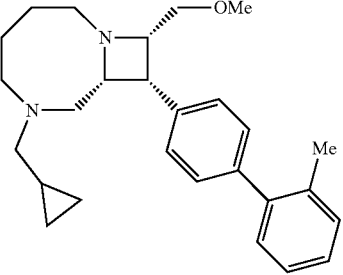 [SMILES: COC[C@@H]1[C@H](c2ccc(-c3ccccc3C)cc2)[C@@H]2CN(CC3CC3)CCCCN12] 768-OMe
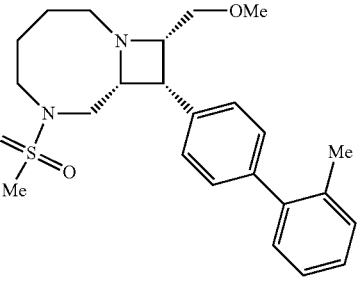 077-OMe
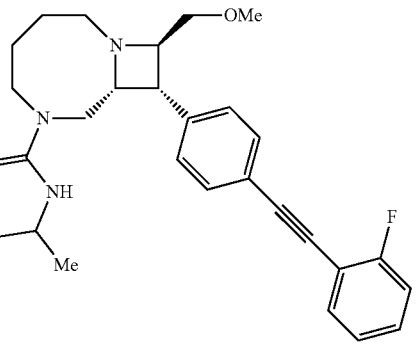 304
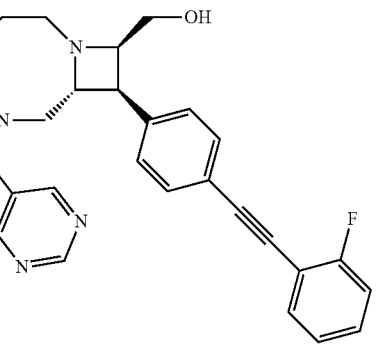 683
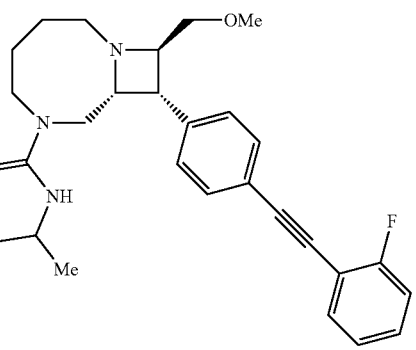 304-OMe TABLE 1-continued
Exemplary compounds of Formula (I).
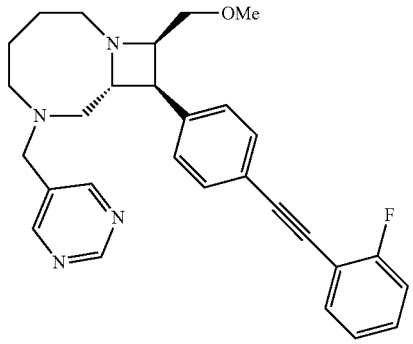 [SMILES: COC[C@H]1[C@@H](c2ccc(C#Cc3ccccc3F)cc2)[C@@H]2CN(Cc3cncnc3)CCCCN12] 683-OMe
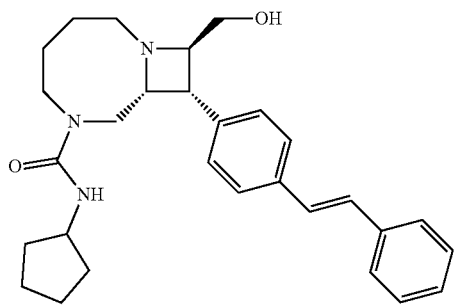 [SMILES: O=C(NC1CCCC1)N1CCCCN2[C@@H](CO)[C@H](c3ccc(/C=C/c4ccccc4)cc3)[C@@H]2C1] 346
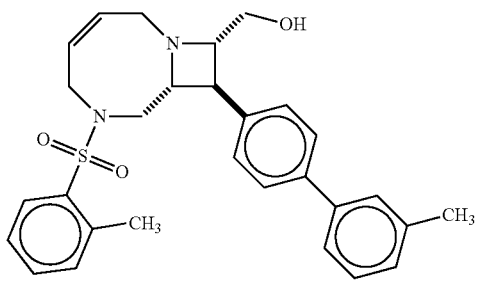 K1
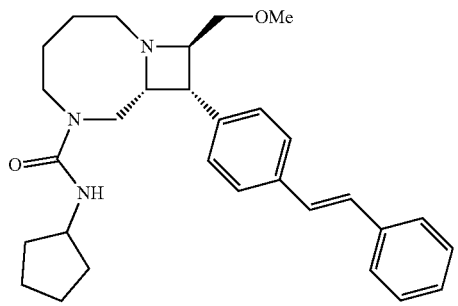 [SMILES: COC[C@H]1[C@H](c2ccc(/C=C/c3ccccc3)cc2)[C@@H]2CN(C(=O)NC3CCCC3)CCCCN12] 346-OMe
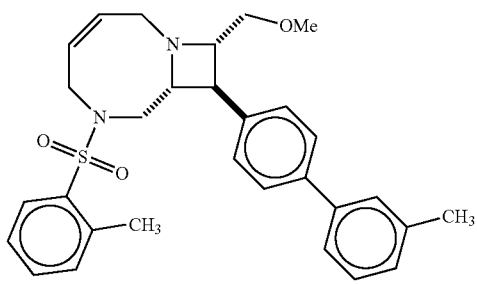 K1-OMe TABLE 1-continued
Exemplary compounds of Formula (I).
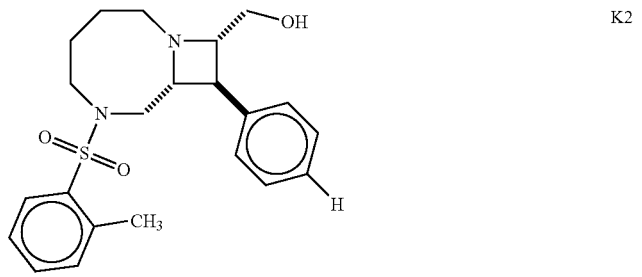 K2
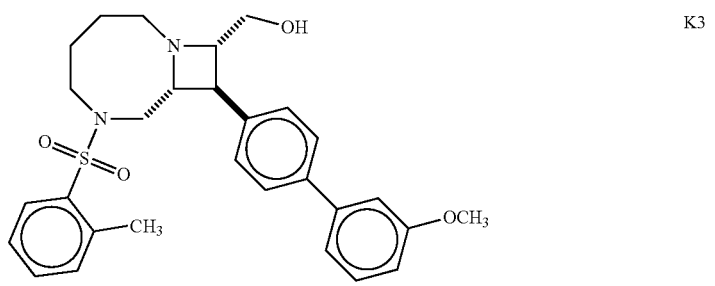 K3
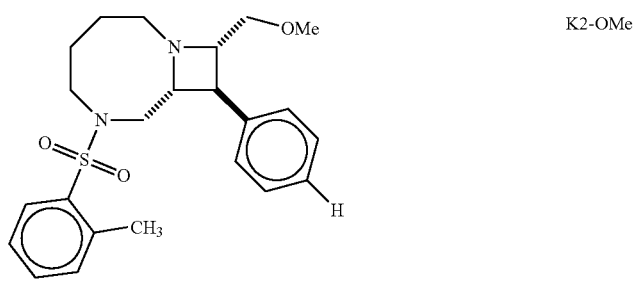 K2-OMe
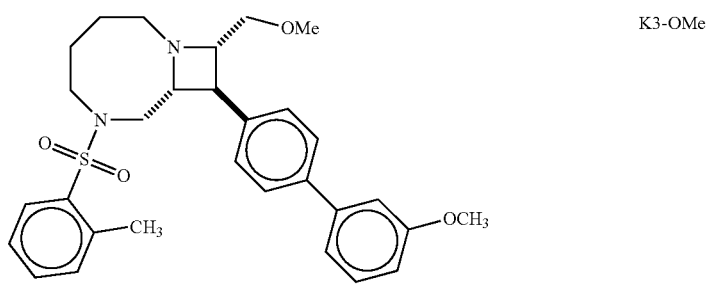 K3-OMe
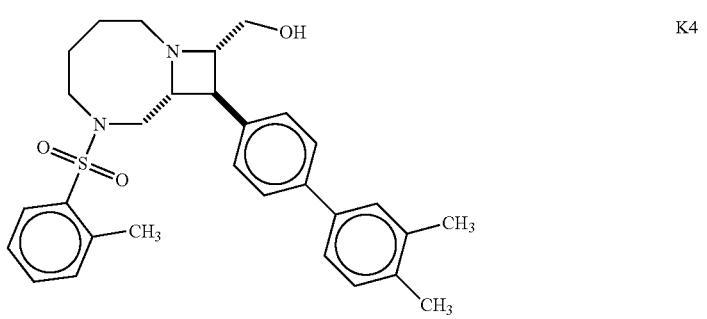 K4

TABLE 1-continued
Exemplary compounds of Formula (I).
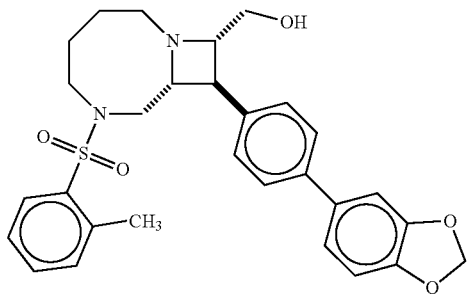 K5
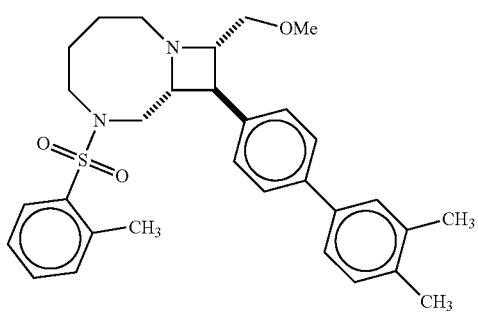 K4-OMe
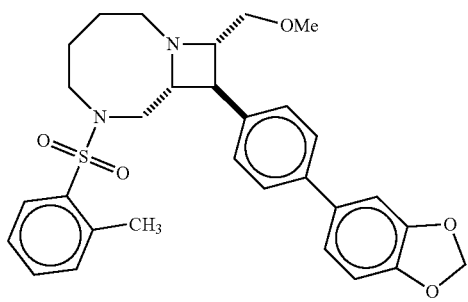 K5-OMe
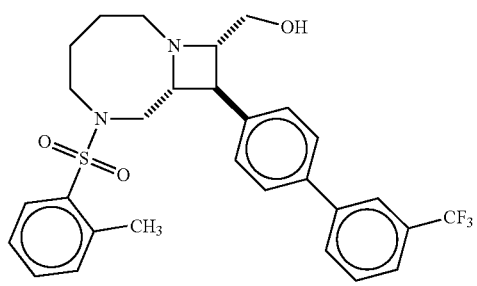 K6
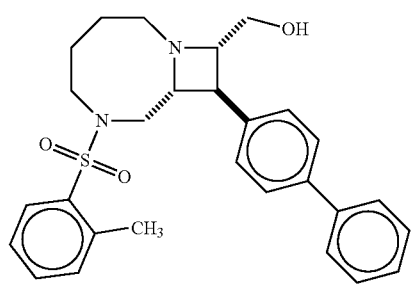 K7

TABLE 1-continued
Exemplary compounds of Formula (I).
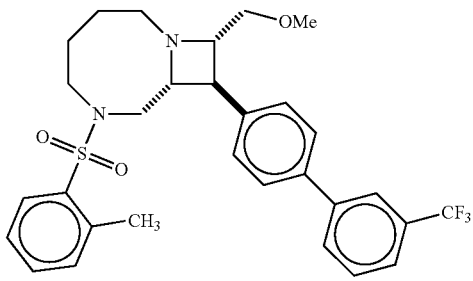 K6-OMe
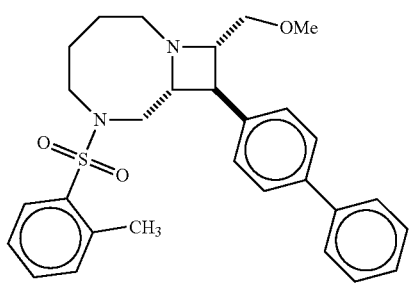 K7-OMe
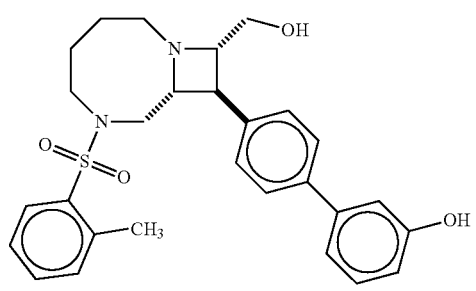 K8
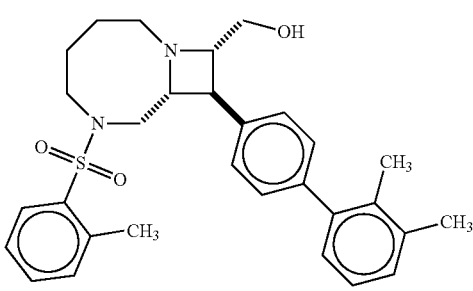 K9
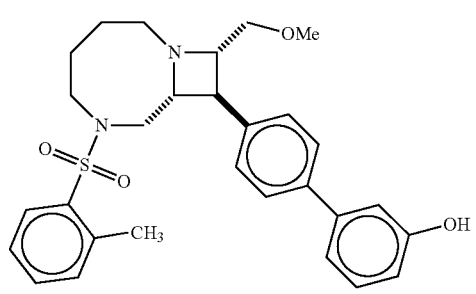 K8-OMe TABLE 1-continued
Exemplary compounds of Formula (I).
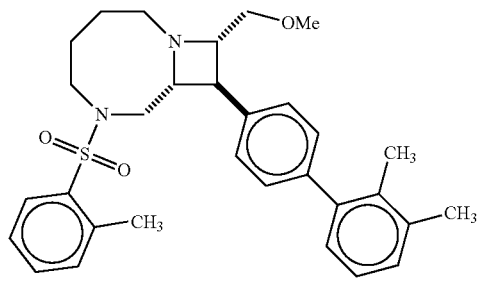 K9-OMe
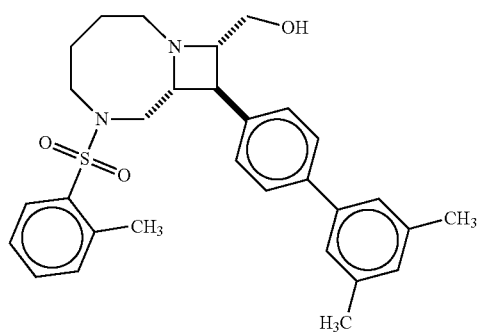 K10
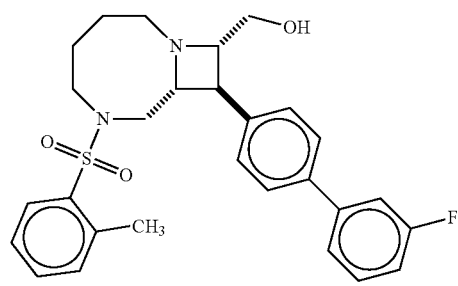 K11
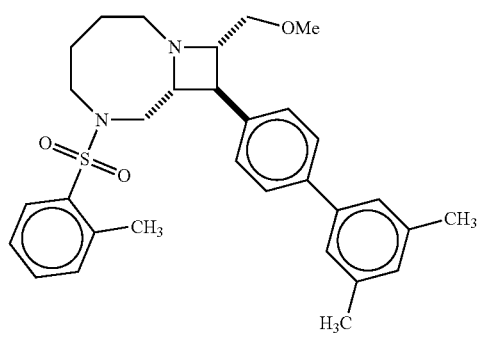 K10-OMe
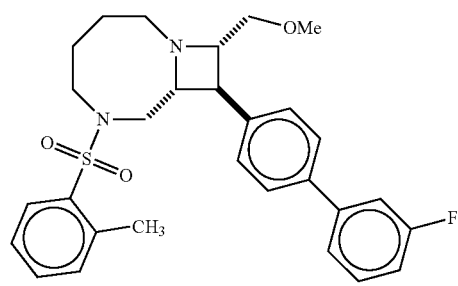 K11-OMe TABLE 1-continued
Exemplary compounds of Formula (I).
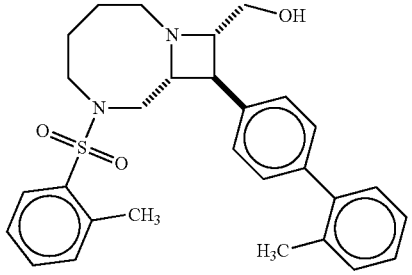 K12
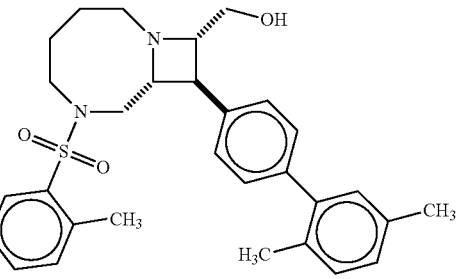 K13
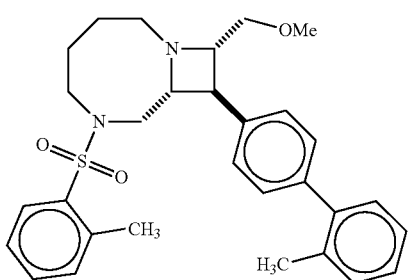 K12-OMe
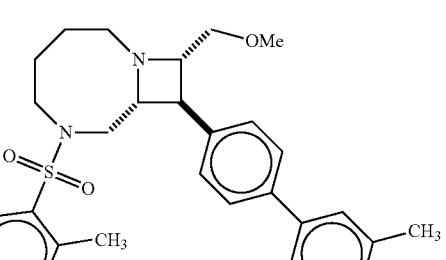 K13-OMe
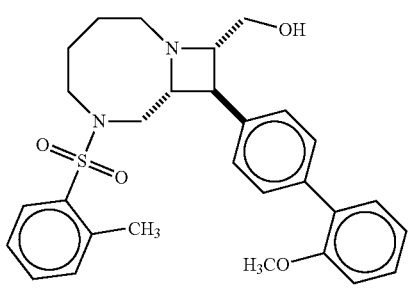 K14

TABLE 1-continued
Exemplary compounds of Formula (I).
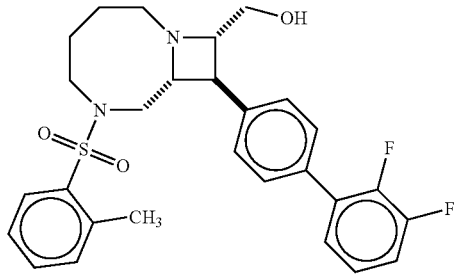 K15
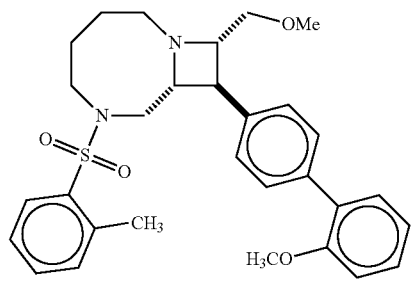 K14-OMe
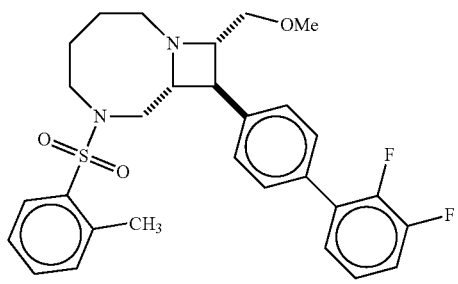 K15-OMe
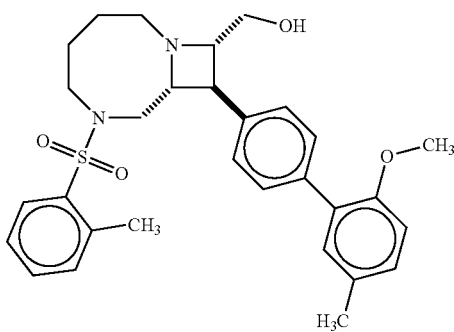 K16
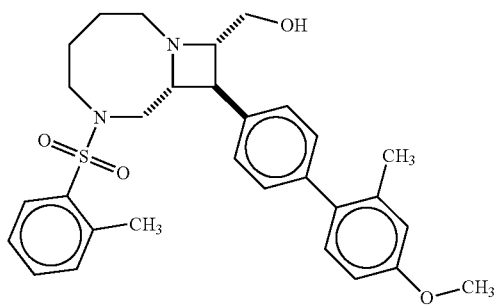 K17

TABLE 1-continued
Exemplary compounds of Formula (I).
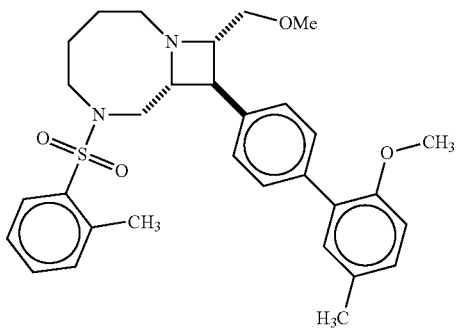 K16-OMe
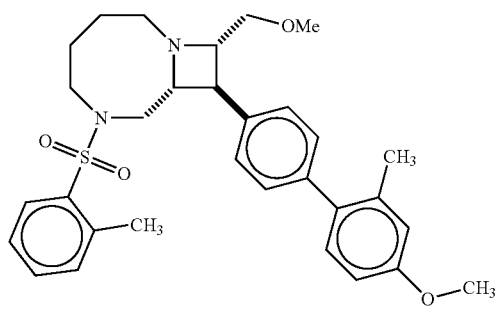 K17-OMe
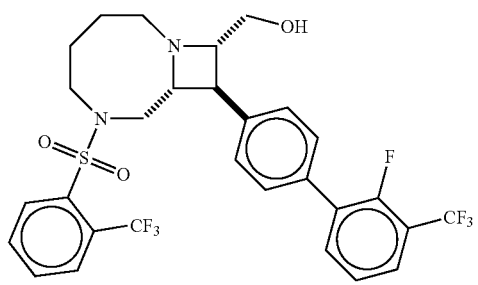 K18
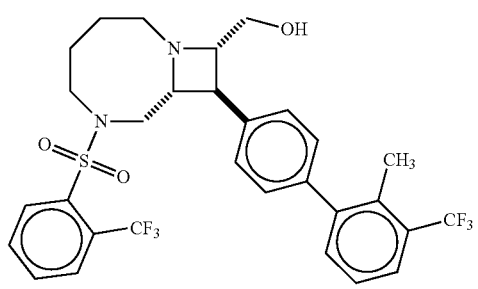 K19
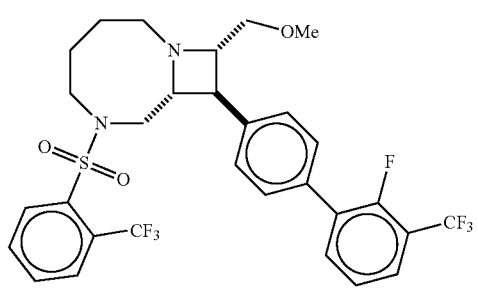 K18-OMe TABLE 1-continued
Exemplary compounds of Formula (I).
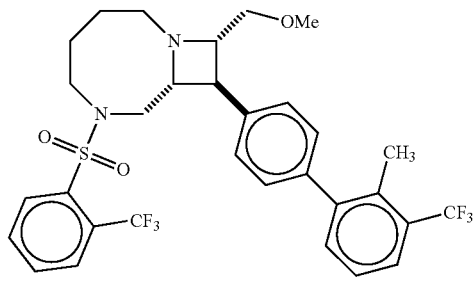 K19-OMe
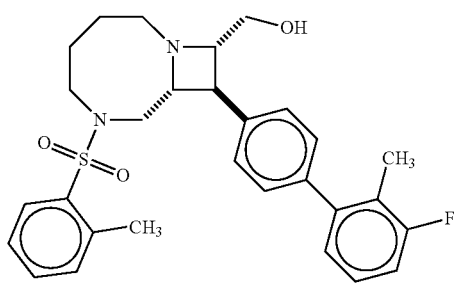 K20
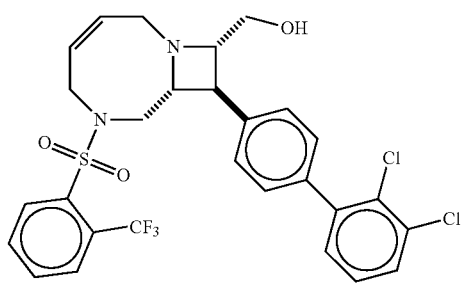 K21
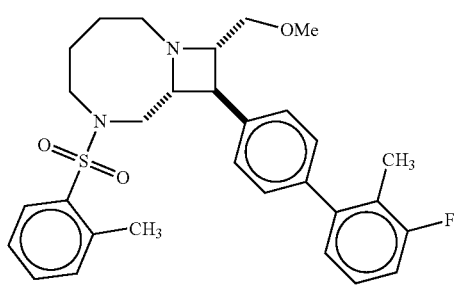 K20-OMe
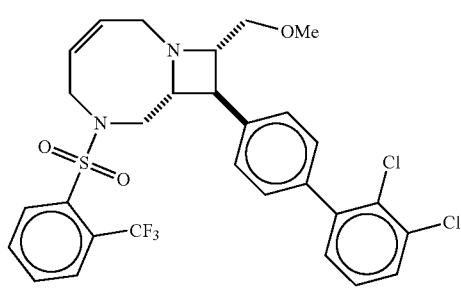 K21-OMe TABLE 1-continued
Exemplary compounds of Formula (I).
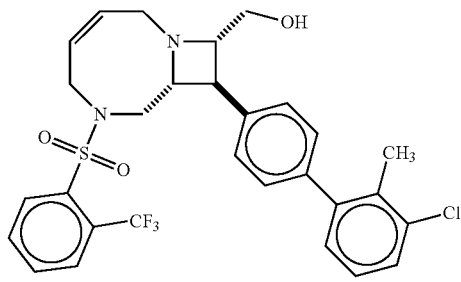 K22
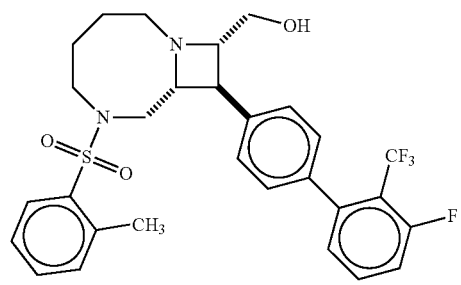 K23
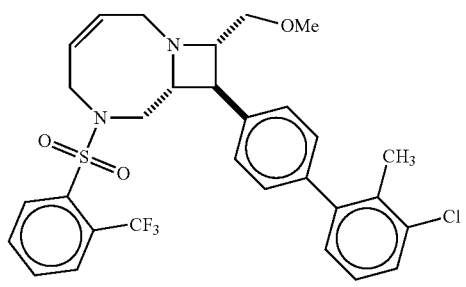 K22-OMe
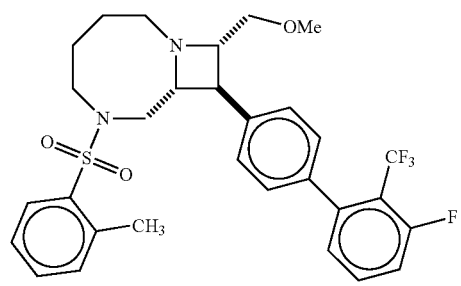 K23-OMe
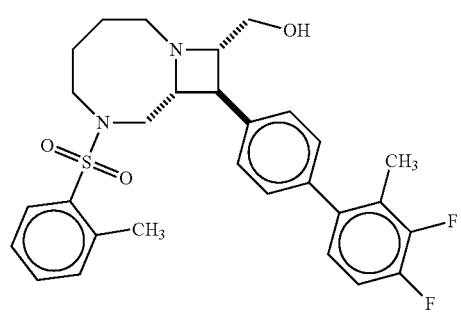 K24

TABLE 1-continued
Exemplary compounds of Formula (I).
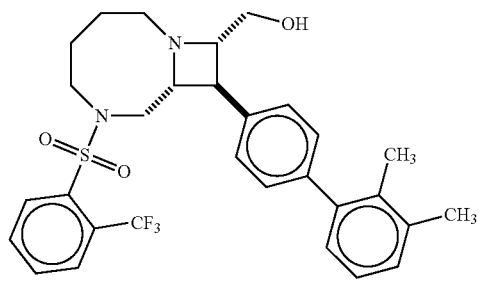 K25
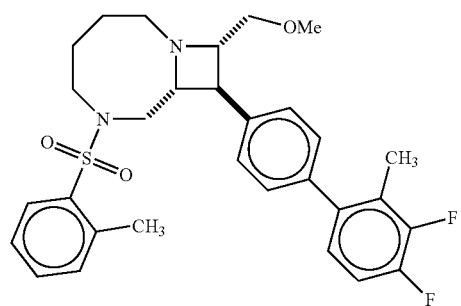 K24-OMe
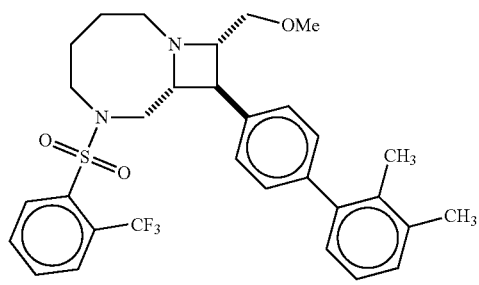 K25-OMe
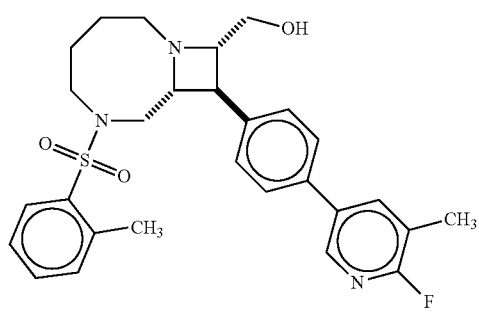 K26
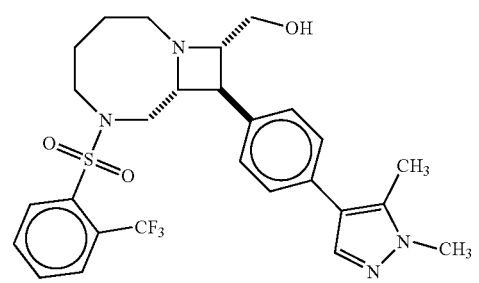 K27

TABLE 1-continued
Exemplary compounds of Formula (I).
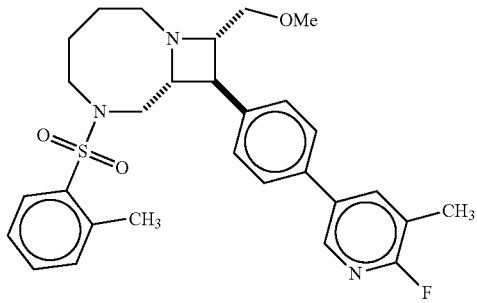 K26-OMe
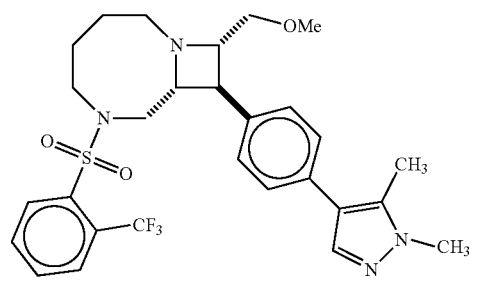 K27-OMe
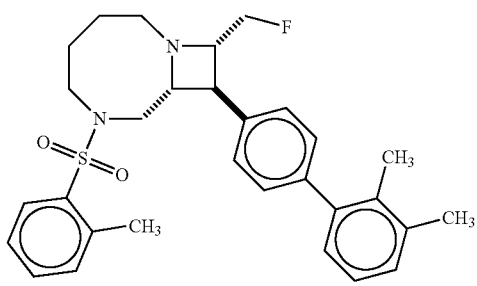 K28
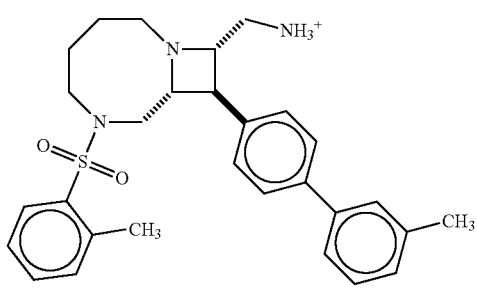 K29
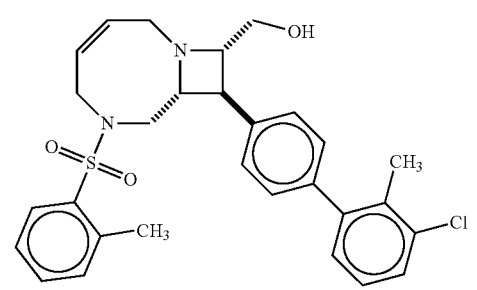 JP-28

TABLE 1-continued
Exemplary compounds of Formula (I).
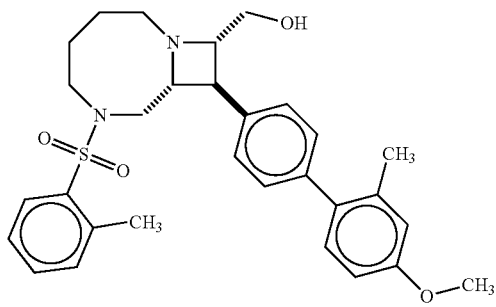 JP-29
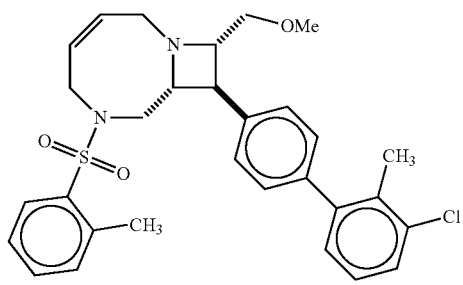 JP-28-OMe
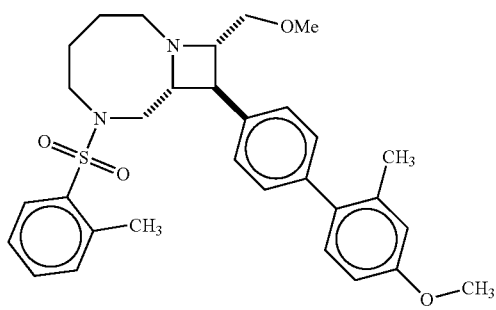 JP-29-OMe
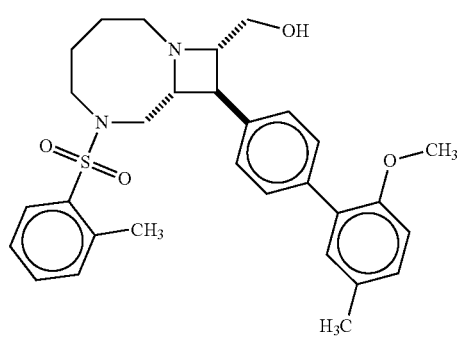 JP-30a
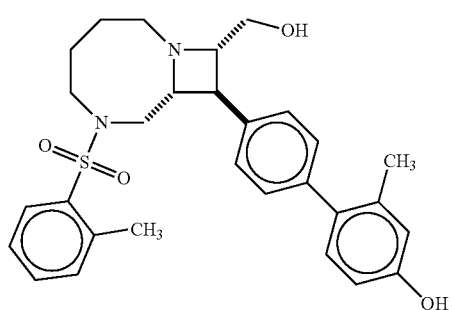 JP-31

TABLE 1-continued
Exemplary compounds of Formula (I).
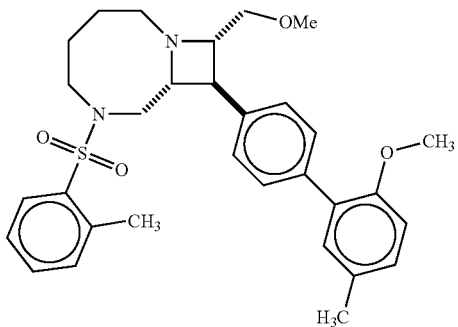 JP-30a-OMe
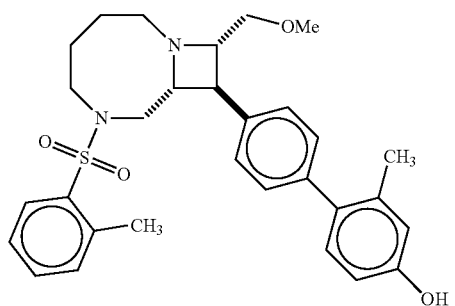 JP-31-OMe
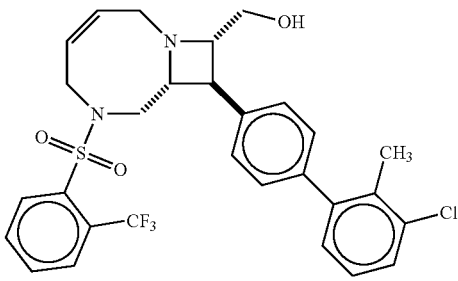 JP-37
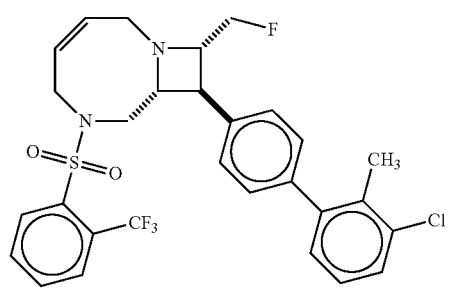 JP-38
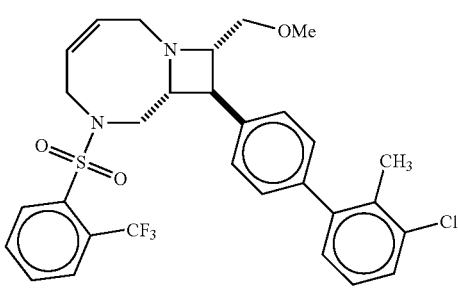 JP-37-OMe TABLE 1-continued
Exemplary compounds of Formula (I).
| | |
|---|---|
| 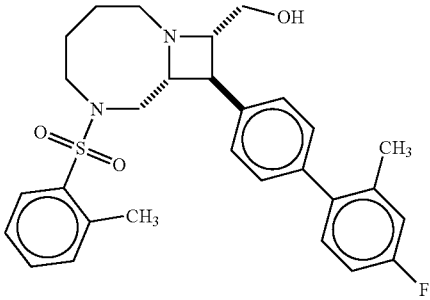 | JP-39 |
| 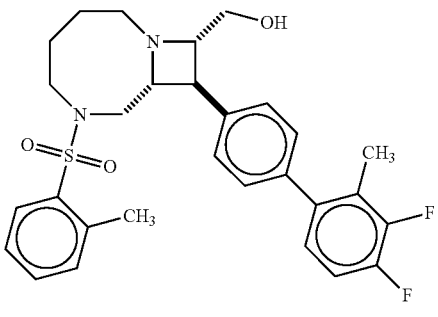 | JP-40 |
| 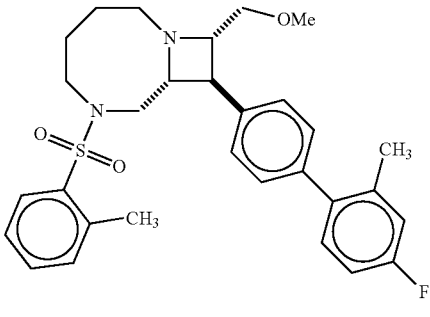 | JP-39-OMe |
| 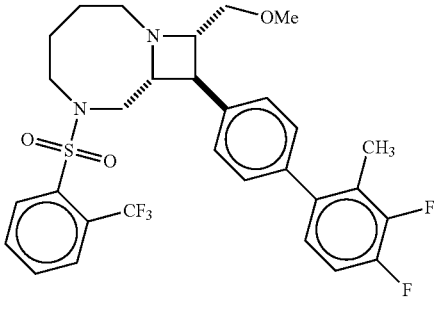 | JP-40-OMe |
| 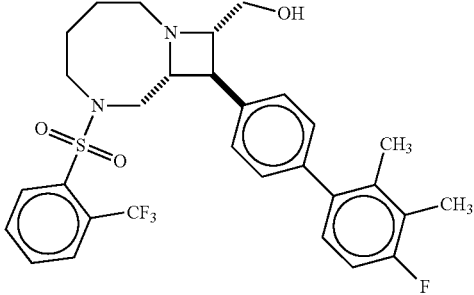 | JP-41 |

US 11,040,976 B2
221                                                                 222
TABLE 1-continued
Exemplary compounds of Formula (I).
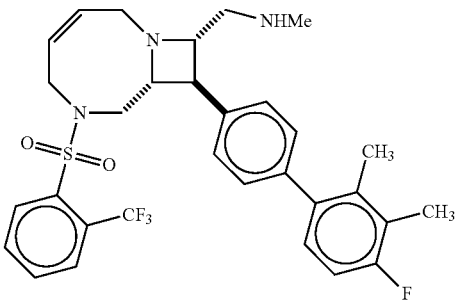 JP-41-NHMe
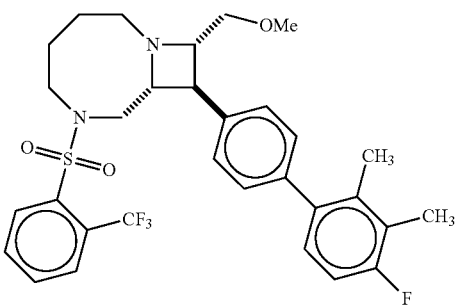 JP-41-OMe
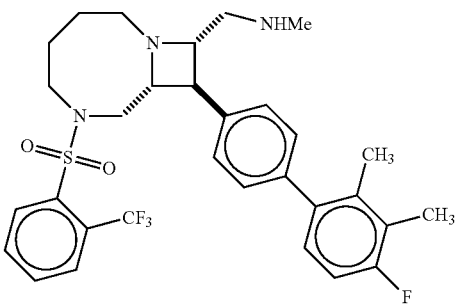 JP-41-NHMe
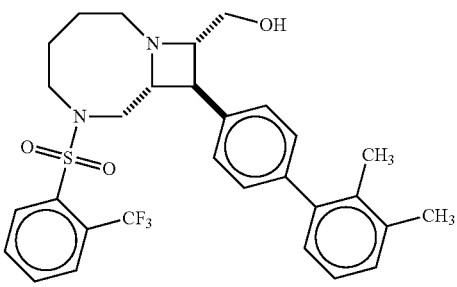 JP-17
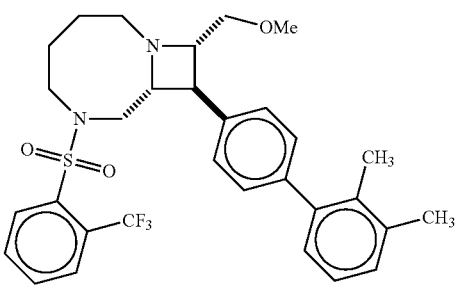 JP-17-OMe TABLE 1-continued
Exemplary compounds of Formula (I).
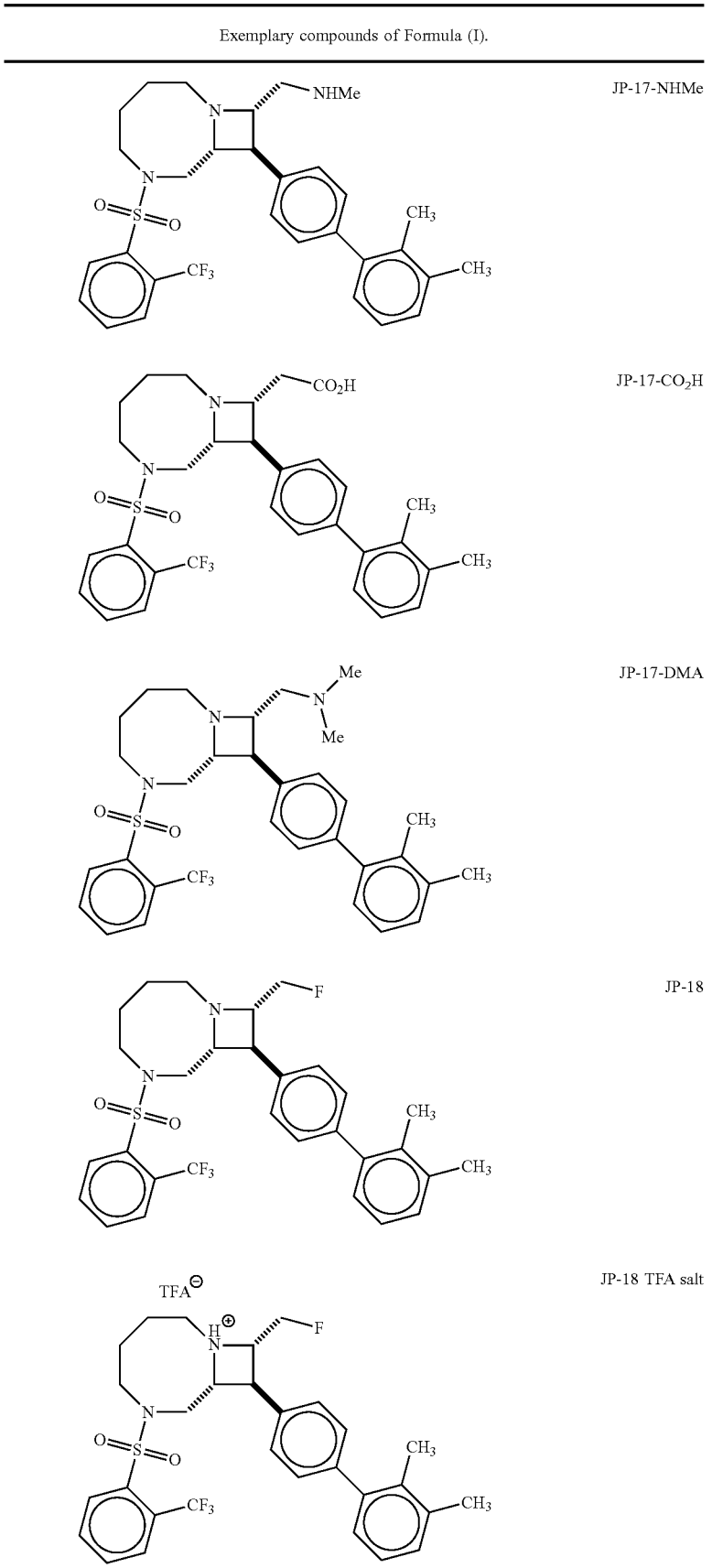
JP-17-NHMe
JP-17-CO2H
JP-17-DMA
JP-18
JP-18 TFA salt TABLE 1-continued
Exemplary compounds of Formula (I).
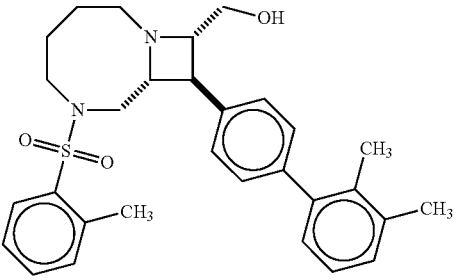 JP-8
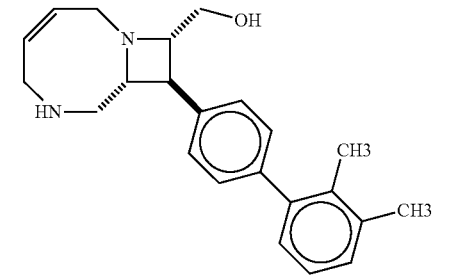 Int211
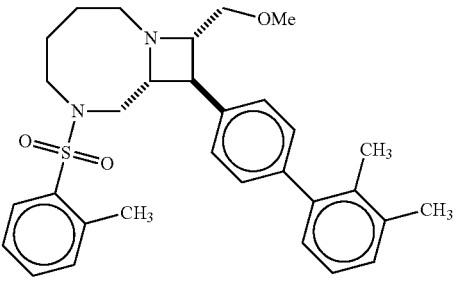 JP-8-OMe
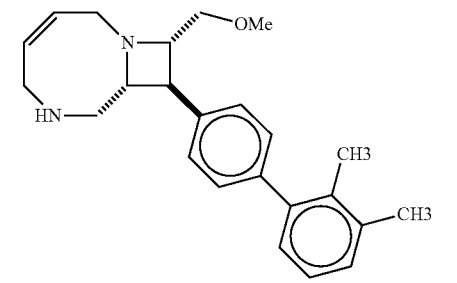 Int211-OMe
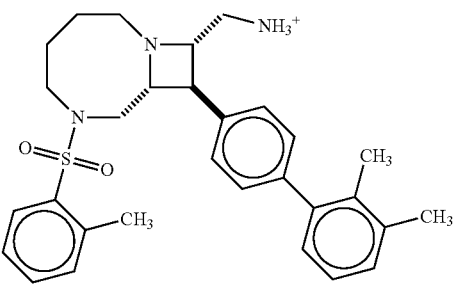 JP-8N TABLE 1-continued
Exemplary compounds of Formula (I).
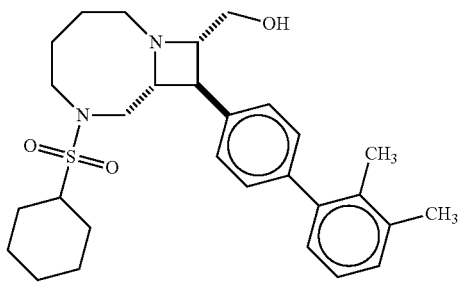 JP-S2
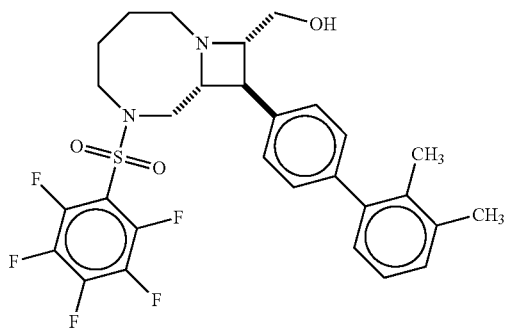 JP-S4
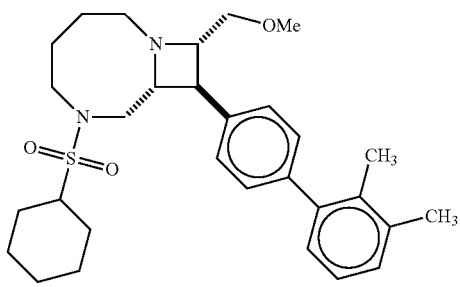 JP-S2-OMe
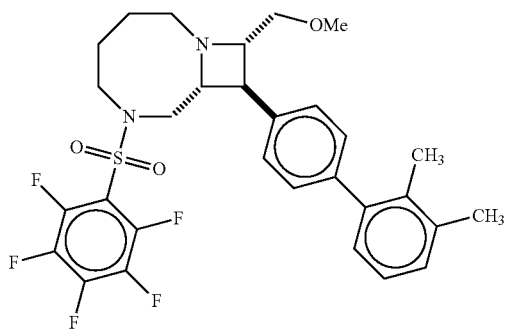 JP-S4-OMe
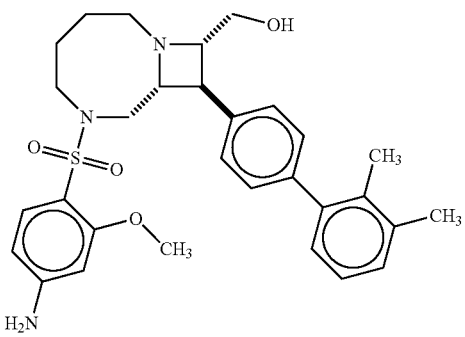 JP-S5

TABLE 1-continued

Exemplary compounds of Formula (I).

| Structure | ID |
|---|---|
| (structure) | JP-S7 |
| (structure) | JP-S5-OMe |
| (structure) | JP-S7-OMe |
| (structure) | JP-S10 |
| (structure) | JP-S11 |

TABLE 1-continued
Exemplary compounds of Formula (I).
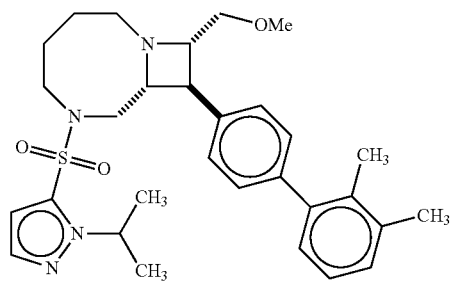 JP-S10-OMe
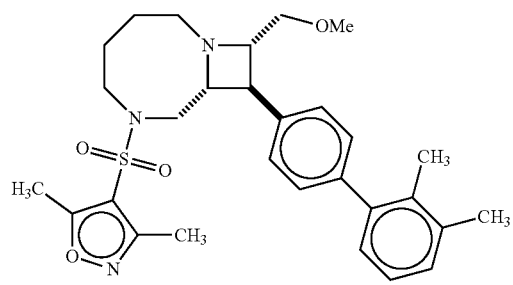 JP-S11-OMe
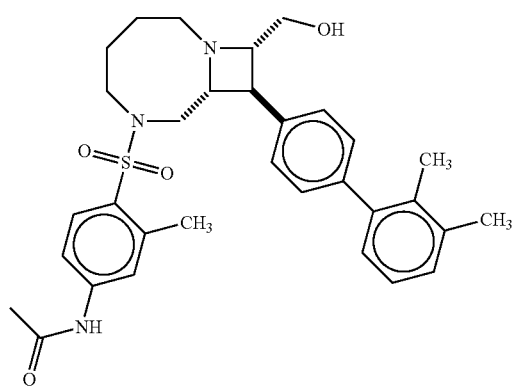 JP-S12
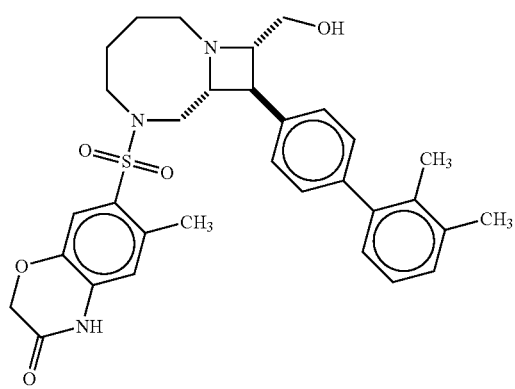 JP-S13

TABLE 1-continued
Exemplary compounds of Formula (I).
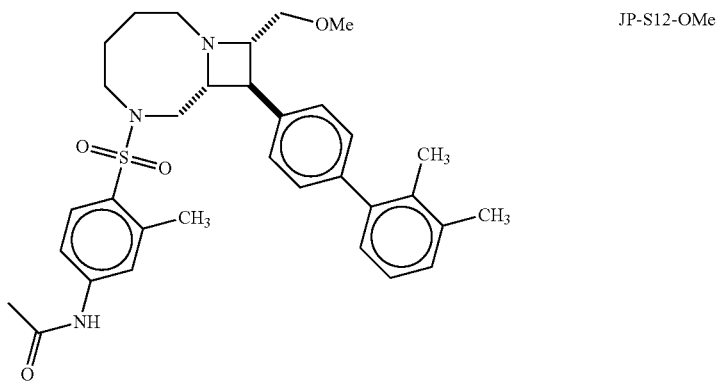
JP-S12-OMe
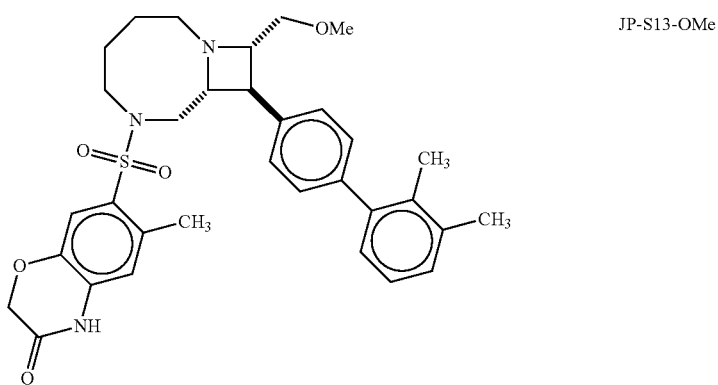
JP-S13-OMe
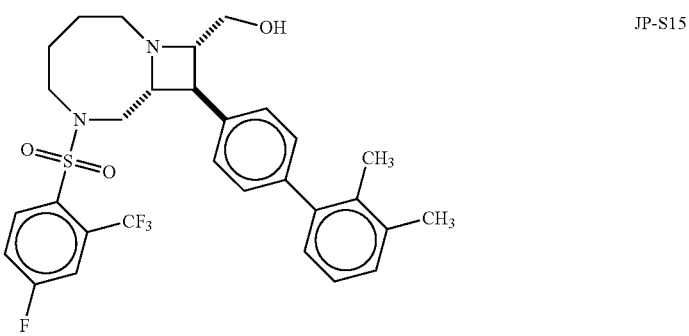
JP-S15
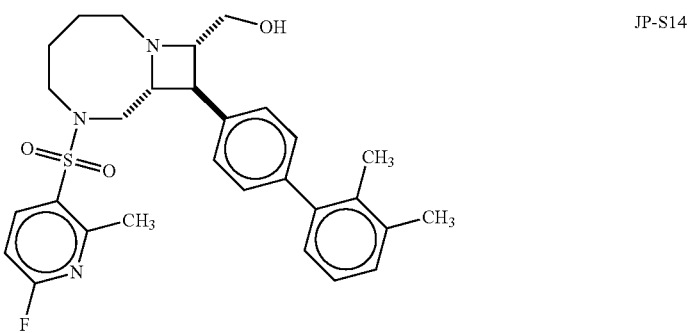
JP-S14

TABLE 1-continued
Exemplary compounds of Formula (I).
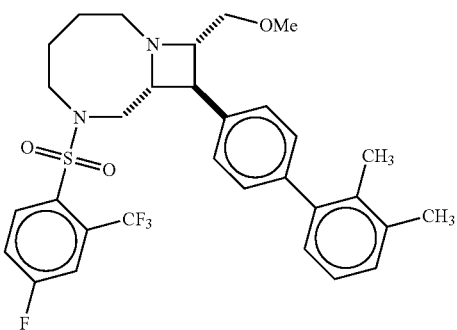 JP-S15-OMe
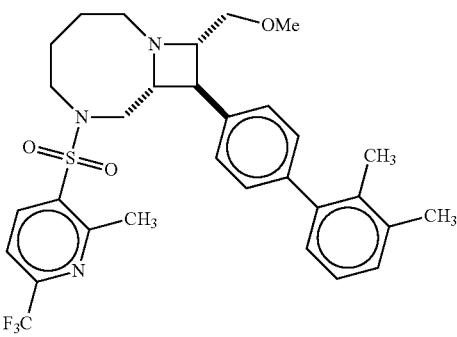 JP-S14-OMe
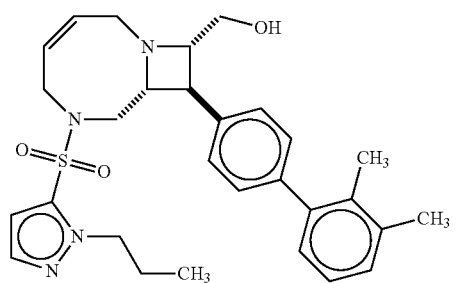 JP-S16
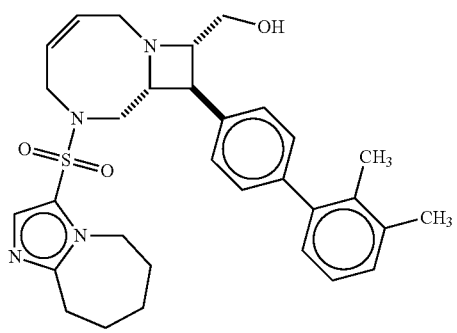 JP-S17
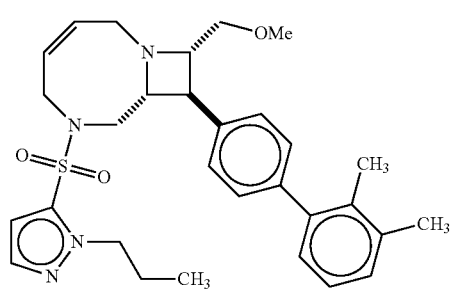 JP-S16-OMe TABLE 1-continued
Exemplary compounds of Formula (I).
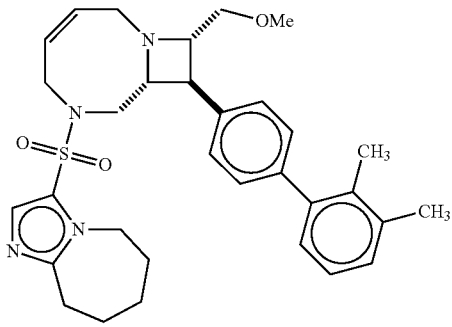 JP-S17-OMe
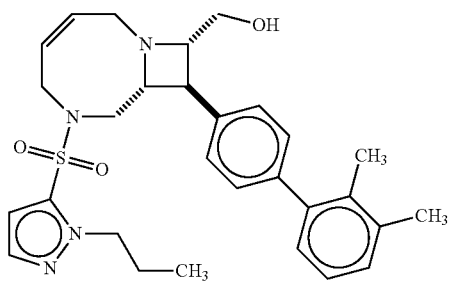 JP-S16-H2
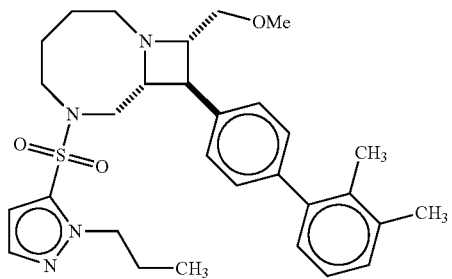 JP-S16-H2-OMe
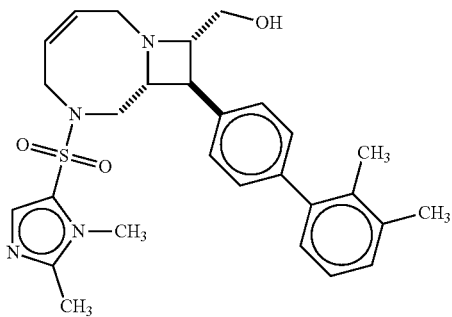 JP-S18
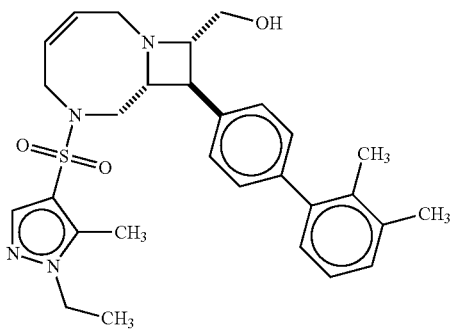 JP-S19

TABLE 1-continued
Exemplary compounds of Formula (I).
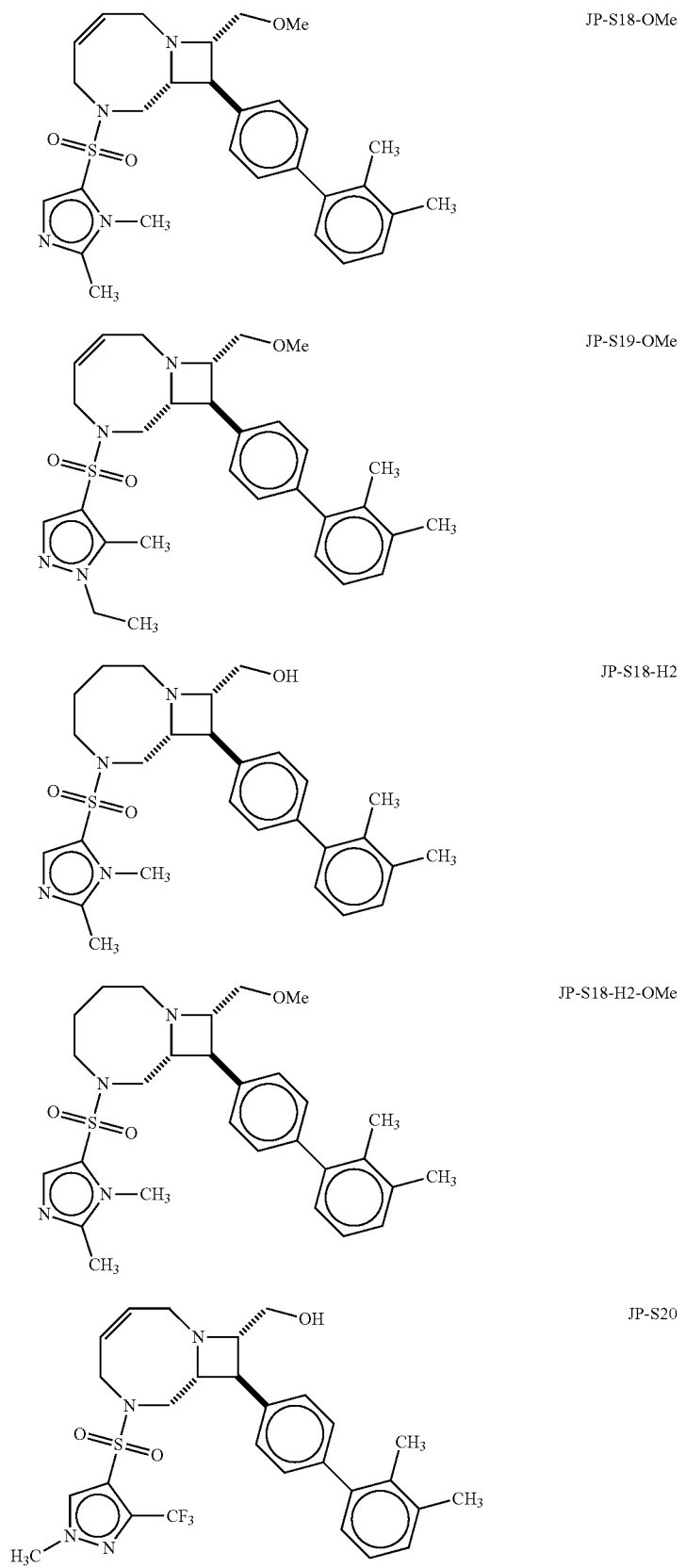
JP-S18-OMe
JP-S19-OMe
JP-S18-H2
JP-S18-H2-OMe
JP-S20

TABLE 1-continued
Exemplary compounds of Formula (I).
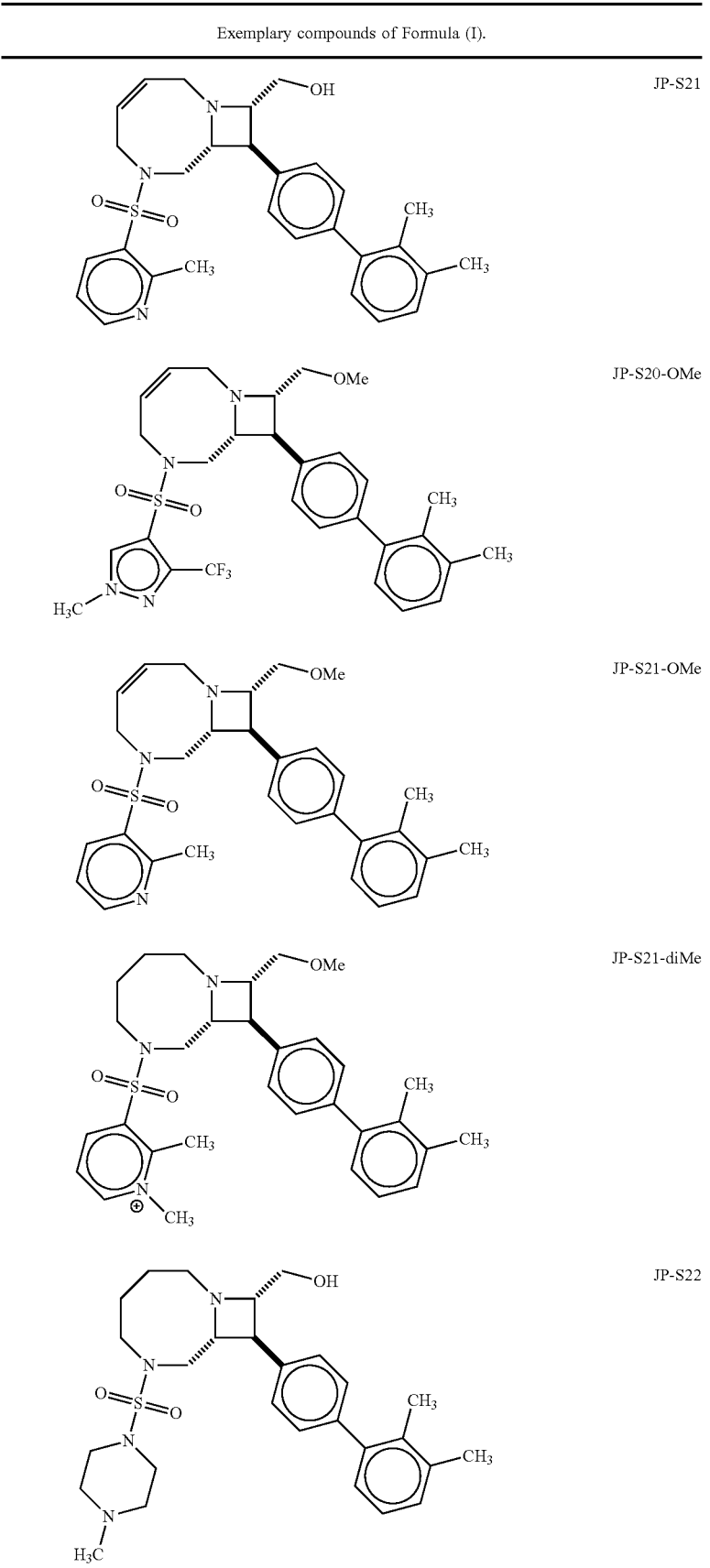
JP-S21
JP-S20-OMe
JP-S21-OMe
JP-S21-diMe
JP-S22

TABLE 1-continued
Exemplary compounds of Formula (I).
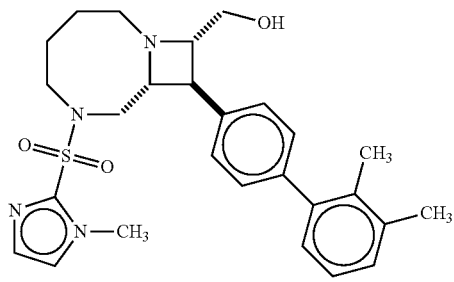 JP-S23
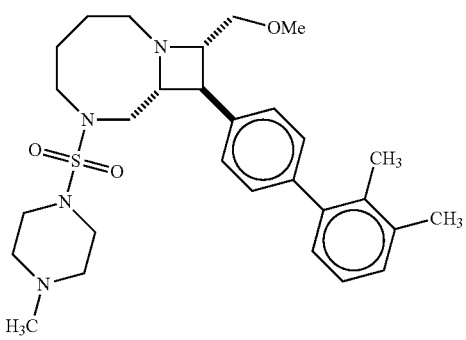 JP-S22-OMe
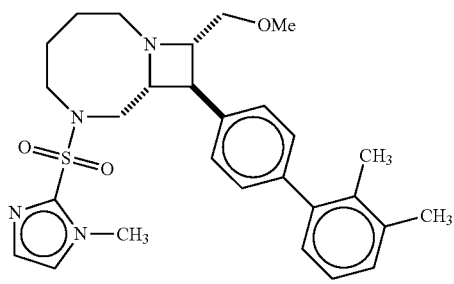 JP-S23-OMe
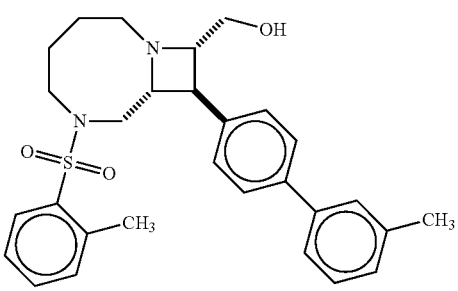 BRD-297
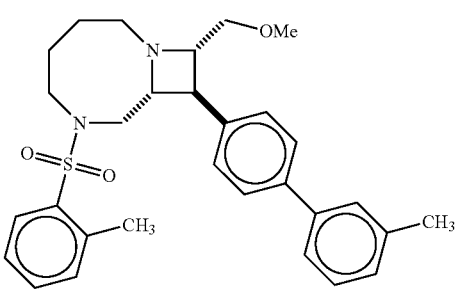 BRD-297-OMe TABLE 1-continued
Exemplary compounds of Formula (I).
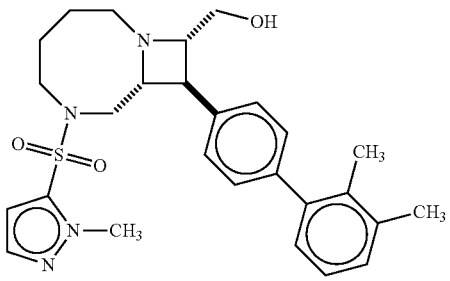
JP-S24
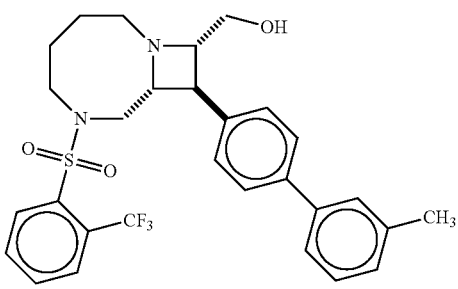
BRD-298
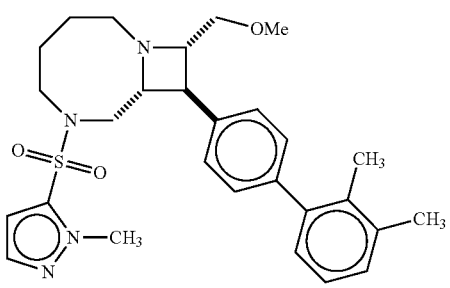
JP-S24-OMe
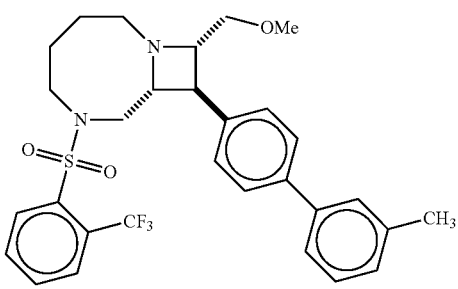
BRD-298-OMe
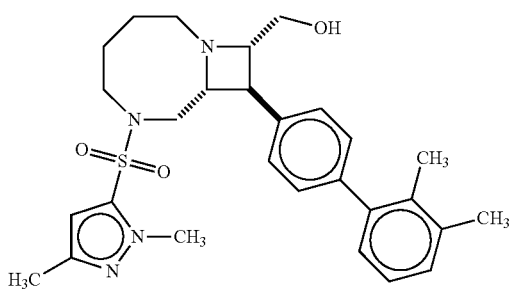
JP-S25

TABLE 1-continued
Exemplary compounds of Formula (I).
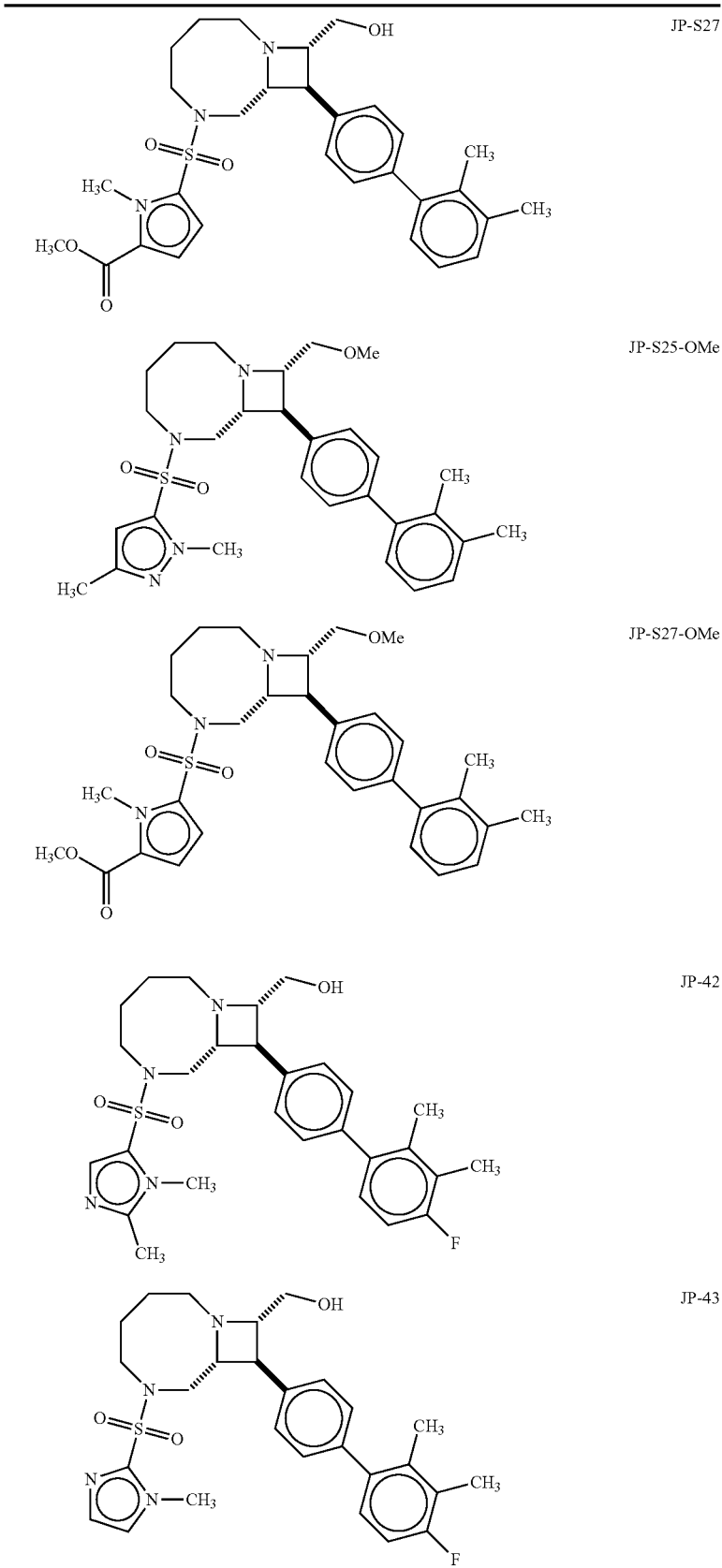
JP-S27
JP-S25-OMe
JP-S27-OMe
JP-42
JP-43

TABLE 1-continued
Exemplary compounds of Formula (I).
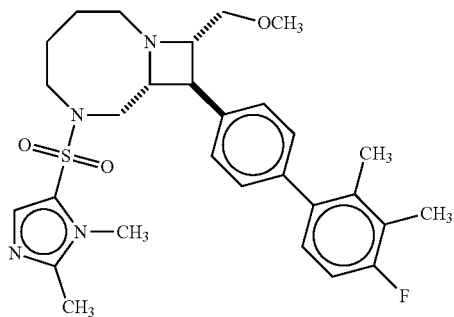 JP-42-OMe
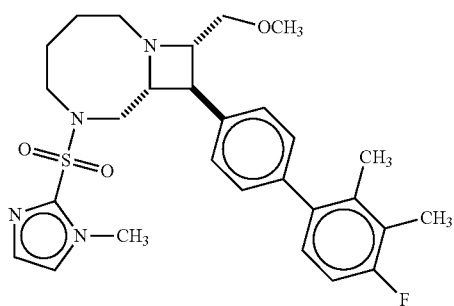 JP-43-OMe
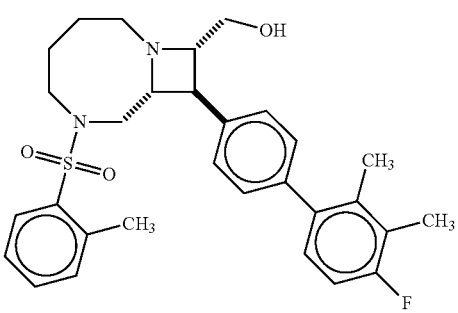 JP-44
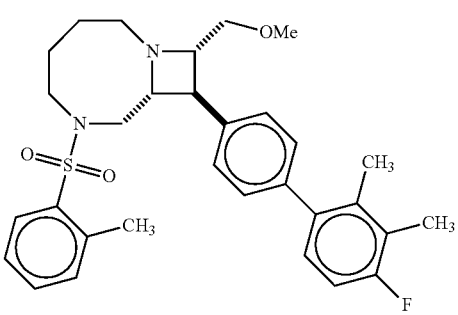 JP-44-OMe TABLE 2
Exemplary compounds of Formula (I).
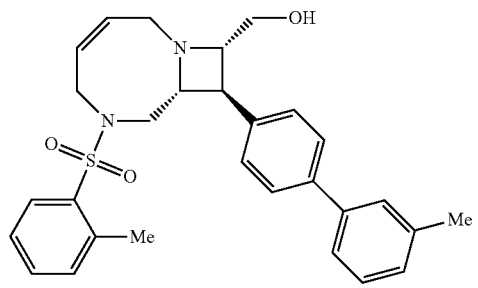 B1
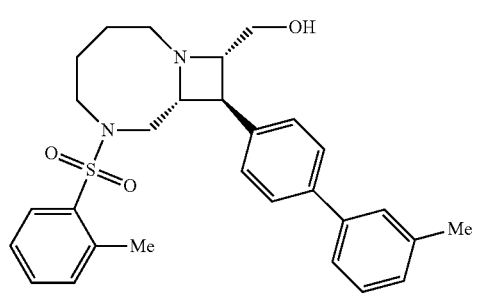 [SMILES: Cc1cccc(-c2ccc([C@@H]3[C@@H](CO)N4CCCCN(S(=O)(=O)c5ccccc5C)C[C@@H]34)cc2)c1] B2
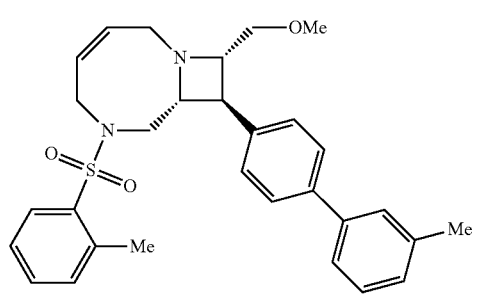 [SMILES: COC[C@@H]1[C@@H](c2ccc(-c3cccc(C)c3)cc2)[C@@H]2CN(S(=O)(=O)c3ccccc3C)C/C=C\CN12] B1-OMe
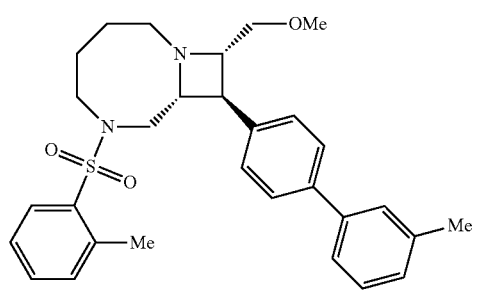 B2-OMe
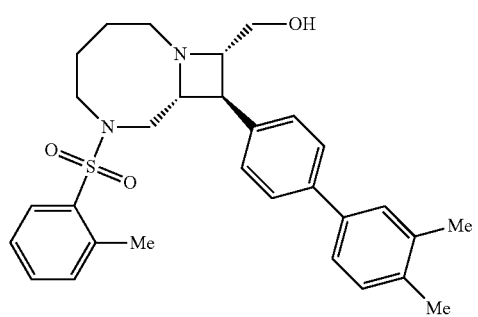 [SMILES: Cc1ccc(-c2ccc([C@@H]3[C@@H](CO)N4CCCCN(S(=O)(=O)c5ccccc5C)C[C@@H]34)cc2)cc1C] B3
TABLE 2-continued
Exemplary compounds of Formula (I).
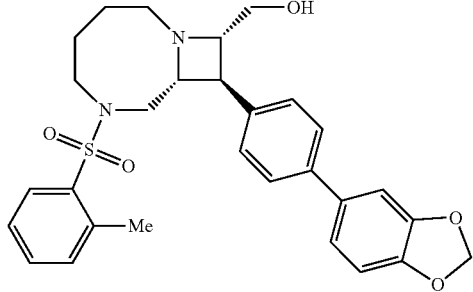 [SMILES: Cc1ccccc1S(=O)(=O)N1CCCCN2[C@H](CO)[C@@H](c3ccc(-c4ccc5c(c4)OCO5)cc3)[C@@H]2C1] B4
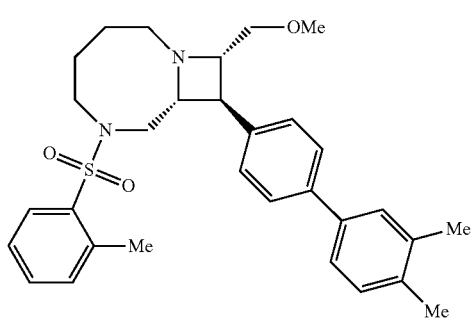 [SMILES: COC[C@@H]1[C@@H](c2ccc(-c3ccc(C)c(C)c3)cc2)[C@@H]2CN(S(=O)(=O)c3ccccc3C)CCCCN12] B3-OMe
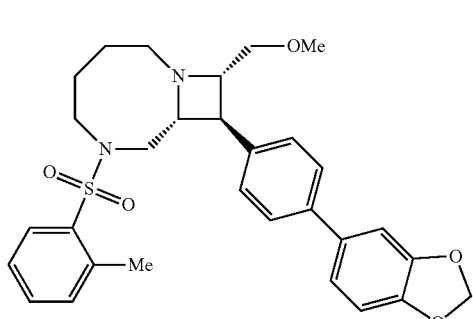 B4-OMe
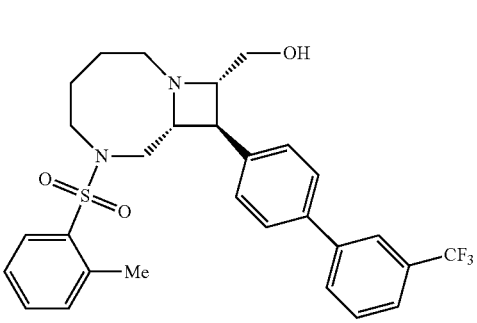 [SMILES: Cc1ccccc1S(=O)(=O)N1CCCCN2[C@H](CO)[C@@H](c3ccc(-c4cccc(C(F)(F)F)c4)cc3)[C@@H]2C1] B5
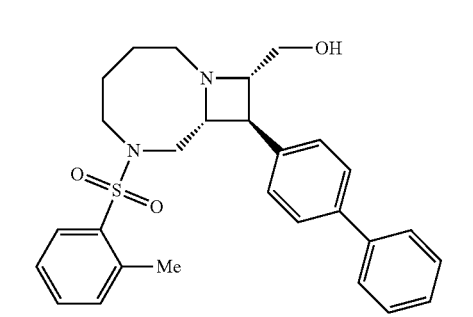 [SMILES: Cc1ccccc1S(=O)(=O)N1CCCCN2[C@H](CO)[C@@H](c3ccc(-c4ccccc4)cc3)[C@@H]2C1] B6

TABLE 2-continued
Exemplary compounds of Formula (I).
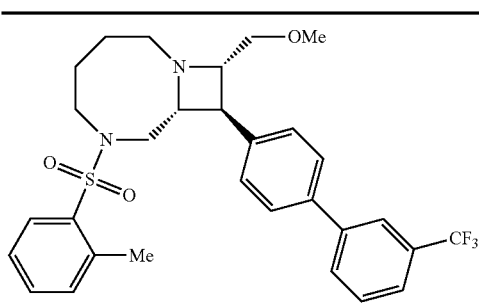 B5-OMe
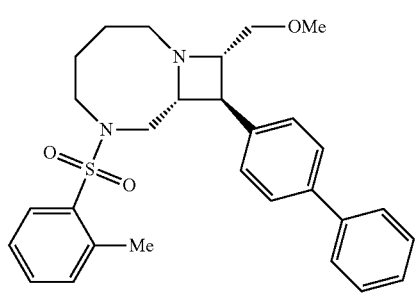 [SMILES: COC[C@@H]1[C@@H](c2ccc(-c3ccccc3)cc2)[C@@H]2CN(S(=O)(=O)c3ccccc3C)CCCCN12] B6-OMe
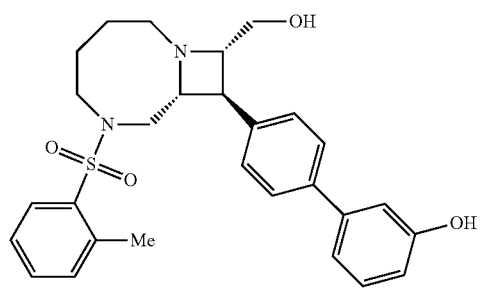 [SMILES: Cc1ccccc1S(=O)(=O)N1CCCCN2[C@H](CO)[C@@H](c3ccc(-c4cccc(O)c4)cc3)[C@@H]2C1] B7
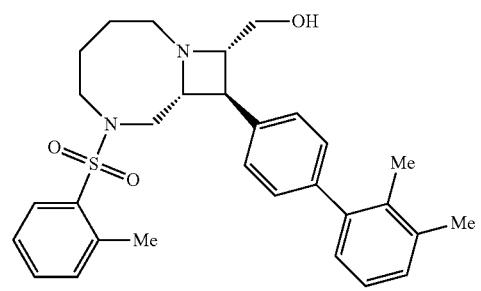 B8
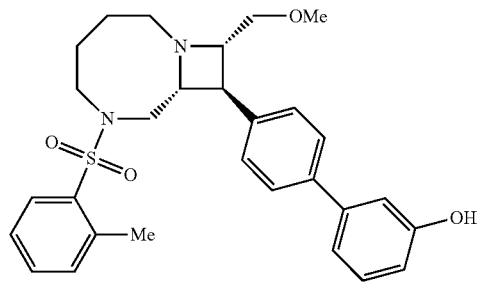 [SMILES: COC[C@@H]1[C@@H](c2ccc(-c3cccc(O)c3)cc2)[C@@H]2CN(S(=O)(=O)c3ccccc3C)CCCCN12] B7-OMe
TABLE 2-continued
Exemplary compounds of Formula (I).
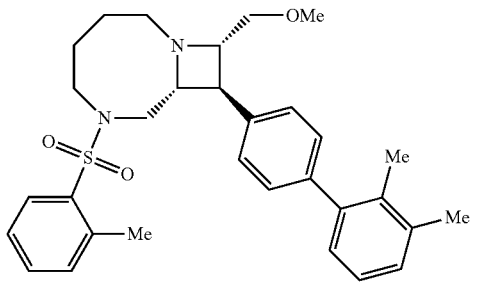 [SMILES: COC[C@@H]1[C@@H](c2ccc(-c3cccc(C)c3C)cc2)[C@@H]2CN(S(=O)(=O)c3ccccc3C)CCCCN12] B8-OMe
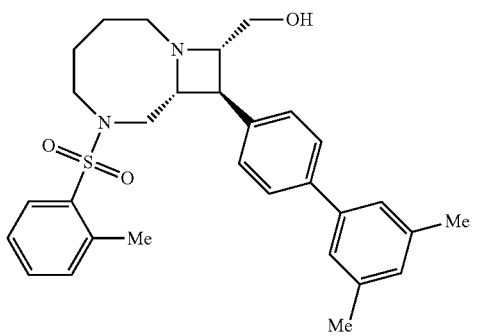 [SMILES: Cc1cc(C)cc(-c2ccc([C@@H]3[C@@H](CO)N4CCCCN(S(=O)(=O)c5ccccc5C)C[C@@H]34)cc2)c1] B9
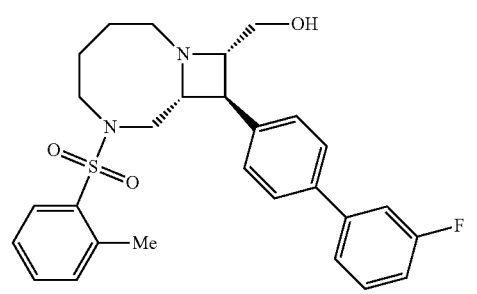 [SMILES: Cc1ccccc1S(=O)(=O)N1CCCCN2[C@H](CO)[C@@H](c3ccc(-c4cccc(F)c4)cc3)[C@@H]2C1] B10
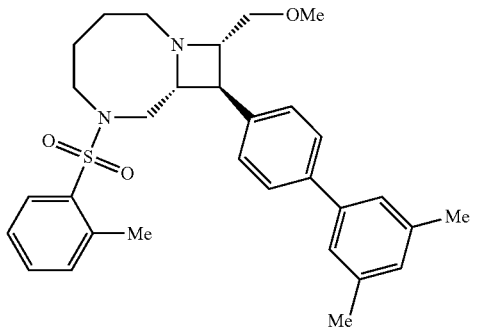 [SMILES: COC[C@@H]1[C@@H](c2ccc(-c3cc(C)cc(C)c3)cc2)[C@@H]2CN(S(=O)(=O)c3ccccc3C)CCCCN12] B9-OMe
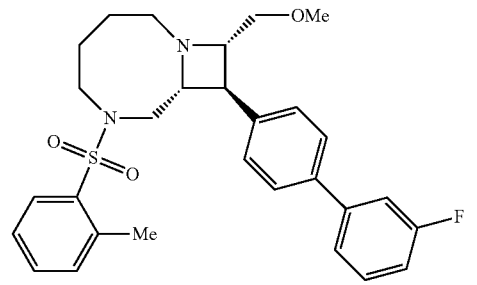 [SMILES: COC[C@@H]1[C@@H](c2ccc(-c3cccc(F)c3)cc2)[C@@H]2CN(S(=O)(=O)c3ccccc3C)CCCCN12] B10-OMe TABLE 2-continued Exemplary compounds of Formula (I).

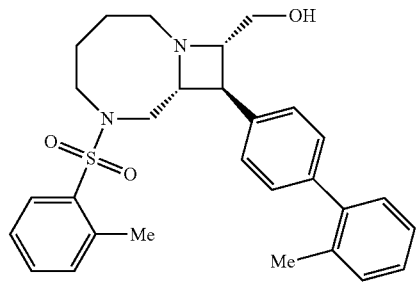 [SMILES: Cc1ccccc1-c1ccc([C@@H]2[C@@H](CO)N3CCCCN(S(=O)(=O)c4ccccc4C)C[C@@H]23)cc1]
B11

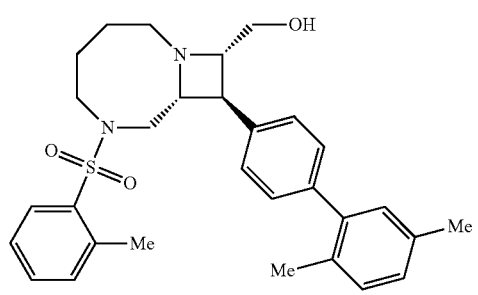 [SMILES: Cc1ccc(C)c(-c2ccc([C@@H]3[C@@H](CO)N4CCCCN(S(=O)(=O)c5ccccc5C)C[C@@H]34)cc2)c1]
B12

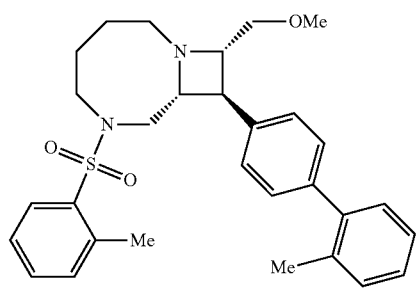 [SMILES: COC[C@@H]1[C@@H](c2ccc(-c3ccccc3C)cc2)[C@@H]2CN(S(=O)(=O)c3ccccc3C)CCCCN12]
B11-OMe

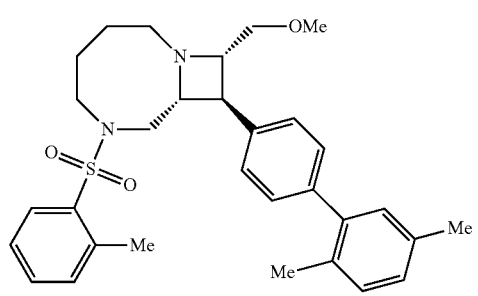 [SMILES: COC[C@@H]1[C@@H](c2ccc(-c3cc(C)ccc3C)cc2)[C@@H]2CN(S(=O)(=O)c3ccccc3C)CCCCN12]
B12-OMe

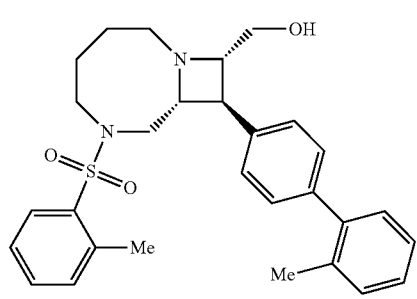 [SMILES: Cc1ccccc1-c1ccc([C@@H]2[C@@H](CO)N3CCCCN(S(=O)(=O)c4ccccc4C)C[C@@H]23)cc1]
B13

TABLE 2-continued

Exemplary compounds of Formula (I).

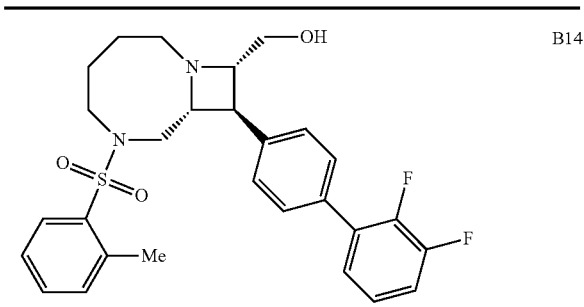
B14

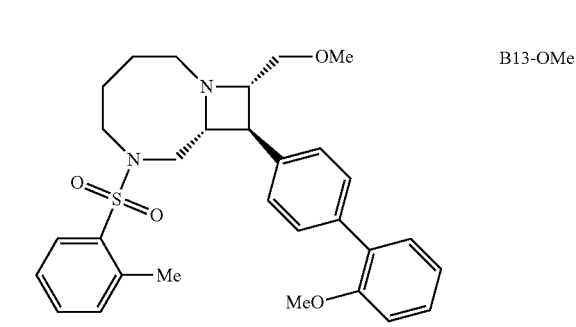
B13-OMe

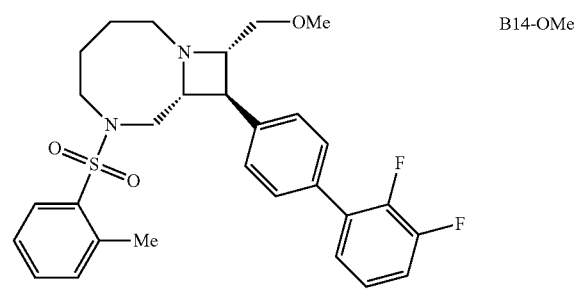
B14-OMe

In certain embodiments, the compound of Formula (I) is of formula:

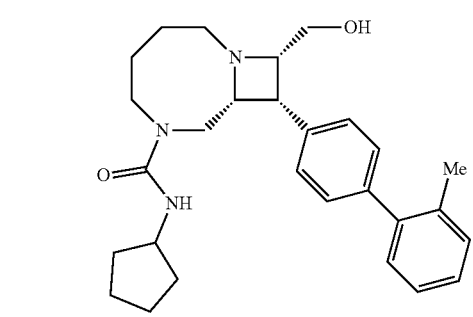 [SMILES: Cc1ccccc1-c1ccc([C@H]2[C@@H](CO)N3CCCCN(C(=O)NC4CCCC4)C[C@@H]23)cc1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

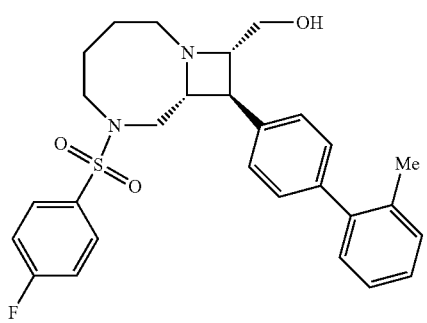 [SMILES: Cc1ccccc1-c1ccc([C@@H]2[C@@H](CO)N3CCCCN(S(=O)(=O)c4ccc(F)cc4)C[C@@H]23)cc1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

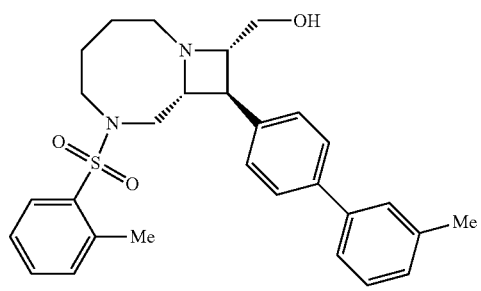 [SMILES: Cc1cccc(-c2ccc([C@@H]3[C@@H](CO)N4CCCCN(S(=O)(=O)c5ccccc5C)C[C@@H]34)cc2)c1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

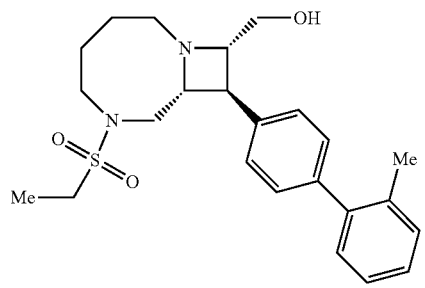 [SMILES: CCS(=O)(=O)N1CCCCN2[C@H](CO)[C@@H](c3ccc(-c4ccccc4C)cc3)[C@@H]2C1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

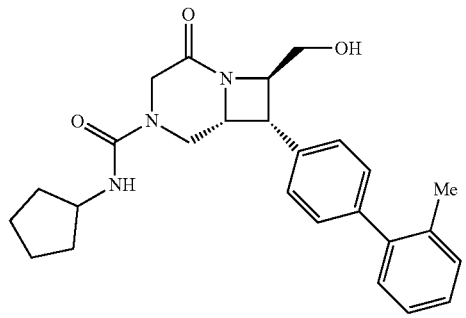 [SMILES: Cc1ccccc1-c1ccc([C@H]2[C@H](CO)N3C(=O)CN(C(=O)NC4CCCC4)C[C@@H]23)cc1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

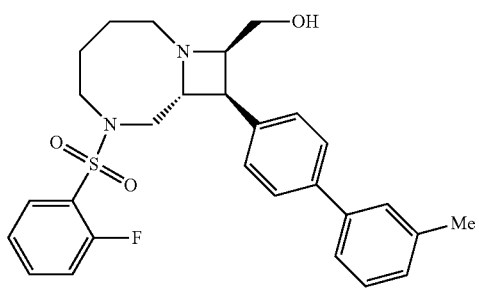 [SMILES: Cc1cccc(-c2ccc([C@@H]3[C@H](CO)N4CCCCN(S(=O)(=O)c5ccccc5F)C[C@@H]34)cc2)c1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

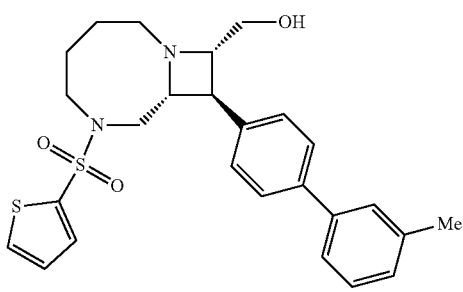 [SMILES: Cc1cccc(-c2ccc([C@@H]3[C@@H](CO)N4CCCCN(S(=O)(=O)c5cccs5)C[C@@H]34)cc2)c1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

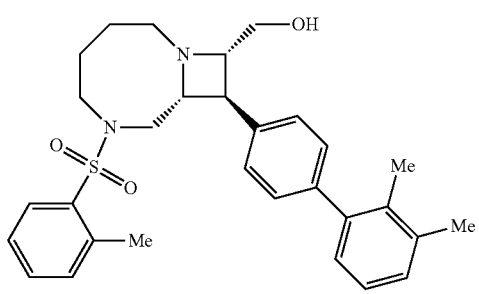 [SMILES: Cc1ccccc1S(=O)(=O)N1CCCCN2[C@H](CO)[C@@H](c3ccc(-c4cccc(C)c4C)cc3)[C@@H]2C1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

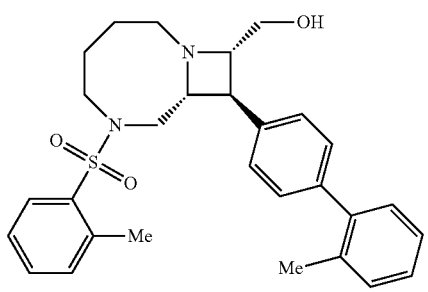 [SMILES: Cc1ccccc1-c1ccc([C@@H]2[C@@H](CO)N3CCCCN(S(=O)(=O)c4ccccc4C)C[C@@H]23)cc1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) is of formula:

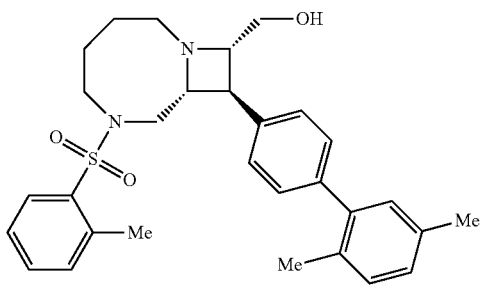 [SMILES: Cc1ccc(C)c(-c2ccc([C@@H]3[C@@H](CO)N4CCCCN(S(=O)(=O)c5ccccc5C)C[C@@H]34)cc2)c1]

or a pharmaceutically acceptable salt, solvate, hydrate, polymorph, co-crystal, tautomer, stereoisomer, prodrug, or isotopically labeled derivative thereof.

In certain embodiments, the compound of Formula (I) includes a moiety comprising Ring A and Ring B, wherein the rings are not free to rotate about the bond or linker connecting the two rings. In certain embodiments, the compound comprises a locked ring moiety comprising Ring A and Ring B directly attached by a single bond, wherein the rings are independently optionally substituted aryl or optionally substituted heteroaryl. In certain embodiments, the locked ring moiety comprises Ring A and Ring B directly attached by a single bond, wherein the rings are independently optionally substituted aryl or optionally substituted heteroaryl, and at least one of the rings has a non-hydrogen group ortho to the single bond.

In certain embodiments, the rotational energy barrier between rings A and B is at least about 6 kcal/mol. In certain embodiments, the rotational energy barrier between rings A and B is at least about 10 kcal/mol, at least about 15 kcal/mol, at least about 20 kcal/mol, or at least about 30 kcal/mol. In certain embodiments, the equilibrium dihedral angle between rings A and B is between about 20° and between about 160°, inclusive. In certain embodiments, the equilibrium dihedral angle between rings A and B is between about 40° and between about 140°, between about 60° and between about 120°, between about 90° and between about 100°, inclusive. In certain embodiments, the equilibrium dihedral angle between rings A and B is between about 20° and between about 160°, inclusive, when bound to IDE. In certain embodiments, the equilibrium dihedral angle between rings A and B is between about 40° and between about 140°, between about 60° and between about 120°, between about 90° and between about 100°, inclusive, when bound to IDE.

Compounds of Formula (II)

In certain embodiments, the invention provides a compound of Formula (II):

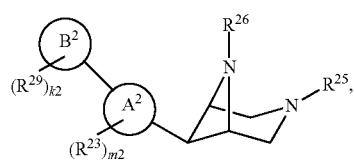

(II)

or a pharmaceutically acceptable salt, solvate, hydrate, polymorph, co-crystal, tautomer, stereoisomer, prodrug, or isotopically labeled derivative thereof,
wherein:
$R^{25}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$R$^{25a}$, —S(=O)$_2$OR$^{25a}$, —S(=O)$_2$N(R$^{25a}$)$_2$, or a nitrogen protecting group, wherein each $R^{25a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{25a}$ are joined to form an optionally substituted heteroaryl or optionally substituted heterocyclic ring;

$R^{26}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$R$^{26a}$, —S(=O)$_2$OR$^{26a}$, —S(=O)$_2$N(R$^{26a}$)$_2$, or a nitrogen protecting group, wherein each $R^{26a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{26a}$ are joined to form an optionally substituted heteroaryl or optionally substituted heterocyclic ring;

Ring $A^2$ is carbocyclylene, heterocyclylene, arylene or heteroarylene;

each $R^{23}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{23a}$, —N(R$^{23a}$)$_2$, or two $R^{23}$ are joined to form an optionally substituted carbocyclic, heterocyclic, aryl, or heteroaryl ring, wherein each $R^{23a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{23a}$ are joined to form an optionally substituted heteroaryl or optionally substituted heterocyclic ring;

Ring $B^2$ is a carbocyclic, heterocyclic, aryl or heteroaryl ring;

each $R^{29}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, $-NO_2$, $-CN$, $-OR^{29a}$, $-N(R^{29a})_2$, $-S(=O)_2R^{29a}$, $-S(=O)_2OR^{29a}$, or $-S(=O)_2N(R^{29a})_2$, or two $R^{29}$ are joined to form an optionally substituted carbocyclic, heterocyclic, aryl, or heteroaryl ring, wherein each $R^{29a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{29a}$ are joined to form an optionally substituted heteroaryl or optionally substituted heterocyclic ring; and m2 is 0, 1, 2, 3, or 4; and k2 is 0, 1, 2, 3, 4, or 5.

In certain embodiments, the compound of Formula (II) selectively inhibits the activity of IDE for degradation of a first substrate over the activity of IDE for degradation of a second substrate. In certain embodiments, the compound of Formula (II) selectively inhibits the activity of IDE for degradation of insulin over the activity of IDE for degradation of a second substrate (e.g., glucagon, amylin). In certain embodiments, the compound of Formula (II) selectively inhibits the activity of IDE for degradation of insulin over the activity of IDE for degradation of glucagon. In certain embodiments, the compound of Formula (II) selectively inhibits the activity of IDE for degradation of insulin over the activity of IDE for degradation of more than one other substrate.

A provided compound may be any possible stereoisomer of Formula (II). The carbon attached to ring $A^2$ may be in either the (R)- or (S)-configuration. In certain embodiments, a compound of Formula (II) is a stereoisomer of formula:

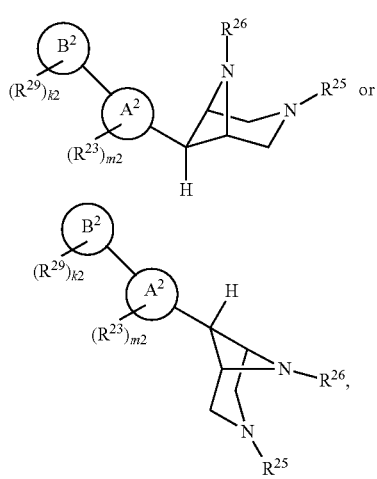

or a pharmaceutically acceptable salt, solvate, hydrate, polymorph, co-crystal, prodrug, or isotopically labeled derivative thereof.

In certain embodiments, the compound of Formula (II) is a compound of Formula (II-a):

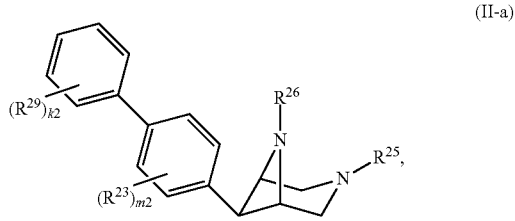

(II-a)

or a pharmaceutically acceptable salt, solvate, hydrate, polymorph, co-crystal, tautomer, stereoisomer, prodrug, or isotopically labeled derivative thereof, wherein $R^{23}$, $R^{25}$, $R^{26}$, $R^{29}$, m2, and k2 are as described herein.

In certain embodiments, the compound of Formula (II) is a compound of Formula (II-b):

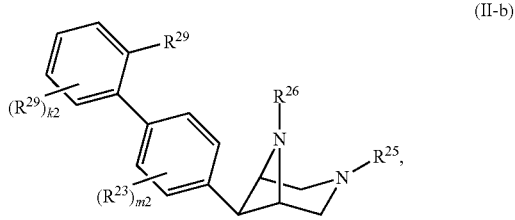

(II-b)

or a pharmaceutically acceptable salt, solvate, hydrate, polymorph, co-crystal, tautomer, stereoisomer, prodrug, or isotopically labeled derivative thereof, wherein $R^{23}$, $R^{25}$, $R^{26}$, $R^{29}$, m2, and k2 are as described herein.

In certain embodiments, the compound of Formula (II) is a compound of Formula (II-c):

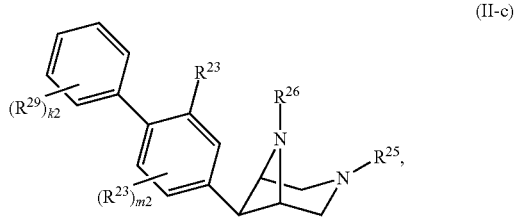

(II-c)

or a pharmaceutically acceptable salt, solvate, hydrate, polymorph, co-crystal, tautomer, stereoisomer, prodrug, or isotopically labeled derivative thereof, wherein $R^{23}$, $R^{25}$, $R^{26}$, $R^{29}$, m2, and k2 are as described herein.

In certain embodiments, the compound of Formula (II) is a compound of Formula (II-d):

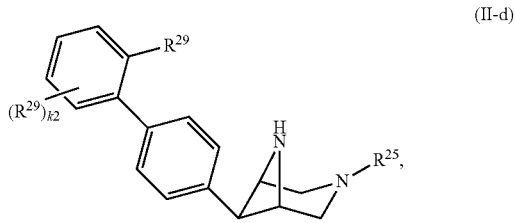

(II-d)

or a pharmaceutically acceptable salt, solvate, hydrate, polymorph, co-crystal, tautomer, stereoisomer, prodrug, or isotopically labeled derivative thereof, wherein $R^{25}$, $R^{29}$, and k2 are as described herein.

In certain embodiments, the compound of Formula (II) is a compound of Formula:

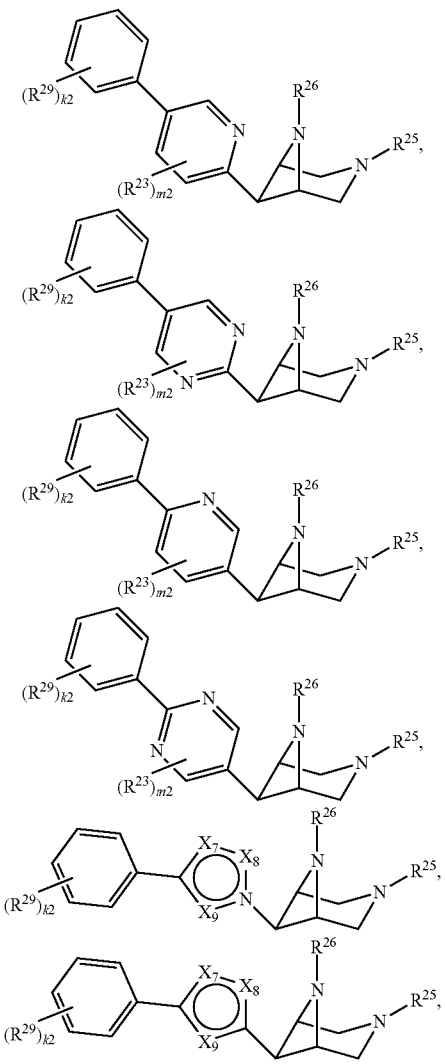

or a pharmaceutically acceptable salt, solvate, hydrate, polymorph, co-crystal, tautomer, stereoisomer, prodrug, or isotopically labeled derivative thereof, wherein $R^{23}$, $R^{25}$, $R^{26}$, $R^{29}$, m2, and k2 are as described herein, m2 is 0, 1, or 2; and $X_7$, $X_8$, and $X_9$ are selected from the group consisting of C, CH, $C(R^{23})$, O, S, N, and $N(R^{23a})$, as valency permits.
Ring $A^2$ and $R^{23}$ As generally defined herein, Ring $A^2$ is carbocyclylene, heterocyclylene, arylene, or heteroarylene. In certain embodiments, Ring $A^2$ and Ring $B^2$ are both phenyl rings, such that Ring $A^2$ and $B^2$ together form a biphenyl group. Ring $A^2$ may be substituted with 0, 1, 2, 3, or 4 independent $R^{23}$, valency permitting. In certain embodiments, m2 is 0 or 1. In certain embodiments, m2 is 0. In certain embodiments, m2 is 1. In certain embodiments, m2 is 2. In certain embodiments, m2 is 3. In certain embodiments, m2 is 4.

In certain embodiments, Ring $A^2$ is arylene, e.g., phenylene. In certain embodiments, Ring $A^2$ is heteroarylene, e.g., 5- to 6-membered heteroarylene. In some embodiments, Ring $A^2$ is pyridylene, pyrimidylene, or imidazylene. In certain embodiments, Ring $A^2$ is carbocyclylene, e.g., 3- to 6-membered carbocyclylene. In some embodiments, Ring $A^2$ is cyclohexylene, cyclopentylene, cyclobutylene, or cyclopropylene. In certain embodiments, Ring $A^2$ is heterocyclylene, e.g., 5- to 6-membered heterocyclylene. In some embodiments, Ring $A^2$ is piperidinylene or piperizinylene.

In certain embodiments, Ring $A^2$ is of formula:

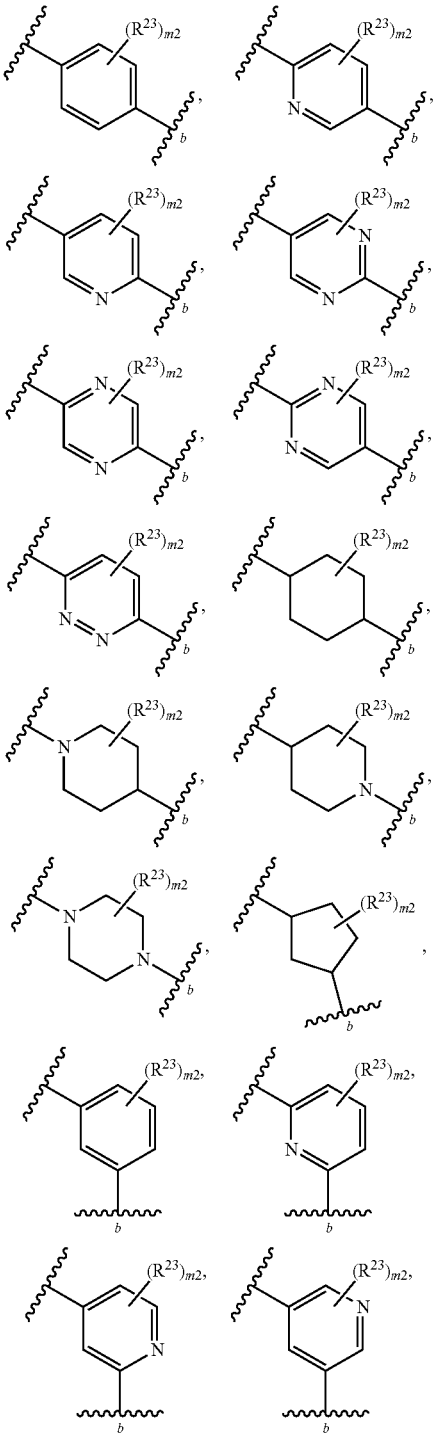

-continued
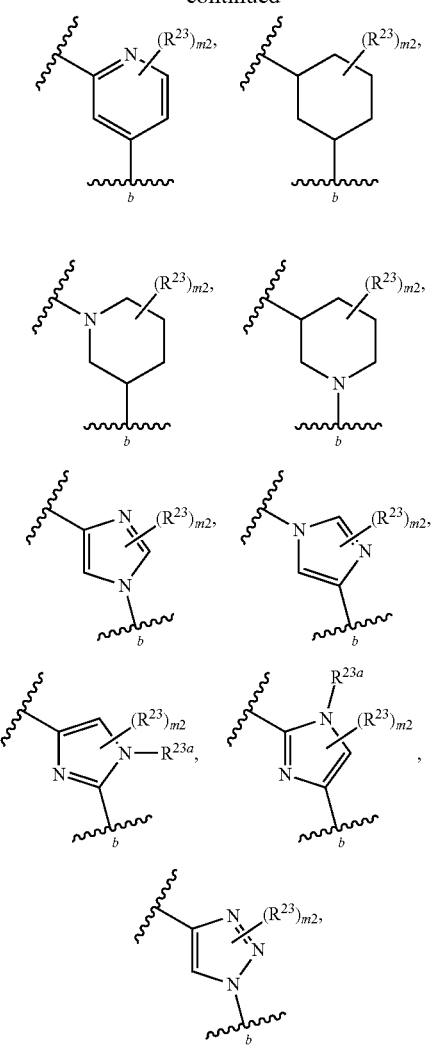
wherein the position labeled b is attached to Ring B², and m2 is 0, 1, 2, 3, or 4, valency permitting.
In certain embodiments, Ring A² is of formula:
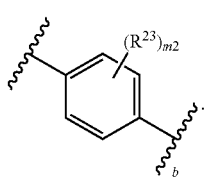
In certain embodiments, Ring A² is of formula:
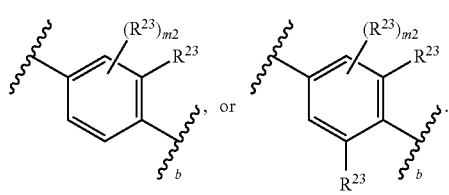
In certain embodiments, Ring A² is of formula:
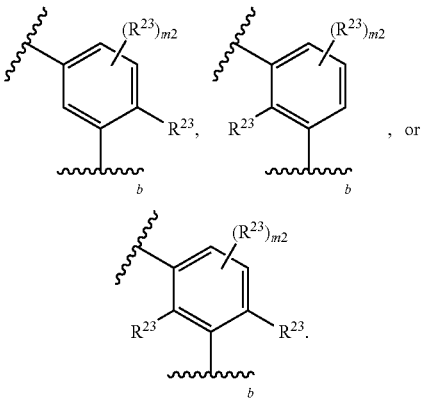
In certain embodiments, Ring A² is of formula:
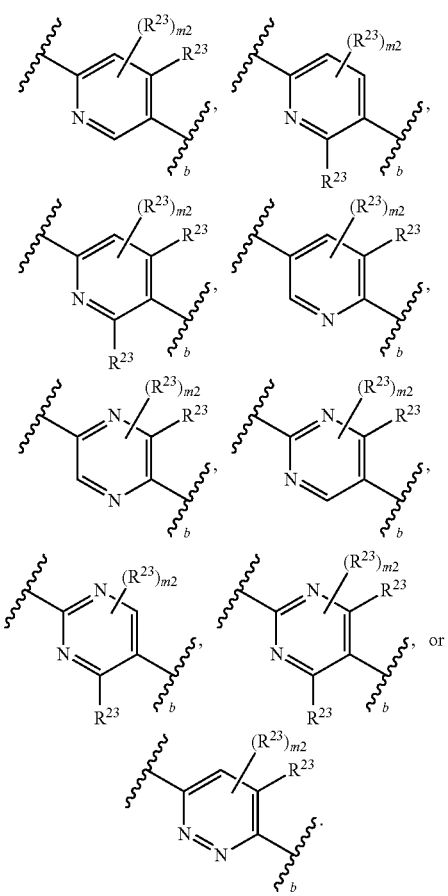
In certain embodiments, Ring A² is of formula:
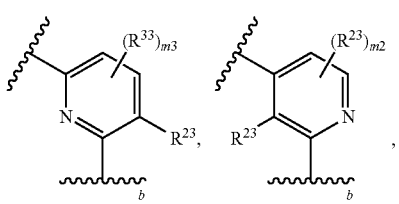

-continued
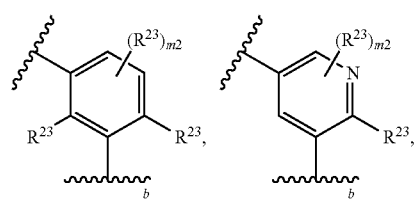
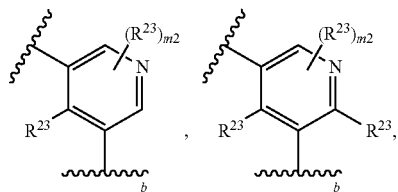
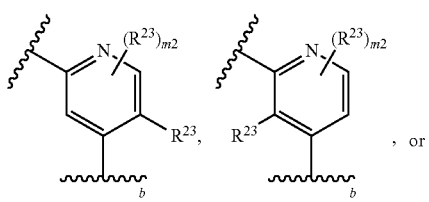
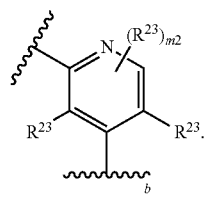
In certain embodiments, Ring A² is of formula:
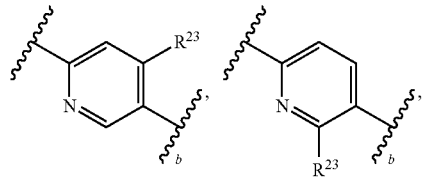
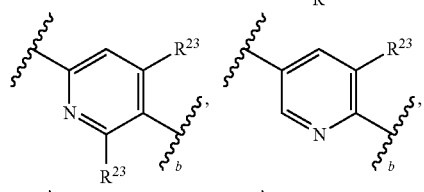
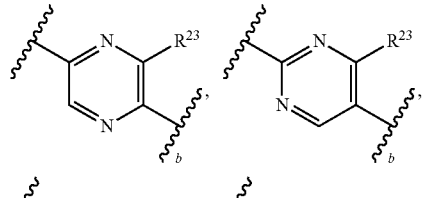
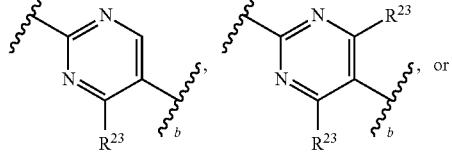, or
-continued
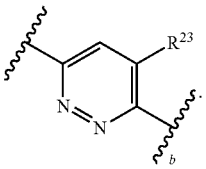.
In certain embodiments, Ring A² is of formula:
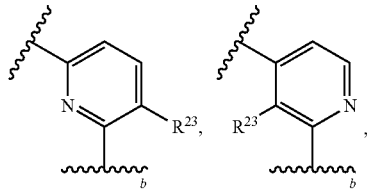
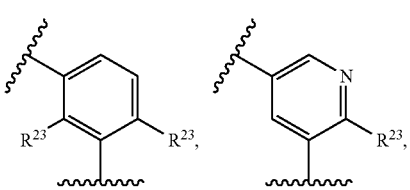
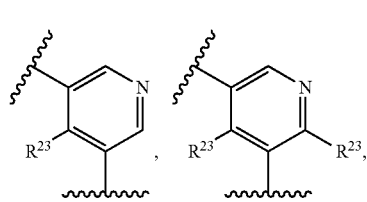
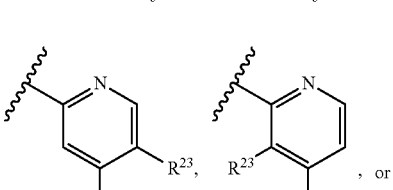, or
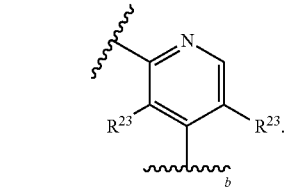.
In certain embodiments, Ring A² is of formula:
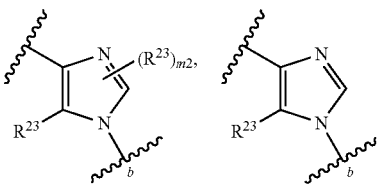

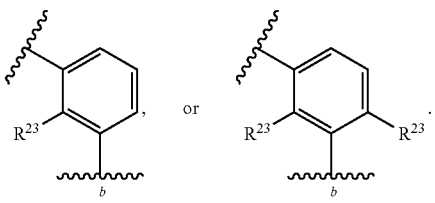
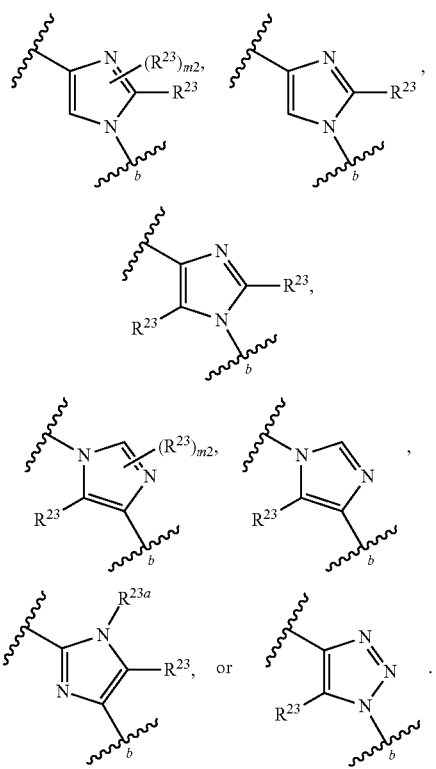
In certain embodiments, Ring A² is of formula:
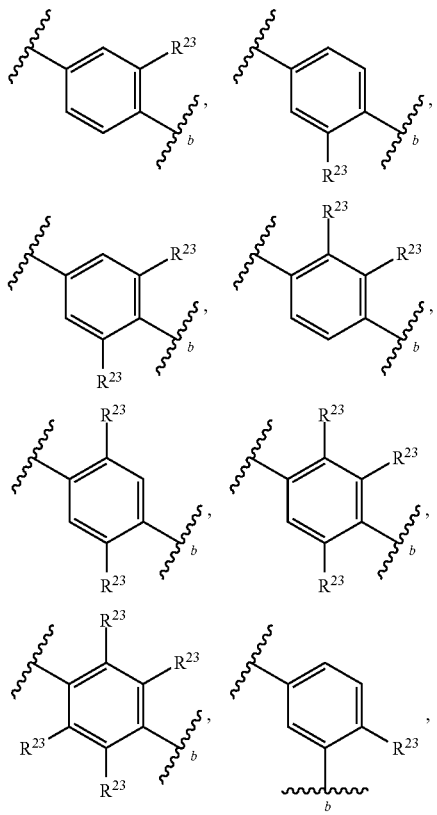
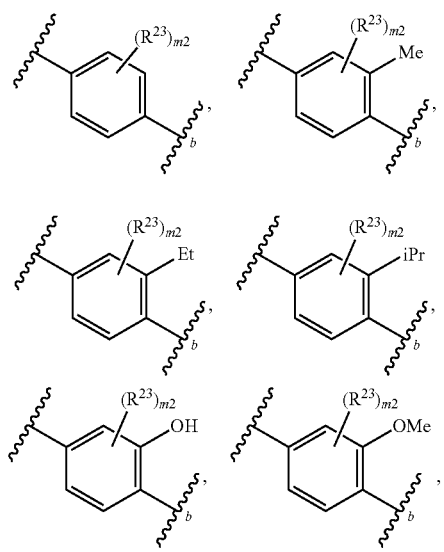
In certain embodiments, Ring A² is of formula:
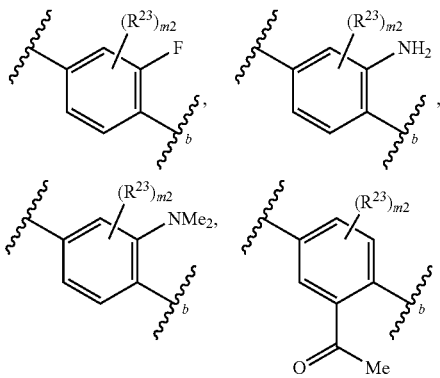
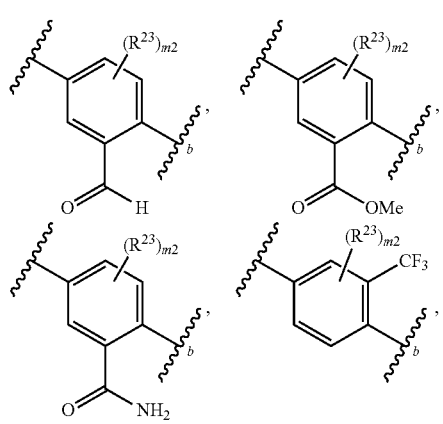

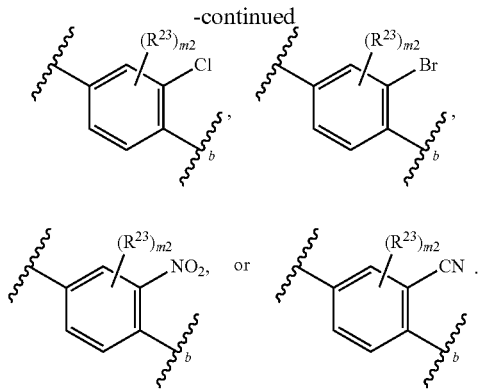

In certain embodiments, Ring $A^2$ is of formula:

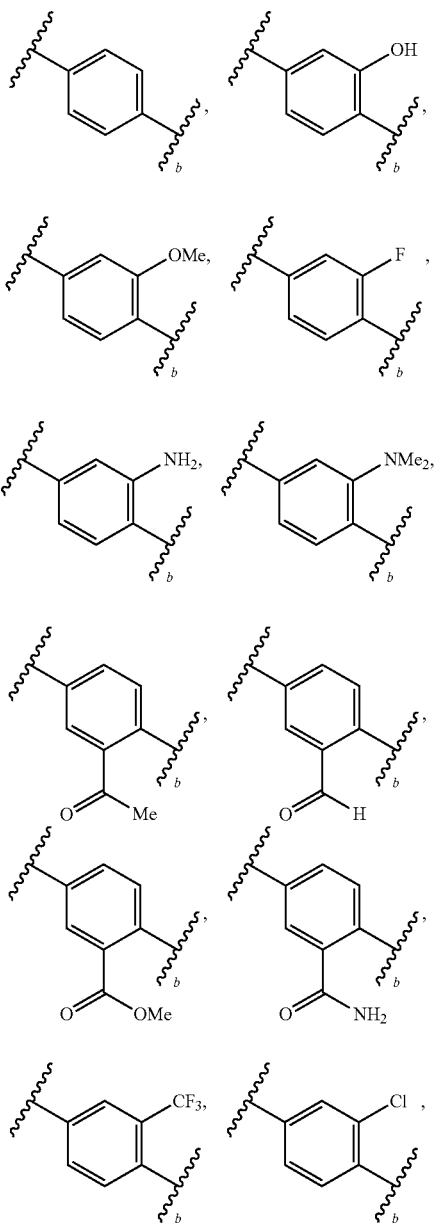

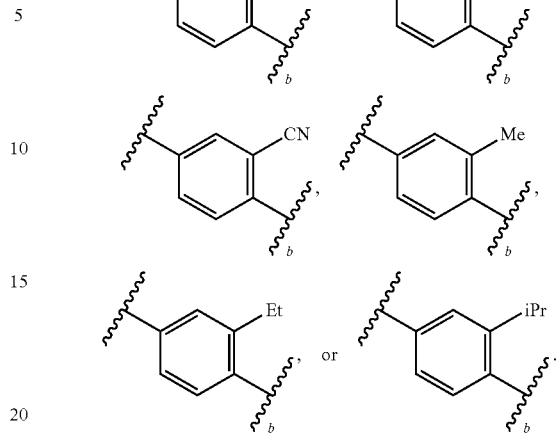

In certain embodiments, Ring $A^2$ is of formula:

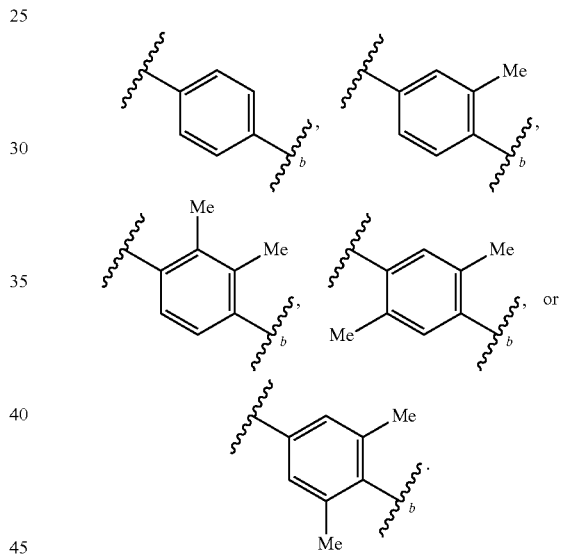

As generally defined herein, each $R^{23}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{23a}$, or —N(R$^{23a}$)$_2$, or two R$^{23}$ are joined to form an optionally substituted carbocyclic, heterocyclic, aryl, or heteroaryl ring, wherein each $R^{23a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{23a}$ are joined to form an optionally substituted heteroaryl or optionally substituted heterocyclic ring.

In certain embodiments, at least one $R^{23}$ is —$NO_2$. In certain embodiments, at least one $R^{23}$ is —CN. In certain embodiments, at least one $R^{23}$ is halogen. In some embodiments, at least one $R^{23}$ is —F. In some embodiments, at least one $R^{23}$ is —Cl, —Br, or —I. In certain embodiments, at least one $R^{23}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{23}$ is methyl. In certain embodiments, at least one $R^{23}$ is ethyl, propyl, or butyl. In certain embodiments, at least one $R^{23}$ is optionally substituted alkenyl, e.g., optionally substituted $C_{2-6}$ alkenyl. In certain embodiments, at least one $R^{23}$ is vinyl, allyl, or prenyl. In certain embodiments, at least one $R^{23}$ is optionally substituted alkynyl, e.g., $C_{2-6}$ alkynyl.

In certain embodiments, at least one $R^{23}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{23}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{23}$ is optionally substituted aryl, e.g., optionally substituted phenyl. In certain embodiments, at least one $R^{23}$ is optionally substituted heteroaryl, e.g., optionally substituted 5-6 membered heteroaryl or optionally substituted 9-10 membered bicyclic heteroaryl. In certain embodiments, at least one $R^{23}$ is optionally substituted aralkyl, e.g., optionally substituted benzyl. In certain embodiments, at least one $R^{23}$ is optionally substituted heteroaralkyl, e.g., methyl substituted with a 5-6 membered heteroaryl ring.

In certain embodiments, at least one $R^{23}$ is optionally substituted acyl, e.g., —CHO, —$CO_2H$, or —C(=O)$NH_2$. In certain embodiments, at least one $R^{23}$ is —C(=O)$R^{23a}$, —C(=O)$OR^{23a}$, —C(=O)NH($R^{23a}$), or —C(=O)N($R^{23a}$)$_2$. In certain embodiments, at least one $R^{23}$ is —C(=O)$R^{23a}$, and $R^{23a}$ is optionally substituted alkyl, e.g., $R^{23}$ is —C(=O)Me. In certain embodiments, at least one $R^{23}$ is —C(=O)$R^{23a}$, and $R^{23a}$ is optionally substituted alkenyl. In certain embodiments, at least one $R^{23}$ is —C(=O)$R^{23a}$, and $R^{23a}$ is optionally substituted carbocyclyl, heterocyclyl, aryl, or heteroaryl. In certain embodiments, at least one $R^{23}$ is —C(=O)$OR^{23a}$, and $R^{23a}$ is optionally substituted alkyl. In certain embodiments, at least one $R^{23}$ is —C(=O)$OR^{23a}$, and $R^{23a}$ is optionally substituted alkenyl. In certain embodiments, at least one $R^{23}$ is —C(=O)$OR^{23a}$, and $R^{23a}$ is optionally substituted carbocyclyl, heterocyclyl, aryl, or heteroaryl. In certain embodiments, at least one $R^{23}$ is —C(=O)N($R^{23a}$)$_2$, and at least one $R^{23a}$ is optionally substituted alkyl. In certain embodiments, at least one $R^{23}$ is —C(=O)$NHR^{23a}$, and $R^{23a}$ is optionally substituted alkyl. In certain embodiments, at least one $R^{23}$ is —C(=O)$NHR^{23a}$, and $R^{23a}$ is optionally substituted alkenyl. In certain embodiments, at least one $R^{23}$ is —C(=O)$NHR^{23a}$, and $R^{23a}$ is optionally substituted carbocyclyl, heterocyclyl, aryl, or heteroaryl.

In certain embodiments, at least one $R^{23}$ is —$OR^{23a}$, e.g., —OH. In certain embodiments, at least one $R^{23}$ is —$OR^{23a}$, and $R^{23a}$ is optionally substituted alkyl. In certain embodiments, at least one $R^{23}$ is —$OR^{23a}$, and $R^{23a}$ is optionally alkenyl. In certain embodiments, at least one $R^{23}$ is —$OR^{23a}$, and $R^{23a}$ is optionally substituted carbocyclyl, optionally substituted heterocyclyl, optionally substituted aryl optionally substituted heteroaryl. In certain embodiments, at least one $R^{23}$ is —$OR^{23a}$, and $R^{23a}$ is optionally substituted acyl, e.g., $R^{23}$ is —OC(=O)$R^{23a}$, —OC(=O)$OR^{23a}$, or —OC(=O)N($R^{23a}$)$_2$. In certain embodiments, at least one $R^{23}$ is —$OR^{23a}$, and $R^{23a}$ is an oxygen protecting group.

In certain embodiments, at least one $R^{23}$ is —N($R^{23a}$)$_2$, e.g., —$NH_2$, —$NHR^{23a}$. In certain embodiments, at least one $R^{23}$ is —NH($R^{23a}$), and $R^{23a}$ is optionally substituted alkyl. In certain embodiments, at least one $R^{23}$ is —N($R^{23a}$)$_2$, and at least one $R^{23a}$ is optionally substituted alkyl. In certain embodiments, at least one $R^{23}$ is —$NHR^{23a}$, and $R^{23a}$ is optionally substituted carbocyclyl, optionally substituted heterocyclyl, optionally substituted aryl, or optionally substituted heteroaryl. In certain embodiments, at least one $R^{23}$ is —$NHR^{23a}$, and $R^{23a}$ is optionally substituted acyl, e.g., $R^{23}$ is —NHC(=O)$R^{23a}$, —NHC(=O)$OR^{23a}$, or —NHC(=O)$NHR^{23a}$. In certain embodiments, at least one $R^{23}$ is —N($R^{23a}$)$_2$, and at least one $R^{23a}$ is a nitrogen protecting group. In certain embodiments, at least one $R^{23}$ is —N($R^{23a}$)$_2$, and $R^{23a}$ are joined to form an optionally substituted heterocyclic or optionally substituted heteroaryl ring.

In certain embodiments, an $R^{23}$ ortho to the bond between Ring $A^2$ and Ring $B^2$ is —$NO_2$. In certain embodiments, an $R^{23}$ ortho to the bond between Ring $A^2$ and Ring $B^2$ is —CN. In certain embodiments, an $R^{23}$ ortho to the bond between Ring $A^2$ and Ring $B^2$ is halogen. In some embodiments, an $R^{23}$ ortho to the bond between Ring $A^2$ and Ring $B^2$ is —F. In some embodiments, an $R^{23}$ ortho to the bond between Ring $A^2$ and Ring $B^2$ is —Cl, —Br, or —I. In certain embodiments, an $R^{23}$ ortho to the bond between Ring $A^2$ and Ring $B^2$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^{23}$ ortho to the bond between Ring $A^2$ and Ring $B^2$ is methyl. In certain embodiments, an $R^{23}$ ortho to the bond between Ring $A^2$ and Ring $B^2$ is ethyl, propyl, or butyl. In certain embodiments, an $R^{23}$ ortho to the bond between Ring $A^2$ and Ring $B^2$ is optionally substituted alkenyl, e.g., optionally substituted $C_{2-6}$ alkenyl. In certain embodiments, an $R^{23}$ ortho to the bond between Ring $A^2$ and Ring $B^2$ is vinyl, allyl, or prenyl. In certain embodiments, an $R^{23}$ ortho to the bond between Ring $A^2$ and Ring $B^2$ is optionally substituted alkynyl, e.g., $C_{2-6}$ alkynyl.

In certain embodiments, an $R^{23}$ ortho to the bond between Ring $A^2$ and Ring $B^2$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^{23}$ ortho to the bond between Ring $A^2$ and Ring $B^2$ is optionally substituted heterocyclyl, e.g., optionally substituted 3-6 membered heterocyclyl, optionally substituted 3-$^2$ membered heterocyclyl, optionally substituted $^2$-5 membered heterocyclyl, or optionally substituted 5-6 membered heterocyclyl.

In certain embodiments, an $R^{23}$ ortho to the bond between Ring $A^2$ and Ring $B^2$ is optionally substituted aryl, e.g., optionally substituted phenyl. In certain embodiments, an $R^{23}$ ortho to the bond between Ring $A^2$ and Ring $B^2$ is optionally substituted heteroaryl, e.g., optionally substituted 5-6 membered heteroaryl or optionally substituted 9-10 membered bicyclic heteroaryl. In certain embodiments, an $R^{23}$ ortho to the bond between Ring $A^2$ and Ring $B^2$ is optionally substituted aralkyl, e.g., optionally substituted benzyl. In certain embodiments, an $R^{23}$ ortho to the bond between Ring $A^2$ and Ring $B^2$ is optionally substituted heteroaralkyl, e.g., methyl substituted with a 5-6 membered heteroaryl ring.

In certain embodiments, an $R^{23}$ ortho to the bond between Ring $A^2$ and Ring $B^2$ is optionally substituted acyl, e.g., —CHO, —CO$_2$H, or —C(=O)NH$_2$. In certain embodiments, an $R^{23}$ ortho to the bond between Ring $A^2$ and Ring $B^2$ is —C(=O)R$^{23a}$, —C(=O)OR$^{23a}$, —C(=O)NH(R$^{23a}$), or —C(=O)N(R$^{23a}$)$_2$. In certain embodiments, an $R^{23}$ ortho to the bond between Ring $A^2$ and Ring $B^2$ is —C(=O)R$^{23a}$, and R$^{23a}$ is optionally substituted alkyl, e.g., $R^{23}$ is —C(=O)Me. In certain embodiments, an $R^{23}$ ortho to the bond between Ring $A^2$ and Ring $B^2$ is —C(=O)R$^{23a}$, and R$^{23a}$ is optionally substituted alkenyl. In certain embodiments, an $R^{23}$ ortho to the bond between Ring $A^2$ and Ring $B^2$ is —C(=O)R$^{23a}$, and R$^{23a}$ is optionally substituted carbocyclyl, heterocyclyl, aryl, or heteroaryl. In certain embodiments, an $R^{23}$ ortho to the bond between Ring $A^2$ and Ring $B^2$ is —C(=O)OR$^{23a}$, and R$^{23a}$ is optionally substituted alkyl. In certain embodiments, an $R^{23}$ ortho to the bond between Ring $A^2$ and Ring $B^2$ is —C(=O)OR$^{23a}$, and R$^{23a}$ is optionally substituted alkenyl. In certain embodiments, an $R^{23}$ ortho to the bond between Ring $A^2$ and Ring $B^2$ is —C(=O)OR$^{23a}$, and R$^{23a}$ is optionally substituted carbocyclyl, heterocyclyl, aryl, or heteroaryl. In certain embodiments, an $R^{23}$ ortho to the bond between Ring $A^2$ and Ring $B^2$ is —C(=O)N(R$^{23a}$)$_2$, and at least one R$^{23a}$ is optionally substituted alkyl. In certain embodiments, an $R^{23}$ ortho to the bond between Ring $A^2$ and Ring $B^2$ is —C(=O)NHR$^{23a}$, and R$^{23a}$ is optionally substituted alkyl. In certain embodiments, an $R^{23}$ ortho to the bond between Ring $A^2$ and Ring $B^2$ is —C(=O)NHR$^{23a}$, and R$^{23a}$ is optionally substituted alkenyl. In certain embodiments, an $R^{23}$ ortho to the bond between Ring $A^2$ and Ring $B^2$ is —C(=O)NHR$^{23a}$, and R$^{23a}$ is optionally substituted carbocyclyl, heterocyclyl, aryl, or heteroaryl.

In certain embodiments, an $R^{23}$ ortho to the bond between Ring $A^2$ and Ring $B^2$ is —OR$^{23a}$, e.g., —OH. In certain embodiments, an $R^{23}$ ortho to the bond between Ring $A^2$ and Ring $B^2$ is —OR$^{23a}$, and R$^{23a}$ is optionally substituted alkyl. In certain embodiments, an $R^{23}$ ortho to the bond between Ring $A^2$ and Ring $B^2$ is —OR$^{23a}$, and R$^{23a}$ is optionally alkenyl. In certain embodiments, an $R^{23}$ ortho to the bond between Ring $A^2$ and Ring $B^2$ is —OR$^{23a}$, and R$^{23a}$ is optionally substituted carbocyclyl, optionally substituted heterocyclyl, optionally substituted aryl or optionally substituted heteroaryl. In certain embodiments, an $R^{23}$ ortho to the bond between Ring $A^2$ and Ring $B^2$ is —OR$^{23a}$, and R$^{23a}$ is optionally substituted acyl, e.g., $R^{23}$ is —OC(=O)R$^{23a}$, —OC(=O)OR$^{23a}$, or —OC(=O)N(R$^{23a}$)$_2$. In certain embodiments, an $R^{23}$ ortho to the bond between Ring $A^2$ and Ring $B^2$ is —OR$^{23a}$, and R$^{23a}$ is an oxygen protecting group.

In certain embodiments, an $R^{23}$ ortho to the bond between Ring $A^2$ and Ring $B^2$ is —N(R$^{23a}$)$_2$, e.g., —NH$_2$, —NHR$^{23a}$. In certain embodiments, an $R^{23}$ ortho to the bond between Ring $A^2$ and Ring $B^2$ is —NH(R$^{23a}$), and R$^{23a}$ is optionally substituted alkyl. In certain embodiments, an $R^{23}$ ortho to the bond between Ring $A^2$ and Ring $B^2$ is —N(R$^{23a}$)$_2$, and at least one R$^{23a}$ is optionally substituted alkyl. In certain embodiments, an $R^{23}$ ortho to the bond between Ring $A^2$ and Ring $B^2$ is —NHR$^{23a}$, and R$^{23a}$ is optionally substituted carbocyclyl, optionally substituted heterocyclyl, optionally substituted aryl, or optionally substituted heteroaryl. In certain embodiments, an $R^{23}$ ortho to the bond between Ring $A^2$ and Ring $B^2$ is —NHR$^{23a}$, and R$^{23a}$ is optionally substituted acyl, e.g., $R^{23}$ is —NHC(=O)R$^{23a}$, —NHC(=O)OR$^{23a}$, or —NHC(=O)NHR$^{23a}$. In certain embodiments, an $R^{23}$ ortho to the bond between Ring $A^2$ and Ring $B^2$ is —N(R$^{23a}$)$_2$, and at least one R$^{23a}$ is a nitrogen protecting group. In certain embodiments, an $R^{23}$ ortho to the bond between Ring $A^2$ and Ring $B^2$ is —N(R$^{23a}$)$_2$, and R$^{23a}$ are joined to form an optionally substituted heterocyclic or optionally substituted heteroaryl ring.

Ring $B^2$ and $R^{29}$

As generally defined herein, is Ring $B^2$ is a carbocyclic, heterocyclic, aryl or heteroaryl ring. In certain embodiments, Ring $A^2$ and Ring $B^2$ are both phenyl rings, such that Ring $A^2$ and $B^2$ together form a biphenyl group. Ring $B^2$ may be substituted with 0, 1, 2, 3, 4, or 5 independent $R^{29}$, valency permitting. In certain embodiments, k2 is 0 or 1. In certain embodiments, k2 is 0. In certain embodiments, k2 is 1. In certain embodiments, k2 is 2. In certain embodiments, k2 is 3. In certain embodiments, k2 is 4. In certain embodiments, k2 is 5.

In certain embodiments, Ring $B^2$ is aryl, e.g., phenyl. In certain embodiments, Ring $B^2$ is heteroaryl, e.g., 5- to 6-membered heteroaryl. In some embodiments, Ring $B^2$ is pyridyl, pyrimidyl, or imidazyl. In certain embodiments, Ring $B^2$ is carbocyclyl, e.g., 3- to 6-membered carbocyclyl. In some embodiments, Ring $B^2$ is cyclohexyl, cyclopentyl, cyclobutyl, or cyclopropyl. In certain embodiments, Ring $B^2$ is heterocyclyl, e.g., 5- to 6-membered heterocyclyl. In some embodiments, Ring $B^2$ is piperidinyl, piperizinyl, or morpholinyl.

In certain embodiments, Ring $B^2$ is of formula:

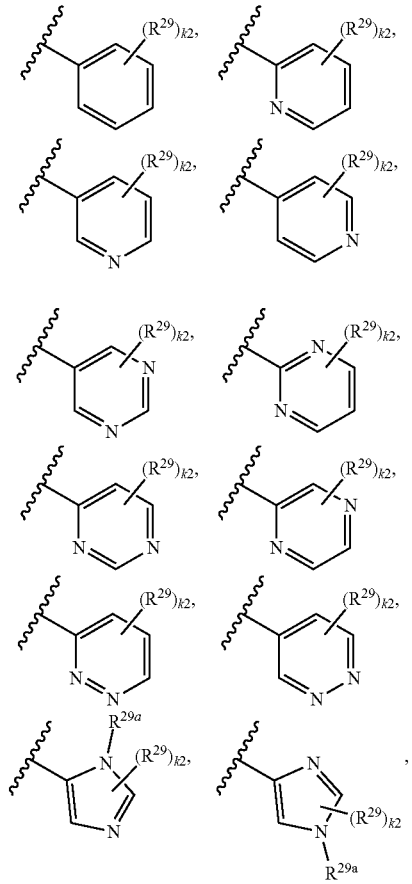

-continued
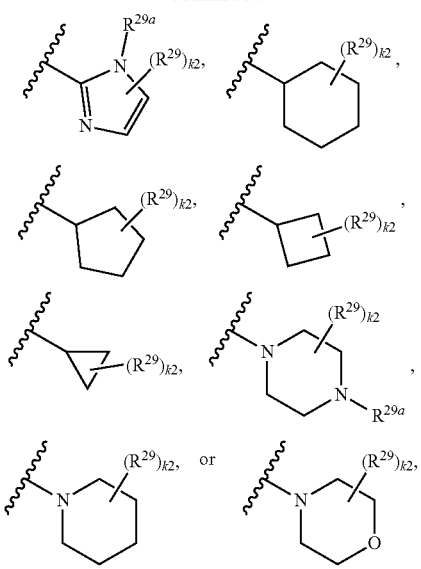
wherein k2 is 0, 1, 2, 3, 4, or 5, valency permitting.
In certain embodiments, Ring B² is of formula:
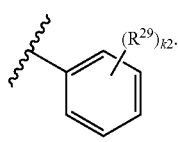
In certain embodiments, Ring B² is of formula:
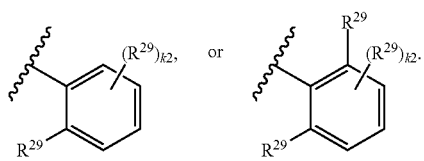
In certain embodiments, Ring B² is of formula:
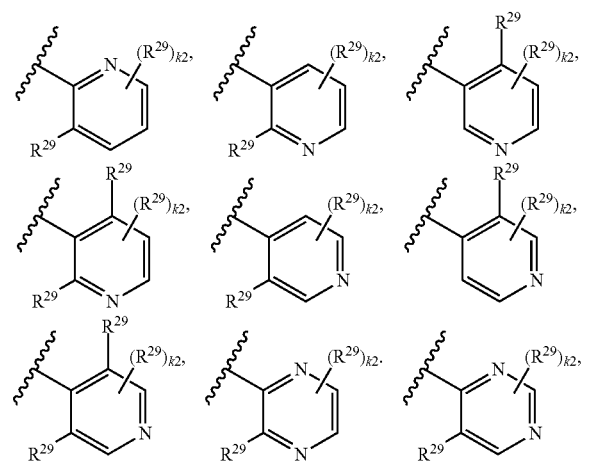
-continued
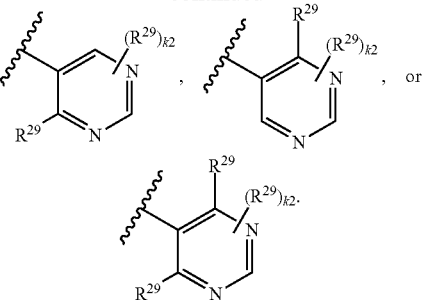
In certain embodiments, Ring B² is of formula:
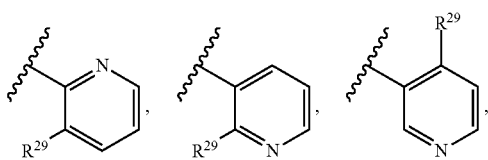
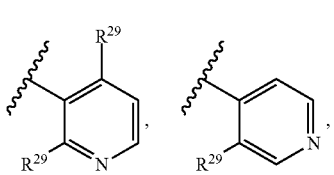
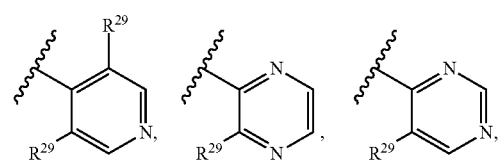
In certain embodiments, Ring B² is of formula:
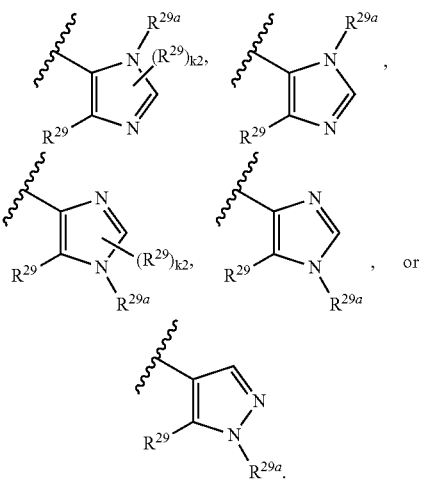

In certain embodiments, Ring B² is of formula:
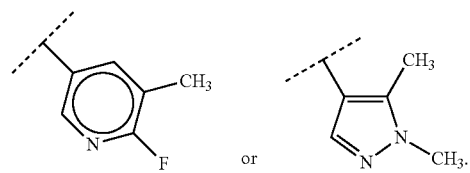
In certain embodiments, Ring B² is of formula:
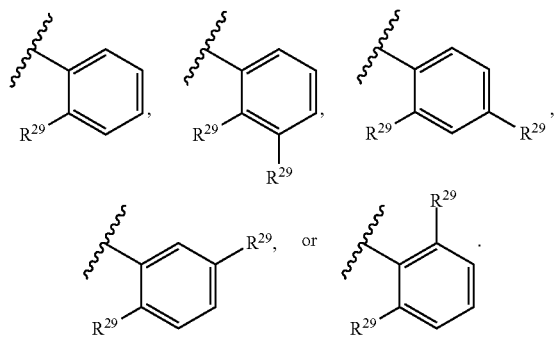
In certain embodiments, Ring B² is of formula:
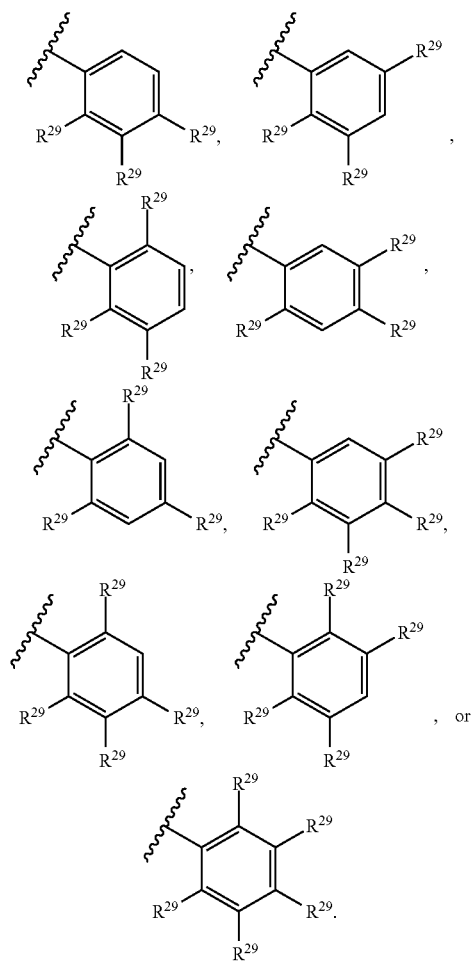
In certain embodiments, Ring B² is of formula:
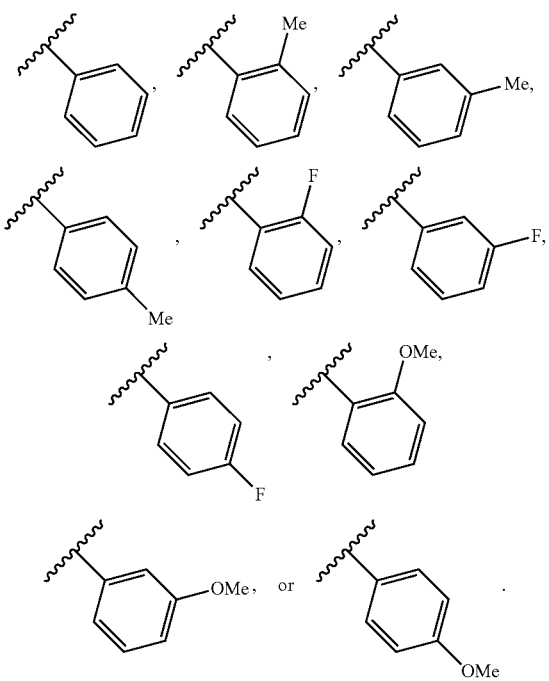
In certain embodiments, Ring B² is of formula:
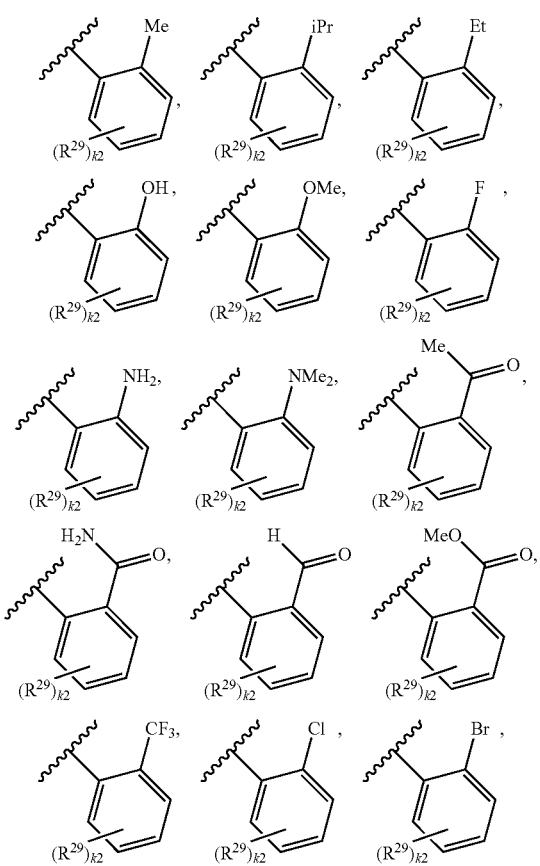

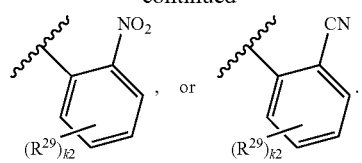
In certain embodiments, Ring B² is of formula:
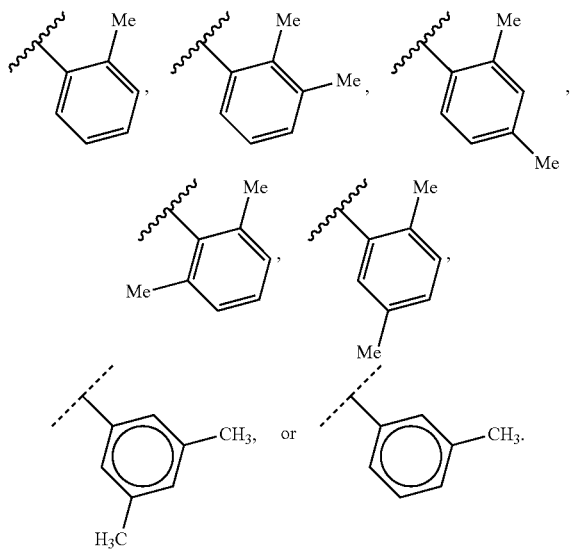
In certain embodiments, Ring B² is of formula:
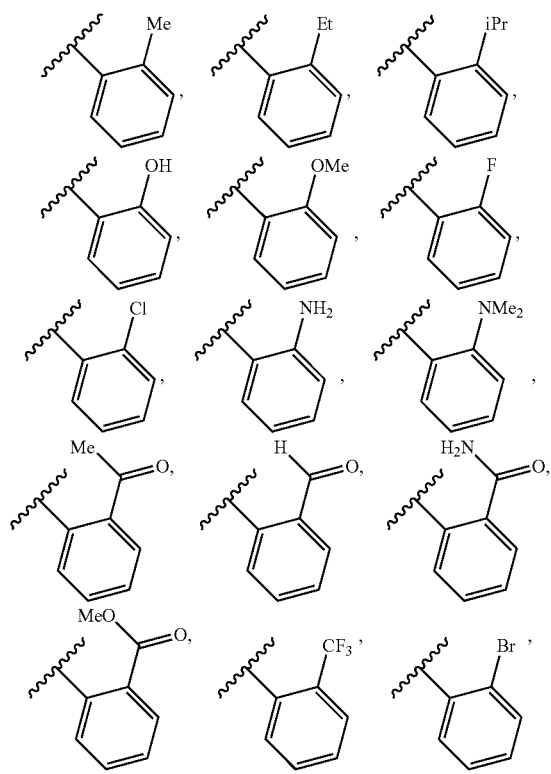
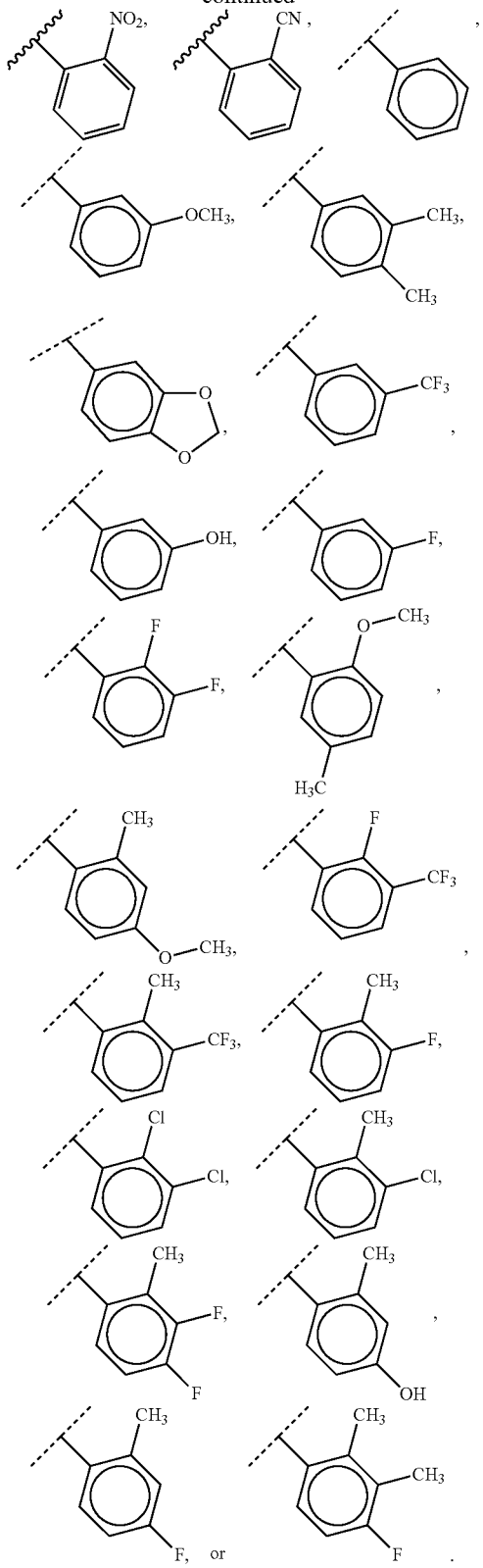
As generally described herein, each $R^{29}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{29a}$, —N(R$^{29a}$)$_2$, —S(=O)$_2$R$^{29a}$, —S(=O)$_2$OR$^{29a}$, or —S(=O)$_2$N(R$^{29a}$)$_2$, or two R$^{29}$ are joined to form an optionally substituted carbocyclic, heterocyclic, aryl, or heteroaryl ring, wherein each R$^{29a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R$^{29a}$ are joined to form an optionally substituted heteroaryl or optionally substituted heterocyclic ring.

In certain embodiments, at least one R$^{29}$ is —NO$_2$. In certain embodiments, at least one R$^{29}$ is —CN. In certain embodiments, at least one R$^{29}$ is halogen. In some embodiments, at least one R$^{29}$ is —F. In some embodiments, at least one R$^{29}$ is —Cl, —Br, or —I. In certain embodiments, at least one R$^{29}$ is optionally substituted alkyl, e.g., optionally substituted C$_{1-6}$ alkyl, optionally substituted C$_{1-2}$ alkyl, optionally substituted C$_{2-3}$ alkyl, optionally substituted C$_{3-4}$ alkyl, optionally substituted C$_{4-5}$ alkyl, or optionally substituted C$_{5-6}$ alkyl. In certain embodiments, at least one R$^{29}$ is methyl. In certain embodiments, at least one R$^{29}$ is ethyl, propyl, or butyl. In certain embodiments, at least one R$^{29}$ is optionally substituted alkenyl, e.g., optionally substituted C$_{2-6}$ alkenyl. In certain embodiments, at least one R$^{29}$ is vinyl, allyl, or prenyl. In certain embodiments, at least one R$^{29}$ is optionally substituted alkynyl, e.g., C$_{2-6}$ alkynyl.

In certain embodiments, at least one R$^{29}$ is optionally substituted carbocyclyl, e.g., optionally substituted C$_{3-6}$ carbocyclyl, optionally substituted C$_{3-4}$ carbocyclyl, optionally substituted C$_{4-5}$ carbocyclyl, or optionally substituted C$_{5-6}$ carbocyclyl. In certain embodiments, at least one R$^{29}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one R$^{29}$ is optionally substituted aryl, e.g., optionally substituted phenyl. In certain embodiments, at least one R$^{29}$ is optionally substituted heteroaryl, e.g., optionally substituted 5-6 membered heteroaryl or optionally substituted 9-10 membered bicyclic heteroaryl. In certain embodiments, at least one R$^{29}$ is optionally substituted aralkyl, e.g., optionally substituted benzyl. In certain embodiments, at least one R$^{29}$ is optionally substituted heteroaralkyl, e.g., methyl substituted with a 5-6 membered heteroaryl ring.

In certain embodiments, at least one R$^{29}$ is optionally substituted acyl, e.g., —CHO, —CO$_2$H, or —C(=O)NH$_2$. In certain embodiments, at least one R$^{29}$ is —C(=O)R$^{29a}$, —C(=O)OR$^{29a}$, —C(=O)NH(R$^{29a}$), or —C(=O)N(R$^{29a}$)$_2$. In certain embodiments, at least one R$^{29}$ is —C(=O)R$^{29a}$, and R$^{29a}$ is optionally substituted alkyl, e.g., R$^{29}$ is —C(=O)Me. In certain embodiments, at least one R$^{29}$ is —C(=O)R$^{29a}$, and R$^{29a}$ is optionally substituted alkenyl. In certain embodiments, at least one R$^{29}$ is —C(=O)R$^{29a}$, and R$^{29a}$ is optionally substituted carbocyclyl, heterocyclyl, aryl, or heteroaryl. In certain embodiments, at least one R$^{29}$ is —C(=O)OR$^{29a}$, and R$^{29a}$ is optionally substituted alkyl. In certain embodiments, at least one R$^{29}$ is —C(=O)OR$^{29a}$, and R$^{29a}$ is optionally substituted alkenyl. In certain embodiments, at least one R$^{29}$ is —C(=O)OR$^{29a}$, and R$^{29a}$ is optionally substituted carbocyclyl, heterocyclyl, aryl, or heteroaryl. In certain embodiments, at least one R$^{29}$ is —C(=O)N(R$^{29a}$)$_2$, and at least one R$^{29a}$ is optionally substituted alkyl. In certain embodiments, at least one R$^{29}$ is —C(=O)NHR$^{29a}$, and R$^{29a}$ is optionally substituted alkyl. In certain embodiments, at least one R$^{29}$ is —C(=O)NHR$^{29a}$, and R$^{29a}$ is optionally substituted alkenyl. In certain embodiments, at least one R$^{29}$ is —C(=O)NHR$^{29a}$, and R$^{29a}$ is optionally substituted carbocyclyl, heterocyclyl, aryl, or heteroaryl.

In certain embodiments, at least one R$^{29}$ is —OR$^{29a}$, e.g., —OH. In certain embodiments, at least one R$^{29}$ is —OR$^{29a}$, and R$^{29a}$ is optionally substituted alkyl. In certain embodiments, at least one R$^{29}$ is —OR$^{29a}$, and R$^{29a}$ is optionally alkenyl. In certain embodiments, at least one R$^{29}$ is —OR$^{29a}$, and R$^{29a}$ is optionally substituted carbocyclyl, optionally substituted heterocyclyl, optionally substituted aryl optionally substituted heteroaryl. In certain embodiments, at least one R$^{29}$ is —OR$^{29a}$, and R$^{29a}$ is optionally substituted acyl, e.g., R$^{29}$ is —OC(=O)R$^{29a}$, —OC(=O)OR$^{29a}$, or —OC(=O)N(R$^{29a}$)$_2$. In certain embodiments, at least one R$^{29}$ is —OR$^{29a}$, and R$^{29a}$ is an oxygen protecting group.

In certain embodiments, at least one R$^{29}$ is —N(R$^{29a}$)$_2$, e.g., —NH$_2$, —NHR$^{29a}$. In certain embodiments, at least one R$^{29}$ is —NH(R$^{29a}$), and R$^{29a}$ is optionally substituted alkyl. In certain embodiments, at least one R$^{29}$ is —N(R$^{29a}$)$_2$, and at least one R$^{29a}$ is optionally substituted alkyl. In certain embodiments, at least one R$^{29}$ is —NHR$^{29a}$, and R$^{29a}$ is optionally substituted carbocyclyl, optionally substituted heterocyclyl, optionally substituted aryl, or optionally substituted heteroaryl. In certain embodiments, at least one R$^{29}$ is —NHR$^{29a}$, and R$^{29a}$ is optionally substituted acyl, e.g., R$^{29}$ is —NHC(=O)R$^{29a}$, —NHC(=O)OR$^{29a}$, or —NHC(=O)NHR$^{29a}$. In certain embodiments, at least one R$^{29}$ is —N(R$^{29a}$)$_2$, and at least one R$^{29a}$ is a nitrogen protecting group. In certain embodiments, at least one R$^{29}$ is —N(R$^{29a}$)$_2$, and R$^{29a}$ are joined to form an optionally substituted heterocyclic or optionally substituted heteroaryl ring.

In certain embodiments, at least one R$^{29}$ is —S(=O)$_2$R$^{29a}$. In certain embodiments, at least one R$^{29}$ is —S(=O)$_2$R$^{29a}$, and R$^{29a}$ is optionally substituted alkyl, e.g., R$^{29}$ is —S(=O)$_2$Me. In certain embodiments, at least one R$^{29}$ is —S(=O)$_2$R$^{29a}$, and R$^{29a}$ is optionally substituted alkenyl. In certain embodiments, at least one R$^{29}$ is —S(=O)$_2$R$^{29a}$, and R$^{29a}$ is optionally substituted carbocyclyl, heterocyclyl, aryl, or heteroaryl. In certain embodiments, at least one R$^{29}$ is —S(=O)$_2$OR$^{29a}$. In certain embodiments, at least one R$^{29}$ is —S(=O)$_2$OR$^{29a}$, and R$^{29a}$ is optionally substituted alkyl. In certain embodiments, at least one R$^{29}$ is —S(=O)$_2$OR$^{29a}$, and R$^{29a}$ is optionally substituted alkenyl. In certain embodiments, at least one R$^{29}$ is —S(=O)$_2$OR$^{29a}$, and R$^{29a}$ is optionally substituted carbocyclyl, heterocyclyl, aryl, or heteroaryl. In certain embodiments, at least one R$^{29}$ is —S(=O)$_2$N(R$^{29a}$)$_2$ or —S(=O)$_2$NHR$^{29a}$. In certain embodiments, at least one R$^{29}$ is —S(=O)$_2$N(R$^{29a}$)$_2$, and at least one R$^{29a}$ is optionally substituted alkyl. In certain embodiments, at least one R$^{29}$ is —S(=O)$_2$NHR$^{29a}$, and R$^{29a}$ is optionally substituted alkyl. In certain embodiments, at least one R$^{29}$ is —S(=O)$_2$NHR$^{29a}$, and R$^{29a}$ is optionally substituted alkenyl. In certain embodiments, at least one R$^{29}$ is —S(=O)$_2$NHR$^{29a}$, and R$^{29a}$ is optionally substituted carbocyclyl, heterocyclyl, aryl, or heteroaryl.

In certain embodiments, an $R^{29}$ ortho to the bond connecting Ring $A^2$ and Ring $B^2$ is —$NO_2$. In certain embodiments, an $R^{29}$ ortho to the bond connecting Ring $A^2$ and Ring $B^2$ is —CN. In certain embodiments, an $R^{29}$ ortho to the bond connecting Ring $A^2$ and Ring $B^2$ is halogen. In some embodiments, an $R^{29}$ ortho to the bond connecting Ring $A^2$ and Ring $B^2$ is —F. In some embodiments, an $R^{29}$ ortho to the bond connecting Ring $A^2$ and Ring $B^2$ is —Cl, —Br, or —I. In certain embodiments, an $R^{29}$ ortho to the bond connecting Ring $A^2$ and Ring $B^2$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^{29}$ ortho to the bond connecting Ring $A^2$ and Ring $B^2$ is methyl. In certain embodiments, an $R^{29}$ ortho to the bond connecting Ring $A^2$ and Ring $B^2$ is ethyl, propyl, or butyl. In certain embodiments, an $R^{29}$ ortho to the bond connecting Ring $A^2$ and Ring $B^2$ is optionally substituted alkenyl, e.g., optionally substituted $C_{2-6}$ alkenyl. In certain embodiments, an $R^{29}$ ortho to the bond connecting Ring $A^2$ and Ring $B^2$ is vinyl, allyl, or prenyl. In certain embodiments, an $R^{29}$ ortho to the bond connecting Ring $A^2$ and Ring $B^2$ is optionally substituted alkynyl, e.g., $C_{2-6}$ alkynyl.

In certain embodiments, an $R^{29}$ ortho to the bond connecting Ring $A^2$ and Ring $B^2$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^{29}$ ortho to the bond connecting Ring $A^2$ and Ring $B^2$ is optionally substituted heterocyclyl, e.g., optionally substituted 3-6 membered heterocyclyl, optionally substituted 3-² membered heterocyclyl, optionally substituted ²-5 membered heterocyclyl, or optionally substituted 5-6 membered heterocyclyl.

In certain embodiments, an $R^{29}$ ortho to the bond connecting Ring $A^2$ and Ring $B^2$ is optionally substituted aryl, e.g., optionally substituted phenyl. In certain embodiments, an $R^{29}$ ortho to the bond connecting Ring $A^2$ and Ring $B^2$ is optionally substituted heteroaryl, e.g., optionally substituted 5-6 membered heteroaryl or optionally substituted 9-10 membered bicyclic heteroaryl. In certain embodiments, an $R^{29}$ ortho to the bond connecting Ring $A^2$ and Ring $B^2$ is optionally substituted aralkyl, e.g., optionally substituted benzyl. In certain embodiments, an $R^{29}$ ortho to the bond connecting Ring $A^2$ and Ring $B^2$ is optionally substituted heteroaralkyl, e.g., methyl substituted with a 5-6 membered heteroaryl ring.

In certain embodiments, an $R^{29}$ ortho to the bond connecting Ring $A^2$ and Ring $B^2$ is optionally substituted acyl, e.g., —CHO, —$CO_2H$, or —C(=O)$NH_2$. In certain embodiments, an $R^{29}$ ortho to the bond connecting Ring $A^2$ and Ring $B^2$ is —C(=O)$R^{29a}$, —C(=O)$OR^{29a}$, —C(=O)NH($R^{29a}$), or —C(=O)N($R^{29a}$)$_2$. In certain embodiments, an $R^{29}$ ortho to the bond connecting Ring $A^2$ and Ring $B^2$ is —C(=O)$R^{29a}$, and $R^{29a}$ is optionally substituted alkyl, e.g., $R^{29}$ is —C(=O)Me. In certain embodiments, an $R^{29}$ ortho to the bond connecting Ring $A^2$ and Ring $B^2$ is —C(=O)$R^{29a}$, and $R^{29a}$ is optionally substituted alkenyl. In certain embodiments, an $R^{29}$ ortho to the bond connecting Ring $A^2$ and Ring $B^2$ is —C(=O)$R^{29a}$, and $R^{29a}$ is optionally substituted carbocyclyl, heterocyclyl, aryl, or heteroaryl. In certain embodiments, an $R^{29}$ ortho to the bond connecting Ring $A^2$ and Ring $B^2$ is —C(=O)$OR^{29a}$, and $R^{29a}$ is optionally substituted alkyl. In certain embodiments, an $R^{29}$ ortho to the bond connecting Ring $A^2$ and Ring $B^2$ is —C(=O)$OR^{29a}$, and $R^{29a}$ is optionally substituted alkenyl. In certain embodiments, an $R^{29}$ ortho to the bond connecting Ring $A^2$ and Ring $B^2$ is —C(=O)$OR^{29a}$, and $R^{29a}$ is optionally substituted carbocyclyl, heterocyclyl, aryl, or heteroaryl. In certain embodiments, an $R^{29}$ ortho to the bond connecting Ring $A^2$ and Ring $B^2$ is —C(=O)N($R^{29a}$)$_2$, and at least one $R^{29a}$ is optionally substituted alkyl. In certain embodiments, an $R^{29}$ ortho to the bond connecting Ring $A^2$ and Ring $B^2$ is —C(=O)NH$R^{29a}$, and $R^{29a}$ is optionally substituted alkyl. In certain embodiments, an $R^{29}$ ortho to the bond connecting Ring $A^2$ and Ring $B^2$ is —C(=O)NH$R^{29a}$, and $R^{29a}$ is optionally substituted alkenyl. In certain embodiments, an $R^{29}$ ortho to the bond connecting Ring $A^2$ and Ring $B^2$ is —C(=O)NH$R^{29a}$, and $R^{29a}$ is optionally substituted carbocyclyl, heterocyclyl, aryl, or heteroaryl.

In certain embodiments, an $R^{29}$ ortho to the bond connecting Ring $A^2$ and Ring $B^2$ is —$OR^{29a}$, e.g., —OH. In certain embodiments, an $R^{29}$ ortho to the bond connecting Ring $A^2$ and Ring $B^2$ is —$OR^{29a}$, and $R^{29a}$ is optionally substituted alkyl. In certain embodiments, an $R^{29}$ ortho to the bond connecting Ring $A^2$ and Ring $B^2$ is —$OR^{29a}$, and $R^{29a}$ is optionally alkenyl. In certain embodiments, an $R^{29}$ ortho to the bond connecting Ring $A^2$ and Ring $B^2$ is —$OR^{29a}$, and $R^{29a}$ is optionally substituted carbocyclyl, optionally substituted heterocyclyl, optionally substituted aryl optionally substituted heteroaryl. In certain embodiments, an $R^{29}$ ortho to the bond connecting Ring $A^2$ and Ring $B^2$ is —$OR^{29a}$, and $R^{29a}$ is optionally substituted acyl, e.g., $R^{29}$ is —OC(=O)$R^{29a}$, —OC(=O)$OR^{29a}$, or —OC(=O)N($R^{29a}$)$_2$. In certain embodiments, an $R^{29}$ ortho to the bond connecting Ring $A^2$ and Ring $B^2$ is —$OR^{29a}$, and $R^{29a}$ is an oxygen protecting group.

In certain embodiments, an $R^{29}$ ortho to the bond connecting Ring $A^2$ and Ring $B^2$ is —N($R^{29a}$)$_2$, e.g., —$NH_2$, —NH$R^{29a}$. In certain embodiments, an $R^{29}$ ortho to the bond connecting Ring $A^2$ and Ring $B^2$ is —NH($R^{29a}$), and $R^{29a}$ is optionally substituted alkyl. In certain embodiments, an $R^{29}$ ortho to the bond connecting Ring $A^2$ and Ring $B^2$ is —N($R^{29a}$)$_2$, and at least one $R^{29a}$ is optionally substituted alkyl. In certain embodiments, an $R^{29}$ ortho to the bond connecting Ring $A^2$ and Ring $B^2$ is —NH$R^{29a}$, and $R^{29a}$ is optionally substituted carbocyclyl, optionally substituted heterocyclyl, optionally substituted aryl, or optionally substituted heteroaryl. In certain embodiments, an $R^{29}$ ortho to the bond connecting Ring $A^2$ and Ring $B^2$ is —NH$R^{29a}$, and $R^{29a}$ is optionally substituted acyl, e.g., $R^{29}$ is —NHC(=O)$R^{29a}$, —NHC(=O)$OR^{29a}$, or —NHC(=O)NH$R^{29a}$. In certain embodiments, an $R^{29}$ ortho to the bond connecting Ring $A^2$ and Ring $B^2$ is —N($R^{29a}$)$_2$, and at least one $R^{29a}$ is a nitrogen protecting group. In certain embodiments, an $R^{29}$ ortho to the bond connecting Ring $A^2$ and Ring $B^2$ is —N($R^{29a}$)$_2$, and $R^{29a}$ are joined to form an optionally substituted heterocyclic or optionally substituted heteroaryl ring.

In certain embodiments, an $R^{29}$ ortho to the bond connecting Ring $A^2$ and Ring $B^2$ is —S(=O)$_2R^{29a}$. In certain embodiments, an $R^{29}$ ortho to the bond connecting Ring $A^2$ and Ring $B^2$ is —S(=O)$_2R^{29a}$, and $R^{29a}$ is optionally substituted alkyl, e.g., $R^{29}$ is —S(=O)$_2$Me. In certain embodiments, an $R^{29}$ ortho to the bond connecting Ring $A^2$ and Ring $B^2$ is —S(=O)$_2R^{29a}$, and $R^{29a}$ is optionally substituted alkenyl. In certain embodiments, an $R^{29}$ ortho to the bond connecting Ring $A^2$ and Ring $B^2$ is —S(=O)$_2R^{29a}$, and $R^{29a}$ is optionally substituted carbocyclyl, heterocyclyl, aryl, or heteroaryl. In certain embodiments, an $R^{29}$ ortho to the bond connecting Ring $A^2$ and Ring $B^2$ is —S(=O)$_2OR^{29a}$. In certain embodiments, an $R^{29}$ ortho to the bond connecting Ring $A^2$ and Ring $B^2$ is —S(=O)$_2OR^{29a}$, and $R^{29a}$ is optionally substituted alkyl. In certain embodiments, an $R^{29}$ ortho to the bond connecting Ring $A^2$ and Ring $B^2$ is —S(=O)$_2OR^{29a}$, and $R^{29a}$ is optionally substituted alkenyl. In certain embodiments, an $R^{29}$ ortho to the bond connecting Ring $A^2$ and Ring $B^2$ is —S(=O)$_2OR^{29a}$, and $R^{29a}$ is optionally substituted carbocyclyl, heterocyclyl, aryl, or heteroaryl. In certain embodiments, an $R^{29}$ ortho to the bond connecting Ring $A^2$ and Ring $B^2$ is —S(=O)$_2$N($R^{29a}$)$_2$ or —S(=O)$_2$NH$R^{29a}$. In certain embodiments, an $R^{29}$ ortho to the bond connecting Ring $A^2$ and Ring $B^2$ is —S(=O)$_2$N($R^{29a}$)$_2$, and at least one $R^{29a}$ is optionally substituted alkyl. In certain embodiments, an $R^{29}$ ortho to the bond connecting Ring $A^2$ and Ring $B^2$ is —S(=O)$_2$NH$R^{29a}$, and $R^{29a}$ is optionally substituted alkyl. In certain embodiments, an $R^{29}$ ortho to the bond connecting Ring $A^2$ and Ring $B^2$ is —S(=O)$_2$NH$R^{29a}$, and $R^{29a}$ is optionally substituted alkenyl. In certain embodiments, an $R^{29}$ ortho to the bond connecting Ring $A^2$ and Ring $B^2$ is —S(=O)$_2$NH$R^{29a}$, and $R^{29a}$ is optionally substituted carbocyclyl, heterocyclyl, aryl, or heteroaryl.

$R^{25}$

As generally defined herein, $R^{25}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$$R^{25a}$, —S(=O)$_2$O$R^{25a}$, —S(=O)$_2$N($R^{25a}$)$_2$, or a nitrogen protecting group, wherein each $R^{25a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{25a}$ are joined to form an optionally substituted heteroaryl or optionally substituted heterocyclic ring.

In certain embodiments, $R^{25}$ is a non-hydrogen group. In certain embodiments, $R^{25}$ is not alkyl. In certain embodiments, $R^{25}$ is a non-hydrogen group and is not alkyl, —C(=O)$R^{25a}$, or —S(=O)$_2$$R^{25a}$. In certain embodiments, $R^{25}$ is a non-hydrogen group and is not methyl, —C(=O)$R^{25a}$, or —S(=O)$_2$$R^{25a}$. In certain embodiments, $R^{25}$ is not nosyl. In certain embodiments, $R^{25}$ is not —CH$_3$, —C(=O)Me, or —S(=O)$_2$Me. In certain embodiments, $R^{25}$ is a nitrogen protecting group.

In certain embodiments, $R^{25}$ is hydrogen. In certain embodiments, $R^{25}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{25}$ is optionally substituted $C_{2-6}$ alkyl. In certain embodiments, $R^{25}$ is methyl. In certain embodiments, $R^{25}$ is ethyl, propyl, or butyl. In certain embodiments, $R^{25}$ is optionally substituted alkenyl, e.g., optionally substituted $C_{2-6}$ alkenyl. In certain embodiments, $R^{25}$ is vinyl, allyl, or prenyl. In certain embodiments, $R^{25}$ is optionally substituted alkynyl, e.g., $C_{2-6}$ alkynyl.

In certain embodiments, $R^{25}$ is of formula:

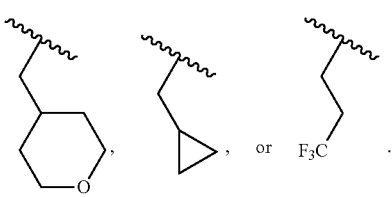 [SMILES: *CC1CCOCC1 ; *CC1CC1 ; *CCC(F)(F)F]

In certain embodiments, $R^{25}$ is optionally substituted aralkyl, e.g., optionally substituted benzyl. In certain embodiments, $R^{25}$ is optionally substituted heteroaralkyl, e.g., methyl substituted with a 5- to 6-membered heteroaryl ring.

In certain embodiments, $R^{25}$ is of formula:

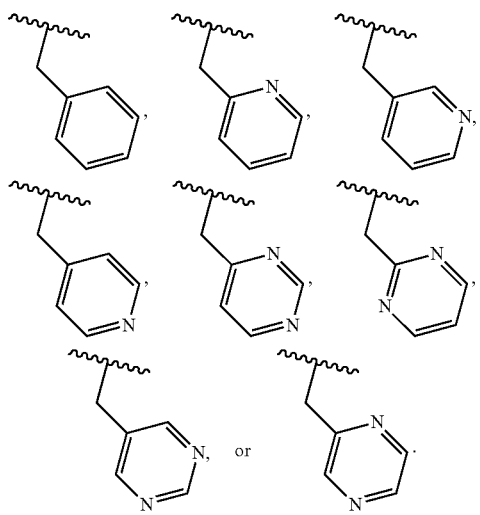

In certain embodiments, $R^{25}$ is optionally substituted acyl, e.g., —CHO, —CO$_2$H, or —C(=O)NH$_2$. In certain embodiments, $R^{25}$ is —C(=O)$R^{25a}$, —C(=O)O$R^{25a}$, —C(=O)NH($R^{25a}$), or —C(=O)N($R^{25a}$)$_2$. In certain embodiments, $R^{25}$ is —C(=O)$R^{25a}$, and $R^{25a}$ is optionally substituted alkyl, e.g., —C(=O)Me. In certain embodiments, $R^{25}$ is —C(=O)$R^{25a}$, and $R^{25a}$ is optionally substituted $C_{1-6}$ alkyl. In certain embodiments, $R^{25}$ is —C(=O)$R^{25a}$, and $R^{25a}$ is optionally substituted $C_{2-6}$ alkyl. In certain embodiments, $R^{25}$ is —C(=O)$R^{25a}$, and $R^{25a}$ is optionally substituted alkenyl. In certain embodiments, $R^{25}$ is —C(=O)$R^{25a}$, and $R^{25a}$ is optionally substituted carbocyclyl, heterocyclyl, aryl, or heteroaryl. In certain embodiments, $R^{25}$ is —C(=O)O$R^{25a}$, and $R^{25a}$ is optionally substituted alkyl. In certain embodiments, $R^{25}$ is —C(=O)O$R^{25a}$, and $R^{25a}$ is optionally substituted alkenyl. In certain embodiments, $R^{25}$ is —C(=O)O$R^{25a}$, and $R^{25a}$ is optionally substituted carbocyclyl, heterocyclyl, aryl, or heteroaryl. In certain embodiments, $R^{25}$ is —C(=O)N($R^{25a}$)$_2$, and at least one $R^{25a}$ is optionally substituted alkyl. In certain embodiments, $R^{25}$ is —C(=O)NH$R^{25a}$, and $R^{25a}$ is optionally substituted alkyl. In certain embodiments, $R^{25}$ is —C(=O)NH$R^{25a}$, and $R^{25a}$ is optionally substituted alkenyl. In certain embodiments, $R^{25}$ is —C(=O)NH$R^{25a}$, and $R^{25a}$ is optionally substituted carbocyclyl, heterocyclyl, aryl, or heteroaryl.

In certain embodiments, $R^{25}$ is of formula:

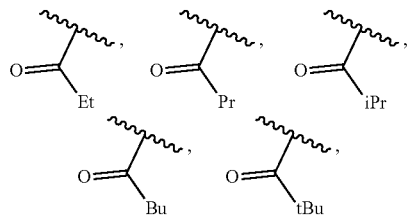

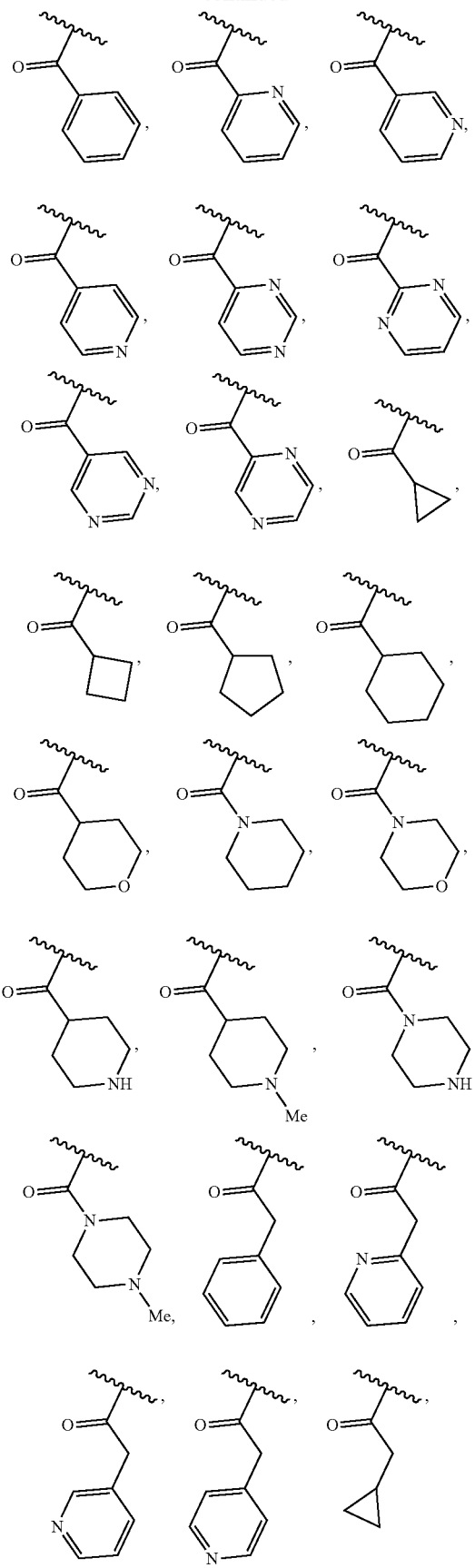
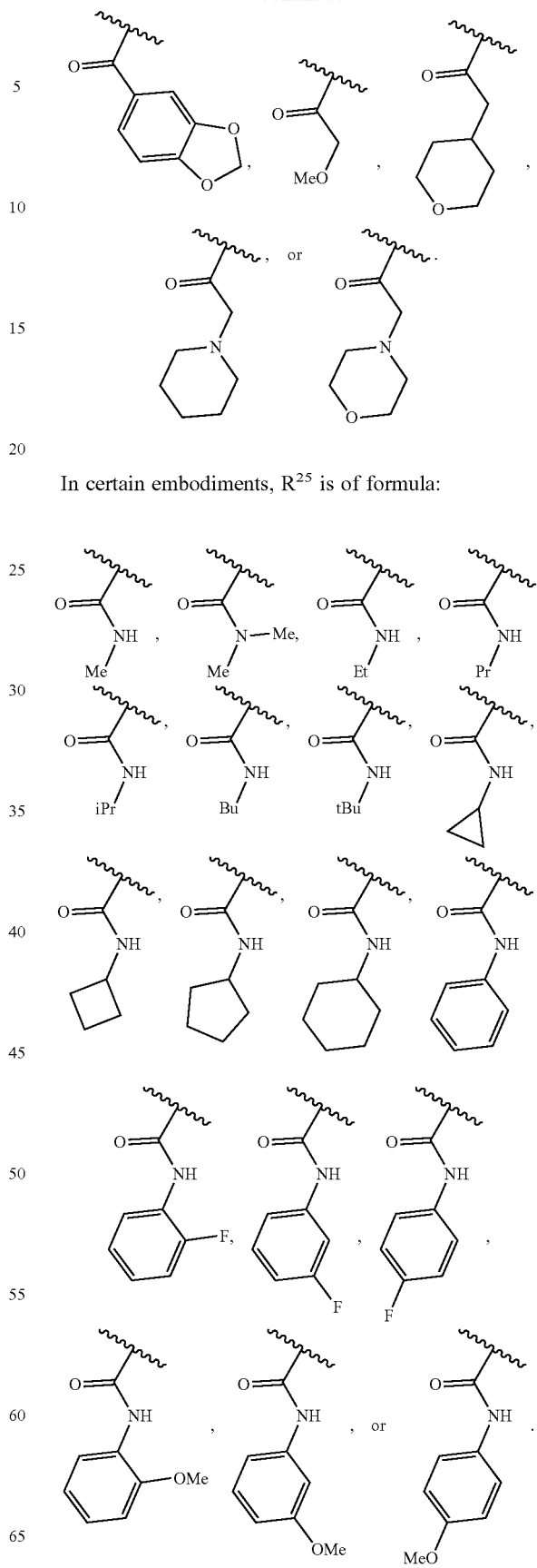
In certain embodiments, $R^{25}$ is of formula:

In certain embodiments, $R^{25}$ is —S(=O)$_2$R$^{25a}$. In certain embodiments, $R^{25}$ is —S(=O)$_2$R$^{25a}$, and R$^{25a}$ is optionally substituted alkyl, e.g., $R^{25}$ is —S(=O)$_2$Me. In certain embodiments, $R^{25}$ is —S(=O)$_2$R$^{25a}$, and R$^{25a}$ is optionally substituted $C_{1-6}$ alkyl. In certain embodiments, $R^{25}$ is —S(=O)$_2$R$^{25a}$, and R$^{25a}$ is optionally substituted $C_{2-6}$ alkyl. In certain embodiments, $R^{25}$ is —S(=O)$_2$R$^{25a}$, and R$^{25a}$ is optionally substituted alkenyl. In certain embodiments, $R^{25}$ is —S(=O)$_2$R$^{25a}$, and R$^{25a}$ is optionally substituted carbocyclyl, heterocyclyl, aryl, or heteroaryl. In certain embodiments, $R^{25}$ is —S(=O)$_2$R$^{25a}$. In certain embodiments, $R^{25}$ is —S(=O)$_2$R$^{25a}$, and R$^{25a}$ is optionally substituted alkyl. In certain embodiments, $R^{25}$ is —S(=O)$_2$OR$^{25a}$, and R$^{25a}$ is optionally substituted alkenyl. In certain embodiments, $R^{25}$ is —S(=O)$_2$R$^{25a}$, and R$^{25a}$ is optionally substituted carbocyclyl, heterocyclyl, aryl, or heteroaryl. In certain embodiments, $R^{25}$ is —S(=O)$_2$N(R$^{25a}$)$_2$ or —S(=O)$_2$NHR$^{25a}$. In certain embodiments, $R^{25}$ is —S(=O)$_2$N(R$^{25a}$)$_2$, and at least one R$^{25a}$ is optionally substituted alkyl. In certain embodiments, $R^{25}$ is —S(=O)$_2$NHR$^{25a}$, and R$^{25a}$ is optionally substituted alkenyl. In certain embodiments, $R^{25}$ is —S(=O)$_2$NHR$^{25a}$, and R$^{25a}$ is optionally substituted carbocyclyl, heterocyclyl, aryl, or heteroaryl.

In certain embodiments, $R^{25}$ is of formula:

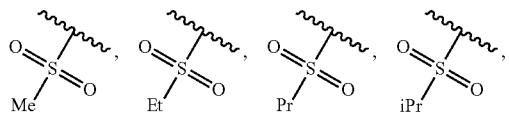

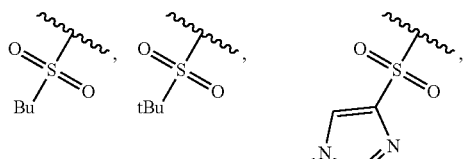

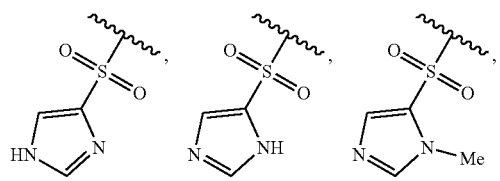

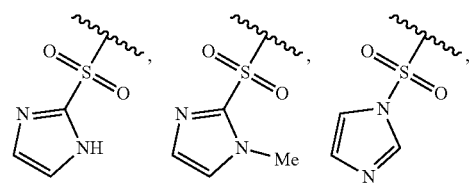

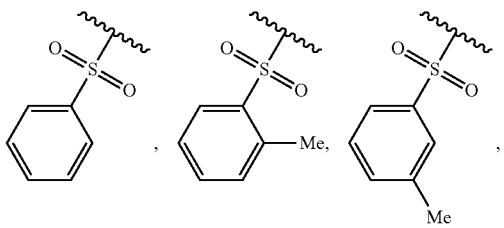

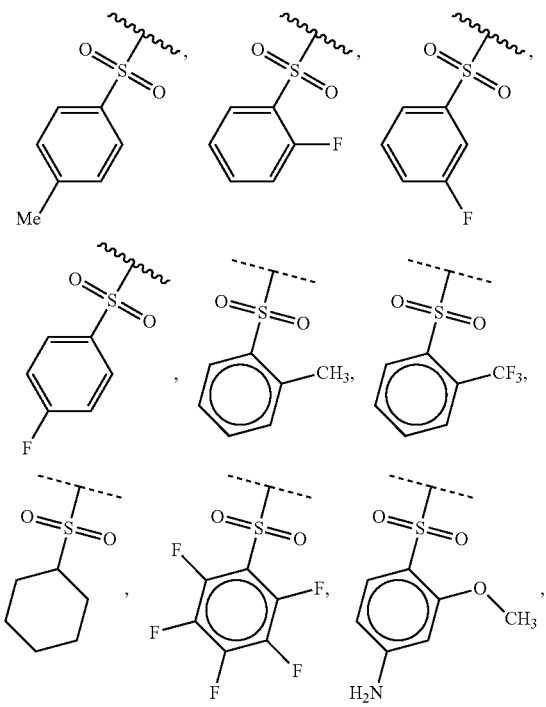

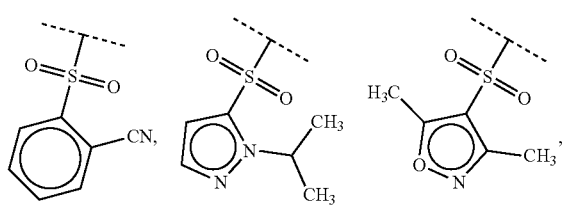

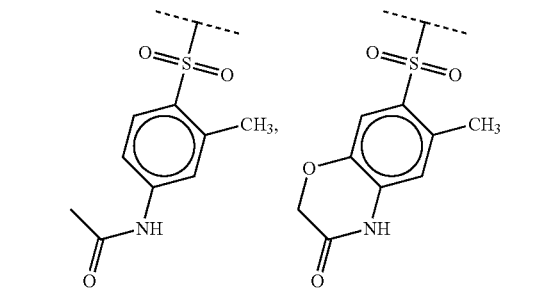

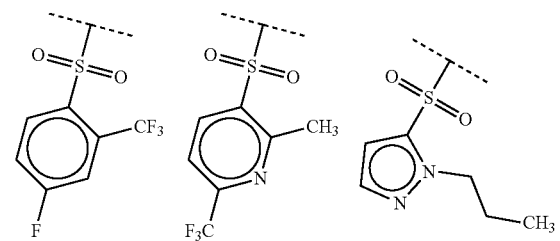

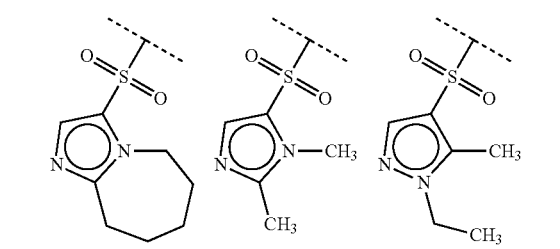

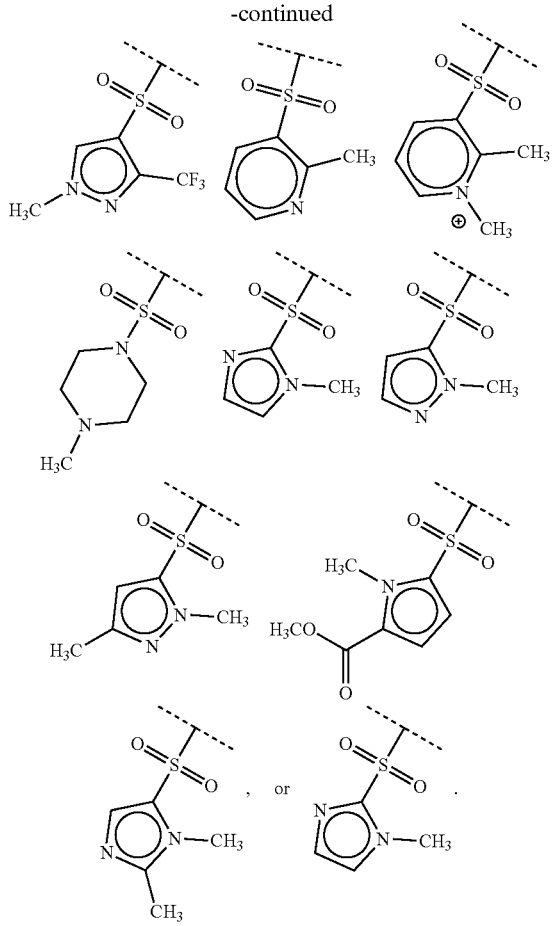

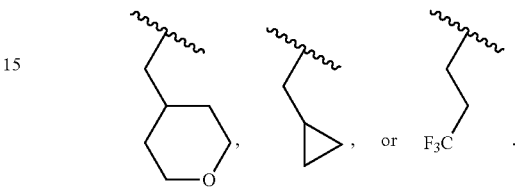

$R^{26}$

As generally defined herein, $R^{26}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$R$^{26a}$, —S(=O)$_2$OR$^{26a}$, —S(=O)$_2$N(R$^{26a}$)$_2$, or a nitrogen protecting group, wherein each $R^{26a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{26a}$ are joined to form an optionally substituted heteroaryl or optionally substituted heterocyclic ring.

In certain embodiments, $R^{26}$ is a non-hydrogen group. In certain embodiments, $R^{26}$ is not alkyl. In certain embodiments, $R^{26}$ is a non-hydrogen group and is not alkyl, —C(=O)R$^{26a}$, or —S(=O)$_2$R$^{26a}$. In certain embodiments, $R^{26}$ is a non-hydrogen group and is not methyl, —C(=O)R$^{26a}$, or —S(=O)$_2$R$^{26a}$. In certain embodiments, $R^{26}$ is not nosyl. In certain embodiments, $R^{26}$ is not —CH$_3$, —C(=O)Me, or —S(=O)$_2$Me. In certain embodiments, $R^{26}$ is a nitrogen protecting group.

In certain embodiments, $R^{26}$ is hydrogen. In certain embodiments, $R^{26}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{26}$ is optionally substituted $C_{2-6}$ alkyl. In certain embodiments, $R^{26}$ is methyl. In certain embodiments, $R^{26}$ is ethyl, propyl, or butyl. In certain embodiments, $R^{26}$ is optionally substituted alkenyl, e.g., optionally substituted $C_{2-6}$ alkenyl. In certain embodiments, $R^{26}$ is vinyl, allyl, or prenyl. In certain embodiments, $R^{26}$ is optionally substituted alkynyl, e.g., $C_{2-6}$ alkynyl.

In certain embodiments, $R^{26}$ is of formula:

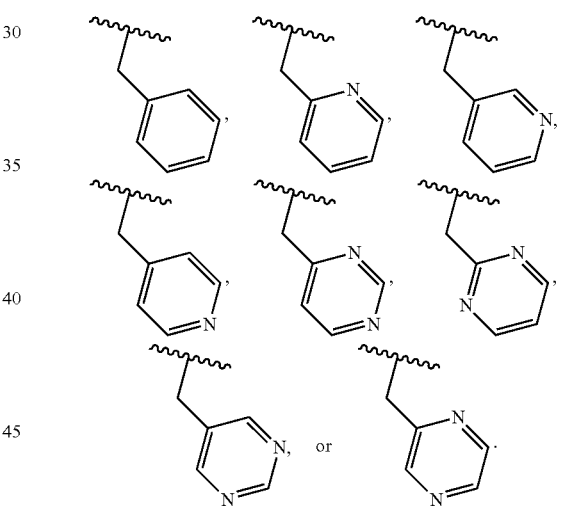

In certain embodiments, $R^{26}$ is optionally substituted aralkyl, e.g., optionally substituted benzyl. In certain embodiments, $R^{26}$ is optionally substituted heteroaralkyl, e.g., methyl substituted with a 5- to 6-membered heteroaryl ring.

In certain embodiments, $R^{26}$ is of formula:

In certain embodiments, $R^{26}$ is optionally substituted acyl, e.g., —CHO, —CO$_2$H, or —C(=O)NH$_2$. In certain embodiments, $R^{26}$ is —C(=O)R$^{26a}$, —C(=O)OR$^{26a}$, —C(=O)NH(R$^{26a}$), or —C(=O)N(R$^{26a}$)$_2$. In certain embodiments, $R^{26}$ is —C(=O)R$^{26a}$, and $R^{26a}$ is optionally substituted alkyl, e.g., —C(=O)Me. In certain embodiments, $R^{26}$ is —C(=O)R$^{26a}$, and $R^{26a}$ is optionally substituted $C_{1-6}$ alkyl. In certain embodiments, $R^{26}$ is —C(=O)R$^{26a}$, and $R^{26a}$ is optionally substituted $C_{2-6}$ alkyl. In certain embodiments, $R^{26}$ is —C(=O)R$^{26a}$, and $R^{26a}$ is optionally substituted alkenyl. In certain embodiments, $R^{26}$ is —C(=O)R$^{26a}$, and $R^{26a}$ is optionally substituted carbocyclyl, heterocyclyl, aryl, or heteroaryl. In certain embodiments, $R^{26}$ is —C(=O)OR$^{26a}$, and $R^{26a}$ is optionally substituted alkyl. In certain embodiments, $R^{26}$ is —C(=O)OR$^{26a}$, and $R^{26a}$ is optionally substituted alkenyl. In certain embodiments, $R^{26}$ is —C(=O)OR$^{26a}$, and $R^{26a}$ is optionally substituted carbocyclyl, heterocyclyl, aryl, or heteroaryl. In certain embodiments, $R^{26}$ is —C(=O)N($R^{26a}$)$_2$, and at least one $R^{26a}$ is optionally substituted alkyl. In certain embodiments, $R^{26}$ is —C(=O)NH$R^{26a}$, and $R^{26a}$ is optionally substituted alkyl. In certain embodiments, $R^{26}$ is —C(=O)NH$R^{26a}$, and $R^{26a}$ is optionally substituted alkenyl. In certain embodiments, $R^{26}$ is —C(=O)NH$R^{26a}$, and $R^{26a}$ is optionally substituted carbocyclyl, heterocyclyl, aryl, or heteroaryl.

In certain embodiments, $R^{26}$ is of formula:

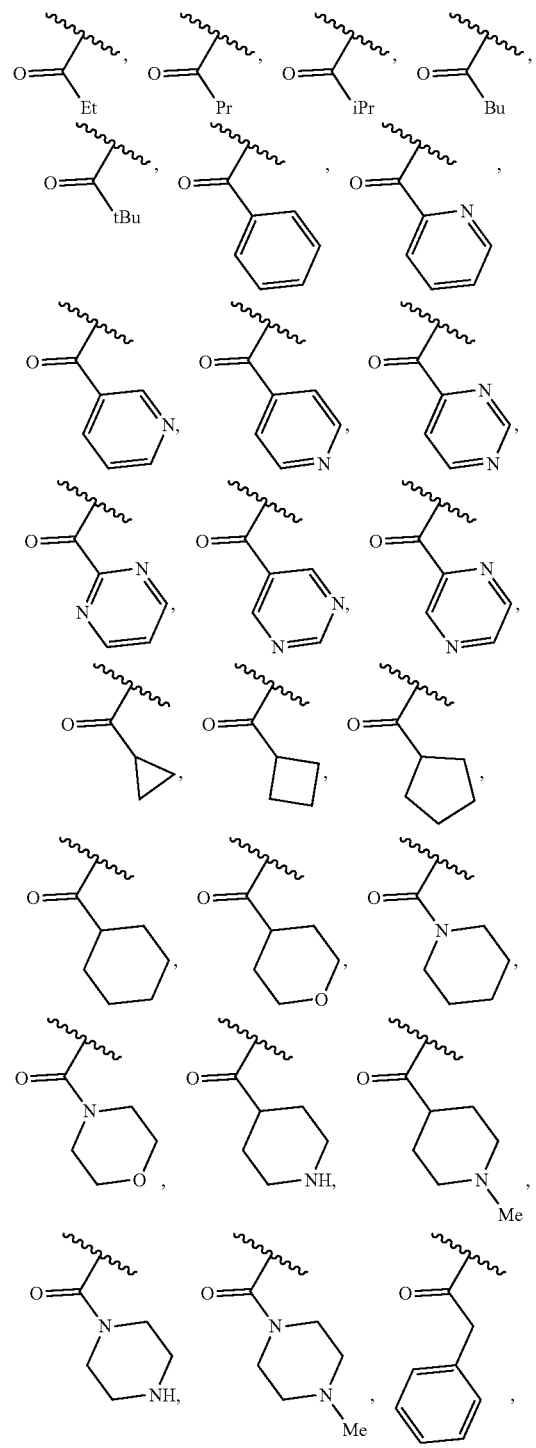

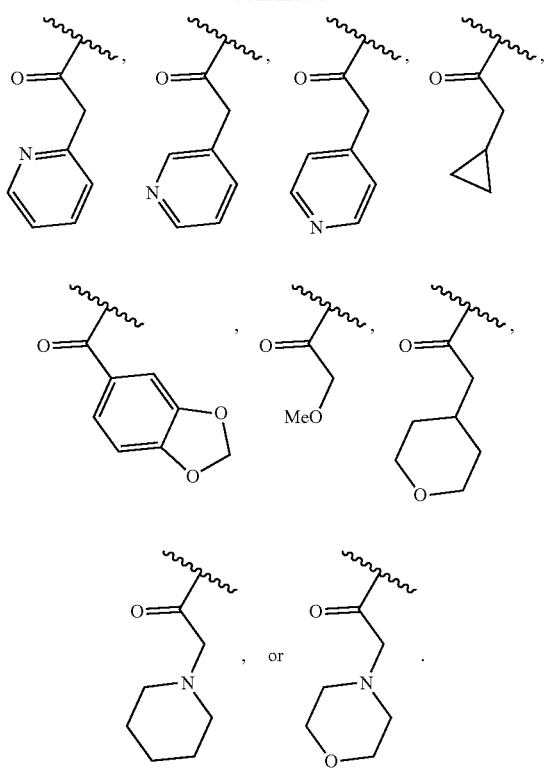

In certain embodiments, $R^{26}$ is of formula:

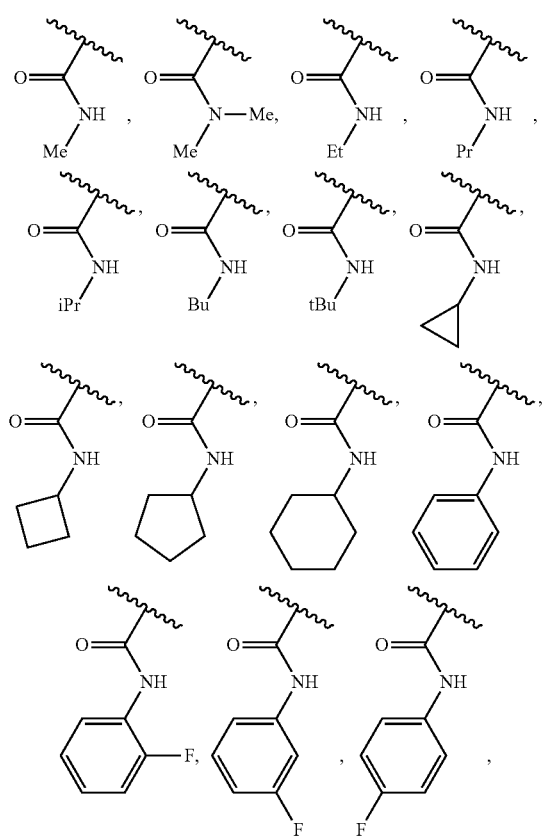

-continued

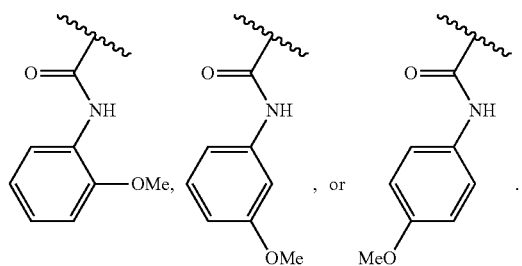

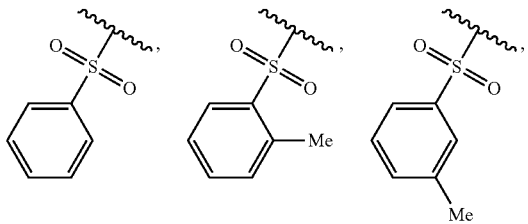

-continued

In certain embodiments, $R^{26}$ is $-S(=O)_2R^{26a}$. In certain embodiments, $R^{26}$ is $-S(=O)_2R^{26a}$, and $R^{26a}$ is optionally substituted alkyl, e.g., $R^{26}$ is $-S(=O)_2Me$. In certain embodiments, $R^{26}$ is $-S(=O)_2R^{26a}$, and $R^{26a}$ is optionally substituted $C_{1-6}$ alkyl. In certain embodiments, $R^{26}$ is $-S(=O)_2R^{26a}$, and $R^{26a}$ is optionally substituted $C_{2-6}$ alkyl. In certain embodiments, $R^{26}$ is $-S(=O)_2R^{26a}$, and $R^{26a}$ is optionally substituted alkenyl. In certain embodiments, $R^{26}$ is $-S(=O)_2R^{26a}$, and $R^{26a}$ is optionally substituted carbocyclyl, heterocyclyl, aryl, or heteroaryl. In certain embodiments, $R^{26}$ is $-S(=O)_2R^{26a}$. In certain embodiments, $R^{26}$ is $-S(=O)_2R^{26a}$, and $R^{26a}$ is optionally substituted alkyl. In certain embodiments, $R^{26}$ is $-S(=O)_2OR^{26a}$, and $R^{26a}$ is optionally substituted alkenyl. In certain embodiments, $R^{26}$ is $-S(=O)_2R^{26a}$, and $R^{26a}$ is optionally substituted carbocyclyl, heterocyclyl, aryl, or heteroaryl. In certain embodiments, $R^{26}$ is $-S(=O)_2N(R^{26a})_2$ or $-S(=O)_2NHR^{26a}$. In certain embodiments, $R^{26}$ is $-S(=O)_2N(R^{26a})_2$, and at least one $R^{26a}$ is optionally substituted alkyl. In certain embodiments, $R^{26}$ is $-S(=O)_2NHR^{26a}$, and $R^{26a}$ is optionally substituted alkenyl. In certain embodiments, $R^{26}$ is $-S(=O)_2NHR^{26a}$, and $R^{26a}$ is optionally substituted carbocyclyl, heterocyclyl, aryl, or heteroaryl.

In certain embodiments, $R^{26}$ is of formula:

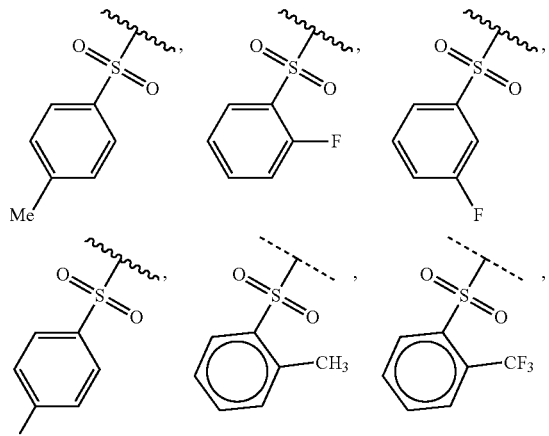

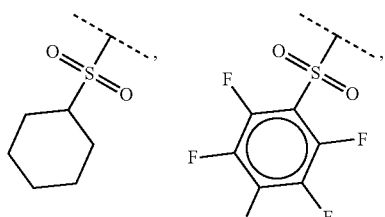

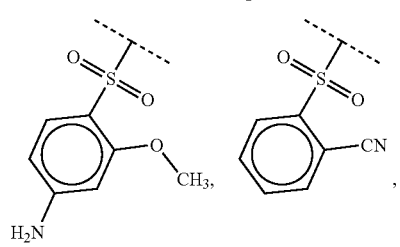

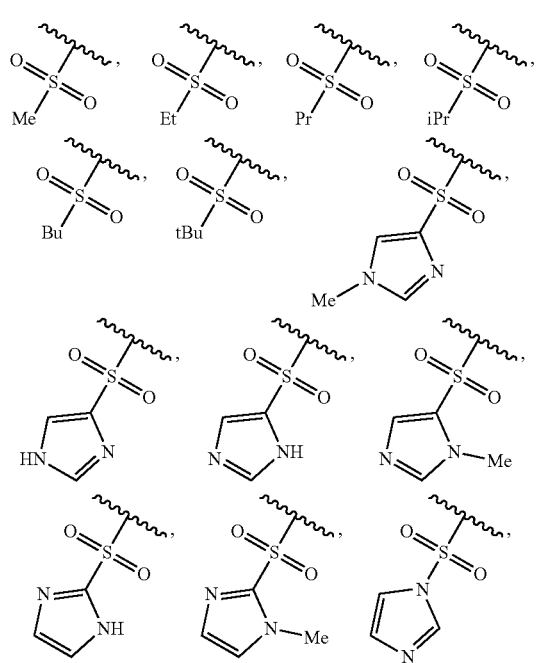

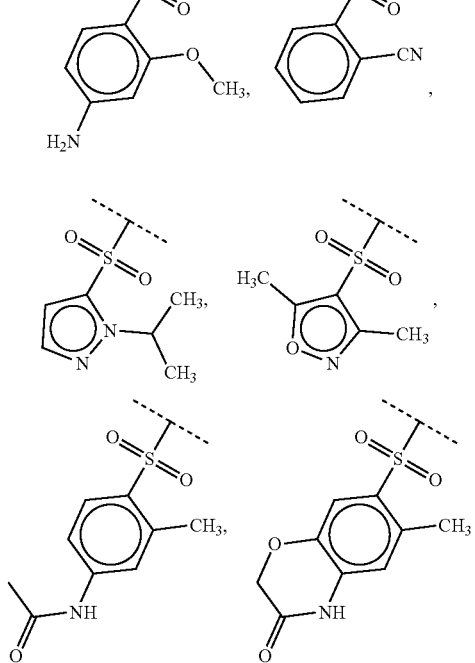

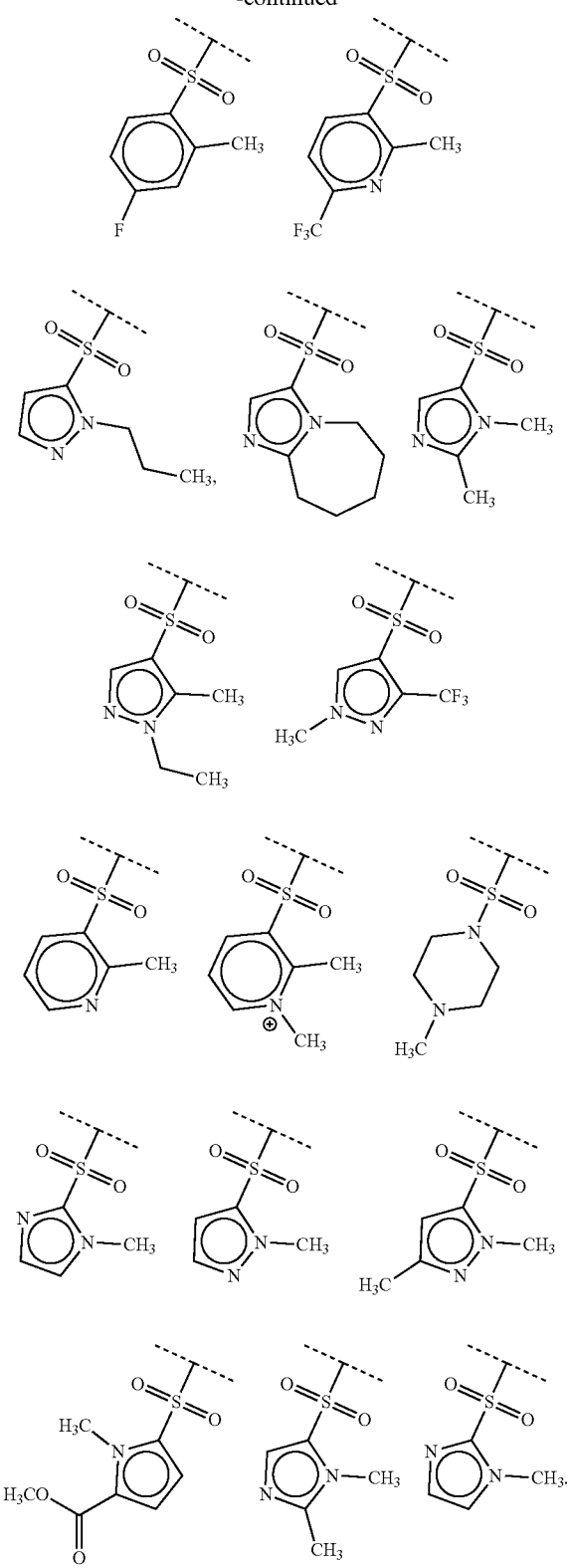
In certain embodiments, the compound of Formula (II) is a compound in Table 3, or a pharmaceutically acceptable salt, solvate, hydrate, polymorph, co-crystal, tautomer, stereoisomer, prodrug, or isotopically labeled derivative thereof.
TABLE 3
Exemplary compounds of Formula (II).
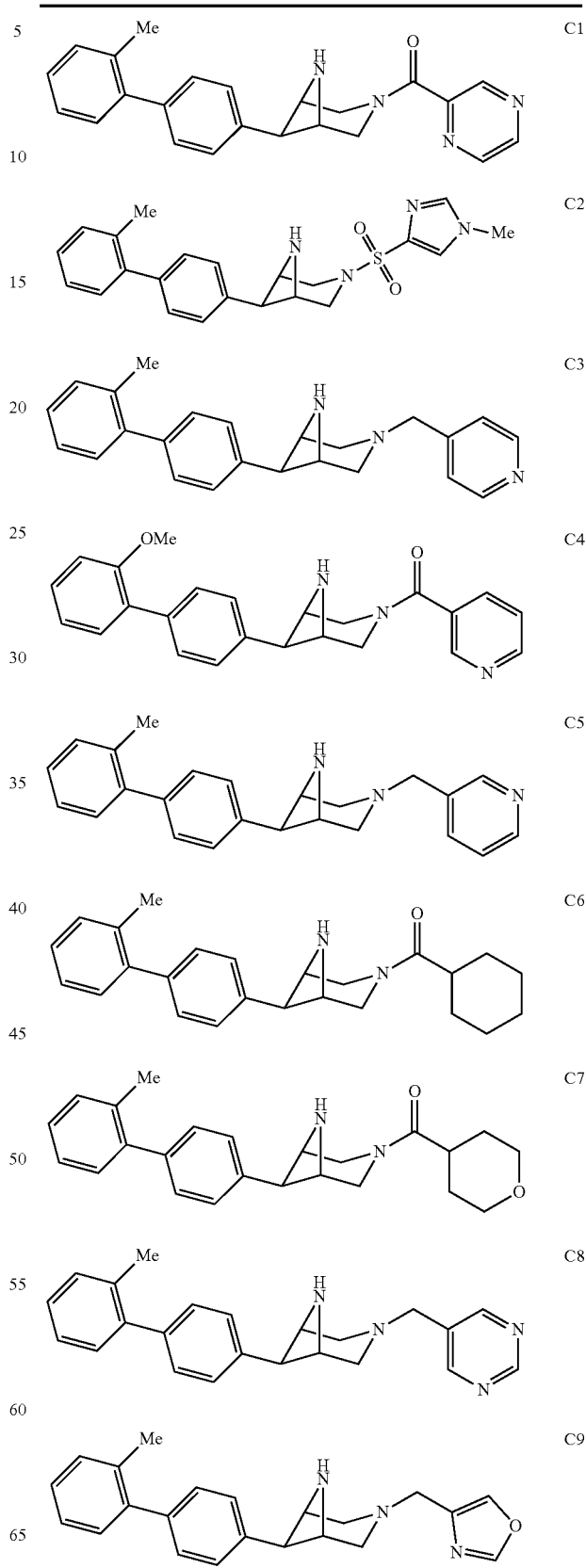

TABLE 3-continued

Exemplary compounds of Formula (II).

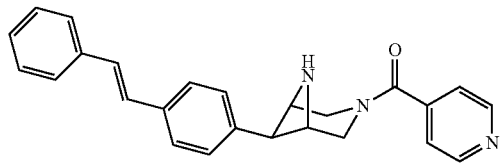 [SMILES: O=C(c1ccncc1)N1CC2NC(C1)C2c1ccc(/C=C/c2ccccc2)cc1]

C10

In certain embodiments, the compound of Formula (I) includes a moiety comprising Ring $A^2$ and Ring $B^2$, wherein the rings are not free to rotate about the bond or linker connecting the two rings. In certain embodiments, the compound comprises a locked ring moiety comprising Ring $A^2$ and Ring $B^2$ directly attached by a single bond, wherein the rings are independently optionally substituted aryl or optionally substituted heteroaryl. In certain embodiments, the locked ring moiety comprises Ring $A^2$ and Ring $B^2$ directly attached by a single bond, wherein the rings are independently optionally substituted aryl or optionally substituted heteroaryl, and at least one of the rings has a non-hydrogen group ortho to the single bond.

In certain embodiments, the rotational energy barrier between rings $A^2$ and $B^2$ is at least about 6 kcal/mol. In certain embodiments, the rotational energy barrier between rings $A^2$ and $B^2$ is at least about 10 kcal/mol, at least about 15 kcal/mol, at least about 20 kcal/mol, or at least about 30 kcal/mol. In certain embodiments, the equilibrium dihedral angle between rings $A^2$ and $B^2$ is between about 20° and between about 160°, inclusive. In certain embodiments, the equilibrium dihedral angle between rings $A^2$ and $B^2$ is between about 40° and between about 140°, between about 60° and between about 120°, between about 90° and between about 100°, inclusive. In certain embodiments, the equilibrium dihedral angle between rings $A^2$ and $B^2$ is between about 20° and between about 160°, inclusive, when bound to IDE. In certain embodiments, the equilibrium dihedral angle between rings $A^2$ and $B^2$ is between about 40° and between about 140°, between about 60° and between about 120°, between about 90° and between about 100°, inclusive, when bound to IDE.

Compounds of Formula (III)

In certain embodiments, the invention provides a compound of Formula (III):

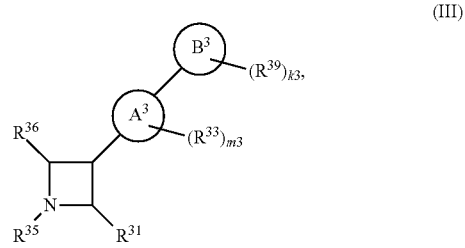

(III)

or a pharmaceutically acceptable salt, solvate, hydrate, polymorph, co-crystal, tautomer, stereoisomer, prodrug, or isotopically labeled derivative thereof,
wherein:
$R^{31}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$CH_2OR^{31a}$, or —$CH_2N(R^{31a})_2$, wherein each $R^{31a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, a sulfur protecting group when attached to a sulfur atom, or a nitrogen protecting group when attached to a nitrogen atom, or two $R^{31a}$ are joined to form an optionally substituted heteroaryl or optionally substituted heterocyclic ring $R^{35}$ is hydrogen, optionally substituted alkyl, optionally substituted alkenyl, optionally substituted alkynyl, optionally substituted aralkyl, optionally substituted heteroaralkyl, optionally substituted acyl, —$S(=O)_2R^{35a}$, —$S(=O)_2OR^{35a}$, —$S(=O)_2N(R^{35a})_2$, or a nitrogen protecting group, wherein each $R^{35}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{35a}$ are joined to form an optionally substituted heteroaryl or optionally substituted heterocyclic ring;

$R^{36}$ is —CN or —$CH_2N(R^{36a})_2$, wherein each $R^{36a}$ is independently hydrogen, optionally substituted alkyl, optionally substituted acyl, or a nitrogen protecting group, or two $R^{36a}$ are joined to form an optionally substituted heterocyclic or optionally substituted heteroaryl ring; Ring $A^3$ is carbocyclylene, heterocyclylene, arylene or heteroarylene;

each $R^{33}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{33a}$, —$N(R^{33a})_2$, or two $R^{33}$ are joined to form an optionally substituted carbocyclic, heterocyclic, aryl, or heteroaryl ring, wherein each $R^{33a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{33a}$ are joined to form an optionally substituted heteroaryl or optionally substituted heterocyclic ring;

Ring $B^3$ is a carbocyclic, heterocyclic, aryl or heteroaryl ring;

each $R^{39}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{39a}$, —$N(R^{39a})_2$, —$S(=O)_2R^{39a}$, —S(=O)$_2$OR$^{39a}$, or —S(=O)$_2$N(R$^{39a}$)$_2$, or two R$^{39}$ are joined to form an optionally substituted carbocyclic, heterocyclic, aryl, or heteroaryl ring, wherein each R$^{39a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R$^{39a}$ are joined to form an optionally substituted heteroaryl or optionally substituted heterocyclic ring; and m3 is 0, 1, 2, 3, or 4; and k3 is 0, 1, 2, 3, 4, or 5.

In certain embodiments, the compound of Formula (III) selectively inhibits the activity of IDE for degradation of a first substrate over the activity of IDE for degradation of a second substrate. In certain embodiments, the compound of Formula (III) selectively inhibits the activity of IDE for degradation of insulin over the activity of IDE for degradation of a second substrate (e.g., glucagon, amylin). In certain embodiments, the compound of Formula (III) selectively inhibits the activity of IDE for degradation of insulin over the activity of IDE for degradation of glucagon. In certain embodiments, the compound of Formula (III) selectively inhibits the activity of IDE for degradation of insulin over the activity of IDE for degradation of more than one other substrate.

A provided compound may be any possible stereoisomer of Formula (III). The azetidines ring comprises three chiral centers, which each may independently be in either the (R)- or (S)-configuration. In certain embodiments, a compound of Formula (III) is a stereoisomer of formula:

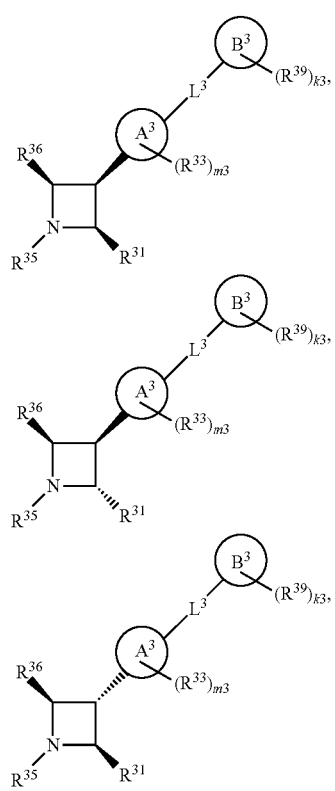

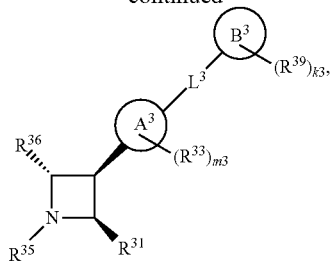

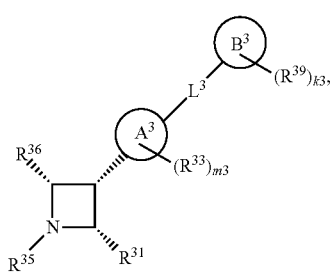

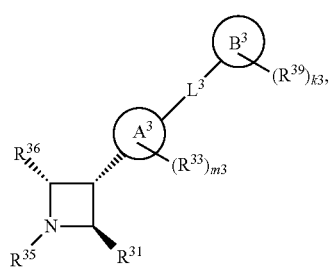

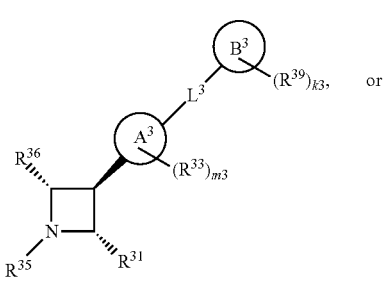

or

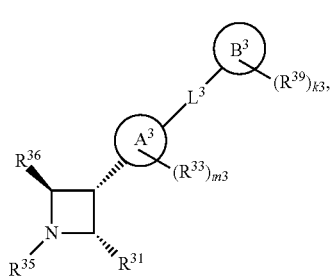

or a pharmaceutically acceptable salt, solvate, hydrate, polymorph, co-crystal, prodrug, or isotopically labeled derivative thereof.

In certain embodiments, the compound of Formula (III) is a compound of Formula (III-a):

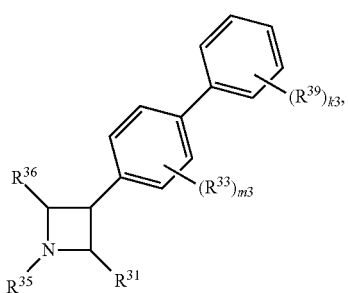

(III-a)

or a pharmaceutically acceptable salt, solvate, hydrate, polymorph, co-crystal, prodrug, or isotopically labeled derivative thereof, wherein $R^{31}$, $R^{33}$, $R^{35}$, $R^{36}$, $R^{39}$, m3, and k3 are as described herein.

In certain embodiments, the compound of Formula (III) is a compound of Formula (III-b):

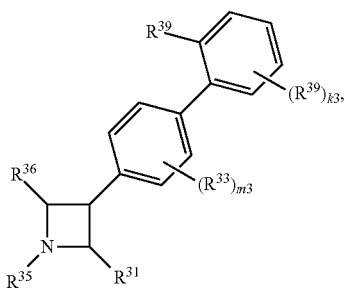

(III-b)

or a pharmaceutically acceptable salt, solvate, hydrate, polymorph, co-crystal, prodrug, or isotopically labeled derivative thereof, wherein $R^{31}$, $R^{33}$, $R^{35}$, $R^{36}$, $R^{39}$, m3, and k3 are as described herein.

In certain embodiments, the compound of Formula (III) is a compound of Formula (III-c):

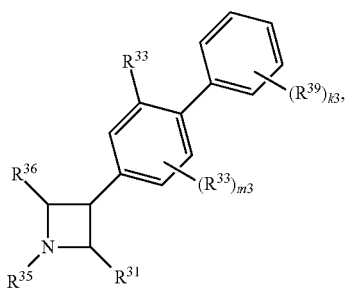

(III-c)

or a pharmaceutically acceptable salt, solvate, hydrate, polymorph, co-crystal, prodrug, or isotopically labeled derivative thereof, wherein $R^{31}$, $R^{33}$, $R^{35}$, $R^{36}$, $R^{39}$, m3, and k3 are as described herein.

In certain embodiments, the compound of Formula (III) is a compound of Formula (III-d):

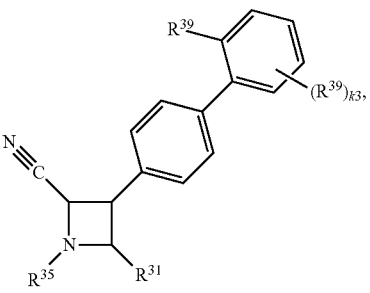

(III-d)

or a pharmaceutically acceptable salt, solvate, hydrate, polymorph, co-crystal, prodrug, or isotopically labeled derivative thereof, wherein $R^{31}$, $R^{35}$, $R^{36}$, $R^{39}$, and k3 are as described herein.

In certain embodiments, the compound of Formula (III) is a compound of Formula:

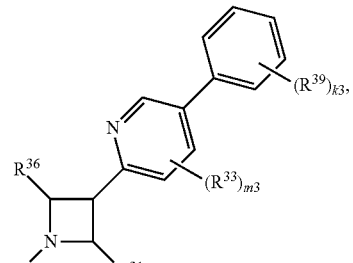

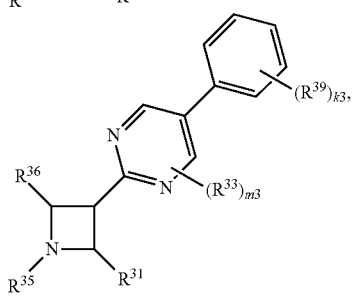

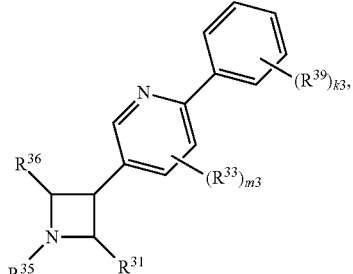

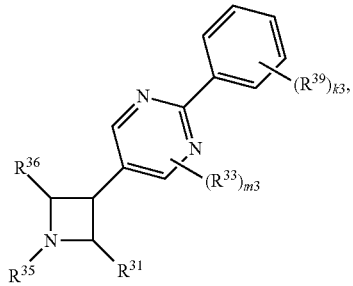

-continued

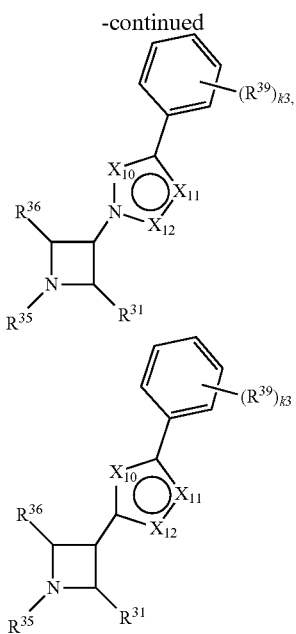

or a pharmaceutically acceptable salt, solvate, hydrate, polymorph, co-crystal, prodrug, or isotopically labeled derivative thereof, wherein $R^{31}$, $R^{33}$, $R^{35}$, $R^{36}$, $R^{39}$, m3, and k3 are as described herein, m3 is 0, 1, or 2; and $X_{10}$, $X_{11}$, and $X_{12}$ are selected from the group consisting of C, CH, C($R^{33}$), O, S, N, and N($R^{33a}$), as valency permits.

$R^{31}$

As generally defined herein, $R^{31}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH$_2$OR$^{31a}$, —CH$_2$SR$^{31a}$ or —CH$_2$N(R$^{31a}$)$_2$, wherein each $R^{31a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{31a}$ are joined to form an optionally substituted heteroaryl or optionally substituted heterocyclic ring.

In certain embodiments, $R^{31}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, or —CH$_2$N(R$^{31a}$)$_2$.

In certain embodiments, $R^{31}$ is hydrogen. In certain embodiments, $R^{31}$ is a non-hydrogen group, and the carbon to which $R^{31}$ attached is a stereocenter of the (R)-configuration. In certain embodiments, $R^{31}$ is a non-hydrogen group, and the carbon to which $R^{31}$ attached is a stereocenter of the (S)-configuration.

In certain embodiments, $R^{31}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, or —CH$_2$N(R$^{31a}$)$_2$.

In certain embodiments, $R^{31}$ is halogen. In some embodiments, $R^{31}$ is —F. In some embodiments, $R^{31}$ is —Cl, —Br, or —I. In certain embodiments, $R^{31}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{31}$ is methyl. In certain embodiments, $R^{31}$ is ethyl, propyl, or butyl. In certain embodiments, $R^{31}$ is optionally substituted alkenyl, e.g., optionally substituted $C_{2-6}$ alkenyl. In certain embodiments, $R^{31}$ is vinyl, allyl, or prenyl. In certain embodiments, $R^{31}$ is optionally substituted alkynyl, e.g., $C_{2-6}$ alkynyl.

In certain embodiments, $R^{31}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^{31}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{31}$ is optionally substituted aryl, e.g., optionally substituted phenyl. In certain embodiments, $R^{31}$ is optionally substituted heteroaryl, e.g., optionally substituted 5-6 membered heteroaryl, or optionally substituted 9-10 membered bicyclic heteroaryl. In certain embodiments, $R^{31}$ is optionally substituted aralkyl, e.g., optionally substituted benzyl. In certain embodiments, $R^{31}$ is optionally substituted heteroaralkyl, e.g., methyl substituted with a 5-6 membered heteroaryl ring.

In certain embodiments, $R^{31}$ is optionally substituted acyl, e.g., —CHO, —CO$_2$H, or —C(=O)NH$_2$. In certain embodiments, $R^{31}$ is —C(=O)R$^{31a}$, —C(=O)OR$^{31a}$, —C(=O)NH(R$^{31a}$), or —C(=O)N(R$^{31a}$)$_2$. In certain embodiments, $R^{31}$ is —C(=O)R$^{31a}$, and $R^{31a}$ is optionally substituted alkyl, e.g., —C(=O)Me. In certain embodiments, $R^{31}$ is —C(=O)R$^{31a}$, and $R^{31a}$ is optionally substituted alkenyl. In certain embodiments, $R^{31}$ is —C(=O)R$^{31a}$, and $R^{31a}$ is optionally substituted carbocyclyl, heterocyclyl, aryl, or heteroaryl. In certain embodiments, $R^{31}$ is —C(=O)OR$^{31a}$, and $R^{31a}$ is optionally substituted alkyl. In certain embodiments, $R^{31}$ is —C(=O)OR$^{31a}$, and $R^{31a}$ is optionally substituted alkenyl. In certain embodiments, $R^{31}$ is —C(=O)OR$^{31a}$, and $R^{31a}$ is optionally substituted carbocyclyl, heterocyclyl, aryl, or heteroaryl. In certain embodiments, $R^{31}$ is —C(=O)N(R$^{31a}$)$_2$, and at least one $R^{31a}$ is optionally substituted alkyl. In certain embodiments, $R^{31}$ is —C(=O)NHR$^{31a}$, and $R^{31a}$ is optionally substituted alkyl. In certain embodiments, $R^{31}$ is —C(=O)NHR$^{31a}$, and $R^{31a}$ is optionally substituted alkenyl. In certain embodiments, $R^{31}$ is —C(=O)NHR$^{31a}$, and $R^{31a}$ is optionally substituted carbocyclyl, heterocyclyl, aryl, or heteroaryl.

In certain embodiments, $R^{31}$ is —(CH$_2$)$_n$OR$^{31a}$, wherein n is 0, 1, 2, 3, or 4. In certain embodiments, $R^{31}$ is —CH$_2$OR$^{31a}$, e.g., —CH$_2$OH. In certain embodiments, $R^{31}$ is —CH$_2$OR$^{31a}$, and $R^{31a}$ is hydrogen, optionally substituted alkyl, or an oxygen protecting group. In certain embodiments, $R^{31}$ is —CH$_2$OR$^{31a}$, and $R^{31a}$ is optionally substituted alkyl or an oxygen protecting group. In certain embodiments, $R^{31}$ is —$CH_2OR^{31a}$, and $R^{31a}$ is optionally substituted alkyl. In certain embodiments, $R^{31}$ is —$CH_2OR^{31a}$, and $R^{31a}$ is optionally alkenyl. In certain embodiments, $R^{31}$ is —$CH_2OR^{31a}$, and $R^{31a}$ is optionally substituted carbocyclyl, optionally substituted heterocyclyl, optionally substituted aryl optionally substituted heteroaryl. In certain embodiments, $R^{31}$ is —$CH_2OR^{31a}$, and $R^{31a}$ is optionally substituted acyl, e.g., $R^{31}$ is —$CH_2OC(=O)R^{31a}$, —$CH_2OC(=O)OR^{31a}$, or —$CH_2OC(=O)N(R^{31a})_2$. In certain embodiments, $R^{31}$ is —$OR^{31a}$, and $R^{31a}$ is an oxygen protecting group, e.g., $R^{31}$ is —$CH_2OCPh_3$. In certain embodiments, $R^{31}$ is —$CH_2OH$. In certain embodiments, $R^{31}$ is not —$CH_2OH$.

In certain embodiments, $R^{31}$ is —$(CH_2)_nSR^{31a}$, wherein n is 0, 1, 2, 3, or 4. In certain embodiments, $R^{31}$ is —$CH_2SR^{31a}$, e.g., —$CH_2SH$. In certain embodiments, $R^{31}$ is —$CH_2SR^{31a}$ and $R^{31a}$ is hydrogen, optionally substituted alkyl, or a sulfur protecting group. In certain embodiments, $R^{31}$ is —$CH_2SR^{31a}$, and $R^{31a}$ is optionally substituted alkyl or a sulfur protecting group. In certain embodiments, $R^{31}$ is —$CH_2SR^{31a}$, and $R^{31a}$ is optionally substituted alkyl. In certain embodiments, $R^{31}$ is —$CH_2SR^{31a}$, and $R^{31a}$ is optionally alkenyl. In certain embodiments, $R^{31}$ is —$CH_2SR^{31a}$, and $R^{31a}$ is optionally substituted carbocyclyl, optionally substituted heterocyclyl, optionally substituted aryl optionally substituted heteroaryl. In certain embodiments, $R^{31}$ is —$CH_2SR^{31a}$, and $R^{31a}$ is optionally substituted acyl, e.g., $R^{31}$ is —$CH_2SC(=O)R^{31a}$, —$CH_2SC(=O)OR^{31a}$, or —$CH_2SC(=O)N(R^{31a})_2$. In certain embodiments, $R^{31}$ is —$SR^{31a}$, and $R^{31a}$ is a sulfur protecting group.

In certain embodiments, $R^{31}$ is —$(CH_2)_n N(R^{31a})_2$, wherein n is 0, 1, 2, 3, or 4. In certain embodiments, $R^{31}$ is —$CH_2N(R^{31a})_2$, e.g., —$CH_2NH_2$, —$CH_2NHR^{31a}$. In certain embodiments, $R^{31}$ is —$CH_2NH(R^{31a})$, and $R^{31a}$ is optionally substituted alkyl. In certain embodiments, $R^{31}$ is —$CH_2N(R^{31a})_2$, and at least one $R^{31a}$ is optionally substituted alkyl. In certain embodiments, $R^{31}$ is —$CH_2NHR^{31a}$, and $R^{31a}$ is optionally substituted carbocyclyl, optionally substituted heterocyclyl, optionally substituted aryl, or optionally substituted heteroaryl. In certain embodiments, $R^{31}$ is —$CH_2NHR^{31}$, and $R^{31a}$ is optionally substituted acyl, e.g., $R^{31}$ is —$CH_2NHC(=O)R^{31a}$, —$CH_2NHC(=O)OR^{31a}$, or —$CH_2NHC(=O)NHR^{31}$. In certain embodiments, $R^{31}$ is —$CH_2N(R^{31a})_2$, and at least one $R^{31a}$ is a nitrogen protecting group. In certain embodiments, $R^{31}$ is —$CH_2N(R^{31a})_2$, and both $R^{31a}$ are joined to form an optionally substituted heterocyclic or optionally substituted heteroaryl ring.

Ring $A^3$ and $R^{33}$

As generally defined herein, Ring $A^3$ is carbocyclylene, heterocyclylene, arylene, or heteroarylene. In certain embodiments, Ring $A^3$ and Ring $B^3$ are both phenyl rings, such that Ring $A^3$ and $B^3$ together form a biphenyl group. Ring $A^3$ may be substituted with 0, 1, 2, 3, or 4 independent $R^{33}$, valency permitting. In certain embodiments, m3 is 0 or 1. In certain embodiments, m3 is 0. In certain embodiments, m3 is 1. In certain embodiments, m3 is 2. In certain embodiments, m3 is 3. In certain embodiments, m3 is 4.

In certain embodiments, Ring $A^3$ is arylene, e.g., phenylene. In certain embodiments, Ring $A^3$ is heteroarylene, e.g., 5- to 6-membered heteroarylene. In some embodiments, Ring $A^3$ is pyridylene, pyrimidylene, or imidazylene.

In certain embodiments, Ring $A^3$ is carbocyclylene, e.g., 3- to 6-membered carbocyclylene. In some embodiments, Ring $A^3$ is cyclohexylene, cyclopentylene, cyclobutylene, or cyclopropylene. In certain embodiments, Ring $A^3$ is heterocyclylene, e.g., 5- to 6-membered heterocyclylene. In some embodiments, Ring $A^3$ is piperidinylene or piperizinylene.

In certain embodiments, Ring $A^3$ is of formula:

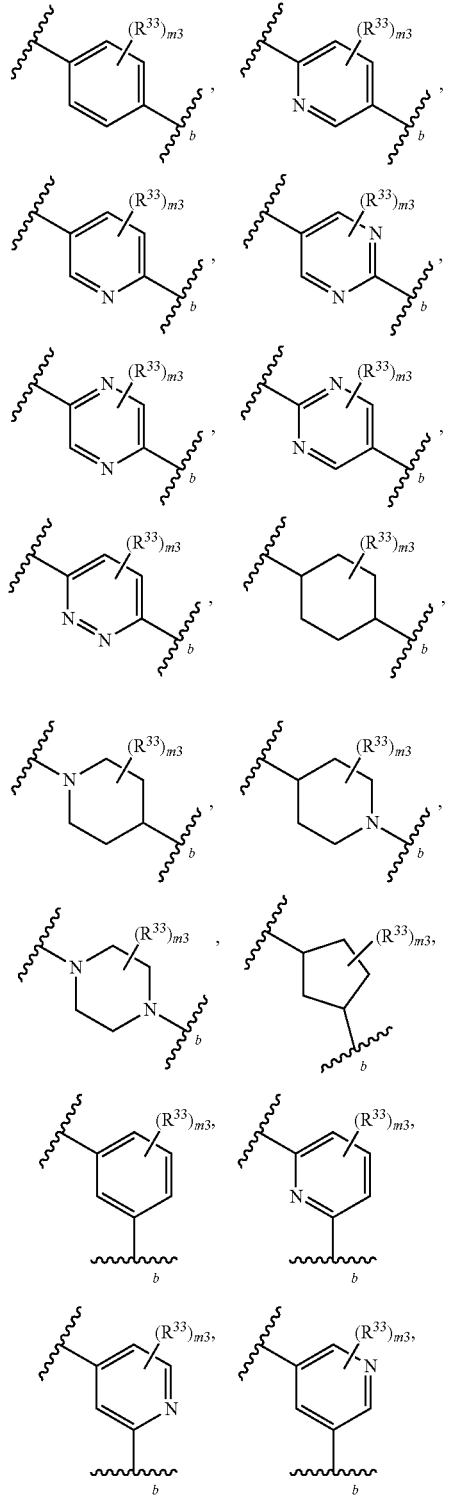

-continued
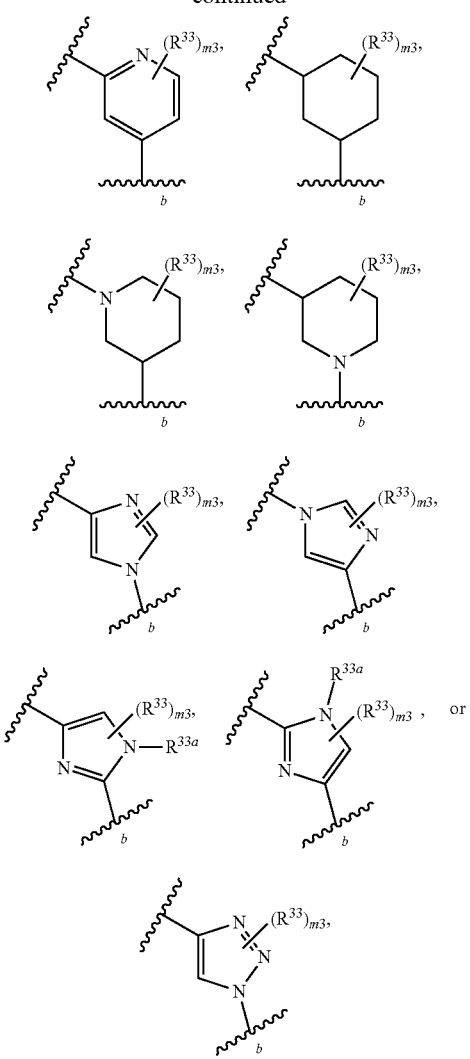
wherein the position labeled b is attached to Ring B³, and m3 is 0, 1, 2, 3, or 4, valency permitting.
In certain embodiments, Ring A³ is of formula:
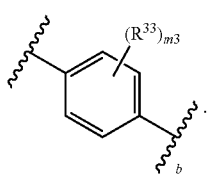
In certain embodiments, Ring A³ is of formula:
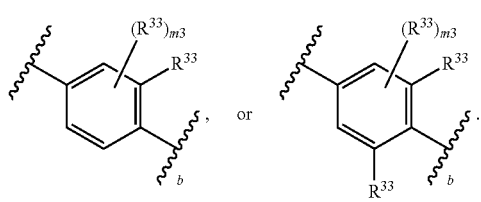
In certain embodiments, Ring A³ is of formula:
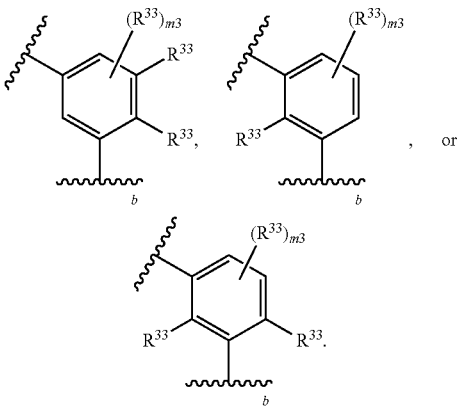
In certain embodiments, Ring A³ is of formula:
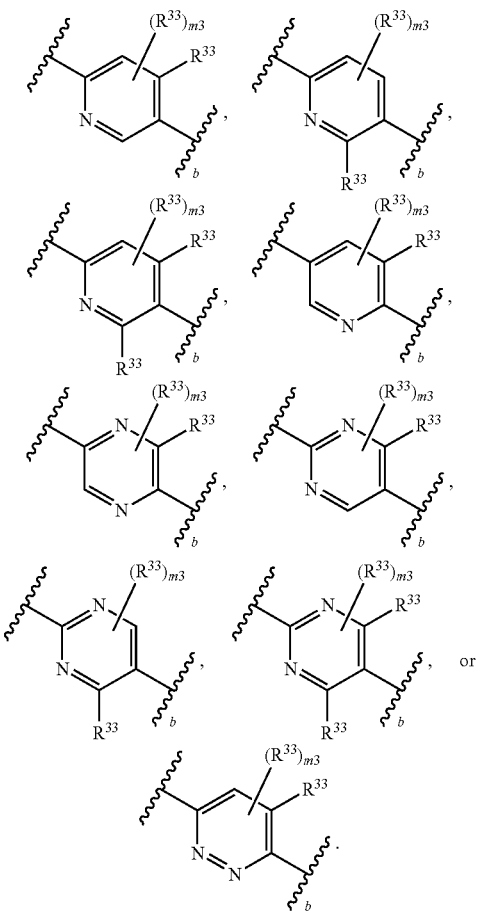
In certain embodiments, Ring A³ is of formula:
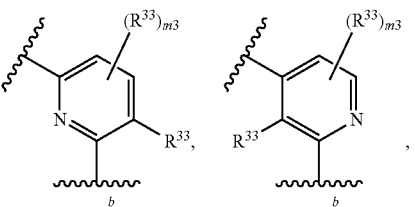

-continued
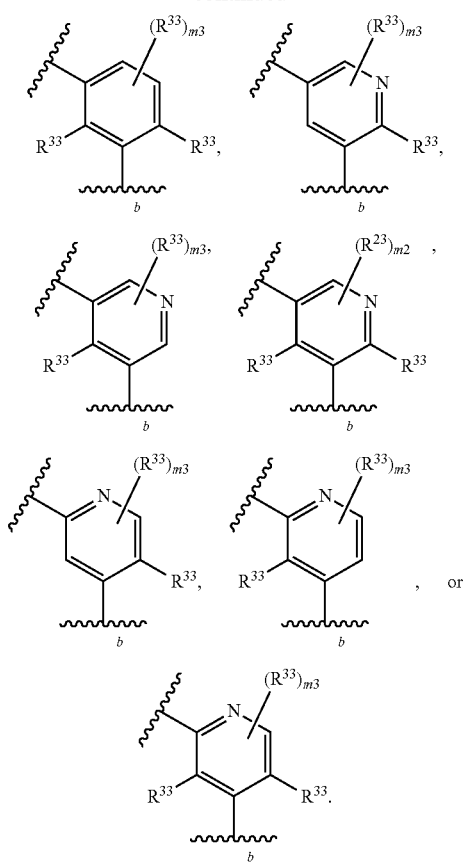
In certain embodiments, Ring A³ is of formula:
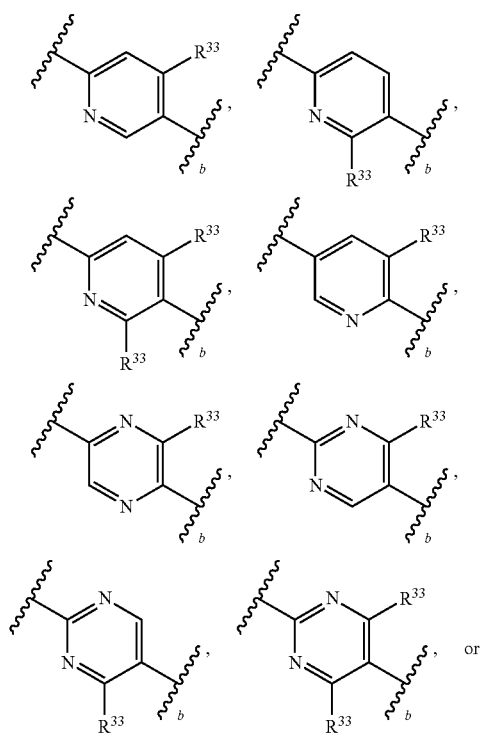
-continued
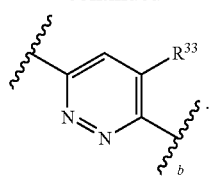
In certain embodiments, Ring A³ is of formula:
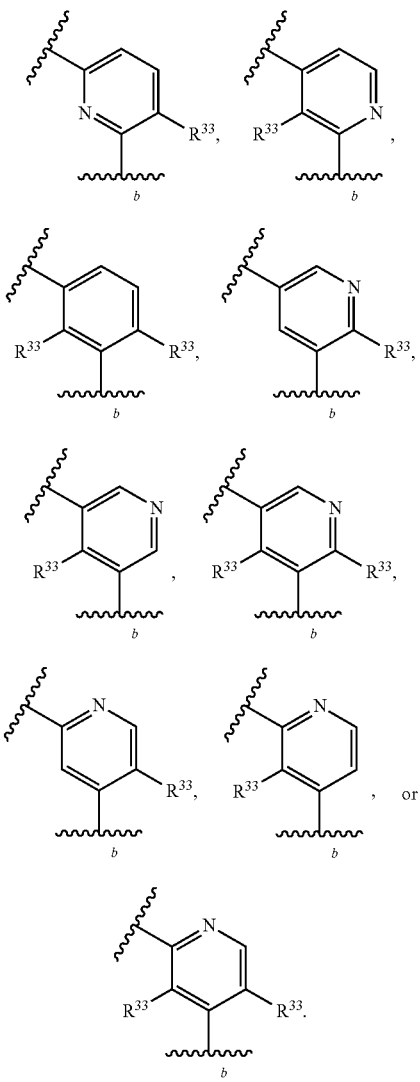
In certain embodiments, Ring A³ is of formula:
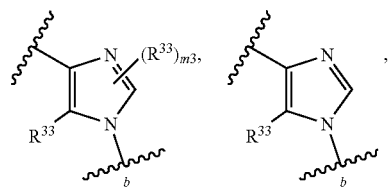

-continued
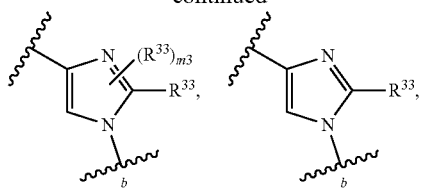
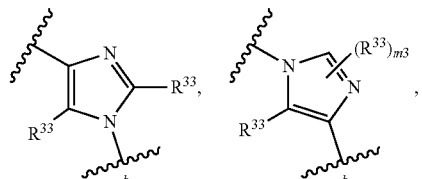
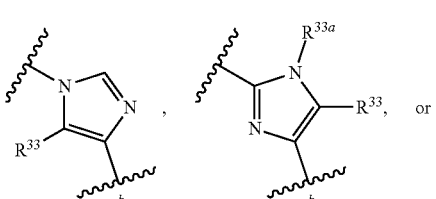
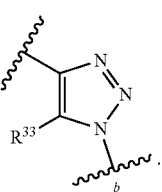
In certain embodiments, Ring A³ is of formula:
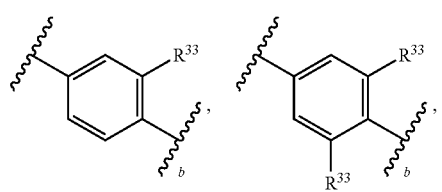
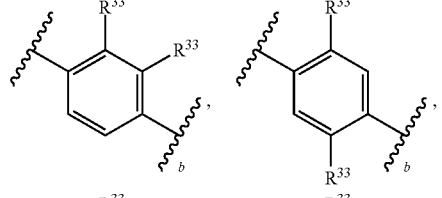
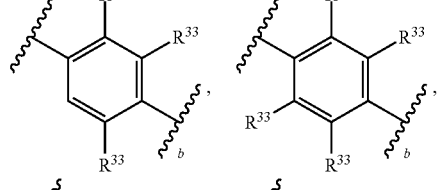
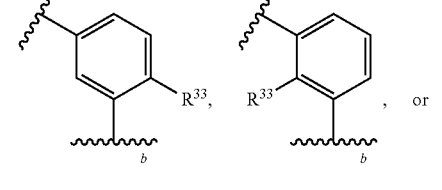
-continued
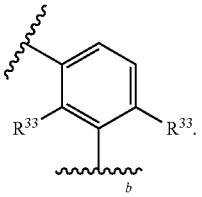
In certain embodiments, Ring A³ is of formula:
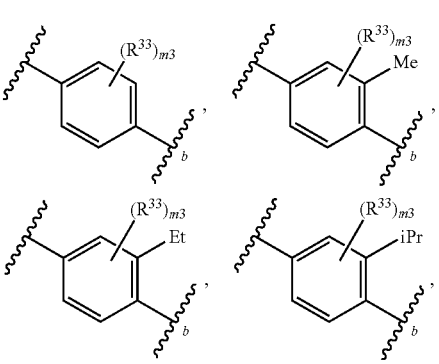
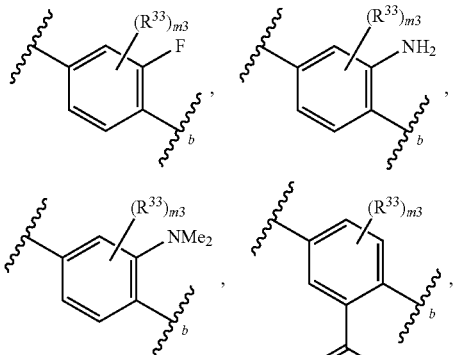
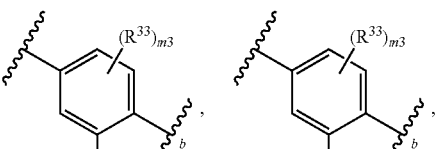
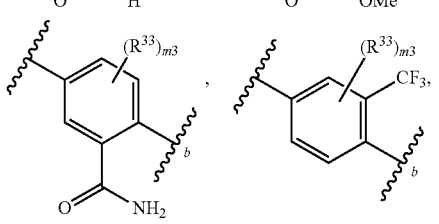

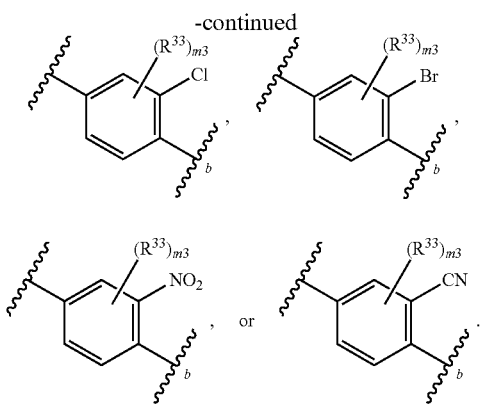

In certain embodiments, Ring $A^3$ is of formula:

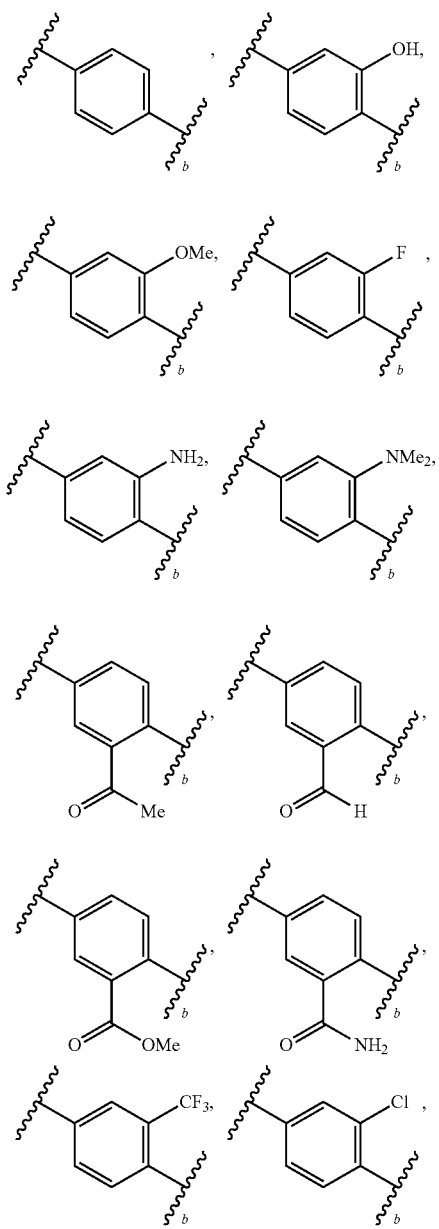

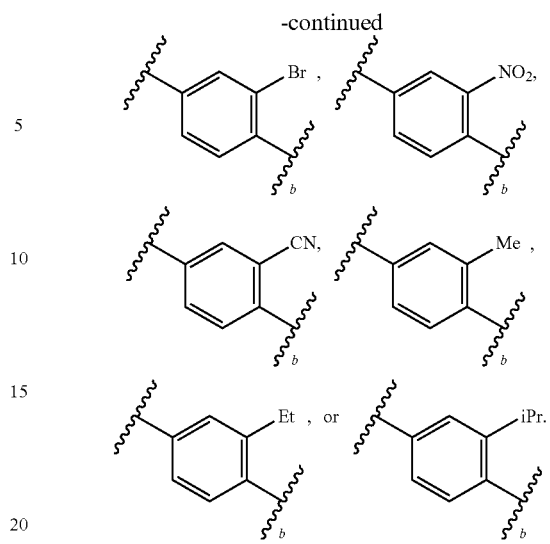

In certain embodiments, Ring $A^3$ is of formula:

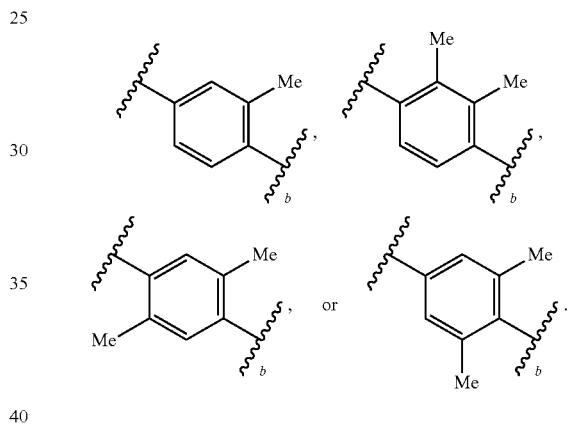

As generally defined herein, each $R^{33}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{33a}$, or —$N(R^{33a})_2$, or two $R^{33}$ are joined to form an optionally substituted carbocyclic, heterocyclic, aryl, or heteroaryl ring, wherein each $R^{33a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{33a}$ are joined to form an optionally substituted heteroaryl or optionally substituted heterocyclic ring.

In certain embodiments, at least one $R^{33}$ is —$NO_2$. In certain embodiments, at least one $R^{33}$ is —CN. In certain embodiments, at least one $R^{33}$ is halogen. In some embodiments, at least one $R^{33}$ is —F. In some embodiments, at least one $R^{33}$ is —Cl, —Br, or —I. In certain embodiments, at least one $R^{33}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{33}$ is methyl. In certain embodiments, at least one $R^{33}$ is ethyl, propyl, or butyl. In certain embodiments, at least one $R^{33}$ is optionally substituted alkenyl, e.g., optionally substituted $C_{2-6}$ alkenyl. In certain embodiments, at least one $R^{33}$ is vinyl, allyl, or prenyl. In certain embodiments, at least one $R^{33}$ is optionally substituted alkynyl, e.g., $C_{2-6}$ alkynyl.

In certain embodiments, at least one $R^{33}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{33}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{33}$ is optionally substituted aryl, e.g., optionally substituted phenyl. In certain embodiments, at least one $R^{33}$ is optionally substituted heteroaryl, e.g., optionally substituted 5-6 membered heteroaryl or optionally substituted 9-10 membered bicyclic heteroaryl. In certain embodiments, at least one $R^{33}$ is optionally substituted aralkyl, e.g., optionally substituted benzyl. In certain embodiments, at least one $R^{33}$ is optionally substituted heteroaralkyl, e.g., methyl substituted with a 5-6 membered heteroaryl ring.

In certain embodiments, at least one $R^{33}$ is optionally substituted acyl, e.g., —CHO, —CO$_2$H, or —C(=O)NH$_2$. In certain embodiments, at least one $R^{33}$ is —C(=O)R$^{33a}$, —C(=O)OR$^{33a}$, —C(=O)NH(R$^{33a}$), or —C(=O)N(R$^{33a}$)$_2$. In certain embodiments, at least one $R^{33}$ is —C(=O)R$^{33a}$, and R$^{33a}$ is optionally substituted alkyl, e.g., $R^{33}$ is —C(=O)Me. In certain embodiments, at least one $R^{33}$ is —C(=O)R$^{33a}$, and R$^{33a}$ is optionally substituted alkenyl. In certain embodiments, at least one $R^{33}$ is —C(=O)R$^{33a}$, and R$^{33a}$ is optionally substituted carbocyclyl, heterocyclyl, aryl, or heteroaryl. In certain embodiments, at least one $R^{33}$ is —C(=O)OR$^{33a}$, and R$^{33a}$ is optionally substituted alkyl. In certain embodiments, at least one $R^{33}$ is —C(=O)OR$^{33a}$, and R$^{33a}$ is optionally substituted alkenyl. In certain embodiments, at least one $R^{33}$ is —C(=O)OR$^{33a}$, and R$^{33a}$ is optionally substituted carbocyclyl, heterocyclyl, aryl, or heteroaryl. In certain embodiments, at least one $R^{33}$ is —C(=O)N(R$^{33a}$)$_2$, and at least one R$^{33a}$ is optionally substituted alkyl. In certain embodiments, at least one $R^{33}$ is —C(=O)NHR$^{33a}$, and R$^{33a}$ is optionally substituted alkyl. In certain embodiments, at least one $R^{33}$ is —C(=O)NHR$^{33a}$, and R$^{33a}$ is optionally substituted alkenyl. In certain embodiments, at least one $R^{33}$ is —C(=O)NHR$^{33a}$, and R$^{33a}$ is optionally substituted carbocyclyl, heterocyclyl, aryl, or heteroaryl.

In certain embodiments, at least one $R^{33}$ is —OR$^{33a}$, e.g., —OH. In certain embodiments, at least one $R^{33}$ is —OR$^{33a}$, and R$^{33a}$ is optionally substituted alkyl. In certain embodiments, at least one $R^{33}$ is —OR$^{33a}$, and R$^{33a}$ is optionally substituted alkenyl. In certain embodiments, at least one $R^{33}$ is —OR$^{33a}$, and R$^{33a}$ is optionally substituted carbocyclyl, optionally substituted heterocyclyl, optionally substituted aryl optionally substituted heteroaryl. In certain embodiments, at least one $R^{33}$ is —OR$^{33a}$, and R$^{33a}$ is optionally substituted acyl, e.g., $R^{33}$ is —OC(=O)R$^{33a}$, —OC(=O)OR$^{33a}$, or —OC(=O)N(R$^{33a}$)$_2$. In certain embodiments, at least one $R^{33}$ is —OR$^{33a}$, and R$^{33a}$ is an oxygen protecting group.

In certain embodiments, at least one $R^{33}$ is —N(R$^{33a}$)$_2$, e.g., —NH$_2$, —NHR$^{33a}$. In certain embodiments, at least one $R^{33}$ is —NH(R$^{33a}$), and R$^{33a}$ is optionally substituted alkyl. In certain embodiments, at least one $R^{33}$ is —N(R$^{33a}$)$_2$, and at least one R$^{33a}$ is optionally substituted alkyl. In certain embodiments, at least one $R^{33}$ is —NHR$^{33a}$, and R$^{33a}$ is optionally substituted carbocyclyl, optionally substituted heterocyclyl, optionally substituted aryl, or optionally substituted heteroaryl. In certain embodiments, at least one $R^{33}$ is —NHR$^{33a}$, and R$^{33a}$ is optionally substituted acyl, e.g., $R^{33}$ is —NHC(=O)R$^{33a}$, —NHC(=O)OR$^{33a}$, or —NHC(=O)NHR$^{33a}$. In certain embodiments, at least one $R^{33}$ is —N(R$^{33a}$)$_2$, and at least one R$^{33a}$ is a nitrogen protecting group. In certain embodiments, at least one $R^{33}$ is —N(R$^{33a}$)$_2$, and R$^{33a}$ are joined to form an optionally substituted heterocyclic or optionally substituted heteroaryl ring.

In certain embodiments, an $R^{33}$ ortho to the bond between Ring $A^3$ and Ring $B^3$ is —NO$_2$. In certain embodiments, an $R^{33}$ ortho to the bond between Ring $A^3$ and Ring $B^3$ is —CN. In certain embodiments, an $R^{33}$ ortho to the bond between Ring $A^3$ and Ring $B^3$ is halogen. In some embodiments, an $R^{33}$ ortho to the bond between Ring $A^3$ and Ring $B^3$ is —F. In some embodiments, an $R^{33}$ ortho to the bond between Ring $A^3$ and Ring $B^3$ is —Cl, —Br, or —I. In certain embodiments, an $R^{33}$ ortho to the bond between Ring $A^3$ and Ring $B^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^{33}$ ortho to the bond between Ring $A^3$ and Ring $B^3$ is methyl. In certain embodiments, an $R^{33}$ ortho to the bond between Ring $A^3$ and Ring $B^3$ is ethyl, propyl, or butyl. In certain embodiments, an $R^{33}$ ortho to the bond between Ring $A^3$ and Ring $B^3$ is optionally substituted alkenyl, e.g., optionally substituted $C_{2-6}$ alkenyl. In certain embodiments, an $R^{33}$ ortho to the bond between Ring $A^3$ and Ring $B^3$ is vinyl, allyl, or prenyl. In certain embodiments, an $R^{33}$ ortho to the bond between Ring $A^3$ and Ring $B^3$ is optionally substituted alkynyl, e.g., $C_{2-6}$ alkynyl.

In certain embodiments, an $R^{33}$ ortho to the bond between Ring $A^3$ and Ring $B^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^{33}$ ortho to the bond between Ring $A^3$ and Ring $B^3$ is optionally substituted heterocyclyl, e.g., optionally substituted 3-6 membered heterocyclyl, optionally substituted 3-$^3$ membered heterocyclyl, optionally substituted $^3$-5 membered heterocyclyl, or optionally substituted 5-6 membered heterocyclyl.

In certain embodiments, an $R^{33}$ ortho to the bond between Ring $A^3$ and Ring $B^3$ is optionally substituted aryl, e.g., optionally substituted phenyl. In certain embodiments, an $R^{33}$ ortho to the bond between Ring $A^3$ and Ring $B^3$ is optionally substituted heteroaryl, e.g., optionally substituted 5-6 membered heteroaryl or optionally substituted 9-10 membered bicyclic heteroaryl. In certain embodiments, an $R^{33}$ ortho to the bond between Ring $A^3$ and Ring $B^3$ is optionally substituted aralkyl, e.g., optionally substituted benzyl. In certain embodiments, an $R^{33}$ ortho to the bond between Ring $A^3$ and Ring $B^3$ is optionally substituted heteroaralkyl, e.g., methyl substituted with a 5-6 membered heteroaryl ring.

In certain embodiments, an $R^{33}$ ortho to the bond between Ring $A^3$ and Ring $B^3$ is optionally substituted acyl, e.g., —CHO, —CO$_2$H, or —C(=O)NH$_2$. In certain embodiments, an $R^{33}$ ortho to the bond between Ring $A^3$ and Ring $B^3$ is —C(=O)R$^{33a}$, —C(=O)OR$^{33a}$, —C(=O)NH(R$^{33a}$), or —C(=O)N(R$^{33a}$)$_2$. In certain embodiments, an $R^{33}$ ortho to the bond between Ring $A^3$ and Ring $B^3$ is —C(=O)R$^{33a}$, and R$^{33a}$ is optionally substituted alkyl, e.g., $R^{33}$ is —C(=O)Me. In certain embodiments, an $R^{33}$ ortho to the bond between Ring $A^3$ and Ring $B^3$ is —C(=O)R$^{33a}$, and R$^{33a}$ is optionally substituted alkenyl. In certain embodiments, an $R^{33}$ ortho to the bond between Ring $A^3$ and Ring $B^3$ is —C(=O)R$^{33a}$, and R$^{33a}$ is optionally substituted carbocyclyl, heterocyclyl, aryl, or heteroaryl. In certain embodiments, an $R^{33}$ ortho to the bond between Ring $A^3$ and Ring $B^3$ is —C(=O)OR$^{33a}$, and R$^{33a}$ is optionally substituted alkyl. In certain embodiments, an $R^{33}$ ortho to the bond between Ring $A^3$ and Ring $B^3$ is —C(=O)OR$^{33a}$, and R$^{33a}$ is optionally substituted alkenyl. In certain embodiments, an $R^{33}$ ortho to the bond between Ring $A^3$ and Ring $B^3$ is —C(=O)OR$^{33a}$, and R$^{33a}$ is optionally substituted carbocyclyl, heterocyclyl, aryl, or heteroaryl. In certain embodiments, an $R^{33}$ ortho to the bond between Ring $A^3$ and Ring $B^3$ is —C(=O)N(R$^{33a}$)$_2$, and at least one R$^{33a}$ is optionally substituted alkyl. In certain embodiments, an $R^{33}$ ortho to the bond between Ring $A^3$ and Ring $B^3$ is —C(=O)NHR$^{33a}$, and R$^{33a}$ is optionally substituted alkyl. In certain embodiments, an $R^{33}$ ortho to the bond between Ring $A^3$ and Ring $B^3$ is —C(=O)NHR$^{33a}$, and R$^{33a}$ is optionally substituted alkenyl. In certain embodiments, an $R^{33}$ ortho to the bond between Ring $A^3$ and Ring $B^3$ is —C(=O)NHR$^{33a}$, and R$^{33a}$ is optionally substituted carbocyclyl, heterocyclyl, aryl, or heteroaryl.

In certain embodiments, an $R^{33}$ ortho to the bond between Ring $A^3$ and Ring $B^3$ is —OR$^{33a}$, e.g., —OH. In certain embodiments, an $R^{33}$ ortho to the bond between Ring $A^3$ and Ring $B^3$ is —OR$^{33a}$, and R$^{33a}$ is optionally substituted alkyl. In certain embodiments, an $R^{33}$ ortho to the bond between Ring $A^3$ and Ring $B^3$ is —OR$^{33a}$, and R$^{33a}$ is optionally alkenyl. In certain embodiments, an $R^{33}$ ortho to the bond between Ring $A^3$ and Ring $B^3$ is —OR$^{33a}$, and R$^{33a}$ is optionally substituted carbocyclyl, optionally substituted heterocyclyl, optionally substituted aryl or optionally substituted heteroaryl. In certain embodiments, an $R^{33}$ ortho to the bond between Ring $A^3$ and Ring $B^3$ is —OR$^{33a}$, and R$^{33a}$ is optionally substituted acyl, e.g., $R^{33}$ is —OC(=O)R$^{33a}$, —OC(=O)OR$^{33a}$, or —OC(=O)N(R$^{33a}$)$_2$. In certain embodiments, an $R^{33}$ ortho to the bond between Ring $A^3$ and Ring $B^3$ is —OR$^{33a}$, and R$^{33a}$ is an oxygen protecting group.

In certain embodiments, an $R^{33}$ ortho to the bond between Ring $A^3$ and Ring $B^3$ is —N(R$^3$)$_2$, e.g., —NH$_2$, —NHR$^{33a}$. In certain embodiments, an $R^{33}$ ortho to the bond between Ring $A^3$ and Ring $B^3$ is —NH(R$^{33a}$), and R$^{33a}$ is optionally substituted alkyl. In certain embodiments, an $R^{33}$ ortho to the bond between Ring $A^3$ and Ring $B^3$ is —N(R$^{33a}$)$_2$, and at least one R$^{33a}$ is optionally substituted alkyl. In certain embodiments, an $R^{33}$ ortho to the bond between Ring $A^3$ and Ring $B^3$ is —NHR$^{33a}$, and R$^{33a}$ is optionally substituted carbocyclyl, optionally substituted heterocyclyl, optionally substituted aryl, or optionally substituted heteroaryl. In certain embodiments, an $R^{33}$ ortho to the bond between Ring $A^3$ and Ring $B^3$ is —NHR$^{33a}$, and R$^{33a}$ is optionally substituted acyl, e.g., $R^{33}$ is —NHC(=O)R$^{33a}$, —NHC(=O)OR$^{33a}$, or —NHC(=O)NHR$^{33a}$. In certain embodiments, an $R^{33}$ ortho to the bond between Ring $A^3$ and Ring $B^3$ is —N(R$^{33a}$)$_2$, and at least one R$^{33a}$ is a nitrogen protecting group. In certain embodiments, an $R^{33}$ ortho to the bond between Ring $A^3$ and Ring $B^3$ is —N(R$^{33a}$)$_2$, and R$^{33a}$ are joined to form an optionally substituted heterocyclic or optionally substituted heteroaryl ring.

Ring $B^3$ and $R^{39}$

As generally defined herein, is Ring $B^3$ is a carbocyclic, heterocyclic, aryl or heteroaryl ring. In certain embodiments, Ring $A^3$ and Ring $B^3$ are both phenyl rings, such that Ring $A^3$ and $B^3$ together form a biphenyl group. Ring $B^3$ may be substituted with 0, 1, 2, 3, 4, or 5 independent $R^{39}$, valency permitting. In certain embodiments, k3 is 0 or 1. In certain embodiments, k3 is 0. In certain embodiments, k3 is 1. In certain embodiments, k3 is 2. In certain embodiments, k3 is 3. In certain embodiments, k3 is 4. In certain embodiments, k3 is 5.

In certain embodiments, Ring $B^3$ is aryl, e.g., phenyl. In certain embodiments, Ring $B^3$ is heteroaryl, e.g., 5- to 6-membered heteroaryl. In some embodiments, Ring $B^3$ is pyridyl, pyrimidyl, or imidazyl. In certain embodiments, Ring $B^3$ is carbocyclyl, e.g., 3- to 6-membered carbocyclyl. In some embodiments, Ring $B^3$ is cyclohexyl, cyclopentyl, cyclobutyl, or cyclopropyl. In certain embodiments, Ring $B^3$ is heterocyclyl, e.g., 5- to 6-membered heterocyclyl. In some embodiments, Ring $B^3$ is piperidinyl, piperizinyl, or morpholinyl.

In certain embodiments, Ring $B^3$ is of formula:

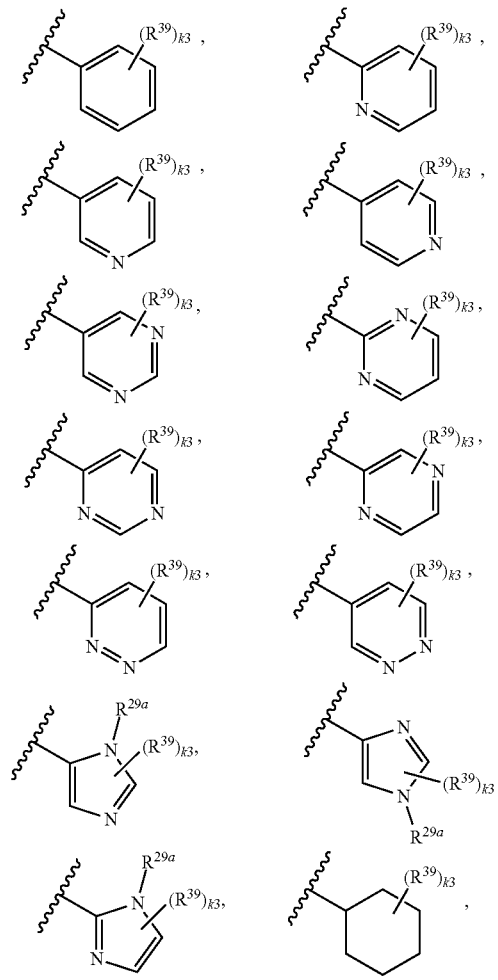

-continued
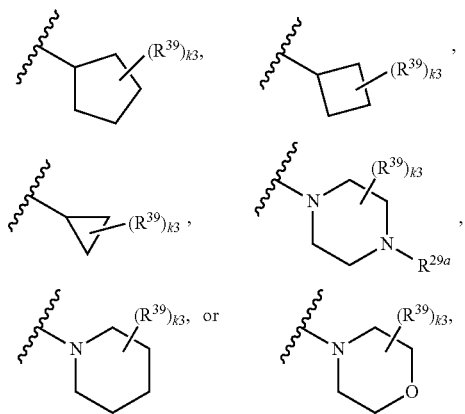
wherein k3 is 0, 1, 2, 3, 4, or 5, valency permitting.
In certain embodiments, Ring B³ is of formula:
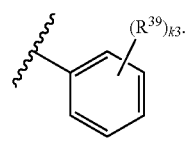
In certain embodiments, Ring B³ is of formula:
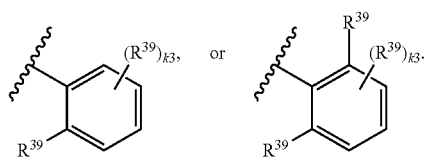
In certain embodiments, Ring B³ is of formula:
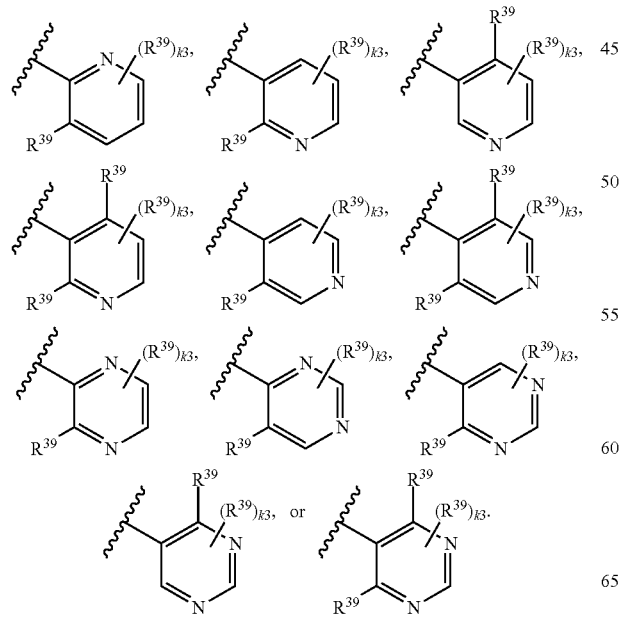
In certain embodiments, Ring B³ is of formula:
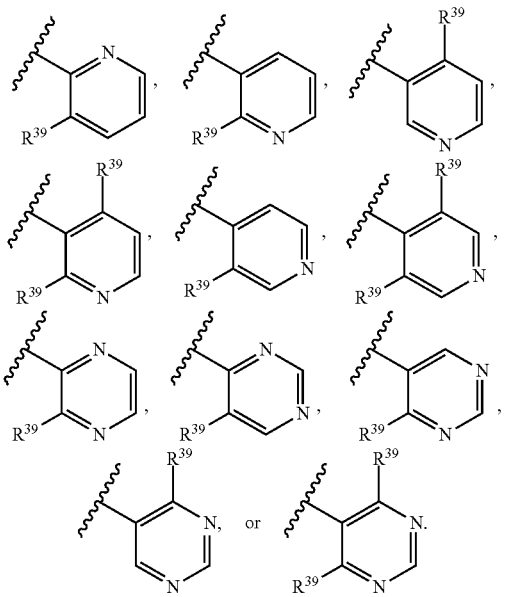
In certain embodiments, Ring B³ is of formula:
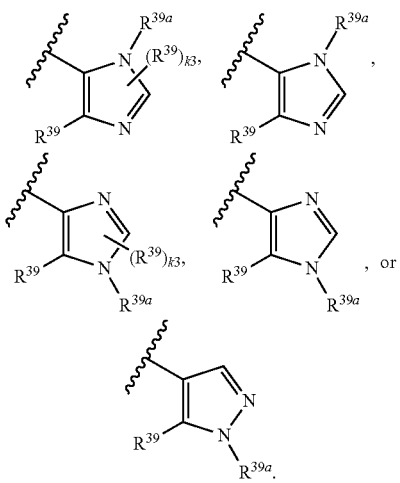
In certain embodiments, Ring B³ is of formula:
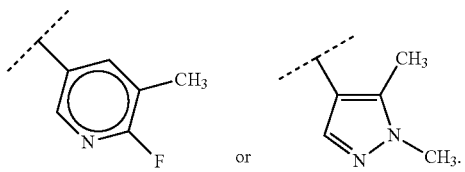
In certain embodiments, Ring B³ is of formula:
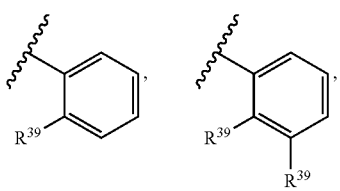

-continued
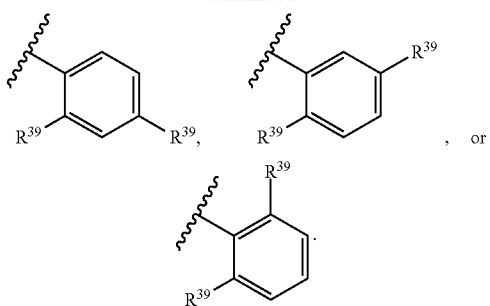
In certain embodiments, Ring $B^3$ is of formula:
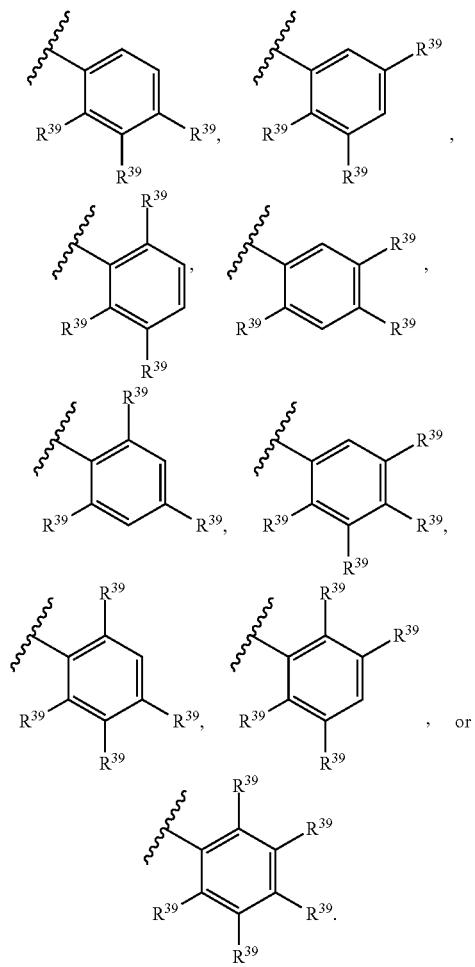
In certain embodiments, Ring $B^3$ is of formula:
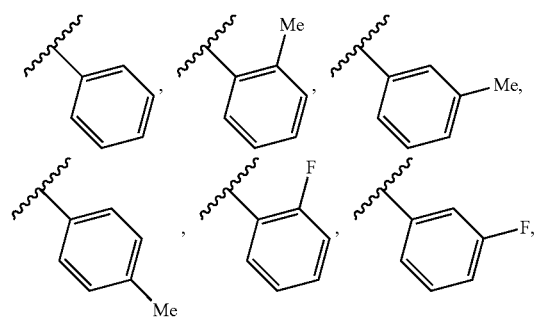
-continued
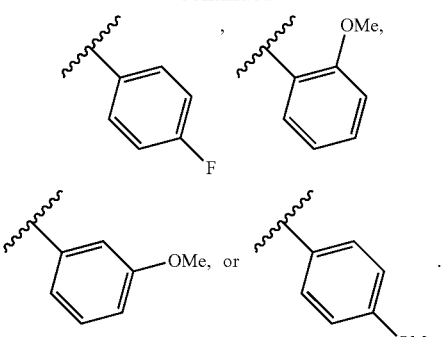
In certain embodiments, Ring $B^3$ is of formula:
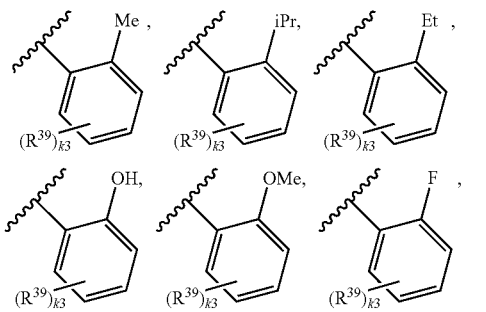
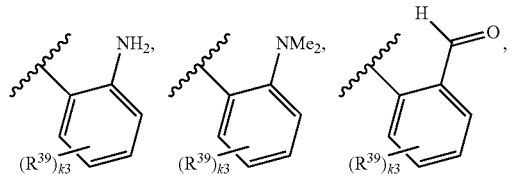
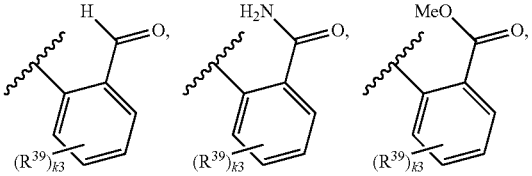
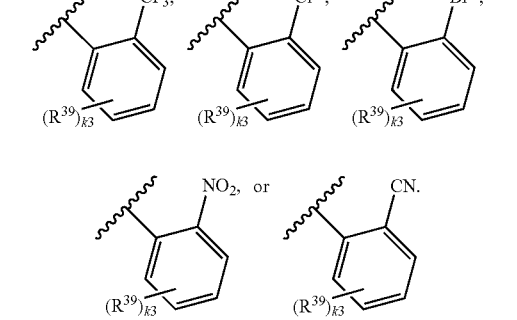
In certain embodiments, Ring $B^3$ is of formula:
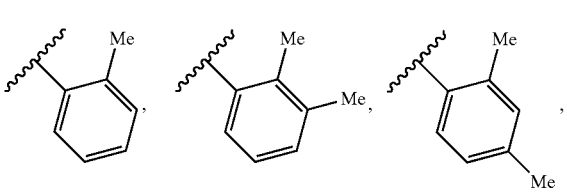

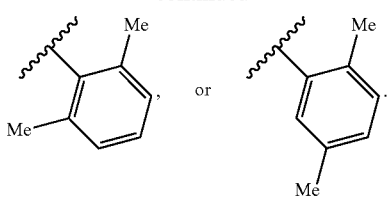

In certain embodiments, Ring B³ is of formula:

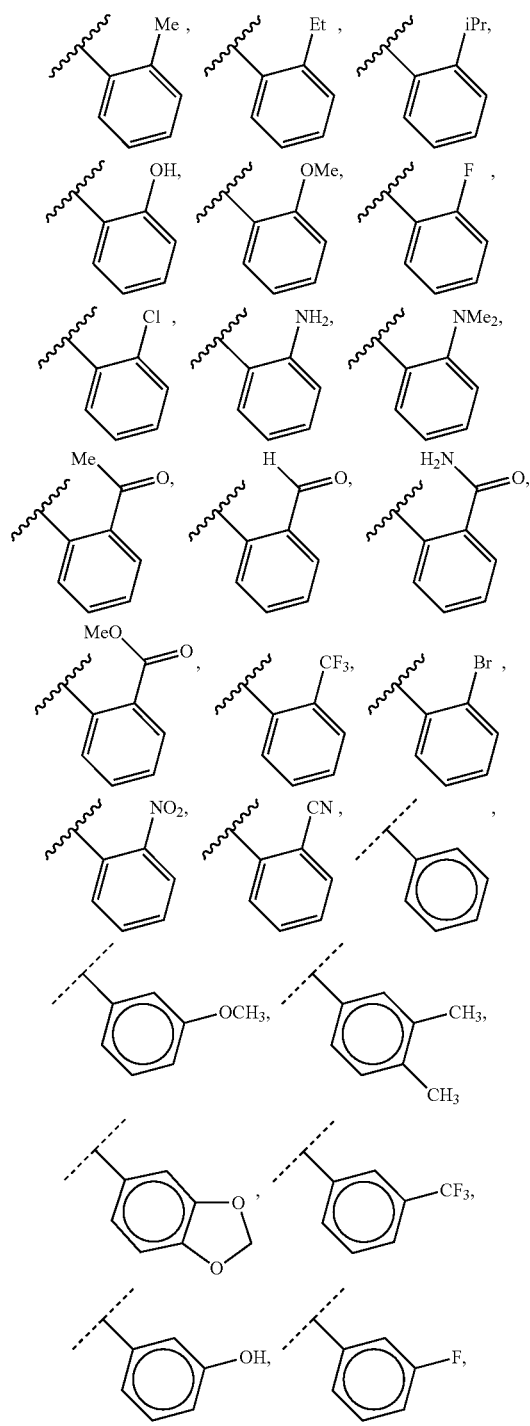

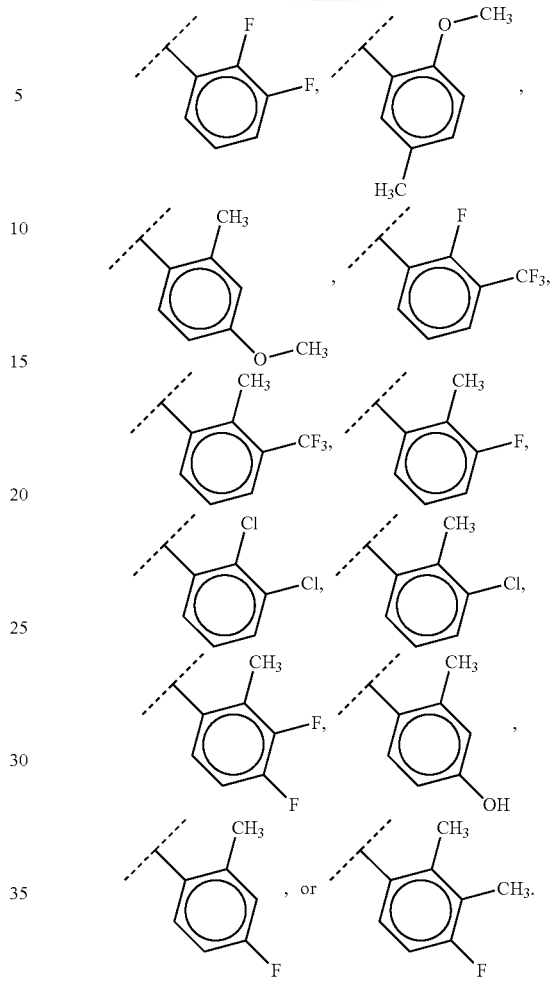

As generally described herein, each R³⁹ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO₂, —CN, —OR³⁹ᵃ, —N(R³⁹ᵃ)₂, —S(=O)₂R³⁹ᵃ, —S(=O)₂OR³⁹ᵃ, or —S(=O)₂N(R³⁹ᵃ)₂, or two R³⁹ are joined to form an optionally substituted carbocyclic, heterocyclic, aryl, or heteroaryl ring, wherein each R³⁹ᵃ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R³⁹ᵃ are joined to form an optionally substituted heteroaryl or optionally substituted heterocyclic ring.

In certain embodiments, at least one R³⁹ is —NO₂. In certain embodiments, at least one R³⁹ is —CN. In certain embodiments, at least one R³⁹ is halogen. In some embodiments, at least one R³⁹ is —F. In some embodiments, at least one R³⁹ is —Cl, —Br, or —I. In certain embodiments, at least one R³⁹ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{39}$ is methyl. In certain embodiments, at least one $R^{39}$ is ethyl, propyl, or butyl. In certain embodiments, at least one $R^{39}$ is optionally substituted alkenyl, e.g., optionally substituted $C_{2-6}$ alkenyl. In certain embodiments, at least one $R^{39}$ is vinyl, allyl, or prenyl. In certain embodiments, at least one $R^{39}$ is optionally substituted alkynyl, e.g., $C_{2-6}$ alkynyl.

In certain embodiments, at least one $R^{39}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{39}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{39}$ is optionally substituted aryl, e.g., optionally substituted phenyl. In certain embodiments, at least one $R^{39}$ is optionally substituted heteroaryl, e.g., optionally substituted 5-6 membered heteroaryl or optionally substituted 9-10 membered bicyclic heteroaryl. In certain embodiments, at least one $R^{39}$ is optionally substituted aralkyl, e.g., optionally substituted benzyl. In certain embodiments, at least one $R^{39}$ is optionally substituted heteroaralkyl, e.g., methyl substituted with a 5-6 membered heteroaryl ring.

In certain embodiments, at least one $R^{39}$ is optionally substituted acyl, e.g., —CHO, —CO$_2$H, or —C(=O)NH$_2$. In certain embodiments, at least one $R^{39}$ is —C(=O)R$^{39a}$, —C(=O)OR$^{39a}$, —C(=O)NH(R$^{39a}$), or —C(=O)N(R$^{39a}$)$_2$. In certain embodiments, at least one $R^{39}$ is —C(=O)R$^{39a}$, and $R^{39a}$ is optionally substituted alkyl, e.g., $R^{39}$ is —C(=O)Me. In certain embodiments, at least one $R^{39}$ is —C(=O)R$^{39a}$, and $R^{39a}$ is optionally substituted alkenyl. In certain embodiments, at least one $R^{39}$ is —C(=O)R$^{39a}$, and $R^{39a}$ is optionally substituted carbocyclyl, heterocyclyl, aryl, or heteroaryl. In certain embodiments, at least one $R^{39}$ is —C(=O)OR$^{39a}$, and $R^{39a}$ is optionally substituted alkyl. In certain embodiments, at least one $R^{39}$ is —C(=O)OR$^{39a}$, and $R^{39a}$ is optionally substituted alkenyl. In certain embodiments, at least one $R^{39}$ is —C(=O)OR$^{39a}$, and $R^{39a}$ is optionally substituted carbocyclyl, heterocyclyl, aryl, or heteroaryl. In certain embodiments, at least one $R^{39}$ is —C(=O)N(R$^{39a}$)$_2$, and at least one $R^{39a}$ is optionally substituted alkyl. In certain embodiments, at least one $R^{39}$ is —C(=O)NHR$^{39a}$, and $R^{39a}$ is optionally substituted alkyl. In certain embodiments, at least one $R^{39}$ is —C(=O)NHR$^{39a}$, and $R^{39a}$ is optionally substituted alkenyl. In certain embodiments, at least one $R^{39}$ is —C(=O)NHR$^{39a}$, and $R^{39a}$ is optionally substituted carbocyclyl, heterocyclyl, aryl, or heteroaryl.

In certain embodiments, at least one $R^{39}$ is —OR$^{39a}$, e.g., —OH. In certain embodiments, at least one $R^{39}$ is —OR$^{39a}$, and $R^{39a}$ is optionally substituted alkyl. In certain embodiments, at least one $R^{39}$ is —OR$^{39a}$, and $R^{39a}$ is optionally substituted alkenyl. In certain embodiments, at least one $R^{39}$ is —OR$^{39a}$, and $R^{39a}$ is optionally substituted carbocyclyl, optionally substituted heterocyclyl, optionally substituted aryl optionally substituted heteroaryl. In certain embodiments, at least one $R^{39}$ is —OR$^{39a}$, and $R^{39a}$ is optionally substituted acyl, e.g., $R^{39}$ is —OC(=O)R$^{39a}$, —OC(=O) OR$^{39a}$, or —OC(=O)N(R$^{39a}$)$_2$. In certain embodiments, at least one $R^{39}$ is —OR$^{39a}$, and $R^{39a}$ is an oxygen protecting group.

In certain embodiments, at least one $R^{39}$ is —N(R$^{39a}$)$_2$, e.g., —NH$_2$, —NHR$^{39a}$. In certain embodiments, at least one $R^{39}$ is —NH(R$^{39a}$), and $R^{39a}$ is optionally substituted alkyl. In certain embodiments, at least one $R^{39}$ is —N(R$^{39a}$)$_2$, and at least one $R^{39a}$ is optionally substituted alkyl. In certain embodiments, at least one $R^{39}$ is —NHR$^{39a}$, and $R^{39a}$ is optionally substituted carbocyclyl, optionally substituted heterocyclyl, optionally substituted aryl, or optionally substituted heteroaryl. In certain embodiments, at least one $R^{39}$ is —NHR$^{39a}$, and $R^{39a}$ is optionally substituted acyl, e.g., $R^{39}$ is —NHC(=O)R$^{39a}$, —NHC(=O)OR$^{39a}$, or —NHC(=O)NHR$^{39a}$. In certain embodiments, at least one $R^{39}$ is —N(R$^{39a}$)$_2$, and at least one $R^{39a}$ is a nitrogen protecting group. In certain embodiments, at least one $R^{39}$ is —N(R$^{39a}$)$_2$, and $R^{39a}$ are joined to form an optionally substituted heterocyclic or optionally substituted heteroaryl ring.

In certain embodiments, at least one $R^{39}$ is —S(=O)$_2$R$^{39a}$. In certain embodiments, at least one $R^{39}$ is —S(=O)$_2$R$^{39a}$, and $R^{39a}$ is optionally substituted alkyl, e.g., $R^{39}$ is —S(=O)$_2$Me. In certain embodiments, at least one $R^{39}$ is —S(=O)$_2$R$^{39a}$, and $R^{39a}$ is optionally substituted alkenyl. In certain embodiments, at least one $R^{39}$ is —S(=O)$_2$R$^{39a}$, and $R^{39a}$ is optionally substituted carbocyclyl, heterocyclyl, aryl, or heteroaryl. In certain embodiments, at least one $R^{39}$ is —S(=O)$_2$OR$^{39a}$. In certain embodiments, at least one $R^{39}$ is —S(=O)$_2$OR$^{39a}$, and $R^{39a}$ is optionally substituted alkyl. In certain embodiments, at least one $R^{39}$ is —S(=O)$_2$OR$^{39a}$, and $R^{39a}$ is optionally substituted alkenyl. In certain embodiments, at least one $R^{39}$ is —S(=O)$_2$OR$^{39a}$, and $R^{39a}$ is optionally substituted carbocyclyl, heterocyclyl, aryl, or heteroaryl. In certain embodiments, at least one $R^{39}$ is —S(=O)$_2$N(R$^{39a}$)$_2$ or —S(=O)$_2$NHR$^{39a}$ In certain embodiments, at least one $R^{39}$ is —S(=O)$_2$N(R$^{39a}$)$_2$, and at least one $R^{39a}$ is optionally substituted alkyl. In certain embodiments, at least one $R^{39}$ is —S(=O)$_2$NHR$^{39a}$, and $R^{39a}$ is optionally substituted alkyl. In certain embodiments, at least one $R^{39}$ is —S(=O)$_2$NHR$^{39a}$, and $R^{39a}$ is optionally substituted alkenyl. In certain embodiments, at least one $R^{39}$ is —S(=O)$_2$NHR$^{39a}$, and $R^{39a}$ is optionally substituted carbocyclyl, heterocyclyl, aryl, or heteroaryl.

In certain embodiments, an $R^{39}$ ortho to the bond connecting Ring $A^3$ and Ring $B^3$ is —NO$_2$. In certain embodiments, an $R^{39}$ ortho to the bond connecting Ring $A^3$ and Ring $B^3$ is —CN. In certain embodiments, an $R^{39}$ ortho to the bond connecting Ring $A^3$ and Ring $B^3$ is halogen. In some embodiments, an $R^{39}$ ortho to the bond connecting Ring $A^3$ and Ring $B^3$ is —F. In some embodiments, an $R^{39}$ ortho to the bond connecting Ring $A^3$ and Ring $B^3$ is —Cl, —Br, or —I. In certain embodiments, an $R^{39}$ ortho to the bond connecting Ring $A^3$ and Ring $B^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^{39}$ ortho to the bond connecting Ring $A^3$ and Ring $B^3$ is methyl. In certain embodiments, an $R^{39}$ ortho to the bond connecting Ring $A^3$ and Ring $B^3$ is ethyl, propyl, or butyl. In certain embodiments, an $R^{39}$ ortho to the bond connecting Ring $A^3$ and Ring $B^3$ is optionally substituted alkenyl, e.g., optionally substituted $C_{2-6}$ alkenyl. In certain embodiments, an $R^{39}$ ortho to the bond connecting Ring $A^3$ and Ring $B^3$ is vinyl, allyl, or prenyl. In certain embodiments, an $R^{39}$ ortho to the bond connecting Ring $A^3$ and Ring $B^3$ is optionally substituted alkynyl, e.g., $C_{2-6}$ alkynyl.

In certain embodiments, an $R^{39}$ ortho to the bond connecting Ring $A^3$ and Ring $B^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^{39}$ ortho to the bond connecting Ring $A^3$ and Ring $B^3$ is optionally substituted heterocyclyl, e.g., optionally substituted 3-6 membered heterocyclyl, optionally substituted 3-³ membered heterocyclyl, optionally substituted ³-5 membered heterocyclyl, or optionally substituted 5-6 membered heterocyclyl.

In certain embodiments, an $R^{39}$ ortho to the bond connecting Ring $A^3$ and Ring $B^3$ is optionally substituted aryl, e.g., optionally substituted phenyl. In certain embodiments, an $R^{39}$ ortho to the bond connecting Ring $A^3$ and Ring $B^3$ is optionally substituted heteroaryl, e.g., optionally substituted 5-6 membered heteroaryl or optionally substituted 9-10 membered bicyclic heteroaryl. In certain embodiments, an $R^{39}$ ortho to the bond connecting Ring $A^3$ and Ring $B^3$ is optionally substituted aralkyl, e.g., optionally substituted benzyl. In certain embodiments, an $R^{39}$ ortho to the bond connecting Ring $A^3$ and Ring $B^3$ is optionally substituted heteroaralkyl, e.g., methyl substituted with a 5-6 membered heteroaryl ring.

In certain embodiments, an $R^{39}$ ortho to the bond connecting Ring $A^3$ and Ring $B^3$ is optionally substituted acyl, e.g., —CHO, —CO$_2$H, or —C(=O)NH$_2$. In certain embodiments, an $R^{39}$ ortho to the bond connecting Ring $A^3$ and Ring $B^3$ is —C(=O)R$^{39a}$, —C(=O)OR$^{39a}$, —C(=O)NH(R$^{39a}$), or —C(=O)N(R$^{39a}$)$_2$. In certain embodiments, an $R^{39}$ ortho to the bond connecting Ring $A^3$ and Ring $B^3$ is —C(=O)R$^{39a}$, and R$^{39a}$ is optionally substituted alkyl, e.g., $R^{39}$ is —C(=O)Me. In certain embodiments, an $R^{39}$ ortho to the bond connecting Ring $A^3$ and Ring $B^3$ is —C(=O)R$^{39a}$, and R$^{39a}$ is optionally substituted alkenyl. In certain embodiments, an $R^{39}$ ortho to the bond connecting Ring $A^3$ and Ring $B^3$ is —C(=O)R$^{39a}$, and R$^{39a}$ is optionally substituted carbocyclyl, heterocyclyl, aryl, or heteroaryl. In certain embodiments, an $R^{39}$ ortho to the bond connecting Ring $A^3$ and Ring $B^3$ is —C(=O)OR$^{39a}$, and R$^{39a}$ is optionally substituted alkyl. In certain embodiments, an $R^{39}$ ortho to the bond connecting Ring $A^3$ and Ring $B^3$ is —C(=O)OR$^{39a}$, and R$^{39a}$ is optionally substituted alkenyl. In certain embodiments, an $R^{39}$ ortho to the bond connecting Ring $A^3$ and Ring $B^3$ is —C(=O)OR$^{39a}$, and R$^{39a}$ is optionally substituted carbocyclyl, heterocyclyl, aryl, or heteroaryl. In certain embodiments, an $R^{39}$ ortho to the bond connecting Ring $A^3$ and Ring $B^3$ is —C(=O)N(R$^{39a}$)$_2$, and at least one R$^{39a}$ is optionally substituted alkyl. In certain embodiments, an $R^{39}$ ortho to the bond connecting Ring $A^3$ and Ring $B^3$ is —C(=O)NHR$^{39a}$, and R$^{39a}$ is optionally substituted alkyl. In certain embodiments, an $R^{39}$ ortho to the bond connecting Ring $A^3$ and Ring $B^3$ is —C(=O)NHR$^{39a}$, and R$^{39a}$ is optionally substituted alkenyl. In certain embodiments, an $R^{39}$ ortho to the bond connecting Ring $A^3$ and Ring $B^3$ is —C(=O)NHR$^{39a}$, and R$^{39a}$ is optionally substituted carbocyclyl, heterocyclyl, aryl, or heteroaryl.

In certain embodiments, an $R^{39}$ ortho to the bond connecting Ring $A^3$ and Ring $B^3$ is —OR$^{39a}$, e.g., —OH. In certain embodiments, an $R^{39}$ ortho to the bond connecting Ring $A^3$ and Ring $B^3$ is —OR$^{39a}$, and R$^{39a}$ is optionally substituted alkyl. In certain embodiments, an $R^{39}$ ortho to the bond connecting Ring $A^3$ and Ring $B^3$ is —OR$^{39a}$, and R$^{39a}$ is optionally alkenyl. In certain embodiments, an $R^{39}$ ortho to the bond connecting Ring $A^3$ and Ring $B^3$ is —OR$^{39a}$, and R$^{39a}$ is optionally substituted carbocyclyl, optionally substituted heterocyclyl, optionally substituted aryl optionally substituted heteroaryl. In certain embodiments, an $R^{39}$ ortho to the bond connecting Ring $A^3$ and Ring $B^3$ is —OR$^{39a}$, and R$^{39a}$ is optionally substituted acyl, e.g., $R^{39}$ is —OC(=O)R$^{39a}$, —OC(=O)OR$^{39a}$, or —OC(=O)N(R$^{39a}$)$_2$. In certain embodiments, an $R^{39}$ ortho to the bond connecting Ring $A^3$ and Ring $B^3$ is —OR$^{39a}$, and R$^{39a}$ is an oxygen protecting group.

In certain embodiments, an $R^{39}$ ortho to the bond connecting Ring $A^3$ and Ring $B^3$ is —N(R$^{39a}$)$_2$, e.g., —NH$_2$, —NHR$^{39a}$. In certain embodiments, an $R^{39}$ ortho to the bond connecting Ring $A^3$ and Ring $B^3$ is —NH(R$^{39a}$), and R$^{39a}$ is optionally substituted alkyl. In certain embodiments, an $R^{39}$ ortho to the bond connecting Ring $A^3$ and Ring $B^3$ is —N(R$^{39a}$)$_2$, and at least one R$^{39a}$ is optionally substituted alkyl. In certain embodiments, an $R^{39}$ ortho to the bond connecting Ring $A^3$ and Ring $B^3$ is —NHR$^{39a}$, and R$^{39a}$ is optionally substituted carbocyclyl, optionally substituted heterocyclyl, optionally substituted aryl, or optionally substituted heteroaryl. In certain embodiments, an $R^{39}$ ortho to the bond connecting Ring $A^3$ and Ring $B^3$ is —NHR$^{39a}$, and R$^{39a}$ is optionally substituted acyl, e.g., $R^{39}$ is —NHC(=O)R$^{39a}$, —NHC(=O)OR$^{39a}$, or —NHC(=O)NHR$^{39a}$. In certain embodiments, an $R^{39}$ ortho to the bond connecting Ring $A^3$ and Ring $B^3$ is —N(R$^{39a}$)$_2$, and at least one R$^{39a}$ is a nitrogen protecting group. In certain embodiments, an $R^{39}$ ortho to the bond connecting Ring $A^3$ and Ring $B^3$ is —N(R$^{39a}$)$_2$, and R$^{39a}$ are joined to form an optionally substituted heterocyclic or optionally substituted heteroaryl ring.

In certain embodiments, an $R^{39}$ ortho to the bond connecting Ring $A^3$ and Ring $B^3$ is —S(=O)$_2$R$^{39a}$. In certain embodiments, an $R^{39}$ ortho to the bond connecting Ring $A^3$ and Ring $B^3$ is —S(=O)$_2$R$^{39a}$, and R$^{39a}$ is optionally substituted alkyl, e.g., $R^{39}$ is —S(=O)$_2$Me. In certain embodiments, an $R^{39}$ ortho to the bond connecting Ring $A^3$ and Ring $B^3$ is —S(=O)$_2$R$^{39a}$, and R$^{39a}$ is optionally substituted alkenyl. In certain embodiments, an $R^{39}$ ortho to the bond connecting Ring $A^3$ and Ring $B^3$ is —S(=O)$_2$R$^{39a}$, and R$^{39a}$ is optionally substituted carbocyclyl, heterocyclyl, aryl, or heteroaryl. In certain embodiments, an $R^{39}$ ortho to the bond connecting Ring $A^3$ and Ring $B^3$ is —S(=O)$_2$OR$^{39a}$. In certain embodiments, an $R^{39}$ ortho to the bond connecting Ring $A^3$ and Ring $B^3$ is —S(=O)$_2$OR$^{39a}$, and R$^{39a}$ is optionally substituted alkyl. In certain embodiments, an $R^{39}$ ortho to the bond connecting Ring $A^3$ and Ring $B^3$ is —S(=O)$_2$OR$^{39a}$, and R$^{39a}$ is optionally substituted alkenyl. In certain embodiments, an $R^{39}$ ortho to the bond connecting Ring $A^3$ and Ring $B^3$ is —S(=O)$_2$OR$^{39a}$, and R$^{39a}$ is optionally substituted carbocyclyl, heterocyclyl, aryl, or heteroaryl. In certain embodiments, an $R^{39}$ ortho to the bond connecting Ring $A^3$ and Ring $B^3$ is —S(=O)$_2$N(R$^{39a}$)$_2$ or —S(=O)$_2$NHR$^{39a}$. In certain embodiments, an $R^{39}$ ortho to the bond connecting Ring $A^3$ and Ring $B^3$ is —S(=O)$_2$N(R$^{39a}$)$_2$, and at least one R$^{39a}$ is optionally substituted alkyl. In certain embodiments, an $R^{39}$ ortho to the bond connecting Ring $A^3$ and Ring $B^3$ is —S(=O)$_2$NHR$^{39a}$, and R$^{39a}$ is optionally substituted alkyl. In certain embodiments, an $R^{39}$ ortho to the bond connecting Ring $A^3$ and Ring $B^3$ is —S(=O)$_2$NHR$^{39a}$, and R$^{39a}$ is optionally substituted alkenyl. In certain embodiments, an $R^{39}$ ortho to the bond connecting Ring $A^3$ and Ring $B^3$ is —S(=O)$_2$NHR$^{39a}$, and R$^{39a}$ is optionally substituted carbocyclyl, heterocyclyl, aryl, or heteroaryl.

$R^{35}$

As generally defined herein, $R^{35}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$R$^{35a}$, —S(=O)$_2$OR$^{35a}$, —S(=O)$_2$N(R$^{35a}$)$_2$, or a nitrogen protecting group, wherein each $R^{35a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{35a}$ are joined to form an optionally substituted heteroaryl or optionally substituted heterocyclic ring.

In certain embodiments, $R^{35}$ is a non-hydrogen group. In certain embodiments, $R^{35}$ is not alkyl. In certain embodiments, $R^{35}$ is a non-hydrogen group and is not alkyl, —C(=O)R$^{35a}$, or —S(=O)$_2$R$^{35a}$. In certain embodiments, $R^{35}$ is a non-hydrogen group and is not methyl, —C(=O)R$^{35a}$, or —S(=O)$_2$R$^{35a}$. In certain embodiments, $R^{35}$ is not nosyl. In certain embodiments, $R^{35}$ is not —CH$_3$, —C(=O)Me, or —S(=O)$_2$Me. In certain embodiments, $R^{35}$ is a nitrogen protecting group.

In certain embodiments, $R^{35}$ is hydrogen. In certain embodiments, $R^{35}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{35}$ is optionally substituted $C_{2-6}$ alkyl. In certain embodiments, $R^{35}$ is methyl. In certain embodiments, $R^{35}$ is ethyl, propyl, or butyl. In certain embodiments, $R^{35}$ is optionally substituted alkenyl, e.g., optionally substituted $C_{2-6}$ alkenyl. In certain embodiments, $R^{35}$ is vinyl, allyl, or prenyl. In certain embodiments, $R^{35}$ is optionally substituted alkynyl, e.g., $C_{2-6}$ alkynyl.

In certain embodiments, $R^{35}$ is of formula:

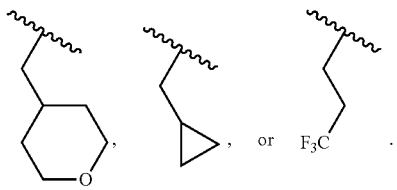 [SMILES: *CC1CCOCC1 ; *CC1CC1 ; *CCC(F)(F)F]

In certain embodiments, $R^{35}$ is optionally substituted aralkyl, e.g., optionally substituted benzyl. In certain embodiments, $R^{35}$ is optionally substituted heteroaralkyl, e.g., methyl substituted with a 5- to 6-membered heteroaryl ring.

In certain embodiments, $R^{35}$ is of formula:

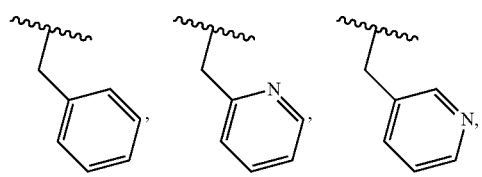

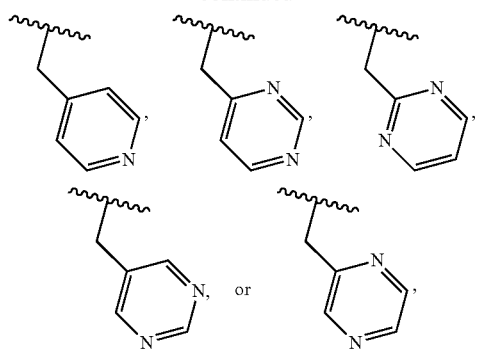

In certain embodiments, $R^{35}$ is optionally substituted acyl, e.g., —CHO, —CO$_2$H, or —C(=O)NH$_2$. In certain embodiments, $R^{35}$ is —C(=O)R$^{35a}$, —C(=O)OR$^{35a}$, —C(=O)NH(R$^{35a}$), or —C(=O)N(R$^{35a}$)$_2$. In certain embodiments, $R^{35}$ is —C(=O)R$^{35a}$, and $R^{35a}$ is optionally substituted alkyl, e.g., —C(=O)Me. In certain embodiments, $R^{35}$ is —C(=O)R$^{35a}$, and $R^{35a}$ is optionally substituted $C_{1-6}$ alkyl. In certain embodiments, $R^{35}$ is —C(=O)R$^{35a}$, and $R^{35a}$ is optionally substituted $C_{2-6}$ alkyl. In certain embodiments, $R^{35}$ is —C(=O)R$^{35a}$, and $R^{35a}$ is optionally substituted alkenyl. In certain embodiments, $R^{35}$ is —C(=O)R$^{35a}$, and $R^{35a}$ is optionally substituted carbocyclyl, heterocyclyl, aryl, or heteroaryl. In certain embodiments, $R^{35}$ is —C(=O)OR$^{35a}$, and $R^{35a}$ is optionally substituted alkyl. In certain embodiments, $R^{35}$ is —C(=O)OR$^{35a}$, and $R^{35a}$ is optionally substituted alkenyl. In certain embodiments, $R^{35}$ is —C(=O)OR$^{3a}$, and $R^{35a}$ is optionally substituted carbocyclyl, heterocyclyl, aryl, or heteroaryl. In certain embodiments, $R^{35}$ is —C(=O)N(R$^{35a}$)$_2$, and at least one $R^{35a}$ is optionally substituted alkyl. In certain embodiments, $R^{35}$ is —C(=O)NHR$^{35a}$, and $R^{35}$ is optionally substituted alkyl. In certain embodiments, $R^{35}$ is —C(=O)NHR$^{35a}$, and $R^{35a}$ is optionally substituted alkenyl. In certain embodiments, $R^{35}$ is —C(=O)NHR$^{35a}$, and $R^{35a}$ is optionally substituted carbocyclyl, heterocyclyl, aryl, or heteroaryl.

In certain embodiments, $R^{35}$ is of formula:

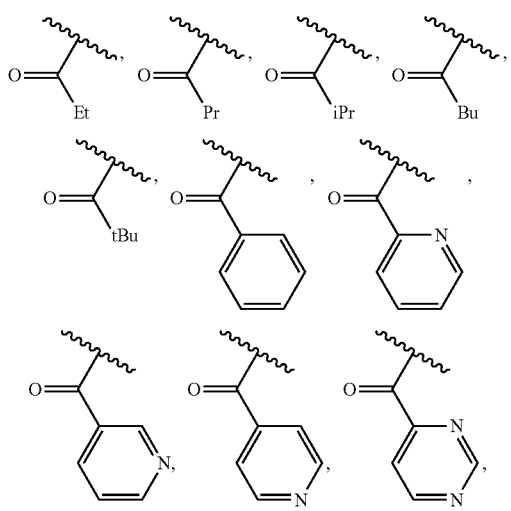

-continued

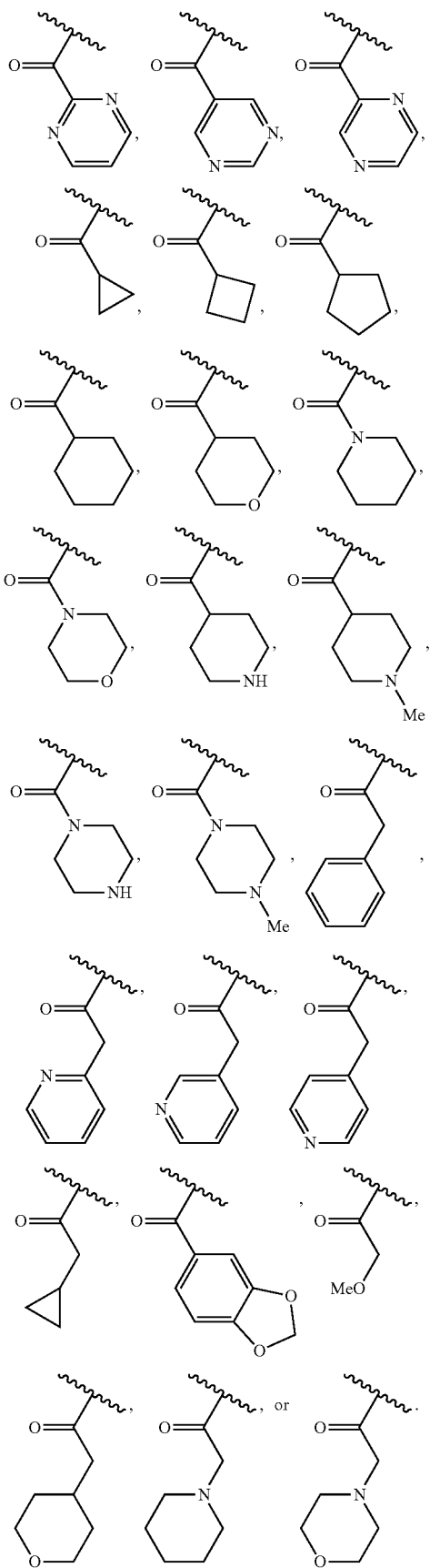

In certain embodiments, $R^{35}$ is of formula:

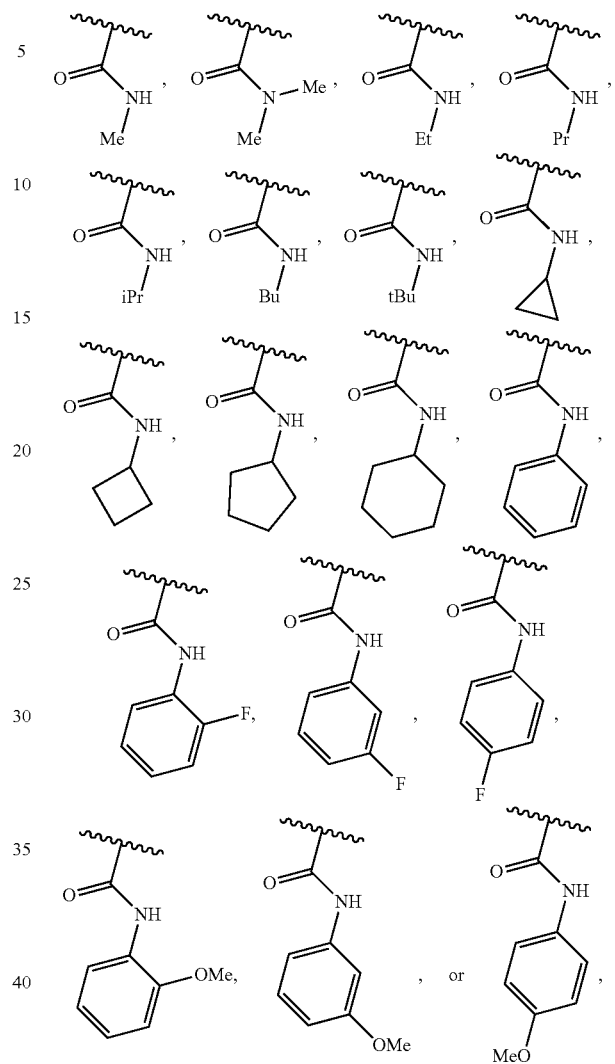

In certain embodiments, $R^{35}$ is $-S(=O)_2R^{35a}$. In certain embodiments, $R^{35}$ is $-S(=O)_2R^{35a}$, and $R^{35a}$ is optionally substituted alkyl, e.g., $R^{35}$ is $-S(=O)_2Me$. In certain embodiments, $R^{35}$ is $-S(=O)_2R^{35a}$, and $R^{3a}$ is optionally substituted $C_{1-6}$ alkyl. In certain embodiments, $R^{35}$ is $-S(=O)_2R^{35a}$, and $R^{35a}$ is optionally substituted $C_{2-6}$ alkyl. In certain embodiments, $R^{35}$ is $-S(=O)_2R^{35a}$, and $R^{35a}$ is optionally substituted alkenyl. In certain embodiments, $R^{35}$ is $-S(=O)_2R^{35a}$, and $R^{35a}$ is optionally substituted carbocyclyl, heterocyclyl, aryl, or heteroaryl. In certain embodiments, $R^{35}$ is $-S(=O)_2OR^{35a}$. In certain embodiments, $R^{35}$ is $-S(=O)_2OR^{35a}$, and $R^{35a}$ is optionally substituted alkyl. In certain embodiments, $R^{35}$ is $-S(=O)_2OR^{35a}$, and $R^{35a}$ is optionally substituted alkenyl. In certain embodiments, $R^{35}$ is $-S(=O)_2OR^{35a}$, and $R^{35a}$ is optionally substituted carbocyclyl, heterocyclyl, aryl, or heteroaryl. In certain embodiments, $R^{35}$ is $-S(=O)_2N(R^{35a})_2$ or $-S(=O)_2NHR^{35a}$. In certain embodiments, $R^{35}$ is $-S(=O)_2N(R^{35a})_2$, and at least one $R^{35a}$ is optionally substituted alkyl. In certain embodiments, $R^{35}$ is $-S(=O)_2NHR^{3a}$, and $R^{35a}$ is optionally substituted alkyl. In certain embodiments, $R^{35}$ is $-S(=O)_2NHR^{35a}$, and $R^{35a}$ is optionally substituted alkenyl. In certain embodiments, $R^{35}$ is $-S(=O)_2NHR^{35a}$, and $R^{35a}$ is optionally substituted carbocyclyl, heterocyclyl, aryl, or heteroaryl.

In certain embodiments, $R^{35}$ is of formula:
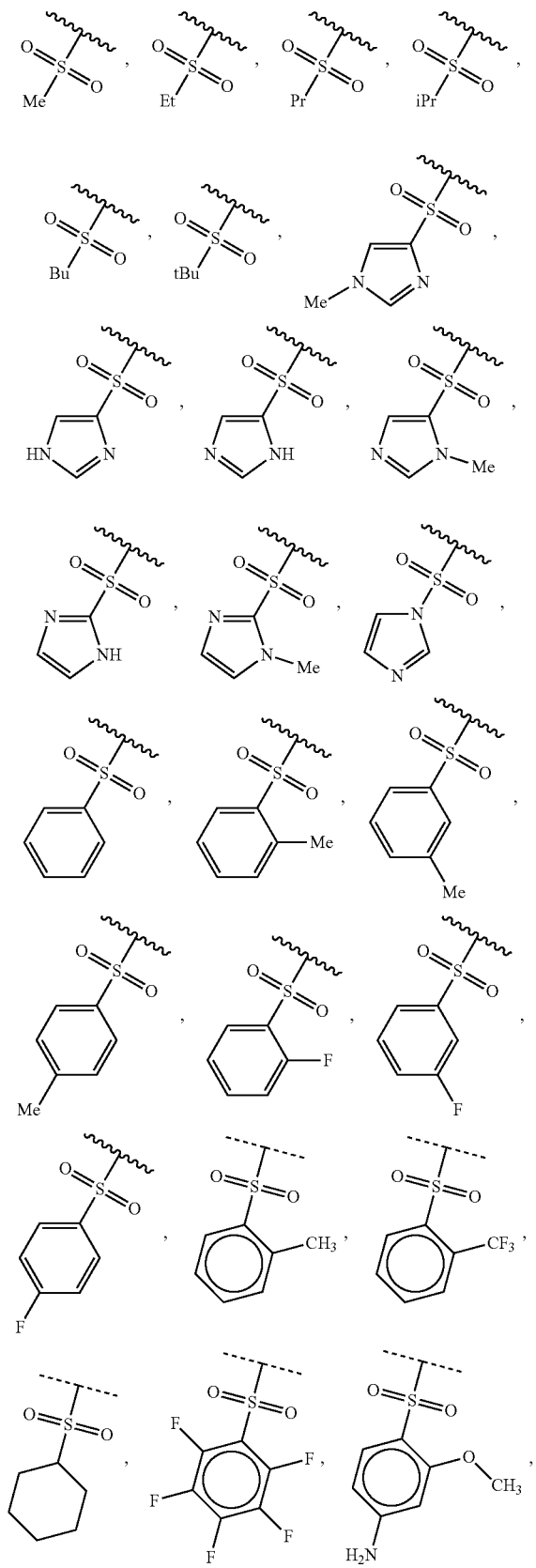
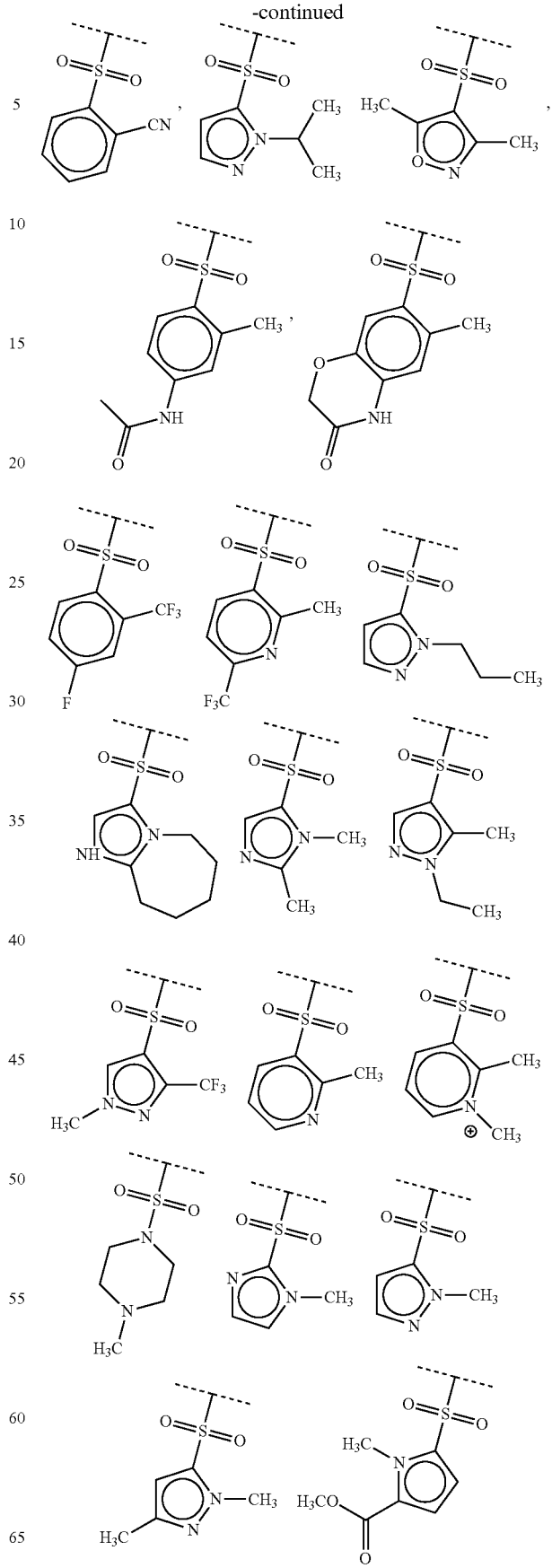

-continued

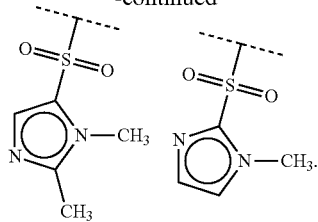

Group R$^{36}$

As generally described herein, R$^{36}$ is —CN or —CH$_2$N(R$^{36a}$)$_2$, wherein each R$^{36a}$ is independently hydrogen, optionally substituted alkyl, optionally substituted acyl, or a nitrogen protecting group, or two R$^{36a}$ are joined to form an optionally substituted heterocyclic or optionally substituted heteroaryl ring. In certain embodiments, R$^{36}$ is —CN. In certain embodiments, two R$^{36a}$ are joined to form an optionally substituted heterocyclic ring.

In certain embodiments, R$^{36}$ is —CH$_2$N(R$^{36a}$)$_2$. In certain embodiments, R$^{36}$ is —CH$_2$NHR$^{36a}$. In some embodiments, R$^{36}$ is —CH$_2$NHR$^{36a}$, and R$^{36a}$ is hydrogen. In some embodiments, R$^{36}$ is —CH$_2$NHR$^{36a}$, and R$^{36a}$ is optionally substituted alkyl. In some embodiments, R$^{36}$ is —CH$_2$NHR$^{36}$, and R$^{36a}$ is unsubstituted C$_{1-6}$ alkyl, e.g., methyl, ethyl, propyl, butyl. In some embodiments, R$^{36}$ is —CH$_2$NHR$^{36}$, and R$^{36a}$ is optionally substituted acyl. In some embodiments, R$^{36}$ is —CH$_2$NHR$^{36}$, and R$^{36a}$ is —C(=O)(alkyl), e.g., —C(=O)Me. In some embodiments, R$^{36}$ is —CH$_2$NHR$^{36a}$, and R$^{36a}$ is —C(=O)(heterocyclyl), e.g., cyclopentyl, cyclohexyl.

In certain embodiments, R$^{36}$ is —CH$_2$NHR$^{36a}$, and R$^{36a}$ is of formula:

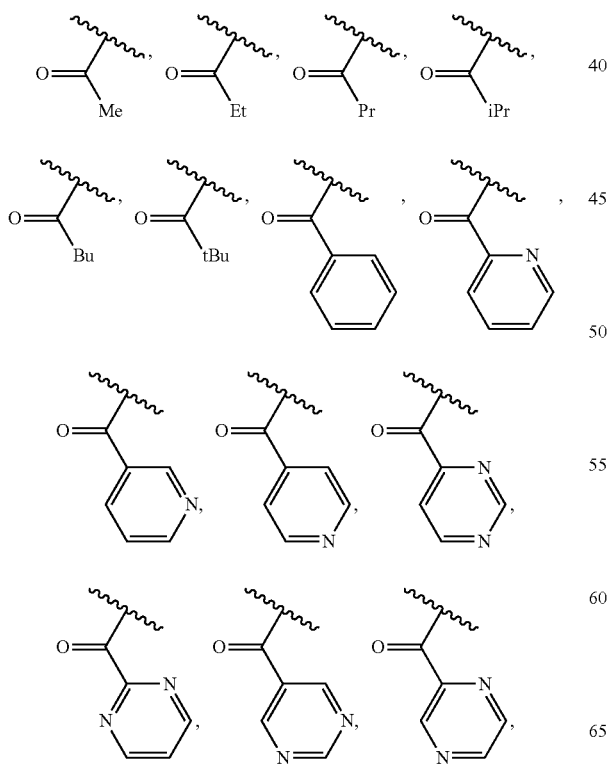

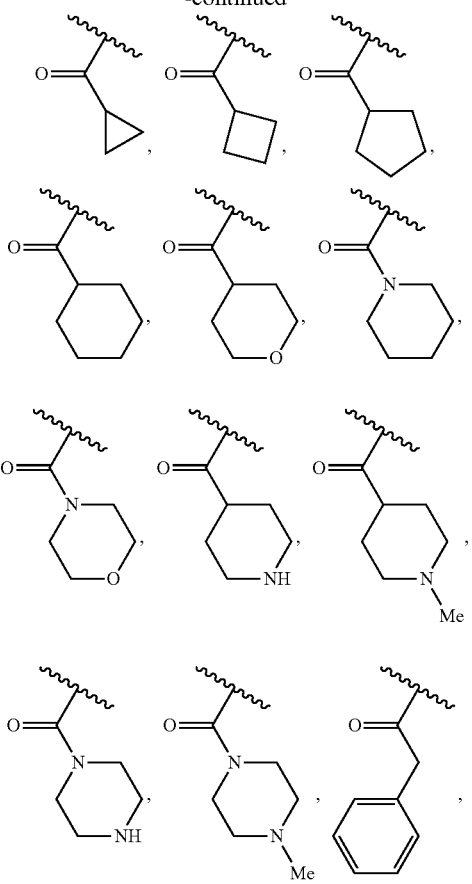

In certain embodiments, the compound of Formula (III) is a compound in Table 4, or a pharmaceutically acceptable salt, solvate, hydrate, polymorph, co-crystal, tautomer, stereoisomer, prodrug, or isotopically labeled derivative thereof.
TABLE 4
Exemplary compounds of Formula (III).
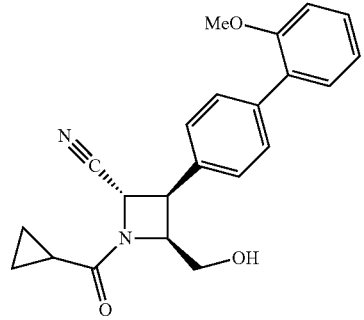 [SMILES: COc1ccccc1-c1ccc([C@@H]2[C@@H](C#N)N(C(=O)C3CC3)[C@@H]2CO)cc1]
D1
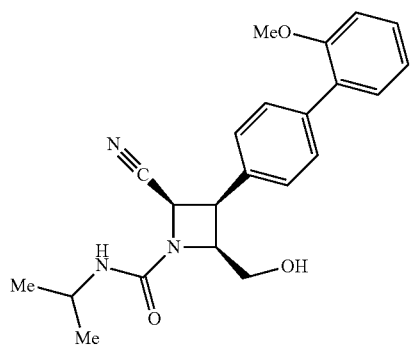 [SMILES: COc1ccccc1-c1ccc([C@H]2[C@@H](CO)N(C(=O)NC(C)C)[C@H]2C#N)cc1]
D2
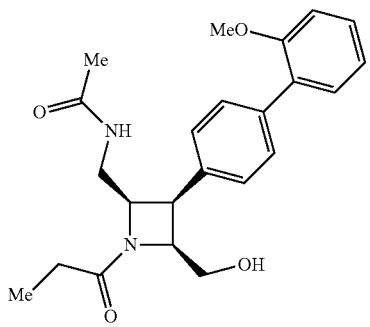 [SMILES: CCC(=O)N1[C@H](CO)[C@H](c2ccc(-c3ccccc3OC)cc2)[C@@H]1CNC(C)=O]
D3
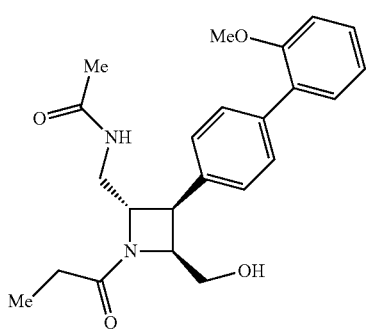 [SMILES: CCC(=O)N1[C@H](CO)[C@H](c2ccc(-c3ccccc3OC)cc2)[C@H]1CNC(C)=O]
D4
TABLE 4-continued
Exemplary compounds of Formula (III).
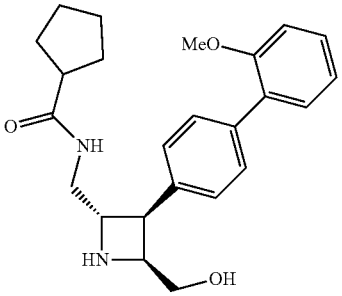 [SMILES: COc1ccccc1-c1ccc([C@H]2[C@@H](CO)N[C@@H]2CNC(=O)C2CCCC2)cc1]
D5
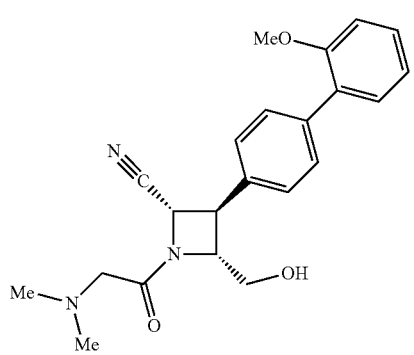 [SMILES: COc1ccccc1-c1ccc([C@@H]2[C@@H](C#N)N(C(=O)CN(C)C)[C@H]2CO)cc1]
D6
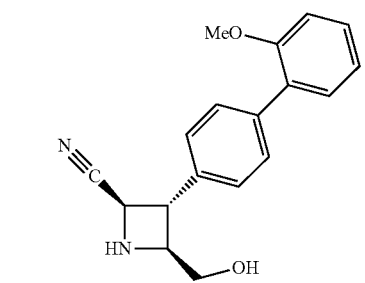 [SMILES: COc1ccccc1-c1ccc([C@H]2[C@H](C#N)N[C@@H]2CO)cc1]
D7
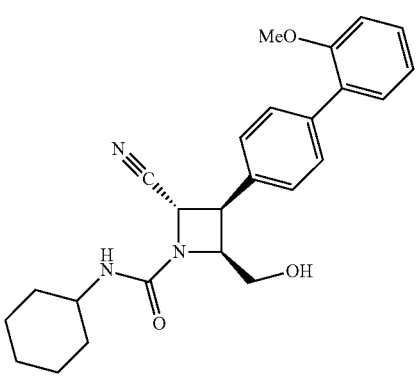 [SMILES: COc1ccccc1-c1ccc([C@@H]2[C@@H](C#N)N(C(=O)NC3CCCCC3)[C@@H]2CO)cc1]
D8

TABLE 4-continued

Exemplary compounds of Formula (III).

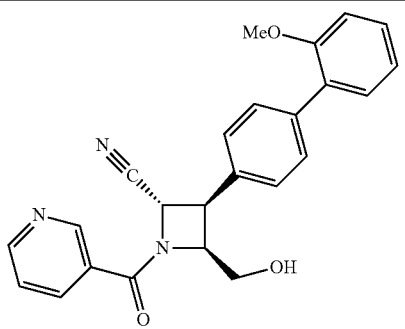

D9

In certain embodiments, the compound of Formula (I) includes a moiety comprising Ring $A^3$ and Ring $B^3$, wherein the rings are not free to rotate about the bond or linker connecting the two rings. In certain embodiments, the compound comprises a locked ring moiety comprising Ring $A^3$ and Ring $B^3$ directly attached by a single bond, wherein the rings are independently optionally substituted aryl or optionally substituted heteroaryl. In certain embodiments, the locked ring moiety comprises Ring $A^3$ and Ring $B^3$ directly attached by a single bond, wherein the rings are independently optionally substituted aryl or optionally substituted heteroaryl, and at least one of the rings has a non-hydrogen group ortho to the single bond.

In certain embodiments, the rotational energy barrier between rings $A^3$ and $B^3$ is at least about 6 kcal/mol. In certain embodiments, the rotational energy barrier between rings $A^3$ and $B^3$ is at least about 10 kcal/mol, at least about 15 kcal/mol, at least about 20 kcal/mol, or at least about 30 kcal/mol. In certain embodiments, the equilibrium dihedral angle between rings $A^3$ and $B^3$ is between about 20° and between about 160°, inclusive. In certain embodiments, the equilibrium dihedral angle between rings $A^3$ and $B^3$ is between about 40° and between about 140°, between about 60° and between about 120°, between about 90° and between about 100°, inclusive. In certain embodiments, the equilibrium dihedral angle between rings $A^3$ and $B^3$ is between about 20° and between about 160°, inclusive, when bound to IDE. In certain embodiments, the equilibrium dihedral angle between rings $A^3$ and $B^3$ is between about 40° and between about 140°, between about 60° and between about 120°, between about 90° and between about 100°, inclusive, when bound to IDE.

Compounds of Formula (IV)

In certain embodiments, the invention provides a compound of Formula (IV):

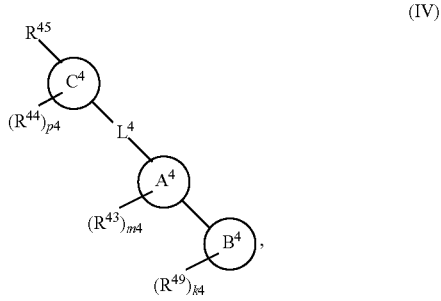

(IV)

or a pharmaceutically acceptable salt, solvate, hydrate, polymorph, co-crystal, tautomer, stereoisomer, prodrug, or isotopically labeled derivative thereof, wherein:

$R^{45}$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$OR^{45a}$, —$N(R^{45a})_2$, —$S(=O)_2R^{45a}$, —$S(=O)_2OR^{45a}$, or —$S(=O)_2N(R^{45a})_2$ wherein each $R^{45a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{45a}$ are joined to form an optionally substituted heteroaryl or optionally substituted heterocyclic ring;

Ring $C^4$ is carbocyclylene, heterocyclylene, arylene or heteroarylene;

$L^4$ is a bond, optionally substituted alkylene, optionally substituted alkenylene, optionally substituted alkynylene, —O—, —$NR^L$—, —$C(=O)$—, —$C(=O)NR^L$—, —$NR^LC(=O)$—, wherein $R^L$ is hydrogen, optionally substituted $C_{1-6}$ alkyl, or a nitrogen protecting group; each $R^{44}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{44a}$, —$N(R^{44a})_2$, or two $R^{44}$ are joined to form an optionally substituted carbocyclic, heterocyclic, aryl, or heteroaryl ring, wherein each $R^{44a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{44a}$ are joined to form an optionally substituted heteroaryl or optionally substituted heterocyclic ring;

Ring $A^4$ is 6-membered arylene or 5-7 membered heteroarylene;

Ring $B^4$ is 6 membered aryl, or 5-7 membered heteroaryl;

each $R^{43}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{43a}$, —$N(R^{43a})_2$, or two $R^{43}$ are joined to form an optionally substituted carbocyclic, heterocyclic, aryl, or heteroaryl ring, wherein each $R^{43a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{43a}$ are joined to form an optionally substituted heteroaryl or optionally substituted heterocyclic ring;

each $R^{49}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{49a}$, —N(R$^{49a}$)$_2$, —S(=O)$_2$R$^{49a}$, —S(=O)$_2$OR$^{49a}$, or —S(=O)$_2$N(R$^{49a}$)$_2$, or two $R^{49}$ are joined to form an optionally substituted carbocyclic, heterocyclic, aryl, or heteroaryl ring, wherein each $R^{49a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{49a}$ are joined to form an optionally substituted heteroaryl or optionally substituted heterocyclic ring;

m4 is 0, 1, 2, 3, or 4;

p4 is 0, 1, 2, 3, or 4; and k4 is 0, 1, 2, 3, 4, or 5;

wherein the sum of m4 and k4 is at least one, and at least one $R^{43}$ or $R^{49}$ is attached ortho to the bond between Rings $A^4$ and $B^4$.

In certain embodiments, the compound of Formula (IV) selectively inhibits the activity of IDE for degradation of a first substrate over the activity of IDE for degradation of a second substrate. In certain embodiments, the compound of Formula (IV) selectively inhibits the activity of IDE for degradation of insulin over the activity of IDE for degradation of a second substrate (e.g., glucagon, amylin). In certain embodiments, the compound of Formula (IV) selectively inhibits the activity of IDE for degradation of insulin over the activity of IDE for degradation of glucagon. In certain embodiments, the compound of Formula (IV) selectively inhibits the activity of IDE for degradation of insulin over the activity of IDE for degradation of more than one other substrate.

In certain embodiments, the compound of Formula (IV) is a compound of Formula:

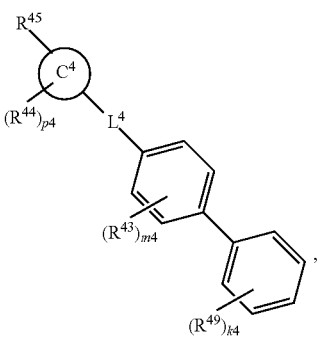

,

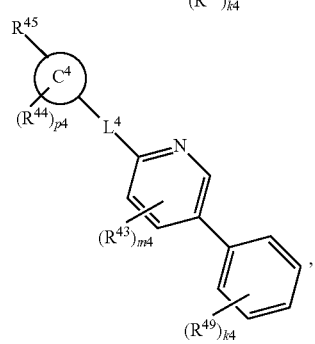

,

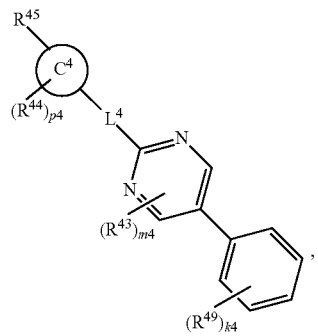

,

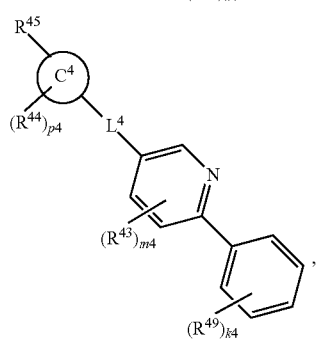

,

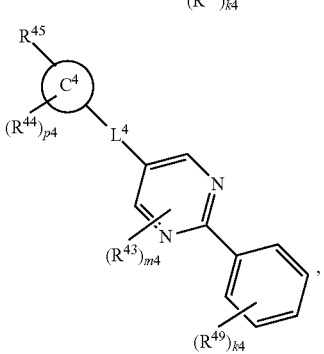

,

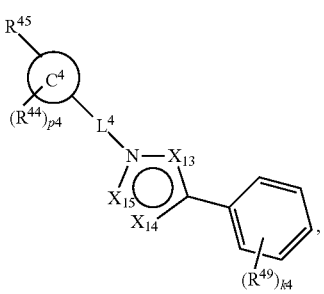

,

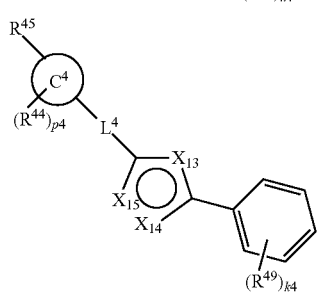

, or a pharmaceutically acceptable salt, solvate, hydrate, polymorph, co-crystal, tautomer, stereoisomer, prodrug, or isotopically labeled derivative thereof, wherein Ring $C^4$, $L^4$, $R^{43}$, $R^{44}$, $R^{45}$, $R^{49}$, m4, p4, and k4 are as described herein, m4 is 0, 1, or 2; and $X_{13}$, $X_{14}$, and $X_{15}$ are selected from the group consisting of C, CH, C($R^{43}$), O, S, N, and N($R^{43a}$), as valency permits.

In certain embodiments, the compound of Formula (IV) is a compound of Formula (IV-a-1) or (IV-a-2):

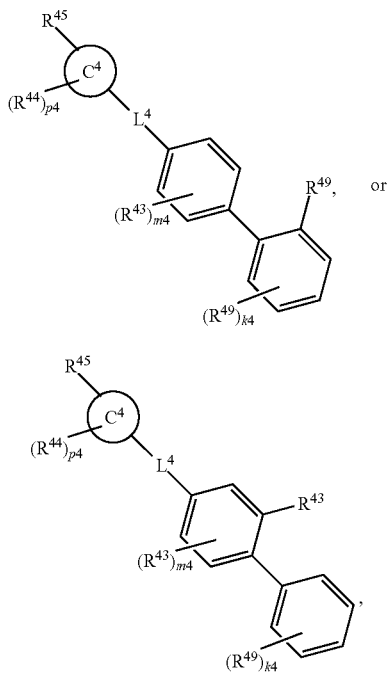

(IV-a-1)

(IV-a-2)

or a pharmaceutically acceptable salt, solvate, hydrate, polymorph, co-crystal, tautomer, stereoisomer, prodrug, or isotopically labeled derivative thereof, wherein Ring $C^4$, $L^4$, $R^{43}$, $R^{44}$, $R^{45}$, $R^{49}$, m4, p4, and k4 are as described herein.

In certain embodiments, the compound of Formula (IV) is a compound of Formula (IV-b-1) or (IV-b-2)

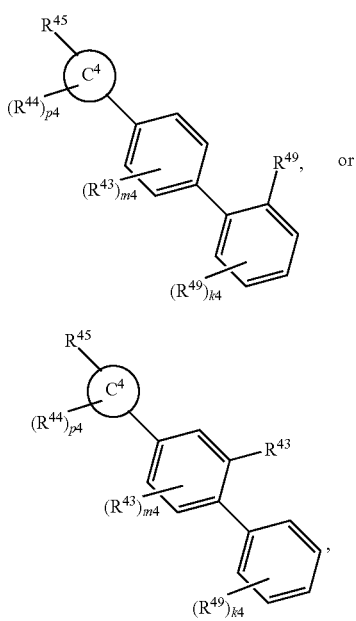

(IV-b-1)

(IV-b-2)

or a pharmaceutically acceptable salt, solvate, hydrate, polymorph, co-crystal, tautomer, stereoisomer, prodrug, or isotopically labeled derivative thereof, wherein Ring $C^4$, $R^{43}$, $R^{44}$, $R^{45}$, $R^{49}$, m4, p4, and k4 are as described herein.

In certain embodiments, the compound of Formula (IV) is a compound of Formula (IV-c-1) or (IV-c-2):

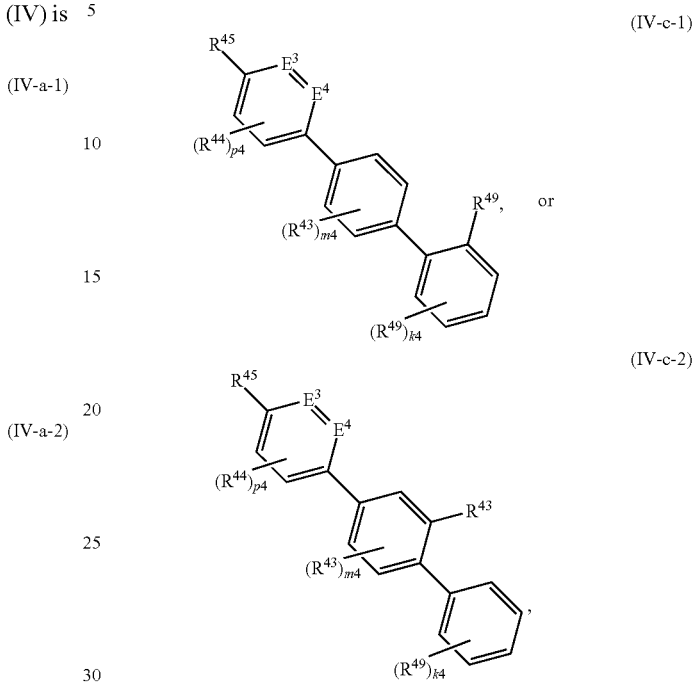

(IV-c-1)

(IV-c-2)

or a pharmaceutically acceptable salt, solvate, hydrate, polymorph, co-crystal, tautomer, stereoisomer, prodrug, or isotopically labeled derivative thereof, wherein each of $E^3$ and $E^4$ is N, CH, or $CR^{44}$, and $R^{43}$, $R^{44}$, $R^{45}$, $R^{49}$, m4, p4, and k4 are as described herein.

In certain embodiments, the compound of Formula (IV) is a compound of Formula (IV-d-1) or (IV-d-2):

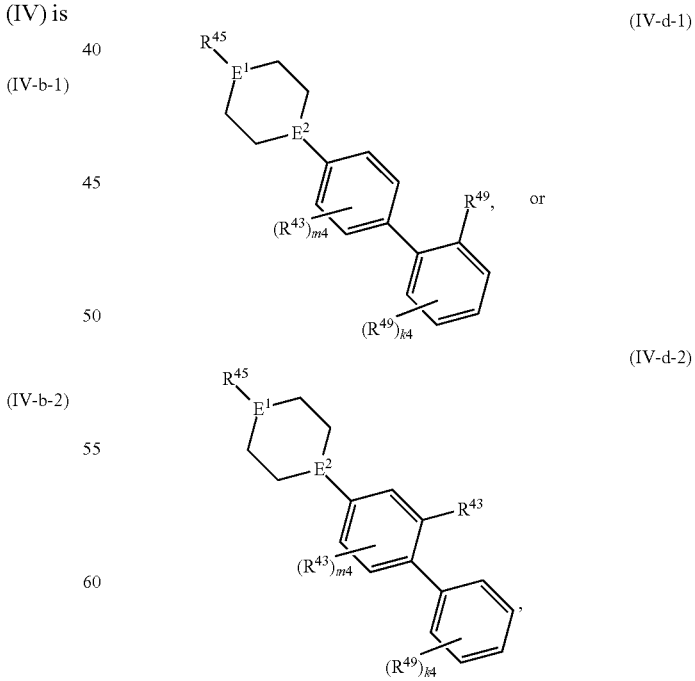

(IV-d-1)

(IV-d-2)

or a pharmaceutically acceptable salt, solvate, hydrate, polymorph, co-crystal, tautomer, stereoisomer, prodrug, or isotopically labeled derivative thereof, wherein:

each of $E^1$ and $E^2$ is independently N or $CR^E$;
each $R^E$ is independently hydrogen, halogen, optionally substituted alkyl, or $-OR^{Ea}$, wherein each $R^{Ea}$ is independently hydrogen, optionally substituted alkyl, optionally substituted acyl, or an oxygen protecting group; and $R^{43}$, $R^{45}$, $R^{49}$, m4, and k4 are as described herein.

In certain embodiments, the compound of Formula (IV) is a compound of Formula (IV-e-1) or (IV-e-2):

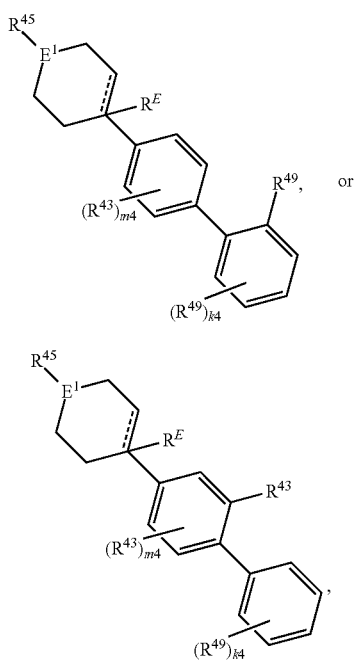

or a pharmaceutically acceptable salt, solvate, hydrate, polymorph, co-crystal, tautomer, stereoisomer, prodrug, or isotopically labeled derivative thereof, wherein:
$E^1$ N or $CR^E$;
each $R^E$ is independently hydrogen, halogen, optionally substituted alkyl, or $-OR^{Ea}$, wherein each $R^{Ea}$ is independently hydrogen, optionally substituted alkyl, optionally substituted acyl, or an oxygen protecting group;
=== is a single or double bond, wherein if === is a double bond the attached $R^E$ is absent; and $R^{43}$, $R^{45}$, $R^{49}$, m4, and k4 are as described herein.

Ring $C^4$ and $R^{44}$

As generally defined herein, Ring $C^4$ is carbocyclylene, heterocyclylene, arylene, or heteroarylene. Ring $C^4$ may be substituted with 0, 1, 2, 3, or 4 independent $R^{43}$, valency permitting. In certain embodiments, p4 is 0 or 1. In certain embodiments, p4 is 0. In certain embodiments, p4 is 1. In certain embodiments, p4 is 2. In certain embodiments, p4 is 3. In certain embodiments, p4 is 4.

In certain embodiments, Ring $C^4$ is arylene, e.g., phenylene. In certain embodiments, Ring $C^4$ is heteroarylene, e.g., 5- to 6-membered heteroarylene. In some embodiments, Ring $C^4$ is pyridylene, pyrimidylene, or imidazylene. In certain embodiments, Ring $C^4$ is carbocyclylene, e.g., 3- to 6-membered carbocyclylene. In some embodiments, Ring $C^4$ is cyclohexylene, cyclopentylene, cyclobutylene, or cyclopropylene. In certain embodiments, Ring $C^4$ is heterocyclylene, e.g., 5- to 6-membered heterocyclylene. In some embodiments, Ring $C^4$ is piperidinylene or piperizinylene.

In certain embodiments, Ring $C^4$ is of formula:

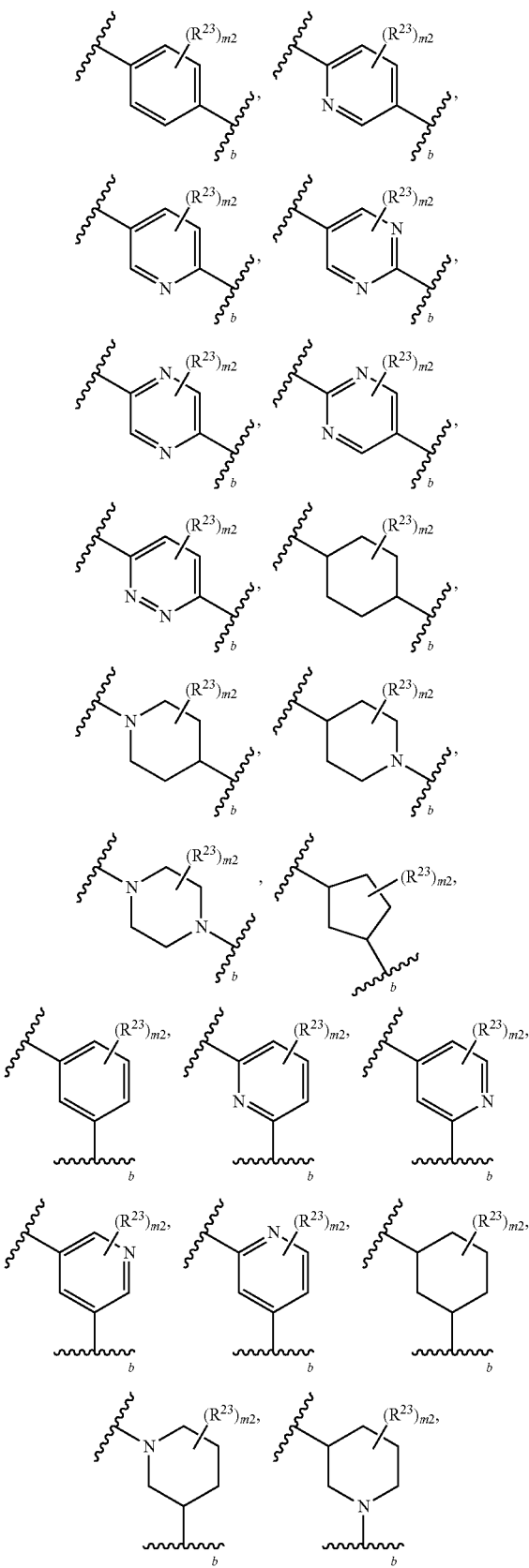

-continued

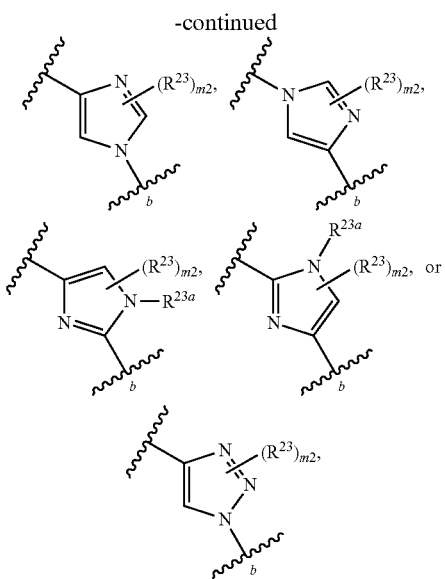

wherein the position labeled b is attached to $L^4$, and p4 is 0, 1, 2, 3, or 4, valency permitting.

In certain embodiments, Ring $C^4$ is of formula:

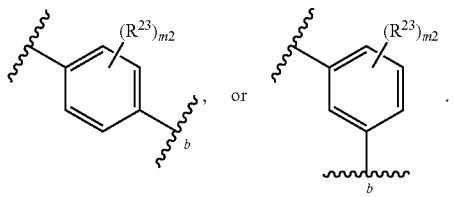

In certain embodiments, Ring $C^4$ is of formula:

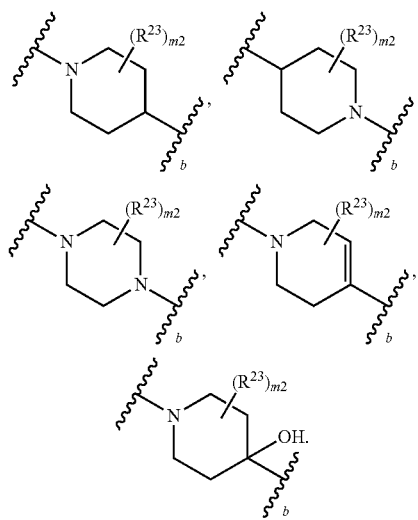

In certain embodiments, Ring $C^4$ is of formula:

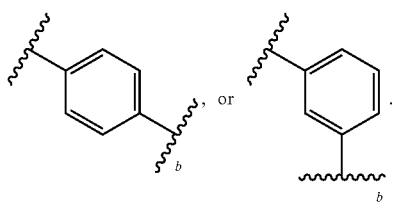 [SMILES: *c1ccc(*)cc1 ; *c1cccc(*)c1]

In certain embodiments, Ring $C^4$ is of formula:

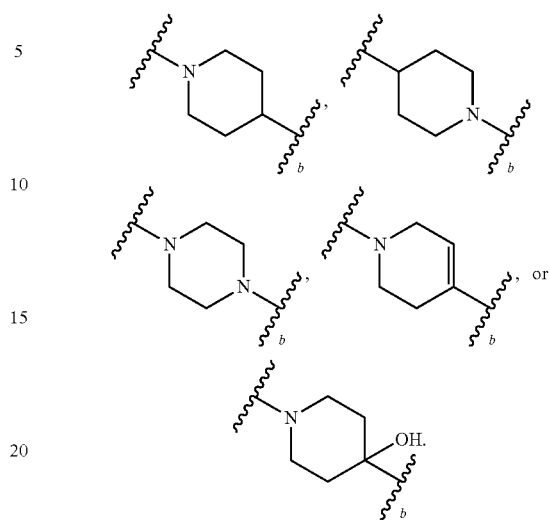

As generally defined herein, each $R^{43}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —$NO_2$, —CN, —$OR^{43a}$, or —$N(R^{43a})_2$, wherein each $R^{43a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{43a}$ are joined to form an optionally substituted heteroaryl or optionally substituted heterocyclic ring.

In certain embodiments, at least one $R^{43}$ is —$NO_2$. In certain embodiments, at least one $R^{43}$ is —CN. In certain embodiments, at least one $R^{43}$ is halogen. In some embodiments, at least one $R^{43}$ is —F. In some embodiments, at least one $R^{43}$ is —Cl, —Br, or —I. In certain embodiments, at least one $R^{43}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one $R^{43}$ is methyl. In certain embodiments, at least one $R^{43}$ is ethyl, propyl, or butyl. In certain embodiments, at least one $R^{43}$ is optionally substituted alkenyl, e.g., optionally substituted $C_{2-6}$ alkenyl. In certain embodiments, at least one $R^{43}$ is vinyl, allyl, or prenyl. In certain embodiments, at least one $R^{43}$ is optionally substituted alkynyl, e.g., $C_{2-6}$ alkynyl.

In certain embodiments, at least one $R^{43}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, at least one $R^{43}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{43}$ is optionally substituted aryl, e.g., optionally substituted phenyl. In certain embodiments, at least one $R^{43}$ is optionally substituted heteroaryl, e.g., optionally substituted 5-6 membered heteroaryl or optionally substituted 9-10 membered bicyclic heteroaryl. In certain embodiments, at least one $R^{43}$ is optionally substituted aralkyl, e.g., optionally substituted benzyl. In certain embodiments, at least one $R^{43}$ is optionally substituted heteroaralkyl, e.g., methyl substituted with a 5-6 membered heteroaryl ring.

In certain embodiments, at least one $R^{43}$ is optionally substituted acyl, e.g., —CHO, —CO$_2$H, or —C(=O)NH$_2$. In certain embodiments, at least one $R^{43}$ is —C(=O)R$^{43a}$, —C(=O)OR$^{43a}$, —C(=O)NH(R$^{43a}$), or —C(=O)N(R$^{43a}$)$_2$. In certain embodiments, at least one $R^{43}$ is —C(=O)R$^{43a}$, and $R^{43a}$ is optionally substituted alkyl, e.g., $R^{43}$ is —C(=O)Me. In certain embodiments, at least one $R^{43}$ is —C(=O)R$^{43a}$, and $R^{43a}$ is optionally substituted alkenyl. In certain embodiments, at least one $R^{43}$ is —C(=O)R$^{43a}$, and $R^{43a}$ is optionally substituted carbocyclyl, heterocyclyl, aryl, or heteroaryl. In certain embodiments, at least one $R^{43}$ is —C(=O)OR$^{43a}$, and $R^{43a}$ is optionally substituted alkyl. In certain embodiments, at least one $R^{43}$ is —C(=O)OR$^{43a}$, and $R^{43a}$ is optionally substituted alkenyl. In certain embodiments, at least one $R^{43}$ is —C(=O)OR$^{43a}$, and $R^{43a}$ is optionally substituted carbocyclyl, heterocyclyl, aryl, or heteroaryl. In certain embodiments, at least one $R^{43}$ is —C(=O)N(R$^{43a}$)$_2$, and at least one $R^{43a}$ is optionally substituted alkyl. In certain embodiments, at least one $R^{43}$ is —C(=O)NHR$^{43a}$, and $R^{43a}$ is optionally substituted alkyl. In certain embodiments, at least one $R^{43}$ is —C(=O)NHR$^{43a}$, and $R^{43a}$ is optionally substituted alkenyl. In certain embodiments, at least one $R^{43}$ is —C(=O)NHR$^{43a}$, and $R^{43a}$ is optionally substituted carbocyclyl, heterocyclyl, aryl, or heteroaryl.

In certain embodiments, at least one $R^{43}$ is —OR$^{43a}$, e.g., —OH. In certain embodiments, at least one $R^{43}$ is —OR$^{43a}$, and $R^{43a}$ is optionally substituted alkyl. In certain embodiments, at least one $R^{43}$ is —OR$^{43a}$, and $R^{43a}$ is optionally substituted alkenyl. In certain embodiments, at least one $R^{43}$ is —OR$^{43a}$, and $R^{43a}$ is optionally substituted carbocyclyl, optionally substituted heterocyclyl, optionally substituted aryl optionally substituted heteroaryl. In certain embodiments, at least one $R^{43}$ is —OR$^{43a}$, and $R^{43a}$ is optionally substituted acyl, e.g., $R^{43}$ is —OC(=O)R$^{43a}$, —OC(=O)OR$^{43a}$, or —OC(=O)N(R$^{43a}$)$_2$. In certain embodiments, at least one $R^{43}$ is —OR$^{43a}$, and $R^{43a}$ is an oxygen protecting group.

In certain embodiments, at least one $R^{43}$ is —N(R$^{43a}$)$_2$, e.g., —NH$_2$, —NHR$^{43a}$. In certain embodiments, at least one $R^{43}$ is —NH(R$^{43a}$), and $R^{43a}$ is optionally substituted alkyl. In certain embodiments, at least one $R^{43}$ is —N(R$^{43a}$)$_2$, and at least one $R^{43a}$ is optionally substituted alkyl. In certain embodiments, at least one $R^{43}$ is —NHR$^{43a}$, and $R^{43a}$ is optionally substituted carbocyclyl, optionally substituted heterocyclyl, optionally substituted aryl, or optionally substituted heteroaryl. In certain embodiments, at least one $R^{43}$ is —NHR$^{43a}$, and $R^{43a}$ is optionally substituted acyl, e.g., $R^{43}$ is —NHC(=O)R$^{43a}$, —NHC(=O)OR$^{43a}$, or —NHC(=O)NHR$^{43a}$. In certain embodiments, at least one $R^{43}$ is —N(R$^{43a}$)$_2$, and at least one $R^{43a}$ is a nitrogen protecting group. In certain embodiments, at least one $R^{43}$ is —N(R$^{43a}$)$_2$, and $R^{43a}$ are joined to form an optionally substituted heterocyclic or optionally substituted heteroaryl ring.

$L^4$

As generally described herein, $L^4$ is a bond, optionally substituted alkylene, optionally substituted alkenylene, optionally substituted alkynylene, —O—, —NR$^L$—, —C(=O)—, —C(=O)NR$^L$—, or —NR$^L$C(=O)—, wherein $R^L$ is hydrogen, optionally substituted $C_{1-6}$ alkyl, or a nitrogen protecting group.

In certain embodiments, $L^4$ is a bond, such that Ring $C^4$ and Ring $A^4$ are directly attached. In certain embodiments, $L^4$ is optionally substituted alkylene. In certain embodiments, $L^4$ is optionally substituted alkenylene. In certain embodiments, $L^4$ is optionally substituted alkynylene. In certain embodiments, $L^4$ is —C≡C—. In certain embodiments, $L^4$ is —O—. In certain embodiments, $L^4$ is —NR$^L$—, e.g., —NH—. In certain embodiments, $L^4$ is —C(=O)—. In certain embodiments, $L^4$ is —C(=O)NR$^L$—, e.g., —C(=O)NH—. In certain embodiments, $L^4$ is —NR$^L$C(=O)—, e.g., —NHC(=O)—.

In certain embodiments, $R^L$ is hydrogen. In certain embodiments, $R^L$ is optionally substituted $C_{1-6}$ alkyl. In certain embodiments, $R^L$ is a nitrogen protecting group.

$R^{45}$

As generally defined herein, $R^{45}$ is hydrogen, optionally substituted alkyl, optionally substituted alkenyl, optionally substituted alkynyl, optionally substituted aralkyl, optionally substituted heteroaralkyl, optionally substituted acyl, —S(=O)$_2$R$^{45a}$, —S(=O)$_2$OR$^{45a}$, —S(=O)$_2$N(R$^{45a}$)$_2$, or a nitrogen protecting group, wherein each $R^{45a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{45a}$ are joined to form an optionally substituted heteroaryl or optionally substituted heterocyclic ring.

In certain embodiments, $R^{45}$ is a non-hydrogen group. In certain embodiments, $R^{45}$ is not alkyl. In certain embodiments, $R^{45}$ is a non-hydrogen group and is not alkyl, —C(=O)R$^{45a}$, or —S(=O)$_2$R$^{45a}$. In certain embodiments, $R^{45}$ is a non-hydrogen group and is not methyl, —C(=O)R$^{45a}$, or —S(=O)$_2$R$^{45a}$. In certain embodiments, $R^{45}$ is not nosyl. In certain embodiments, $R^{45}$ is not —CH$_3$, —C(=O)Me, or —S(=O)$_2$Me. In certain embodiments, $R^{45}$ is a nitrogen protecting group.

In certain embodiments, $R^{45}$ is hydrogen. In certain embodiments, $R^{45}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{45}$ is optionally substituted $C_{2-6}$ alkyl. In certain embodiments, $R^{45}$ is methyl. In certain embodiments, $R^{45}$ is ethyl, propyl, or butyl. In certain embodiments, $R^{45}$ is optionally substituted alkenyl, e.g., optionally substituted $C_{2-6}$ alkenyl. In certain embodiments, $R^{45}$ is vinyl, allyl, or prenyl. In certain embodiments, $R^{45}$ is optionally substituted alkynyl, e.g., $C_{2-6}$ alkynyl.

In certain embodiments, $R^{45}$ is of formula:

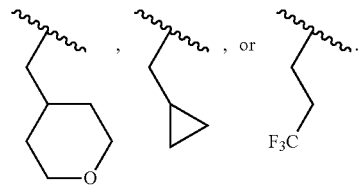

In certain embodiments, $R^{45}$ is optionally substituted aralkyl, e.g., optionally substituted benzyl. In certain embodiments, $R^{45}$ is optionally substituted heteroaralkyl, e.g., methyl substituted with a 5- to 6-membered heteroaryl ring.

In certain embodiments, $R^{45}$ is of formula:

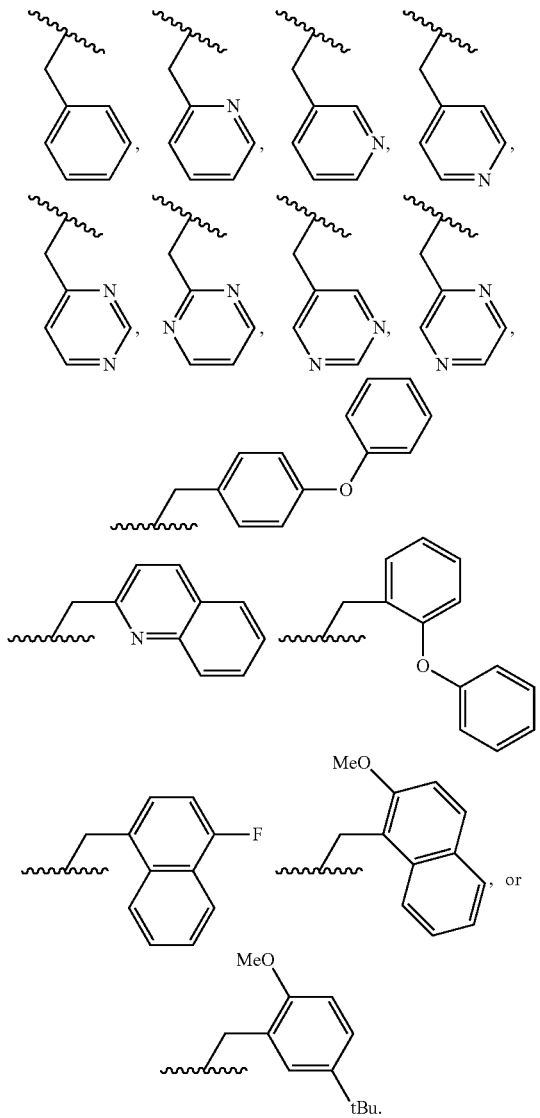

In certain embodiments, $R^{45}$ is optionally substituted acyl, e.g., —CHO, —CO$_2$H, or —C(=O)NH$_2$. In certain embodiments, $R^{45}$ is —C(=O)R$^{45a}$, —C(=O)OR$^{45a}$, —C(=O)NH(R$^{45a}$), or —C(=O)N(R$^{45a}$)$_2$. In certain embodiments, $R^{45}$ is —C(=O)R$^{45a}$, and R$^{45a}$ is optionally substituted alkyl, e.g., —C(=O)Me. In certain embodiments, $R^{45}$ is —C(=O)R$^{45a}$, and R$^{45a}$ is optionally substituted C$_{1-6}$ alkyl. In certain embodiments, $R^{45}$ is —C(=O)R$^{45a}$, and R$^{45a}$ is optionally substituted C$_{2-6}$ alkyl. In certain embodiments, $R^{45}$ is —C(=O)R$^{45a}$, and R$^{45a}$ is optionally substituted alkenyl. In certain embodiments, $R^{45}$ is —C(=O)R$^{45a}$, and R$^{45a}$ is optionally substituted carbocyclyl, heterocyclyl, aryl, or heteroaryl. In certain embodiments, $R^{45}$ is —C(=O)OR$^{45a}$, and R$^{45a}$ is optionally substituted alkyl. In certain embodiments, $R^{45}$ is —C(=O)OR$^{45a}$, and R$^{45a}$ is optionally substituted alkenyl. In certain embodiments, $R^{45}$ is —C(=O)OR$^{45a}$, and R$^{45}$ is optionally substituted carbocyclyl, heterocyclyl, aryl, or heteroaryl. In certain embodiments, $R^{45}$ is —C(=O)N(R$^{45a}$)$_2$, and at least one R$^{45a}$ is optionally substituted alkyl. In certain embodiments, $R^{45}$ is —C(=O)NHR$^{45a}$, and R$^{45a}$ is optionally substituted alkyl. In certain embodiments, $R^{45}$ is —C(=O)NHR$^{45a}$, and R$^{45a}$ is optionally substituted alkenyl. In certain embodiments, $R^{45}$ is —C(=O)NHR$^{45a}$, and R$^{45a}$ is optionally substituted carbocyclyl, heterocyclyl, aryl, or heteroaryl.

In certain embodiments, $R^{45}$ is of formula:

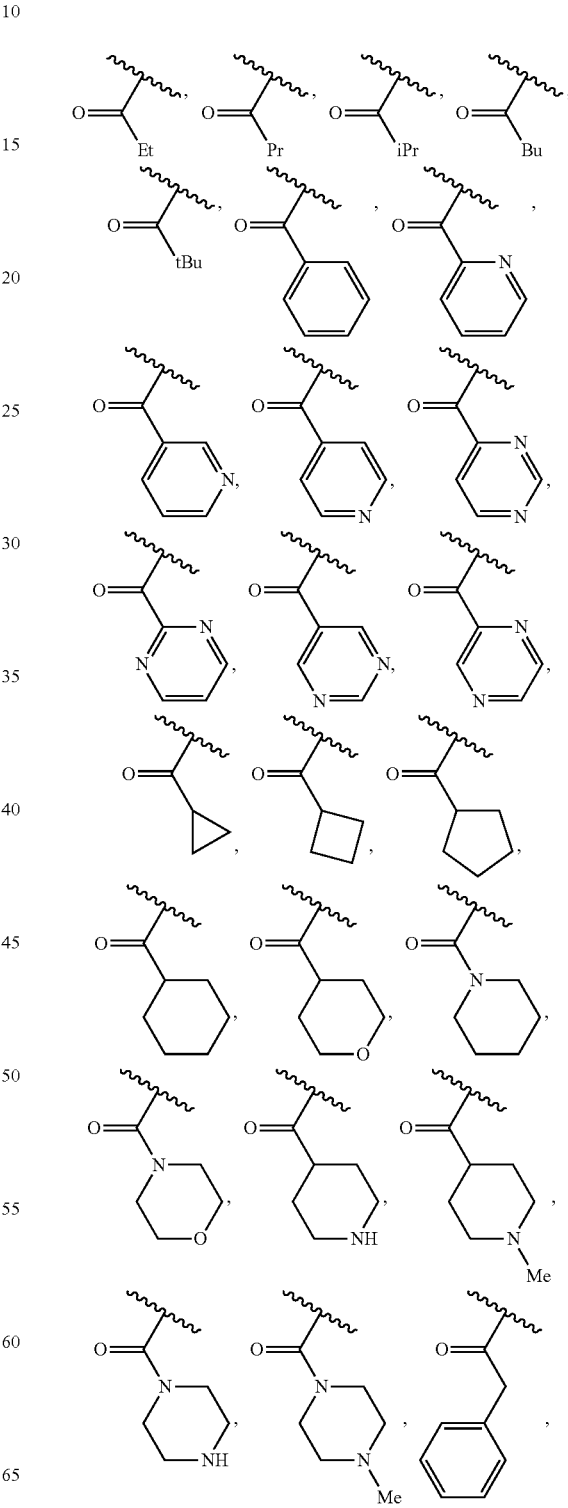

-continued
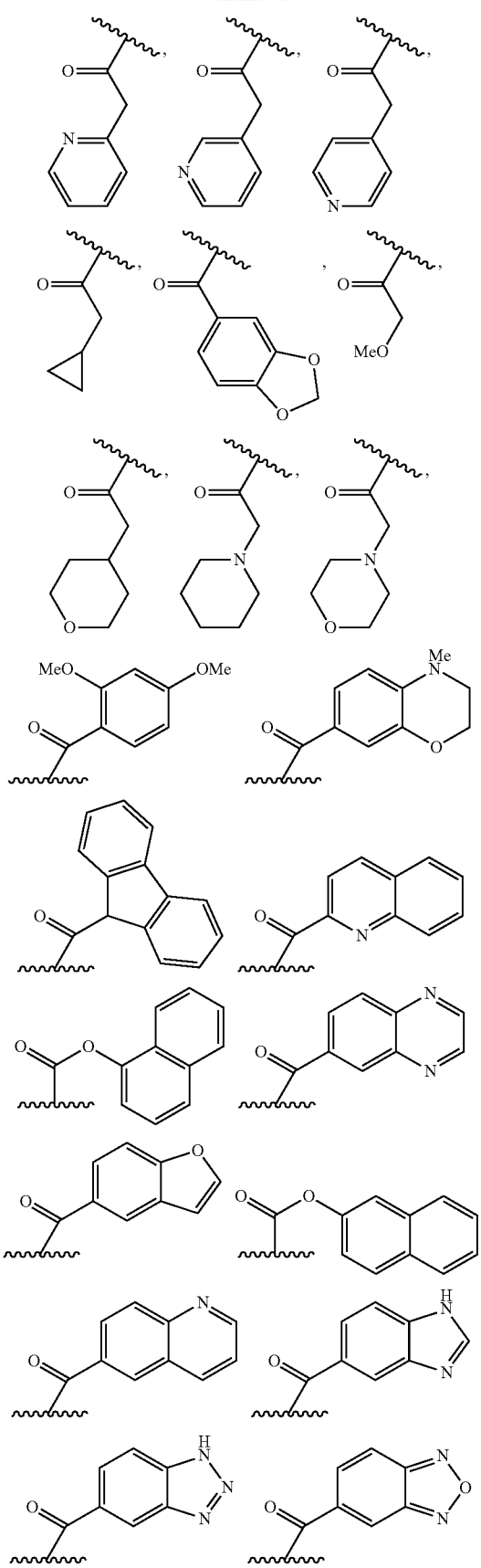
-continued
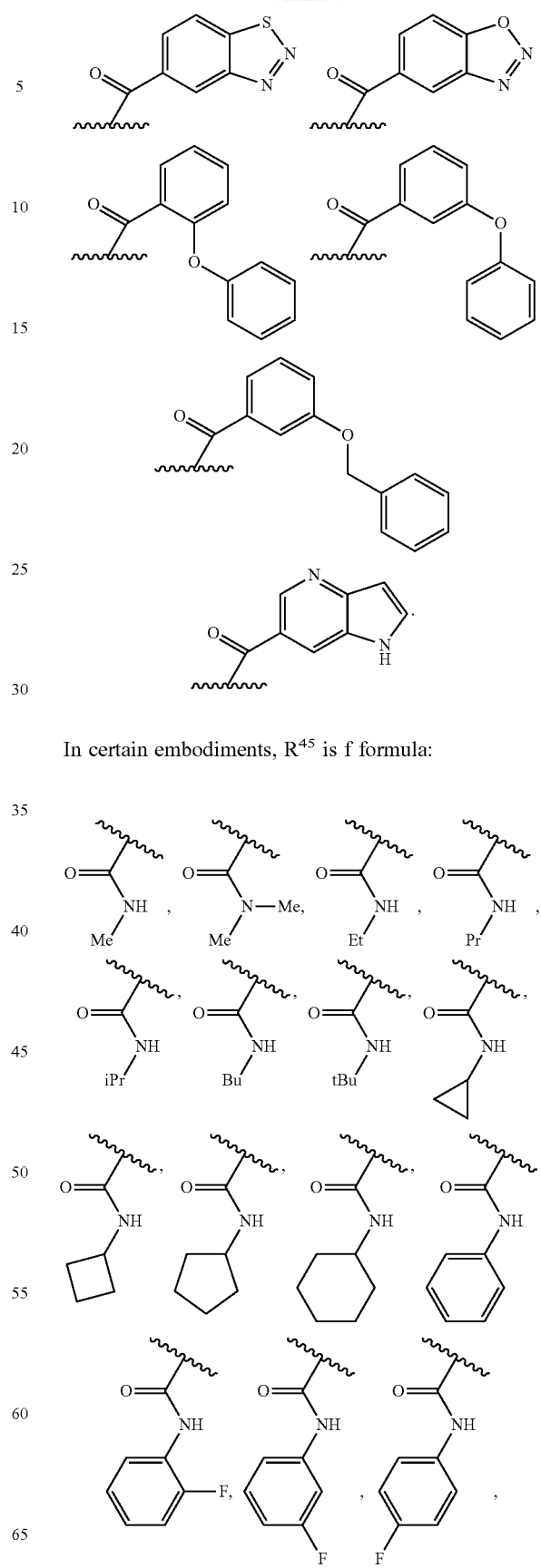
In certain embodiments, $R^{45}$ is f formula:

-continued

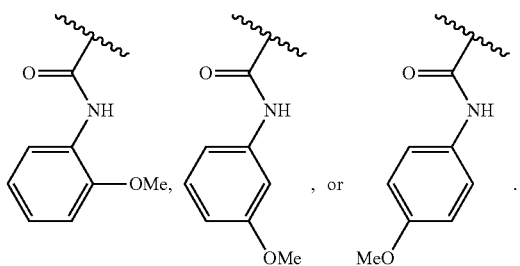

In certain embodiments, $R^{45}$ is $-S(=O)_2R^{45a}$. In certain embodiments, $R^{45}$ is $-S(=O)_2R^{45a}$, and $R^{45a}$ is optionally substituted alkyl, e.g., $R^{45}$ is $-S(=O)_2Me$. In certain embodiments, $R^{45}$ is $-S(=O)_2R^{45a}$, and $R^{45a}$ is optionally substituted $C_{1-6}$ alkyl. In certain embodiments, $R^{45}$ is $-S(=O)_2R^{45a}$, and $R^{45a}$ is optionally substituted $C_{2-6}$ alkyl. In certain embodiments, $R^{45}$ is $-S(=O)_2R^{45a}$, and $R^{45a}$ is optionally substituted alkenyl. In certain embodiments, $R^{45}$ is $-S(=O)_2R^{45a}$, and $R^{45a}$ is optionally substituted carbocyclyl, heterocyclyl, aryl, or heteroaryl. In certain embodiments, $R^{45}$ is $-S(=O)_2OR^{45a}$. In certain embodiments, $R^{45}$ is $-S(=O)_2OR^{45a}$, and $R^{45a}$ is optionally substituted alkyl. In certain embodiments, $R^{45}$ is $-S(=O)_2OR^{45a}$, and $R^{45a}$ is optionally substituted alkenyl. In certain embodiments, $R^{45}$ is $-S(=O)_2OR^{45a}$, and $R^{45a}$ is optionally substituted carbocyclyl, heterocyclyl, aryl, or heteroaryl. In certain embodiments, $R^{45}$ is $-S(=O)_2N(R^{45a})_2$ or $-S(=O)_2NHR^{45a}$. In certain embodiments, $R^{45}$ is $-S(=O)_2N(R^{45a})_2$, and at least one $R^{45a}$ is optionally substituted alkyl. In certain embodiments, $R^{45}$ is $-S(=O)_2NHR^{45a}$, and $R^{45a}$ is optionally substituted alkenyl. In certain embodiments, $R^{45}$ is $-S(=O)_2NHR^{45a}$, and $R^{45a}$ is optionally substituted carbocyclyl, heterocyclyl, aryl, or heteroaryl.

In certain embodiments, $R^{45}$ is of formula:

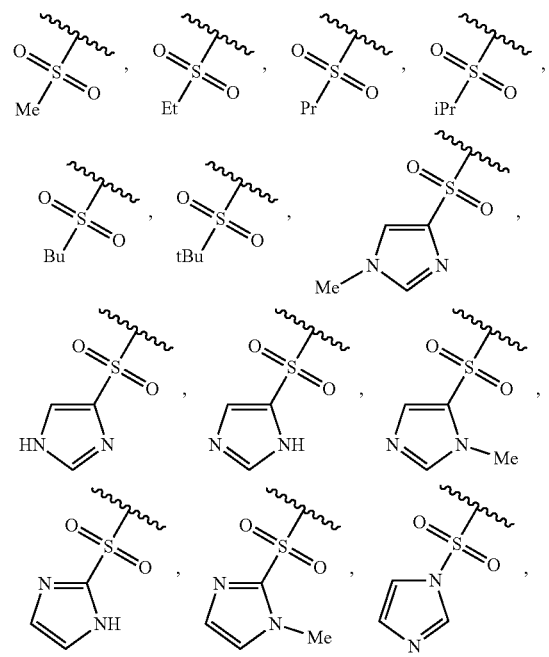

-continued

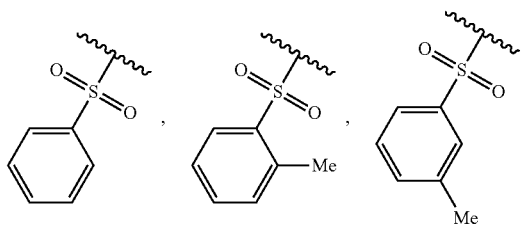

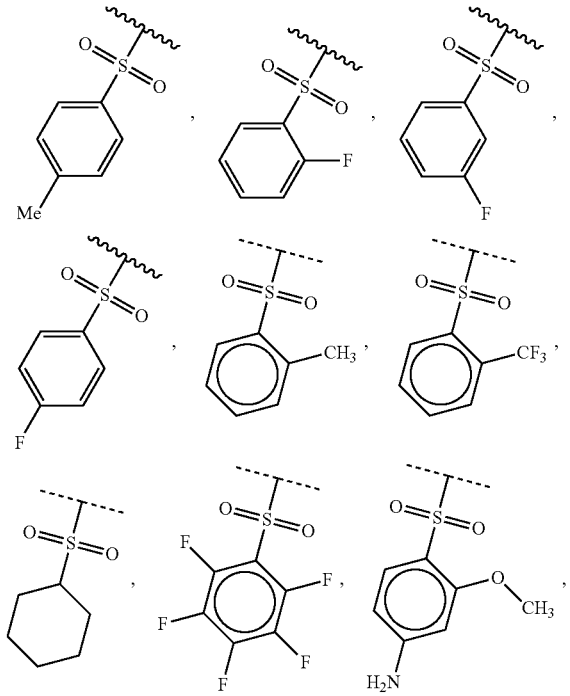

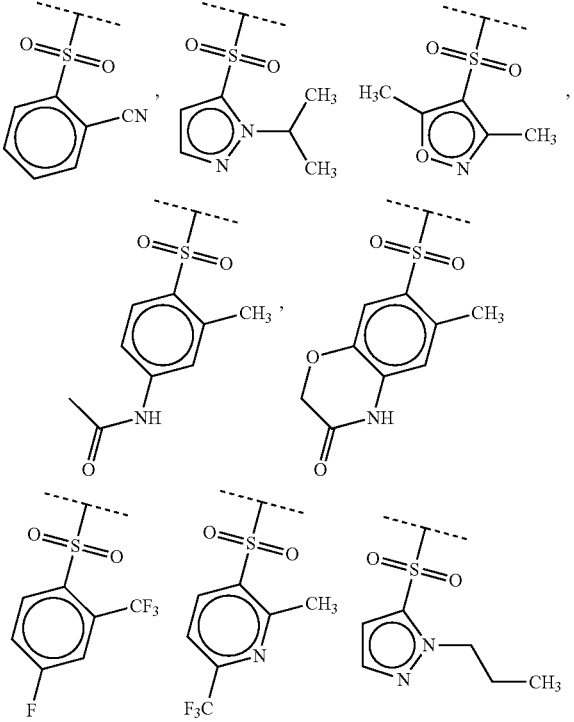

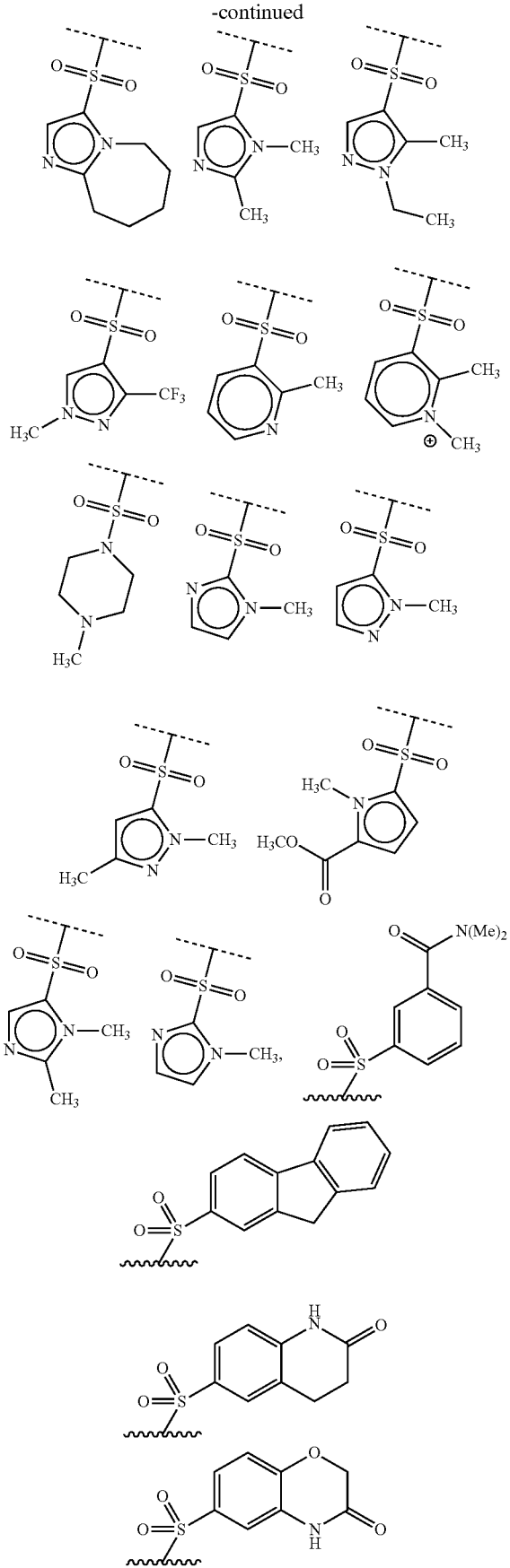
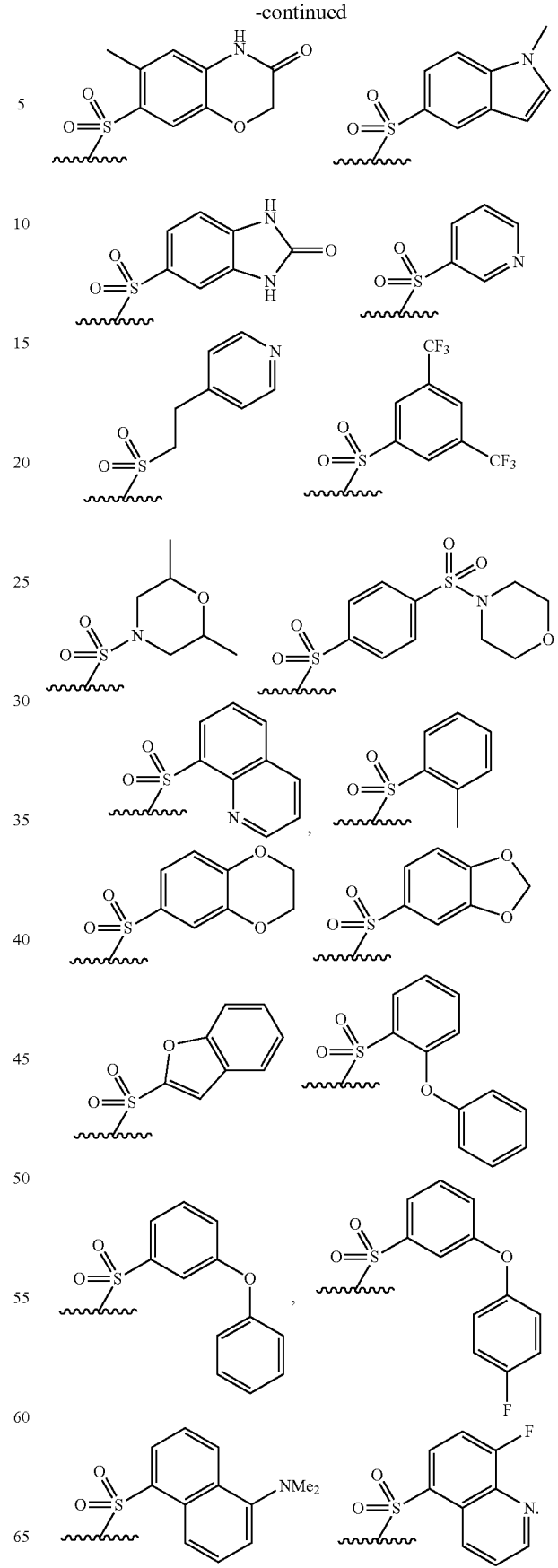

Compounds of Formula (V)

In certain embodiments, the invention provides a compound of Formula (V):

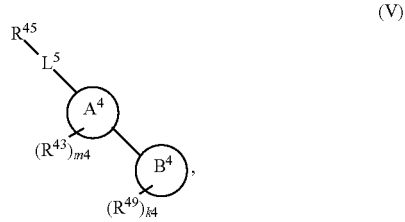

or a pharmaceutically acceptable salt, solvate, hydrate, polymorph, co-crystal, tautomer, stereoisomer, prodrug, or isotopically labeled derivative thereof,
wherein:

$R^{45}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, $-OR^{45a}$, $-N(R^{45a})_2$, $-S(=O)_2R^{45a}$, $-S(=O)_2OR^{45a}$, or $-S(=O)_2N(R^{45a})_2$ wherein each $R^{45a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{45a}$ are joined to form an optionally substituted heteroaryl or optionally substituted heterocyclic ring;

$L^5$ is a bond, optionally substituted alkylene, optionally substituted alkenylene, optionally substituted alkynylene, optionally substituted heteroalkylene, optionally substituted, heteroalkenylene, optionally substituted heteroalkynylene, or optionally substituted acylene;

Ring $A^4$ is 6-membered arylene or 5-7 membered heteroarylene;

Ring $B^4$ is 6 membered aryl, or 5-7 membered heteroaryl;

each $R^{43}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, $-NO_2$, $-CN$, $-OR^{43a}$, $-N(R^{43a})_2$, or two $R^{43}$ are joined to form an optionally substituted carbocyclic, heterocyclic, aryl, or heteroaryl ring, wherein each $R^{43a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{43a}$ are joined to form an optionally substituted heteroaryl or optionally substituted heterocyclic ring;

each $R^{49}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, $-NO_2$, $-CN$, $-OR^{49a}$, $-N(R^{49a})_2$, $-S(=O)_2R^{49a}$, $-S(=O)_2OR^{49a}$, or $-S(=O)_2N(R^{49a})_2$, or two $R^{49}$ are joined to form an optionally substituted carbocyclic, heterocyclic, aryl, or heteroaryl ring, wherein each $R^{49a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two $R^{49a}$ are joined to form an optionally substituted heteroaryl or optionally substituted heterocyclic ring;

m4 is 0, 1, 2, 3, or 4; and k4 is 0, 1, 2, 3, 4, or 5;

wherein the sum of m4 and k4 is at least one, and at least one $R^{43}$ or $R^{49}$ is attached ortho to the bond between Rings $A^4$ and $B^4$.

In certain embodiments, the compound of Formula (V) selectively inhibits the activity of IDE for degradation of a first substrate over the activity of IDE for degradation of a second substrate. In certain embodiments, the compound of Formula (V) selectively inhibits the activity of IDE for degradation of insulin over the activity of IDE for degradation of a second substrate (e.g., glucagon, amylin). In certain embodiments, the compound of Formula (V) selectively inhibits the activity of IDE for degradation of insulin over the activity of IDE for degradation of glucagon. In certain embodiments, the compound of Formula (V) selectively inhibits the activity of IDE for degradation of insulin over the activity of IDE for degradation of more than one other substrate.

In certain embodiments, the compound of Formula (V) is a compound of Formula:

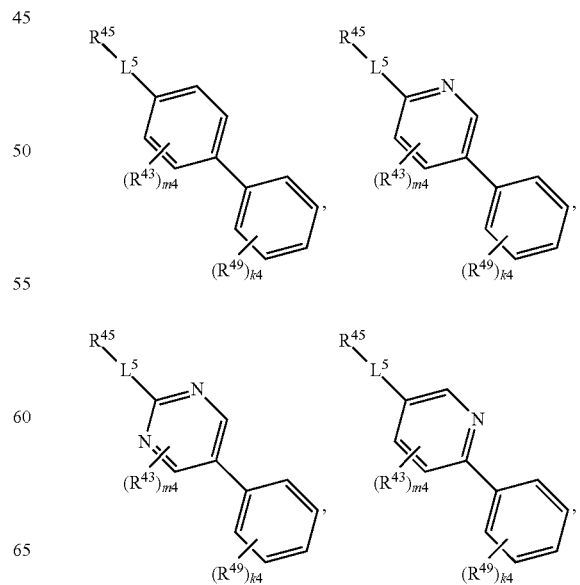

-continued

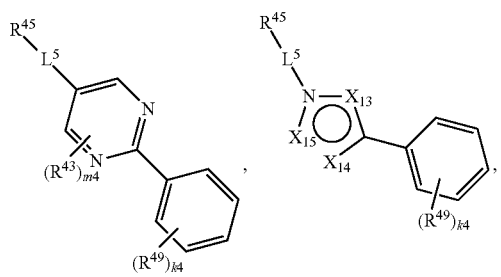

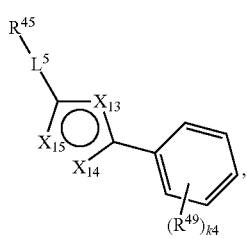

or a pharmaceutically acceptable salt, solvate, hydrate, polymorph, co-crystal, tautomer, stereoisomer, prodrug, or isotopically labeled derivative thereof, wherein $L^4$, $R^{43}$, $R^{45}$, $R^{49}$, m4, and k4 are as described herein, m4 is 0, 1, or 2; and $X_{13}$, $X_{14}$, and $X_{15}$ are selected from the group consisting of C, CH, C($R^{43}$), O, S, N, and N($R^{43a}$), as valency permits.

In certain embodiments, the compound of Formula (V) is a compound of Formula (V-a-1) or (V-a-2):

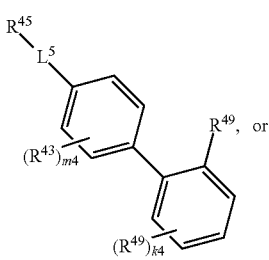

(V-a-1)

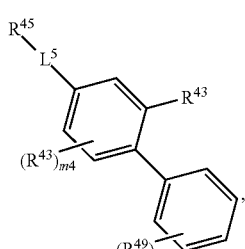

(V-a-2)

or a pharmaceutically acceptable salt, solvate, hydrate, polymorph, co-crystal, tautomer, stereoisomer, prodrug, or isotopically labeled derivative thereof, wherein $L^4$, $R^{43}$, $R^{45}$, $R^{49}$ m4, and k4 are as described herein.

In certain embodiments, the compound of Formula (V) is a compound of Formula (V-b-1) or (V-b-2):

(V-b-1)

(V-b-2)

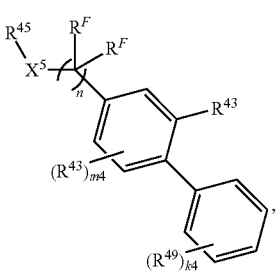

or a pharmaceutically acceptable salt, solvate, hydrate, polymorph, co-crystal, tautomer, stereoisomer, prodrug, or isotopically labeled derivative thereof, wherein:

each $R^F$ is independently hydrogen, halogen, optionally substituted alkyl, optionally substituted acyl, —$OR^{Fa}$, or —$N(R^{Fa})_2$, wherein each $R^{Fa}$ is independently hydrogen, optionally substituted alkyl, optionally substituted acyl, an oxygen protecting group, or a nitrogen protecting group, or two $R^{Fa}$ are joined to form an optionally substituted heterocyclic or optionally substituted heteroaryl ring;

n is 1, 2, 3, 4, 5, or 6.

$R^{43}$, $R^{45}$, $R^{49}$, m4, and k4 are as described herein.

In certain embodiments, the compound of Formula (V) is a compound of Formula (V-c-1) or (V-c-2):

(V-c-1)

(V-c-2)

or a pharmaceutically acceptable salt, solvate, hydrate, polymorph, co-crystal, tautomer, stereoisomer, prodrug, or isotopically labeled derivative thereof, wherein:

$X^5$ is —O— or —NR$^X$—, and R$^X$ is hydrogen, optionally substituted $C_{1-6}$ alkyl, optionally substituted acyl, or a nitrogen protecting group;

each R$^F$ is independently hydrogen, halogen, optionally substituted alkyl, optionally substituted acyl, —OR$^{Fa}$, or —N(R$^{Fa}$)$_2$, wherein each R$^{Fa}$ is independently hydrogen, optionally substituted alkyl, optionally substituted acyl, an oxygen protecting group, or a nitrogen protecting group, or two R$^{Fa}$ are joined to form an optionally substituted heterocyclic or optionally substituted heteroaryl ring;

n is 1, 2, 3, 4, 5, or 6.

R$^{43}$, R$^{45}$, R$^{49}$, m4, and k4 are as described herein.

L$^5$

As generally described herein, L$^5$ is a bond, optionally substituted alkylene, optionally substituted alkenylene, optionally substituted alkynylene, optionally substituted heteroalkylene, optionally substituted, heteroalkenylene, optionally substituted heteroalkynylene, or optionally substituted acylene.

In certain embodiments, L$^5$ is a bond, such that R$^{45}$ and Ring A$^4$ are directly attached. In certain embodiments, L$^5$ is optionally substituted alkylene. In certain embodiments, L$^5$ is optionally substituted alkenylene. In certain embodiments, L$^5$ is optionally substituted alkynylene. In certain embodiments, L$^5$ is —C≡C—. In certain embodiments, L$^5$ is —C(=O)—.

In certain embodiments, L$^5$ is optionally substituted heteroalkylene. In some embodiments, L$^5$ is optionally substituted heteroalkylene, wherein one carbon atom is replaced with oxygen. In some embodiments, L$^5$ is optionally substituted heteroalkylene, wherein one carbon atom is replaced with nitrogen. In certain embodiments, L$^5$ is optionally substituted heteroalkenylene. In certain embodiments, L$^5$ is optionally substituted heteroalkynylene.

In certain embodiments, L$^5$ is optionally substituted acylene. In certain embodiments, L$^5$ is —C(=O)NR$^L$—, e.g., —C(=O)NH—. In certain embodiments, L$^5$ is —NR$^L$C(=O)—, e.g., —NHC(=O)—. In certain embodiments, R$^L$ is hydrogen. In certain embodiments, R$^L$ is optionally substituted $C_{1-6}$ alkyl. In certain embodiments, R$^L$ is a nitrogen protecting group.

In certain embodiments, L$^5$ is —(CR$^{F2}$)$_n$—, wherein each R$^F$ is independently hydrogen, halogen, optionally substituted alkyl, optionally substituted acyl, —OR$^{Fa}$, or —N(R$^{Fa}$)$_2$; each R$^{Fa}$ is independently hydrogen, optionally substituted alkyl, optionally substituted acyl, an oxygen protecting group, or a nitrogen protecting group, or two R$^{Fa}$ are joined to form an optionally substituted heterocyclic or optionally substituted heteroaryl ring; and n is 1, 2, 3, 4, 5, or 6.

In certain embodiments, n is 1. In certain embodiments, n is 2. In certain embodiments, n is 3. In certain embodiments, n is 4. In certain embodiments, n is 5. In certain embodiments, n is 6.

In certain embodiments, at least one R$^F$ is halogen, e.g., F, Cl, Br, I. In certain embodiments, at least one R$^F$ is optionally substituted alkyl. In certain embodiments, at least one R$^F$ is optionally substituted acyl, e.g., —C(=O)Me, —C(=O)OH, —C(=O)OMe. In certain embodiments, at least one R$^F$ is —OR$^{Fa}$, e.g., —OH. In certain embodiments, at least one R$^F$ is —N(R$^{Fa}$)$_2$, e.g., —NH$_2$.

In certain embodiments, L$^5$ is —(CR$^{F2}$)$_n$X$^5$—, wherein X$^5$ is —O— or —NR$^X$—, and R$^X$ is hydrogen, optionally substituted $C_{1-6}$ alkyl, optionally substituted acyl, or a nitrogen protecting group, and R$^F$ and n are as described herein. In some embodiments, X$^5$ is —O—, In some embodiments, X$^5$ is —NR$^X$—, e.g., —NH—.

In certain embodiments, the compound of Formula (IV) or (V) is a compound in Table 5, or a pharmaceutically acceptable salt, solvate, hydrate, polymorph, co-crystal, tautomer, stereoisomer, prodrug, or isotopically labeled derivative thereof.

TABLE 5

Exemplary compounds of Formula (IV) or (V).

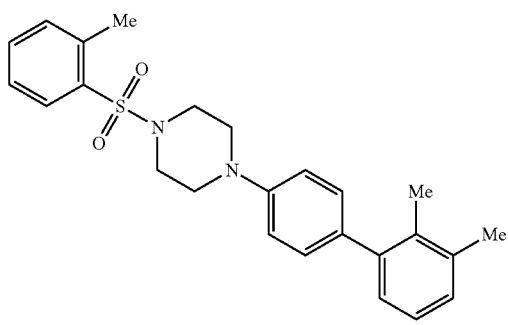 [SMILES: Cc1ccccc1S(=O)(=O)N1CCN(c2ccc(-c3cccc(C)c3C)cc2)CC1]

J1

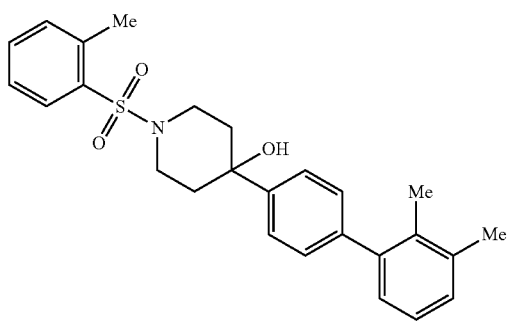 [SMILES: Cc1ccccc1S(=O)(=O)N1CCC(O)(c2ccc(-c3cccc(C)c3C)cc2)CC1]

J2

TABLE 5-continued
Exemplary compounds of Formula (IV) or (V).
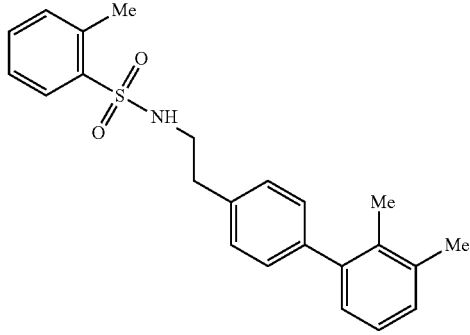 [SMILES: Cc1ccccc1S(=O)(=O)NCCc1ccc(-c2cccc(C)c2C)cc1]
J3
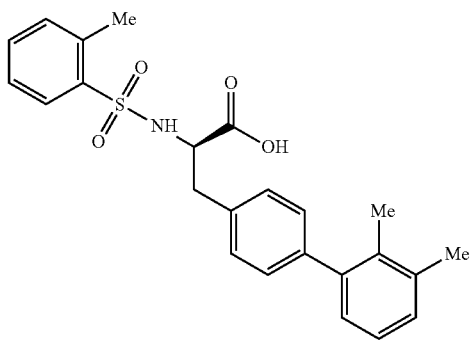 [SMILES: Cc1ccccc1S(=O)(=O)N[C@H](Cc1ccc(-c2cccc(C)c2C)cc1)C(=O)O]
J4
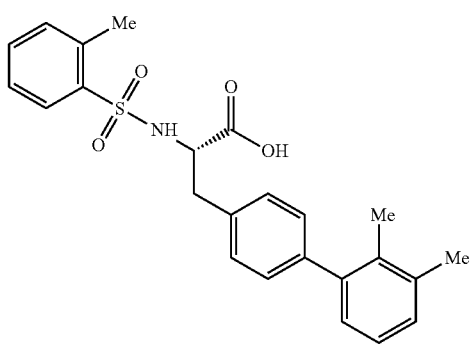 [SMILES: Cc1ccccc1S(=O)(=O)N[C@@H](Cc1ccc(-c2cccc(C)c2C)cc1)C(=O)O]
J5
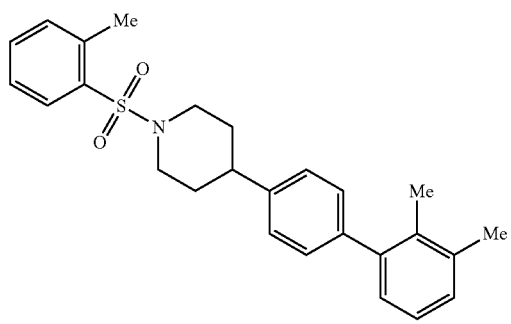 [SMILES: Cc1ccccc1S(=O)(=O)N1CCC(c2ccc(-c3cccc(C)c3C)cc2)CC1]
J6

TABLE 5-continued
Exemplary compounds of Formula (IV) or (V).
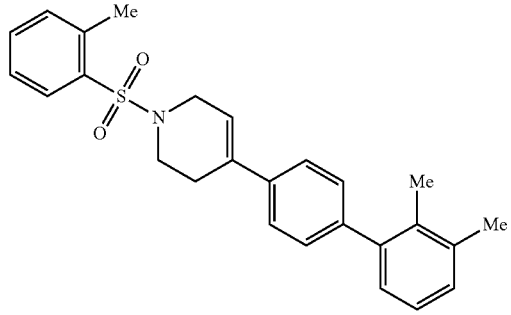 [SMILES: Cc1ccccc1S(=O)(=O)N1CC=C(c2ccc(-c3cccc(C)c3C)cc2)CC1]
J7
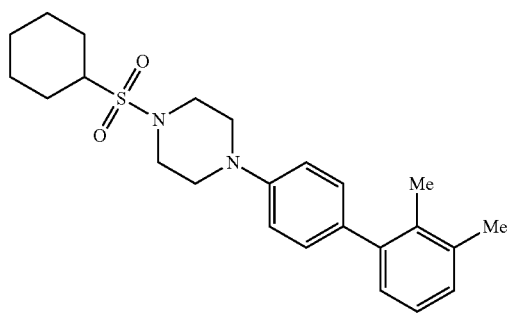 [SMILES: Cc1cccc(-c2ccc(N3CCN(S(=O)(=O)C4CCCCC4)CC3)cc2)c1C]
J8
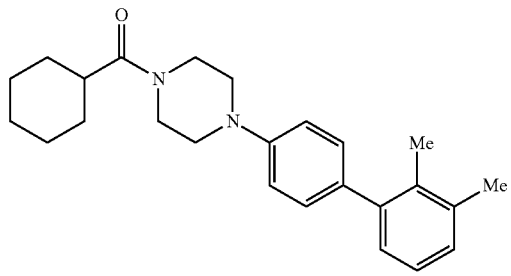 [SMILES: Cc1cccc(-c2ccc(N3CCN(C(=O)C4CCCCC4)CC3)cc2)c1C]
J9
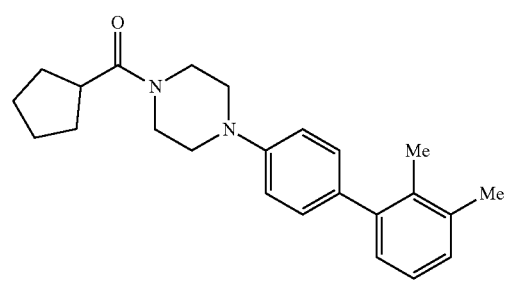 [SMILES: Cc1cccc(-c2ccc(N3CCN(C(=O)C4CCCC4)CC3)cc2)c1C]
J10
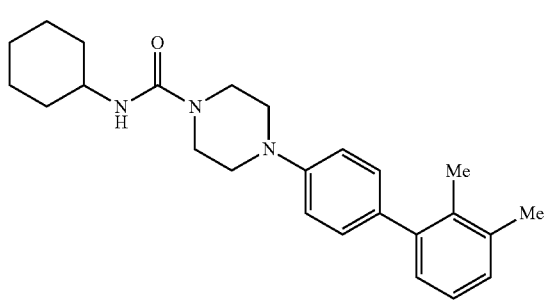 [SMILES: Cc1cccc(-c2ccc(N3CCN(C(=O)NC4CCCCC4)CC3)cc2)c1C]
J11

TABLE 5-continued
Exemplary compounds of Formula (IV) or (V).
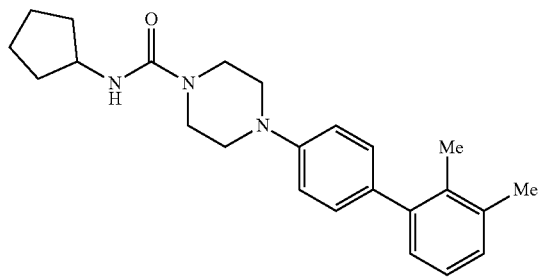 [SMILES: Cc1cccc(-c2ccc(N3CCN(C(=O)NC4CCCC4)CC3)cc2)c1C]
J12
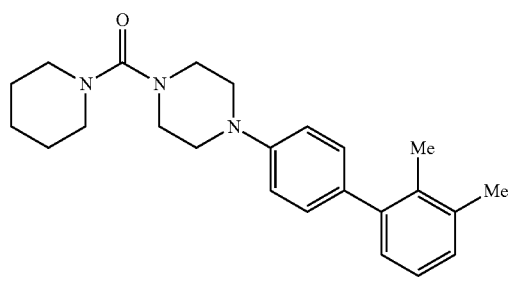 [SMILES: Cc1cccc(-c2ccc(N3CCN(C(=O)N4CCCCC4)CC3)cc2)c1C]
J13
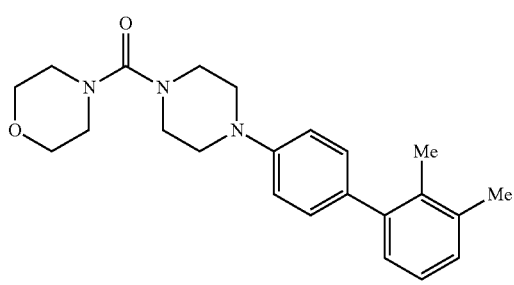 [SMILES: Cc1cccc(-c2ccc(N3CCN(C(=O)N4CCOCC4)CC3)cc2)c1C]
J14
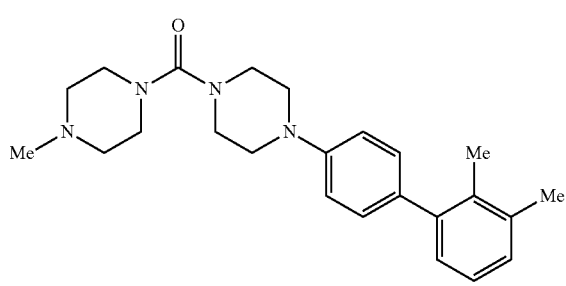 [SMILES: Cc1cccc(-c2ccc(N3CCN(C(=O)N4CCN(C)CC4)CC3)cc2)c1C]
J15
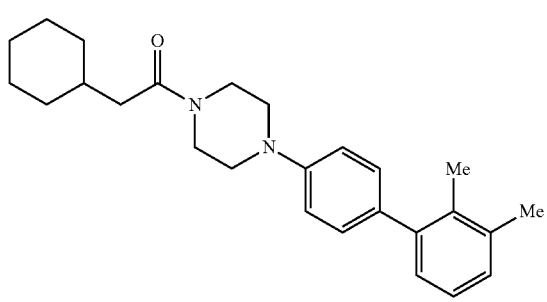 [SMILES: Cc1cccc(-c2ccc(N3CCN(C(=O)CC4CCCCC4)CC3)cc2)c1C]
J16

TABLE 5-continued
Exemplary compounds of Formula (IV) or (V).
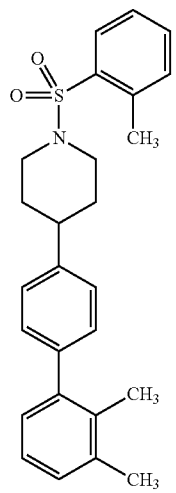 [SMILES: Cc1ccccc1S(=O)(=O)N1CCC(c2ccc(-c3cccc(C)c3C)cc2)CC1] JPM-6
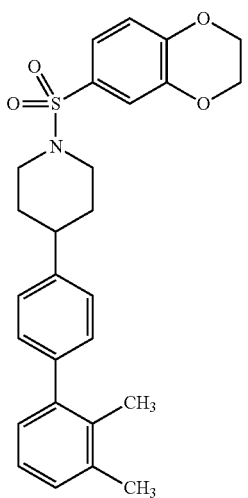 [SMILES: Cc1cccc(-c2ccc(C3CCN(S(=O)(=O)c4ccc5c(c4)OCCO5)CC3)cc2)c1C] A01
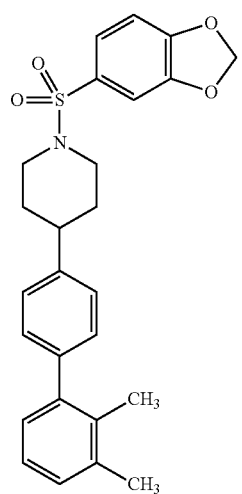 [SMILES: Cc1cccc(-c2ccc(C3CCN(S(=O)(=O)c4ccc5c(c4)OCO5)CC3)cc2)c1C] A02

TABLE 5-continued
Exemplary compounds of Formula (IV) or (V).
A03
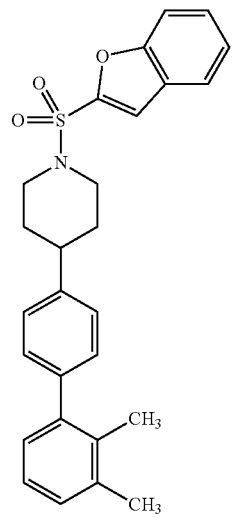 [SMILES: Cc1cccc(-c2ccc(C3CCN(S(=O)(=O)c4cc5ccccc5o4)CC3)cc2)c1C]
A04
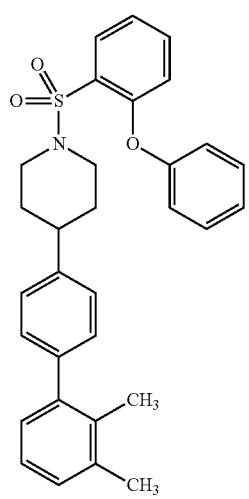 [SMILES: Cc1cccc(-c2ccc(C3CCN(S(=O)(=O)c4ccccc4Oc4ccccc4)CC3)cc2)c1C]
A05
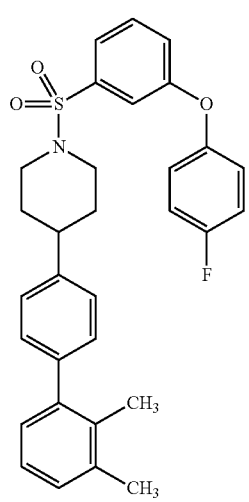 [SMILES: Cc1cccc(-c2ccc(C3CCN(S(=O)(=O)c4cccc(Oc5ccc(F)cc5)c4)CC3)cc2)c1C]

TABLE 5-continued
Exemplary compounds of Formula (IV) or (V).
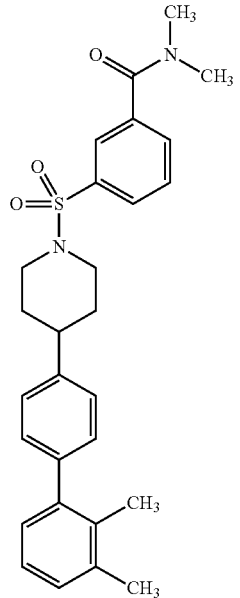 [SMILES: Cc1cccc(-c2ccc(C3CCN(S(=O)(=O)c4cccc(C(=O)N(C)C)c4)CC3)cc2)c1C]
A06
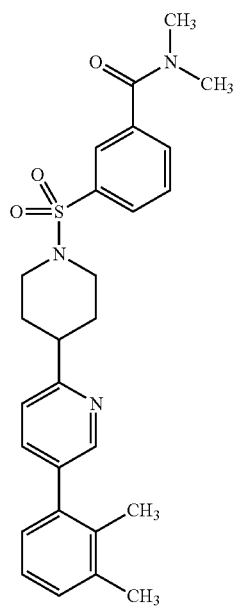 [SMILES: Cc1cccc(-c2ccc(C3CCN(S(=O)(=O)c4cccc(C(=O)N(C)C)c4)CC3)nc2)c1C]
A06-2-py TABLE 5-continued
Exemplary compounds of Formula (IV) or (V).
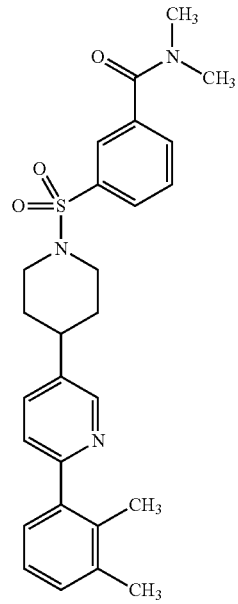 [SMILES: Cc1cccc(-c2ccc(C3CCN(S(=O)(=O)c4cccc(C(=O)N(C)C)c4)CC3)cn2)c1C]
A06-3-py
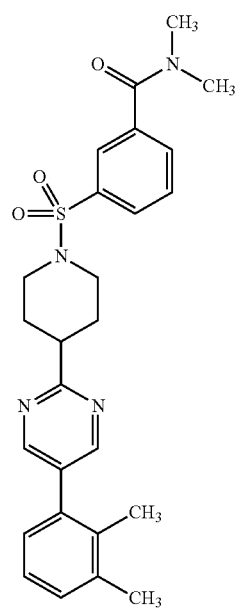 [SMILES: Cc1cccc(-c2cnc(C3CCN(S(=O)(=O)c4cccc(C(=O)N(C)C)c4)CC3)nc2)c1C]
A06-2-pyrimid TABLE 5-continued
Exemplary compounds of Formula (IV) or (V).
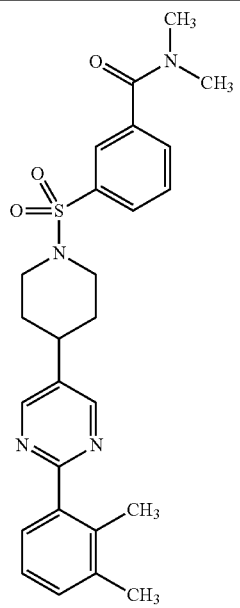
A06-5-pyrimid
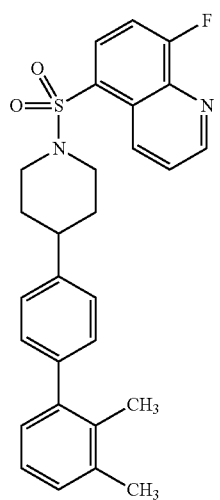 [SMILES: Cc1cccc(-c2ccc(C3CCN(S(=O)(=O)c4ccc(F)c5ncccc45)CC3)cc2)c1C]
A07
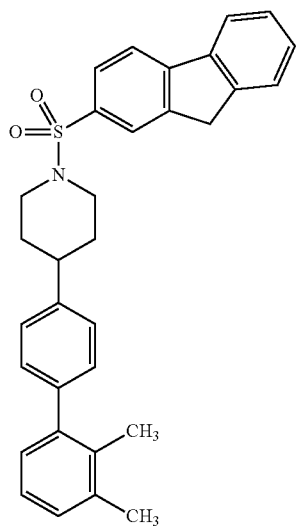 [SMILES: Cc1cccc(-c2ccc(C3CCN(S(=O)(=O)c4ccc5c(c4)Cc4ccccc4-5)CC3)cc2)c1C]
A08

TABLE 5-continued
Exemplary compounds of Formula (IV) or (V).
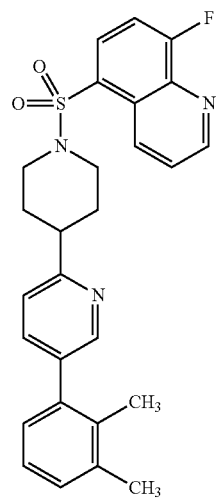 [SMILES: Cc1cccc(-c2ccc(C3CCN(S(=O)(=O)c4ccc(F)c5ncccc45)CC3)nc2)c1C] A07-2-py
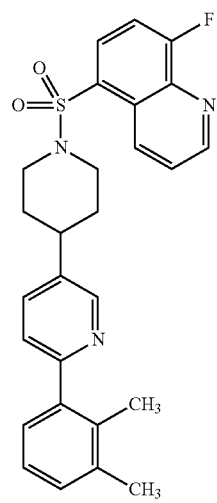 [SMILES: Cc1cccc(-c2ccc(C3CCN(S(=O)(=O)c4ccc(F)c5ncccc45)CC3)cn2)c1C] A07-3-py
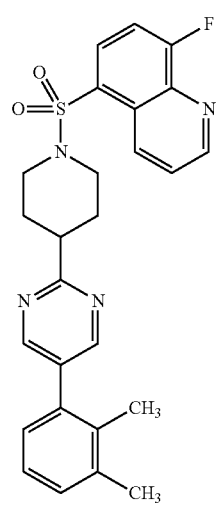 [SMILES: Cc1cccc(-c2cnc(C3CCN(S(=O)(=O)c4ccc(F)c5ncccc45)CC3)nc2)c1C] A07-2-pyrimid TABLE 5-continued
Exemplary compounds of Formula (IV) or (V).
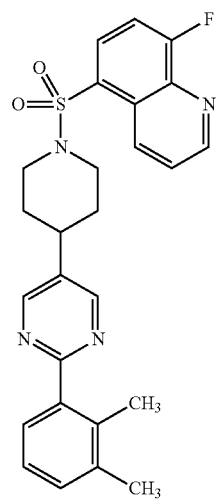 [SMILES: Cc1cccc(-c2ncc(C3CCN(S(=O)(=O)c4ccc(F)c5ncccc45)CC3)cn2)c1C]
A07-5-pyrimid
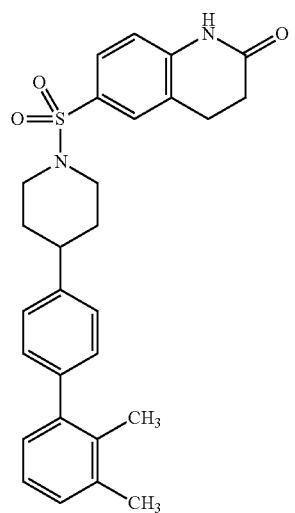 [SMILES: Cc1cccc(-c2ccc(C3CCN(S(=O)(=O)c4ccc5c(c4)CCC(=O)N5)CC3)cc2)c1C]
A10
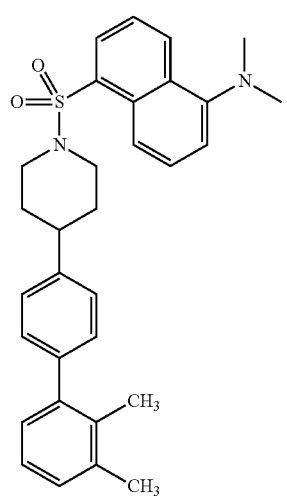 [SMILES: Cc1cccc(-c2ccc(C3CCN(S(=O)(=O)c4cccc5c(N(C)C)cccc45)CC3)cc2)c1C]
A11

TABLE 5-continued
Exemplary compounds of Formula (IV) or (V).
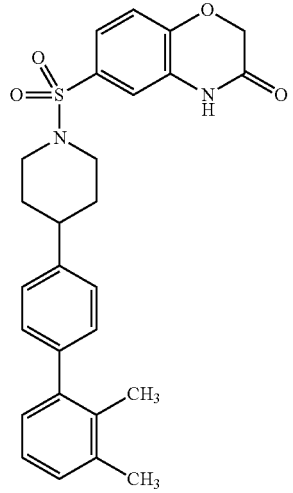 [SMILES: Cc1cccc(-c2ccc(C3CCN(S(=O)(=O)c4ccc5c(c4)NC(=O)CO5)CC3)cc2)c1C] A12
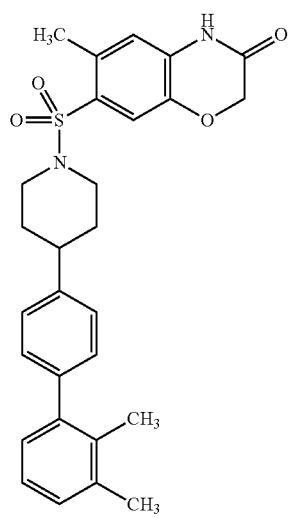 [SMILES: Cc1cc2c(cc1S(=O)(=O)N1CCC(c3ccc(-c4cccc(C)c4C)cc3)CC1)OCC(=O)N2] A13
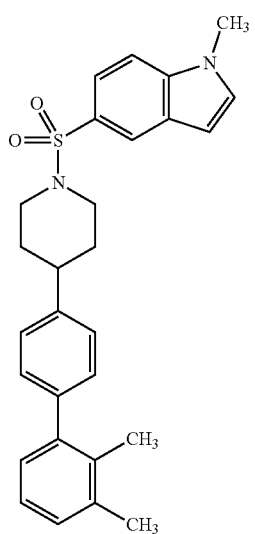 [SMILES: Cc1cccc(-c2ccc(C3CCN(S(=O)(=O)c4ccc5c(ccn5C)c4)CC3)cc2)c1C] A14

TABLE 5-continued
Exemplary compounds of Formula (IV) or (V).
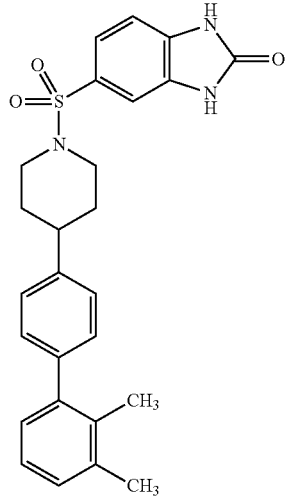 [SMILES: Cc1cccc(-c2ccc(C3CCN(S(=O)(=O)c4ccc5[nH]c(=O)[nH]c5c4)CC3)cc2)c1C]
A15
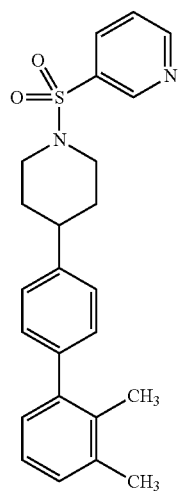 [SMILES: Cc1cccc(-c2ccc(C3CCN(S(=O)(=O)c4cccnc4)CC3)cc2)c1C]
A16
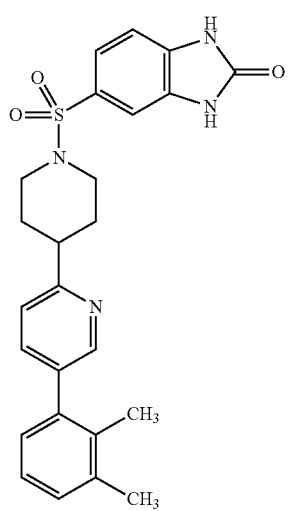 [SMILES: Cc1cccc(-c2ccc(C3CCN(S(=O)(=O)c4ccc5[nH]c(=O)[nH]c5c4)CC3)nc2)c1C]
A15-2-py TABLE 5-continued
Exemplary compounds of Formula (IV) or (V).
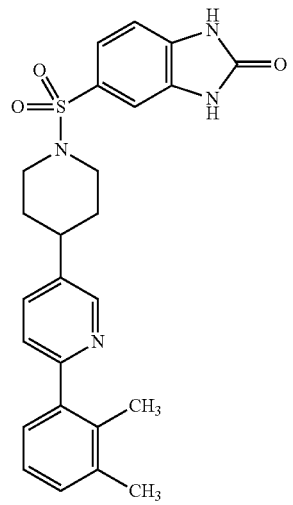
A15-3-py
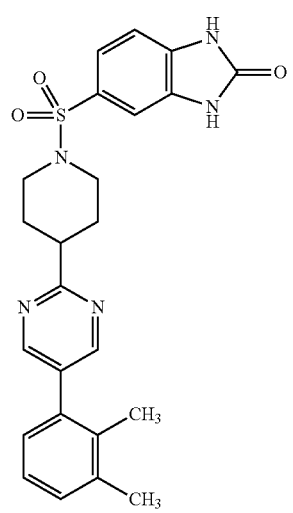 [SMILES: Cc1cccc(-c2cnc(C3CCN(S(=O)(=O)c4ccc5[nH]c(=O)[nH]c5c4)CC3)nc2)c1C]
A15-2-pyrimid
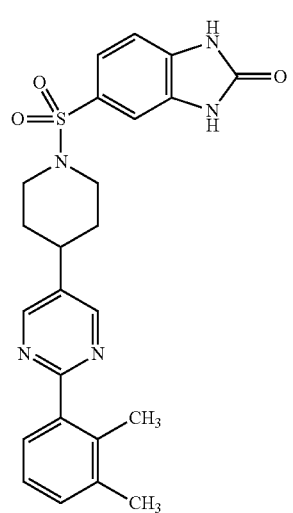 [SMILES: Cc1cccc(-c2ncc(C3CCN(S(=O)(=O)c4ccc5[nH]c(=O)[nH]c5c4)CC3)cn2)c1C]
A15-5-pyrimid TABLE 5-continued
Exemplary compounds of Formula (IV) or (V).
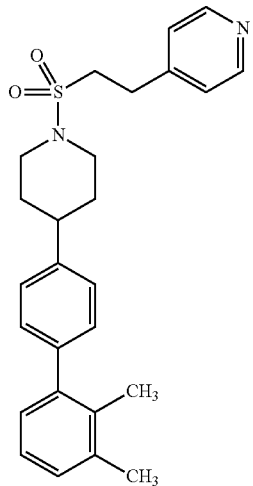 [SMILES: Cc1cccc(-c2ccc(C3CCN(S(=O)(=O)CCc4ccncc4)CC3)cc2)c1C]
A17
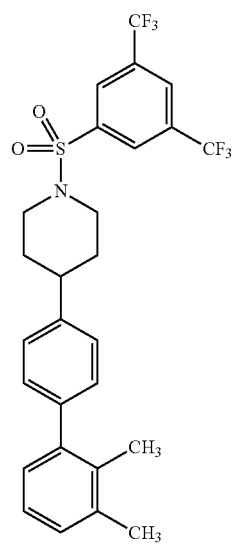 [SMILES: Cc1cccc(-c2ccc(C3CCN(S(=O)(=O)c4cc(C(F)(F)F)cc(C(F)(F)F)c4)CC3)cc2)c1C]
A18
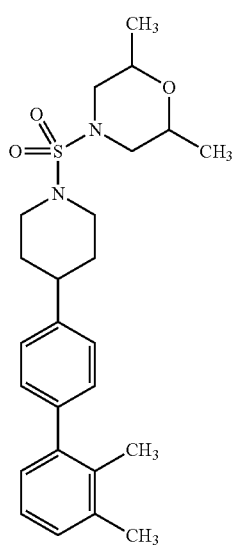 [SMILES: Cc1cccc(-c2ccc(C3CCN(S(=O)(=O)N4CC(C)OC(C)C4)CC3)cc2)c1C]
A19

TABLE 5-continued
Exemplary compounds of Formula (IV) or (V).
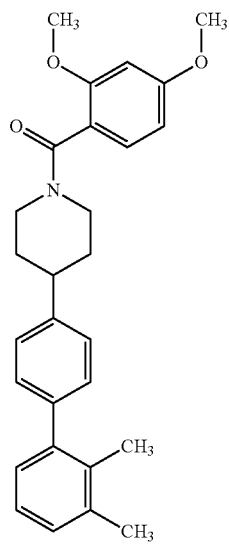 [SMILES: COc1ccc(C(=O)N2CCC(c3ccc(-c4cccc(C)c4C)cc3)CC2)c(OC)c1]
A21
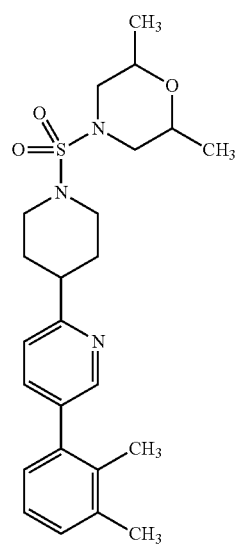 [SMILES: Cc1cccc(-c2ccc(C3CCN(S(=O)(=O)N4CC(C)OC(C)C4)CC3)nc2)c1C]
A19-2-py
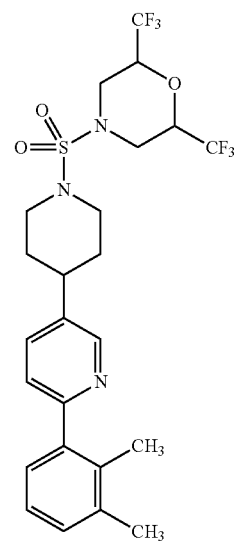 [SMILES: Cc1cccc(-c2ccc(C3CCN(S(=O)(=O)N4CC(C(F)(F)F)OC(C(F)(F)F)C4)CC3)cn2)c1C]
A19-3-py TABLE 5-continued
Exemplary compounds of Formula (IV) or (V).
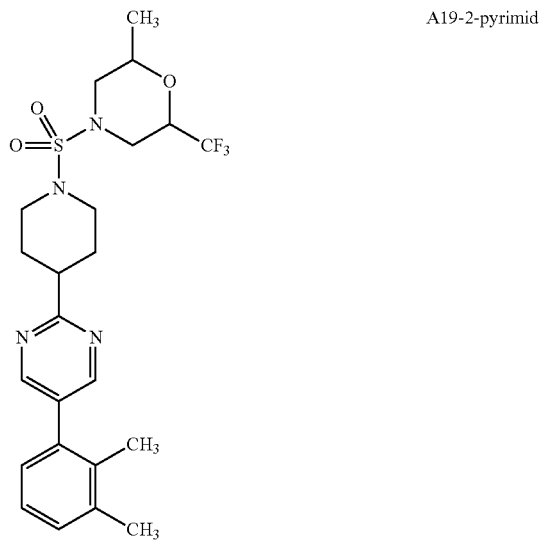
A19-2-pyrimid
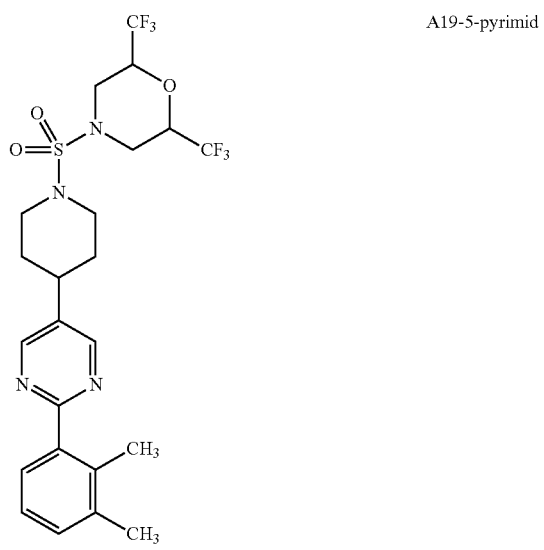
A19-5-pyrimid
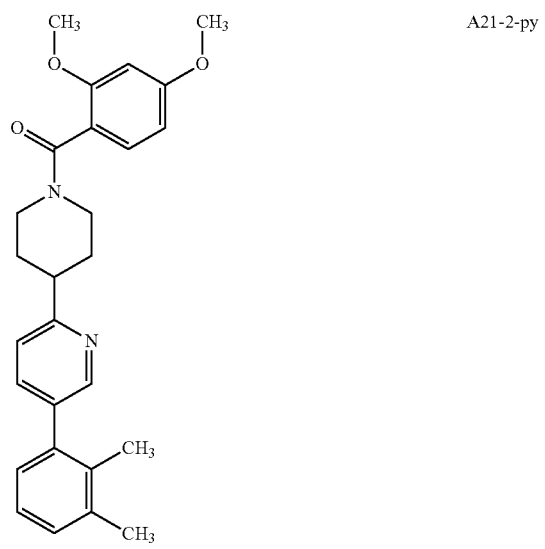
A21-2-py TABLE 5-continued
Exemplary compounds of Formula (IV) or (V).
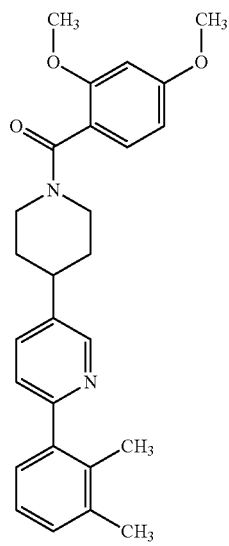
A21-3-py
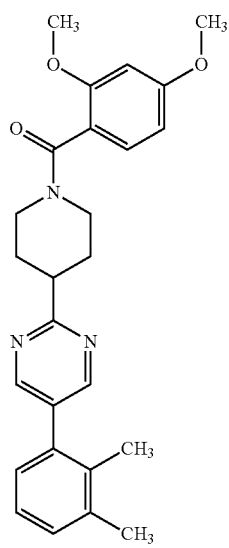 [SMILES: COc1ccc(C(=O)N2CCC(c3ccc(-c4cccc(C)c4C)cn3)CC2)c(OC)c1]
A21-2-pyrimid
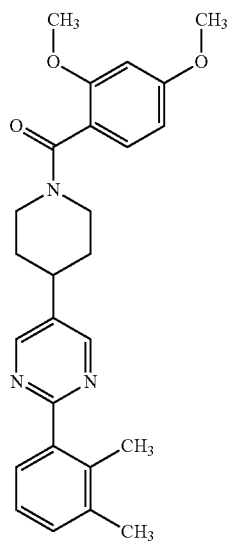 [SMILES: COc1ccc(C(=O)N2CCC(c3ccc(-c4cccc(C)c4C)nc3)CC2)c(OC)c1]
A21-5-pyrimid TABLE 5-continued
Exemplary compounds of Formula (IV) or (V).
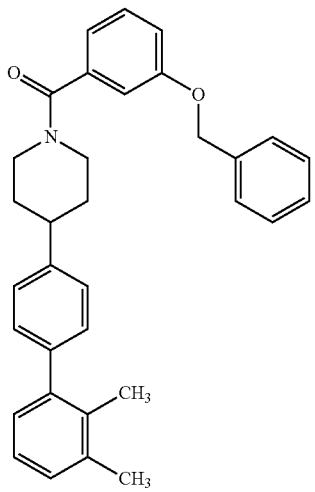 [SMILES: Cc1cccc(-c2ccc(C3CCN(C(=O)c4cccc(OCc5ccccc5)c4)CC3)cc2)c1C]
A22
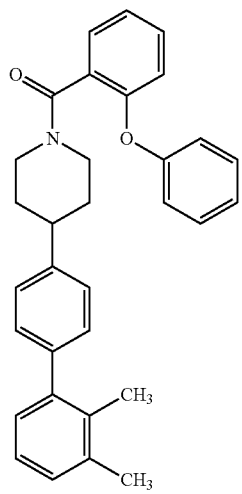 [SMILES: Cc1cccc(-c2ccc(C3CCN(C(=O)c4ccccc4Oc4ccccc4)CC3)cc2)c1C]
A23
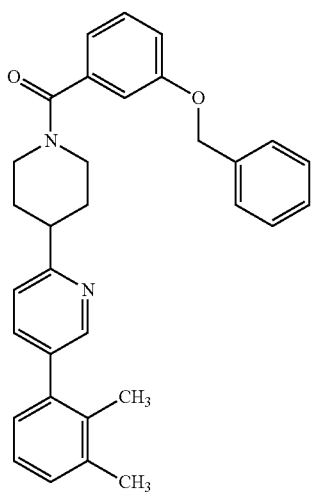 [SMILES: Cc1cccc(-c2ccc(C3CCN(C(=O)c4cccc(OCc5ccccc5)c4)CC3)nc2)c1C]
A22-2-py TABLE 5-continued
Exemplary compounds of Formula (IV) or (V).
A22-3-py
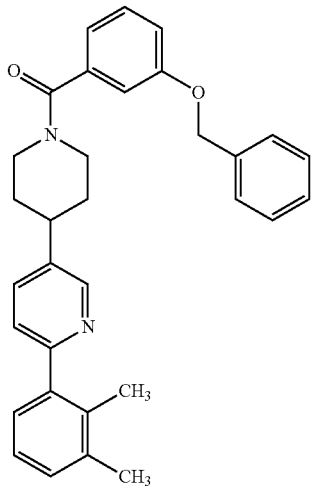 [SMILES: Cc1cccc(-c2ccc(C3CCN(C(=O)c4cccc(OCc5ccccc5)c4)CC3)cn2)c1C]
A22-2-pyrimid
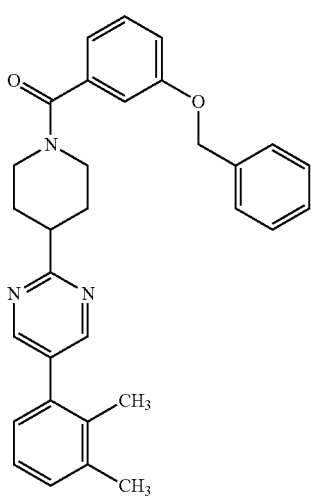 [SMILES: Cc1cccc(-c2cnc(C3CCN(C(=O)c4cccc(OCc5ccccc5)c4)CC3)nc2)c1C]
A22-5-pyrimid
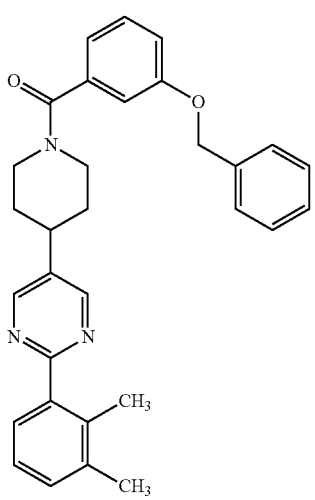 [SMILES: Cc1cccc(-c2ncc(C3CCN(C(=O)c4cccc(OCc5ccccc5)c4)CC3)cn2)c1C]

TABLE 5-continued
Exemplary compounds of Formula (IV) or (V).
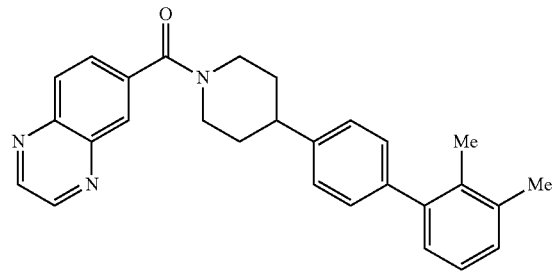 [SMILES: Cc1cccc(-c2ccc(C3CCN(C(=O)c4ccc5nccnc5c4)CC3)cc2)c1C]
J17
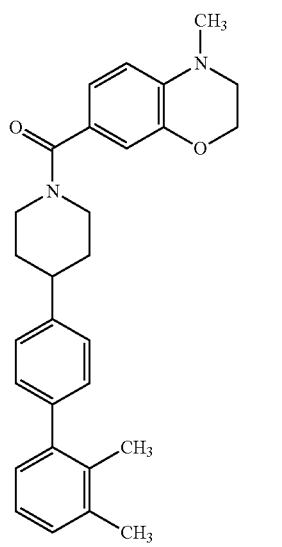 [SMILES: Cc1cccc(-c2ccc(C3CCN(C(=O)c4ccc5c(c4)OCCN5C)CC3)cc2)c1C]
A25
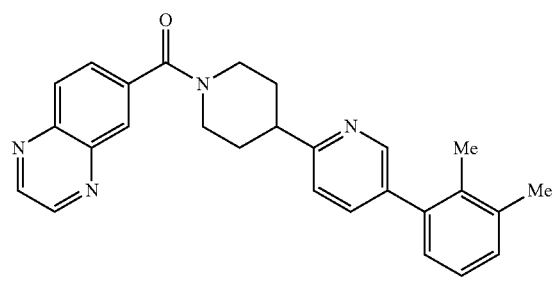 [SMILES: Cc1cccc(-c2ccc(C3CCN(C(=O)c4ccc5nccnc5c4)CC3)nc2)c1C]
J17-2-py
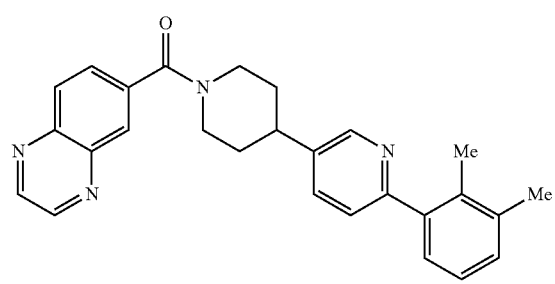 [SMILES: Cc1cccc(-c2ccc(C3CCN(C(=O)c4ccc5nccnc5c4)CC3)cn2)c1C]
J17-3-py TABLE 5-continued
Exemplary compounds of Formula (IV) or (V).
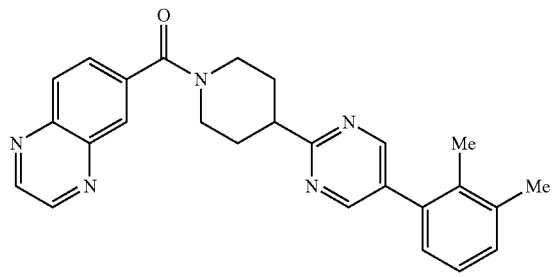 [SMILES: Cc1cccc(-c2cnc(C3CCN(C(=O)c4ccc5nccnc5c4)CC3)nc2)c1C]
J17-2-pyrimid
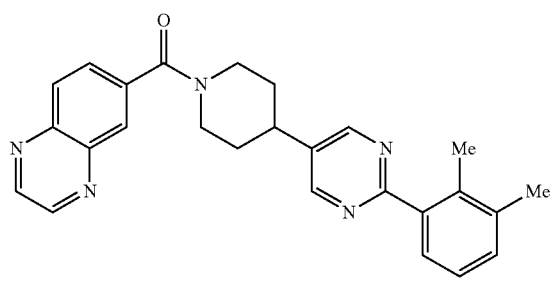 [SMILES: Cc1cccc(-c2ncc(C3CCN(C(=O)c4ccc5nccnc5c4)CC3)cn2)c1C]
J17-5-pyrimid
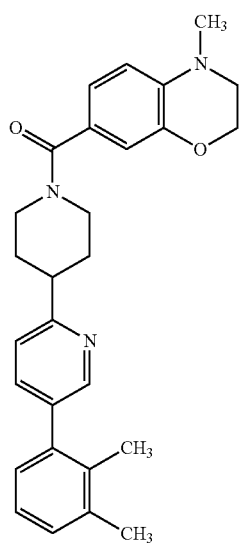
A25-2-py TABLE 5-continued
Exemplary compounds of Formula (IV) or (V).
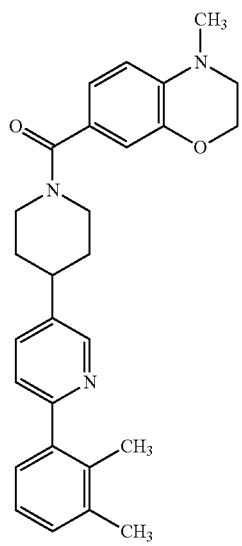
A25-3-py
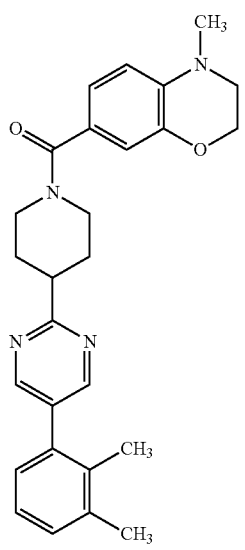 [SMILES: Cc1cccc(-c2ccc(C3CCN(C(=O)c4ccc5c(c4)OCCN5C)CC3)nc2)c1C]
A25-2-pyrimid
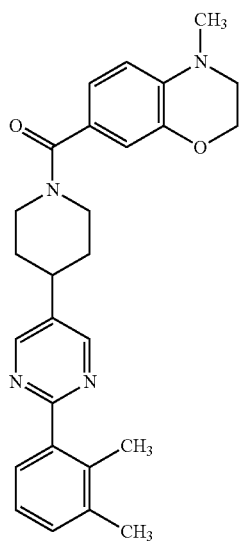 [SMILES: Cc1cccc(-c2ccc(C3CCN(C(=O)c4ccc5c(c4)OCCN5C)CC3)cn2)c1C]
A25-5-pyrimid TABLE 5-continued
Exemplary compounds of Formula (IV) or (V).
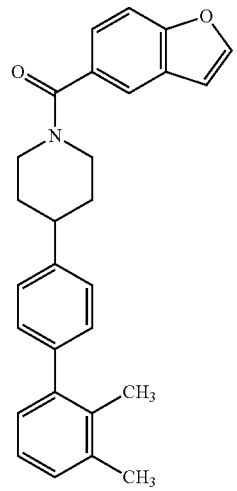 [SMILES: Cc1cccc(-c2ccc(C3CCN(C(=O)c4ccc5occc5c4)CC3)cc2)c1C]
A26
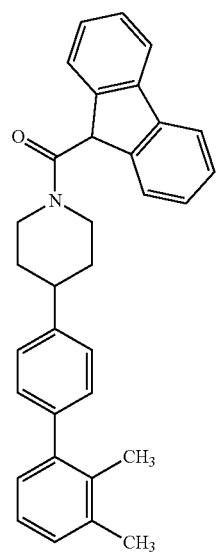 [SMILES: Cc1cccc(-c2ccc(C3CCN(C(=O)C4c5ccccc5-c5ccccc54)CC3)cc2)c1C]
A27
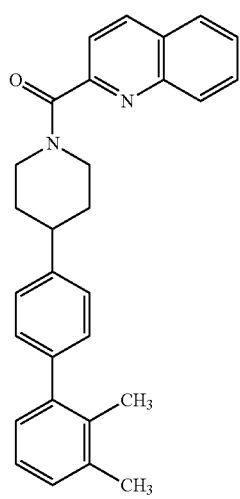 [SMILES: Cc1cccc(-c2ccc(C3CCN(C(=O)c4ccc5ccccc5n4)CC3)cc2)c1C]
A28

TABLE 5-continued
Exemplary compounds of Formula (IV) or (V).
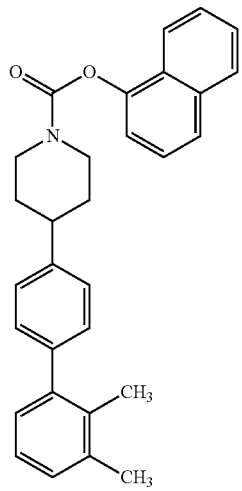 [SMILES: Cc1cccc(-c2ccc(C3CCN(C(=O)Oc4cccc5ccccc45)CC3)cc2)c1C]
A29
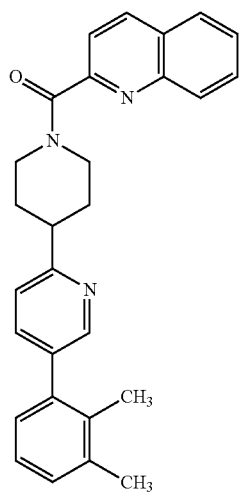
A28-2-py
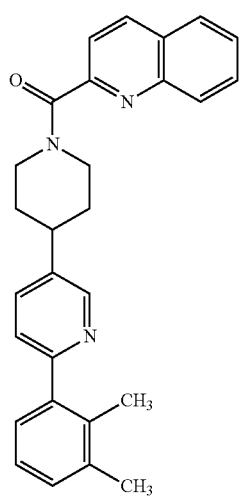
A28-3-py TABLE 5-continued
Exemplary compounds of Formula (IV) or (V).
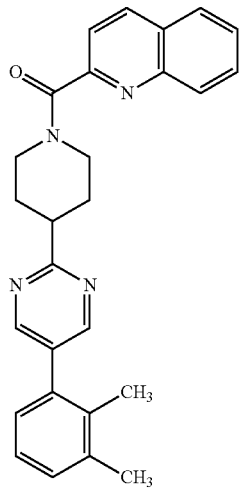 [SMILES: Cc1cccc(-c2ccc(C3CCN(C(=O)c4ccc5ccccc5n4)CC3)nc2)c1C]
A28-2-pyrimid
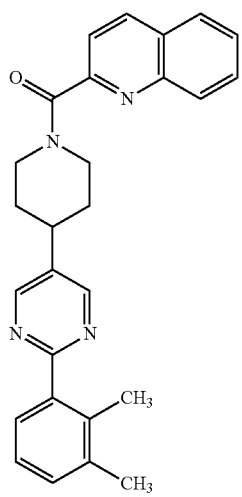 [SMILES: Cc1cccc(-c2ccc(C3CCN(C(=O)c4ccc5ccccc5n4)CC3)cn2)c1C]
A28-5-pyrimid
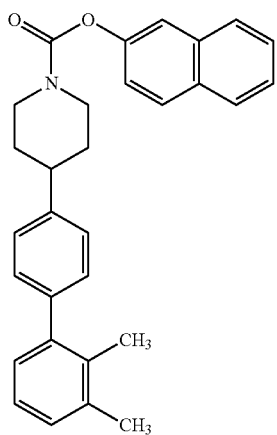 [SMILES: Cc1cccc(-c2ccc(C3CCN(C(=O)Oc4ccc5ccccc5c4)CC3)cc2)c1C]
A30

TABLE 5-continued
Exemplary compounds of Formula (IV) or (V).
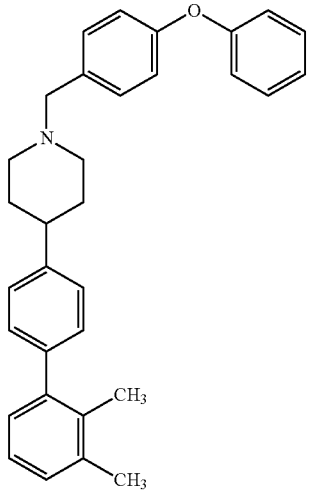 [SMILES: Cc1cccc(-c2ccc(C3CCN(Cc4ccc(Oc5ccccc5)cc4)CC3)cc2)c1C]
A31
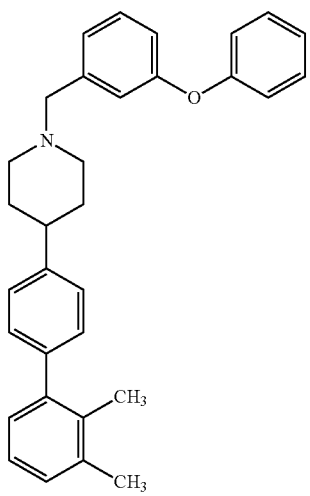 [SMILES: Cc1cccc(-c2ccc(C3CCN(Cc4cccc(Oc5ccccc5)c4)CC3)cc2)c1C]
A32
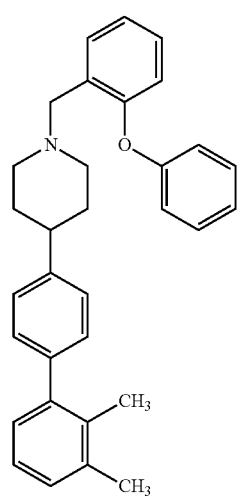 [SMILES: Cc1cccc(-c2ccc(C3CCN(Cc4ccccc4Oc4ccccc4)CC3)cc2)c1C]
A33

TABLE 5-continued
Exemplary compounds of Formula (IV) or (V).
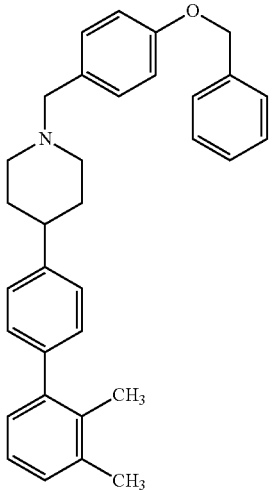 [SMILES: Cc1cccc(-c2ccc(C3CCN(Cc4ccc(OCc5ccccc5)cc4)CC3)cc2)c1C]
A34
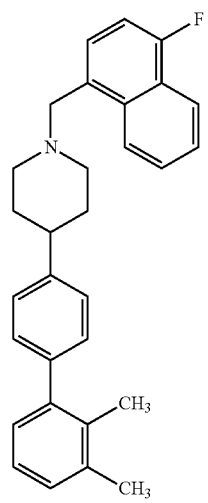 [SMILES: Cc1cccc(-c2ccc(C3CCN(Cc4ccc(F)c5ccccc45)CC3)cc2)c1C]
A35
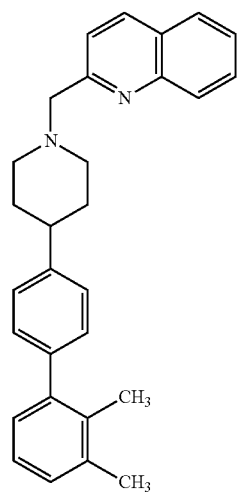 [SMILES: Cc1cccc(-c2ccc(C3CCN(Cc4ccc5ccccc5n4)CC3)cc2)c1C]
A39

TABLE 5-continued
Exemplary compounds of Formula (IV) or (V).
A40
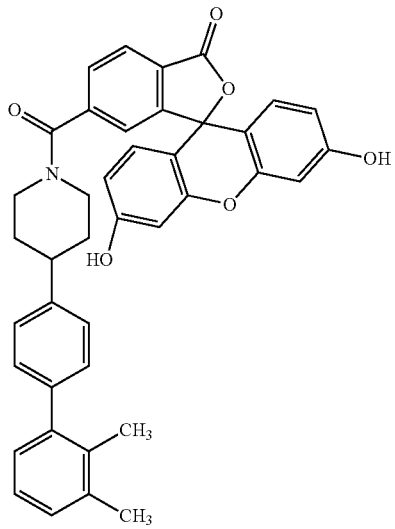 [SMILES: Cc1cccc(-c2ccc(C3CCN(C(=O)c4ccc5c(c4)C4(OC5=O)c5ccc(O)cc5Oc5cc(O)ccc54)CC3)cc2)c1C]
A50
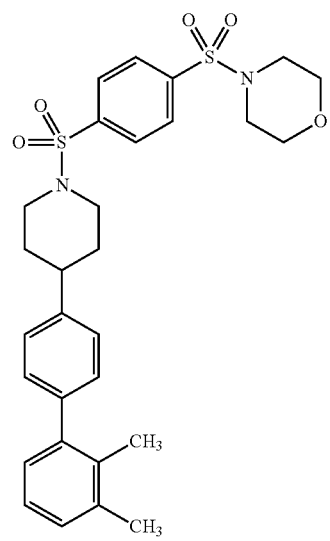 [SMILES: Cc1cccc(-c2ccc(C3CCN(S(=O)(=O)c4ccc(S(=O)(=O)N5CCOCC5)cc4)CC3)cc2)c1C]
A51
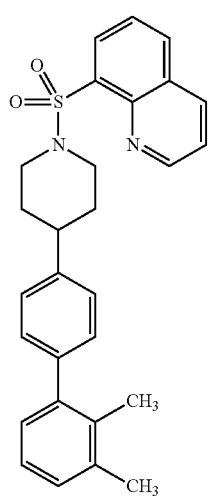 [SMILES: Cc1cccc(-c2ccc(C3CCN(S(=O)(=O)c4cccc5cccnc45)CC3)cc2)c1C]

TABLE 5-continued
Exemplary compounds of Formula (IV) or (V).
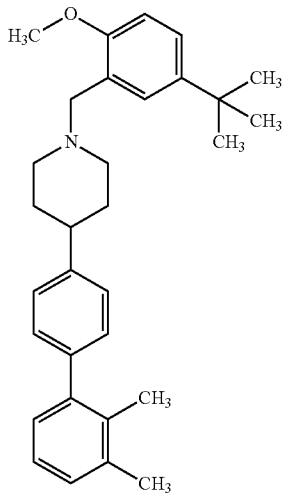 [SMILES: COc1ccc(C(C)(C)C)cc1CN1CCC(c2ccc(-c3cccc(C)c3C)cc2)CC1]
A52
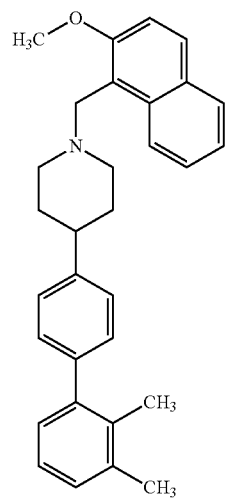 [SMILES: COc1ccc2ccccc2c1CN1CCC(c2ccc(-c3cccc(C)c3C)cc2)CC1]
A53
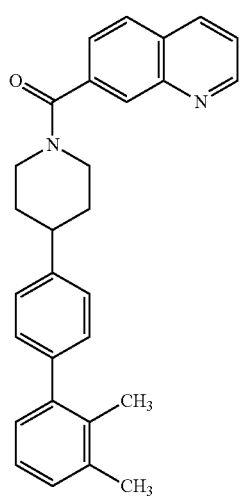 [SMILES: Cc1cccc(-c2ccc(C3CCN(C(=O)c4ccc5cccnc5c4)CC3)cc2)c1C]
A54

TABLE 5-continued
Exemplary compounds of Formula (IV) or (V).
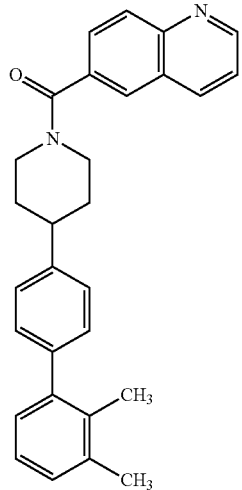 [SMILES: Cc1cccc(-c2ccc(C3CCN(C(=O)c4ccc5ncccc5c4)CC3)cc2)c1C]
A55
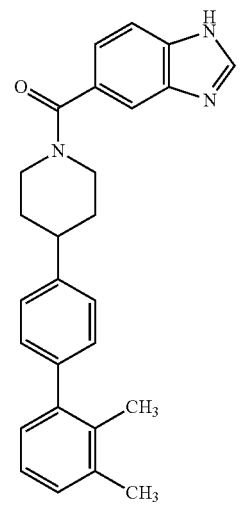 [SMILES: Cc1cccc(-c2ccc(C3CCN(C(=O)c4ccc5[nH]cnc5c4)CC3)cc2)c1C]
A56
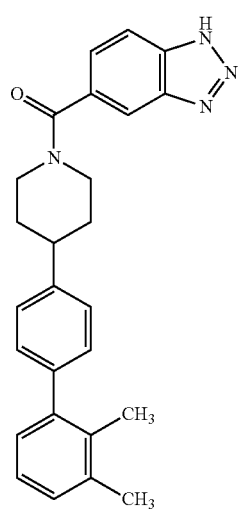 [SMILES: Cc1cccc(-c2ccc(C3CCN(C(=O)c4ccc5[nH]nnc5c4)CC3)cc2)c1C]
A57

TABLE 5-continued

Exemplary compounds of Formula (IV) or (V).

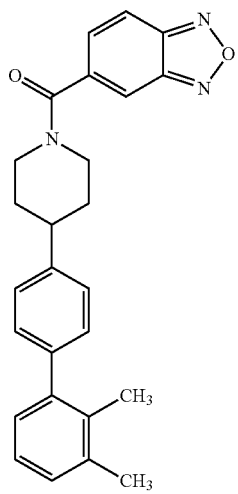

A58

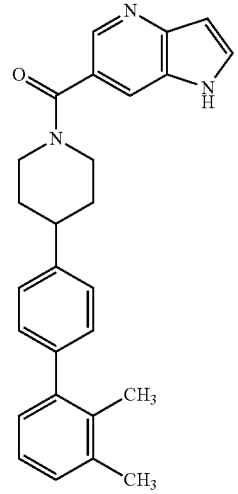 [SMILES: Cc1cccc(-c2ccc(C3CCN(C(=O)c4cnc5cc[nH]c5c4)CC3)cc2)c1C]

A59

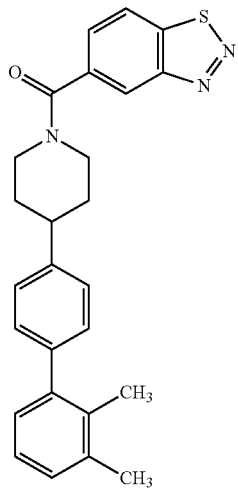 [SMILES: Cc1cccc(-c2ccc(C3CCN(C(=O)c4ccc5snnc5c4)CC3)cc2)c1C]

A60

Methods of Preparation

Compounds of the invention may be synthesized according to the schemes described below and those presented in the Examples. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.). The synthesis of fused azetidines-monoketopiperazines and fused azetidine-diazocanes is described by Lowe et al. (*J. Org. Chem.* 2012, 77, 7187-7211), which is incorporated by reference herein.

In one aspect, the present invention provides methods for the preparation of compounds of Formula (I), (II), (III), (IV), or (V), and intermediates thereto. Exemplary synthetic methods are shown in Schemes 1 to 10. Unless otherwise stated, variables depicted in the schemes below are as defined herein for compounds of Formula (I), (II), (III), (IV), or (V), and also include the following variables:

$R^a$ is hydrogen, optionally substituted alkyl, or a nitrogen protecting group, or $R^a$ and R1 are joined to form an optionally substituted heterocyclic ring;

$R^b$ is hydrogen, optionally substituted alkyl, or an oxygen protecting group; each instance of LG is an independent leaving group (exemplary leaving groups include, but are not limited to, halogen (e.g., F, Cl, Br, I), sulfonic acid ester (e.g., tosylate, mesylate, triflate), —OH, alkoxy, aryloxy, alkoxycarbonyloxy, aryloxycarbonyloxy, alkylcarbonyloxy, and arylcarbonyloxy);

$R^{2'}$ is hydrogen, halogen, —OH, amino, alkenyl, alkynyl, zinc halide, magnesium halide, silyl, stannyl, boronyl, acyl, or LG, or is $R^2$, as defined herein;

p' is 0, 1, or 2, valency permitting; and $P^2$ is hydrogen, halogen, —OH, amino, alkenyl, alkynyl, zinc halide, magnesium halide, silyl, stannyl, boronyl, acyl, or LG.

Scheme 1.

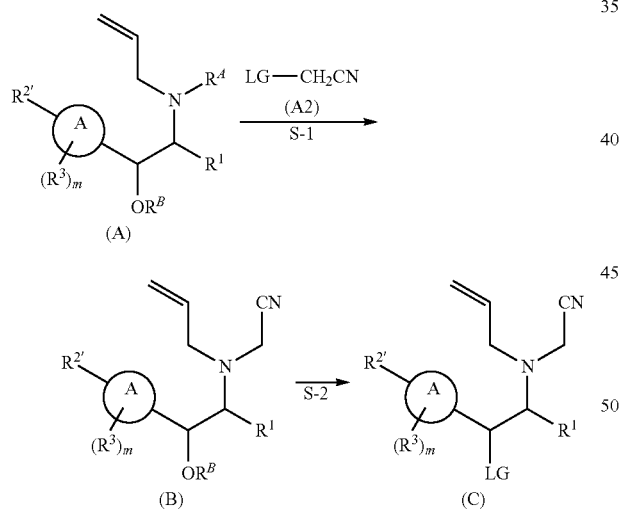

Step S-1 comprises adding the methylcyano group to an allyl amine of Formula (A) by adding LG-CH$_2$CN (e.g., ClCH$_2$CN, BrCH$_2$CN) to form the N-allyl-N-methylcyano amine of Formula (B) In some embodiments, the step of adding the methylcyano group is performed in the presence of a base (e.g., a carbonate). In some embodiments, step S-1 further comprises adding a protecting group to a nitrogen, oxygen, or sulfur atom (e.g., a nitrogen, oxygen, or sulfur atom of group $R^1$). In some embodiments, $R^1$ is —CH$_2$OH, and the protecting group is triphenylmethyl. The intermediates (C), (D), (E), (F), or (J) are depicted with an unsubstituted allyl group in the Schemes below, but the allyl group may be substituted. In certain embodiments, the allyl group is substituted with 1, 2, 3, or 4 $R^4$.

Step S-2 comprises replacing —OR$^b$ in a compound of Formula (B) with a leaving group (LG) to form a compound of Formula (C). In some embodiments, the step of replacing —OR$^b$ is performed in the presence of a halogenating reagent (e.g., Cl$_2$, Br$_2$, I$_2$, SOCl$_2$, POCl$_3$, N-halosuccinimide). In some embodiments, the leaving group (LG) of a compound of Formula (C) is —Cl, —Br, or —I.

Scheme 2.

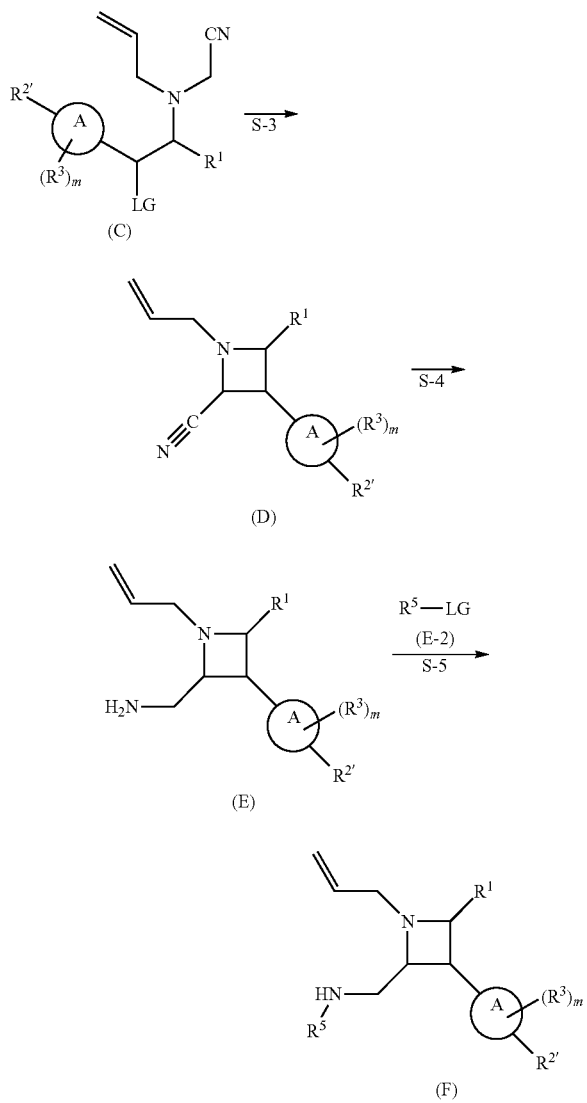

Step S-3 comprises cyclizing a compound of Formula (C) to form an azetidine of Formula (D). In some embodiments, the step of cyclizing is performed in the presence of a base. In some embodiments, the base is LiN(SiMe$_3$)$_2$, NaN(SiMe$_3$)$_2$, or KN(SiMe$_3$)$_2$. In certain embodiments, the step of cyclizing provides an azetidines of Formula (D) as a diastereomeric mixture. In some embodiments, the diastereomeric mixture will be comprise one diastereomer in greater yield than another diastereomer. In some embodiments, the diastereomeric ratio is at least about 2:1, at least about 5:1, at least about 10:1, at least about 20:1, or at least about 50:1. The choice of base may affect the diastereomeric ratio of the product. For example, in some embodiment, use of LiN(SiMe$_3$)$_2$ will give a diastereomeric ratio of 20:1, but use of KN(SiMe$_3$)$_2$ will give a diastereomeric ratio of 1:20. The possible stereoisomers of the azetidines of Formula (D) may also be determined by the stereoisomer of the compound of Formula (C) which is cyclized, as shown in Scheme 3A. In some embodiments, step S-3 further comprises a separation of stereoisomers.

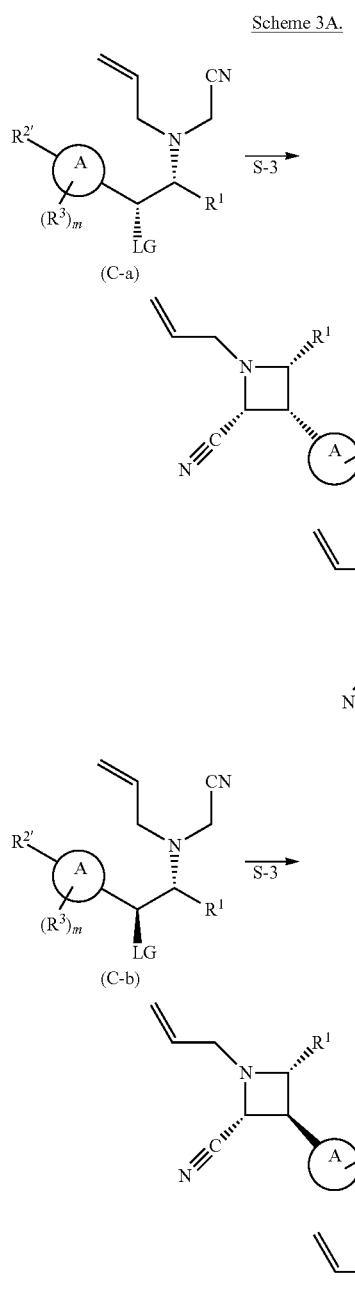

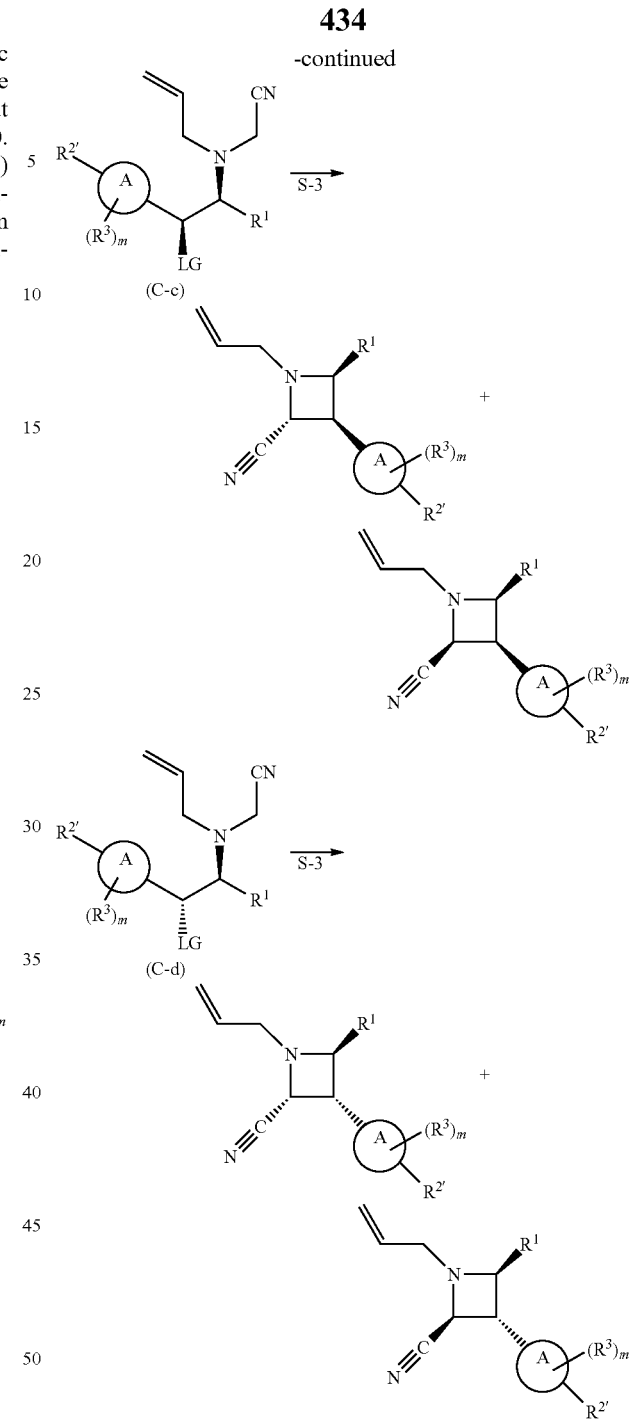

Step S-4 comprises reducing a cyano group of Formula (D) to form an amine of Formula (E). In some embodiments, the step of reducing a cyano group is performed in the presence of a reducing agent selected from H$_2$, sodium borohydride, lithium aluminum hydride, and diisobutylaluminum hydride (DIBAL). In some embodiments, the reducing agent is DIBAL. In some embodiments, the step of reducing is performed in the presence of a cobalt, rhodium, iridium, nickel, palladium, or platinum catalyst (e.g., Wilkinson's catalyst, palladium on carbon, palladium hydroxide, Raney nickel).

Step S-5 comprises adding R$^5$-LG to an amine of Formula (E) to form a compound of Formula (F). In certain embodiments, R$^5$ is a protecting group. In certain embodiments, R$^5$ is sulfonyl (e.g., nosyl, mesyl, tosyl, brosyl). In certain embodiments, $R^5$ is alkoxycarbonyl (e.g., tert-butyloxycarbonyl).

Scheme 3B.

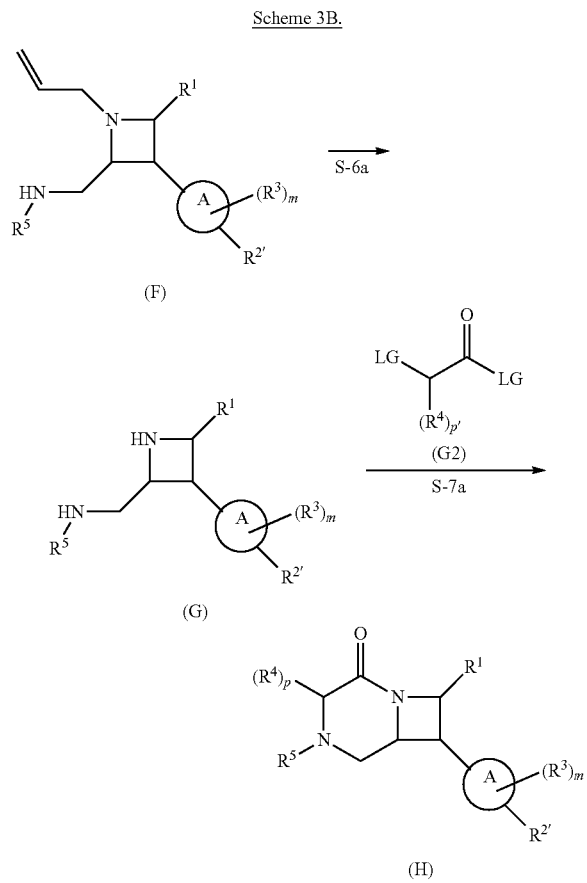

Scheme 3B describes a method of preparing compounds of Formula (I-a). Step S-6a comprises removing the allyl group from the azetidine of Formula (F) to form an azetidine of Formula (G). In some embodiments, the step of removing the allyl group is performed in the presence of a palladium complex (e.g., $Pd(PPh_3)_4$).

Step 7-a comprises coupling a compound of Formula (G) with a compound of Formula (G2) to form a compound of Formula (H). In certain embodiments, the compound of Formula (G2) is an a-halo-acyl halide (e.g., bromoacetyl chloride, iodoacetyl chloride, chloroacetyl chloride). In certain embodiments, p' is 0, such that the compound of Formula (G2) is $LG\text{-}CH_2\text{—}C(\!=\!O)\text{-}LG$. In some embodiments, the step of coupling is performed in the presence of a base (e.g., a carbonate).

Scheme 4.

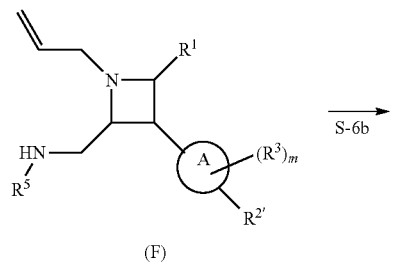

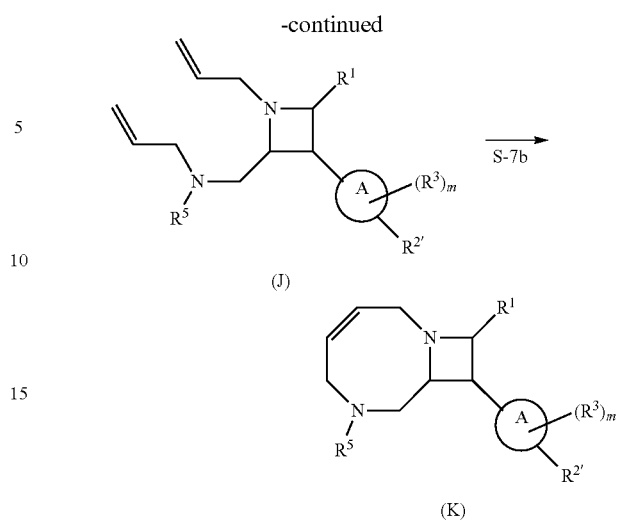

Scheme 4 and 5 describe a method of preparing compounds of Formula (I-b) and (I-c). Step S-6b comprises adding an allyl group to a compound of Formula (F) to form a compound of Formula (J). In certain embodiments, the allyl group is unsubstituted. In certain embodiments, the allyl group is substituted with 1, 2, 3, or 4 $R^4$. In certain embodiments, the step of adding an allyl group is performed in the presence of an allyl halide (e.g., allyl-Br). In some embodiments, the step of adding an allyl group is performed in the presence of a base (e.g., a carbonate).

Step S-7b comprises cyclizing a compound of Formula (J) via olefin metathesis to form a compound of Formula (K). In some embodiments, the step of cyclizing via olefin metathesis is performed in the presence of a molybdenum or ruthenium catalyst (e.g., a Grubbs catalyst, a Hoveyda-Grubbs catalyst).

Scheme 5.

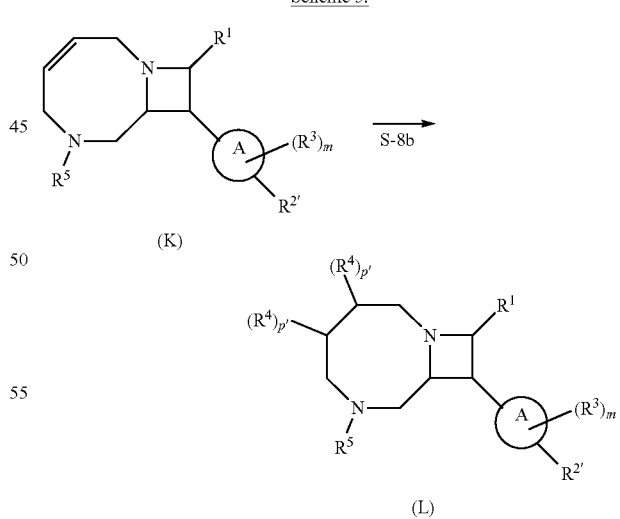

Step S-8b comprises reducing an alkene bond of a compound of Formula (K) to form a diazocane of Formula (L). In certain embodiments, the step of reducing is performed in the presence of a reducing agent selected from $H_2$, sodium borohydride, lithium aluminum hydride, and diisobutylaluminum hydride (DIBAL). In some embodiments, the reducing agent H$_2$. In some embodiments, the step of reducing is performed in the presence of a cobalt, rhodium, iridium, nickel, palladium, or platinum catalyst (e.g., Wilkinson's catalyst, palladium on carbon, palladium hydroxide, Raney nickel). In some embodiments, the catalyst is Wilkinson's catalyst.

Scheme 6.

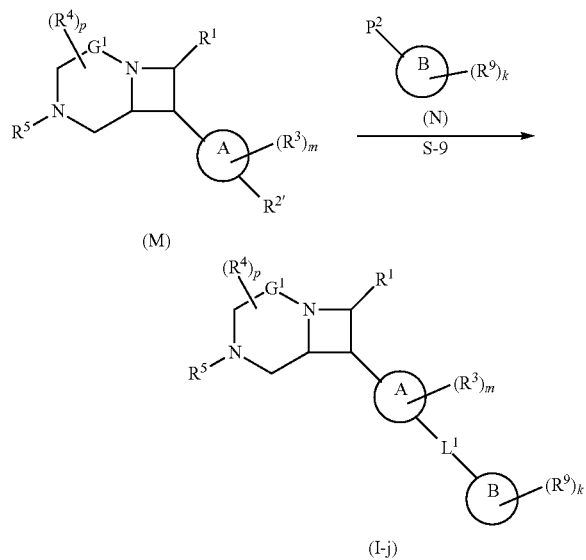

In certain embodiments, R$^{2\prime}$ is R$^2$ such that compounds of Formula (H), (K), and (L) are compounds of Formula (I). Compounds of Formula (H), (K), and (L) may also be considered sub-formula of Formula (M), wherein G$^1$, R$^4$, and p, are as defined herein, and may be further modified to afford compounds of Formula (I-c), as shown in Scheme 6. Step S-9 comprises coupling a compound of Formula (M) with a compound of Formula (N) to yield a compound of Formula (I-j). In certain embodiments, R$^{2\prime}$ is halogen (e.g., —Cl, —Br, —I). In some embodiments, R$^{2\prime}$ is halogen, and P$^2$ is —OH, amino, alkenyl, alkynyl, zinc halide, stannyl, boronyl, or silyl. In some embodiments, R$^{2\prime}$ is halogen, and P$^2$ is alkenyl (e.g., —CH=CH$_2$). In some embodiments, R$^{2\prime}$ is halogen, and P$^2$ is alkynyl (e.g., —C≡CH). In some embodiments, R$^{2\prime}$ is halogen, and P$^2$ is boronyl (e.g., —B(OH)$_2$). In certain embodiments, R$^{2\prime}$ is —OH, amino, alkenyl, alkynyl, zinc halide, stannyl, boronyl, or silyl, and P$^2$ is halogen. In some embodiments, R$^{2\prime}$ is alkenyl (e.g., —CH=CH$_2$), and P$^2$ is halogen. In certain embodiments, R$^{2\prime}$ is alkynyl (e.g., —C≡CH), and P$^2$ is halogen. In certain embodiments, (R$^{2\prime}$ is boronyl (e.g., —B(OH)$_2$), and P$^2$ is halogen.

Scheme 7.

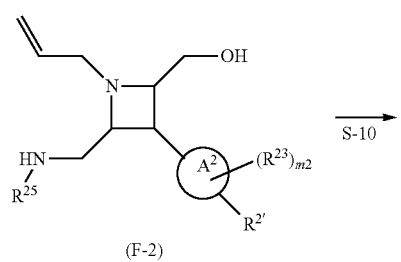

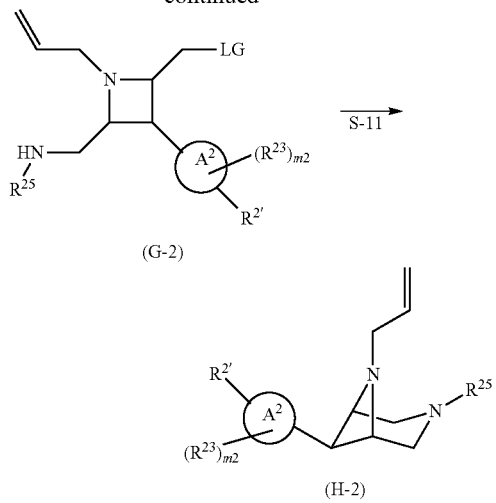

A compound of Formula (F-2) may be prepared according to the methods described herein for preparing a compound of Formula (F). The compound of Formula (F-2) may be converted to a precursor of a compound of Formula (II), according to Scheme 7. Step S-10 comprises protecting the alcohol of a compound of Formula (F-2) to yield a compound of Formula (G-2). In certain embodiments, LG is a sulfonyl ester. In some embodiments, LG is mesylate.

Step S-11 comprises cyclizing a compound of Formula (G-2) to yield the bicyclic compound of Formula (H-2). In certain embodiments, the step of cyclizing further comprises heating in the presence of a base. In some embodiments, the base is a carbonate, e.g., sodium carbonate, potassium carbonate.

Scheme 8.

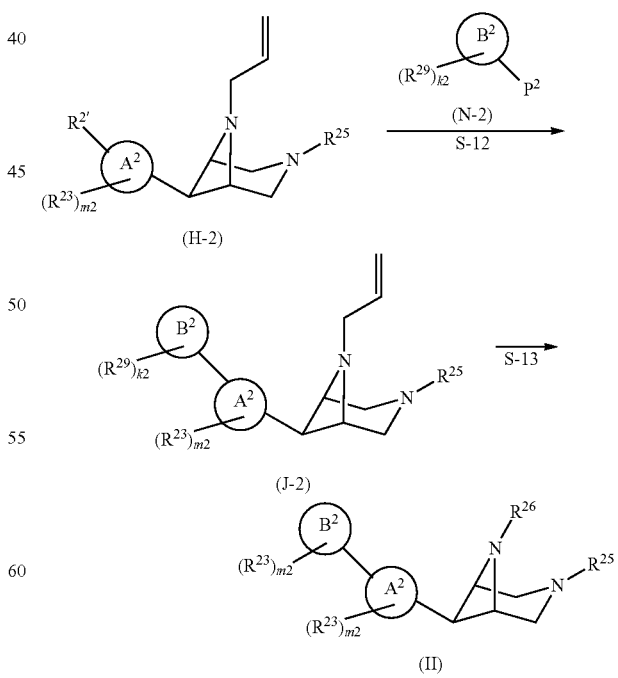

Compounds of Formula (H-2) may be further modified to afford compounds of Formula (II), as shown in Scheme 8.

Step S-12 comprises coupling a compound of Formula (H-2) with a compound of Formula (N-2) to yield a compound of Formula (J-2). In certain embodiments, $R^{2\prime}$ is halogen (e.g., —Cl, —Br, —I). In some embodiments, $R^{2\prime}$ is halogen, and $P^2$ is —OH, amino, alkenyl, alkynyl, zinc halide, stannyl, boronyl, or silyl. In some embodiments, $R^{2\prime}$ is halogen, and $P^2$ is alkenyl (e.g., —CH=CH$_2$). In some embodiments, $R^{2\prime}$ is halogen, and $P^2$ is alkynyl (e.g., —C≡CH). In some embodiments, $R^{2\prime}$ is halogen, and $P^2$ is boronyl (e.g., —B(OH)$_2$). In certain embodiments, $R^{2\prime}$ is —OH, amino, alkenyl, alkynyl, zinc halide, stannyl, boronyl, or silyl, and $P^2$ is halogen. In some embodiments, $R^{2\prime}$ is alkenyl (e.g., —CH=CH$_2$), and $P^2$ is halogen. In certain embodiments, $R^{2\prime}$ is alkynyl (e.g., —C≡CH), and $P^2$ is halogen. In certain embodiments, ($R^{2\prime}$ is boronyl (e.g., —B(OH)$_2$), and $P^2$ is halogen.

Step S-13 comprises removing the allyl group of a compound of Formula (J-2) and optionally adding $R^{26}$-LG to the amine from which the allyl group is removed. In some embodiments, the step of removing the allyl group is performed in the presence of a palladium complex (e.g., Pd(PPh$_3$)$_4$). In some embodiments, $R^{26}$ is hydrogen. In certain embodiments, $R^{26}$ is a protecting group. In certain embodiments, $R^{26}$ is sulfonyl (e.g., nosyl, mesyl, tosyl, brosyl). In certain embodiments, $R^{26}$ is acyl (e.g., —C(=O)(alkyl), —C(=O)(carbocyclyl), —C(=O)(heterocyclyl), —C(=O)NH(alkyl), —C(=O)NH(carbocyclyl), —C(=O)NH(heterocyclyl)). In certain embodiments, $R^{26}$ is alkoxycarbonyl (e.g., tert-butyloxycarbonyl).

Scheme 9.

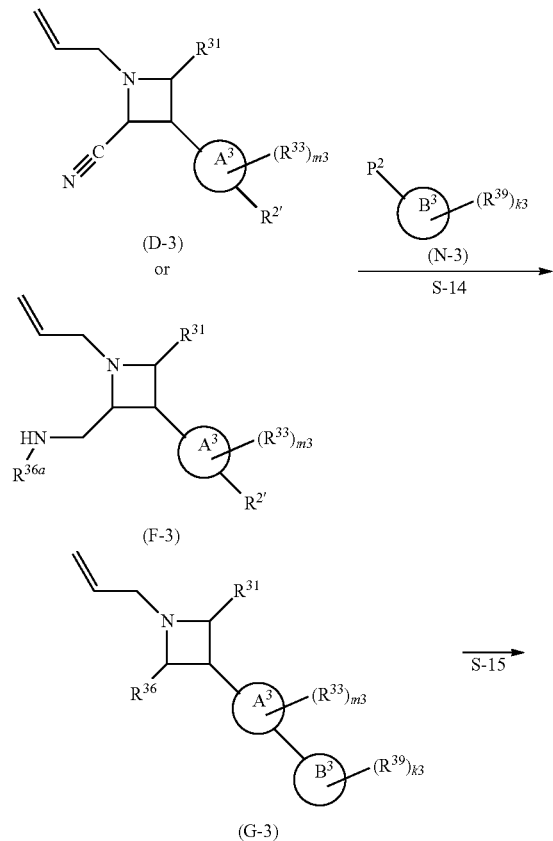

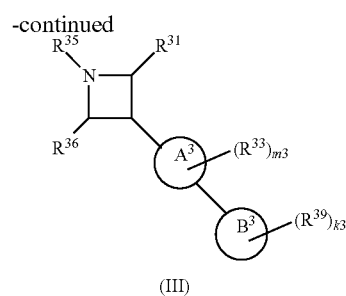

Compound of Formulae (D-3) and (F-3) may be prepared according to the methods described herein for preparing a compounds of Formulae (D) and (F). A compound of Formula (D-3) or (F-3) may be converted to a compound of Formula (III), according to Scheme 9.

Step S-14 comprises coupling a compound of Formula (D-3) or (F-3) with a compound of Formula (N-3) to yield a compound of Formula (G-3). In certain embodiments, $R^{2\prime}$ is halogen (e.g., —Cl, —Br, —I). In some embodiments, $R^{2\prime}$ is halogen, and $P^2$ is —OH, amino, alkenyl, alkynyl, zinc halide, stannyl, boronyl, or silyl. In some embodiments, $R^{2\prime}$ is halogen, and $P^2$ is alkenyl (e.g., —CH=CH$_2$). In some embodiments, $R^{2\prime}$ is halogen, and $P^2$ is alkynyl (e.g., —C≡CH). In some embodiments, $R^{2\prime}$ is halogen, and $P^2$ is boronyl (e.g., —B(OH)$_2$). In certain embodiments, $R^{2\prime}$ is —OH, amino, alkenyl, alkynyl, zinc halide, stannyl, boronyl, or silyl, and $P^2$ is halogen. In some embodiments, $R^{2\prime}$ is alkenyl (e.g., —CH=CH$_2$), and $P^2$ is halogen. In certain embodiments, $R^{2\prime}$ is alkynyl (e.g., —C≡CH), and $P^2$ is halogen. In certain embodiments, ($R^{2\prime}$ is boronyl (e.g., —B(OH)$_2$), and $P^2$ is halogen.

Step S-15 comprises removing the allyl group of a compound of Formula (G-3) and optionally adding $R^{35}$-LG to the amine from which the allyl group is removed. In some embodiments, the step of removing the allyl group is performed in the presence of a palladium complex (e.g., Pd(PPh$_3$)$_4$). In some embodiments, $R^{35}$ is hydrogen. In certain embodiments, $R^{35}$ is a protecting group. In certain embodiments, $R^{35}$ is sulfonyl (e.g., nosyl, mesyl, tosyl, brosyl). In certain embodiments, $R^{35}$ is acyl (e.g., —C(=O)(alkyl), —C(=O)(carbocyclyl), —C(=O)(heterocyclyl), —C(=O)NH(alkyl), —C(=O)NH(carbocyclyl), —C(=O)NH(heterocyclyl)). In certain embodiments, $R^{35}$ is alkoxycarbonyl (e.g., tert-butyloxycarbonyl).

Scheme 10.

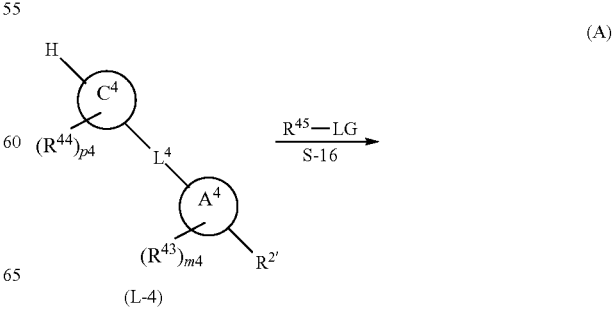

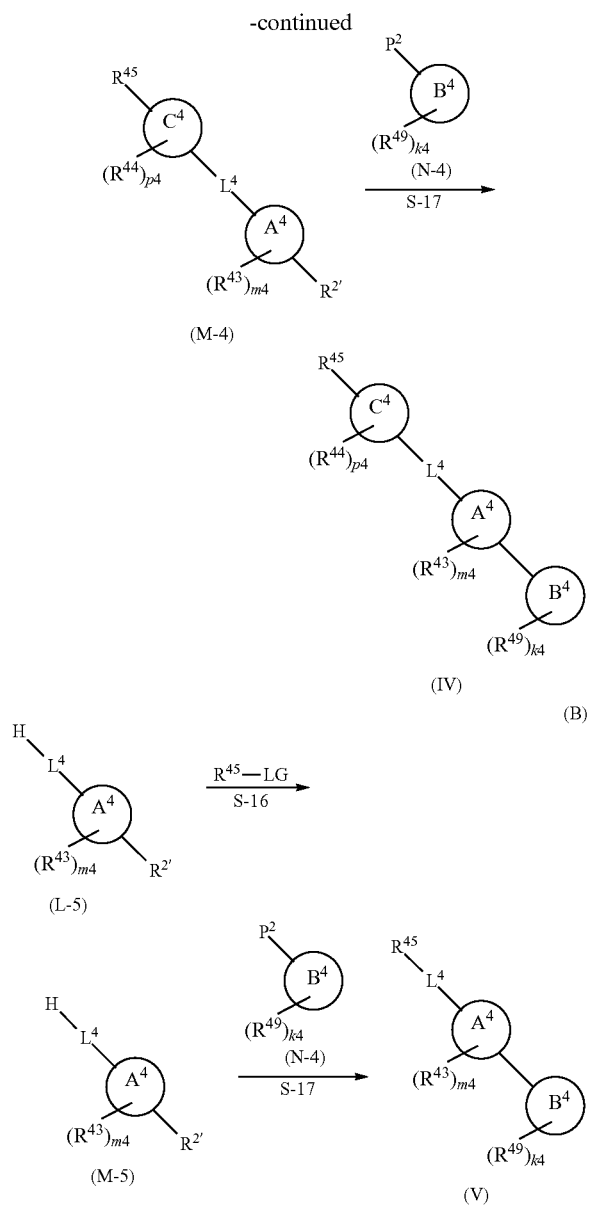

alkenyl, alkynyl, zinc halide, stannyl, boronyl, or silyl. In some embodiments, $R^{2'}$ is halogen, and $P^2$ is alkenyl (e.g., —CH=CH$_2$). In some embodiments, $R^{2'}$ is halogen, and $P^2$ is alkynyl (e.g., —C≡CH). In some embodiments, $R^{2'}$ is halogen, and $P^2$ is boronyl (e.g., —B(OH)$_2$). In certain embodiments, $R^{2'}$ is —OH, amino, alkenyl, alkynyl, zinc halide, stannyl, boronyl, or silyl, and $P^2$ is halogen. In some embodiments, $R^{2'}$ is alkenyl (e.g., —CH=CH$_2$), and $P^2$ is halogen. In certain embodiments, $R^{2'}$ is alkynyl (e.g., —C≡CH), and $P^2$ is halogen. In certain embodiments, ($R^{2'}$ is boronyl (e.g., —B(OH)$_2$), and $P^2$ is halogen.

The method of preparing a compound of Formula (I) or an intermediate thereto optionally further comprises one or more steps of protecting a nitrogen, oxygen, or sulfur atom, or deprotecting a nitrogen, oxygen, or sulfur atom. In certain embodiments, the step of deprotecting or protecting comprises replacing group $R^5$, $R^{25}$, $R^{35}$, or $R^{45}$. In certain embodiments the step of deprotecting or protecting comprises replacing group $R^{26}$ or $R^{36}$. In certain embodiments, the step of deprotecting or protecting involves group $R^1$. In certain embodiments, $R^1$ is —CH$_2$OR$^{1a}$, and the step of protecting or deprotecting comprises replacing group $R^{1a}$.

Pharmaceutical Compositions and Administration

The present invention also provides pharmaceutical compositions comprising a compound described herein (e.g., a compound of Formula (RL), (I), II), (III), (IV), or (V)), or a pharmaceutically acceptable salt, solvate, hydrate, polymorph, co-crystal, tautomer, stereoisomer, or prodrug thereof, and optionally a pharmaceutically acceptable excipient. In certain embodiments, the pharmaceutical composition described herein comprises a compound of Formula (I), or a pharmaceutically acceptable salt, solvate, hydrate, polymorph, co-crystal, tautomer, stereoisomer, prodrug, or isotopically labeled derivative thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a metabolic disorder (e.g., diabetes, hyperglycemia, impaired glucose tolerance, insulin resistance, obesity) in a subject in need thereof. In certain embodiments, the effective amount is an amount effective for preventing a metabolic disorder (e.g., diabetes, hyperglycemia, impaired glucose tolerance, insulin resistance, obesity) in a subject in need thereof. In certain embodiments, the effective amount is an amount effective for reducing the risk of developing a metabolic disorder (e.g., diabetes, hyperglycemia, impaired glucose tolerance, insulin resistance, obesity) in a subject in need thereof. In certain embodiments, the effective amount is an amount effective for inhibiting the activity of a protease (e.g., IDE) in a subject or biological sample. In certain embodiments, the effective amount is an amount effective for treating a cardiac disorder (e.g., hypertension, high blood pressure).

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodi- Compounds of Formula (IV) and (V) may be prepared according to Scheme 10A and B. Step S-16 comprises adding $R^{45}$-LG to an a compound of Formula (L-4) or (L-5) to form a compound of Formula (M-4) or (M-5), respectively. In certain embodiments, Ring $C^4$ is piperidinyl or piperizinyl, such that $R^{45}$ is added to the amine nitrogen of Ring $C^4$. In certain embodiments, $L^4$ is —(CR$^{F2}$)$_n$X$^5$—, and $X^5$ is —NR$^X$—, such that group $R^{45}$ is added to the amine nitrogen of $L^4$. In certain embodiments, $R^{45}$ is a protecting group. In certain embodiments, $R^{45}$ is sulfonyl (e.g., nosyl, mesyl, tosyl, brosyl). In certain embodiments, $R^{45}$ is acyl (e.g., —C(=O)(alkyl), —C(=O)(carbocyclyl), —C(=O)(heterocyclyl), —C(=O)NH(alkyl), —C(=O)NH(carbocyclyl), —C(=O)NH(heterocyclyl)). In certain embodiments, $R^{45}$ is alkoxycarbonyl (e.g., tert-butyloxycarbonyl).

Step S-14 comprises coupling a compound of Formula (M-4) or (M-5) with a compound of Formula (N-4) to yield a compound of Formula (IV) or (V). In certain embodiments, $R^{2'}$ is halogen (e.g., —Cl, —Br, —I). In some embodiments, $R^{2'}$ is halogen, and $P^2$ is —OH, amino, ments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of a metalloprotease by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a metalloprotease by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of IDE by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of IDE by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for a range of inhibition between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophoro), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protease in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-diabetic agents, anti-proliferative agents, anti-cancer agents, anti-angiogenesis agents, anti-inflammatory agents, immunosuppressants, anti-bacterial agents, antiviral agents, cardiovascular agents, cholesterol-lowering agents, anti-allergic agents, contraceptive agents, and pain-relieving agents. In certain embodiments, the additional pharmaceutical agent is an anti-obesity agent. In certain embodiments, the additional pharmaceutical agent is an binder or inhibitor of a protease. In certain embodiments, the additional pharmaceutical agent is an binder or inhibitor of insulin-degrading enzyme (IDE). In certain embodiments, the additional pharmaceutical agent inhibits the degradation of insulin, promotes the release of insulin, or enhances the activity of insulin. In certain embodiments, the additional pharmaceutical agent inhibits the synthesis or release of glucagon.

In certain embodiments, the additional pharmaceutical agent is an anti-diabetic agent. The additional pharmaceutical agents include, but are not limited to, insulins, insulin analogs, insulin sensitizers, insulin secretagogues, incretin mimetics, incretin agonists, dipeptidyl peptidase-4 (DPP4) inhibitors, and sodium glucose co-transporter-2 (SGLT-2) inhibitors. In certain embodiments, the additional pharmaceutical agent is insulin (e.g., humulin). In certain embodiments, the additional pharmaceutical agent is an insulin analog. In certain embodiments, the additional pharmaceutical agent is insulin lispro, insulin aspart, insulin glulisine, insulin detemir, insulin degludec, insulin glargine, or NPH insulin.

In certain embodiments, the additional pharmaceutical agent is an insulin sensitizer. In certain embodiments, the additional pharmaceutical agent is a biguanide. In certain embodiments, the additional pharmaceutical agent is metformin, phenformin, or butformin. In certain embodiments, the additional pharmaceutical agent is a thiazolidinedionze (i.e., a glitzone). In certain embodiments, the additional pharmaceutical agent is rosiglitazone, pioglitazone, or troglitazone.

In certain embodiments, the additional pharmaceutical agent is an insulin secretagogue. In certain embodiments, the additional pharmaceutical agent is a sulfonylurea. In certain embodiments, the sulfonylurea is tolbutamide, acetohexamide, tolazamide, chlorpropamide, glipizide, glibenclamide, glimepiride, gliclazide, glycopyramide, gliquidone. In certain embodiments, the additional pharmaceutical agent is a meglitinide. In certain embodiments, the meglitinide is repaglinide or nateglinide.

In certain embodiments, the additional pharmaceutical agent is an incretin mimetic or incretin agonist. In certain embodiments, the incretin mimetic or incretin agonist is exenatide, liraglutide, taspoglutide, lixisenatide, dulaglutide, or albiglutide. In certain embodiments, the additional pharmaceutical agent is a dipeptidyl peptidase-4 (DPP4) inhibitor. In certain embodiments, the DPP4 inhibitor is vildagliptin, sitagliptin, saxagliptin, linagliptin, alogliptin, or septagliptin. In certain embodiments, the additional pharmaceutical agent is a glycosuric. In certain embodiments, the additional pharmaceutical agent is a sodium glucose co-transporter-2 (SGLT-2) inhibitor. In certain embodiments, the SGLT-2 inhibitor is empagliflozin, canagliflozin, or dapagliflozin. In certain embodiments, the additional pharmaceutical agent is an alpha-glucosidase inhibitor. In certain embodiments, the additional pharmaceutical agent is miglitol, acarbose, or voglibose.

Exemplary anti-diabetic agents include, but are not limited to: Actoplus Met® (pioglitazone HCl and metformin HCl), Actos® (pioglitazone), Amaryl® (glimepride), Avandamet® (rosiglitazone maleate and metformin HCl), Avandia® (rosiglitazone), Bydureon® (exenatide synthetic), Byetta® (exenatide), Deamelin-S® (glyclopyramide), Diabeta® (glibenclamide), Diabinese® (chlorpropamide), Duetact® (pioglitazone HCl and glimepride), Dymelor® (acetohexamide), Farxiga® (dapaglifozin), Galvus® (vildagliptin), Glucotrol® (glipizide), Glurenorm® (gliquidone), Glyset® (miglitol), Invokana® (canagliflozin), Jardiance® (empagliflozin), Janumet® (sitagliptin and metformin HCl), Janumet XR@ (sitagliptin and metformin HCL), Januvia® (sitagliptin phosphate), Jentadueto® (linagliptin and metformin hydrochloride), Juvisync® (sitagliptin and simvastatin), Kombiglize XR@ (saxaglitpin and metoformin HCl), Lucentis® (ranibizumab), Lyxumia® (lixisenatide), Metaglip® (glipizide and metformin HCl), Nesina® (alogliptin), Onglyza® (saxagliptin), Orinase® (tolbutamide), Prandimet® (repaglinide and metformin HCl), Prandin® (repaglinide), Precose® (acarbose), Rezulin® (troglitazone), Starlix® (nateglinide), Symlin® (pramlintide), Tanzeum® (abliglutide), Tolinase® (tolazamide), Tradjenta® (linagliptin), Trulicity® (dulaglutide), Uni Diamicron® (gliclazide), Victoza® (liraglutide), and Voglib® (voglibose).

Exemplary insulin analogs include, but are not limited to: Humulin R® (insulin human), Humulin N® (NPH insulin), Humulin 70/30® (70% NPH insulin and 30% insulin human), Novolin R® (insulin human), Novolin N@ (NPH insulin), Novolin 70/30® (70% NPH insulin and 30% insulin human), Humalog® (insulin lispro), Humalog 50/50@ (50% insulin lispro protamine and 50% insulin lispro), Humalog 75/25® (75% insulin lispro protamine and 25% insulin lispro), Novolog® (insulin aspart), Novolog 70/30® (70% insulin aspart protamine and 30% insulin aspart), Afrezza® (inhalable insulin human), Apidra® (insulin glulisine), Exubera® (inhalable insulin human), Lantus® (insulin glargine), Levemir® (insulin detemir), and Tresiba® (insulin degludec).

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a metabolic disorder (e.g., diabetes, impaired glucose tolerance, insulin resistance, obesity) in a subject in need thereof. In certain embodiments, the kits are useful for preventing a metabolic disorder (e.g., diabetes, impaired glucose tolerance, insulin resistance, obesity) in a subject in need thereof. In certain embodiments, the kits are useful for reducing the risk of developing a metabolic disorder (e.g., diabetes, impaired glucose tolerance, insulin resistance, obesity) in a subject in need thereof. In certain embodiments, the kits are useful for inhibiting the activity of a protease (e.g., IDE) in a subject or biological sample.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a metabolic disorder (e.g., diabetes, impaired glucose tolerance, insulin resistance, obesity) in a subject in need thereof. In certain embodiments, the kits and instructions provide for preventing a metabolic disorder (e.g., diabetes, impaired glucose tolerance, insulin resistance, obesity) in a subject in need thereof. In certain embodiments, the kits and instructions provide for reducing the risk of developing a metabolic disorder (e.g., diabetes, impaired glucose tolerance, insulin resistance, obesity) in a subject in need thereof. In certain embodiments, the kits and instructions provide for inhibiting the activity a protease (e.g., IDE) in a subject or cell. A kit described herein may include one or more additional pharmaceutical agents described herein as a separate composition.

Methods of Treatment and Uses

The present invention also provides methods that may be useful for the treatment or prevention of a disease. In certain embodiments, the disease is a metabolic disorder. In certain embodiments, the disorder is a diabetic condition. In certain embodiments, the disorder is diabetes (e.g., type I diabetes mellitus, type II diabetes mellitus, gestational diabetes). In certain embodiments, the disorder is type I diabetes mellitus. In certain embodiments, the disorder is type II diabetes mellitus. In certain embodiments, the disorder is gestational diabetes. In certain embodiments, the disorder is congenital diabetes, cystic-fibrosis-related diabetes, steroid diabetes, or a monogenic diabetes (e.g., mature onset diabetes of the young). In certain embodiments, the disorder is hyperglycemia, impaired glucose tolerance, or insulin resistance. In certain embodiments, the disorder is hypoglycemia or hyperinsulinemia. In certain embodiments, the disorder is an obesity-related condition. In certain embodiments, the disorder is obesity. In certain embodiments, the disorder is class I obesity, class II obesity, class III obesity, or pre-obesity. In certain embodiments, the disorder is undesired weight gain or an over-eating disorder. In some embodiments, the disorder is impaired insulin signaling or insulin resistance. In some embodiments, the disorder is caused by or associated with an aberrant half-life of a substrate of IDE (e.g., insulin, glucagon, amylin, TGF alpha, beta-endorphin, amyloid beta, bradykinin, kallidin, calcitonin-gene related peptide (CGRP), somatostatin, and/or atrial natriuretic peptide), or that is treatable by modulation of the half-life of a substrate of IDE. In certain embodiments, the disease or condition is associated with elevated blood pressure. In certain embodiments, the disease or condition is hypertension or is associated with hypertension. In certain embodiments, the disease or condition is associated with elevated angiotensin-II. In certain embodiments, the disease or condition is associated with elevated endothelin-1. In certain embodiments, the disease or condition is associated with elevated aldosterone. In certain embodiments, the disease or condition is associated with elevated renin. In certain embodiments, the disease or condition is associated with sodium excretion.

In certain embodiments, the method of treating a metabolic disorder comprises administering a substrate selective inhibitor to a subject in need thereof, wherein the substrate selective inhibitor inhibits the activity of IDE for degradation of a first substrate over activity of IDE for degradation of a second substrate. In some embodiments, the first substrate is insulin and the second substrate is glucagon. In some embodiments, the first substrate is insulin and the second substrate is amylin. In certain embodiments, the disorder is a diabetic condition. In certain embodiments, the disorder is diabetes (e.g., type I diabetes mellitus, type II diabetes mellitus, gestational diabetes). In certain embodiments, the substrate selective inhibitor comprises a locked ring moiety as described herein. In some embodiments, the locked ring moiety comprises two rings connected by a bond and comprising at least one non-hydrogen substituent attached ortho to the bond connecting the two rings.

In certain embodiments, the method of treating a metabolic disorder comprises administering a substrate selective inhibitor to a subject in need thereof, wherein the activity of IDE in the subject for degradation of a first substrate is selectively inhibited over the activity of IDE in the subject for degradation of a second substrate. In some embodiments, the first substrate is insulin and the second substrate is glucagon. In some embodiments, the first substrate is insulin and the second substrate is amylin. In certain embodiments, the disorder is a diabetic condition. In certain embodiments, the disorder is diabetes (e.g., type I diabetes mellitus, type II diabetes mellitus, gestational diabetes). In certain embodiments, the substrate selective inhibitor comprises a locked ring moiety as described herein. In some embodiments, the locked ring moiety comprises two rings connected by a bond and comprising at least one non-hydrogen substituent attached ortho to the bond connecting the two rings.

The compounds described herein (e.g., a compound of Formula (RL), (I), (II), (III), (IV), or (V), may exhibit protease inhibitory activity, may exhibit the ability to inhibit insulin-dependent enzyme (IDE), may exhibit a therapeutic effect and/or preventative effect in the treatment of metabolic disorders, may exhibit a therapeutic and/or preventative effect superior to existing agents for treatment of metabolic disorders, and/or may exhibit the ability to selectively inhibit insulin degradation over glucagon degradation (e.g., by IDE).

In certain embodiments, a compound described herein may exhibit the ability to enhance the degradation of glucagon. In some embodiments, the compound may bind to IDE and alter the affinity of IDE to bind glucagon. Inhibitors often lower the affinity of an enzyme to bind a substrate, for example for competitive inhibitor, by occupying or partly occupying space in the binding pocket that the substrate would occupy during a typical binding interaction. In some embodiments, the compound may bind to IDE and increase the affinity of IDE to bind glucagon. The compound may alter the binding pocket to make the interaction between glucagon and IDE more favorable (e.g., by presenting a hydrophobic or hydrophilic surface not present in wild-type IDE, which forms a stabilizing interaction with a residue or residues of glucagon). The binding pocket may be altered by a conformational change in IDE, by the presence of the inhibitor itself in the binding pocket, or by both. In certain embodiments, a compound described herein may exhibit the ability to enhance the degradation of insulin, amylin, TGF alpha, beta-endorphin, amyloid beta, bradykinin, kallidin, calcitonin-gene related peptide (CGRP), somatostatin, or atrial natriuretic peptide.

The compounds described herein (e.g., a compound of Formula (RL), (I), II), (III), (IV), or (V)), may exhibit selective inhibition of IDE for degradation of one substrate over another substrate. In certain embodiments, the compounds described herein (e.g., a compound of Formula (RL), (I), II), (III), (IV), or (V)) may exhibit selective inhibition of IDE for one or more substrates over another substrates, one or more substrates over one or more other substrates, two or more substrates over another substrate, two or more substrates over one or more substrates, or two or more substrates over two or more substrates. Substrates of IDE include but are not limited to insulin, glucagon, amylin, TGF alpha, beta-endorphin, amyloid beta, bradykinin, kallidin, calcitonin-gene related peptide (CGRP), somatostatin, and atrial natriuretic peptide. In certain embodiments, the compound selectively inhibits insulin degradation over degradation of another substrate. In some embodiments, the compound selectively inhibits insulin degradation over glucagon degradation. In some embodiments, the compound selectively inhibits insulin degradation over amylin degradation. In some embodiments, the compound selectively inhibits insulin degradation over degradation of TGF alpha, beta-endorphin, amyloid beta, bradykinin, kallidin, calcitonin-gene related peptide (CGRP), somatostatin, or atrial natriuretic peptide. In certain embodiments, the compound selectively inhibits glucagon degradation over degradation of another substrate. In some embodiments, the compound selectively inhibits glucagon degradation over amylin degradation. In some embodiments, the compound selectively inhibits glucagon degradation over insulin degradation. In some embodiments, the compound selectively inhibits glucagon degradation over degradation of TGF alpha, beta-endorphin, amyloid beta, bradykinin, kallidin, calcitonin-gene related peptide (CGRP), somatostatin, or atrial natriuretic peptide. In certain embodiments, the compound selectively inhibits amylin degradation over degradation of another substrate. In some embodiments, the compound selectively inhibits amylin degradation over insulin degradation. In some embodiments, the compound selectively inhibits amylin degradation over glucagon degradation. In some embodiments, the compound selectively inhibits amylin degradation over degradation of TGF alpha, beta-endorphin, amyloid beta, bradykinin, kallidin, calcitonin-gene related peptide (CGRP), somatostatin, or atrial natriuretic peptide. In certain embodiments, the compound selectively inhibits TGF alpha degradation over degradation of another substrate. In certain embodiments, the compound selectively inhibits beta-endorphin degradation over degradation of another substrate. In certain embodiments, the compound selectively inhibits amyloid beta degradation over degradation of another substrate. In certain embodiments, the compound selectively inhibits bradykinin degradation over degradation of another substrate. In certain embodiments, the compound selectively inhibits kallidin degradation over degradation of another substrate. In certain embodiments, the compound selectively inhibits atrial natriuretic peptide degradation over degradation of another substrate. In certain embodiments, the compound selectively inhibits calcitonin-gene related peptide (CGRP) degradation over degradation of another substrate. In certain embodiments, the compound selectively inhibits somatostatin degradation over degradation of another substrate. In certain embodiments, the selectivity for inhibiting degradation of one substrate over another is between about 1.1-fold and about 2-fold, between about 2-fold and about 5-fold, between about 5-fold and about 10-fold, between about 10-fold and about 50-fold, between about 50-fold and about 100-fold, inclusive, or greater than about 100-fold. In certain embodiments, there is no selectivity for one substrate over another substrate.

Selectivity of a compound to inhibit degradation of specific substrates of IDE may be measured by comparing an assay for degradation of a first substrate by IDE in the presence of the compound with an assay for degradation of a second substrate by IDE in the presence of the compound. In certain embodiments, the assays comprise fluorescence measurements. In certain embodiments, the assay for the first and second substrate are endpoint assay to determine the quantity of the substrate that was degraded by IDE or not degraded by IDE. In some embodiments, the assay is a homogenous time-resolved FRET (HTRF) assay. In some embodiments, the first substrate is insulin and the HTRF assay is specific for insulin (e.g., FRET is dependent on the concentration of intact insulin). In some embodiments, the second substrate is glucagon and the HTRF assay is specific for glucagon (e.g., FRET is dependent on the concentration of intact glucagon).

In certain embodiments, the selectivity for inhibiting degradation of insulin over degradation of glucagon is between about 1.1-fold and about 2-fold, between about 2-fold and about 5-fold, between about 5-fold and about 10-fold, between about 10-fold and about 50-fold, between about 50-fold and about 100-fold, inclusive, or greater than about 100-fold.

In certain embodiments, the selectivity for inhibiting degradation of insulin over degradation of amylin is between about 1.1-fold and about 2-fold, between about 2-fold and about 5-fold, between about 5-fold and about 10-fold, between about 10-fold and about 50-fold, between about 50-fold and about 100-fold, inclusive, or greater than about 100-fold.

In certain embodiments, the selectivity for inhibiting degradation of amylin over degradation of glucagon is between about 1.1-fold and about 2-fold, between about 2-fold and about 5-fold, between about 5-fold and about 10-fold, between about 10-fold and about 50-fold, between about 50-fold and about 100-fold, inclusive, or greater than about 100-fold.

A compound described herein may interact with IDE to inhibit insulin binding, but not inhibit glucagon binding. The compound may bind near the active site of insulin/glucagon cleavage in IDE and impede binding of insulin, but not impede glucagon or impede binding of glucagon to a lesser extent. The selectivity of the inhibitor will be particular to the size and shape of the compound, and the location and orientation of binding in IDE. Exemplary compounds, which exhibit selectivity for inhibiting insulin degradation over glucagon degradation are listed in Table 2 (see also FIG. 4).

TABLE 6

Exemplary substrate-selective inhibitors of Formula (I).

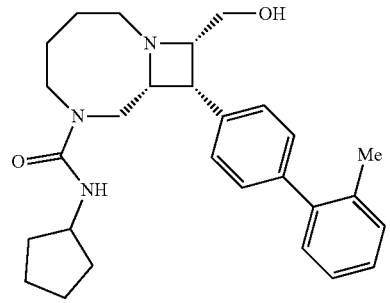 [SMILES: Cc1ccccc1-c1ccc([C@H]2[C@@H](CO)N3CCCCN(C(=O)NC4CCCC4)C[C@@H]23)cc1]
204

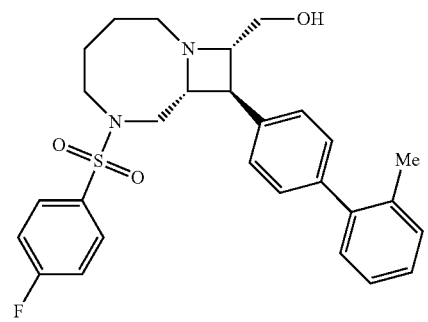 [SMILES: Cc1ccccc1-c1ccc([C@@H]2[C@@H](CO)N3CCCCN(S(=O)(=O)c4ccc(F)cc4)C[C@@H]23)cc1]
217

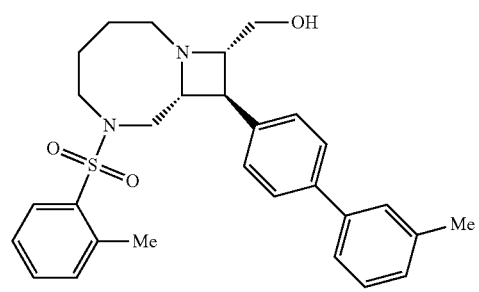 [SMILES: Cc1cccc(-c2ccc([C@@H]3[C@@H](CO)N4CCCCN(S(=O)(=O)c5ccccc5C)C[C@@H]34)cc2)c1]
297

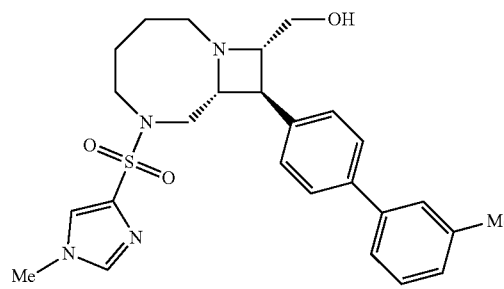
342

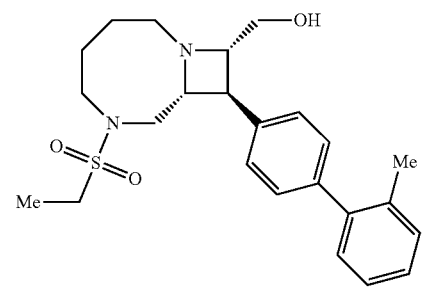 [SMILES: CCS(=O)(=O)N1CCCCN2[C@H](CO)[C@@H](c3ccc(-c4ccccc4C)cc3)[C@@H]2C1]
416

TABLE 6-continued

Exemplary substrate-selective inhibitors of Formula (I).

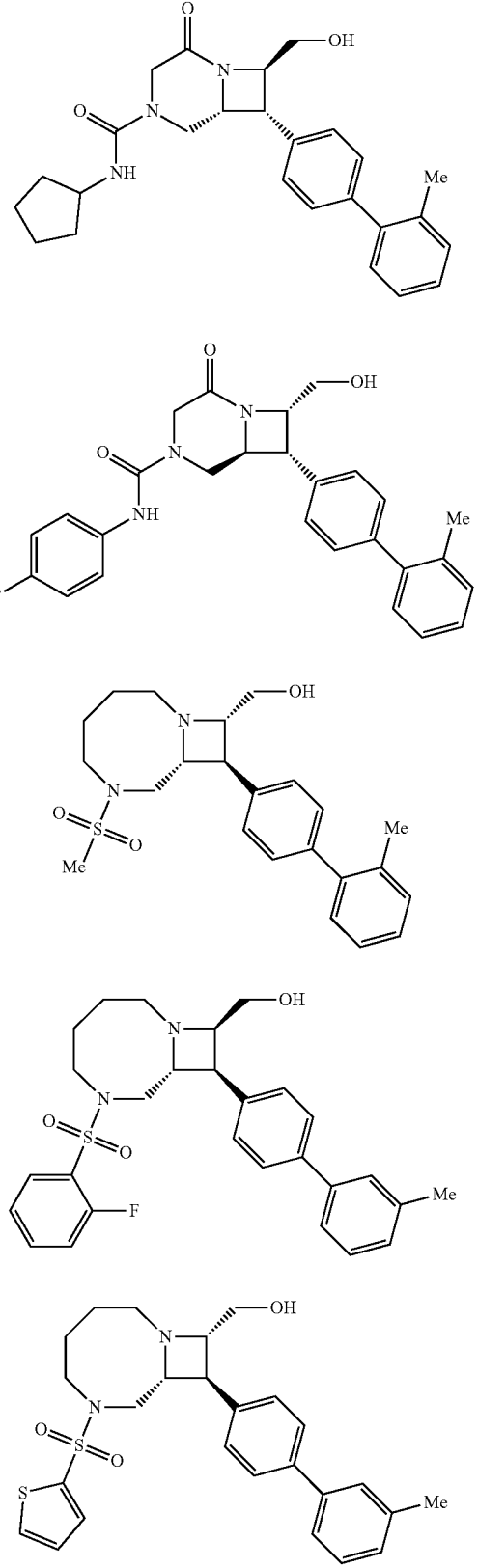

504

510

591

807

945

TABLE 6-continued

Exemplary substrate-selective inhibitors of Formula (I).

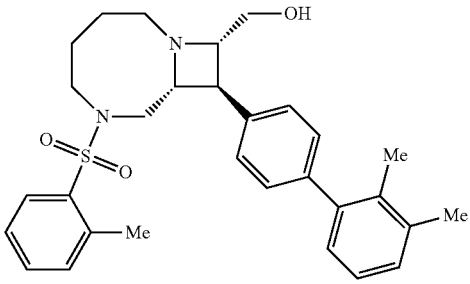 [SMILES: Cc1ccccc1S(=O)(=O)N1CCCCN2[C@H](CO)[C@@H](c3ccc(-c4cccc(C)c4C)cc3)[C@@H]2C1]

B8

The compounds described herein (e.g., a compound of Formula (RL), (I), (II), (III), (IV), or (V)), may exhibit selective inhibition of IDE versus inhibition of other proteases. In certain embodiments, the compound selectively inhibits activity of IDE over activity of one or more other metalloproteases. In certain embodiments, the compound selectively inhibits activity of IDE over activity of neurolysin (NLN), thimet olgiopeptidase-1 (THOP1), neprilysin (NEP), matrix metalloproteinase-1 (MMP1), or angiotensin converting enzyme (ACE). In certain embodiments, the selectivity versus inhibition of another metalloproteases is between about 2-fold and about 10-fold, inclusive. In certain embodiments, the selectivity is between about 10-fold and about 50-fold, inclusive. In certain embodiments, the selectivity is between about 50-fold and about 100-fold, inclusive. In certain embodiments, the selectivity is between about 100-fold and about 500-fold, inclusive. In certain embodiments, the selectivity is between about 500-fold and about 1000-fold, inclusive. In certain embodiments, the selectivity is between about 1000-fold and about 5000-fold, inclusive. In certain embodiments, the selectivity is between about 5000-fold and about 10000-fold, inclusive. In certain embodiments, the selectivity is at least about 10000-fold.

Selectivity towards IDE versus other metalloproteases may be measured by comparing the inhibition of IDE for degrading an IDE suitable substrate in the presence of the compound with the inhibition of another metalloprotease for degrading a substrate suitable for the other metalloprotease in the presence of the compound. In certain embodiments, the inhibition of IDE and/or another metalloprotease is measured by using a substrate with a detectable label. In some embodiments, the detectable label is a fluorophore. In some embodiments, the measurement of inhibition comprises a fluorescence measurement. In some embodiments, the substrate suitable for IDE and the substrate suitable for the other metalloprotease are the same. In some embodiments, the substrate suitable for IDE and the substrate suitable for the other metalloprotease are different. In some embodiments, measurements of inhibition are made at multiple concentrations of the compound for each enzyme (e.g., to determine an $IC_{50}$ or plot a dosage-response curve). In some embodiments, the measurements of inhibition is made at a single concentration of the compound for each enzyme.

Provided are methods that may be useful for the treatment of a metabolic disorder by administering compounds described herein, and pharmaceutically acceptable salts, solvates, hydrates, polymorphs, co-crystals, tautomers, stereoisomers, prodrugs, and isotopically labeled derivatives thereof, and pharmaceutical compositions thereof, to a subject in need thereof. In certain embodiments, the compound is administered as a pharmaceutically acceptable salt, stereoisomer, or tautomer thereof. In certain embodiments, the compound is administered as a pharmaceutically acceptable salt of the compound. In certain embodiments, the compound is administered as a specific stereoisomer or mixture of stereoisomers of the compound. In certain embodiments, the compound is administered as a specific tautomer or mixture of tautomers of the compound. In certain embodiments, the compound is administered as a pharmaceutical composition as described herein comprising the compound.

Also provided are uses of the compounds, and pharmaceutically acceptable salts, solvates, hydrates, polymorphs, co-crystals, tautomers, stereoisomers, prodrugs, and isotopically labeled derivatives thereof, and pharmaceutical compositions thereof, in the manufacture of medicaments for the treatment and prevention of diseases. In certain embodiments, the disease is a metabolic disorder. In certain embodiments, the disorder is a diabetic condition. In certain embodiments, the disorder is diabetes (e.g., type I diabetes mellitus, type II diabetes mellitus, gestational diabetes). In certain embodiments, the disorder is type I diabetes mellitus. In certain embodiments, the disorder is type II diabetes mellitus. In certain embodiments, the disorder is gestational diabetes. In certain embodiments, the disorder is congenital diabetes, cystic-fibrosis related diabetes, steroid diabetes, or a monogenic diabetes (e.g., mature onset diabetes of the young). In certain embodiments, the disorder is hyperglycemia, impaired glucose tolerance, or insulin resistance. In certain embodiments, the disorder is hypoglycemia or hyperinsulinemia. In certain embodiments, the disorder is an obesity-related condition. In certain embodiments, the disorder is obesity. In certain embodiments, the disorder is class I obesity, class II obesity, class III obesity, or pre-obesity. In certain embodiments, the disorder is undesired weight gain or an over-eating disorder. In some embodiments, the disorder is impaired insulin signaling or insulin resistance. In some embodiments, the disorder is caused by or associated with an aberrant half-life of a substrate of IDE (e.g., insulin, glucagon, amylin, calcitonin-gene related peptide (CGRP), amyloid beta-peptide, TGF-alpha, β-endorphin, somatostatin, and/or atrial natriuretic peptide), or that is treatable by modulation of the half-life of a substrate of IDE. In certain embodiments, the disease or condition is associated with elevated blood pressure. In certain embodiments, the disease or condition is hypertension or is associated with hypertension. In certain embodiments, the disease or condition is associated with elevated angiotensin-II. In certain embodiments, the disease or condition is associated with elevated endothelin-1. In certain embodiments, the disease or condition is associated with elevated aldosterone. In certain embodiments, the disease or condition is associated with elevated renin. In certain embodiments, the disease or condition is associated with sodium excretion.

In certain embodiments, provided are methods of administering to the subject an effective amount of a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the effective amount is a therapeutically effective amount. In certain embodiments, the effective amount is a prophylactically effective amount.

In another aspect, provided are methods that may be useful for inhibiting the activity of IDE in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for inhibiting the activity of IDE in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for selectively inhibiting the insulin degrading activity of IDE over the glucagon degrading activity of IDE in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the insulin degrading activity of IDE over the glucagon degrading activity of IDE in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the insulin degrading activity of IDE over the amylin degrading activity of IDE or the amylin degrading activity of IDE over the glucagon degrading activity of IDE in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the insulin degrading activity of IDE over the amylin degrading activity of IDE or the amylin degrading activity of IDE over the glucagon degrading activity of IDE in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, the present invention provides methods that may be useful for selectively inhibiting the glucagon degrading activity of IDE over the insulin degrading activity of IDE, the glucagon degrading activity of IDE over the amylin degrading activity of IDE, or the amylin degrading activity of IDE over the insulin degrading activity of IDE in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the glucagon degrading activity of IDE over the insulin degrading activity of IDE, the glucagon degrading activity of IDE over the amylin degrading activity of IDE, or the amylin degrading activity of IDE over the insulin degrading activity of IDE in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for inhibiting the degradation of insulin in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for inhibiting the degradation of insulin in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are that may be useful for inhibiting the degradation of amylin or glucagon in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for inhibiting the degradation of amylin or glucagon in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for selectively inhibiting the degradation of insulin over the degradation of glucagon in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the degradation of insulin over the degradation of glucagon in a biological sample (e.g., cells, tissues, biopsied tissues, purified or partially purified IDE), by contacting the sample with a compound described (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for enhancing the degradation of glucagon in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for enhancing the degradation of glucagon in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for selectively inhibiting the degradation of insulin over the degradation of amylin or the degradation of amylin over the degradation of glucagon in a subject in need thereof, by administering to the subject a compound described (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the degradation of insulin over the degradation of amylin or the degradation of amylin over the degradation of glucagon in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for selectively inhibiting the degradation of glucagon over the degradation of insulin, the degradation of amylin over the degradation of insulin, or the degradation of glucagon over the degradation of amylin in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-foldm, inclusive. In certain embodiments, the selectivity is at least about 1000-fold.

In another aspect, provided are methods that may be useful for selectively inhibiting the degradation of glucagon over the degradation of insulin, the degradation of amylin over the degradation of insulin, or the degradation of glucagon over the degradation of amylin in a biological sample (e.g., cells, tissues, biopsied tissues, purified or partially purified IDE), by contacting the sample with a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof. In certain embodiments, the selectivity is between about 2-fold and about 5-fold, inclusive. In certain embodiments, the selectivity is between about 5-fold and about 10-fold, inclusive. In certain embodiments, the selectivity is between about 10-fold and about 20-fold, inclusive. In certain embodiments, the selectivity is between about 20-fold and about 50-fold, inclusive. In certain embodiments, the selectivity is between about 50-fold and about 100-fold, inclusive. In certain embodiments, the selectivity is between about 100-fold and about 200-fold, inclusive. In certain embodiments, the selectivity is between about 200-fold and about 500-fold, inclusive. In certain embodiments, the selectivity is between about 500-fold and about 1000-fold, inclusive. In certain embodiments, the selectivity is at least about 1000-fold.

In another aspect, provided are methods that may be useful for increasing blood glucose in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for decreasing blood glucose in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

In another aspect, provided are methods that may be useful for enhancing the uptake of glucose by skeletal or adipose tissue in a subject in need thereof, by administering to the subject a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or a pharmaceutical composition thereof.

Further provided are methods of using a compound described herein (e.g., a compound of Formula (RL), (I), II), (III), (IV), or (V)), or a pharmaceutically acceptable salt, solvate, hydrate, polymorph, co-crystal, tautomer, stereoisomer, prodrug, or isotopically labeled derivative thereof, or pharmaceutical compositions thereof, in research studies in the field of disease pathology, biochemistry, cell biology, nutrition, and other fields associated with metabolic disorders. The compounds of the invention can be used to study the roles of biomolecules (e.g., IDE, insulin, amylin, glucagon, glucose). The compounds of the invention can be used to study metabolic pathways (e.g., glucose regulation, insulin release or degradation, glucagon release or degradation, amylin release or degradation). In certain embodiments, the method comprises use of the compound or composition thereof to inhibit IDE. In certain embodiments, the method comprises use of the compound or composition thereof to selectively inhibit IDE. In certain embodiments, the method comprises determining the concentration of a biomolecule (e.g., insulin, glucagon, glucose) in a subject or biological sample.

Certain methods described herein, may comprise administering one or more additional pharmaceutical agent in combination with the compounds described herein. In certain embodiments, the additional pharmaceutical agent is an anti-diabetic agent. In certain embodiments, the additional pharmaceutical agent is an anti-obesity agent. In certain embodiments, the additional pharmaceutical agent is an binder or inhibitor of a protease. In certain embodiments, the additional pharmaceutical agent is an binder or inhibitor of insulin-degrading enzyme (IDE). In certain embodiments, the additional pharmaceutical agent inhibits the degradation of insulin, promotes the release of insulin, or enhances the activity of insulin. In certain embodiments, the additional pharmaceutical agent inhibits the synthesis or release of glucagon.

In certain embodiments, the additional pharmaceutical agent is an anti-diabetic agent. The additional pharmaceutical agents include, but are not limited to, insulins, insulin analogs, insulin sensitizers, insulin secretagogues, incretin mimetics, incretin agonists, dipeptidyl peptidase-4 (DPP4) inhibitors, and sodium glucose co-transporter-2 (SGLT-2) inhibitors. In certain embodiments, the additional pharmaceutical agent is insulin (e.g., humulin). In certain embodiments, the additional pharmaceutical agent is an insulin analog. In certain embodiments, the additional pharmaceutical agent is insulin lispro, insulin aspart, insulin glulisine, insulin detemir, insulin degludec, insulin glargine, or NPH insulin.

In certain embodiments, the additional pharmaceutical agent is an insulin sensitizer. In certain embodiments, the additional pharmaceutical agent is a biguanide. In certain embodiments, the additional pharmaceutical agent is metformin, phenformin, or butformin. In certain embodiments, the additional pharmaceutical agent is a thiazolidinedionze (i.e., a glitzone). In certain embodiments, the additional pharmaceutical agent is rosiglitazone, pioglitazone, or troglitazone.

In certain embodiments, the additional pharmaceutical agent is an insulin secretagogue. In certain embodiments, the additional pharmaceutical agent is a sulfonylurea. In certain embodiments, the sulfonylurea is tolbutamide, acetohexamide, tolazamide, chlorpropamide, glipizide, glibenclamide, glimepiride, gliclazide, glycopyramide, gliquidone. In certain embodiments, the additional pharmaceutical agent is a meglitinide. In certain embodiments, the meglitinide is repaglinide or nateglinide.

In certain embodiments, the additional pharmaceutical agent is an incretin mimetic or incretin agonist. In certain embodiments, the incretin mimetic or incretin agonist is exenatide, liraglutide, taspoglutide, lixisenatide, dulaglutide, or albiglutide. In certain embodiments, the additional pharmaceutical agent is a dipeptidyl peptidase-4 (DPP4) inhibitor. In certain embodiments, the DPP4 inhibitor is vildagliptin, sitagliptin, saxagliptin, linagliptin, alogliptin, or septagliptin. In certain embodiments, the additional pharmaceutical agent is a glycosuric. In certain embodiments, the additional pharmaceutical agent is a sodium glucose co-transporter-2 (SGLT-2) inhibitor. In certain embodiments, the SGLT-2 inhibitor is empagliflozin, canagliflozin, or dapagliflozin. In certain embodiments, the additional pharmaceutical agent is an alpha-glucosidase inhibitor. In certain embodiments, the additional pharmaceutical agent is miglitol, acarbose, or voglibose.

Substrate Selective Inhibitor Assay

In another aspect, the present invention provides methods of identifying a substrate selective inhibitor of IDE. Substrate selective inhibitors may have an inhibition maximum for IDE which is less than complete (e.g., less than about 100%) inhibition of activity of the enzyme for degradation of a specific substrate. The maximum inhibition ($I_{MAX}$) is defined to be the greatest extent to which IDE is inhibited by any concentration of the candidate inhibitor. The maximum inhibition may be determined by probing the activity of IDE for a specific peptide (e.g., a peptide with a detectable label) in the presence of a candidate inhibitor. In the absence of an inhibitor when the peptide is contacted by IDE no peptide remains uncleaved. Contrastingly, in the presence of a sufficient concentration of a non-selective inhibitor, the IDE is fully inhibited, and all peptide remains uncleaved, i.e. $I_{MAX}$ is about 100%. Those skilled in the art will recognize that all inhibitors have a dosage-response profile, and that even for non-selective inhibitors there will be low concentrations at which the IDE is not fully inhibited. A substrate selective inhibitor will have a dosage-response profile, but will not achieve full inhibition even at high concentrations (e.g., concentrations multiple times higher than the measured or expected $IC_{50}$ of the inhibitor). The dosage-response profile will thus plateau at a level of inhibition at which IDE is not fully inhibited from cleavage of the peptide. The inhibition maximum ($I_{MAX}$) will be less than about 100%. Dosage-response profiles for inhibitors with $I_{MAX}$ of less than 100% are shown in FIG. 2B, along with the dosage-response profile for a non-selective control inhibitor (6bK, $I_{MAX}$=100%). In some embodiments, an $I_{MAX}$ of less than 100% will identify a candidate compound as a substrate selective inhibitor.

In certain embodiments, the method comprises contacting IDE with a candidate compound and a peptide, wherein the IDE is capable of cleaving the peptide; measuring a quantity or percent of the peptide which remains uncleaved; optionally repeating steps (a) and (b) at a number of concentrations of the candidate compound, wherein the number of concentrations is sufficient to determine the inhibition maximum ($I_{MAX}$) of the candidate compound; and determining the inhibition maximum of the candidate compound, wherein if the maximum inhibition of peptide cleavage is less than 100%, then the candidate compound is identified as a substrate-selective inhibitor of IDE.

In certain embodiments, the IDE is human IDE. In certain embodiments, the IDE is from a non-human animal species. In certain embodiments, the IDE is from a microorganism. In certain embodiments, the IDE is wild-type IDE. In certain embodiments, the IDE is a mutant IDE. In certain embodiments, the candidate compound is a compound as described herein (e.g., a compound of Formula (RL), (I), II), (III), (IV), or (V)). In certain embodiments, the candidate compound is not a compound as described herein. In certain embodiments, the peptide is insulin or an insulin analog. In certain embodiments, the peptide is glucagon or a glucagon analog. In certain embodiments, the peptide is amylin or an amylin analog. In certain embodiments, the peptide is TGF alpha, beta-endorphin, amyloid beta, bradykinin, kallidin, calcitonin-gene related peptide (CGRP), somatostatin, or atrial natriuretic peptide, or an analog thereof.

In certain embodiments, the peptide comprises a detectable label. In some embodiments, the detectable label is a fluorophore. In certain embodiments, the peptide comprises a fluorophore and a quencher. In some embodiments, the peptide is conjugated to the detectable label (e.g., fluorophore). In some embodiments, the conjugation is via a direct, covalent bond of the detectable label to the peptide. In some embodiments, the conjugation is via a linker. In some embodiments, the detectable label is conjugated to the peptide in a manner that does not interfere with the binding properties of the peptide to IDE.

In certain embodiments, the detectable label comprises a xanthene derivative, a cyanine derivative, a naphthalene derivative, a dansyl or prodan derivative, a coumarin derivative, an oxadiazole derivative, a pyrene derivative, an oxazine derivative, an acridine derivative, an arylmethine derivative, a tetrapyrole derivative, or a quatum dot.

In certain embodiments, the detectable label comprises fluorescein, rhodamine, Oregon green, eosin, Texas red, cyanine, indocarbocyanine, oxacarbocyanine, thiacarbocyanine, merocyanine, pyridyloxazole, nitrobenzoxadiazole, benzoxadiazole, cascade blue, nile red, nile blue, cresyl violet, oxazine 170, proflavin, acridine orange, acridine yellow, auramine, crystal violet, malachite green, porphin, phthalocyanine, or bilirubin.

In certain embodiments, the detectable label comprises GFP, BFP, CFP, RFP, YFP, Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima, or a derivative thereof.

In certain embodiments, the peptide is a fluorogenic peptide comprising a fluorophore as a detectable label and optionally a quencher. In some embodiments, the peptide or one or more residues or bonds within the peptide may act as the quencher. In certain embodiments, the peptide is the fluorogenic peptide (Mca)-RPPGFSAFK-(Dnp)-OH (SEQ ID NO: 4). In certain embodiments, the fluorogenic peptide comprises (Mca)-RPKPVE-(Nval)-WRK-(Dnp)-NH$_2$ (SEQ ID NO: 10), (Mca)-PLAQAV-(Dpa)-RSSSR—NH$_2$ (SEQ ID NO: 11), (Mca)-SEVNLDAEFRK-(Dnp)-RR—NH$_2$ (SEQ ID NO: 12), (Mca)-PLGL-(Dpa)-AR-NH$_2$ (SEQ ID NO: 13), DADEY-(PO$_3$)-LIPQQG (SEQ ID NO: 14), (Mca)-YVADAPK-(Dnp)-OH (SEQ ID NO: 15), (Cbz)-LR-(AMC), or (Cbz)-FR-(AMC). In certain embodiments, the fluorogenic peptide comprises (Ac)-ASTD-(AMC) (SEQ ID NO: 16), (Cbz)-DQMD-(AFC) (SEQ ID NO: 17), H-His-Phe-(βNA), H-A-(βNA), H-LV-(4MβNA), (Cbz)-VR-(4MβNA), (Cbz)-VLR-(4MβNA), H-KTEEISEVKM-(pNA) (SEQ ID NO: 18), (4-methoxy-Bz)-PF-(pNA), (Suc)-AAP-(Nval)-(pNA) (SEQ ID NO: 19), (Abz)-KPLGL-(Dap)(Dnp)-AR-NH$_2$ (SEQ ID NO: 20), H-APV-(EDANS), (DABCYL)-YVAD-OH (SEQ ID NO: 21), H-Glu (EDANS)-KPAKFFRK(DABCYL)-NH$_2$ (SEQ ID NO: 22), or (Abz-Gly$_1$)-GWTLNSAGYLK(retro-m-nitro-Tyr-H) amide (SEQ ID NO: 23). In these examples, 4M βNA is 4-methyl-β-napthylamide, Ac is acetyl, AFC is 7-amino-4-trifluoromethylcoumarin, AMC is 7-amino-4-methylcoumarin, Abz is 2-aminobenzoic acid, βNA is β-napthylamide, Bz is benzoyl, Cbz is benzyloxycarbonyl, DABCYL is 4-(4-dimethylaminophenylazo)benzoyl, Dap is L-α,β-diaminopropionic acid, Dnp is 2,4-dinitrophenyl, DPA is N-3-

(2,4-dinitrophenyl)-L-2,3-diaminopropionyl, EDANS is 5-[(2-aminoethyl)amino]naphthalene-1-sulfonic acid, Mca is (7-methoxycoumarin-4-yl)acetyl, Nval is norvaline, pNA is p-nitroanilide, and Suc is succinyl. In certain embodiments, the peptide comprises a fluorophore selected from 4MβNA, βNA, Abz, AFC, AMC, EDANS, MCA, and Lys-γN-anthranilamide. In certain embodiments, the peptide comprises a chromphore selected from pNA, DABCYL, DNP, DPA, and 3-nitro-Tyr. In certain embodiments, the peptide comprises a fluorophore selected from 4MβNA, βNA, Abz, AFC, AMC, EDANS, MCA, and Lys-γN-anthranilamide, and a chromophore selected from pNA, DABCYL, DNP, DPA, and 3-nitro-Tyr.

In certain embodiments, the step of contacting comprises contacting the IDE with the candidate compound prior to contacting the IDE with the peptide. In certain embodiments, the step of contacting comprises contacting the IDE with the candidate compound after to contacting the IDE with the peptide. In certain embodiments, the step of contacting comprises contacting the IDE with the candidate compound and the peptide simultaneously or essentially simultaneously. In some embodiments, the IDE is contacted with the probe and the candidate compound in aqueous solution. In some embodiments, the IDE is contacted with the probe and the candidate compound under physiological conditions.

In some embodiments, the method comprises screening a library of different candidate compounds. In some embodiments, the library comprises at least 100, at least 500, at least 1000, at least 5000, at least 10000, different candidate compounds. In some embodiments, the method comprises a parallel assessment of a plurality of different candidate compounds, for example, in a multi-well plate format.

In certain embodiments, the step of measuring comprises a fluorescence assay. In some embodiments, the cleavage of the peptide disrupts the interaction between a fluorophore and quencher providing an observable increase in fluorescence emission. In certain embodiments, the step of measuring comprises calculating the quantity or proportion of peptide which is cleaved from the levels of emitted light (e.g., fluorescence emission) before and after contacting the peptide with the IDE. In some embodiments, the step of measuring comprises calculating a ratio of the levels of emitted light (e.g., fluorescence emission) before and after contacting the peptide with the IDE. In certain embodiments, the step of measuring comprises a Förster resonance energy transfer (FRET) assay. In some embodiments, the cleavage of the peptide disrupts the interaction between two chromophores capable of FRET providing an observable decrease in the FRET efficiency.

Additional suitable assays and detection technologies can be used to determine the level of cleaved/uncleaved peptide in the presence of the candidate compound. Such assays and detection technologies include, without limitation, fluorescence-based, antibody-based, anisotropy-based, plasmon resonance-based, and fluorescence resonance energy transfer (FRET)-based assays. In certain embodiments, the peptide fragments may be detected by a liquid chromatography (LC) assay. In some embodiments, the LC assay comprises a spectroscopic measurement (e.g., LC-UV). In some embodiments, the LC assay comprises a mass spectrometry measurement (e.g., LC-MS). In certain embodiments, the detectable label is the peptide fragment itself, or a sub-fragment or residue within the peptide. For example, the cleaved fragments may be detected by a method to identify peptide fragments (e.g., mass spectrometry, LC-MS, capillary electrophoresis, gel electrophoresis). Additional suitable assays and detection technologies will be apparent to those of skill in the art based on the instant disclosure, and the disclosure is not limited in this respect.

In certain embodiments, the step of repeating is not performed. In certain embodiments, the step of repeating is performed between 1 and 2 times. In certain embodiments, the step of repeating is performed between 3 and 10 times. If the concentration of the candidate compound used is at least about 2 times greater, and preferably at least about 10 times greater, than the expected or known $IC_{50}$ for the compound, and the percent uncleaved peptide is measured to be between above about 0%, the step of repeating may be unnecessary, and the measured uncleaved percent from a single measurement can be taken to be $I_{MAX}$. In certain embodiments, the $IC_{50}$ is not known or cannot be predicted. In certain embodiments, the step of repeating is carried out a number of times that are sufficient to plot an inhibition curve (percent uncleaved vs. concentration of inhibitor). In some embodiments, the number of concentrations that are sufficient to plot an inhibition curve is between 3 and 10.

In certain embodiments, the step of determining involves plotting an inhibition curve (percent uncleaved vs. concentration of inhibitor). In some embodiments, the step of determining involves determining the value at which the inhibition curve stops rising at incrementally higher concentrations. In some embodiments, the step of determining involves estimating or calculating the value at which the inhibition curve reaches an asymptote. In some embodiments, the step of determining involves fitting the inhibition curve data from steps (a), (b), and (c), and analyzing the fit equation to determine $I_{MAX}$. In some embodiments, the step of determining is performed using a computer and software.

In certain embodiments, the candidate compound is identified as a substrate selective inhibitor of IDE if the $I_{MAX}$ is determined to be less than a reference level. In some embodiments, the reference level is about 100%. In some embodiments, the reference level is about 90%. In some embodiments, the reference level is about 80%. In some embodiments, the reference level is about 70%. In some embodiments, the reference level is about 60%. In some embodiments, the reference level is about 50%. In some embodiments, the reference level is about 40%. In some embodiments, the reference level is about 30%. In some embodiments, the reference level is about 20%. In some embodiments, the reference level is about 10%.

In certain embodiments, the candidate compound is identified as a substrate selective inhibitor for inhibiting the activity of IDE for degrading insulin over the activity of IDE for degrading another substrate. In certain embodiments, the candidate compound is identified as a substrate selective inhibitor for activity of degrading insulin over activity of degrading glucagon. In certain embodiments, the candidate compound is identified as a substrate selective inhibitor for activity of degrading insulin over activity of degrading amylin. In certain embodiments, the candidate compound is identified as a substrate selective inhibitor for the activity of degrading insulin over the activity of degrading TGF alpha, beta-endorphin, amyloid beta, bradykinin, kallidin, calcitonin-gene related peptide (CGRP), somatostatin, or atrial natriuretic peptide.

In certain embodiments, the candidate compound is identified as a substrate selective inhibitor for the activity of activity of IDE for degrading amylin over the activity of IDE for degrading another substrate. In certain embodiments, the candidate compound is identified as a substrate selective inhibitor of degrading amylin over activity of degrading insulin. In certain embodiments, the candidate compound is identified as a substrate selective inhibitor for activity of degrading amylin over activity of degrading glucagon. In certain embodiments, the candidate compound is identified as a substrate selective inhibitor for the activity of degrading glucagon over the activity of degrading TGF alpha, beta-endorphin, amyloid beta, bradykinin, kallidin, calcitonin-gene related peptide (CGRP), somatostatin, or atrial natriuretic peptide.

In certain embodiments, the candidate compound is identified as substrate selective modulator for permitting or enhancing the activity of IDE for degrading glucagon over the activity of IDE for degrading another substrate. In certain embodiments, the candidate compound is identified as a substrate selective modulator for permitting or enhancing the activity of degrading glucagon over activity of degrading insulin. In certain embodiments, the candidate compound is identified as a substrate selective modulator for permitting or enhancing the activity of degrading glucagon over activity of degrading amylin. In certain embodiments, the candidate compound is identified as a substrate selective modulator for permitting or enhancing the activity of degrading glucagon over the activity of degrading TGF alpha, beta-endorphin, amyloid beta, bradykinin, kallidin, calcitonin-gene related peptide (CGRP), somatostatin, or atrial natriuretic peptide.

In certain embodiments, the candidate compound is identified as a substrate selective inhibitor for the activity of degrading TGF alpha, beta-endorphin, amyloid beta, bradykinin, kallidin, calcitonin-gene related peptide (CGRP), somatostatin, or atrial natriuretic peptide over the activity of degrading another substrate of IDE. In certain embodiments, the candidate compound is identified as a substrate selective inhibitor for the activity of degrading TGF alpha, beta-endorphin, amyloid beta, bradykinin, kallidin, calcitonin-gene related peptide (CGRP), somatostatin, or atrial natriuretic peptide over the activity of degrading insulin. In certain embodiments, the candidate compound is identified as a substrate selective inhibitor for the activity of degrading TGF alpha, beta-endorphin, amyloid beta, bradykinin, kallidin, calcitonin-gene related peptide (CGRP), somatostatin, or atrial natriuretic peptide over the activity of degrading amylin. In certain embodiments, the candidate compound is identified as a substrate selective inhibitor for the activity of degrading TGF alpha, beta-endorphin, amyloid beta, bradykinin, kallidin, calcitonin-gene related peptide (CGRP), somatostatin, or atrial natriuretic peptide over the activity of degrading glucagon. In certain embodiments, the candidate compound is identified as a substrate selective inhibitor for the activity of degrading TGF alpha, beta-endorphin, amyloid beta, bradykinin, kallidin, calcitonin-gene related peptide (CGRP), somatostatin, or atrial natriuretic peptide over the activity of degrading another substrate of IDE selected from the group consisting of TGF alpha, beta-endorphin, amyloid beta, bradykinin, kallidin, calcitonin-gene related peptide (CGRP), somatostatin, and atrial natriuretic peptide.

In another aspect, provided herein is a compound of compound comprising a locked ring moiety, cavity-interacting moiety, and linker moiety or a compound Formula (RL), (I), (II), (III), (IV), or (V), wherein the compound further comprises a detectable label. In some aspects the detectable label is a fluorophore. In some embodiments, the compound binds to IDE with an $IC_{50}$ of less than 10 µM. In some embodiments, the compound binds to IDE with an $IC_{50}$ of less than 5 µM. In some embodiments, the compound binds to IDE with an $IC_{50}$ of less than 2 µM. In some embodiments, the compound binds to IDE with an $IC_{50}$ of less than 1 µM. In some embodiments, the compound binds to IDE with an $IC_{50}$ of less than 0.5 µM.

In another aspect, provided herein is a method of preparing a compound a compound comprising a locked ring moiety, cavity-interacting moiety, and linker moiety or a compound Formula (RL), (I), (II), (III), (IV), or (V), and further comprising a detectable label, wherein the method comprises coupling a compound comprising a locked ring moiety, cavity-interacting moiety, and linker moiety or a compound Formula (RL), (I), (II), (III), (IV), or (V) with a reagent comprising a detectable label. In some embodiments, the detectable label is a fluorophore. In some embodiments, the reagent comprising a detectable label comprises a leaving group. In some embodiments, the compound comprises a leaving group.

The compound with a detectable label may be used in an assay to identify selective or non-selective inhibitors of insulin-degrading enzyme, as described in PCT application PCT/US2014/064322, which is incorporated herein by reference.

In another aspect, provided is a method of identifying an IDE-binding compounds, the method comprising:
(a) contacting an IDE with:
(i) a probe that binds IDE with an $IC_{50}$ of 10 µM or less, wherein the probe comprises a detectable label; and
(ii) a candidate compound;
under conditions suitable for the probe and the candidate compound to bind the IDE;
(b) determining the level of unbound probe in the presence of the candidate compound; and
(c) comparing the level of unbound probe determined in step (b) to a reference level, wherein if the level of unbound probe in the presence of the candidate compound is higher than the reference level, then the candidate compound is identified as an IDE-binding compound; wherein the probe is a compound described herein. In some embodiments, the probe is a compound comprising a locked ring moiety, cavity-interacting moiety, and linker moiety, wherein the linker moiety connects the locked ring moiety and the cavity-interacting moiety, and further comprising a detectable label. In some embodiments, the probe is a compound of Formula (RL), (I), (II), (III), or (IV) further comprising a detectable label.

In some embodiments, determining the level of unbound probe in the presence of the candidate compound comprises exposing IDE contacted with the probe and the candidate compound to incident, plane-polarized light of a suitable wave length to excite the fluorophore; and detecting the level of fluorescent light emitted by the fluorophore in the same plane of polarization as the incident light, as well as the level of fluorescent light emitted by the fluorophore in a plane different from the plane of polarization of the incident light. In some embodiments, determining the level of unbound probe in the presence of the candidate compound comprises calculating the level of unbound probe from the levels of emitted light detected. In some embodiments, the calculating the level of unbound probe comprises calculating a ratio of the levels of emitted light detected, or calculating a fluorescence anisotropy value.

In some embodiments, the candidate compound is identified as an IDE-binding compound if the level of fluorescent light emitted by the fluorophore in the presence of the candidate compound in a plane different from the plane of polarization of the incident light is higher than a reference level of fluorescent light emitted in that plane measured in the absence of the candidate compound. In some embodiments, the method is carried out repeatedly for a candidate compound at a plurality of IDE concentrations, and the method comprises calculating a ratio of the levels of emitted light detected, or calculating a fluorescence anisotropy value for each concentration; and determining a dynamic IDE concentration range. In some embodiments, the candidate compound is identified as an IDE-binding compound if the level of fluorescent light emitted by the fluorophore in the presence of the candidate compound in a plane different from the plane of polarization of the incident light is at least 1.1-fold, at least 1.2-fold, at least 1.3-fold, at least 1.5-fold, at least 1.75-fold, at least 2-fold, at least 2.5-fold, at least 3-fold, at least 4-fold, at least 5-fold, at least 10-fold, at least 20-fold, at least 30-fold, at least 40-fold, at least 50-fold, at least 100-fold, at least 200-fold, at least 500-fold, or at least 1000-fold higher than a reference level of fluorescent light emitted in that plane measured in the absence of the candidate compound. In some embodiments, the candidate compound is identified as an IDE-binding compound if the fluorescence anisotropy in the presence of the candidate compound is at least 1.1-fold to at least 5-fold, at least 10-fold to at least 100-fold, or at least 200-fold to at least 1000-fold lower than the fluorescence anisotropy in the absence of the candidate compound. In some embodiments, the level of emitted light or the fluorescent anisotropy is measured at a point within the dynamic IDE concentration range. In some embodiments, the detectable label comprises a binding agent. In some embodiments, the binding agent comprises an antibody or an antigen-binding fragment thereof. In some embodiments, the binding agent comprises a ligand. In some embodiments, the ligand is biotin or an avidin derivative. In some embodiments, the detectable label comprises a detectable isotope.

In some embodiments, IDE is contacted with the probe and the candidate compound in aqueous solution. In some embodiments, the IDE is contacted with the probe and the candidate compound under physiological conditions. In some embodiments, the method comprises screening a library of different candidate compounds.

In some embodiments, the reference level represents a level of unbound probe in the absence of the candidate compound. In some embodiments, the reference level is determined by measuring the level of unbound probe in the absence of a candidate compound or in the presence of a compound known to bind IDE with an $IC_{50}$ of more than 10 µM. In some embodiments, the probe comprises an IDE inhibitor, and the candidate compound is identified as an IDE inhibitor if it can successfully compete with the probe for IDE binding.

Exemplary probes include, but are not limited to, probes of the following formula:

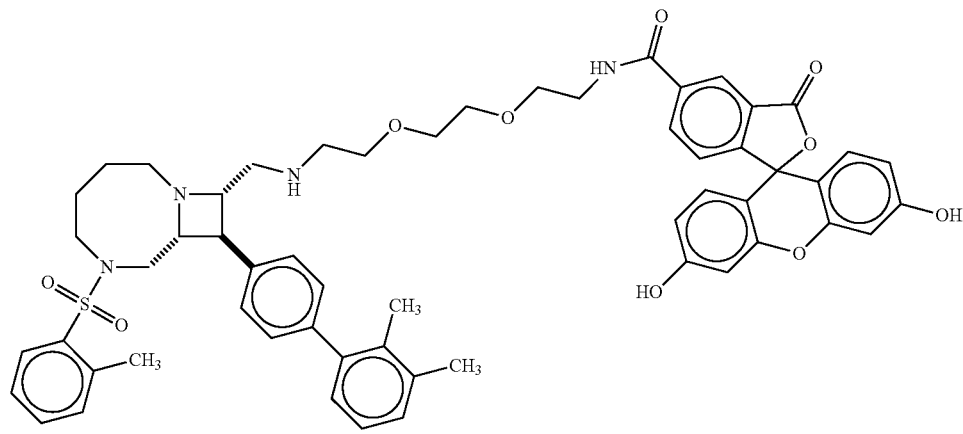

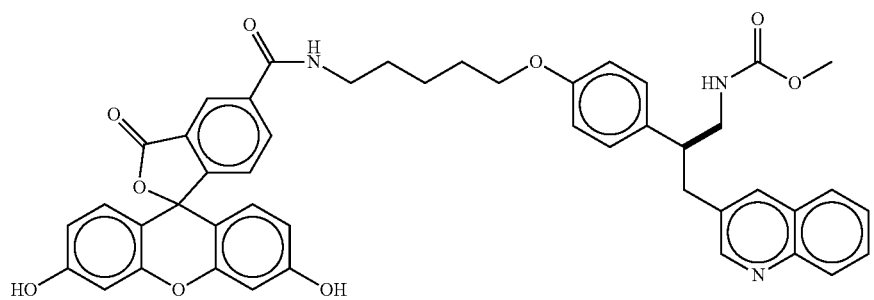

and

-continued

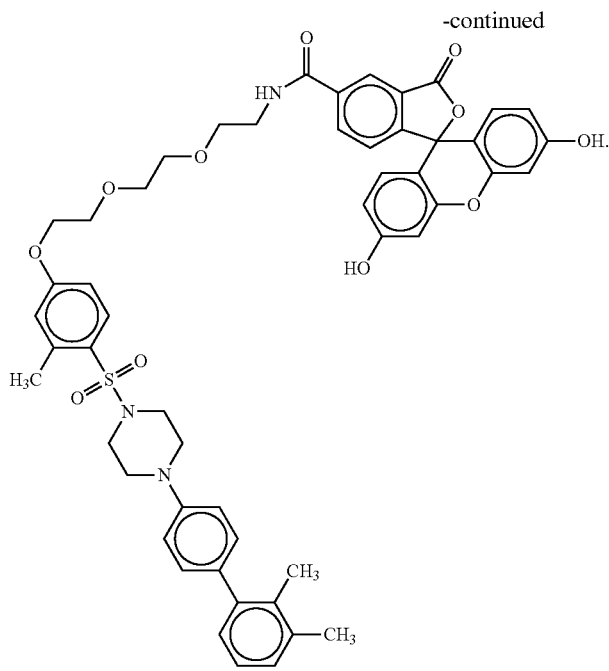

Definitions

Chemical Terms

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, - - - is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are referred to herein as "isotopically labeled derivatives" of the compound having the present structures. Isotopically labeled derivatives are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH_3 or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R—, —SO$_2$R—, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)

($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S) S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$ alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O) S$R^{aa}$, —OC(=O)$R^{aa}$, —OCO$_2$R—, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)R—, —OSO$_2$$R^{aa}$, —OSi($R^{aa}$)$_3$, —OP ($R^{cc}$)$_2$, —OP($R^{cc}$)$_3^+$$X^-$, —OP(O$R^{cc}$)$_2$, —OP(O$R^{cc}$)$_3^+$$X^-$, —OP(=O)($R^{aa}$)$_2$, —OP(=O)(O$R^{cc}$)$_2$, and —OP(=O)(N ($R^{bb}$))$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2$$R^{aa}$, —NHC (=O)N($R^{bb}$)$_2$, —NHC(=N$R^{bb}$)N($R^{bb}$)$_2$, —NHSO$_2$$R^{aa}$, —NHP(=O)(O$R^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}$CO$_2$$R^{aa}$, —$NR^{bb}$C(=O)N($R^{bb}$)$_2$, —$NR^{bb}$C(=N$R^{bb}$)N($R^{bb}$)$_2$, —$NR^{bb}$SO$_2$$R^{aa}$, —$NR^{bb}$P (=O)(O$R^{cc}$)$_2$, and —$NR^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$$X^-$, wherein $R^{bb}$ and $X^-$ are as defined herein.

The term "sulfonyl" refers to a group selected from —SO$_2$N($R^{bb}$)$_2$, —SO$_2$$R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" or "optionally substituted acyl" refers to a group having the general formula —C(=O)$R^{X1}$, —C(=O)O$R^{X1}$, —C(=O)—O—C(=O)$R^{X1}$, —C(=O) S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$) O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "silyl" refers to the group —Si($R^{aa}$)$_3$, wherein $R^{aa}$ is as defined herein.

The term "boronyl" refers to boranes, boronic acids, boronic esters, borinic acids, and borinic esters, e.g., boronyl groups of the formula —B($R^{aa}$)$_2$, —B(O$R^{cc}$)$_2$, and —B$R^{aa}$ (O$R^{cc}$), wherein $R^{aa}$ and $R^{cc}$ are as defined herein.

The term "stannyl" refers to the group —Sn($R^{cc}$)$_3$, wherein $R^{cc}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N ($R^{cc}$)$_2$, —CO$_2$$R^{1a}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)(R)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)

amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^a$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" or "non-hydrogen substituent" refers to any group that is defined for a particular variable that is not hydrogen or an isotope of hydrogen.

The term "leaving group" is given its ordinary meaning in the art of synthetic organic chemistry and refers to an atom or a group capable of being displaced by a nucleophile. As used herein, a leaving group can be an atom or a group capable of being displaced by a nucleophile. See, for example, Smith, March Advanced Organic Chemistry 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$ wherein R$^{aa}$, R$^{bb}$, and R$^{cc}$ are as defined herein).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present invention and one or more other component, including but not limited to, atoms, ions, molecules, or solvent molecules. In certain embodiments, a co-crystal contains a compound of the present invention and one or more solvent molecules. In certain embodiments, a co-crystal contains a compound of the present invention and one or more acid or base. In certain embodiments, a co-crystal contains a compound of the present invention and one or more components related to said compound, including not limited to, an isomer, tautomer, salt, solvate, hydrate, synthetic precursor, synthetic derivative, fragment or impurity of said compound.

The term "prodrug" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); cell fractions, fragments or organelles (such as obtained by lysing cells and separating the components thereof by centrifugation or otherwise); or purified or partially purified biomolecules (e.g., purified or partially purified IDE). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "condition," "disease," and "disorder" are used interchangeably.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type I diabetes, type II diabetes, gestational diabetes), hyperglycemia, hyperinsulinemia, insulin resistance, and obesity.

A "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. type I diabetes results from the body's failure to produce insulin, and presently requires the person to inject insulin or wear an insulin pump. type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

An "obesity-related condition" includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" refers to class I obesity, class II obesity, class III obesity and pre-obesity (e.g., being "over-weight") as defined by the World Health Organization.

As used herein, and unless otherwise specified, the terms "treat," "treating" and "treatment" contemplate an action that occurs while a subject is suffering from the specified metabolic disorder, which reduces the severity of the metabolic disorder, or retards or slows the progression of the metabolic disorder (i.e., "therapeutic treatment"), and also contemplates an action that occurs before a subject begins to suffer from the specified metabolic disorder (i.e., "prophylactic treatment").

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibiting insulin degradation, inhibiting glucagon degradation, or inhibiting activity of insulin-degrading enzyme (IDE). In certain embodiments, a therapeutically effective amount is an amount sufficient for treating a metabolic disorder (e.g., diabetes). In certain embodiments, a therapeutically effective amount is an amount sufficient for inhibiting insulin degradation, inhibiting glucagon degradation, or inhibiting activity of insulin-degrading enzyme (IDE) and for treating a metabolic disorder (e.g., diabetes).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for inhibiting insulin degradation, inhibiting glucagon degradation, or inhibiting activity of insulin-degrading enzyme (IDE). In certain embodiments, a prophylactically effective amount is an amount sufficient for preventing a metabolic disorder (e.g., diabetes). In certain embodiments, a prophylactically effective amount is an amount sufficient for inhibiting insulin degradation, inhibiting glucagon degradation, or inhibiting activity of insulin-degrading enzyme (IDE) and for preventing a metabolic disorder (e.g., diabetes).

As used herein the term "inhibit" or "inhibition" in the context of enzymes, for example, in the context of IDE, refers to a reduction in the activity of the enzyme. In some embodiments, the term refers to a reduction of the level of enzyme activity, e.g., IDE activity, to a level that is statistically significantly lower than an initial level, which may, for example, be a baseline level of enzyme activity. In some embodiments, the term refers to a reduction of the level of enzyme activity, e.g., IDE activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein, the term "insulin degrading enzyme" or "IDE" refers to an insulin-degrading enzyme. IDE (also referred to herein as IDE proteins) and their respective encoding RNA and DNA sequences according to some aspects of this invention include human IDE protein and encoding sequences, as well as, in some embodiments, IDE proteins and encoding sequences from other species, for example, from other mammals (e.g., IDE proteins and encoding sequences from mouse, rat, cat, dog, cattle, goat, sheep, pig, or primate), from other vertebrates, and from insects. In some embodiments, an IDE inhibitor provided herein is specific for an IDE from a species, e.g., for human IDE, mouse IDE, rat IDE, and so on. In some embodiment, an IDE provided herein inhibits IDEs from more than one species, e.g., human IDE and mouse IDE. In some embodiments, an IDE provided herein exhibits equipotent inhibition of IDEs from more than one species, e.g., equipotent inhibition of human and mouse IDEs. The term IDE further includes, in some embodiments, sequence variants and mutations (e.g., naturally occurring or synthetic IDE sequence variants or mutations), and different IDE isoforms. In some embodiments, the term IDE includes protein or encoding sequences that are homologous to an IDE protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with an IDE sequence, for example, with an IDE sequence provided herein. In some embodiments, the term IDE refers to a protein exhibiting IDE activity, for example, a protein exhibiting insulin-targeted protease activity, or a nucleic acid sequence encoding such a protein. In some embodiments, the term IDE included proteins that exhibit at least 50%, at least 60%, at least 70%, at least 80%, at least 90%, at least 95%, or at least 100% insulin-targeting protease activity as compared to a known IDE protein or encoding sequence, for example, as compared to an IDE sequence provided herein. IDE protein and encoding gene sequences are well known to those of skill in the art, and exemplary protein sequences include, but are not limited to, the following sequences. Additional IDE sequences, e.g., IDE homologues from other mammalian species, will be apparent to those of skill in the art, and the invention is not limited to the exemplary sequences provided herein.

```
>gi|155969707|ref|NP_004960.2| insulin-degrading
enzyme isoform 1 [Homo sapiens]
                                     (SEQ ID NO: 1)
MRYRLAWLLHPALPSTERSVLGARLPPPERLCGFQKKTYSKMNNPAIKRI

GNHITKSPEDKREYRGLELANGIKVLLISDPTTDKSSAALDVHIGSLSDP

PNIAGLSHFCEHMLFLGTKKYPKENEYSQFLSEHAGSSNAFTSGEHTNYY

FDVSHEHLEGALDRFAQFFLCPLEDESCKDREVNAVDSEHEKNVMNDAWR

LFQLEKATGNPKHPFSKFGTGNKYTLETRPNQEGIDVRQELLKEHSAYYS

SNLMAVCVLGRESLDDLTNLVVKLFSEVENKNVPLPEFPEHPFQEEHLKQ

LYKIVPIKDIRNLYVTFPIPDLQKYYKSNPGHYLGHLIGHEGPGSLLSEL

KSKGWVNTLVGGQKEGARGEMFFIINVDLTEEGLLHVEDIILHMFQYIQK

LRAEGPQEWVFQECKDLNAVAFREKDKERPRGYTSKIAGILHYYPLEEVL

TAEYLLEEFRPDLIEMVLDKLRPENVRVAISKSFEGKTDRTEEWYGTQY

KQEAIPDEVIKKWQNADLNGKFKLPTKNEFIPTNFEILPLEKEATPYPAL

IKDTAMSKLWFKQDDKFFLPKACLNEEFFSPFAYVDPLHCNMAYLYLELL

KDSLNEYAYAAELAGLSYDLQNTIYGMYLSVKGYNDKQPILLKKIIEKMA

TFEIDEKRFEIIKEAYMRSLNNFRAEQPHQHAMYYLRLLMTEVAWTKDEL

KEALDDVTLPRLKAFIPQLLSRLHIEALLHGNITKQAALGIMQMVEDTLI

EHAHTKPLLPSQLVRYREVQLPDRGWEVYQQRNEVHNNCGIEIYYQTDMQ

STSENMFLELFCQIISEPCFNTLRTKEQLGYIVESGPRRANGIQGLRFII

QSEKPPHYLESRVEAFLITMEKSIEDMTEEAFQKHIQALAIRRLDKPKKL

SAECAKYWGEIISQQYNFDRDNTEVAYLKTLTKEDIIKEYKEMLAVDAPR

RHKVSVHVLAREMDSCPVVGEFPCQNDINLSQAPALPQPEVIQNMTEFKR

GLPLFPLVKPHINFMAAKL

>gi|260099676|ref|NP_001159418.1| insulin-
degrading enzyme isoform 2 [Homo sapiens]
                                     (SEQ ID NO: 2)
MSKLWFKQDDKFFLPKACLNFEFFSPFAYVDPLHCNMAYLYLELLKDSLN

EYAYAAELAGLSYDLQNTIYGMYLSVKGYNDKQPILLKKIIEKMATFEID

EKRFEIIKEAYMRSLNNFRAEQPHQHAMYYLRLLMTEVAWTKDELKEALD

DVTLPRLKAFIPQLLSRLHIEALLHGNITKQAALGIMQMVEDTLIEHAHT

KPLLPSQLVRYREVQLPDRGWEVYQQRNEVHNNCGIEIYYQTDMQSTSEN

MFLELFCQIISEPCFNTLRTKEQLGYIVESGPRRANGIQGLRFIIQSEKP

PHYLESRVEAFLITMEKSIEDMTEEAFQKHIQALAIRRLDKPKKLSAECA

KYWGEIISQQYNFDRDNTEVAYLKTLTKEDIIKEYKEMLAVDAPRRHKVS

VHVLAREMDSCPVVGEFPCQNDINLSQAPALPQPEVIQNMTEFKRGLPLF

PLVKPHINFMAAKL

>gi|121583922|ref|NP_112419.2| insulin-degrading
enzyme [Mus musculus]
                                     (SEQ ID NO: 3)
MRNGLVWLLHPALPGTLRSILGARPPPAKRLCGFPKQTYSTMSNPAIQRI

EDQIVKSPEDKREYRGLELANGIKVLLISDPTTDKSSAALDVHIGSLSDP

PNIPGLSHFCEHMLFLGTKKYPKENEYSQFLSEHAGSSNAFTSGEHTNYY

FDVSHEHLEGALDRFAQFFLCPLFDASCKDREVNAVDSEHEKNVMNDAWR

LFQLEKATGNPKHPFSKFGTGNKYTLETRPNQEGIDVREELLKEHSTYYS

SNLMAICVLGRESLDDLTNLVVKLFSEVENKNVPLPEFPEHPFQEEHLRQ

LYKIVPIKDIRNLYVTFPIPDLQQYYKSNPGHYLGHLIGHEGPGSLLSEL

KSKGWVNTLVGGQKEGARGFMFFIINVDLTEEGLLHVEDIILHMFQYIQK

LRAEGPQEWVFQECKDLNAVAFRFKDKERPRGYTSKIAGKLHYYPLNGVL

TAEYLLEEFRPDLIDMVLDKLRPENVRVAIVSKSFEGKTDRTEQWYGTQY

KQEAIPEDIIQKWQNADLNGKFKLPTKNEFIPTNFEILSLEKDATPYPAL

IKDTAMSKLWFKQDDKFFLPKACLNFEFFSPFAYVDPLHCNMAYLYLELL

KDSLNEYAYAAELAGLSYDLQNTIYGMYLSVKGYNDKQPILLKKITEKMA

TFEIDKKRFEIIKEAYMRSLNNFRAEQPHQHAMYYLRLLMTEVAWTKDEL

KEALDDVTLPRLKAFIPQLLSRLHIEALLHGNITKQAALGVMQMVEDTLI

EHAHTKPLLPSQLVRYREVQLPDRGWFVYQQRNEVHNNCGIEIYYQTDMQ

STSENMFLELFCQIISEPCFNTLRTKEQLGYIVFSGPRRANGIQGLRFII
```

-continued

QSEKPPHYLESRVEAFLITMEKAIEDMTEEAFQKHIQALAIRRLDKPKKL

SAECAKYWGEIISQQYNYDRDNIEVAYLKTLTKDDIIRFYQEMLAVDAPR

RHKVSVHVLAREMDSCPVVGEFPSQNDINLSEAPPLPQPEVIHNMTEFKR

GLPLFPLVKPHINFMAAKL

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Synthesis of the Compounds

Scheme E1 shows the formation of the azetidine and diazocane rings of precursor 5. Epoxide 1 is ring opened in two steps by reaction with allyl isocyanate and base, followed by reaction with sodium hydride, to yield cyclic carbamate 2 (90%, 2 steps). The carbamate is converted to an allyl-cyanomethyl-amine (3) via reaction with cyanomethyl bromide and subsequent protection of the primary alcohol with triphenylmethyl chloride. Addition of thionyl chloride leads to substitution of the secondary alcohol with chloride, followed by cyclization in the presence of potassium hexamethyldisilazide to yield azetidines 4 in a 1:20 diastereomeric ratio. The 8 membered ring is formed in 12% yield over 4 steps: reduction of the nitrile with diisobutylaluminum hydride, nosyl protection of the resulting amine, addition of allyl to the protected amine, and olefin metathesis of the two pendant allyl groups to close the ring.

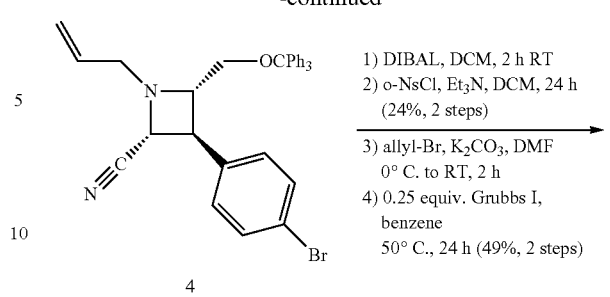

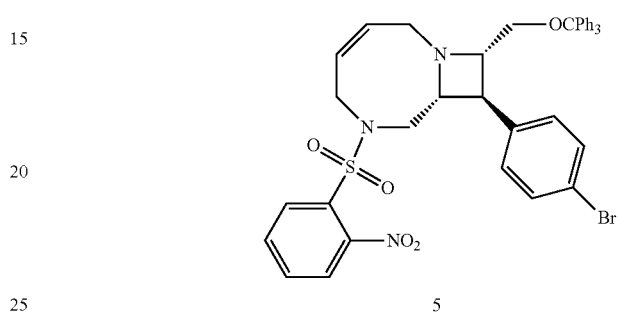

The subsequent modification of precursor 5 to generate compounds 297 and 688 is shown in Scheme E2. The alcohol protecting group is removed with trifluoroacetic acid, and cyclic alkene is reduced by Wilkinson's catalyst to yield 6 in 52% yield (2 steps). The aryl bromide is coupled with an aryl boronic acid to give biphenyl compound 7. Nosyl deprotection followed by addition of an aryl sulfonyl chloride gives either compound 297 or compound 688.

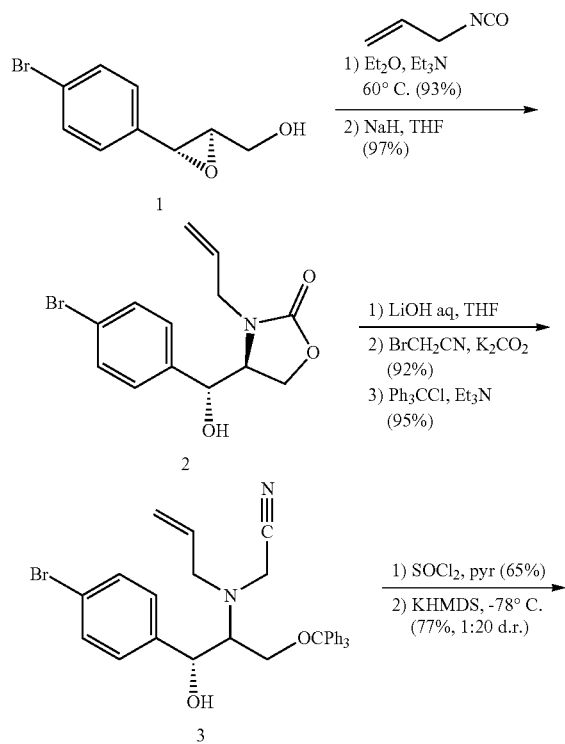

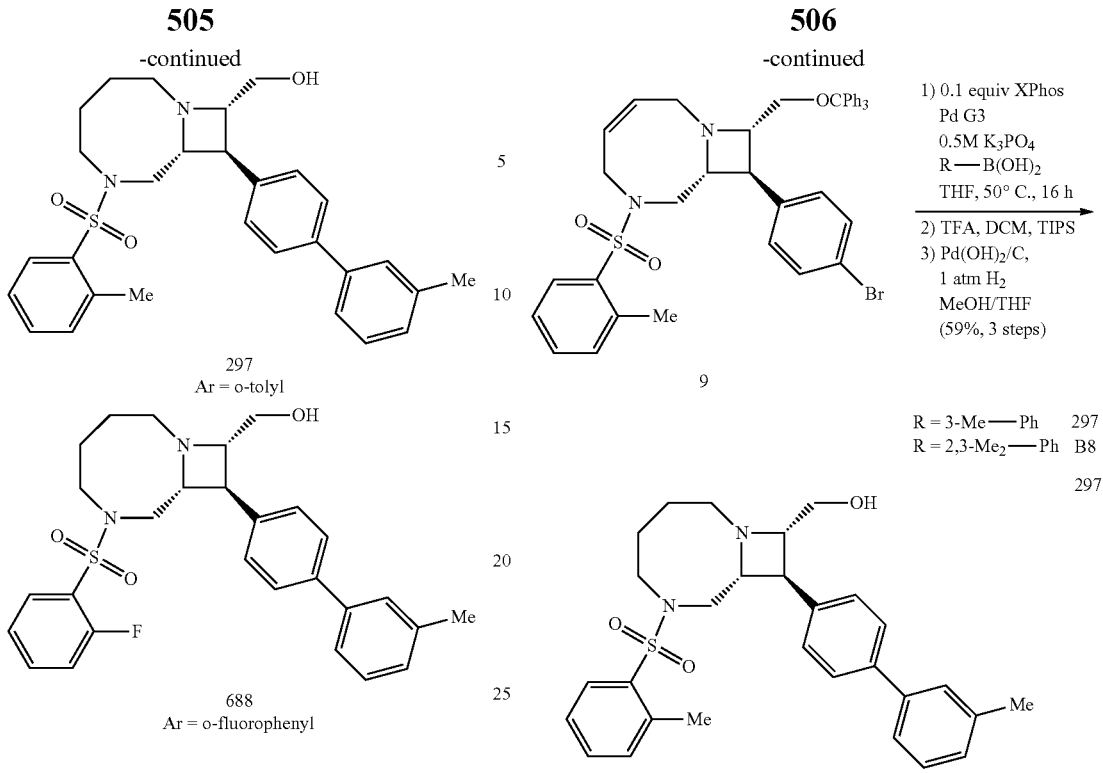

297
Ar = o-tolyl

688
Ar = o-fluorophenyl

An alternative route to compound 297 from azetidine 4 is detailed in Scheme E3. The nitrile of 4 is reduced and directly functionalized with o-methylphenylsulfonyl chloride to yield azetidines 8 (68%, 2 steps). Addition of allyl bromide to the pendant amine and metathesis form the bicyclic species 9 in 66% yield (2 steps). And finally palladium coupling, deprotection, and a reduction of the alkene with $H_2$ over palladium on carbon produces compound 297 in 59% yield for 3 steps.

Scheme E3.

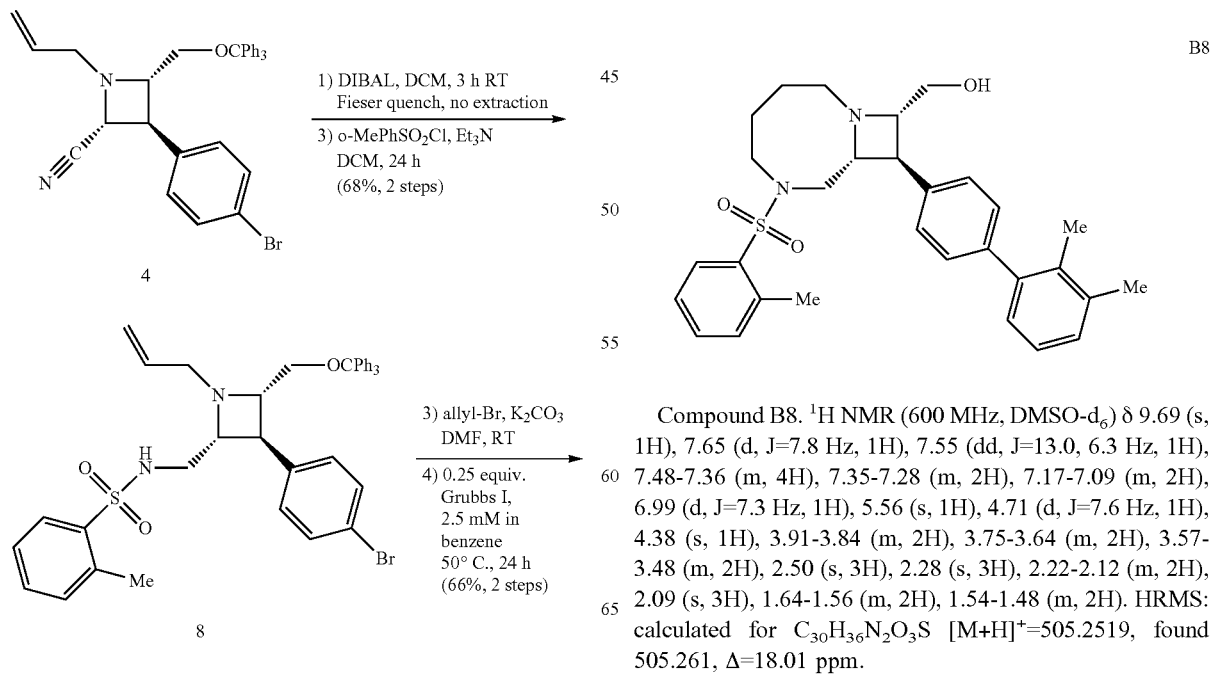

R = 3-Me—Ph  297
R = 2,3-Me$_2$—Ph  B8

297

Compound 297. $^1$H NMR (600 MHz, DMSO-d$_6$) δ 9.21 (s, 1H), 7.13 (m, 2H), 7.10 (d, J=7.8 Hz, 1H), 7.00 (t, J=7.4 Hz, 1H), 6.97-6.92 (m, 3H), 6.90 (d, J=7.1 Hz, 2H), 6.85 (t, J=7.6 Hz, 1H), 6.79 (t, J=7.6 Hz, 1H), 6.63 (d, J=7.4 Hz, 1H), 5.03 (s, 1H), 4.14 (s, 1H), 3.81 (s, 1H), 3.38-3.22 (m, J=17.3 Hz, 3H), 3.20-3.09 (m, 3H), 3.07-2.95 (m, J=27.6 Hz, 1H), 2.62 (d, J=18.7 Hz, 1H), 1.95 (s, 3H), 1.82 (s, 3H), 1.50-1.27 (m, J=43.9, 24.5, 8.9 Hz, 3H), 1.26-1.18 (m, 1H). HRMS: calculated for $C_{29}H_{34}N_2O_3S$ [M+H]$^+$=491.2363, found 491.237, Δ=1.42 ppm.

B8

Compound B8. $^1$H NMR (600 MHz, DMSO-d$_6$) δ 9.69 (s, 1H), 7.65 (d, J=7.8 Hz, 1H), 7.55 (dd, J=13.0, 6.3 Hz, 1H), 7.48-7.36 (m, 4H), 7.35-7.28 (m, 2H), 7.17-7.09 (m, 2H), 6.99 (d, J=7.3 Hz, 1H), 5.56 (s, 1H), 4.71 (d, J=7.6 Hz, 1H), 4.38 (s, 1H), 3.91-3.84 (m, 2H), 3.75-3.64 (m, 2H), 3.57-3.48 (m, 2H), 2.50 (s, 3H), 2.28 (s, 3H), 2.22-2.12 (m, 2H), 2.09 (s, 3H), 1.64-1.56 (m, 2H), 1.54-1.48 (m, 2H). HRMS: calculated for $C_{30}H_{36}N_2O_3S$ [M+H]$^+$=505.2519, found 505.261, Δ=18.01 ppm.

Scheme E4.

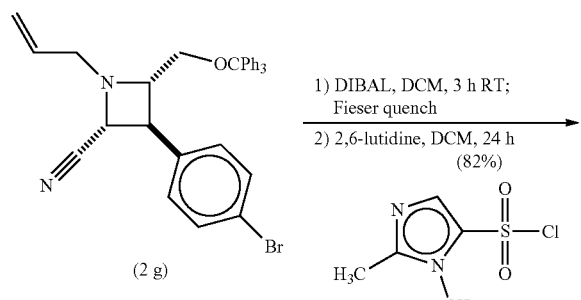

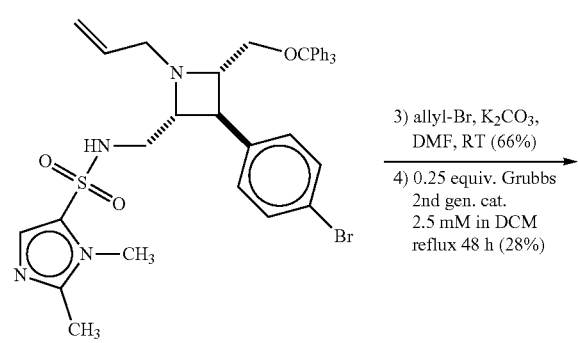

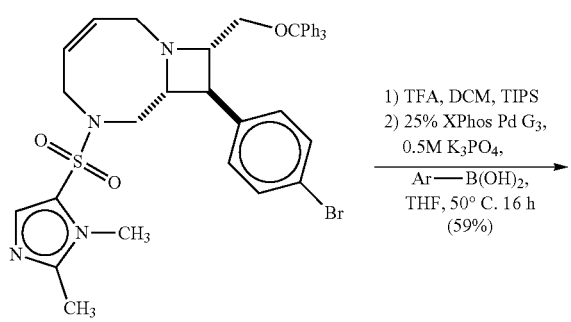

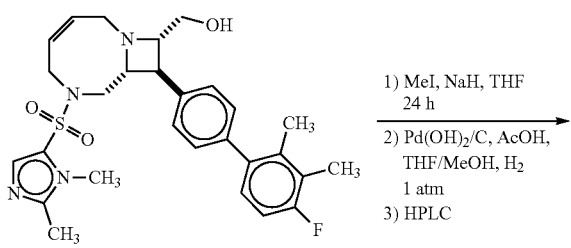

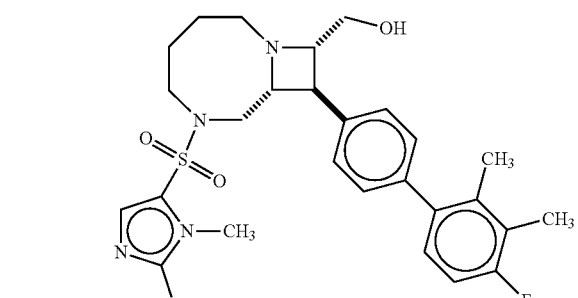

JP-42

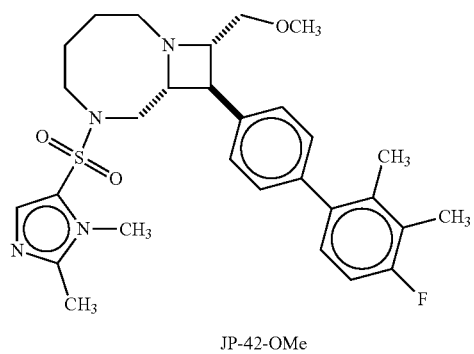

JP-42-OMe

Other exemplary compounds of Formula (I), JP-42 and JP-42-OMe, were synthesized according to Scheme E4.

Scheme E5.

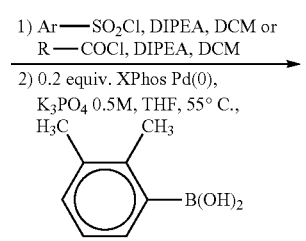

1-(4-bromophenyl) piperazine

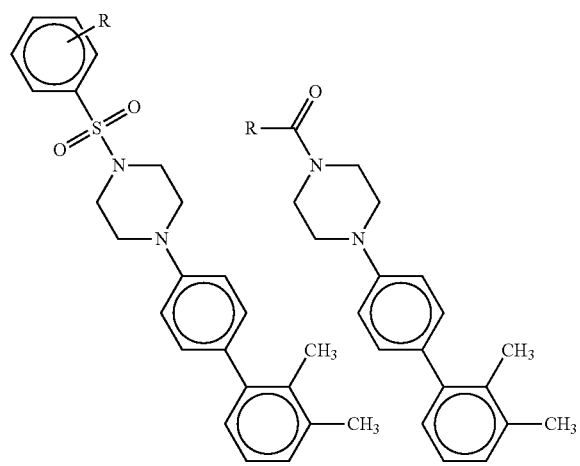

IDE inhibitors (e.g. J1-J16)

Exemplary compounds of Formulae (IV) and were synthesized according to Scheme E5. The amine of 1-(4-bromophenylpiperzine) was sulfonated or acylated with the desired sulfonyl chloride or acyl chloride using diisopropylethylamine (DIPEA) as a base. The biphenyl unit was subsequently synthesized by way of a Suzuki coupling between the aryl bromide and 2,3-dimethylphenylboronic acid, using 0.2 equivalents of XPhos and Pd⁰, and 0.5 M $K_3PO_4$ in THF.

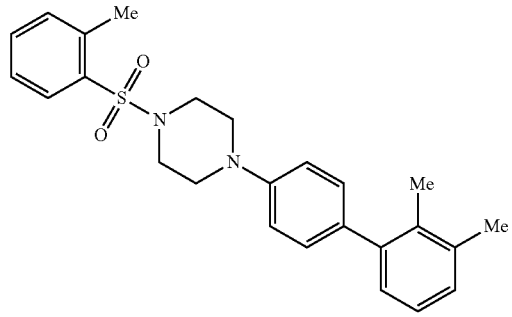

Compound J1. HRMS: calculated for $C_{25}H_{28}N_2O_2S$ [M+H]$^+$=421.1944, found 421.193, Δ=−3.32 ppm. $^1$H NMR (600 MHz, DMSO-d$_6$) δ 7.83 (dd, J=7.9, 1.2 Hz, 1H), 7.59 (td, J=7.5, 1.3 Hz, 1H), 7.46 (dd, J=16.7, 8.0 Hz, 2H), 7.13-7.11 (m, 2H), 7.10-7.05 (m, 2H), 6.97-6.94 (m, 3H), 3.22 (dd, J=6.4, 3.3 Hz, 4H), 3.17 (dd, J=6.3, 3.3 Hz, 4H), 2.59 (s, 3H), 2.25 (s, 3H), 2.07 (s, 3H).

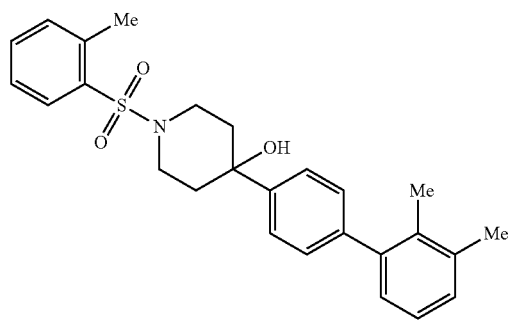

Compound J2. HRMS: calculated for $C_{26}H_{29}NO_3S$ [M+H]$^+$=436.1941, found 436.198, Δ=8.94 ppm. $^1$H NMR (600 MHz, DMSO-d$_6$) δ 7.82 (dd, J=7.9, 1.1 Hz, 1H), 7.58 (td, J=7.5, 1.3 Hz, 1H), 7.49-7.42 (m, 4H), 7.23 (s, 1H), 7.22 (s, J=8.4 Hz, 1H), 7.14 (d, J=7.1 Hz, 1H), 7.10 (t, J=7.5 Hz, 1H), 6.98 (d, J=6.8 Hz, 1H), 5.09 (s, 1H), 3.57-3.52 (m, 2H), 2.91 (td, J=12.1, 2.1 Hz, 2H), 2.60 (s, 3H), 2.26 (s, 3H), 2.07 (s, 3H), 1.98-1.93 (m, 2H), 1.72 (d, J=1.4 Hz, 1H), 1.70 (d, J=1.5 Hz, 1H).

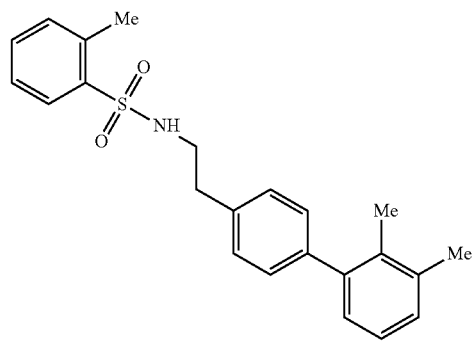

Compound J3. HRMS: calculated for $C_{23}H_{25}NO_2S$ [M+H]$^+$=380.1679, found 380.175, Δ=18.68 ppm. $^1$H NMR (600 MHz, DMSO-d$_6$) δ 7.81 (dd, J=8.2, 1.2 Hz, 1H), 7.78 (t, J=5.7 Hz, 1H), 7.49 (td, J=7.5, 1.2 Hz, 1H), 7.36 (t, J=7.0 Hz, 2H), 7.15-7.12 (m, 5H), 7.10 (t, 1H), 6.96 (d, J=6.6 Hz, 1H), 3.03 (dd, J=13.3, 7.3 Hz, 2H), 2.68 (t, J=7.4 Hz, 2H), 2.50 (s, 3H), 2.26 (s, 3H), 2.06 (s, 3H).

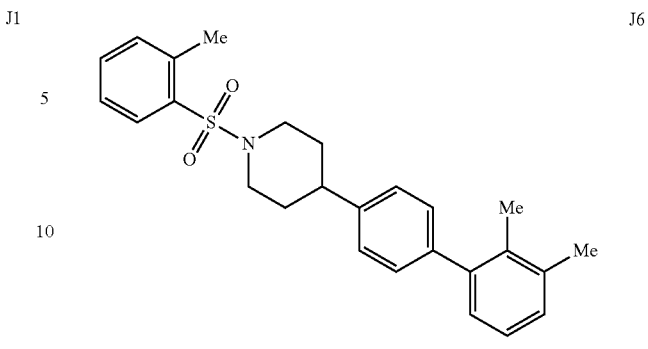

Compound J6. HRMS: calculated for $C_{26}H_{29}NO_2S$ [M+H]$^+$=420.1992, found 420.208, Δ=20.94 ppm. $^1$H NMR (600 MHz, DMSO-d$_6$) δ 7.82 (dd, J=7.9, 1.3 Hz, 1H), 7.58 (td, J=7.5, 1.3 Hz, 1H), 7.46 (d, J=7.6 Hz, 1H), 7.43 (t, J=7.6 Hz, 1H), 7.25 (d, J=8.1 Hz, 2H), 7.21-7.17 (m, 2H), 7.13 (d, J=7.1 Hz, 1H), 7.09 (t, J=7.5 Hz, 1H), 6.97 (d, J=6.6 Hz, 1H), 3.74 (d, J=11.9 Hz, 2H), 2.69-2.61 (m, 3H), 2.59 (s, 3H), 2.26 (s, 3H), 2.06 (s, 3H), 1.88 (d, J=14.3 Hz, 2H), 1.64 (qd, J=12.7, 4.0 Hz, 2H).

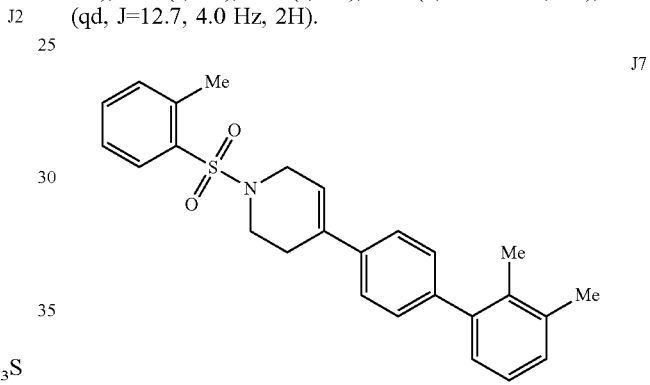

Compound J7. HRMS: calculated for $C_{26}H_{27}NO_2S$ [M+H]$^+$=418.1835, found 418.188, Δ=10.76 ppm. $^1$H NMR (600 MHz, DMSO-d$_6$) δ 7.86 (dd, J=7.9, 1.1 Hz, 1H), 7.57 (dt, J=7.5, 3.8 Hz, 1H), 7.47-7.41 (m, 4H), 7.25 (d, J=1.7 Hz, 1H), 7.24 (d, J=1.7 Hz, 1H), 7.15 (d, J=6.8 Hz, 1H), 7.11 (t, J=7.5 Hz, 1H), 6.99 (d, J=6.6 Hz, 1H), 6.24-6.20 (m, 1H), 3.82 (dd, J=5.8, 2.7 Hz, 2H), 3.40-3.37 (m, 2H), 2.58 (s, 3H), 2.27 (s, 3H), 2.07 (d, J=7.0 Hz, 3H), 1.96 (dd, J=7.1, 5.7 Hz, 2H).

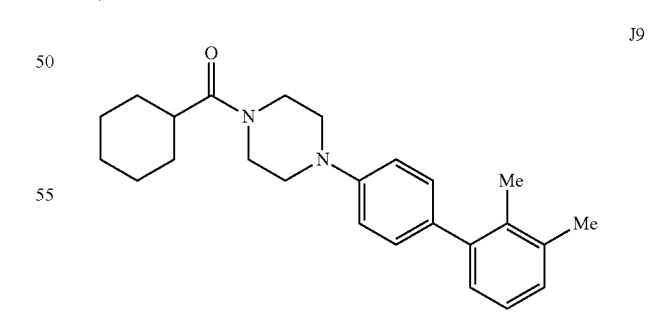

Compound J9. HRMS: calculated for $C_{25}H_{32}N_2O$ [M+H]$^+$=377.2587, found 377.263, Δ=11.40 ppm. $^1$H NMR (600 MHz, DMSO-d$_6$) δ 7.14 (s, 1H), 7.13 (s, 1H), 7.12-7.05 (m, J=23.3 Hz, 2H), 7.01-6.95 (m, 3H), 3.63 (s, 2H), 3.58 (s, 2H), 3.17 (s, 2H), 3.11 (s, 2H), 2.26 (s, 3H), 2.09 (s, 3H), 2.06 (d, J=5.8 Hz, 1H), 1.98-1.93 (m, 2H), 1.72-1.60 (m, 6H), 1.47-1.40 (m, 2H).

J10

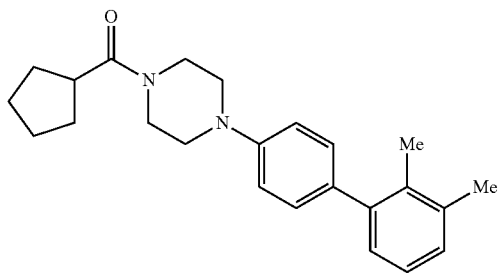

Compound J10. HRMS: calculated for C$_{24}$H$_{30}$N$_2$O [M+H]$^+$=363.2431, found 363.247, Δ=10.74 ppm. $^1$H NMR (600 MHz, DMSO-d$_6$) δ 7.15 (s, 1H), 7.13 (s, 1H), 7.11-7.05 (m, 2H), 7.00 (s, 1H), 6.99 (s, 1H), 6.97 (dd, J=6.8, 1.4 Hz, 1H), 3.67-3.63 (m, 2H), 3.63-3.58 (m, 2H), 3.18-3.15 (m, 2H), 3.14-3.10 (m, 2H), 3.02 (dq, J=15.7, 7.9 Hz, 1H), 2.26 (s, 3H), 2.09 (s, 3H), 1.76 (td, J=11.9, 8.0 Hz, 2H), 1.66 (td, J=14.0, 7.0 Hz, 2H), 1.63-1.55 (m, 2H), 1.55-1.47 (m, 2H).

J16

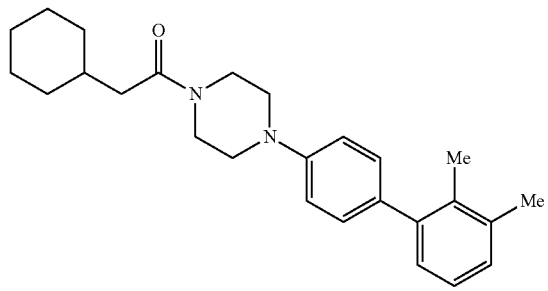

Compound J16. HRMS: calculated for C$_{26}$H$_{34}$N$_2$O [M+H]$^+$=391.2744, found 391.289, Δ=37.31 ppm. $^1$H NMR (600 MHz, DMSO-d$_6$) δ 7.14 (s, 1H), 7.13 (s, 1H), 7.11-7.05 (m, 2H), 7.00 (s, 1H), 6.98 (s, 1H), 6.97 (dd, J=7.2, 1.2 Hz, 1H), 3.63-3.58 (m, 4H), 3.18-3.14 (m, 2H), 3.13-3.10 (m, 2H), 2.26 (s, 3H), 2.22 (d, J=6.5 Hz, 2H), 2.09 (s, 3H), 2.01-1.94 (m, 1H), 1.70-1.55 (m, 7H), 1.14-1.08 (m, 1H), 0.93 (ddd, J=12.1, 1.9 Hz, 1.9 Hz, 2H).

J17

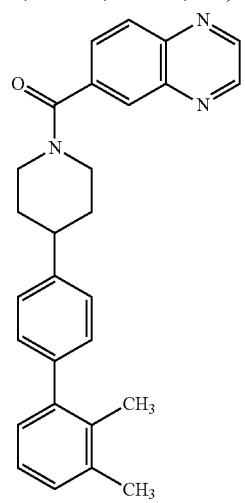

Compound J17. HRMS: calculated for C$_{28}$H$_{27}$N$_3$O [M+H]$^+$=422.2227, found 422.2250, Δ=-5.4 ppm. $^1$H NMR (600 MHz, DMSO-d$_6$) δ 9.00 (dd, J=4.7, 1.8 Hz, 2H), 8.17 (d, J=8.6 Hz, 1H), 8.15 (d, J=1.7 Hz, 1H), 7.91 (dd, J=8.5, 1.8 Hz, 1H), 7.37-7.33 (m, 2H), 7.23-7.19 (m, 2H), 7.13 (d, J=6.7 Hz, 1H), 7.10 (t, J=7.5 Hz, 1H), 6.99 (dd, J=7.4, 1.1 Hz, 1H), 4.71 (d, J=11.0 Hz, 1H), 3.68 (d, J=12.7 Hz, 1H), 3.29-3.20 (m, 1H), 2.93 (t, J=11.9 Hz, 1H), 2.87 (ddd, J=15.6, 11.4, 4.4 Hz, 1H), 2.26 (s, 3H), 2.08 (s, 3H), 1.99-1.91 (m, 1H), 1.73 (s, 3H).

Scheme E6.

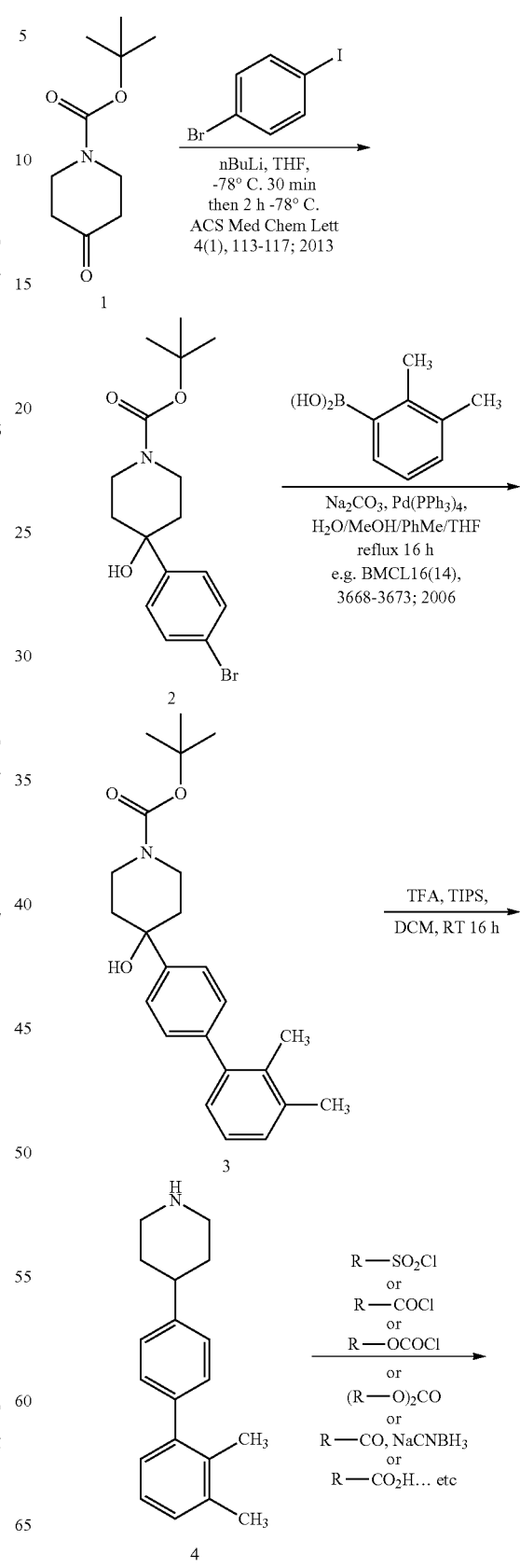

513
-continued
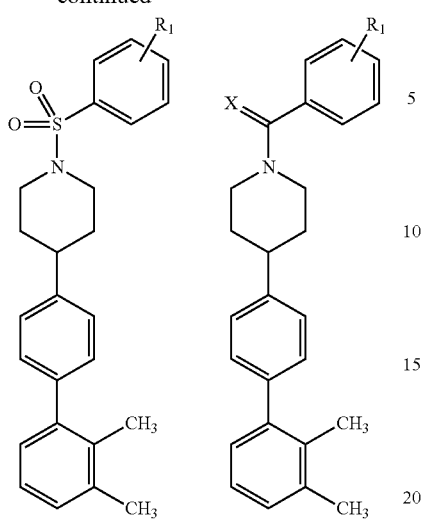
Scheme E7.
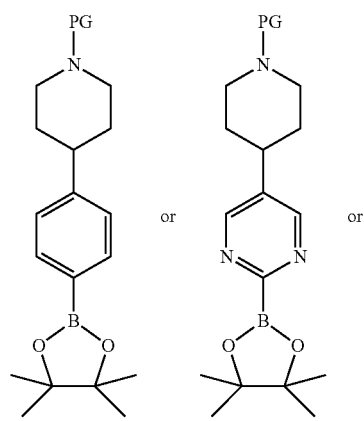
514
-continued
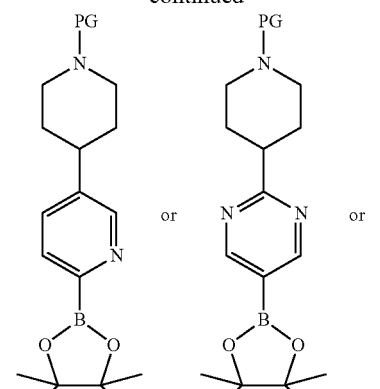
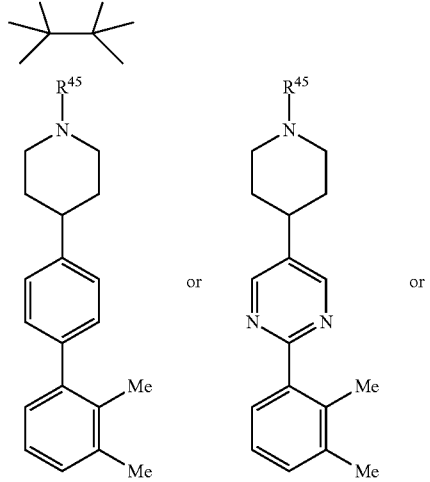
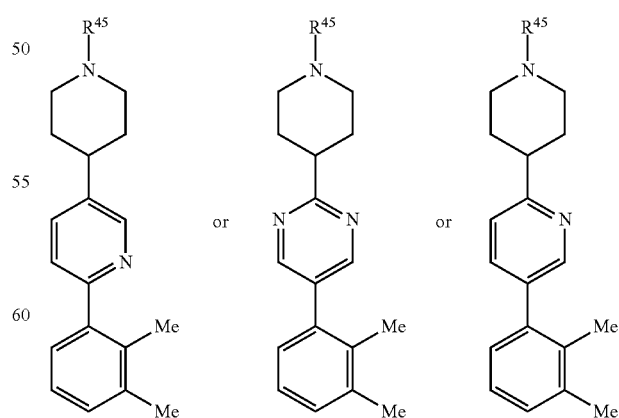
PG = protecting group
$R^{45a}$ = optionally substituted aryl, heteroaryl, carbocyclyl, heterocyclyl Additional compounds may be prepared as provided in Schemes E6 and E7.

Fluorescence Anisotropy High-Throughput Screening Assay.

The fluorescence anisotropy screening method and probe FL-6b are described in PCT application PCT/US2014/064322, incorporated herein by reference.

Figure 1B:
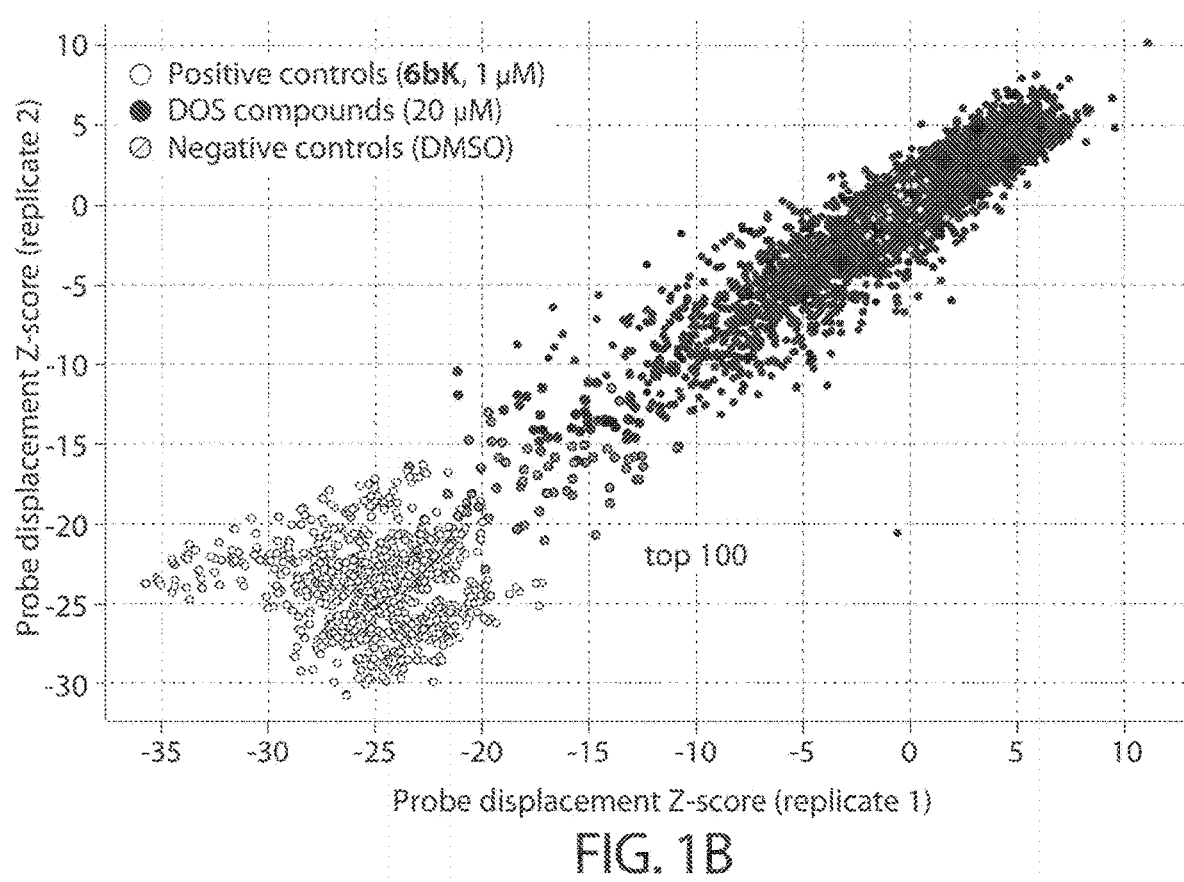

Human N-His$_6$-IDE$_{42\text{-}1019}$ (*E. coli* expressed) was mixed with fluorescein-labeled macrocycle FL-6b:

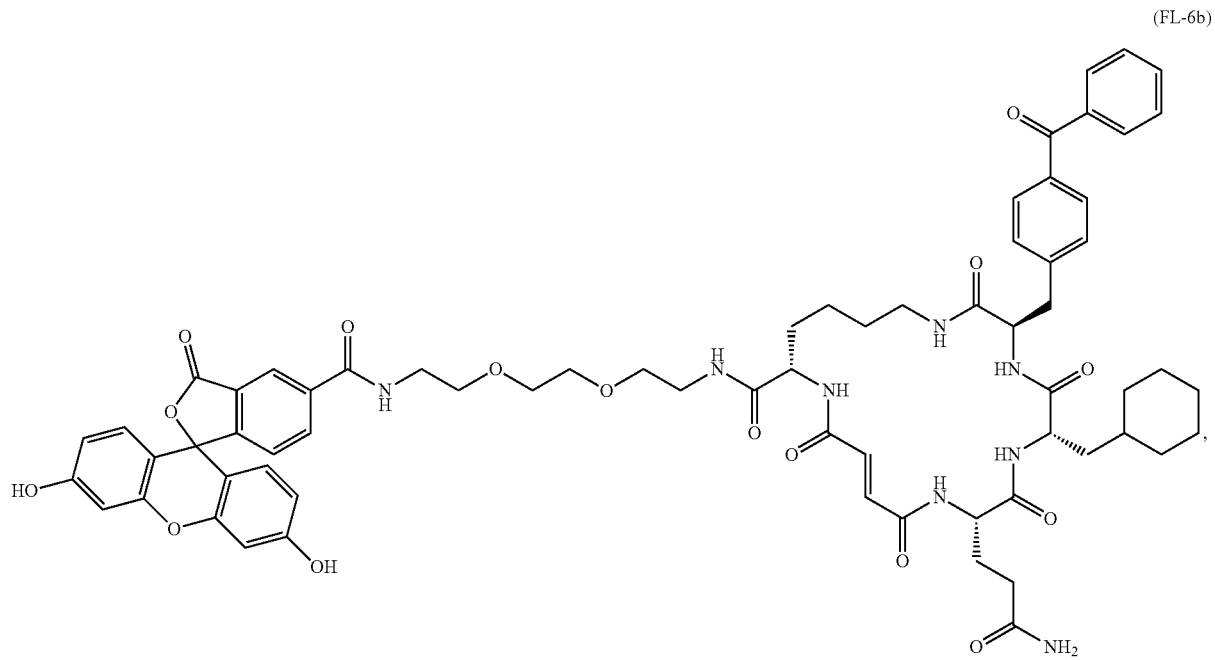 [SMILES: NC(=O)CC[C@@H]1NC(=O)/C=C/C(=O)N[C@H](C(=O)NCCOCCOCCNC(=O)c2ccc3c(c2)C(=O)OC32c3ccc(O)cc3Oc3cc(O)ccc32)CCCCNC(=O)[C@@H](Cc2ccc(C(=O)c3ccccc3)cc2)NC(=O)[C@H](CC2CCCCC2)NC1=O]

in 50 mM Tris buffer pH 8.0, with 1 M NaCl, at 25° C. Optimum signal was obtained using a mixture of 30 mM probe FL-6b and 0.5 µM IDE. The "diversity-oriented (DOS) synthesis informer set" compound plates were pinned onto 384-well plates containing the enzyme-probe mixture (50 µL/well). The azetidine screen was pre-printed on 384-well plates and the enzyme-probe mixture was added (50 µL/well). The final compound concentration was 20 µM. IDE inhibitor 6bK was used as a positive control at a final concentration of 1 µM. After 30 minutes of equilibration, the increase in fluorescence anisotropy was recorded using an EnVision spectrophotometer (excitation 492 nm, emission 523 nm). The fluorescence anisotropy was independently measured twice for each screened compound. The Z-scores for each pair of measurements are plotted in FIG. 1A (DOS informer set) and FIG. 1B (azetidines), and average Z-scores are listed for exemplary compounds in Table E1.

Z-scores were calculated based on the raw anisotropy measured for each well according to Eq. 1, wherein x is the raw anisotropy value of the well, µ is the mean of the anisotropy of the negative control wells (DMSO) for the plate, and σ is the standard deviation in anisotropy of the negative control wells (DMSO) for the plate.

$$Z = \frac{x - \mu}{\sigma} \quad \text{(Eq. 1)}$$

The Z-factor of the assay was determined to be 0.69 for a 384-well plate with half of the wells containing positive control inhibitor 6bK and half containing negative control inactive stereoisomer bisepi-6bK, shown below:

The Z-factor was calculated according to the standard formula (Eq. 2), wherein µ$_p$ and µ$_n$ are the mean of the anisotropy for positive control wells (6bK) and negative control wells (bisepi-6bK), respectively, and $\sigma_p$ and $\sigma_n$ are the standard deviations and in anisotropy of the negative and positive control wells, respectively.

$$Z\text{-factor} = 1 - \frac{3(\sigma_p + \sigma_n)}{|\mu_p - \mu_n|} \quad (\text{Eq. 2})$$

Protease Assays with Fluorogenic Peptide Substrates.

The proteases $IDE_{42\text{-}1019}$, recombinant human $IDE_{42\text{-}1019}$ (R&D Systems), neprilysin (R&D), and angiotensin-converting enzyme (R&D) were assayed using the fluorophore/quencher-tagged peptide substrate Mca-RPPGFSAFK(Dnp)-OH (SEQ ID NO: 24) (R&D) according to the manufacturer's instructions and using the recommended buffers (fluorophore Mca=(7-methoxycourmarin-4-yl)acetyl and quencher Dnp=2,4-dinitrophenyl). For IDE the recommended buffer is 50 mM Tris pH 7.5, 1 M NaCl. The enzyme mixtures (48 µL) were transferred to a 96-well plate and combined with 2 µL of inhibitor in DMSO solutions, in 3-fold dilution series. The mixtures were allowed to equilibrate for 10 minutes and the enzymatic reaction was started by addition of substrate peptide in assay buffer (50 µL), mixed, and monitored on a fluorescence plate reader (excitation at 320 nm, emission at 405 nm). Similarly, thimet oligopeptidase (R&D) and neurolysin (R&D) were assayed using substrate Mca-PLGPK(Dnp)-OH (SEQ ID NO: 25) (R&D) according to the manufacturer's instructions and using the recommended buffers. Matrix metalloproteinase-1 (R&D) was activated and assayed according to the manufacturer's instructions with substrate Mca-KPLGL-Dpa-AR-NH$_2$ (SEQ ID NO: 20) (R&D) (quencher DPA=N-3-(2,4,dinitrophenyl)-L-2,3-diaminopropionyl). All assay data points were obtained in duplicate.

Figure 2A:
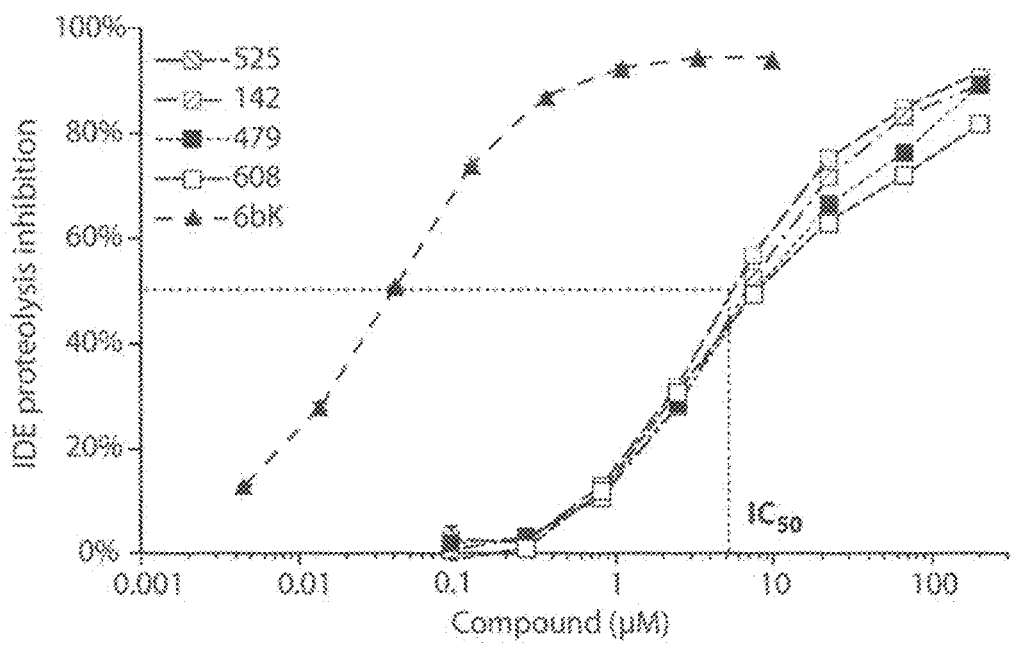
FIGS. 2A-2B. Surrogate proteolysis assay to identify substrate-selective IDE inhibitors that allow IDE-mediated proteolysis of small peptide substrates.
Figure 2B:
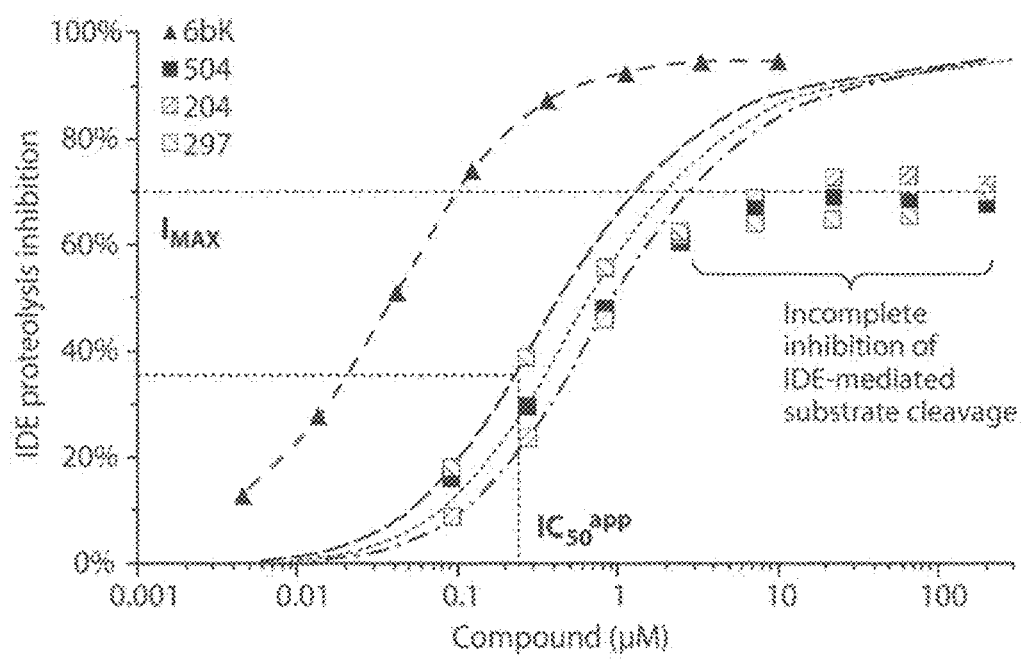

FIG. 2A shows the concentration-dependent IDE inhibition profiles determined via the fluorophore/quencher-tagged peptide assay for compounds 142, 479, 608, 525, and 6bK (control). For the examples the IC$_{50}$ was <10 µM, and the inhibitors displayed an inhibition maximum of approximately 100%. Some compounds (e.g., 297, 204, 504) showed an inhibition of <100%, as shown in FIG. 2B. Compounds with submaximal inhibition were chosen as potential substrate selective inhibitors. IC$_{50}$ or apparent IC$_{50}$ for compounds with submaximal inhibition, and the inhibition maximum (I$_{MAX}$) are listed in Table E1.

A comparison of the inhibition profiles of exemplary inhibitors between IDE and other metalloproteases can be seen in FIGS. 7A-7D. The inhibition curves were determined as described above for the following proteases and tagged peptide substrates: IDE, Mca-RPPGFSAFK(Dnp)-OH (SEQ ID NO: 24); angiotensin converting enzyme (ACE), Mca-RPPGFSAFK(Dnp)-OH (SEQ ID NO: 24); neprilysin (NEP), Mca-RPPGFSAFK(Dnp)-OH (SEQ ID NO: 24); thimet oligopeptidase (THOP1), Mca-PLGPK(Dnp)-OH (SEQ ID NO: 25); neurolysin (NLN), Mca-PLGPK(Dnp)-OH (SEQ ID NO: 25); and matrix metalloproteinase-1 (MMP1), Mca-KPLGL-Dpa-AR-NH$_2$ (SEQ ID NO: 20).

TABLE E1

IC$_{50}$ values of exemplary compounds of Formula (I) for inhibition of IDE.

| Compound No. | IC$_{50}$ (µM) Proteolysis | I$_{max}$ (%) Proteolysis | Average Z-score (Fluorescence anisotropy) |
|---|---|---|---|
| 6bK (control) | 0.05 | 100 | −24.52 |
| 061 | >100 | — | −1.36 |
| 072 | 7.5 | 50 | −14.53 |
| 073 | >50 | — | −0.68 |
| 077 | >100 | — | −2.31 |
| 081 | 2.5 | 50 | −19.85 |
| 089 | 7.5 | — | −4.11 |
| 091 | 7 | 70 | −16.96 |
| 102 | 10 | 80 | −13.56* |
| 106 | 7.5 | 80 | −16.48 |
| 124 | 5 | 70 | −16.49 |
| 130 | >5 | 60 | — |
| 140 | 2.5 | 50 | −17.72 |
| 141 | >100 | — | −17.53* |
| 142 | 6 | 100 | −19.27 |
| 154 | >10 | 20 | −2.84 |
| 1570 | 7 | 40 | −1.37 |
| 1576 | 2.5 | 60 | — |
| 180 | 5 | 80 | −12.26* |
| 187 | >20 | — | −15.91 |
| 204 | 0.4 | 73 | −19.34 |
| 217 | 0.2 | 40 | −17.51 |
| 226 | 7.5 | 30 | −1.67 |
| 231 | 2.5 | 60 | — |
| 236 | >200 | — | −1.64 |
| 255 | 1 | 50 | −17.33 |
| 269 | 7.5 | 30 | −4.36 |
| 291 | >200 | — | — |
| 296 | >100 | — | −3.25 |
| 297 | 0.25 | 65 | −20.26 |
| 304 | 2 | 80 | — |
| 316 | >10 | — | −16.96 |
| 321 | 7.5 | 50 | −17.72 |
| 342 | 0.6 | 50 | −17.53 |
| 3421 | 2.0 | 60 | −17.16 |
| 346 | 1.5 | 80 | — |
| 348 | 7 | 40 | −11.8 |
| 353 | 20 | 50 | −7.98 |
| 397 | 7.5 | 70 | −11.37 |
| 416 | 0.2 | 60 | −18.29 |
| 433 | >100 | — | −2.37 |
| 439 | 2.5 | 50 | −19.08 |
| 443 | >100 | — | −3.13 |
| 469 | 7.5 | 80 | — |
| 479 | 7.5 | 100 | −19.91 |
| 491 | >10 | 70 | −12.38 |
| 496 | 2.5 | 30 | −9.77 |
| 504 | 0.8 | 70 | −20.82 |
| 506 | >100 | — | −3.47 |
| 510 | 0.5 | 30 | −21.34 |
| 525 | 5 | 100 | −16.2 |
| 529 | 5 | 30 | −0.82 |
| 534 | 7 | 70 | −3.03 |
| 559 | >100 | — | −5.28 |
| 564 | >100 | — | −1.33 |
| 580 | 7.5 | 70 | −7.49 |
| 585 | 2.5 | 40 | −12.65* |
| 586 | 7 | 70 | −17.17 |
| 591 | 1.5 | 40 | −17.90 |
| 608 | 7.5 | 90 | −15.34 |
| 612 | 7.5 | 50 | — |
| 644 | >100 | — | — |
| 653 | 10 | 90 | −17.51 |
| 654 | >100 | — | −6.65 |
| 683 | 7 | 80 | — |
| 688 | — | — | −27.23* |
| 712 | >100 | — | −4.78 |
| 736 | 2.5 | 35 | −16.6 |
| 745 | 2.5 | 70 | −19.67 |
| 768 | >100 | — | −3.48 |
| 777 | 10 | 30 | −5.51 |
| 779 | 0.8 | 60 | −22.36 |
| 782 | — | — | −16.08 |

TABLE E1-continued

IC$_{50}$ values of exemplary compounds of Formula (I) for inhibition of IDE.

| Compound No. | IC$_{50}$ (μM) Proteolysis | I$_{max}$ (%) Proteolysis | Average Z-score (Fluorescence anisotropy) |
|---|---|---|---|
| 795 | 1 | 40 | −19.52 |
| 805 | 2.5 | 70 | −17.31 |
| 807 | 7.5 | 30 | −22.09* |
| 836 | 7.5 | 60 | −18.28 |
| 837 | >100 | — | −2.88 |
| 838 | 7.5 | 80 | −17.68 |
| 868 | 2.5 | 40 | −18.53 |
| 890 | >100 | — | −5.69 |
| 900 | >7.5 | — | — |
| 904 | >5 | — | −16.59 |
| 930 | — | — | −10.53* |
| 932 | >20 | 90 | −19.01 |
| 945 | 1 | 30 | −3.77 |
| 959 | >60 | — | −6.79 |
| 964 | 2.5 | 90 | −19.69 |
| 983 | >20 | 90 | −12.81* |
| K1 | 0.2 | — | — |
| K2 | >100 | — | — |
| K3 | 0.4 | 65 | — |
| K4 | 0.2 | 72 | — |
| K5 | 2.5 | 100 | — |
| K6 | 7.5 | — | — |
| K7 | 1.0 | 65 | — |
| K8 | 7.5 | 100 | — |
| K9 | 0.002 | 65 | — |
| K10 | 0.1 | 72 | — |
| K11 | 2.5 | 65 | — |
| K12 | 0.02 | 65 | — |
| K13 | 0.09 | 65 | — |
| K14 | 0.3 | 65 | — |
| K15 | 0.8 | 90 | — |
| K16 | 0.8 | — | — |
| K17 | 0.9 | — | — |
| K18 | 5 | — | — |
| K19 | 0.1 | — | — |
| K20 | 0.1 | — | — |
| K21 | 0.008 | — | — |
| K22 | 0.01 | — | — |
| K23 | 0.3 | — | — |
| K24 | 0.3 | — | — |
| K26 | 4 | 100 | — |
| K27 | 5 | — | — |
| K28 | 0.05 | — | — |
| K29 | 0.25 | — | — |
| JP-28 | 0.003 | — | — |
| JP-29 | 0.9 | — | — |
| JP-30a | 0.8 | — | — |
| JP-31 | 3 | — | — |
| JP-8N | 0.002 | — | — |
| JP-37 | 0.01 | — | — |
| JP-38 | 0.06 | — | — |
| JP-17-DMA | 0.1 | — | — |
| JP-17-CO$_2$H | 0.2 | — | — |
| JP-17-OMe | 0.05 | — | — |
| JP-18 TFA salt | 0.01 | — | — |
| JP-39 | 0.8 | — | — |
| JP-40 | 0.3 | — | — |
| JP-41 | 0.03 | — | — |
| JP-41-OMe | 0.09 | — | — |
| JP-41-NHMe | >1 | — | — |
| JP-17-NHMe | 0.007 | — | — |
| JP-8 | 0.002 | — | — |
| JP-17 | 0.001 | — | — |
| Int211 | >10 | — | — |
| JP-S2 | 0.2 | — | — |
| JP-S4 | 0.2 | — | — |
| JP-S5 | 0.5 | — | — |
| JP-S7 | 0.2 | — | — |
| JP-S10 | 0.015 | — | — |
| JP-S11 | 1 | — | — |
| JP-S12 | 0.03 | — | — |
| JP-S13 | 0.1 | — | — |
| JP-S15 | 0.05 | — | — |
| JP-S14 | 1 | — | — |
| JP-S16 | 0.03 | — | — |
| JP-S17 | 0.09 | — | — |
| JP-S18 | 0.002 | — | — |
| JP-S19 | 0.09 | — | — |
| JP-S20 | 0.03 | — | — |
| JP-S21 | 0.02 | — | — |
| JP-S22 | 0.03 | — | — |
| JP-S23 | 0.0006 | — | — |
| JP-S24 | 0.01 | — | — |
| JP-S25 | 0.02 | — | — |
| JP-S27 | >5 | — | — |
| JP-S10-OMe | >0.2 | — | — |
| JP-S16-OMe | 0.2 | — | — |
| JP-S18-OMe | 0.02 | — | — |
| JP-S21-diMe | >0.2 | — | — |
| BRD-297 | 0.250 | — | — |
| JP-41 | 0.03 | — | — |
| JP-42 | 0.008 | — | — |
| JP-43 | 0.004 | — | — |
| JP-17 | 0.001 | — | — |
| JP-41-OMe | 0.09 | — | — |
| JP-42-OMe | 0.2 | — | — |
| JP-43-OMe | 0.15 | — | — |

*Z-score values from the screen using the diversity-orineted synthesis (DOS) informer set of plates

TABLE E2

IC$_{50}$ values of exemplary compounds of Formula (I) for inhibition of IDE.

| Compound No. | IC$_{50}$ (μM) Proteolysis | I$_{max}$ (%) Proteolysis |
|---|---|---|
| B1 | 0.2 | — |
| B2 | 0.4 | 65 |
| B3 | 0.2 | 72 |
| B4 | 2.5 | 100 |
| B5 | 7.5 | — |
| B6 | 1.0 | 65 |
| B7 | 7.5 | 100 |
| B8 | 0.002 | 60 |
| B9 | 0.1 | 72 |
| B10 | 2.5 | 65 |
| B11 | 0.02 | 65 |
| B12 | 0.09 | 65 |
| B13 | 0.3 | 65 |
| B14 | 0.8 | 90 |

TABLE E3

IC$_{50}$ values of exemplary compounds of Formula (II) for inhibition of IDE.

| Compound No. | IC$_{50}$ (μM) Proteolysis | I$_{max}$ (%) Proteolysis | Average Z-score (Fluorescence anisotropy) |
|---|---|---|---|
| C1 | 2 | 70 | −20.0 |
| C2 | 7 | 50 | −16.62 |
| C3 | 5 | 70 | −9.02 |
| C4 | 7.5 | 70 | −13.76 |
| C5 | — | — | −13.95 |
| C6 | 2 | 60 | −13.8 |
| C7 | 2.5 | 80 | −7.7 |
| C8 | 7.5 | 70 | −2.58 |

TABLE E3-continued

IC$_{50}$ values of exemplary compounds of Formula (II) for inhibition of IDE.

| Compound No. | IC$_{50}$ (μM) Proteolysis | I$_{max}$ (%) Proteolysis | Average Z-score (Fluorescence anisotropy) |
|---|---|---|---|
| C9 | 25 | >60 | −3.01 |
| C10 | 10 | 100 | — |

*Z-score values from the screen using the diversity-orineted synthesis (DOS) informer set of plates

TABLE E4

IC$_{50}$ values of exemplary compounds of Formula (III) for inhibition of IDE.

| Compound No. | IC$_{50}$ (μM) Proteolysis | I$_{max}$ (%) Proteolysis | Average Z-score (Fluorescence anisotropy) |
|---|---|---|---|
| D1 | — | — | −16.97 |
| D2 | 20 | 100 | −16.33 |
| D3 | 7 | 50 | — |
| D4 | >20 | — | — |
| D5 | 7.5 | 60 | — |
| D6 | 5 | 70 | — |
| D7 | — | — | −10.49 |
| D8 | 1 | 40 | −33.77 |
| D9 | 7.5 | 60 | −12.03 |

*Z-score values from the screen using the diversity-orineted synthesis (DOS) informer set of plates

TABLE E5

IC$_{50}$ values of exemplary compounds of Formula (IV) or (V) for inhibition of IDE.

| Compound No. | IC$_{50}$ (μM) Proteolysis |
|---|---|
| J1 | 1 |
| J2 | 2.5 |
| J3 | 2.5 |
| J6 | 0.3 |
| J7 | >100 |
| J9 | 2.5 |
| J10 | 2.5 |
| J16 | 2.5 |
| JPM-6 | 0.3 |
| A01 | >30 |
| A02 | 12 |
| A03 | >100 |
| A04 | 12 |
| A05 | 9 |
| A06 | 1 |
| A08 | 25 |
| A10 | 33 |
| A11 | 10 |
| A12 | 50 |
| A13 | 10 |
| A07 | 3 |
| A14 | 10 |
| A15 | 4 |
| A16 | 12 |
| A17 | 5 |
| A18 | 12 |
| A19 | 4 |
| A21 | 1 |
| A22 | 1 |
| A23 | 10 |
| J17 | 0.2 |
| A25 | 0.9 |
| A26 | 6 |
| A28 | 1 |
| A29 | >50 |
| A30 | 12 |
| A27 | 12 |
| A40 | 12 |
| A39 | 12 |
| A34 | >50 |
| A35 | 12 |
| A31 | 12 |
| A32 | 12 |
| A33 | 7 |

HTRF Assay for IDE-Mediated Degradation of Insulin and Glucagon.

Figure 3:
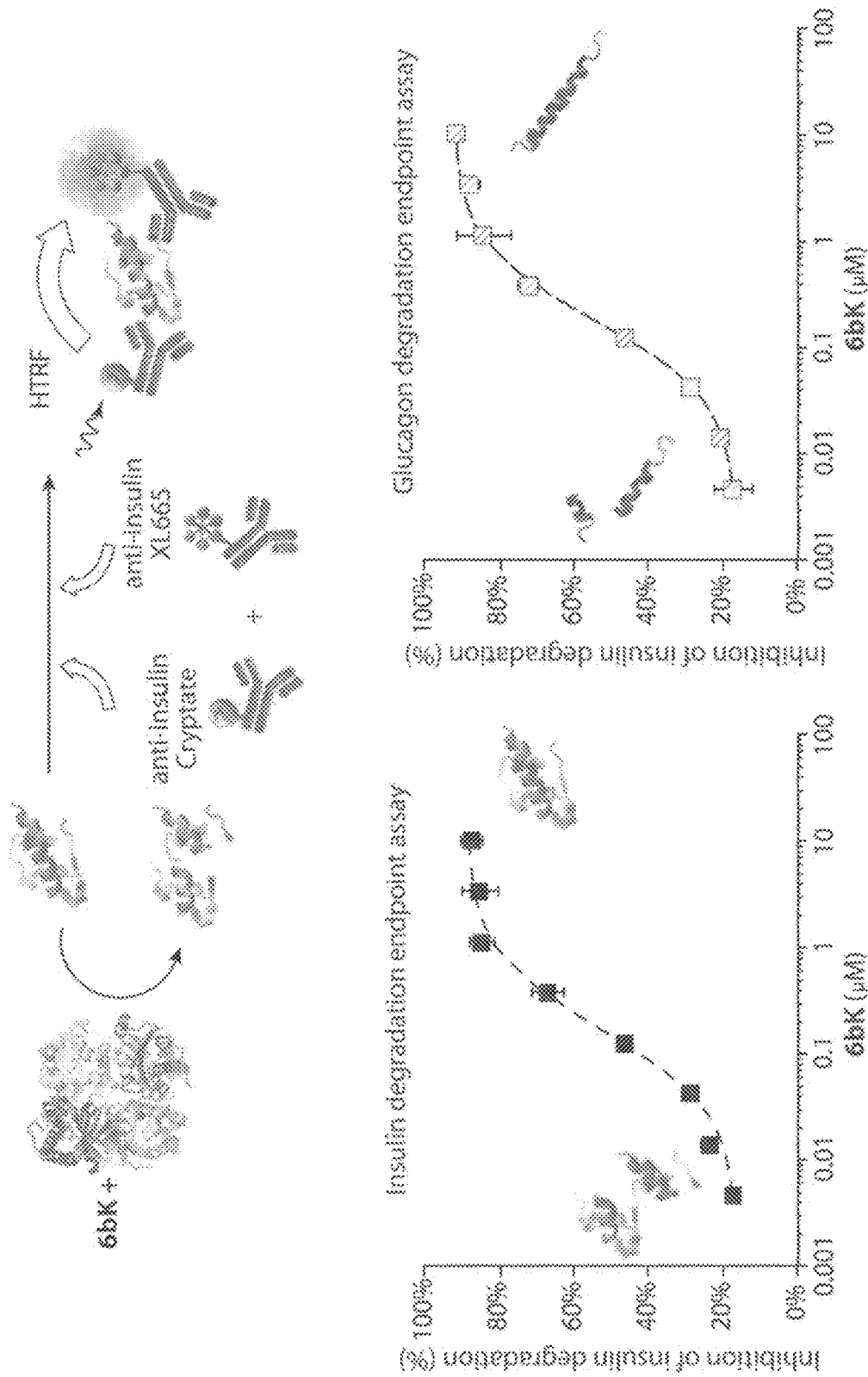
FIG. 3. Optimization of homogeneous time-resolved FRET (HTRF) assays to report on IDE-mediated degradation of insulin and glucagon in the presence of inhibitors. The inhibitor 6bK was used as a positive control to optimize the incubation temperature, the endpoint, the substrate concentration, and the amount of IDE enzyme, in order to generate a sigmoidal profile that reports on 6bK IDE inhibition in a concentration-dependent manner.

A solution of 0.8 μg/mL IDE (R&D) in pH 7.5 buffer containing 20 mM HEPES, 135 mM NaCl (24 μL) was transferred to a 200 μL tube strip, and combined with 1 μL of each inhibitor (10 mM in DMSO, or as a 3-fold dilution series). A solution of insulin in "Assay Diluent" (CisBio, 25 μL) was added to a final concentration of 20 ng/mL, and incubated at 30° C. for 15 minutes. This procedure was optimized to result in ~75% degradation of insulin. The reaction was terminated by adding 25 μL of inhibitor Ii1 (200 nM) and chilled on ice. The remaining insulin was quantified using 10 μL of the quenched enzymatic reaction using the sensitive-range protocol Homogeneous Time-Resolved FRET Insulin assay (CisBio® 62INSPEB, see FIG. 3) in 20 μL total volume according to the manufacturer's instructions (384 well-plate Greiner 784904 non-binding). Fluorescence was measured using a Tecan M1000Pro plate reader (excitation=320 nm, emission=665 and 620 nm, lag time=60 μs) according the assay manufacturer's recommendations. Blank wells and insulin standard curve were included in the assay.

A solution of 0.05 μg/mL IDE (R&D) in "Diluent #5" (CisBio, 24 μL) was transferred to a 200 μL tube strip, and combined with 1 μL of each inhibitor (10 mM in DMSO, or as a 3-fold dilution series). A solution of glucagon in the same buffer (25 μL) was added to a final concentration of 4 ng/mL, and incubated at RT for 10 minutes. This procedure was optimized to result in ~75% degradation of glucagon. The reaction was terminated by 1 μL of inhibitor Ii1 (5 μM) and chilled on ice. The remaining glucagon was quantified using 10 μL of the quenched enzymatic reaction using the sensitive-range protocol Homogeneous Time-Resolved FRET Glucagon assay (CisBio® 62GLCPEF, see FIG. 3) in 20 μL total volume according to the manufacturer's instructions (384 well-plate Greiner 784904 non-binding). Fluorescence was measured using a Tecan M1000Pro plate reader (excitation=340 nm, emission=665 and 620 nm, lag time=60 μs) according the assay manufacturer's recommendations. Blank wells and glucagon standard curve were included in the assay.

Figure 4:
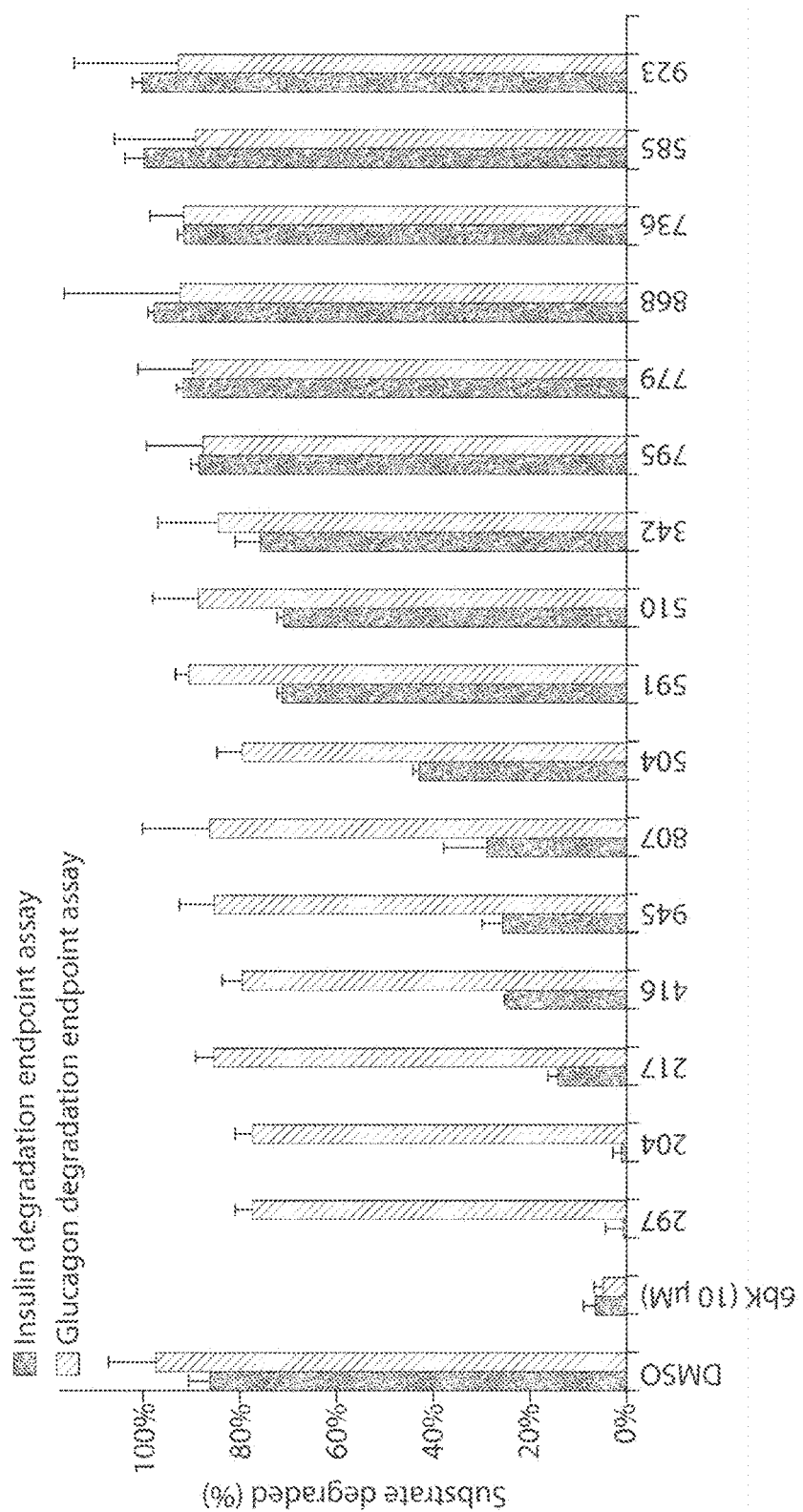
FIG. 4. Focused screen for substrate-selective inhibitory properties using the insulin and glucagon degradation endpoint HTRF assays. Selected hits displaying submaximal inhibition in the range of 40-80% for the surrogate fluorogenic peptide cleavage assay were chosen. All compounds (used at final concentration of 67 μM, >10×$IC_{50}^{app}$) and control incubations were performed in parallel using the same IDE and substrate preparations. Some analogs show a strong discrepancy in IDE-mediated degradation of glucagon versus insulin compared with IDE treated with DMSO alone, or with a positive control 6bK (10 μM).
Figure 5:
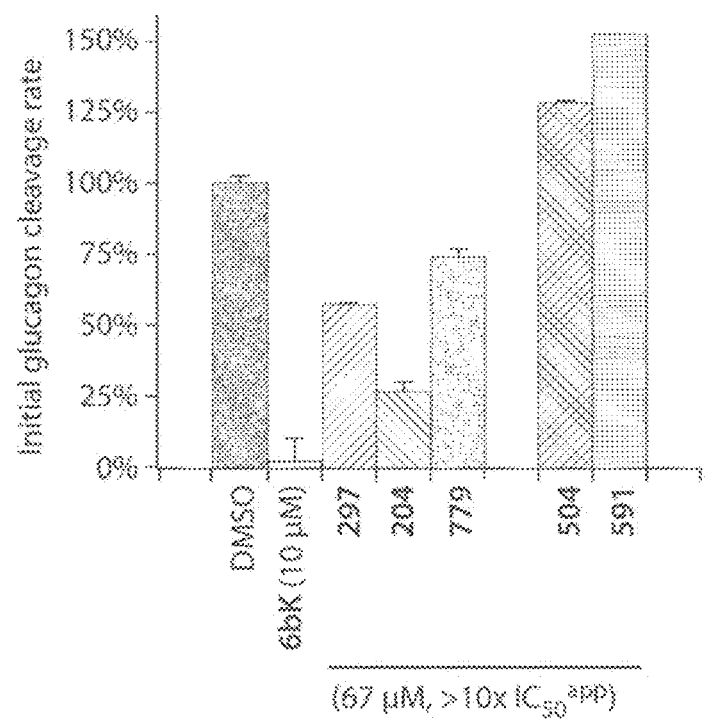
FIG. 5. Study of the initial rates of IDE-mediated glucagon cleavage. The glucagon degradation reaction was incubated in the presence of compounds (67 μM), DMSO alone, or 6bK positive control (10 μM), at 0° C. for 10 minutes to induce partial IDE-mediated degradation, which was measured using the HTRF assay.
Figure 6A:
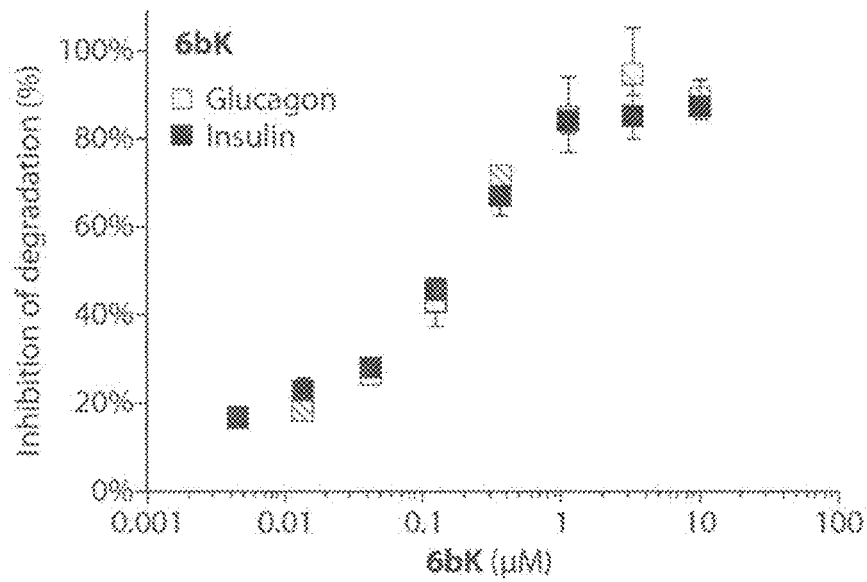
FIGS. 6A-6H. Concentration dependence profiles for certain inhibitors of IDE, including compound 297 (FIG. 6B), compound 204 (FIG. 6C), compound 591 (FIG. 6D), compound 217 (FIG. 6E), compound 416 (FIG. 6F), compound 504 (FIG. 6G), and compound 501 (FIG. 6H). Selected hits that display substrate-selective inhibitory properties were assayed over a range of concentrations using the HTRF endpoint degradation assay for insulin and glucagon. The known non-selective inhibitor 6bK was used as a control (FIG. 6A).
Figure 6B:
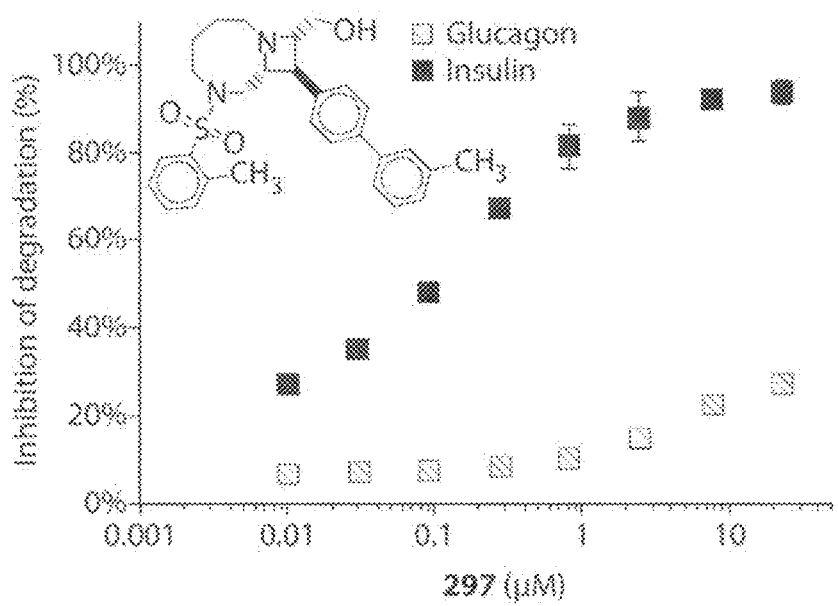
Figure 6C:
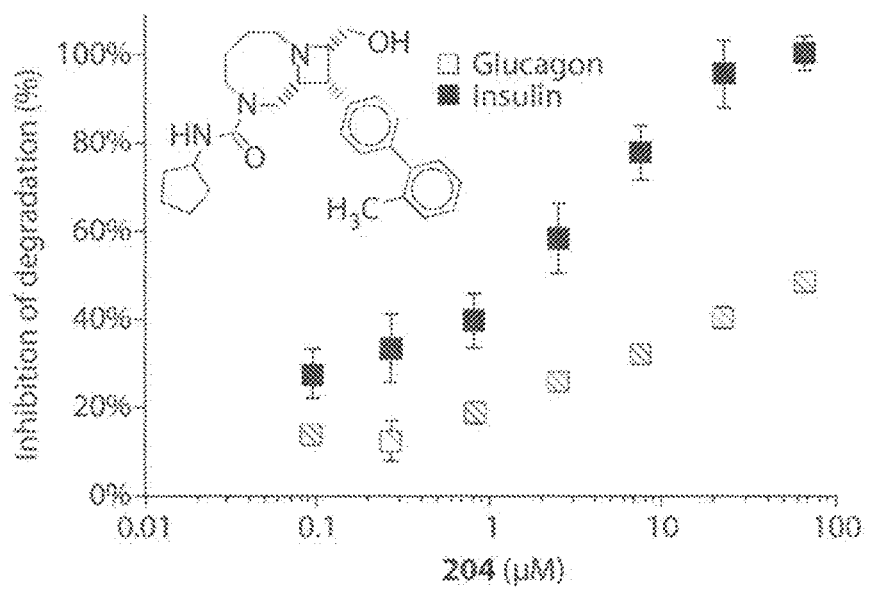
Figure 6D:
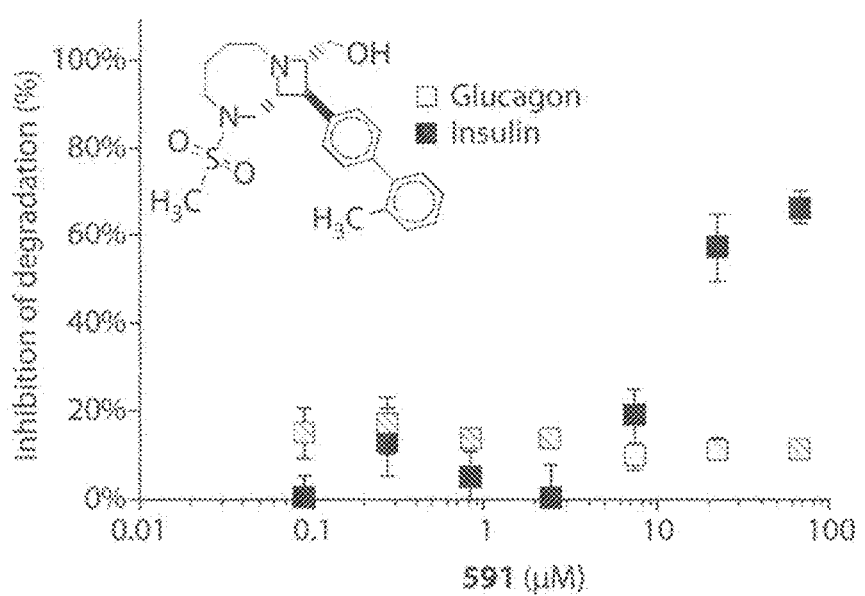
Figure 6E:
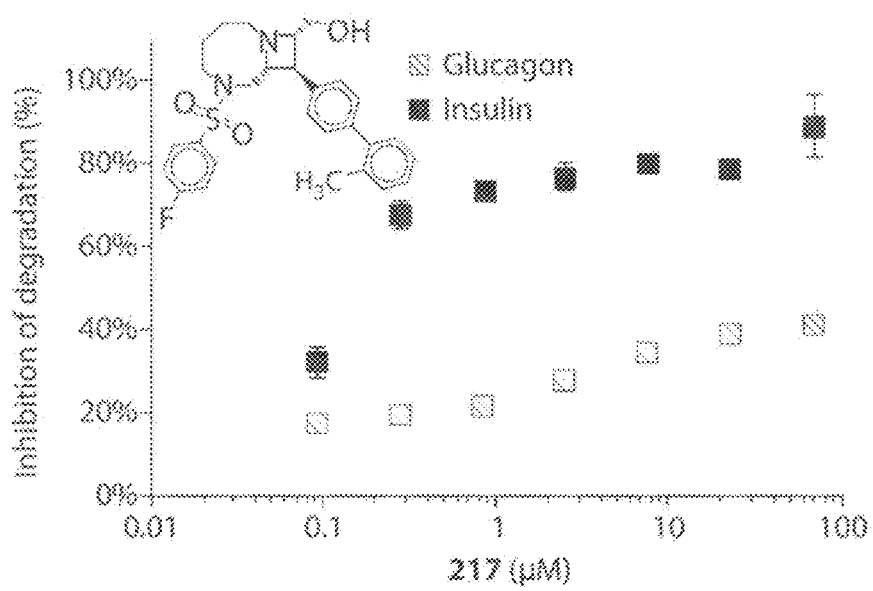
Figure 6F:
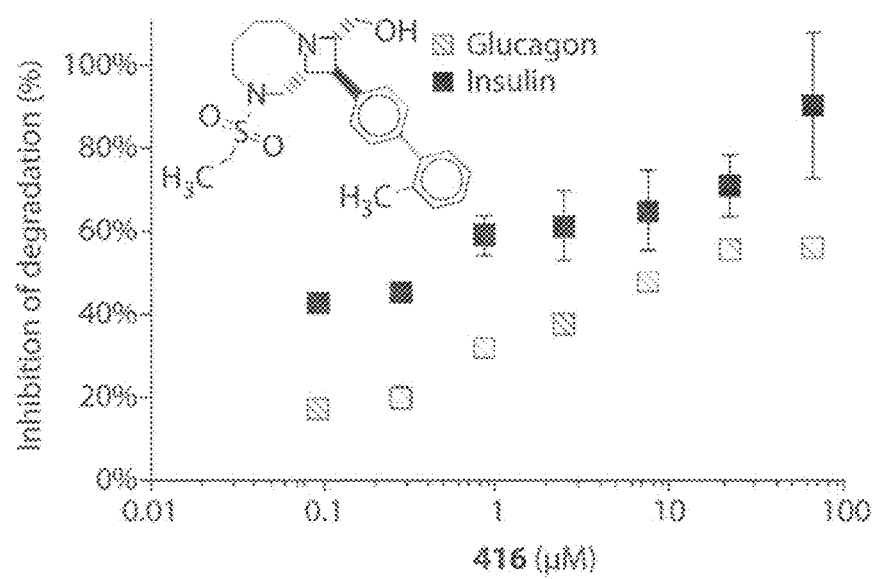
Figure 6G:
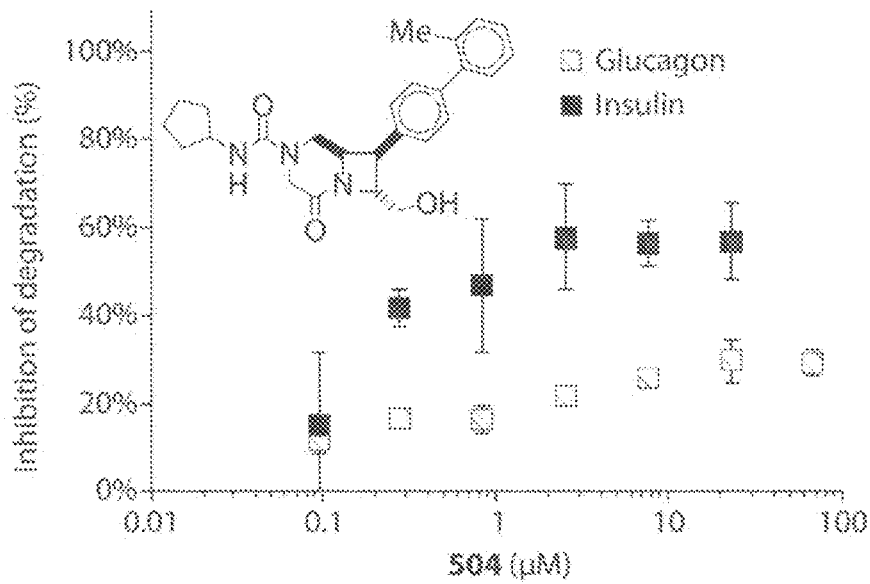
Figure 6H:
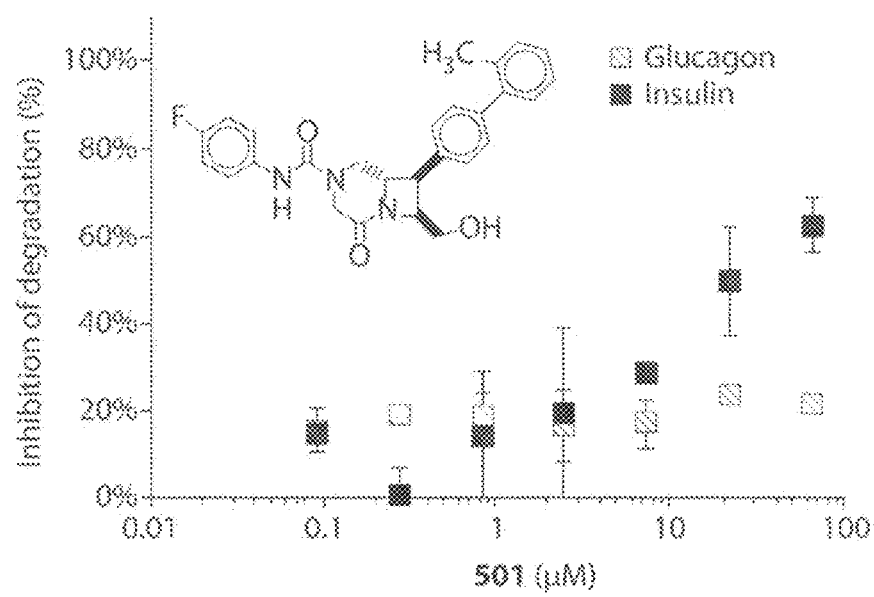
Figure 7A:
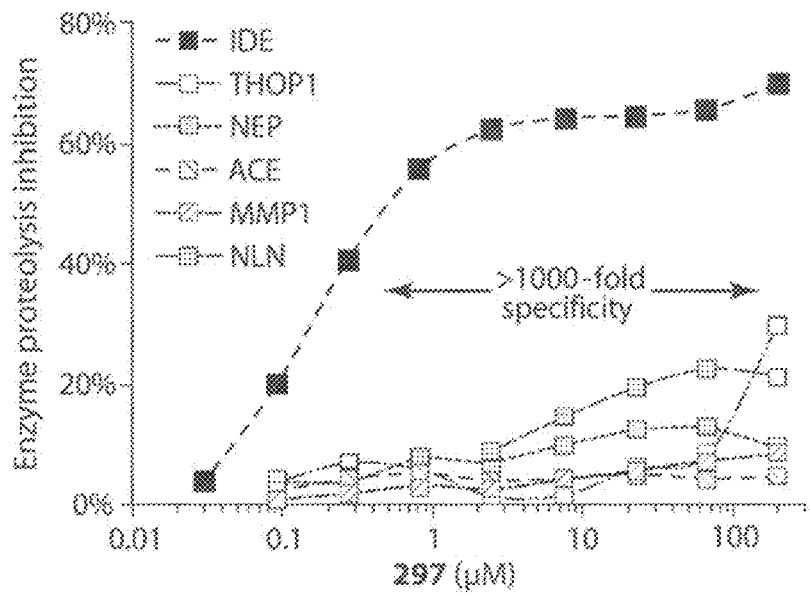
FIGS. 7A-7D. Analysis of metalloprotease specificity for substrate-selective IDE inhibitors, including compound 297 (FIG. 7A), compound 204 (FIG. 7B), compound 779 (FIG. 7C), and compound 504 (FIG. 7D). Concentration dependence profiles for IDE inhibitors with IDE compared with concentration dependent profiles for other metalloproteases tested: thimet oligopeptidase (THOP), neurolysin (NLN), neprilysin (NEP), matrix metalloprotease 1 (MMP1), and angiotensin converting-enzyme (ACE).
Figure 7B:
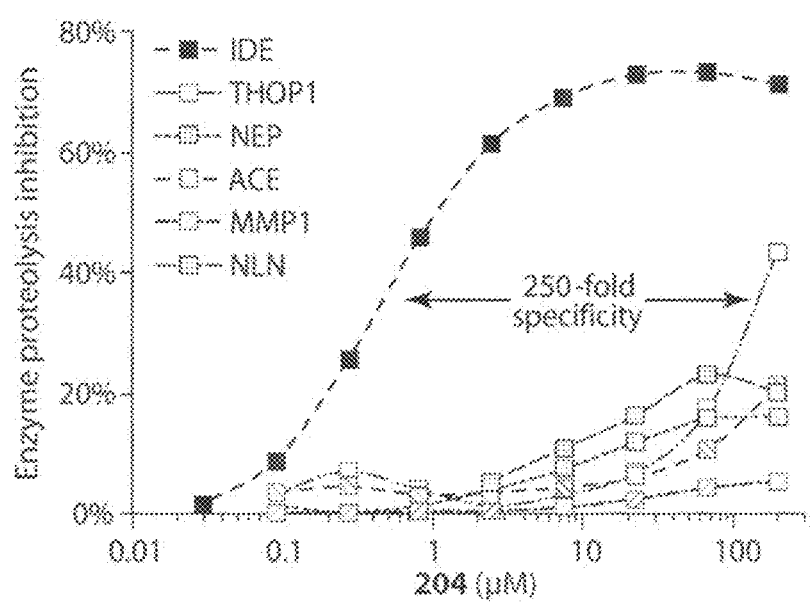
Figure 7C:
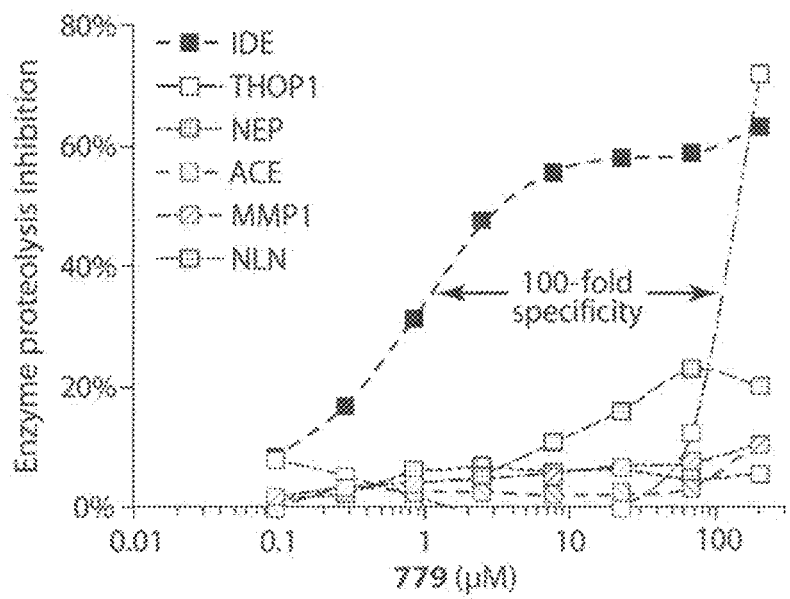
Figure 7D:
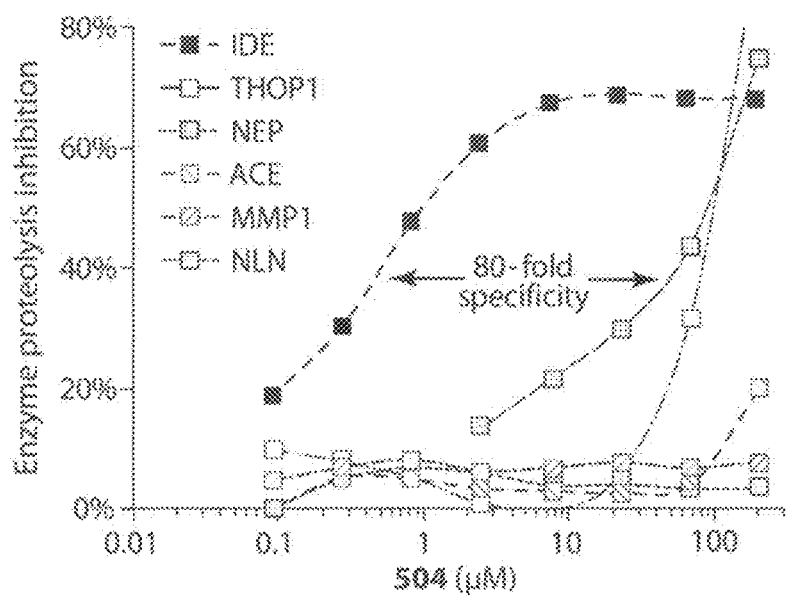

FIG. 4 compares the determined endpoint for insulin degradation with of glucagon degradation for a DMSO control, 6bK at 10 μM, and exemplary compounds of the invention at concentrations of 67 μM. Control and 6bK show no selectivity between insulin in degradation, while several of the inhibitors tested show a significant discrepancy between the two substrates. Initial rates for glucagon cleavage as determined by the HTRF assay are shown in FIG. 5. Tested compounds display both reduced (e.g., compound 297, 204, 779) and enhanced (e.g., 504, 591) rates of glucagon cleavage. The enhanced rates may be a result of the IDE/compound interaction leading to an increased affinity for glucagon versus unaltered IDE ($K_M$~3.5 μM).

The HTRF endpoint assay for insulin and glucagon was performed over a range of concentrations for several potential inhibitors and for 6bK. The concentration-dependent profiles for each substrate are shown in FIG. 6.

vector was amplified for USER cloning with the primers 5'-ATGGCTGGATTATTCATATGATGA-dU-GATGATGAT-GAGAACCC (SEQ ID NO: 28) and 5'-ACTCTGAGGTAT-GGCTAGCA-dU-GACTGGTG (SEQ ID NO: 29). Mutant IDE constructs were generated by amplifying the full vector construct with USER cloning primers introducing a mutant overhang (see Table E6).

TABLE E6

Site directed mutagenesis primers.

| Mutation | Primers (froward, reverse) | SEQ ID NO: |
|---|---|---|
| A198T | AGACTCTTTCAATTGGAAAAAGC-dU-ACAGGG | 30 |
|  | AGCTTTTTCCAATTGAAAGAGTC-dU-CCAGGTATCATTCATCACATTCTTCTCATGTTC | 31 |
| W199F | AGACTCTTTCAATTGGAAAAAGC-dU-ACAGGG | 32 |
|  | AGCTTTTTCCAATTGAAAGAGTC-dU-GAAGGCATCATTCATCACATTCTTCTC | 33 |
| F202R | AGACTCTTTCAATTGGAAAAAGC-dU-ACAGGG | 34 |
|  | ATGAATGATGCCTGGAGAC-dU-CCGTCAATTGGAAAAAGCTACAGGG | 35 |
| Y314F | ACCCATTAAAGATATTAGGAATCTC-dU-TCGTGACATTTCCCATACCTGACCTTC | 36 |
|  | AGAGATTCCTAATATCTTTAATGGG-dU-ACTATTTTG | 37 |
| V360Q | AAAGGGCTGGGTTAATACTCT-dU-CAGGGTGGGCAG | 38 |
|  | AAGAGTATTAACCCAGCCCTT-dU-GACTTAAG | 39 |
| G362Q | AAAGGGCTGGGTTAATACTCT-dU-GTTGGTCAGCAGAAGGAAGGAGCCCGAG | 40 |
|  | AAGAGTATTAACCCAGCCCTT-dU-GACTTAAG | 41 |
| I374Q | ATGTTTTTTCAGATTAATGTGGACT-dU-GACCGAGGAAGG | 42 |
|  | AAGTCCACATTAATCTGAAAAAACA-dU-AAAACCTCGGGCTCCTTC | 43 |
| A479L | ATGTCCGGGTTCTGATAGTTTCTAAA-dU-CTTTTGAAGGAAAAACTG | 44 |
|  | ATTTAGAAACTATCAGAACCCGGACA-dU-TTTCTGGTCTGAG | 45 |

Figure 11A:
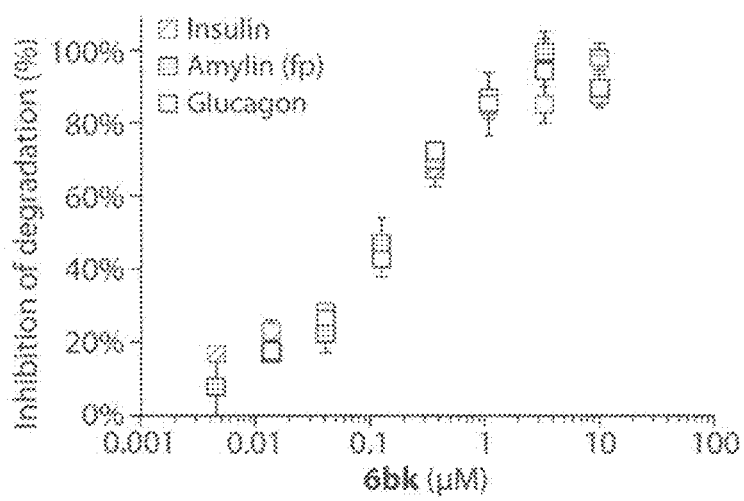
FIGS. 11A-11C. Concentration dependence profiles for certain inhibitors of IDE, including compound 297 (FIG. 11B) and compound 204 (FIG. 11C). Selected hits that display substrate-selective inhibitory properties were assayed over a range of concentrations using the HTRF endpoint degradation assay for insulin and glucagon, and a fluorogenic amylin analog to determine selectivity for amylin. The known non-selective inhibitor 6bK was used as a control. The sequences, from top to bottom, correspond to SEQ ID NOs: 8-9.
Figure 11B:
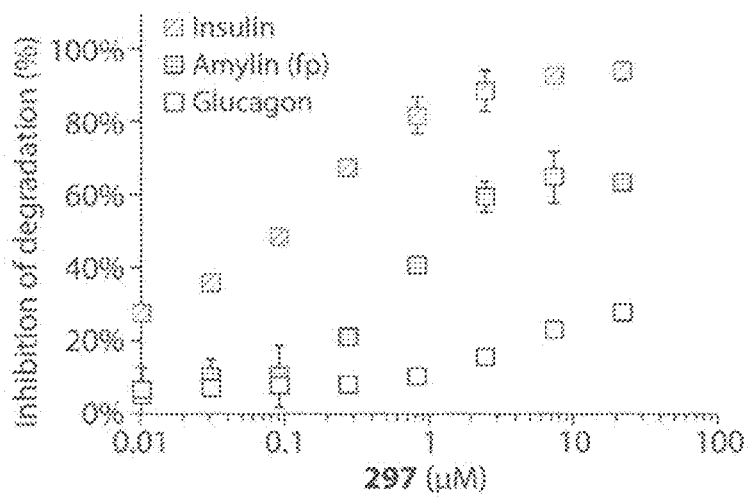
Figure 11C:
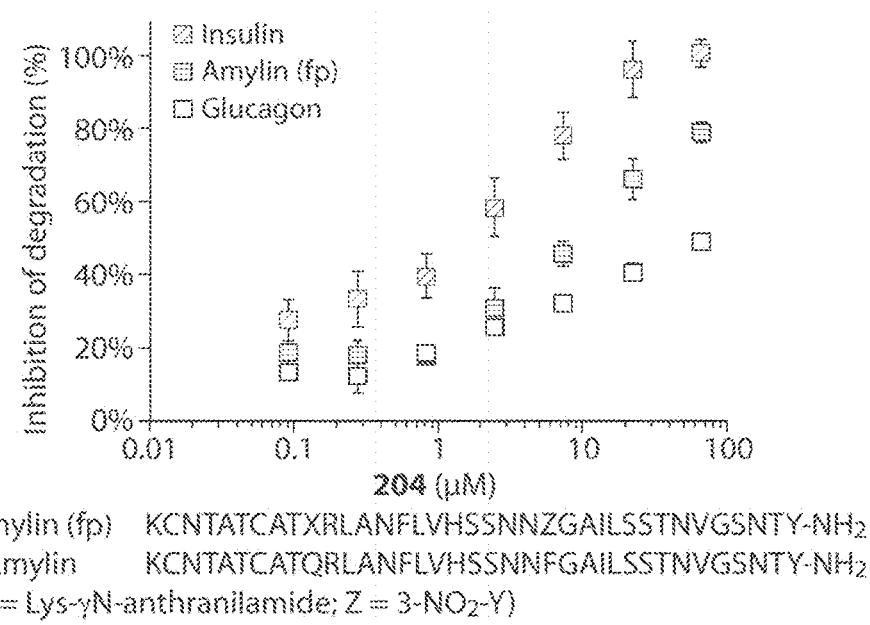
Figure 12:
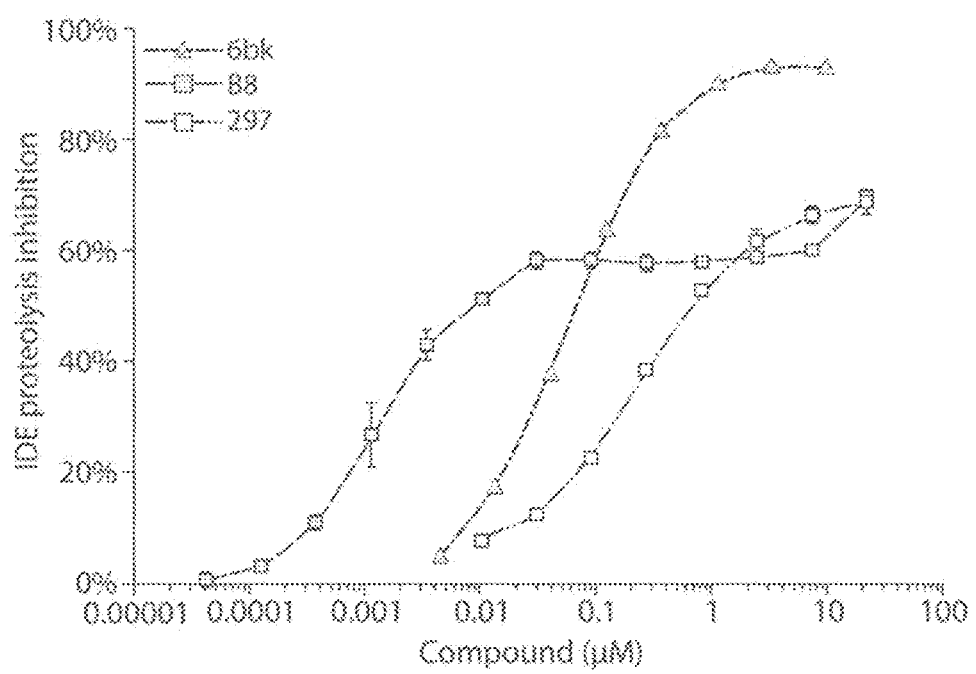
FIG. 12. Concentration dependence profiles for inhibition of IDE to proteolysis of a fluorogenic peptide in the presence of 6bK, 297, and B8. Inhibitors 297 and B8 have an inhibition maximum of less than 100%, indicative of substrate selective inhibitors.
Figure 13A:
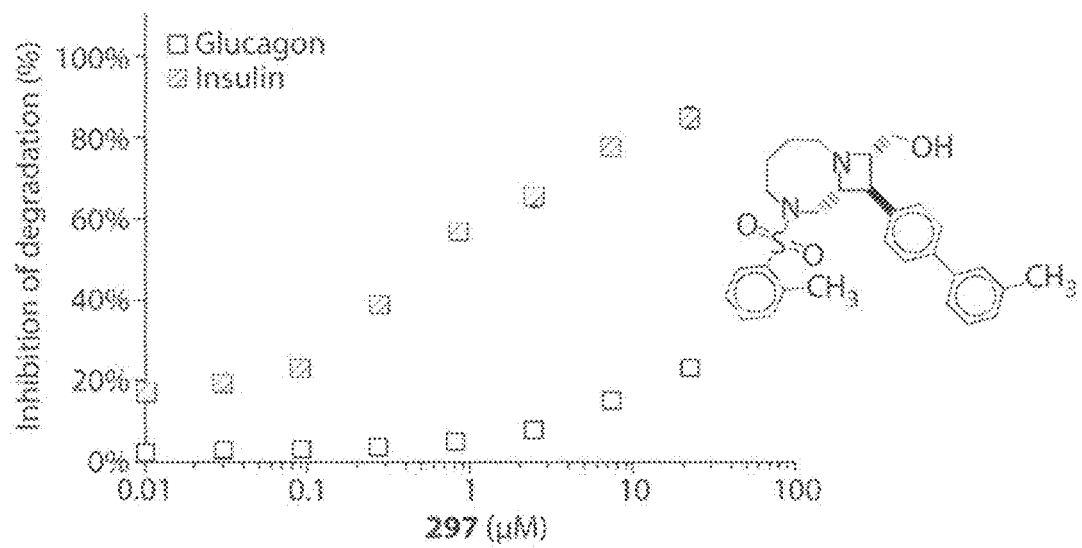
FIGS. 13A-13B. Concentration dependence profiles measured with the HTRF endpoint degradation assay for the inhibition of insulin and glucagon degradation by IDE with inhibitors 297 (FIG. 13A) and B8 (FIG. 13B).
Figure 13B:
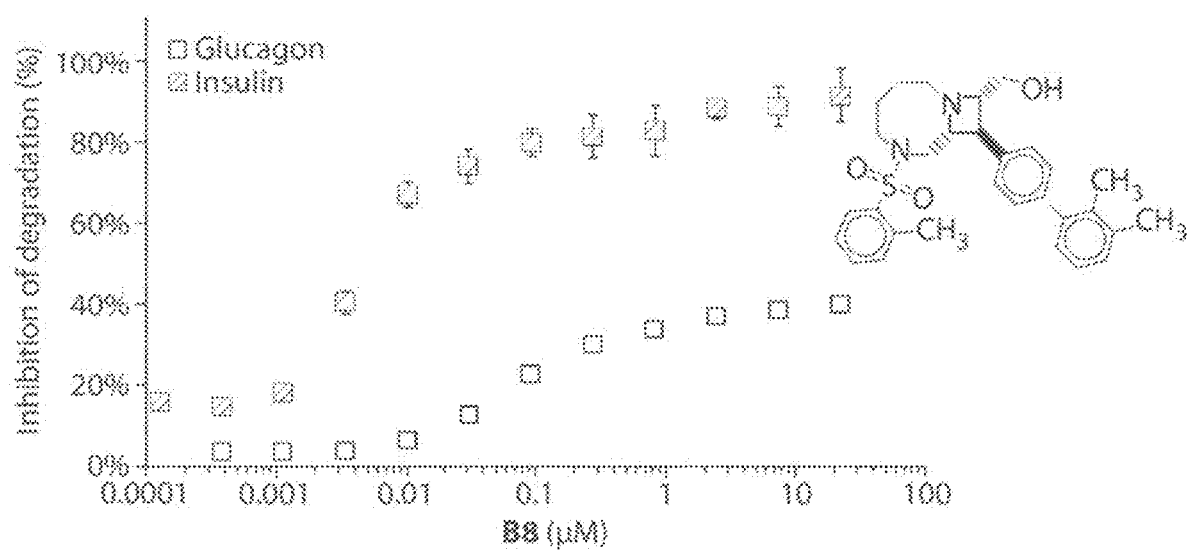
Figure 14A:
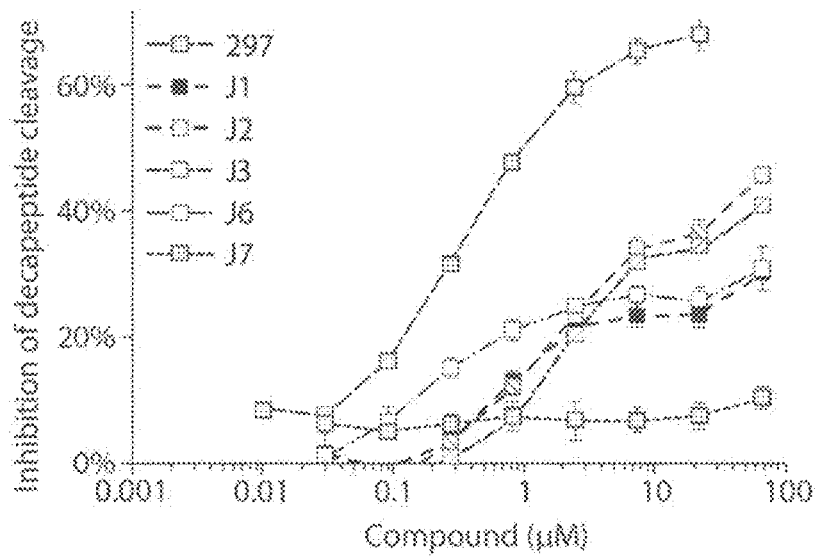
FIGS. 14A-14B.
Figure 14B:
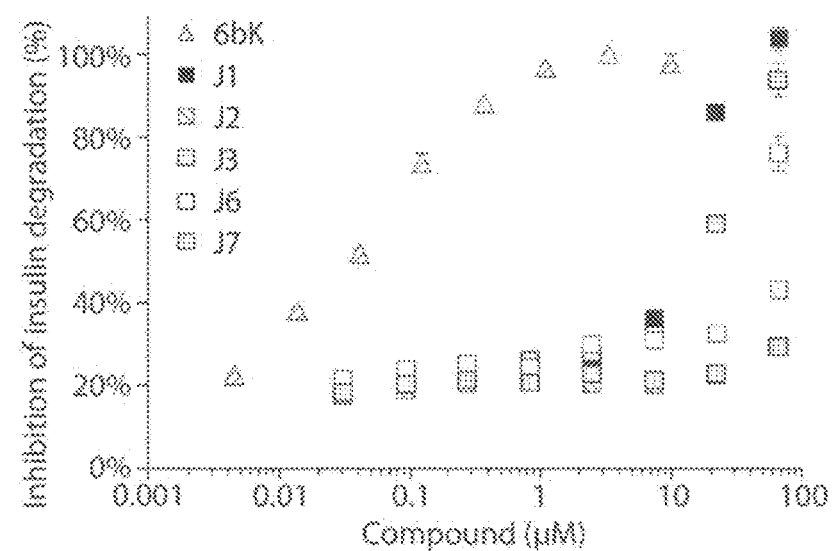

In order to determine the behavior of the inhibitors with respect to amylin, a concentration dependence profile was measured for IDE in the presence of a specified concentration of inhibitor and a fluorogenic amylin analog. The amylin (fp) peptide sequence was KCNTATCATXRLAN-FLVHSSNNZGAILSSTNVGSNTY-$NH_2$ (SEQ ID NO: 8). The residue marked as X is Lys-γN-anthrinilamide, and the residue marked as Z is 3-nitro-Tyr. The sequence of human amylin is KCNTATCATQRLANFLVHSSNNF-GAILSSTNVGSNTY-$NH_2$ (SEQ ID NO: 9). The inhibition for the amylin (fp) peptide is compared with the inhibition curves for insulin and glucagon in FIG. 11A for 6bK (control) and in FIGS. 11B and 11C for compounds 297 and 204, which show selectivity for inhibiting degradation of insulin over degradation of amylin and glucagon, and selectivity for inhibiting degradation of amylin over degradation of glucagon.

Site-Directed Mutagenesis, Expression, and Purification of Human IDE.

N-$His_6$-tagged human $IDE_{42-1019}$ construct was introduced in the expression plasmid pTrcHis-A (Invitrogen) using primers for uracil-specific excision reactions (USER) by Taq (NEB) and Pfu polymerases (PfuTurbo CX®, Agilent), as described in more detail in Maianti et al. (*Nature* (2014), 511, 94-98), which is incorporated by reference herein. The IDE gene was amplified with the primers 5'-ATCATCATATGAATAATCCAGCCA-dU-CAAGAGAAT-AGG (SEQ ID NO: 26) and 5'-ATGCTAGCCATACCT-CAGAG-dU-TTTGCAGCCATGAAG (SEQ ID NO: 27) (underlined sequences represent overhangs, and italics highlight the PCR priming sequence). Similarly, the pTrcHis-A All PCR products were purified on microcentrifuge membrane columns (MinElute®, Qiagen) and quantified by UV absorbance (NanoDrop). Each fragment (0.2 pmol) was combined in a 10 μL reaction mixture containing 20 units DpnI (NEB), 0.75 units of USER mix (Endonuclease VIII and Uracil-DNA Glycosylase, NEB), 20 mM Tris-acetate, 50 mM potassium acetate, 10 mM magnesium acetate, 1 mM dithiothreitol at pH 7.9 (1× NEBuffer 4). The reactions were incubated at 37° C. for 45 minutes, followed by heating to 80° C. and slow cooling to 30° C. (0.2° C./s). The hybridized constructs were directly used for heat-shock transformation of chemically competent NEB turbo *E. coli* cells according to the manufacturer's instructions. Transformants were selected on carbenicillin LB agar, and isolated colonies were cultured overnight in 2 mL LB.

The plasmid was extracted using a microcentrifuge membrane column kit (Miniprep®, Qiagen), and the sequence of genes and vector junctions were confirmed by Sanger sequencing (see Table E7). The plasmid constructs were transformed by heat-shock into chemically-competent expression strain Rosetta 2 (DE3) pLysS *E. coli* cells (EMD Millipore), and selected on carbenicillin/chloramphenicol LB agar. Cells transformed with IDE pTrcHis A constructs were cultured overnight at 37° C. in 2 XYT media (31 g in 1 L) containing 100 μg/mL ampicillin and 34 μg/mL chloramphenicol. Expression of His6-tagged IDE proteins was induced when the culture measured OD600~0.6 by addition of isopropyl-β-D-1-thiogalactopyranoside (IPTG) to 1 mM final concentration, incubated overnight at 37° C., followed by centrifugation at 10,000 g for 30 minutes at 4° C.

TABLE E7

Sequencing primers.

| Sequencing primers | | SEQ ID NO: |
|---|---|---|
| Seq_Fw1 | GATTAACTTTATTATTAAAAATTAAAGAGG | 46 |
| Seq_Re1 | CAACATGTAATAATCCTTCCTCGGTC | 47 |
| Seq_Fw2 | GCATGAAGGTCCTGGAAGTCTG | 48 |
| Seq_Re2 | AGGAAGGGTTACATCATCCAGAGC | 49 |
| Seq_Fw3 | CCATGTACTACCTCCGCTTGC | 50 |
| Seq_Re3 | GCAGATCTCGAGCTCGGATC | 51 |
| Seq_Fw4 | GCTTATGTGGACCCCTTGCACTG | 52 |

Recombinant His6-tagged proteins were purified by Ni(II)-affinity chromatography (IMAC sepharose beads, GE Healthcare®) according to the manufacturer's instructions. The cell pellets were re-suspended in pH 8.0 buffer containing 50 mM phosphate, 300 mM NaCl, 10 mM imidazole, 1% Triton X-100 and 1 mM tris(2-carboxyethyl)phosphine hydrochloride (TCEP), and were lysed by probe sonication for 4 minutes at <4° C., followed by clearing of cell debris by centrifugation at 10,000 g for 25 minutes at 4° C. The supernatant was incubated with Ni(II)-doped IMAC resin (2 mL) for 3 hours at 4° C. The resin was washed twice with the cell re-suspension/lysis buffer, and three times with pH 8.0 buffer containing 50 mM phosphate, 300 mM NaCl, 50 mM imidazole and 1 mM TCEP. Elution was performed in 2 mL aliquots by raising the imidazole concentration to 250 mM and subsequently to 500 mM in the previous buffer. The fractions were combined and the buffer was exchanged to the recommended IDE buffer (R&D) using spin columns with 100 kDa molecular weight cut off membranes (Millipore). Protein yields were typically ~10 µg/L, and >90% purity based on gel electrophoresis analysis (Coomassie stained). IDE-specific protease activity was >95% as assessed by inhibition of degradation of peptide substrate Mca-RPPGFSAFK(Dnp)-OH (SEQ ID NO: 24) (R&D) by 20 µM 6bK, compared with pre-quantitated commercially available human IDE (R&D).

Figure 8A:
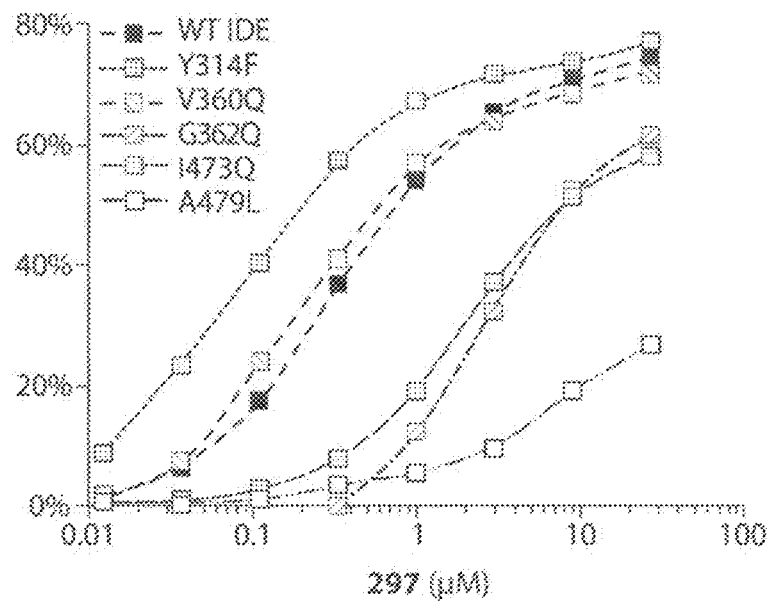
FIGS. 8A-8C. Confirmation of the distal binding site for substrate-selective IDE inhibitors, and a docking model within human IDE.
Figure 8B:
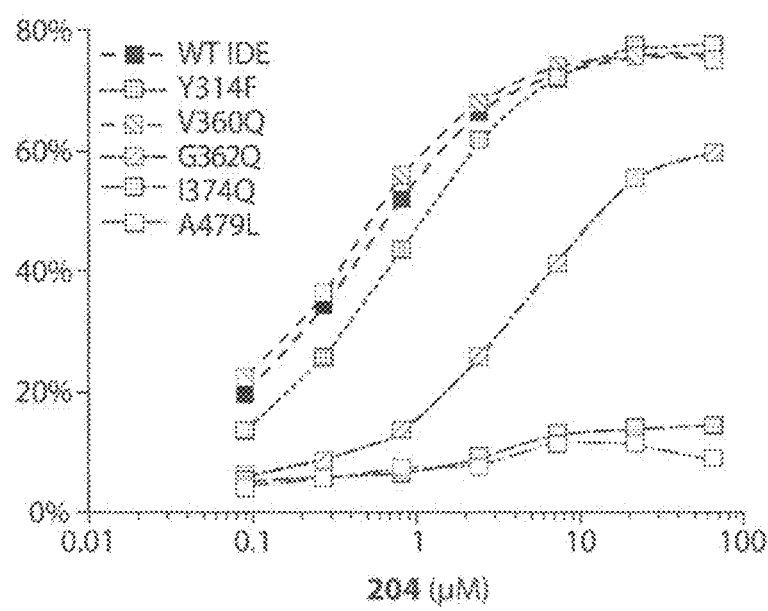

FIGS. 8A and 8B are concentration dependent profiles for inhibitors 297 and 204 with wild type IDE and mutants Y314F, V360Q, G362Q, I473Q, and A479L. Mutagenesis of the residue Ala479Leu hinders the inhibition potency of 297 and 204 by at least >150-fold. This mutation similarly blocks 6bK from inhibiting IDE, suggesting that the inhibitors share the same binding site. The nearby mutations Ile362Gln and Gly362Gln also reduce the inhibition potency of 297 and 204, while other variants like Val360Gln and Tyr314Phe have minor impacts on potency.

Ligand Docking Simulations.

Receptor and ligand preparation was performed in the standard method. DOCKing was performed using version 6.6 with default parameters for flexible ligand and grid-based scoring, and the van der Waals exponent was 9. Because of the mutagenesis data strongly pointing to a role of Ala479, we limited docking of the inhibitor to an area within 15 Å of Ala479.

These models predict multiple steric clashes (shown as circles) that abrogate the interactions of insulin when either (FIG. 9A) 297 or (FIG. 9B) 6b are bound to IDE. For FIGS. 9C and 9D, a 16-residue segment of glucagon (grey surface) is disordered and unresolved in the crystal structure, and only the terminal segments of glucagon are bound to the catalytic site (right) and exo-site (left). The overlaid models predict steric clashes (shown as circles) between 6b and the IDE-bound segments of glucagon (see FIG. 9D), in contrast compound 297 (FIG. 9C) does not abrogate any interactions between IDE and glucagon. The insets in FIG. 9A-9D represent the IDE-mediated cleavage sites (major "a" arrow, minor "b" arrows), the IDE-bound segments of the substrate are underlined, and the circle-backslash symbols highlight predicted steric clashes with the inhibitors.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

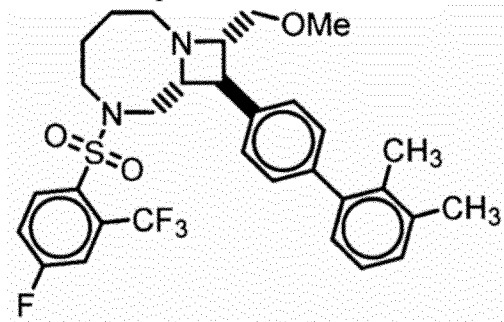

What is claimed is of formula:
1. A compound of Formula (I):

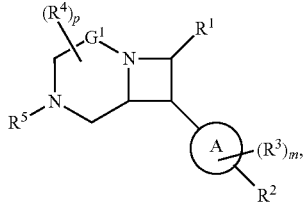
(I)

or a pharmaceutically acceptable salt, solvate, hydrate, polymorph, co-crystal, tautomer, stereoisomer, or isotopically labeled derivative thereof,
wherein:
G¹ is of formula:

;

Ring A is carbocyclylene, heterocyclylene, arylene, or heteroarylene;
R¹ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —CH₂-halo, —CH₂OR$^{1a}$, —CH₂SR$^{1a}$, or —CH₂N(R$^{1a}$)₂, wherein each R$^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, a sulfur protecting group when attached to a sulfur atom, or a nitrogen protecting group when attached to a nitrogen atom, or two R$^{1a}$ are joined to form an optionally substituted heteroaryl or optionally substituted heterocyclic ring;
R² is of formula:

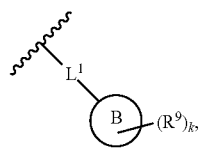

wherein:
L¹ is a bond, and Ring B is a heterocyclic ring,

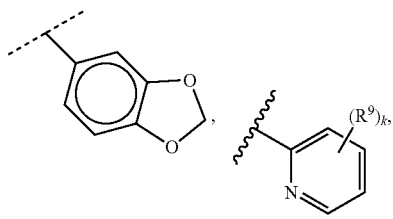

-continued

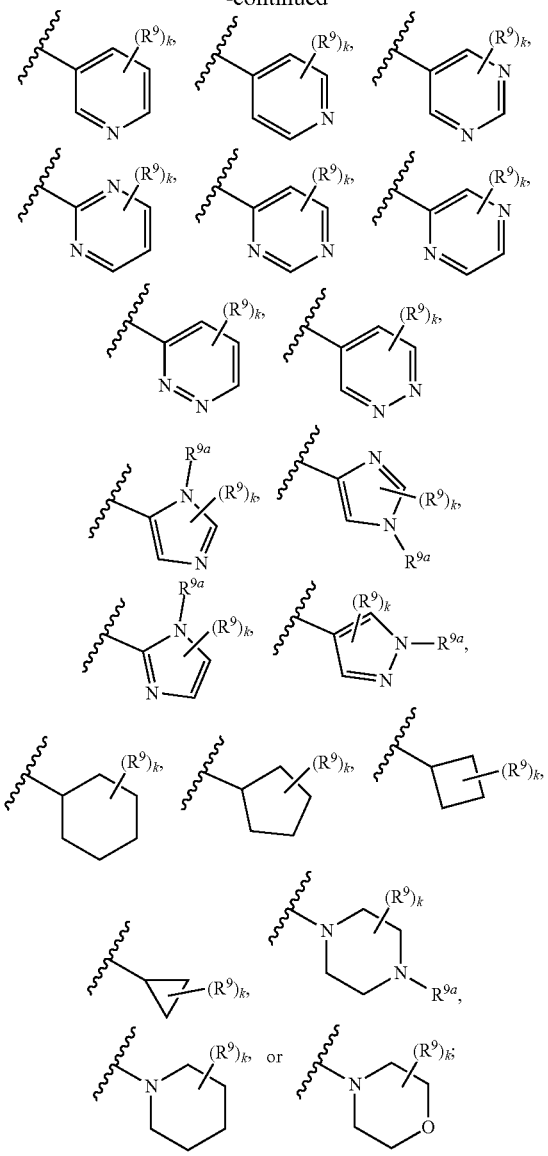

each R⁹ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO₂, —CN, —OR$^{9a}$, —N(R$^{9a}$)₂, —S(=O)₂R$^{9a}$, —S(=O)₂OR$^{9a}$, or —S(=O)₂N(R$^{9a}$)₂, wherein each R$^{9a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R$^{9a}$ are joined to form an optionally substituted heteroaryl or optionally substituted heterocyclic ring; and
k is 0, 1, 2, 3, 4, or 5;

each R³ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO₂, —CN, —OR³ᵃ, or —N(R³ᵃ)₂, wherein each R³ᵃ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R³ᵃ are joined to form an optionally substituted heteroaryl or optionally substituted heterocyclic ring;

each R⁴ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —OR⁴ᵃ, or —N(R⁴ᵃ)₂, wherein each R⁴ᵃ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R⁴ᵃ are joined to form an optionally substituted heteroaryl or optionally substituted heterocyclic ring;

R⁵ is of formula:

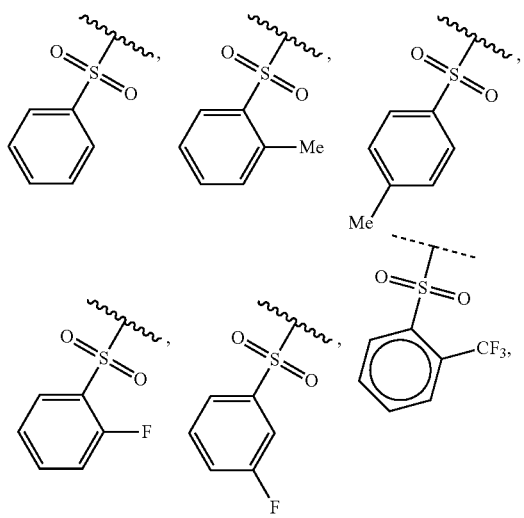

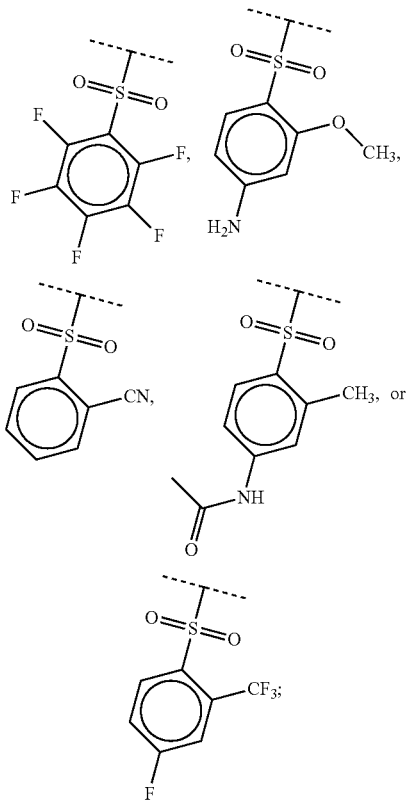

m is 0, 1, 2, 3, or 4; and
p is 0, 1, 2, 3, or 4.

2. The compound of claim 1, wherein R² is of formula:

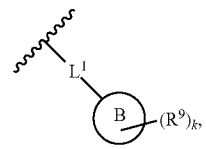

wherein:
L¹ is a bond;
Ring B is

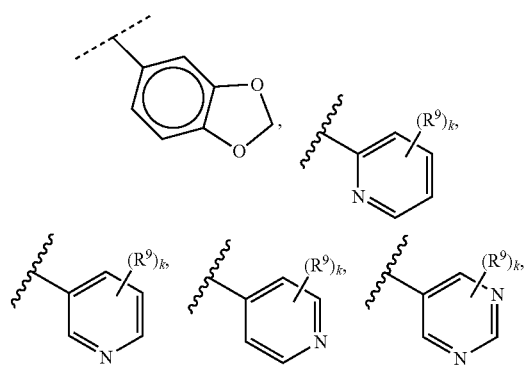

-continued

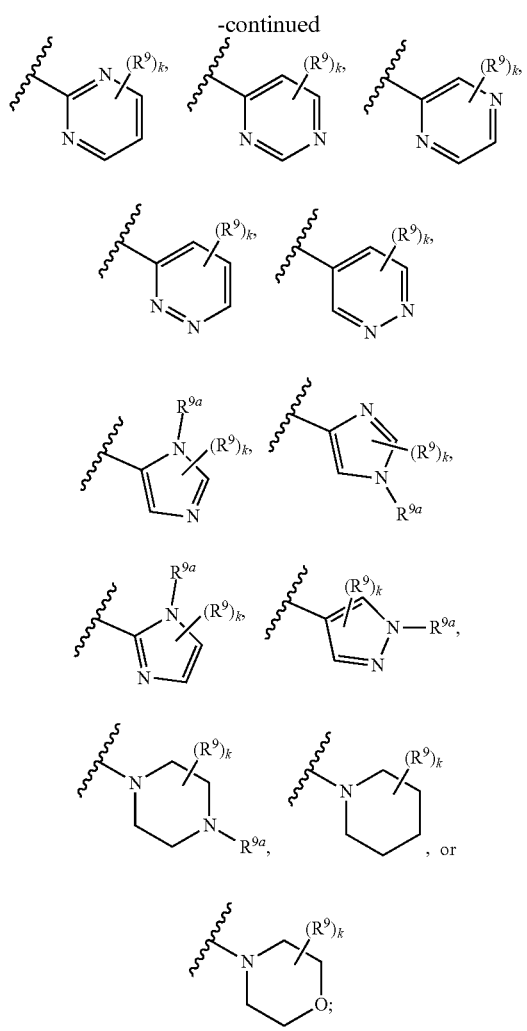

and
each $R^9$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, —NO$_2$, —CN, —OR$^{9a}$, —N(R$^{9a}$)$_2$, —S(=O)$_2$R$^{9a}$, —S(=O)$_2$OR$^{9a}$, or —S(=O)$_2$N(R$^{9a}$)$_2$, wherein each R$^{9a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaralkyl, optionally substituted acyl, an oxygen protecting group when attached to an oxygen atom, or a nitrogen protecting group when attached to a nitrogen atom, or two R$^{9a}$ are joined to form an optionally substituted heteroaryl or optionally substituted heterocyclic ring.

3. The compound of claim 1, wherein R$^1$ is optionally substituted alkyl.

4. The compound of claim 1, wherein k is 0 or 1.

5. The compound of claim 4, wherein R$^9$ is halogen, optionally substituted C$_{1-6}$ alkyl, or —OR$^{9a}$.

6. The compound of claim 1, wherein m is 0 or 1.

7. The compound of claim 1, wherein p is 0 or 1.

8. The compound of claim 1, wherein the compound is of formula:

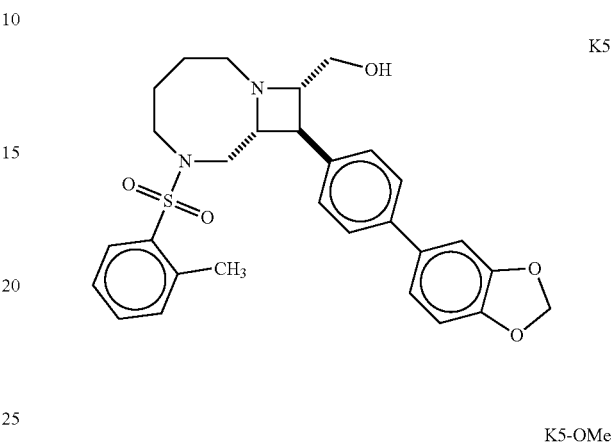

K5

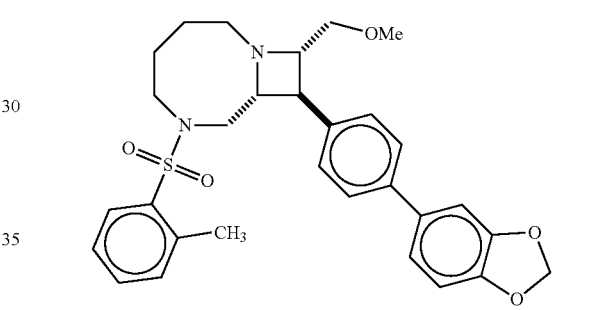

K5-OMe

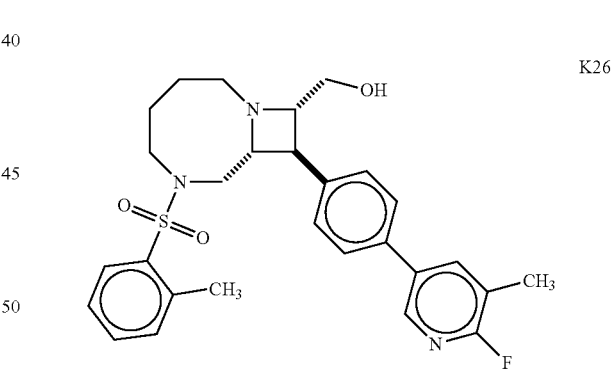

K26

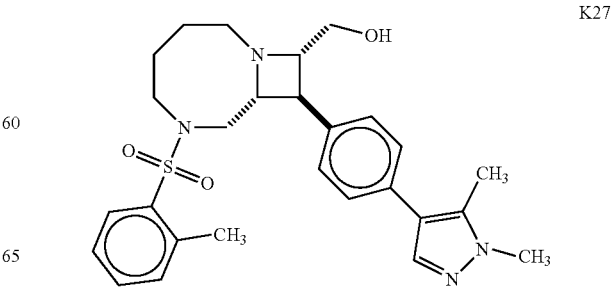

K27

-continued

K26-OMe

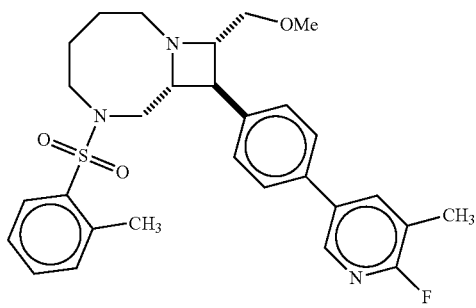

K27-OMe

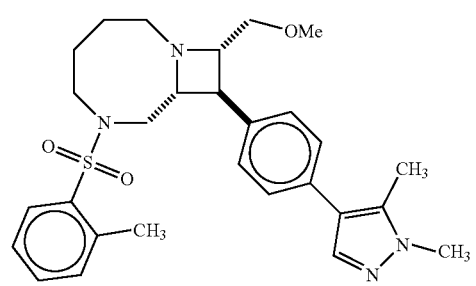

B4

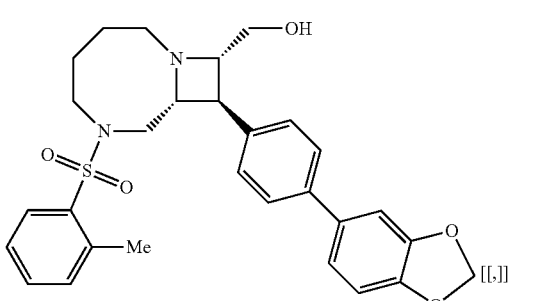

[[,]]

B4-OMe

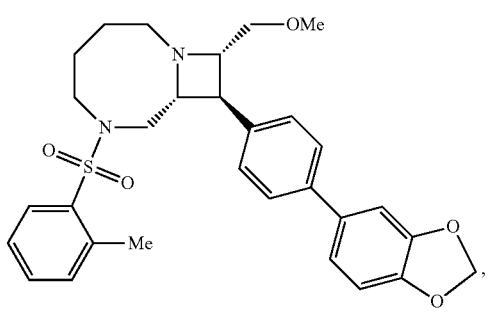

or a pharmaceutically acceptable salt, solvate, hydrate, polymorph, co-crystal, tautomer, stereoisomer, or isotopically labeled derivative thereof.

9. A pharmaceutical composition comprising a compound of claim 1, or a pharmaceutically acceptable salt, solvate, hydrate, polymorph, co-crystal, tautomer, stereoisomer, or isotopically labeled derivative thereof, and a pharmaceutically acceptable excipient.

10. A method of treating a metabolic disorder associated with insulin-degrading enzyme comprising administering a therapeutically effective amount of a compound of claim 1, or pharmaceutically acceptable salt, solvate, hydrate, polymorph, co-crystal, tautomer, stereoisomer, or isotopically labeled derivative thereof, to a subject with the metabolic disorder.

11. The compound of claim 1, wherein the compound is of Formula (I):

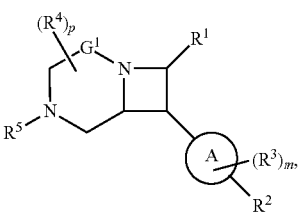

(I)

or a pharmaceutically acceptable salt thereof.

12. The compound of claim 1, wherein $R^1$ is $CH_2OR^{1a}$.

13. The compound of claim 1, wherein $R^5$ is of formula:

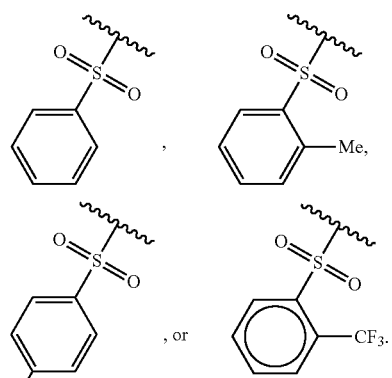

14. The compound of claim 1, wherein $R^5$ is

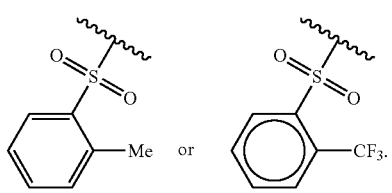

15. A compound of formula:

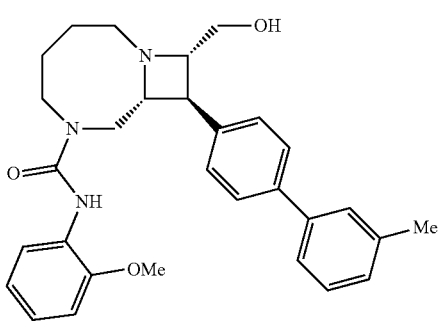

154

-continued
154-OMe
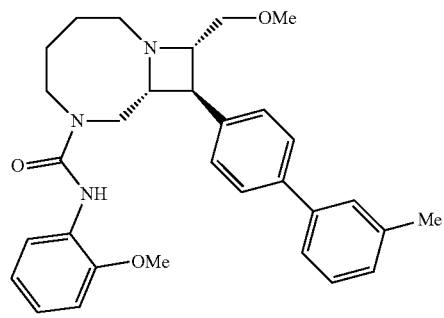
073
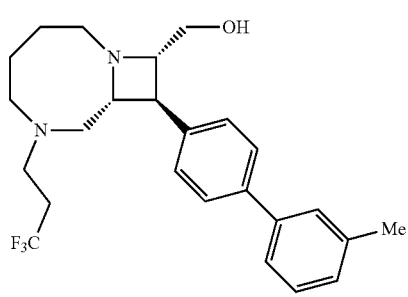
073-OMe
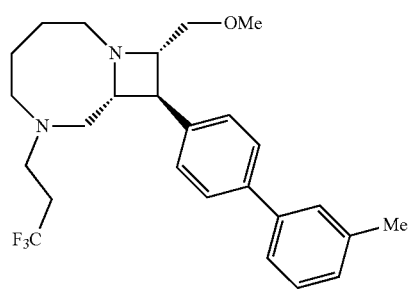
529
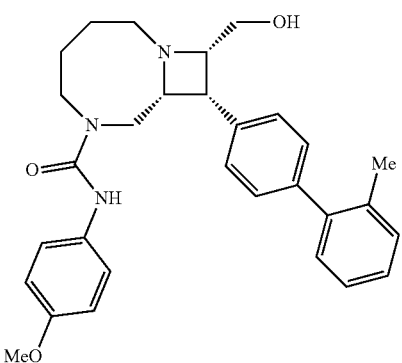
-continued
529-OMe
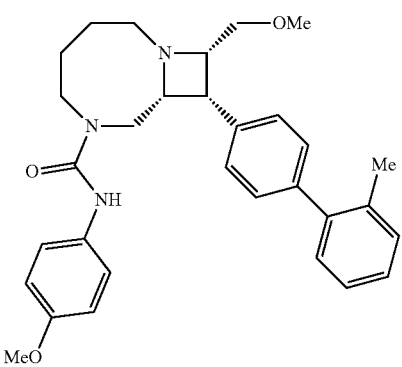
688
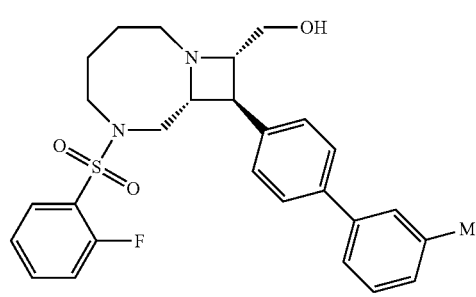
688-OMe
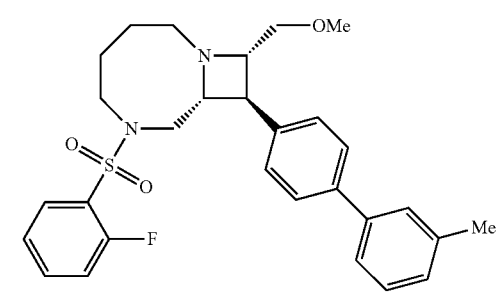
217-OMe
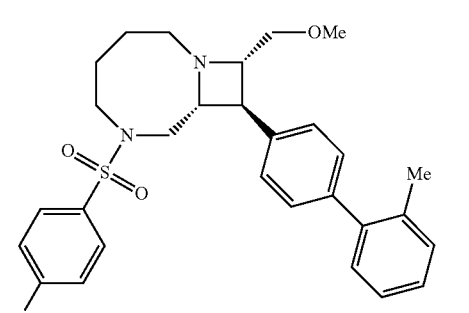
217
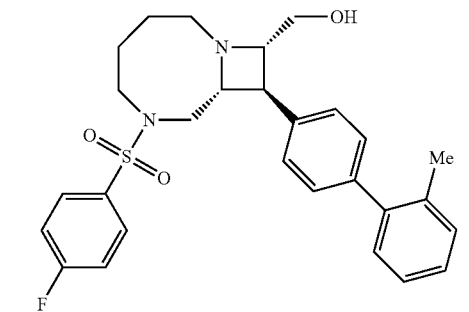

| | |
|---|---|
| 416 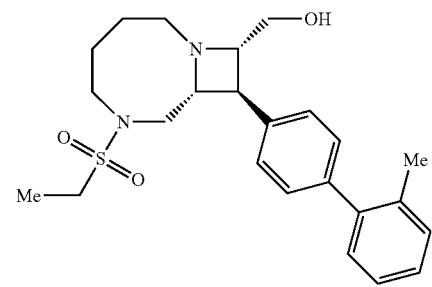 | 297-OMe 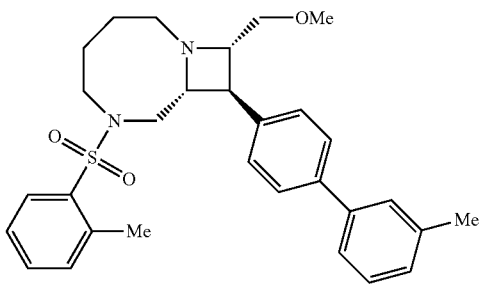 |
| 795 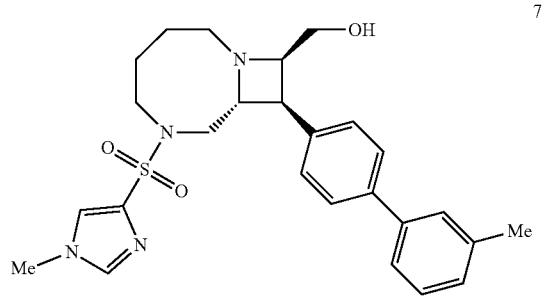 | 591-OMe 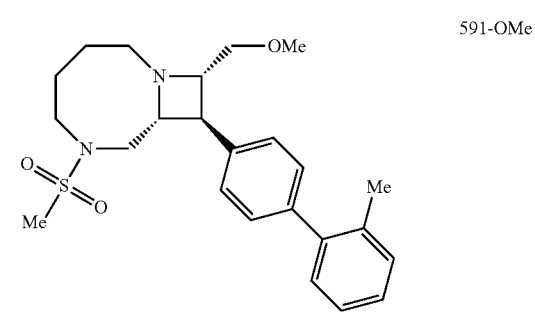 |
| 416-OMe 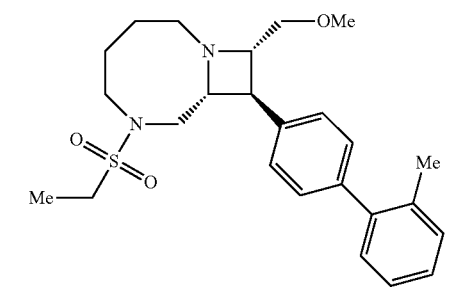 | 868 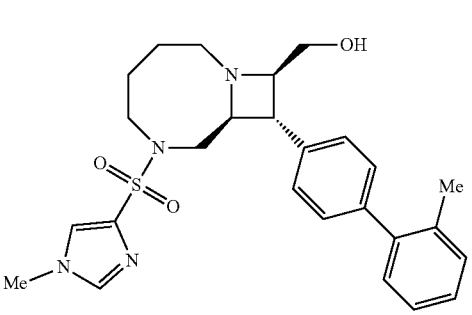 |
| 795-OMe 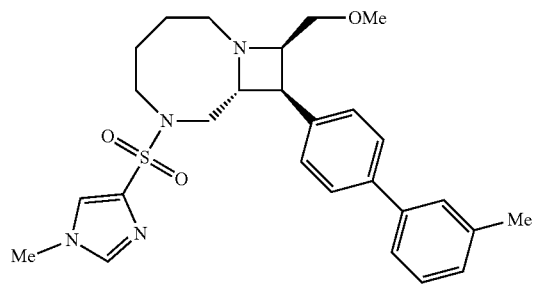 | 342 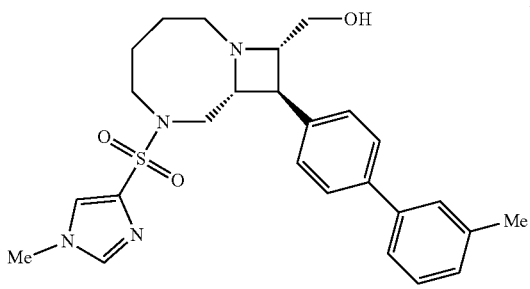 |
| 591 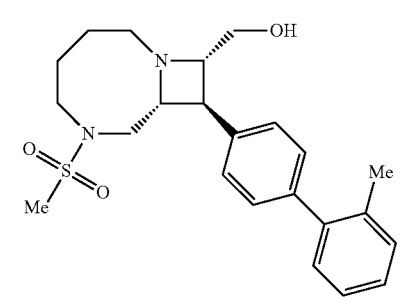 | 868-OMe 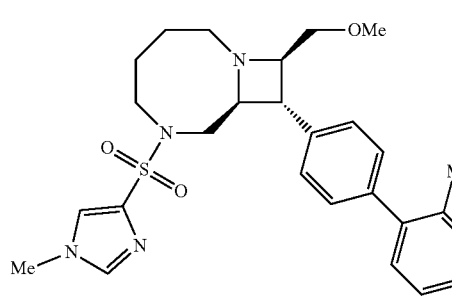 |

-continued
342-OMe
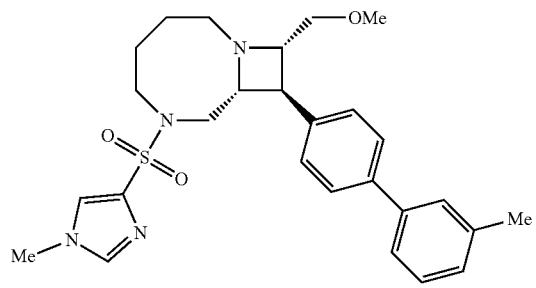
807
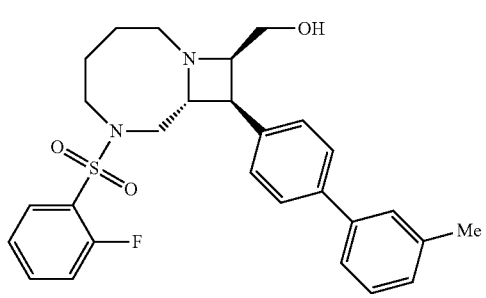
945
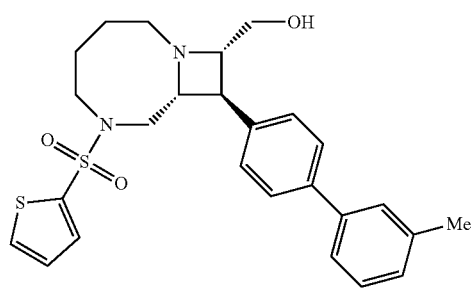
807-OMe
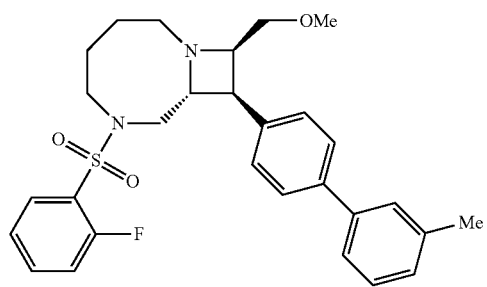
945-OMe
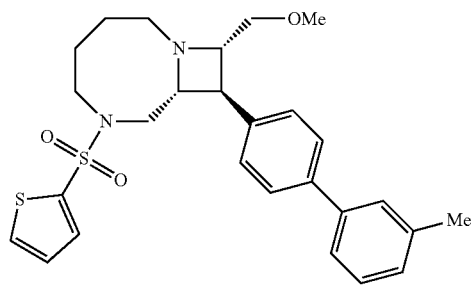
-continued
496-OMe
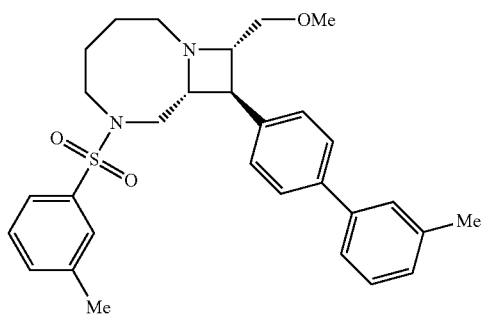
736
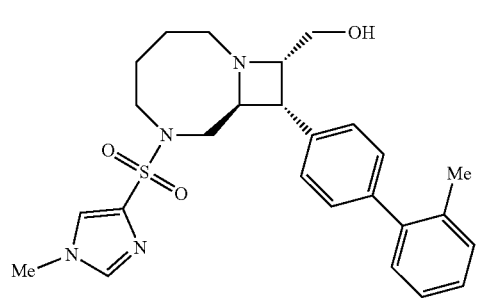
736-OMe
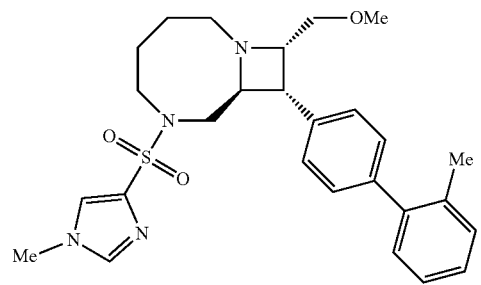
985-OMe
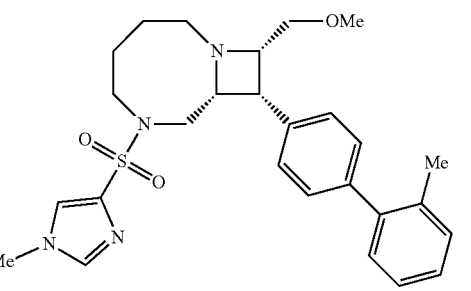
985
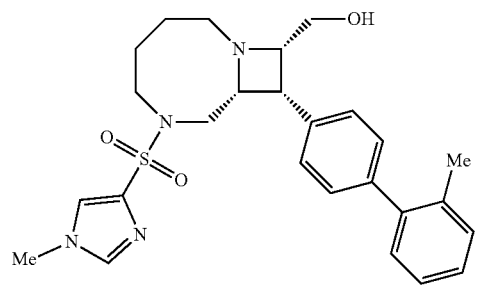

575
-continued
396
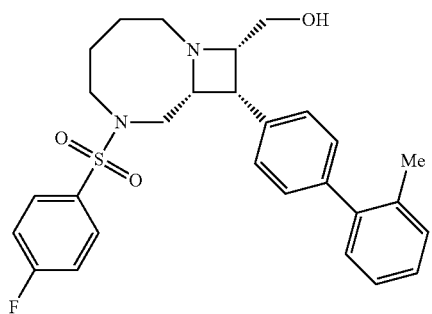
236
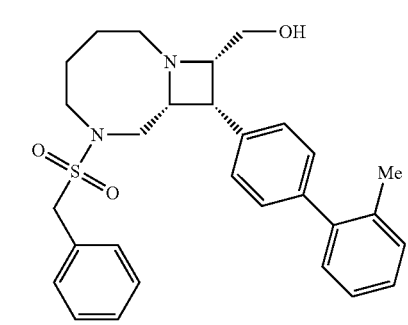
396-OMe
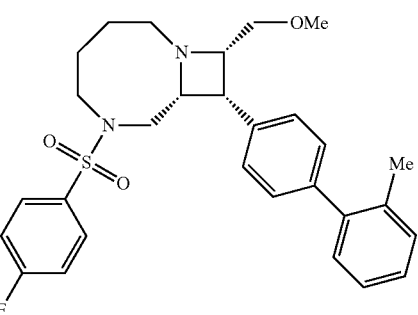
236-OMe
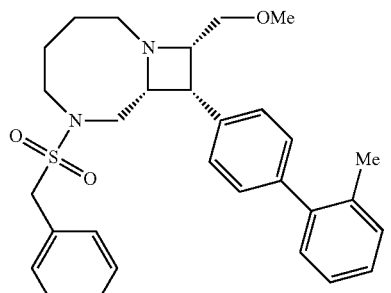
077
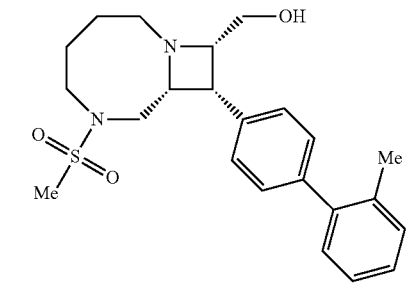
576
-continued
077-OMe
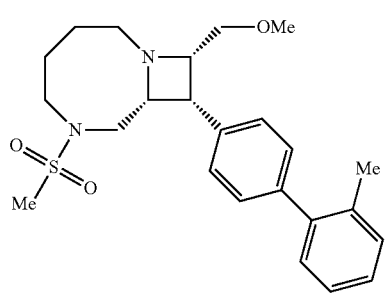
983
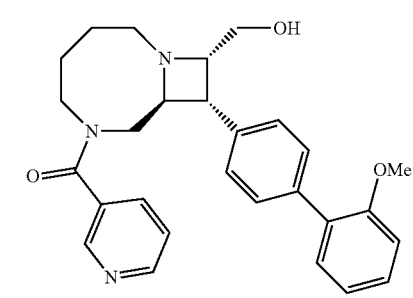
983-OMe
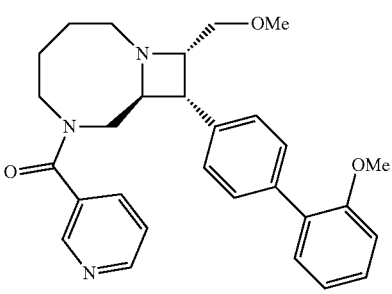
439
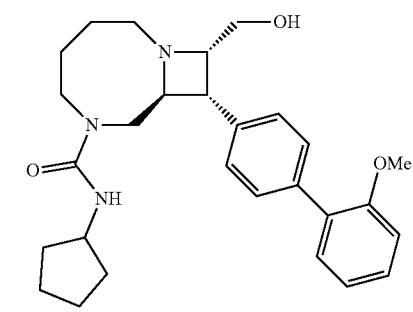
439-OMe
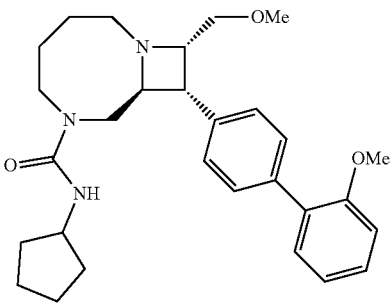

586-OMe
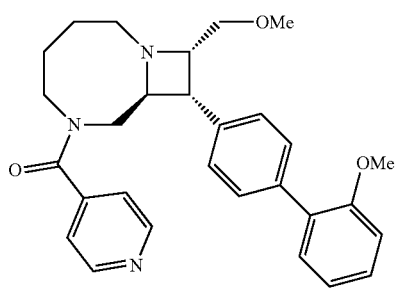
586
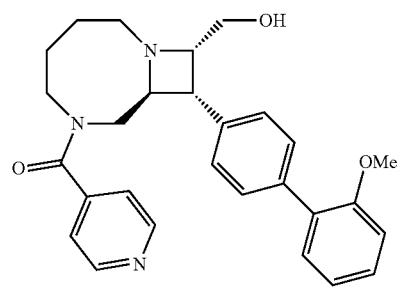
K2
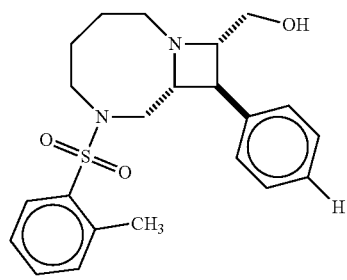
K3
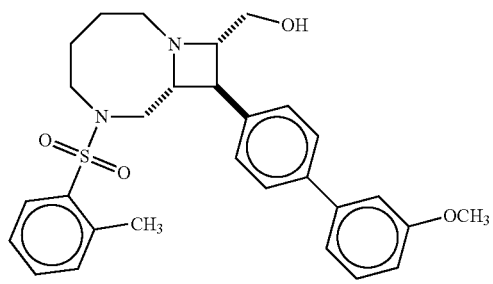
K2-OMe
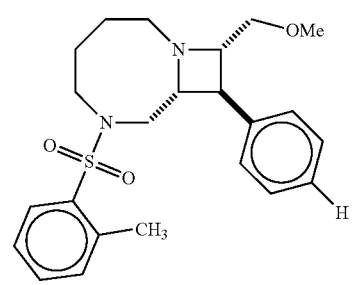
K3-OMe
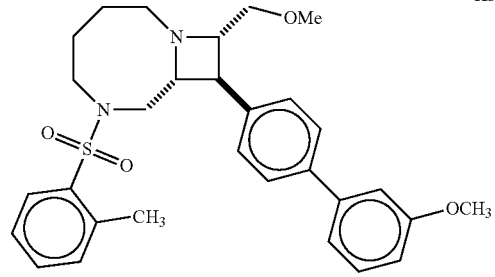
K4
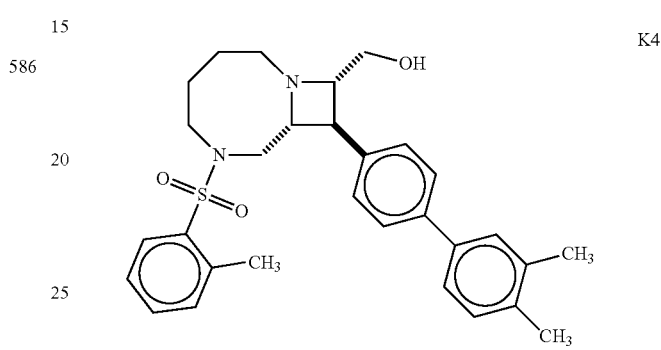
K4-OMe
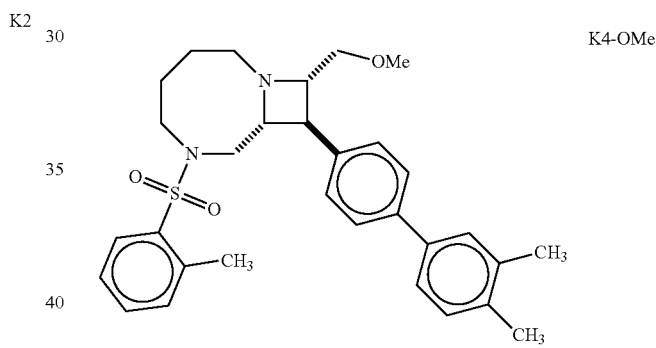
K6
K7

K6-OMe
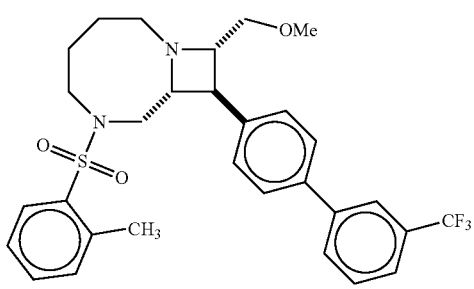
K7-OMe
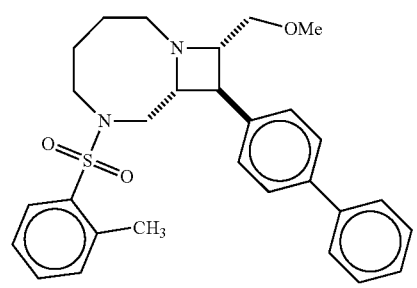
K8
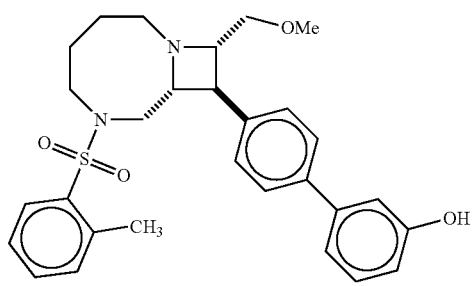
K8-OMe
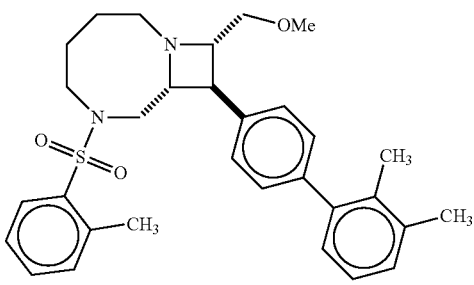
K9-OMe
K9
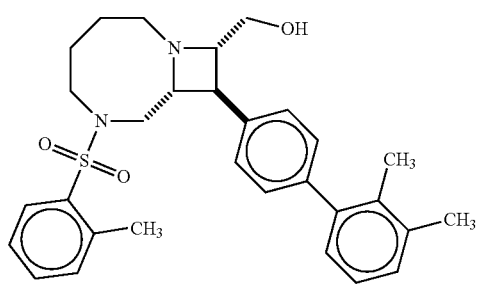
K10
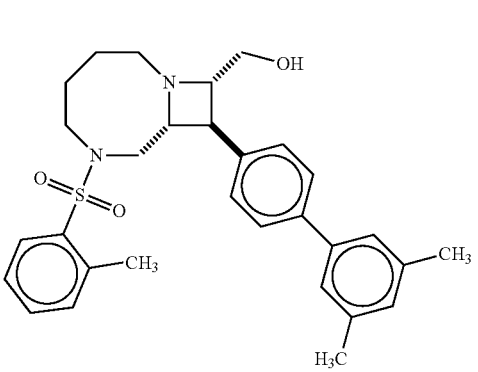
K10-OMe
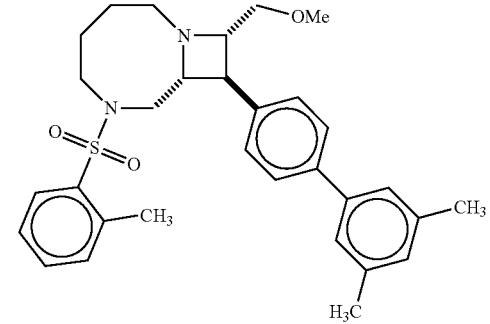
K11
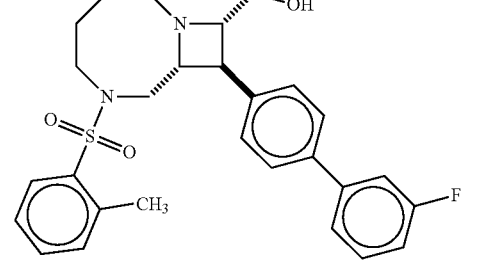
K11-OMe
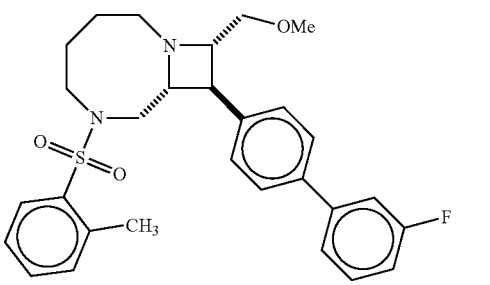

-continued
K12
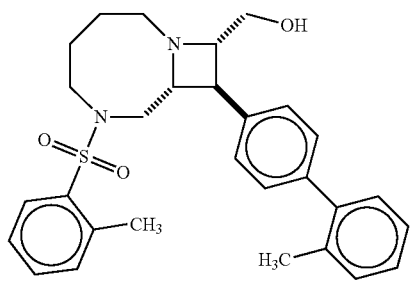
K15
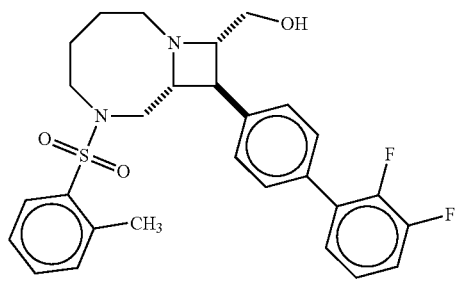
K13
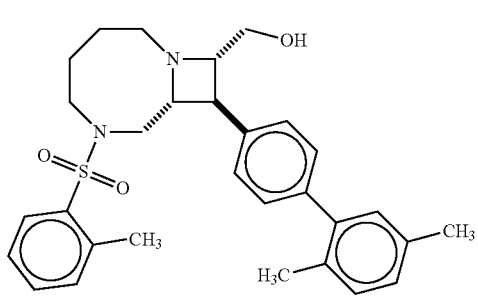
K14-OMe
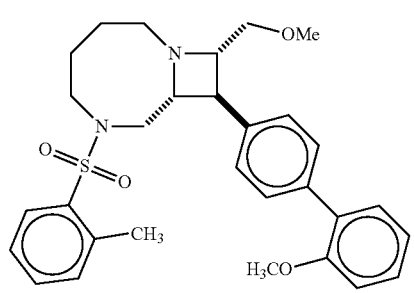
K12-OMe
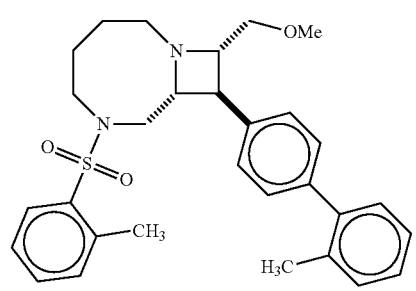
K15-OMe
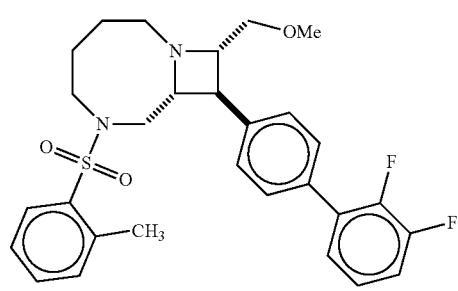
K13-OMe
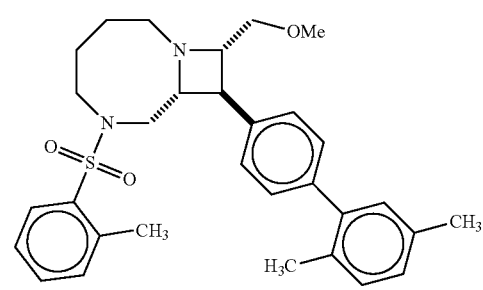
K16
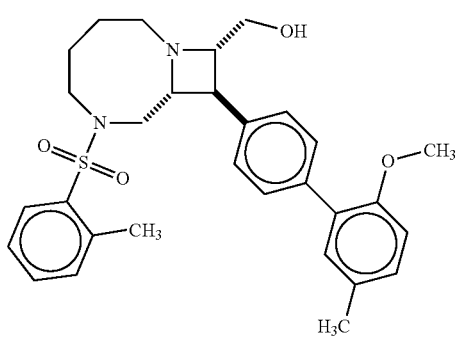
K14
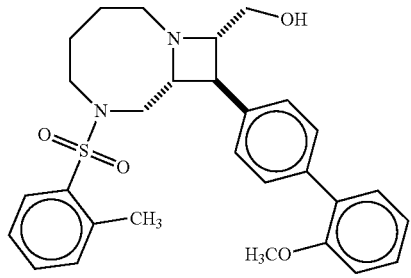
K17
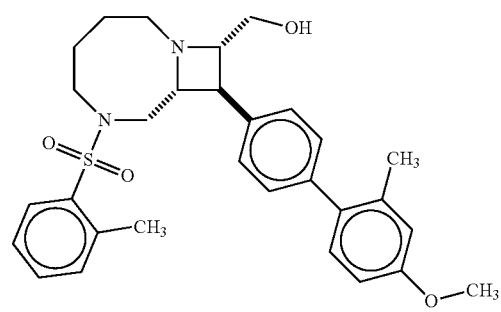

K16-OMe
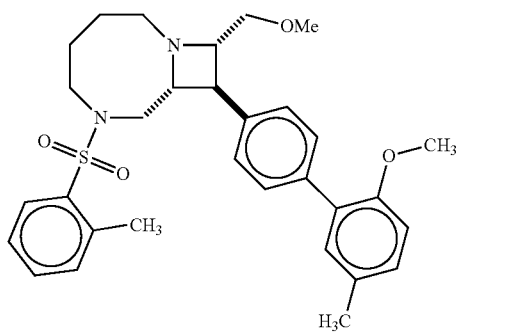
K17-OMe
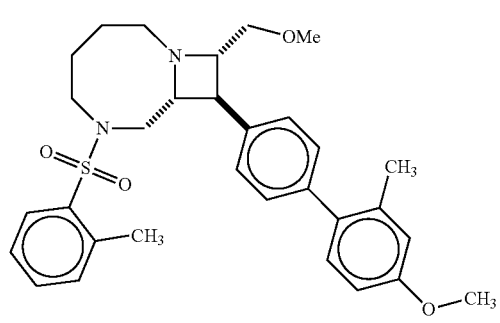
K18
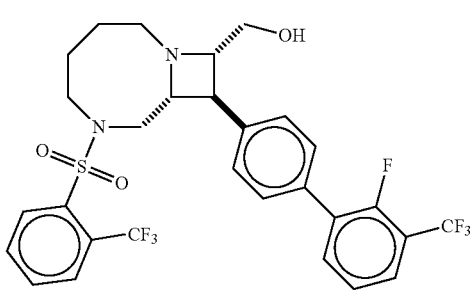
K19
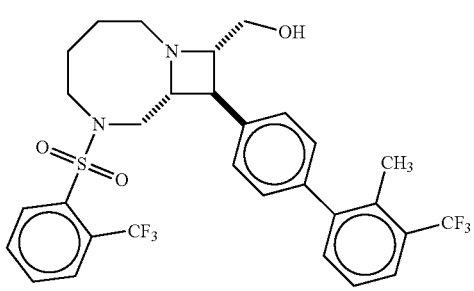
K18-OMe
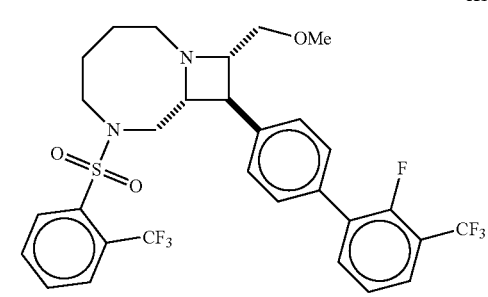
K19-OMe
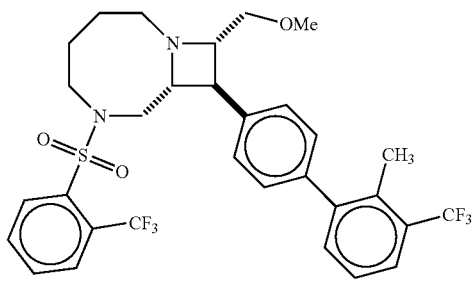
K20
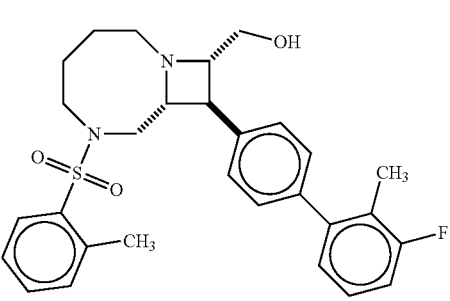
K20-OMe
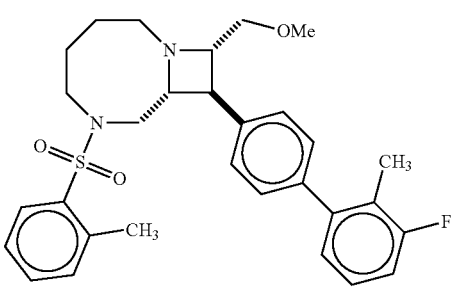
K23
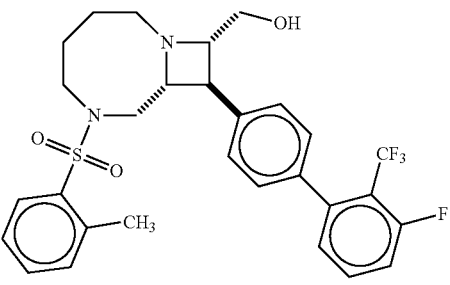
K23-OMe
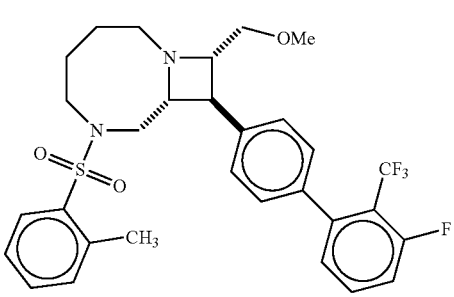

K24
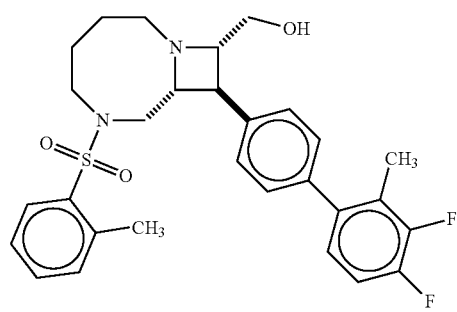
K24-OMe
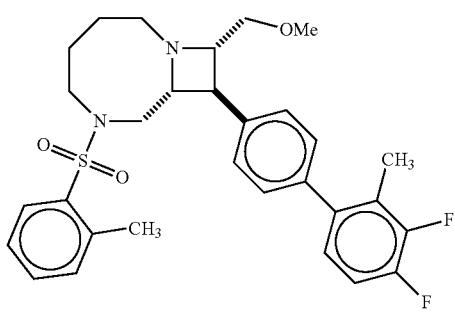
K25-OMe
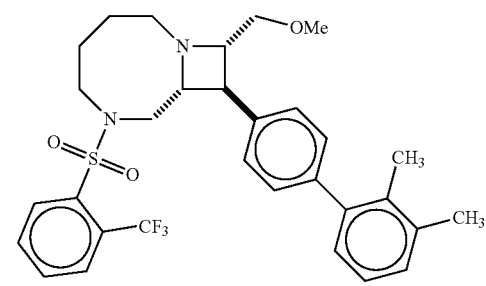
K25
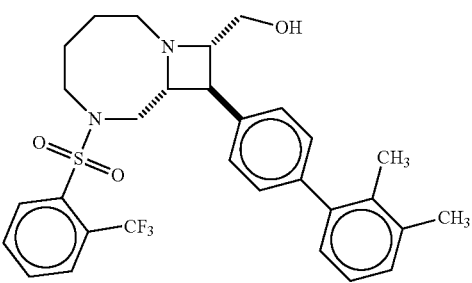
K28
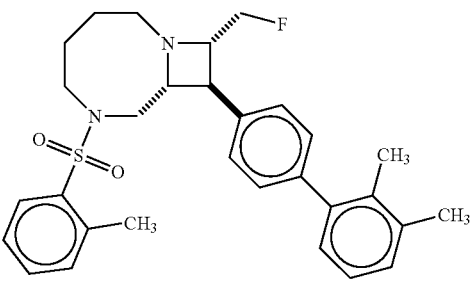
K29
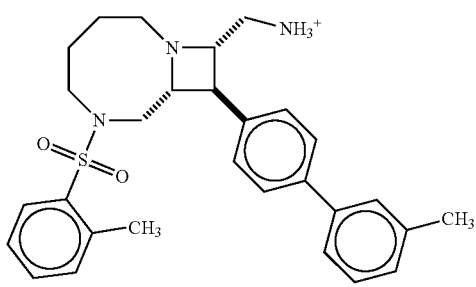
JP-17
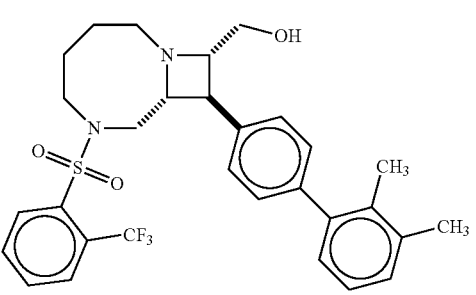
JP-17-OMe
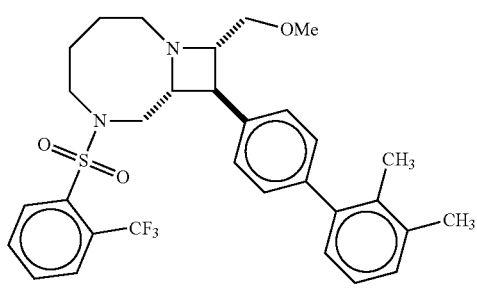
JP-17-NHMe
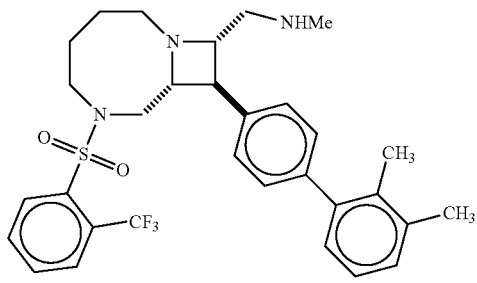
JP-17-CO$_2$H
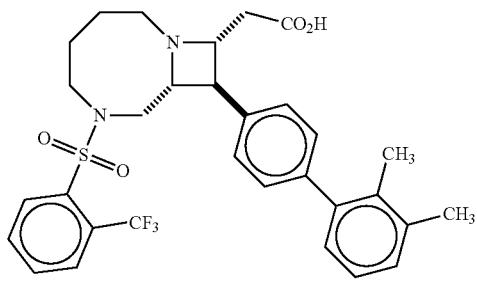

-continued
JP-17-DMA
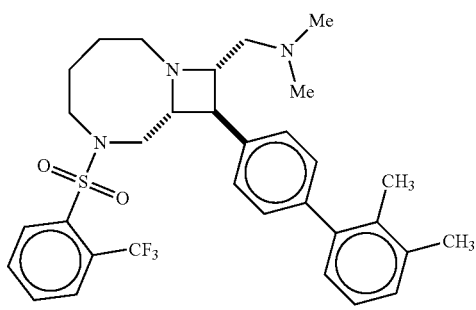
JP-18
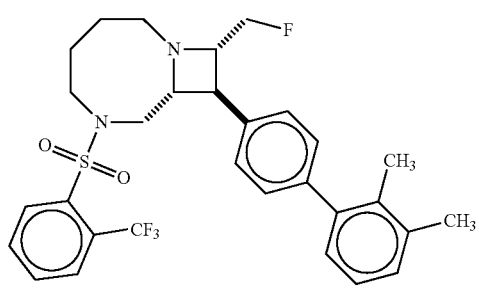
JP-18 TFA salt
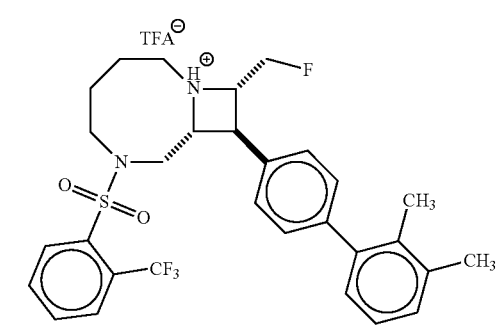
JP-8
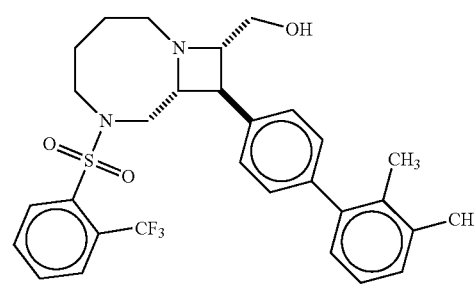
JP-8-OMe
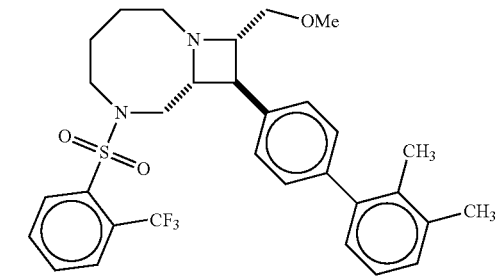
-continued
JP-8N
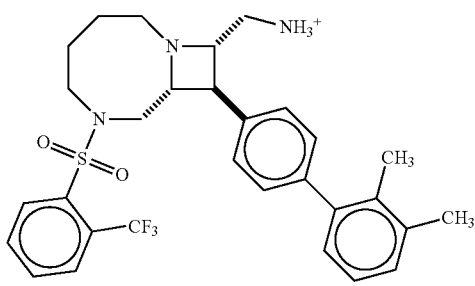
JP-S2
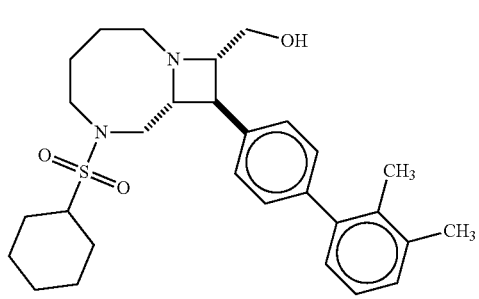
JP-S4
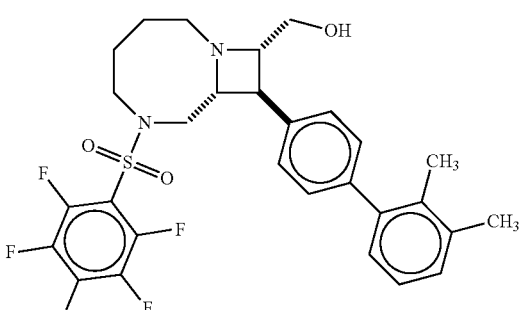
JP-S2-OMe
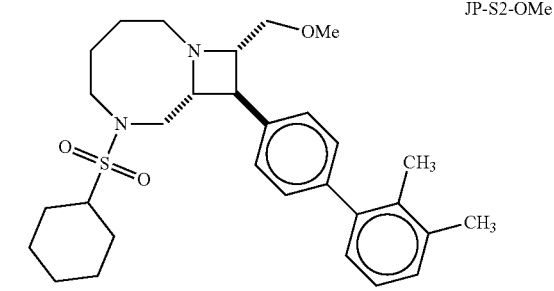
JP-S4-OMe
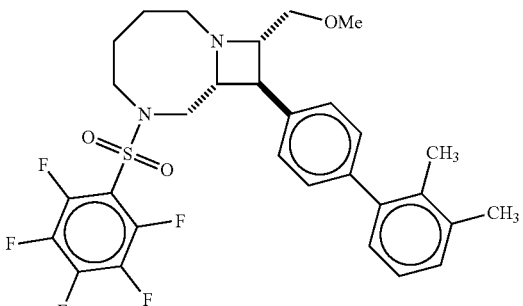

JP-S5
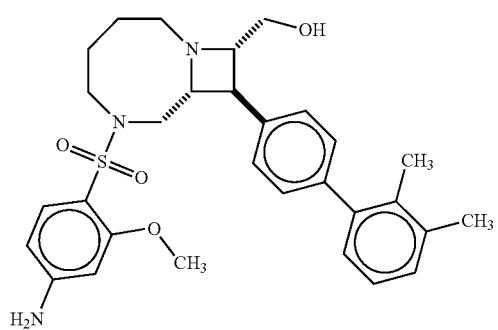
JP-S7
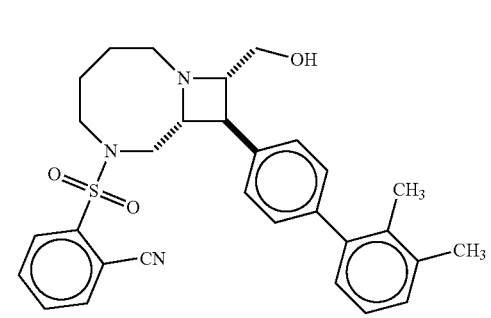
JP-S5-OMe
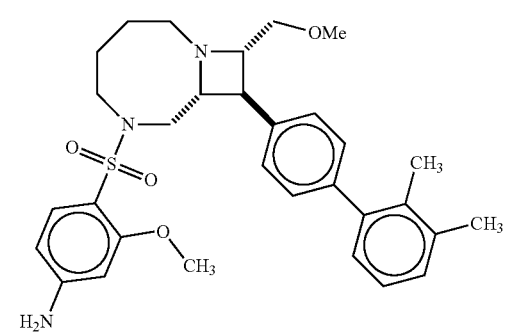
JP-S7-OMe
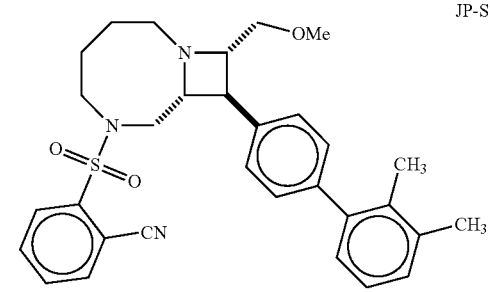
JP-S10
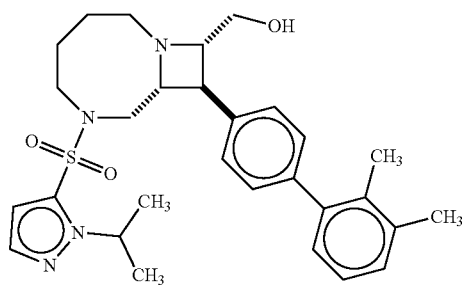
JP-S11
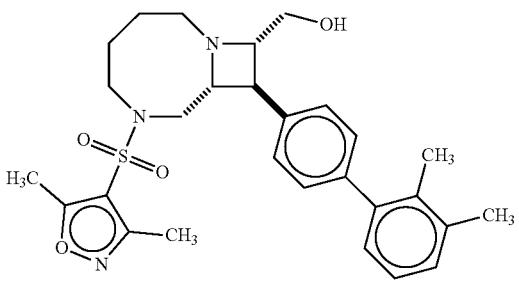
JP-S10-OMe
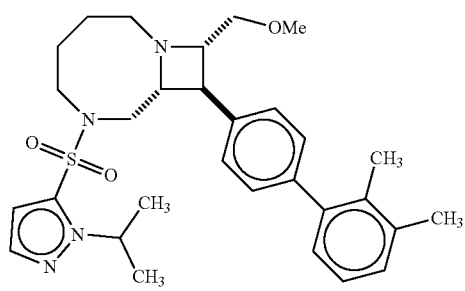
JP-S11-OMe
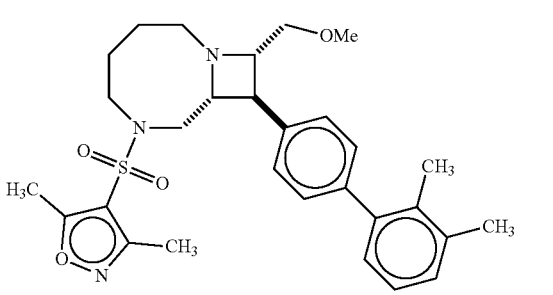
JP-S12
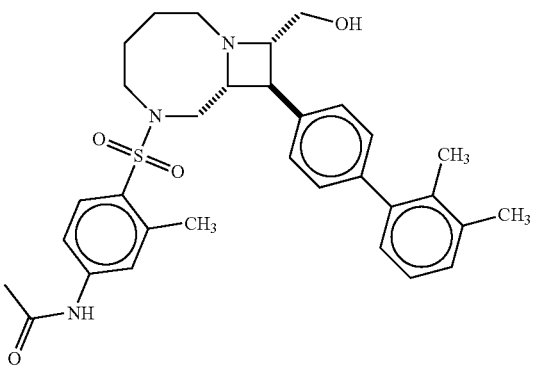

JP-S13
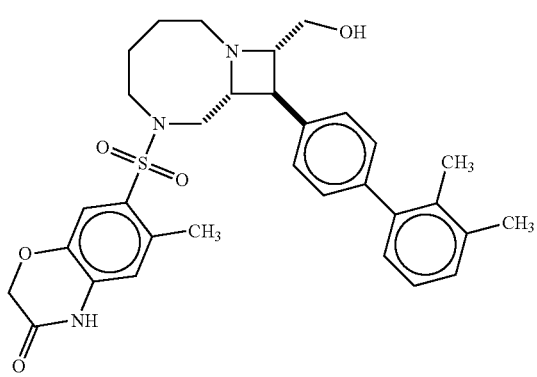
JP-S14
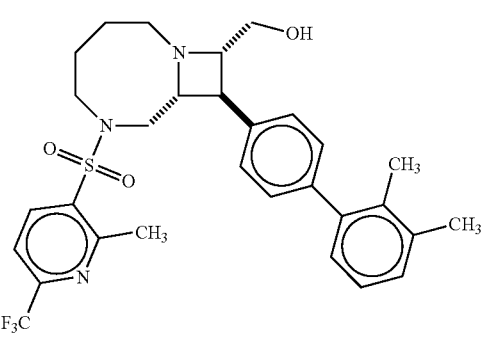
JP-S12-OMe
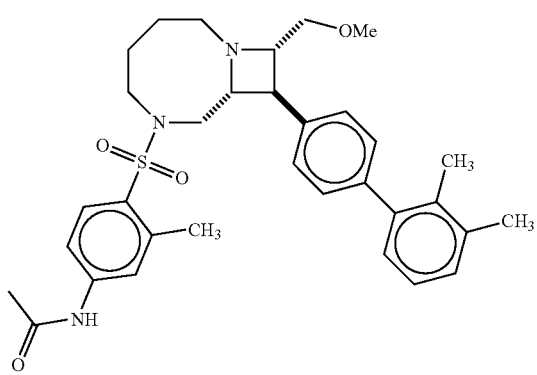
JP-S15-OMe
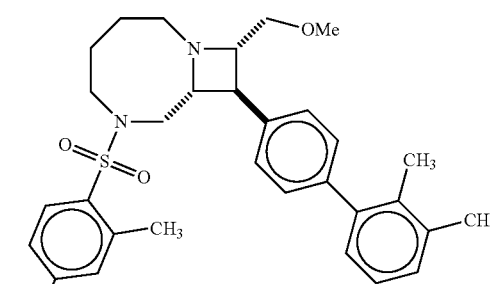
JP-S13-OMe
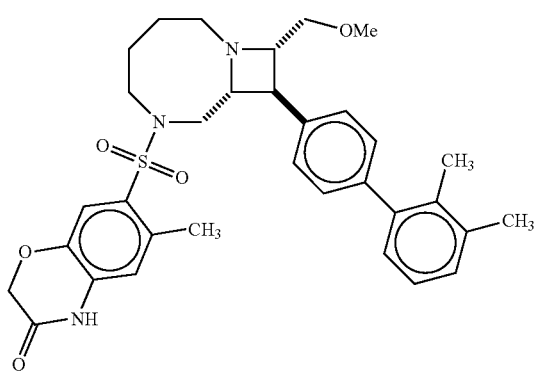
JP-S14-OMe
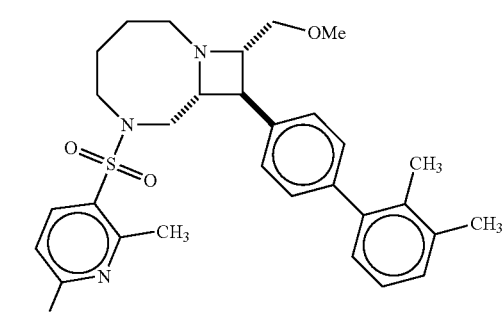
JP-S15
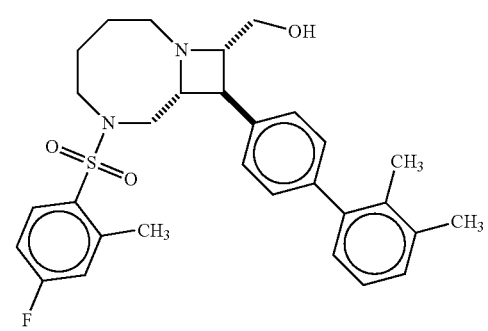
JP-S16-2H
JP-S16-2H-OMe
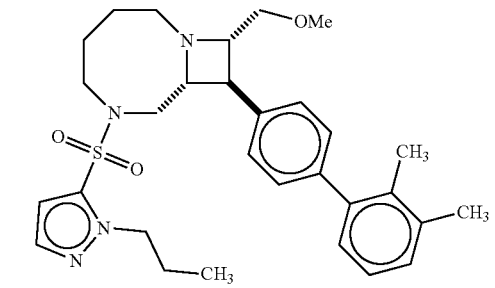

JP-S18-H2
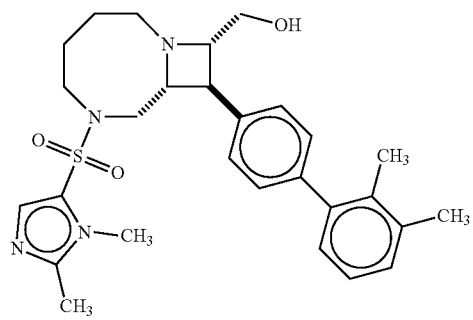
JP-S23
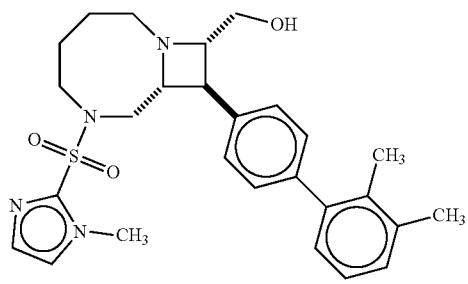
JP-S18-H2-OMe
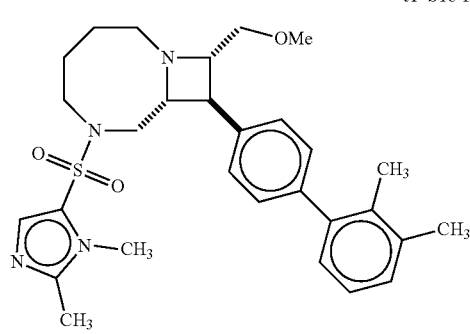
JP-S22-OMe
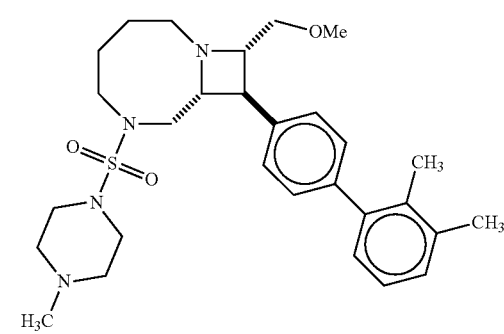
JP-S21-diMe
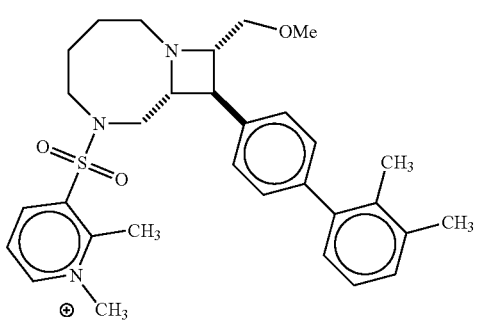
JP-S23-OMe
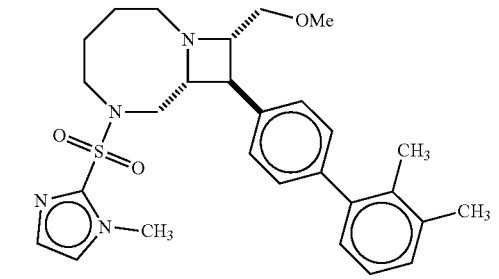
BRD-297-OMe
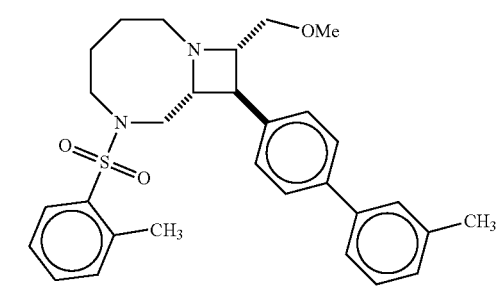
JP-S22
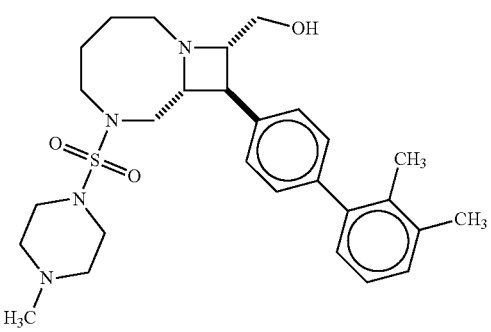
JP-S24
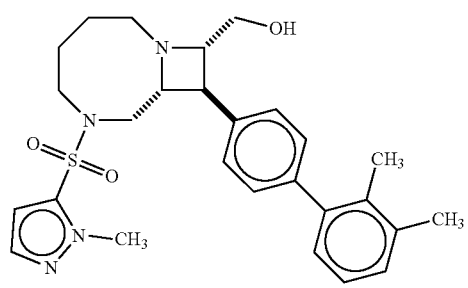

BRD-298
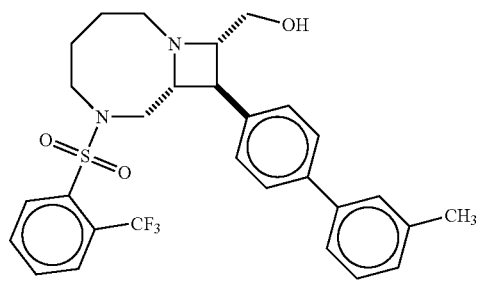
JP-S25-OMe
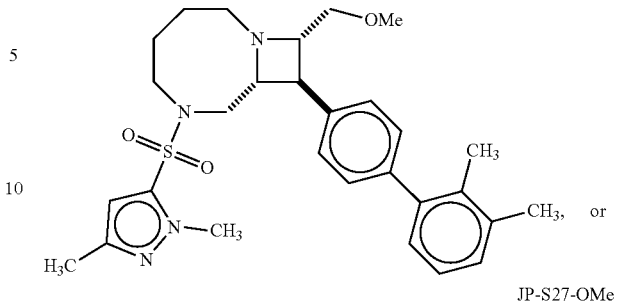
or
JP-S24-OMe
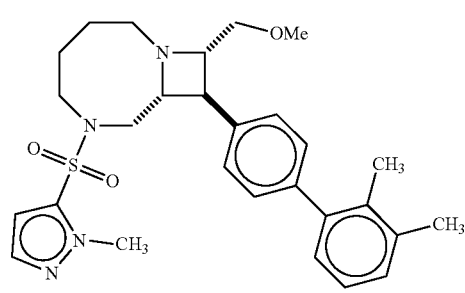
JP-S27-OMe
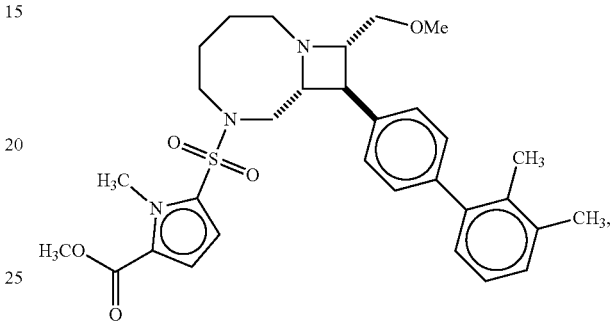
BRD-298-OMe
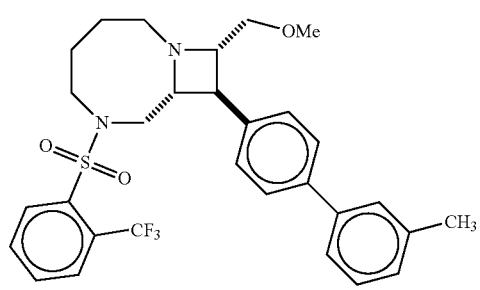
JP-29-OMe
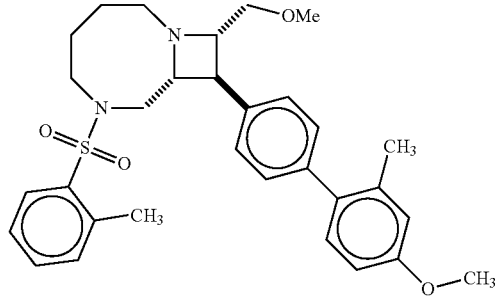
JP-S25
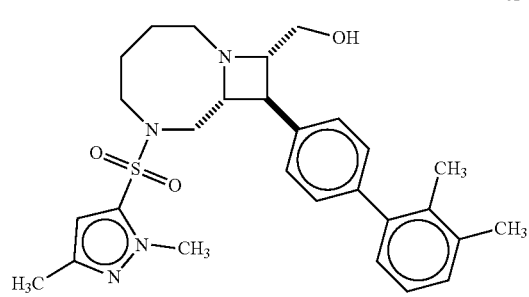
JP-29
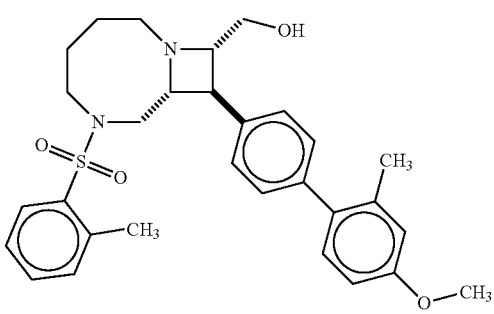
JP-S27
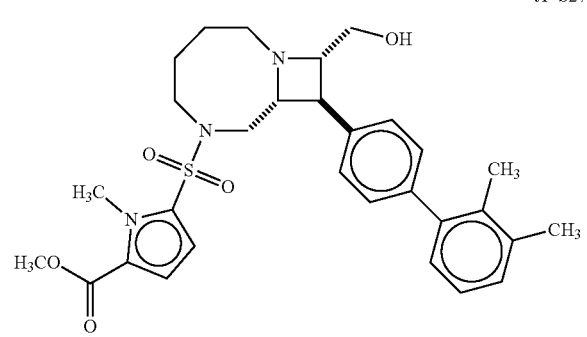
JP-30a
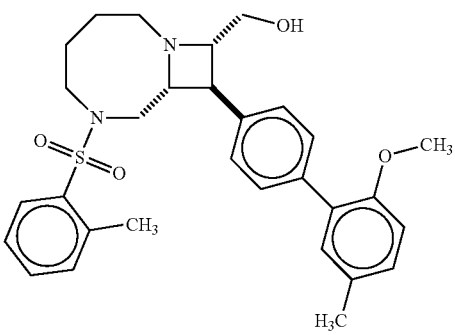

-continued
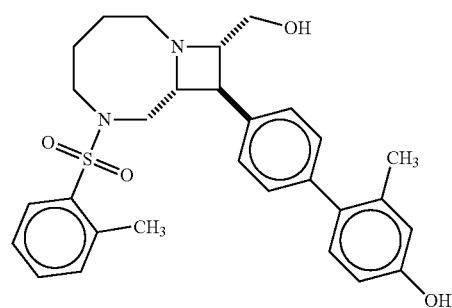
JP-31
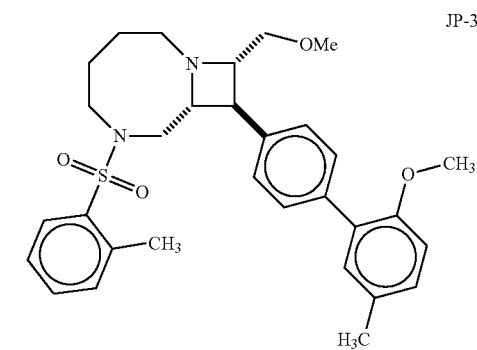
JP-30a-OMe
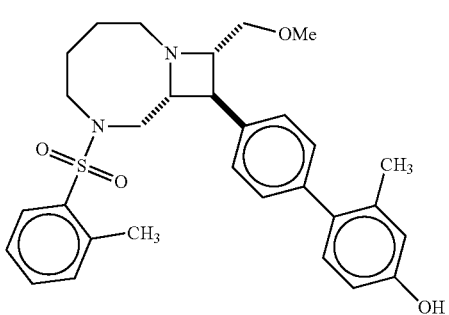
JP-31-OMe
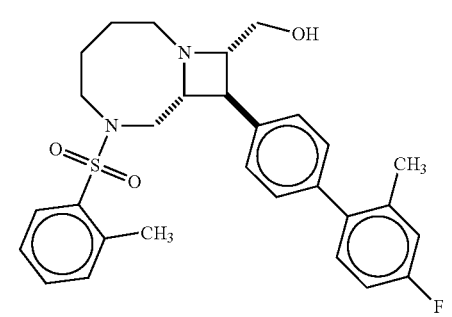
JP-39
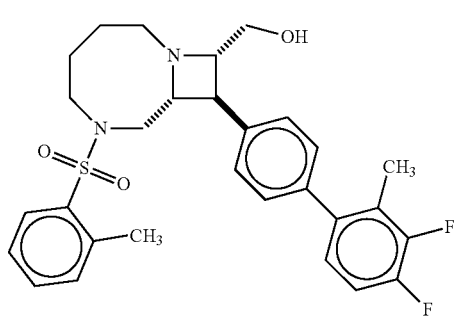
JP-40
-continued
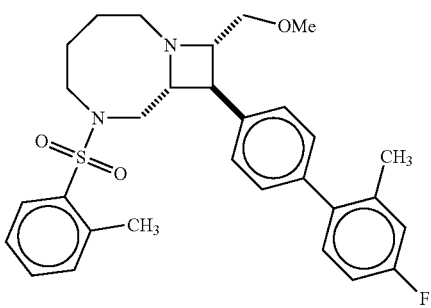
JP-39-OMe
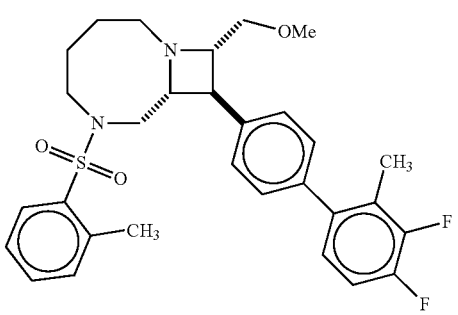
JP-40-OMe
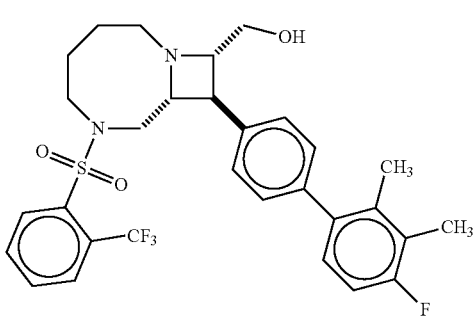
JP-41
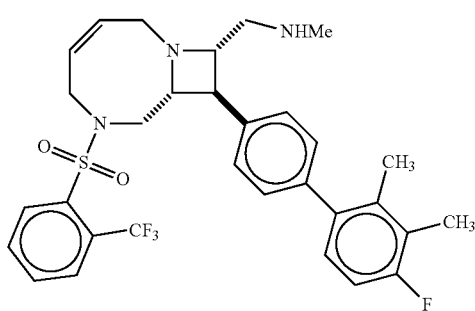
JP-41-NHMe
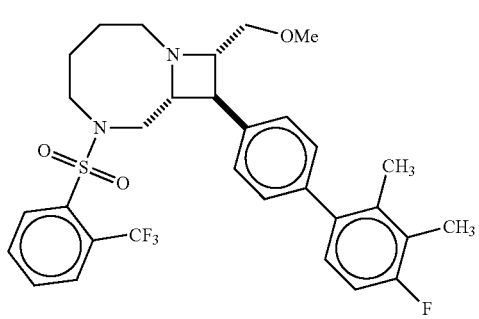
JP-41-OMe 599
-continued
JP-41-NHMe
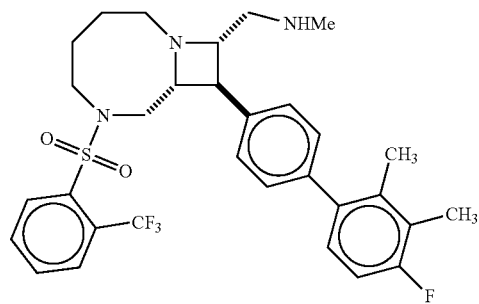
JP-42
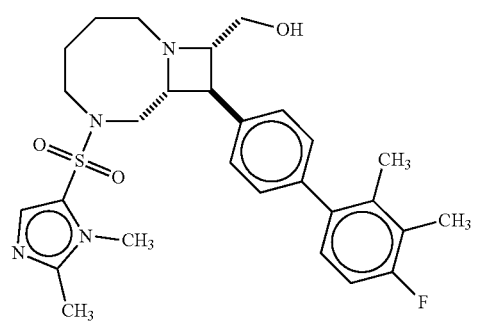
JP-43
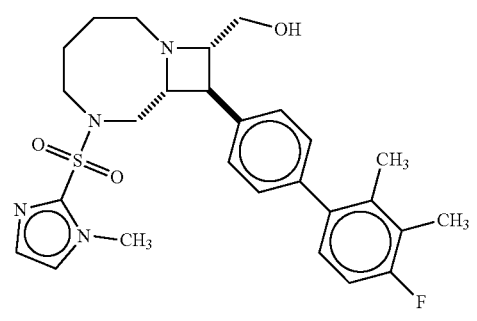
JP-42-OMe
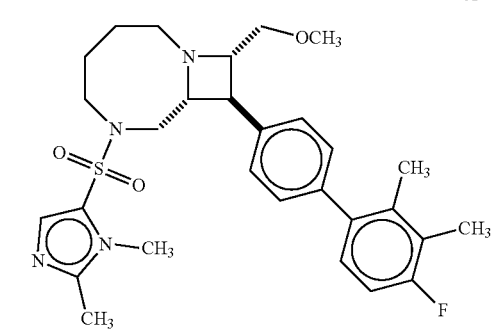
JP-43-OMe
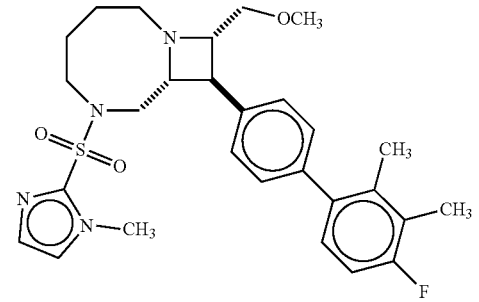
600
-continued
JP-44
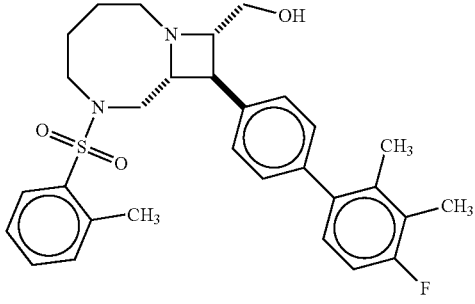
JP-44-OMe
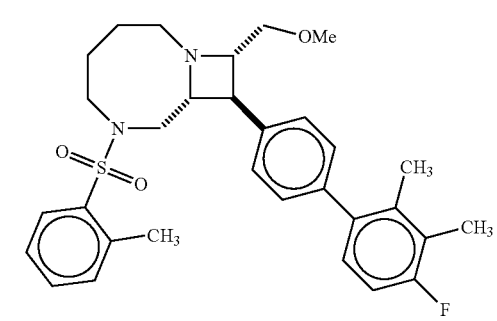
B2-OMe
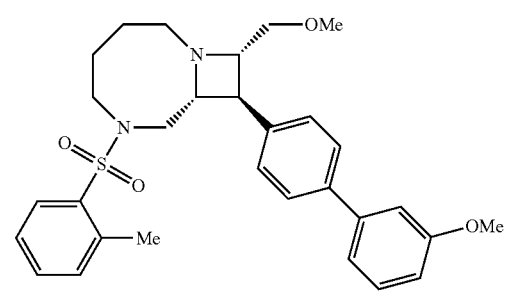
B2
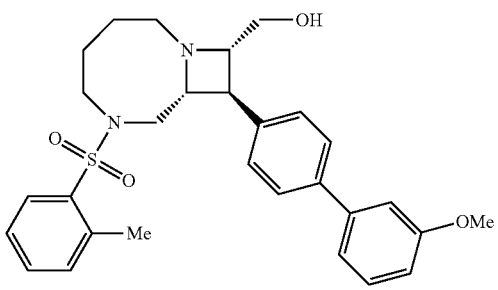
B5
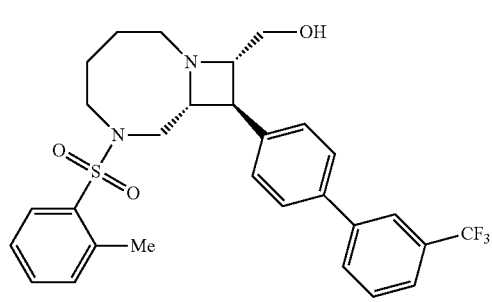

B6
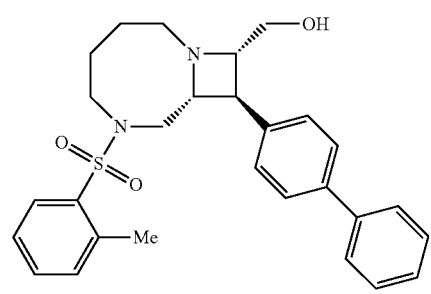
B5-OMe
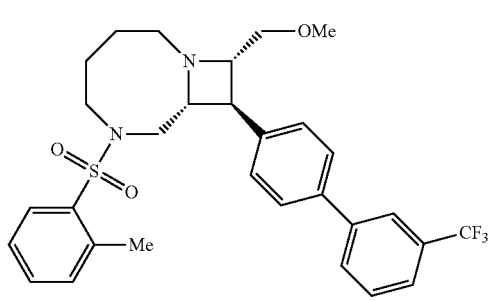
B6-OMe
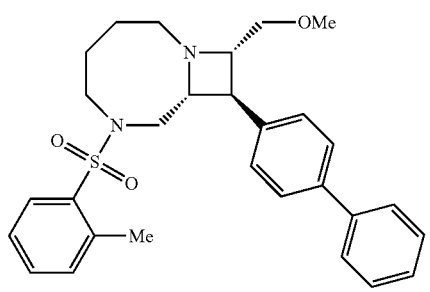
B7
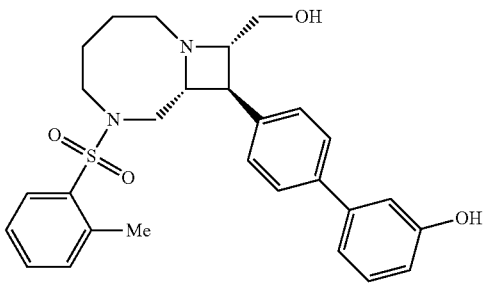
B8
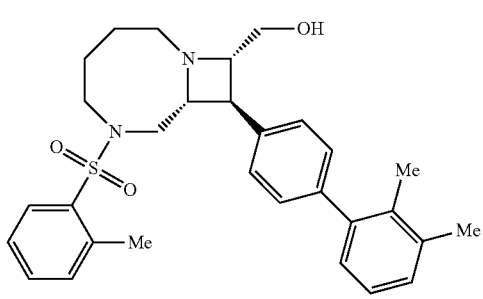
B7-OMe
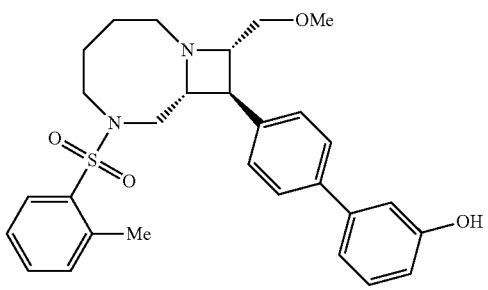
B10
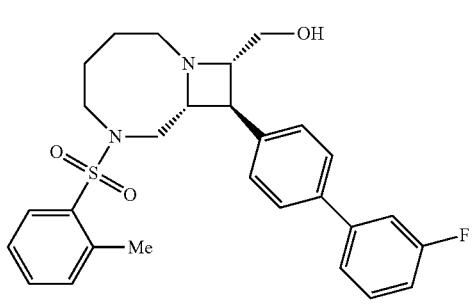
B13
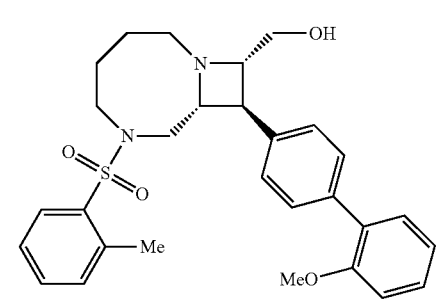
B14
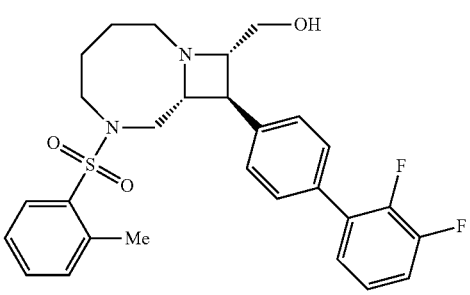
B13-OMe
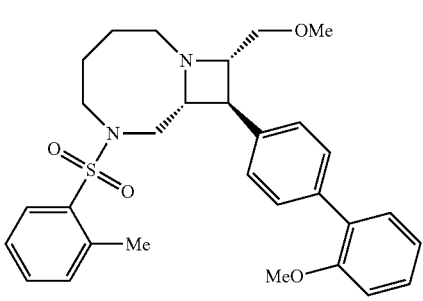

B14-OMe
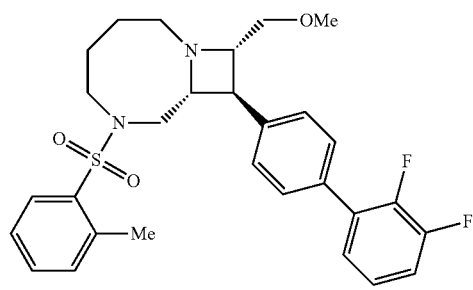
226-OMe
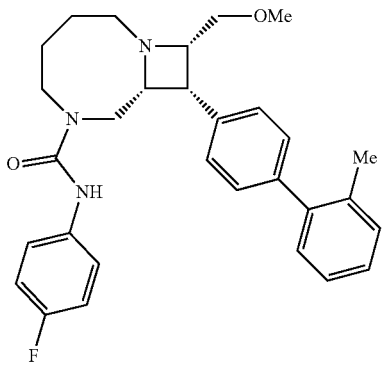
269
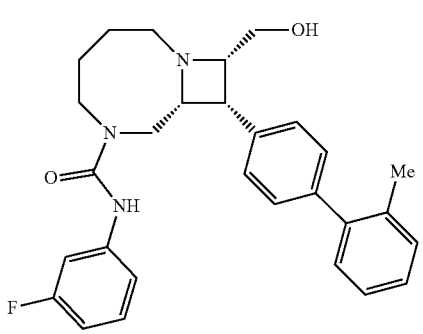
1570
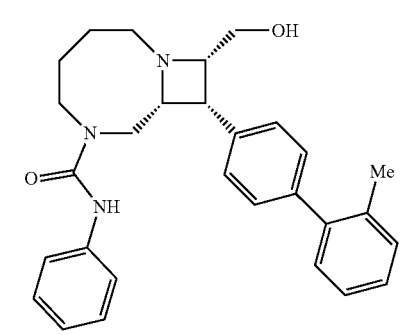
226
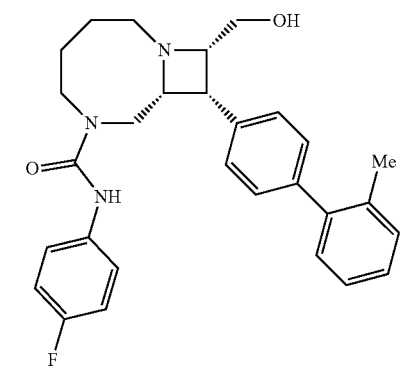
1570-OMe
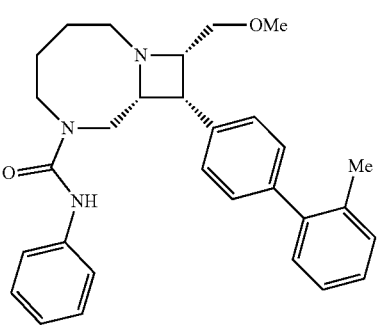
269-OMe
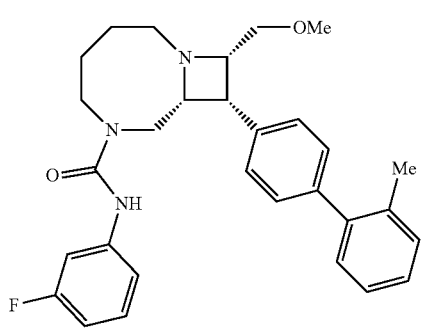
900
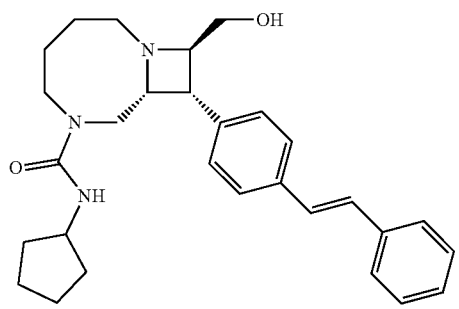

-continued
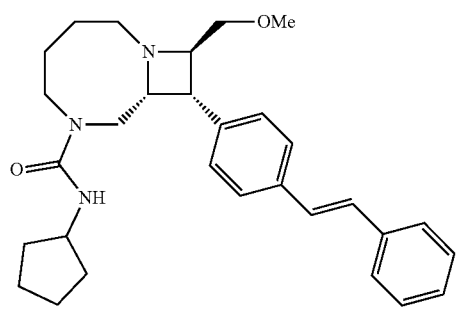
900-OMe
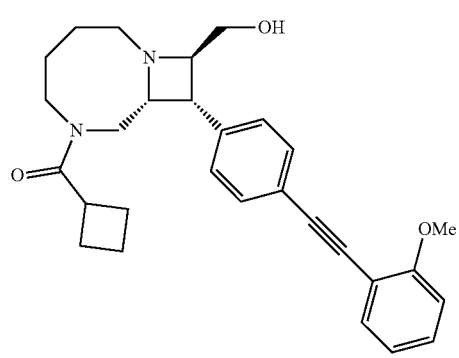
180
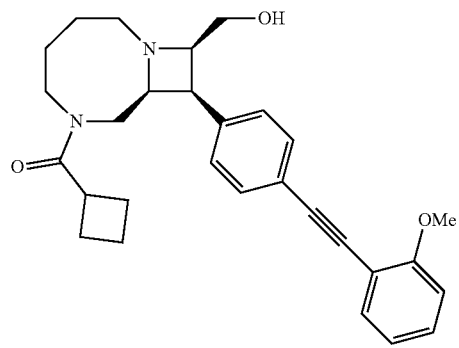
141
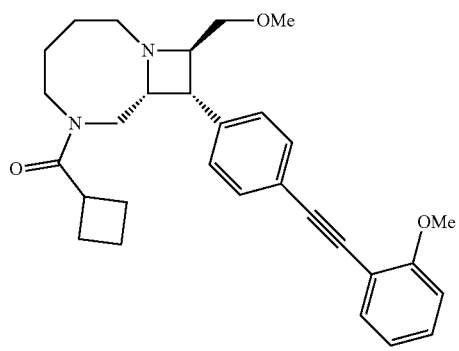
180-OMe
-continued
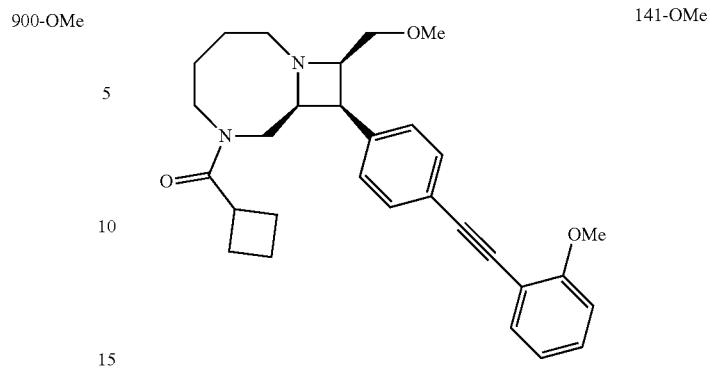
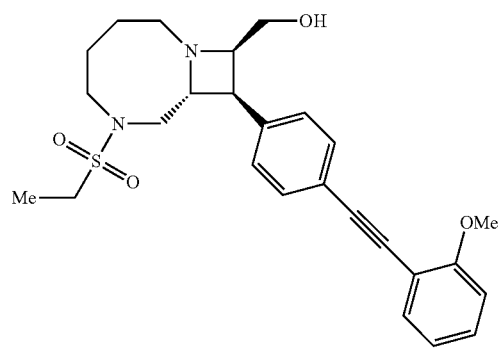

607
-continued
964-OMe
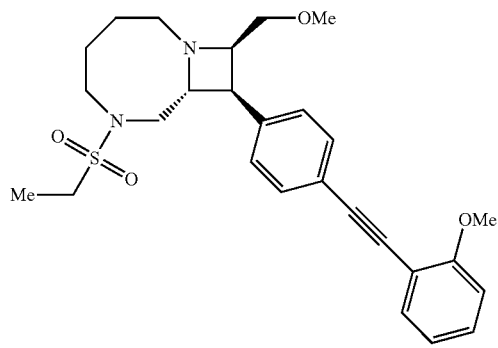
525
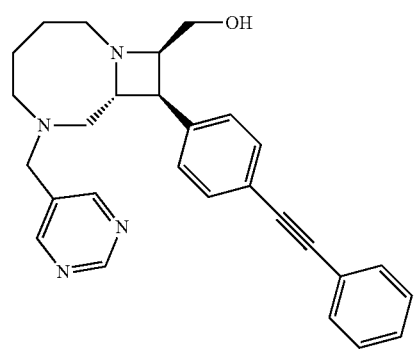
525-OMe
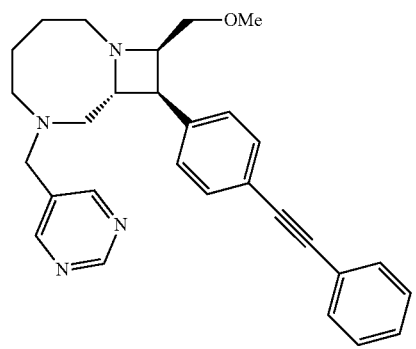
304
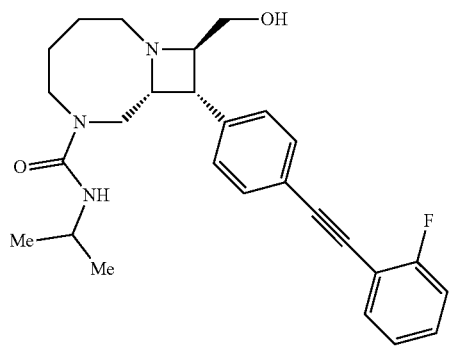
608
-continued
683
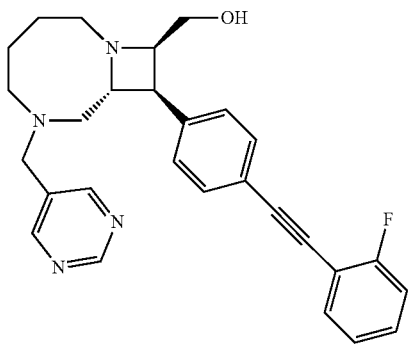
304-OMe
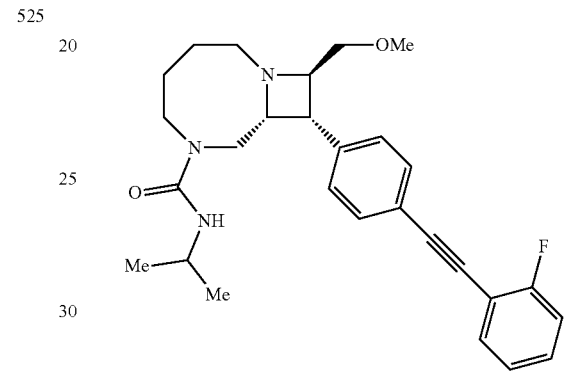
683-OMe
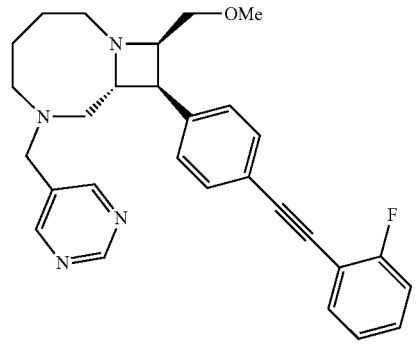
346
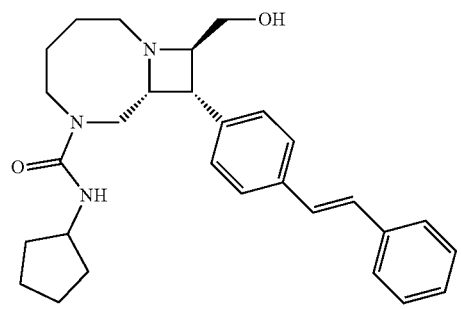

609
-continued
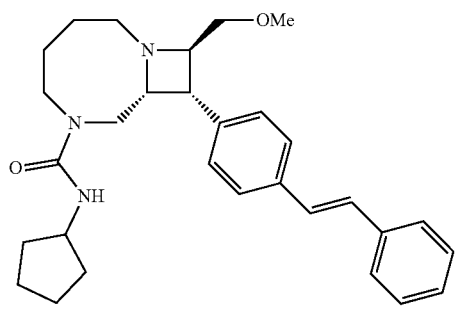
346-OMe
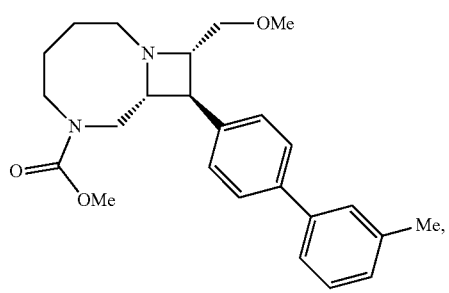
559-OMe
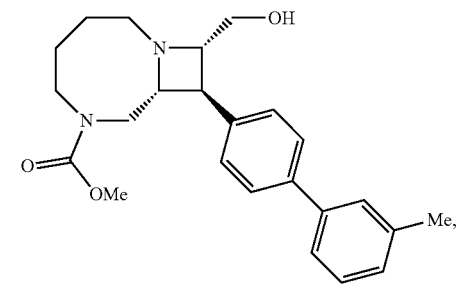
559
or a pharmaceutically acceptable salt, solvate, hydrate, polymorph, co-crystal, tautomer, stereoisomer, or isotopically labeled derivative thereof.
16. A compound of formula:
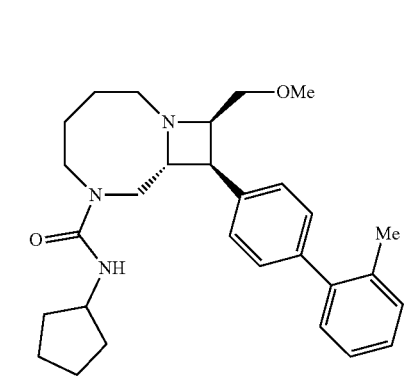
932-OMe
610
-continued
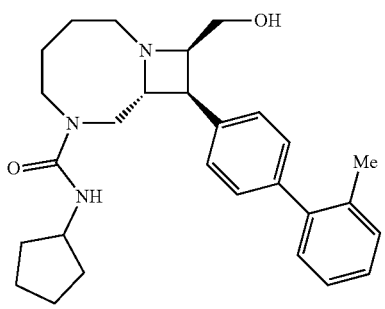
932
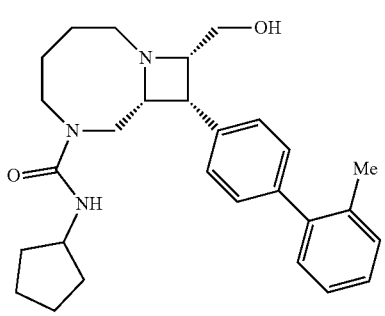
204
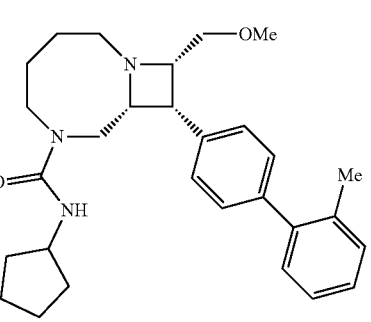
204-OMe
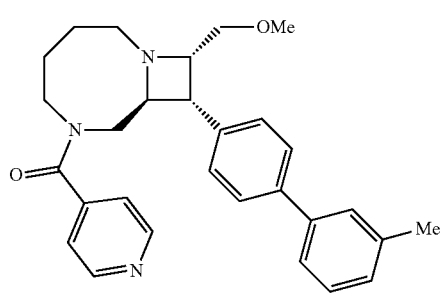
836-OMe
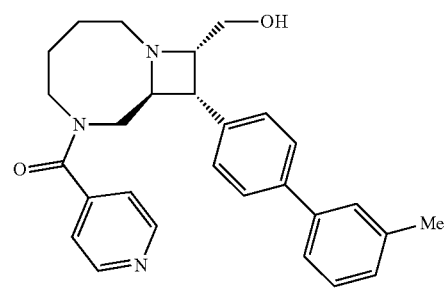
836

611
-continued
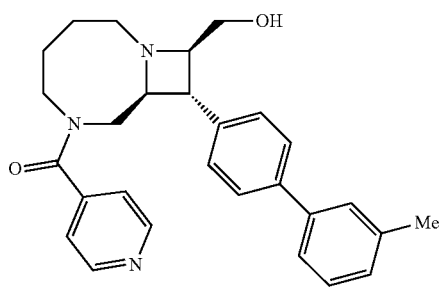
316
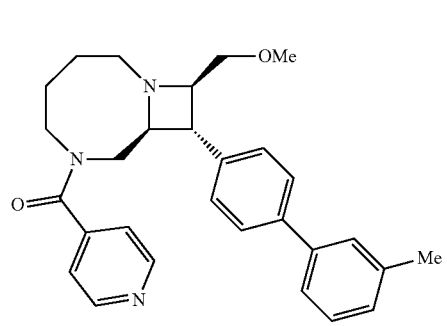
316-OMe
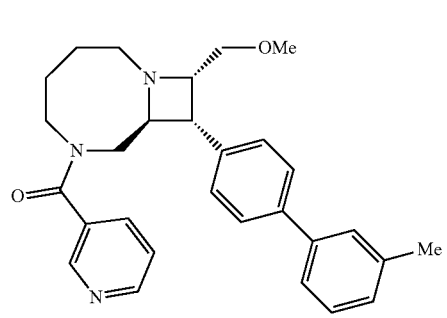
091-OMe
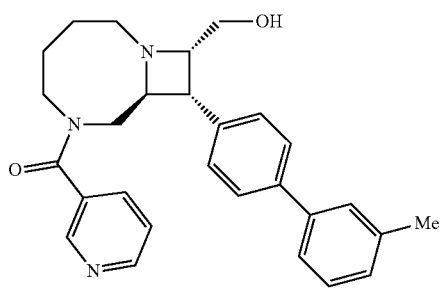
091
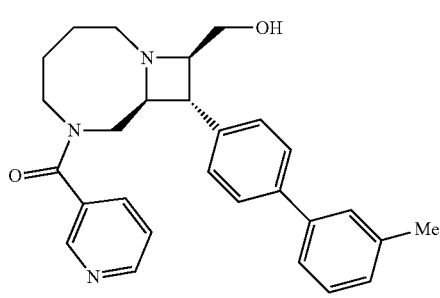
383
612
-continued
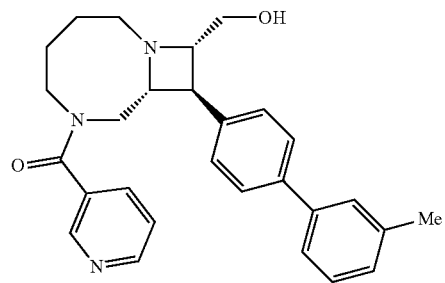
443
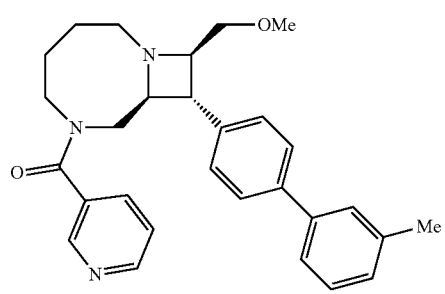
383-OMe
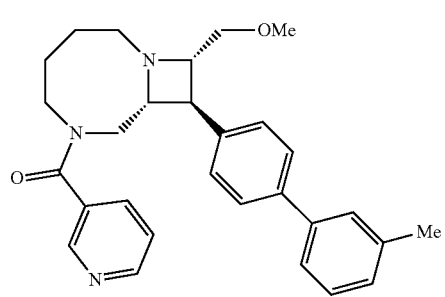
443-OMe
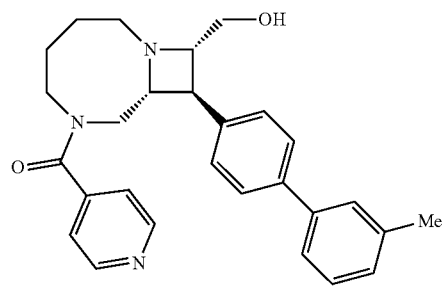
296
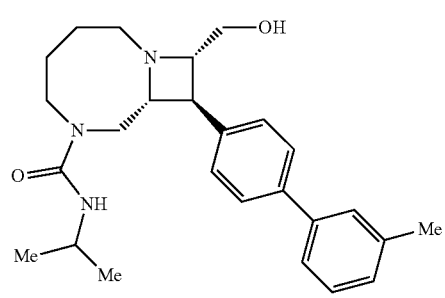
777

| 613 -continued | 614 -continued |
|---|---|
| 296-OMe 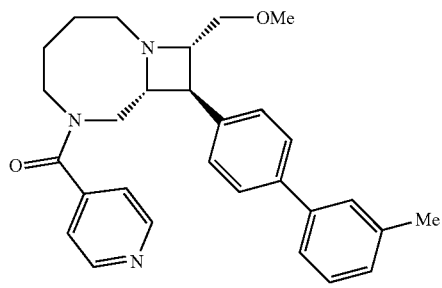 | 507-OMe 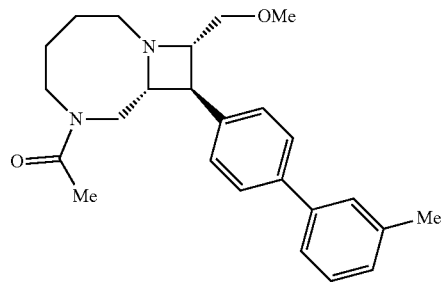 |
| 777-OMe 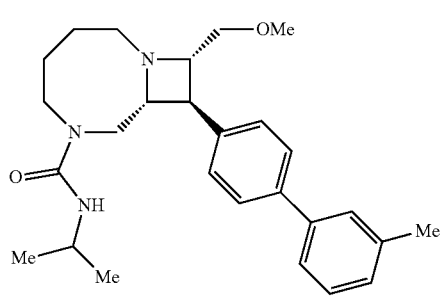 | 291 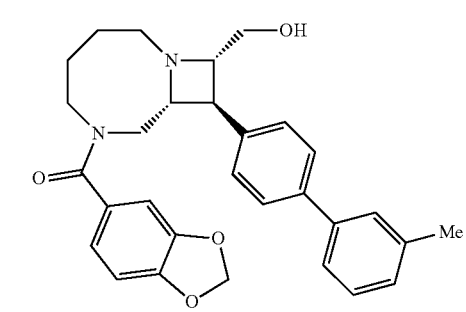 |
| 654 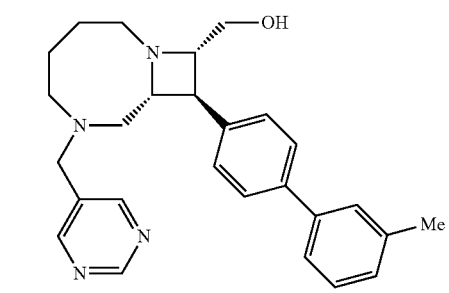 | 291-OMe 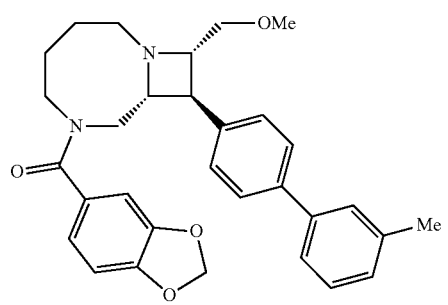 |
| 507 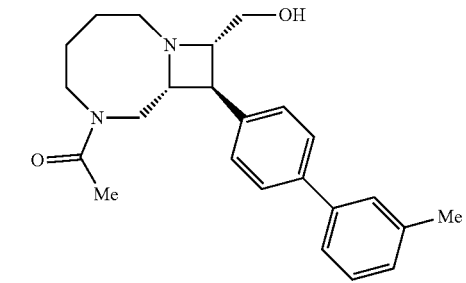 | 959 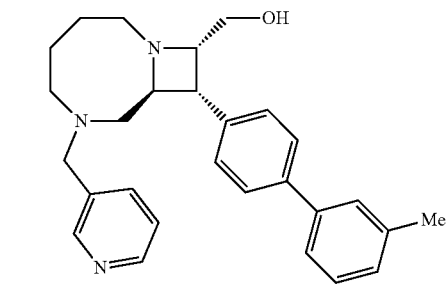 |
| 654-OMe 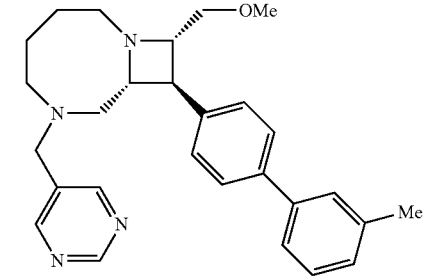 | 433 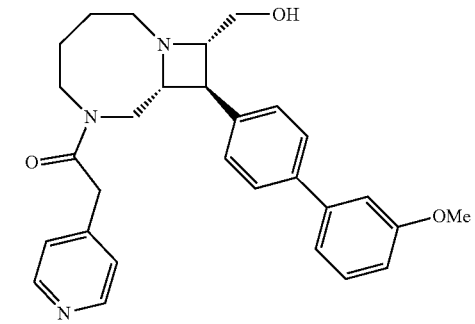 |

615
-continued
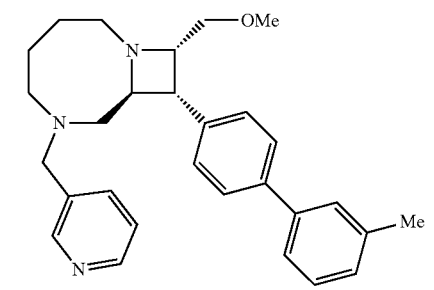
959-OMe
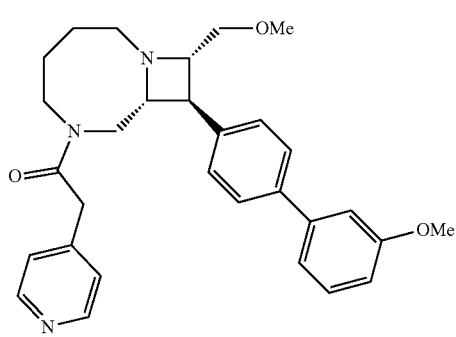
433-OMe
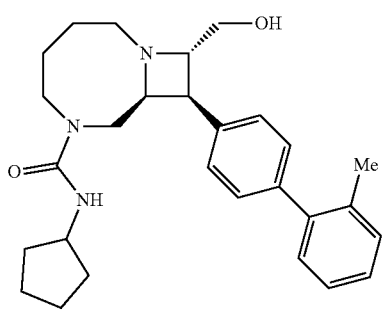
702
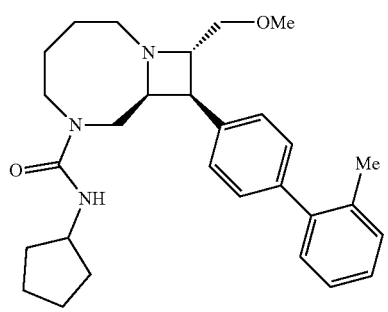
702-OMe
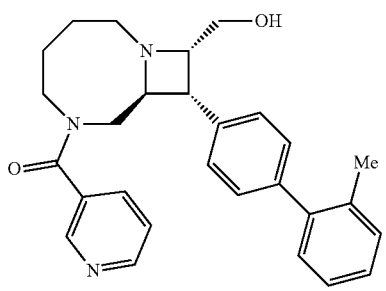
106
616
-continued
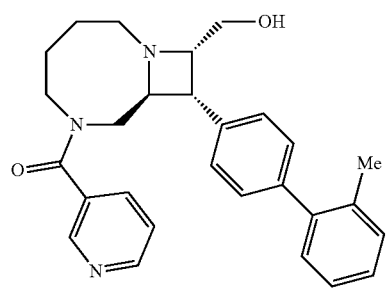
397
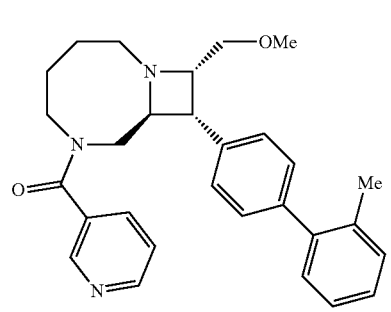
106-OMe
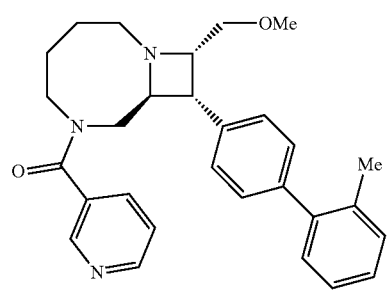
397-OMe
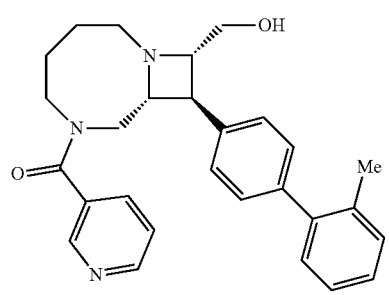
353
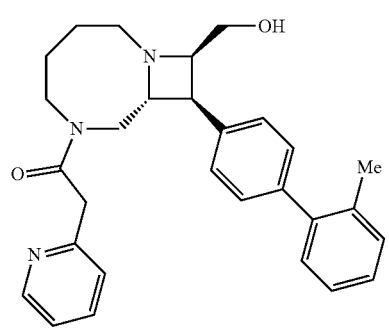
469

353-OMe
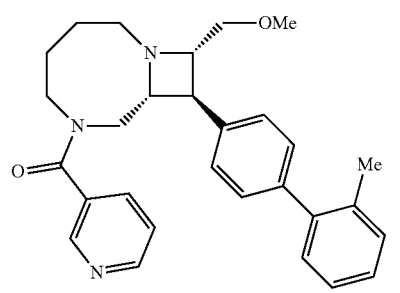
469-OMe
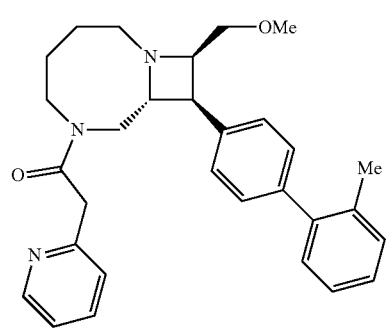
712
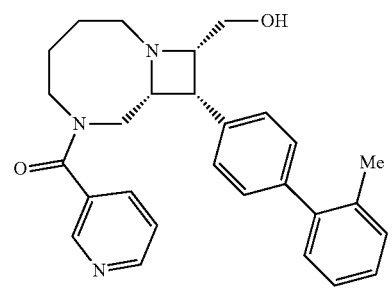
890
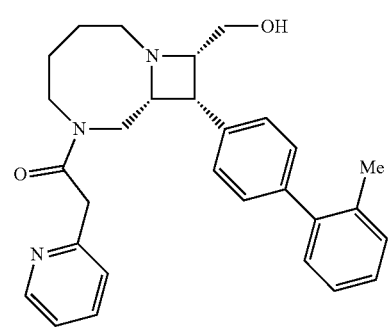
712-OMe
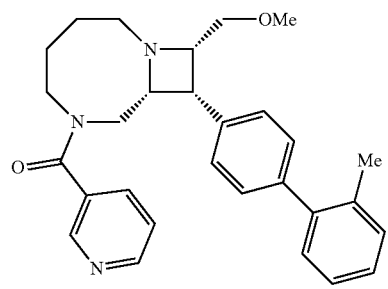
890-OMe
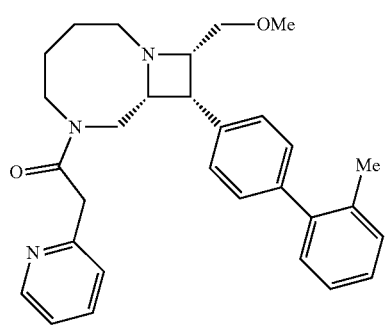
355
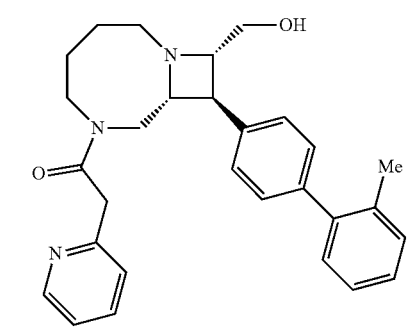
828
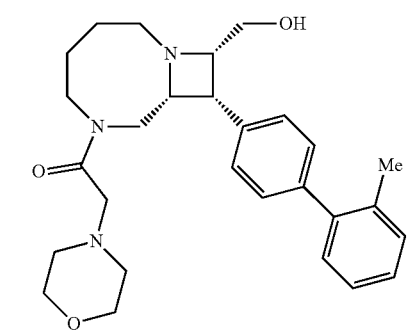
355-OMe
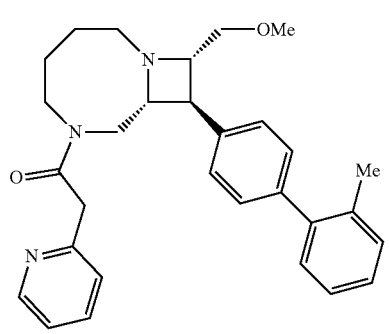
828-OMe
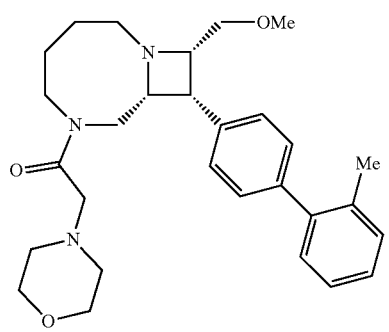

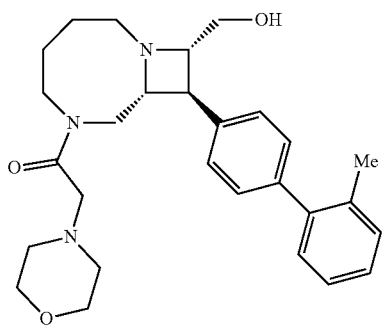
171
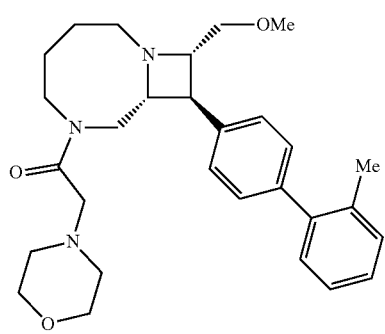
171-OMe
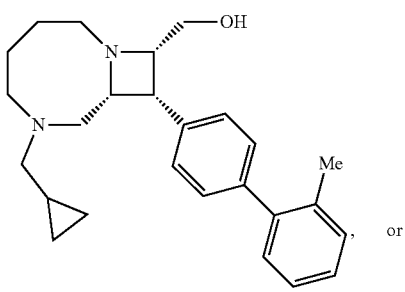
768
, or
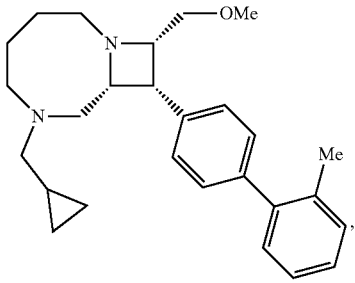
768-OMe
or a pharmaceutically acceptable salt, solvate, hydrate, polymorph, co-crystal, tautomer, stereoisomer, or isotopically labeled derivative thereof.
17. The compound of claim 1, wherein Ring A is arylene.
18. The compound of claim 1, wherein Ring A is phenylene.
19. The compound of claim 1, wherein $R^2$ is of formula:
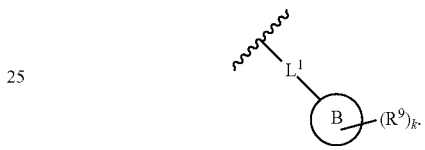
$L^1$ is a bond, and Ring B is
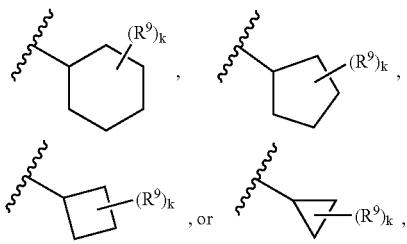
* * * * *

UNITED STATES PATENT AND TRADEMARK OFFICE
CERTIFICATE OF CORRECTION

PATENT NO. : 11,040,976 B2
APPLICATION NO. : 15/568930
DATED : June 22, 2021
INVENTOR(S) : Juan Pablo Maianti et al.

It is certified that error appears in the above-identified patent and that said Letters Patent is hereby corrected as shown below:

In the Claims

In Claim 8, at Column 566, Lines 55-67, the formula for compound K27:

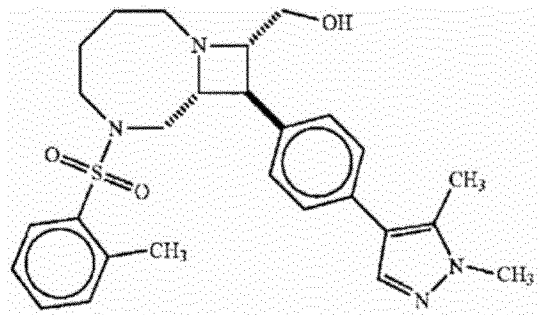

Should be replaced with the formula:

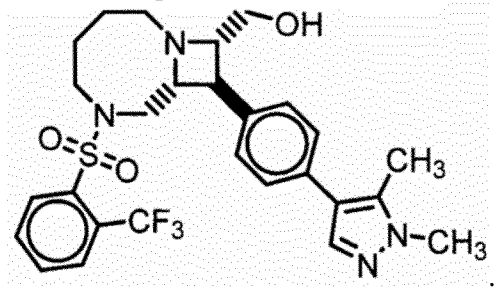

In Claim 8, at Column 567, Lines 15-26, the formula for compound K27-OMe:

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*

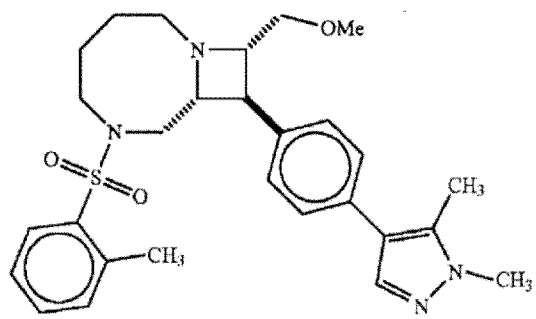
Should be replaced with the formula:
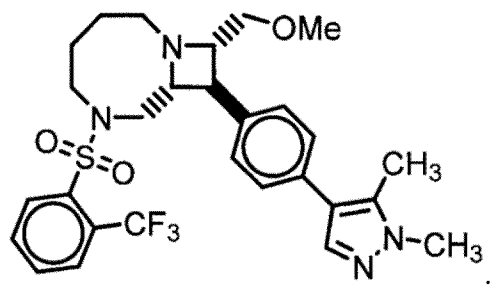
In Claim 8, at Column 567, Line 37, the text "[[,]]" should be deleted.
In Claim 15, at Column 587, Lines 44-54, the formula for compound JP-8:
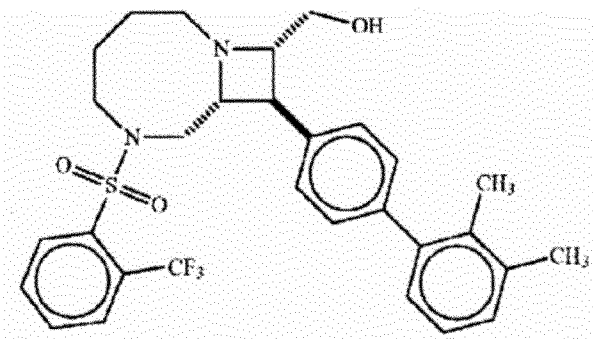
Should be replaced with the formula:
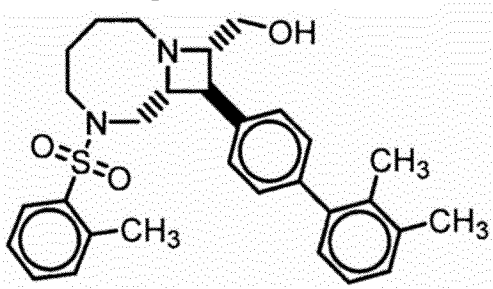
In Claim 15, at Column 587, Lines 55-66, the formula for compound JP-8-OMe:

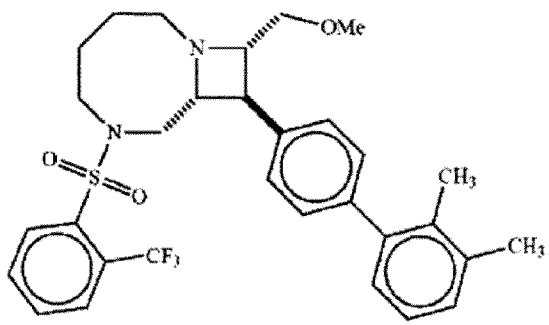
Should be replaced with the formula:
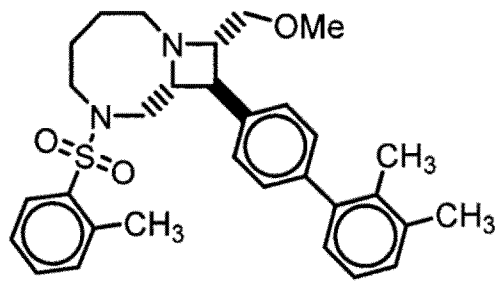
In Claim 15, at Column 588, Lines 3-15, the formula for compound JP-8N:
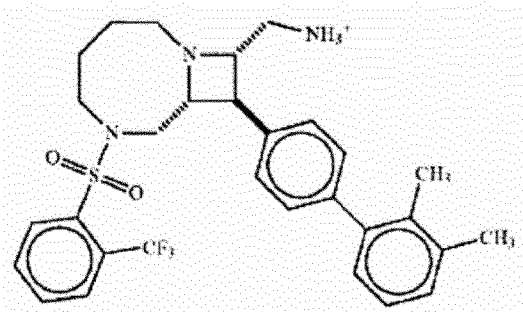
Should be replaced with the formula:
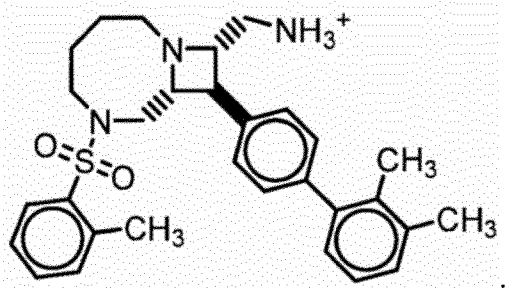
In Claim 15, at Column 591, Lines 54-66, the formula for compound JP-S15:

CERTIFICATE OF CORRECTION (continued)
U.S. Pat. No. 11,040,976 B2

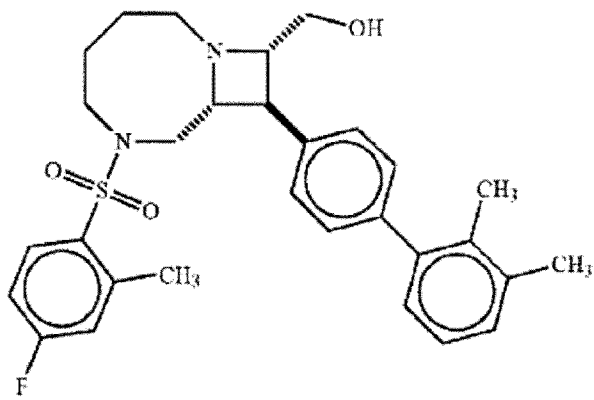

Should be replaced with the formula:

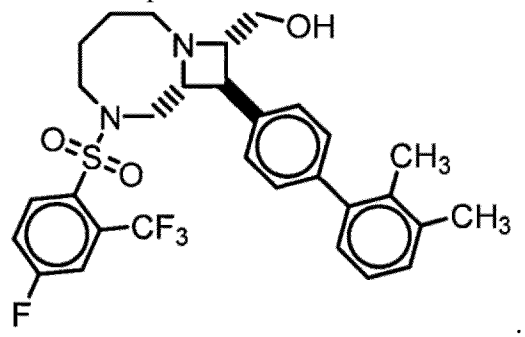

In Claim 15, at Column 592, Lines 16-29, the formula for compound JP-S15-OMe:

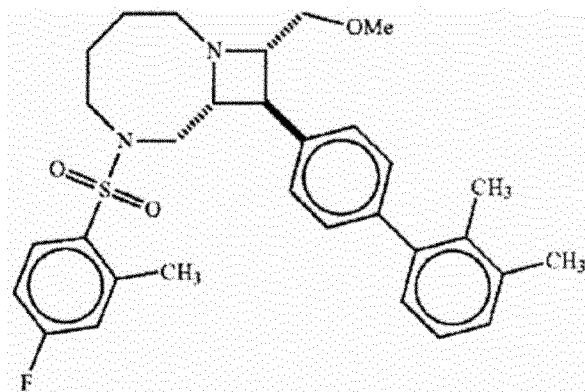

Should be replaced with the formula: